US010946090B2

(12) United States Patent
Haynes et al.

(10) Patent No.: US 10,946,090 B2
(45) Date of Patent: Mar. 16, 2021

(54) CONSENSUS/ANCESTRAL IMMUNOGENS

(71) Applicants: Duke University, Durham, NC (US); The University of Alabama at Birmingham Research Foundation, Birmingham, AL (US); Los Alamos National Security, LLC, Los Alamos, NM (US)

(72) Inventors: Barton F. Haynes, Durham, NC (US); Feng Gao, Durham, NC (US); Bette T. Korber, Los Alamos, NM (US); Beatrice H. Hahn, Birmingham, AL (US); George M. Shaw, Birmingham, AL (US); Denise L. Monti, Birmingham, AL (US); Ying Ying Li, Birmingham, AL (US); Julie Decker, Birmingham, AL (US); Hua-Xin Liao, Durham, NC (US)

(73) Assignees: Duke University, Durham, NC (US); The University of Alabama at Birmingham Research Foundation, Birmingham, AL (US); Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/813,992

(22) Filed: Nov. 15, 2017

(65) Prior Publication Data
US 2018/0296665 A1 Oct. 18, 2018

Related U.S. Application Data

(63) Continuation of application No. 13/137,517, filed on Aug. 2, 2011, now Pat. No. 9,844,589, which is a continuation of application No. 10/572,638, filed as application No. PCT/US2004/030397 on Sep. 17, 2004, now Pat. No. 8,071,107.

(60) Provisional application No. 60/604,722, filed on Aug. 27, 2004, provisional application No. 60/503,460, filed on Sep. 17, 2003.

(51) Int. Cl.
*A61K 39/21* (2006.01)
*C07K 14/005* (2006.01)
*C07K 16/42* (2006.01)
*A61K 39/12* (2006.01)
*A61K 39/00* (2006.01)

(52) U.S. Cl.
CPC ............ *A61K 39/21* (2013.01); *A61K 39/12* (2013.01); *C07K 14/005* (2013.01); *C07K 16/4225* (2013.01); *A61K 2039/53* (2013.01); *A61K 2039/57* (2013.01); *C12N 2740/15022* (2013.01); *C12N 2740/15034* (2013.01); *C12N 2740/16034* (2013.01); *C12N 2740/16122* (2013.01); *C12N 2740/16134* (2013.01); *C12N 2740/16222* (2013.01); *C12N 2740/16322* (2013.01)

(58) Field of Classification Search
CPC .......... A61K 39/21; C12N 2740/16134; C12N 2740/15022; C12N 2740/15034; C12N 2740/16034; C12N 2740/16122; C12N 2740/16222; C12N 2740/16322
See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,703,055 | A | 12/1997 | Felgner et al. |
| 7,172,761 | B2 | 2/2007 | Haynes et al. |
| 8,048,431 | B2 | 11/2011 | Haynes |
| 8,071,107 | B2 | 12/2011 | Haynes et al. |
| 2003/0044421 | A1 | 3/2003 | Emini et al. |
| 2003/0096778 | A1 | 5/2003 | Shiver et al. |
| 2005/0137387 | A1 | 6/2005 | Mullins et al. |
| 2007/0178562 | A1 | 8/2007 | Haynes et al. |
| 2009/0162384 | A1 | 6/2009 | Haynes |

FOREIGN PATENT DOCUMENTS

| | | |
|---|---|---|
| WO | 060838 | 8/2001 |
| WO | 0224149 | 3/2002 |

OTHER PUBLICATIONS

Yang, X., et al., 2003, Role of the gp120 inner domain beta-sandwich in the interaction between the human immunodeficiency virus envelope glycoprotein subunits, Virol. 313:117-125.*
Huang, W., et al., Jun. 2008, Coreceptor tropism can be influenced by amino acid substitutions in the gp41 transmembrane subunit of human immunodeficiency virus type 1 envelope protein, J. Virol. 82(11):5584-5593.*
Murphy, M. K., et al., Feb. 2013, Viral escape from neutralizing antibodies in early subtype A HIV-1 infection drives an increase in autologous neutralization breadth, PLoS Pathogens 9(2):e1003173, pp. 1-20.*
Mathys, L., et al., Jun. 2014, Deletion of the highly conserved N-glycan at Asn260 of HIV-1 gp120 affects folding and lysosomal degradation of gp120, and results in loss of viral infectivity, PLoS One 9(6):e101181, pp. 1-11.*
André et al., "Increased immune response elicited by DNA vaccination with a synthetic gp120 sequence with optimized codon usage," J Virol. Feb. 1998;72(2):1497-503.

(Continued)

*Primary Examiner* — Jeffrey S Parkin
(74) *Attorney, Agent, or Firm* — Baker Donelson

(57) ABSTRACT

The present invention relates, in general, to an immunogen and, in particular, to an immunogen for inducing antibodies that neutralizes a wide spectrum of HIV primary isolates and/or to an immunogen that induces a T cell immune response. The invention also relates to a method of inducing anti-HIV antibodies, and/or to a method of inducing a T cell immune response, using such an immunogen. The invention further relates to nucleic acid sequences encoding the present immunogens.

18 Claims, 178 Drawing Sheets

Figure 2A:
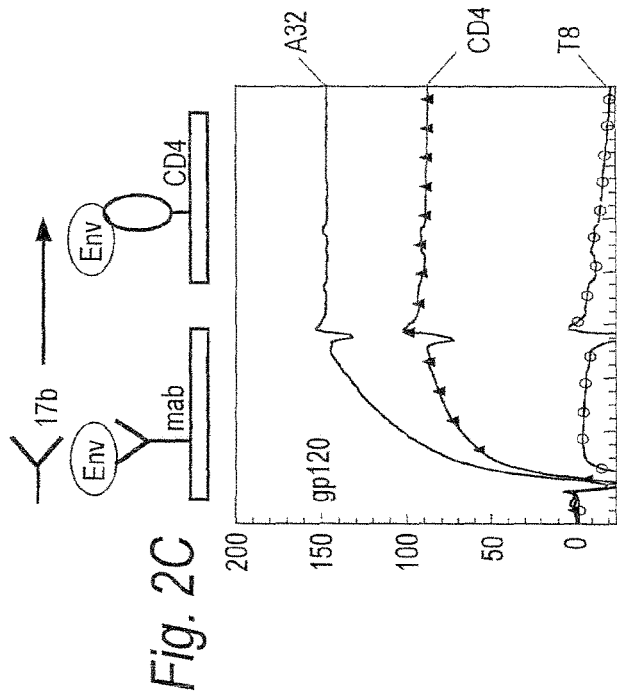

Specification includes a Sequence Listing.

(56) References Cited

OTHER PUBLICATIONS

Australian Patent Application No. 2014240343 Examination Report dated Jan. 21, 2016.
Baldridge et al., "Immunostimulatory activity of aminoalkyl glucosaminide 4-phosphates (AGPs): induction of protective innate immune responses by RC-524 and RC-529," J Endotoxin Res. 2002;8(6):453-8.
Barbeau et al., "Modulation of human immunodeficiency virus type 1-induced syncytium formation by the conformational state of LFA-1 determined by a new luciferase-based syncytium quantitative assay," J Virol. Sep. 1998;72(9):7125-36.
Bartlett et al., "Safety and immunogenicity of an HLA-based HIV envelope polyvalent synthetic peptide immunogen. DATRI 010 Study Group. Division of AIDS Treatment Research Initiative," AIDS. Jul. 30, 1998;12(11)1291-300.
Binley et al; Enhancing the Proteolytic Maturation of Human Immunodeficiency Virus Type 1 Envelope Glycoproteins; Journal of Virology vol. 76, No. 6; Mar. 2002, p. 2606-2616.
Blanchard et al., "Future Vaccines for HIV," Lancet. Dec. 21-28, 1996;348(9043):1741.
Bosch et al.; Mutational Analysis of the Human Immunodeficiency Virus Typle 1 env Gene Product Proteolytic Cleavage Site; Journal of Virology vol. 64, No. 5; May 1990; p. 2337-2344.
Brandt et al., "Association of chemokine-mediated block to HIV entry with coreceptor internalization," J Biol Chem. May 10, 2002;277(19):17291-9. Epub Jan. 8, 2002.
Bures et al., "Immunization with recombinant canarypox vectors expressing membrane-anchored glycoprotein 120 followed by glycoprotein 160," AIDS Res Hum Retroviruses. Dec. 10, 2000;16(18):2019-35.
Bures et al., "Regional clustering of shared neutralization determinants on primary isolates of clade C human immunodeficiency virus type 1 from South Africa," J Virol. Mar. 2002;76(5):2233-44.
Carr et al, Human retroviruses and AIDS 1998: a compilation and analysis of nucleic acid and amino acid sequences, eds. Korber et al (Theoretical Biology and Biophysics Group, Los Alamos National Laboratory, Los Alamos, N. Mex.), pp. III-10-III-19 (1998)).
Chakrabarti et al.; Modifications of the Human Immunodeficiency Virus Envelope Glycoprotein Enhance Immunogenicity for Genetic Immunization; Journal of Virology vol. 76, No. 11; Jun. 2002; p. 5357-5368.
Cho et al., "Polyvalent envelope glycoprotein vaccine elicits a broader neutralizing antibody response but is unable to provide sterilizing protection against heterologous Simian/human immunodeficiency virus infection in pigtailed macaques," J Virol. Mar. 2001;75(5):2224-34.
Cormier et al., "Specific interaction of CCR5 amino-terminal domain peptides containing sulfotyrosines with HIV-1 envelope glycoprotein gp120," Proc Natl Acad Sci U S A. May 23, 2000;97(11):5762-7.
Cornelissen et al., "Human immunodeficiency virus type 1 subtypes defined by env show high frequency of recombinant gag genes. The UNAIDS Network for HIV Isolation and Characterization," J Virol. Nov. 1996;70(11):8209-12.
Demi et al, "Multiple Effects of Codon Usage Optimization on Expression and Immunogenicity of DNA Candidate Vaccines Encoding the Human Immunodeficiency Virust Type 1 Gag Protein", Journal of Virology 75(22): 10991-11001 (2001).
Derdeyn et al., "Sensitivity of human immunodeficiency virus type 1 to the fusion inhibitor T-20 is modulated by coreceptor specificity defined by the V3 loop of gp120," J Virol. Sep. 2000;74(18):8358-67.
Dowling et al., "Forty-one near full-length HIV-1 sequences from Kenya reveal an epidemic of subtype A and A-containing recombinants," AIDS. Sep. 6, 2002;16(13):1809-20.
Ellenberger et al, "Generation of a Consensus Sequence from Prevalent and Incident HIV-1 Infections in West Africa to Guide AIDS Vaccine Development", Virology 302:156-163 (2002).
Evans et al., "A canarypox vaccine expressing multiple human immunodeficiency virus type 1 genes given alone or with rgp120 elicits broad and durable CD8+ cytotoxic T lymphocyte responses in seronegative volunteers," J Infect Dis. Aug. 1999;180(2):290-8.
Ferrari et al., "Identification of highly conserved and broadly cross-reactive HIV type 1 cytotoxic T lymphocyte epitopes as candidate immunogens," AIDS Res Hum Retroviruses. Sep. 20, 2000;16(14):1433-43.
Ferrari et al., "Clade B-based HIV-1 vaccines elicit cross-clade cytotoxic T lymphocyte reactivities in uninfected volunteers," Proc Natl Acad Sci U S A. Feb. 18, 1997;94(4)1396-401.
Fouts et al., "Crosslinked HIV-1 envelope-CD4 receptor complexes elicit broadly cross-reactive neutralizing antibodies in rhesus macaques," Proc Natl Acad Sci U S A. Sep. 3, 2002;99(18):11842-7. Epub Aug. 21, 2002.
Fouts et al., "Neutralization of the human immunodeficiency virus type 1 primary isolate JR-FL by human monoclonal antibodies correlates with antibody binding to the oligomeric form of the envelope glycoprotein complex," J Virol. Apr. 1997;71(4):2779-85.
Gallo, Robert C., "The end or the beginning of the drive to an HIV-preventive vaccine: a view from over 20 years", The Lancet 366:1894-1898 (2005).
Gao et al, "Centralized immunogens as a vaccine strategy to overcome HIV-1 diversity", Expert Rev Vaccines 3(4 Suppl)S 161-8 (2004)-Abstract.
Gao et al, "Codon usage optimization of HIV type 1 subtype C gag, pol, env, and nef genes: in vitro expression and immune responses in DNA-vaccinated mice", AIDS Res. Hum. Retroviruses 19(9):817-823 (2003).
Gao et al. Antigenicity and Immunogenicity of a Synthetic Human Immunodeficiency Virus Type 1 Group M consensus Envelope Glycoprotein; Journal of Virology vol. 79, No. 2; Jan. 2005; p. 1154-1163.
Gaschen et al; Diversity Considerations in HIV-1 Vaccine Selection; Science 296, p. 2354-2360; Jun. 28, 2002.
Guo et al.; Characterization of an HIV-1 Point Mutant Blocked in Envelope Glycoprotein Cleavage; Virology 174, p. 217-224 (1990).
Gürtler, et al., "A new subtype of human immunodeficiency virus type 1 (MVP-5180) from Cameroon," J Virol. Mar. 1994;68(3):1581-5.
Haas et al., "Codon usage limitation in the expression of HIV-1 envelope glycoprotein," Curr Biol. Mar. 1, 1996;6(3):315-24.
Haynes et al., "HIV vaccines: where we are and where we are going," Lancet. Oct. 5, 1996;348(9032):933-7.
Haynes et al., "Induction of HIVMN neutralizing antibodies in primates using a prime-boost regimen of hybrid synthetic gp120 envelope peptides," J Immunol. Aug. 1, 1993;151(3):1646-53.
HIV Sequence Compendium 2003. Leitner T, Foley B, Hahn B, Marx P, McCutchan F, Mellors J, Wolinsky S, and Korber B, Eds. Published by Theoretical Biology and Biophysics Group, Los Alamos National Laboratory, NM, LA-UR 04-7420 (2003).
International Search Report issued in connection with PCT/US04/30397 dated Mar. 8, 2005.
Jiang et al., "A conformation-specific monoclonal antibody reacting with fusion-active gp41 from the human immunodeficiency virus type 1 envelope glycoprotein," J Virol. Dec. 1998;72(12):10213-7.
Kofman et al, "HIV-1 gag expression is quantitatively dependent on the ratio of native and optimized codons", Tsitologiia 45(1):86-93 (2003).
Korber et al., "Evolutionary and immunological implications of contemporary HIV-1 variation", British Medical Bulletin, 58:19-42 (2001).
Korber et al., "Timing the ancestor of the HIV-1 pandemic strains," Science. Jun. 9, 2000;288(5472):1789-96.
Kuiken et al, Human retroviruses and AIDS 2000: a compilation and analysis of nucleic acid and amino acid sequences (Theoretical Biology and Biophysics Group, Los Alamos National Laboratory, Los Alamos, N. Mex.)), pp. 355-456 (2000).
Kwong et al., "Structure of an HIV gp120 envelope glycoprotein in complex with the CD4 receptor and a neutralizing human antibody," Nature. Jun. 18, 1998;393(6686):648-59.
LaCasse et al., "Fusion-competent vaccines: broad neutralization of primary isolates of Hiv," Science. Jan. 15, 1999;283(5400):357-62. [Retracted in Nunberg et al., Science. May 10, 2002;296(5570):1025].

(56) References Cited

OTHER PUBLICATIONS

Leitner et al, eds., "HIV Sequence Compendium 2003", Theoretical Biology and Biophysics Group, Los Alamos National Laboratory, LA-UR No. 04-7420, pp. 513-573 and attached appendix.
Letvin et al., "Prospects for vaccine protection against HIV-1 infection and AIDS," Annu Rev Immunol. 2002;20:73-99. Epub Oct. 4, 2001.
Levine, Arnold J., "Why Do We Not Yet Have a Human Immunodeficiency Virus Vaccine?", Journal of Virology 82(24):11998-1200 (2008).
Li et al.; Control of Expression, Glycosylation, and Secretion of HIV-1 gp 120 by Homologous and Heterologous Signal Sequences; Virology 204, 266-278 (1994).
Li et al.; Effects of inefficient cleavage of the signal sequence of HIV-1 gpl20 on its association with calnexin, folding, and intracellular transport; Proc. Natl. Acad. Sci. USA vol. 93 Sep. 1996 p. 9606-9611.
Liao et al, "A Group M Consensus Envelope Glycoprotein induces Antibodies That Neutralize Subsets of Subtype B and C HIV-1 Primary Viruses", NIH Public Access, pp. 1-30, Published in final edited form as Virology 353(2):268-282 (2006).
Liao et al., "Immunogenicity of constrained monoclonal antibody A32-human immunodeficiency virus (HIV) Env gp120 complexes compared to that of recombinant HIV type 1 gp120 envelope glycoproteins," J Virol. May 2004;78(10):5270-8.
Liao et al.; Antigenicity and Immunogenicity of Transmitted/Founder, Consensus, and Chronic Envelope Glycoproteins of Human Immunodeficiency Virus Type 1; Journal of Virology vol. 87, No. 8; p. 4185-4201; Apr. 2013.
Liao et al; A Group M Consensus Envelope Glycoprotein Induces Antibodies That Neutralize Subsets of Subtype B and C HIV-1 Primary Viruses; Virology 353(2) p. 268-282; Sep. 30, 2006.
Mascola et al., "Protection of Macaques against pathogenic simian/human immunodeficiency virus 89.6PD by passive transfer of neutralizing antibodies," J Virol. May 1999;73(5):4009-18.
Mascola et al., "Protection of macaques against vaginal transmission of a pathogenic HIV-1/SIV chimeric virus by passive infusion of neutralizing antibodies," Nat Med. Feb. 2000;6(2):207-10.
McCune et al; Endoproteolytic Cleavage of gp160 Is Required for the Activation of Human Immunodeficiency Virus; Cell, vol. 53; p. 55-67; Apr. 8, 1988.
McMichael et al., "HIV T cell vaccines, the importance of Glades," Vaccine. May 6, 2002;20(15):1918-21.
Mo et al., "Human immunodeficiency virus type 1 mutants that escape neutralization by human monoclonal antibody IgG1b12. off," J Virol. Sep. 1997;71(9):6869-74.
Moore and Binley, "Envelope's letters boxed into shape," Nature. Jun. 18, 1998;393(6686):630-31.
Moore et al., "Exploration of antigenic variation in gp120 from Glades A through F of human immunodeficiency virus type 1 by using monoclonal antibodies," J Virol. Dec. 1994;68(12):8350-64.
Morris et al., "Characterization and selection of HIV-1 subtype C isolates for use in vaccine development", AIDS Res Hum Retroviruses, 19(2):133-144 (2003)-Abstract.
Muster et al., "Cross-neutralizing activity against divergent human immunodeficiency virus type 1 isolates induced by Ihe gp41 sequence ELDKWAS," J Virol. Jun. 1994;68(6):4031-4.
Nickle et al, "Consensus and Ancestral State HIV Vaccines", Science 299(5612):1515-1518 (2003).
Notice of Allowance dated Jan. 4, 2011 in U.S. Appl. No. 10/572,638.
Notice of Allowance dated May 12, 2011 in U.S. Appl. No. 10/572,638.
Notice of Allowance dated Nov. 15, 2010 in U.S. Appl. No. 11/896,934.
Novitsky et al, "Human Immunodeficiency Virus Type 1 Subtype C Molecular Phylogeny: Consensus Sequences for an AIDS Vaccine Design?", Journal of Virology 66(11 ):5435-5451 (2002).
Nyambi et al., "Multivariate analysis of human immunodeficiency virus type 1 neutralization data," J Virol. Sep. 1996;70(9):6235-43.
Office Action dated Jul. 7, 2010 in U.S. Appl. No. 11/896,934.
Office Action dated Jun. 4, 2010 in U.S. Appl. No. 10/572,638.
Office Action dated Nov. 30, 2009 in U.S. Appl. No. 10/572,638.
Office Action dated Oct. 6, 2009 in U.S. Appl. No. 11/896,934.
Ourmanov et al., "Recombinant modified vaccinia virus ankara expressing the surface gp120 of simian immunodeficiency virus (SIV) primes for a rapid neutralizing antibody response to SIV infection in macaques," J Virol. Mar. 2000;74(6):2960-5.
Pal et al., "ALVAC-SIV-gag-pol-env-based vaccination and macaque major histocompatibility complex class I (A*01) delay simian immunodeficiency virus SIVmac-induced immunodeficiency," J Virol. Jan. 2002;76(1):292-302.
Polacino et al., "Limited breadth of the protective immunity elicited by simian immunodeficiency virus SIVmne gp160 vaccines in a combination immunization regimen," J Virol. Jan. 1999;73(1):618-30.
Rimsky et al., "Determinants of human immunodeficiency virus type 1 resistance to gp41-derived inhibitory peptides," J Virol. Feb. 1998;72(2):986-93.
Roben et al., "Recognition properties of a panel of human recombinant Fab fragments to the CD4 binding site of gp120 that show differing abilities to neutralize human immunodeficiency virus type 1," J Virol. Aug. 1994;68(8):4821-8.
Robertson et al, Human retroviruses and AIDS 1999: a compilation and analysis of nucleic acid and amino acid sequences, eds. Kuiken et al (Theoretical Biology and Biophysics Group, Los Alamos National Laboratory, Los Alamos, N. Mex.), pp. 492-505 (1999)).
Robertson et al., "Recombination in HIV-1," Nature. Mar. 9, 1995;374(6518):124-6.
Rossio et al., "Inactivation of human immunodeficiency virus type 1 infectivity with preservation of conformational and functional integrity of virion surface proteins," J Virol. Oct. 1998;72(10):7992-8001.
Saphire et al., "Crystal structure of a neutralizing human IGG against HIV-1: a template for vaccine design," Science. Aug. 10, 2001;293(5532):1155-9.
Sbai et al., "Use of T cell epitopes for vaccine development," Curr Drug Targets Infect Disord. Nov. 2001;1(3):303-13.
Simon et al., "Identification of a new human immunodeficiency virus type 1 distinct from group M and group O," Nat Med. Sep. 1998;4(9):1032-7.
Supplementary Partial European Search Report dated Aug. 1, 2008—EP Appln. No. 04 78 4298.
Trkola et al., "Human monoclonal antibody 2G12 defines a distinctive neutralization epitope on the gp120 glycoprotein of human immunodeficiency virus type 1," J Virol. Feb. 1996;70(2):1100-8.
Vanden Haesevelde et al., "Genomic cloning and complete sequence analysis of a highly divergent African human immunodeficiency virus isolate," J Virol. Mar. 1994;68(3):1586-96.
Wain Hobson, "More ado about HIV's origins," Nat Med. Sep. 1998;4(9):1001-2.
Walker and Burton, "Toward an AIDS Vaccine", Science 320:760-764 (2008).
Wang, Lai-Xi, "Bioorganic Approaches Towards HIV Vaccine Design", Current Pharmaceutical Design 9:1771-1787 (2003).
Wei et al., "Emergence of resistant human immunodeficiency virus type 1 in patients receiving fusion inhibitor (T-20) monotherapy," Antimicrob Agents Chemother. Jun. 2002;46(6):1896-905.
Williamson et al, "Characterization and selection of HIV-1 subtype C isolates for use in vaccine development", AIDS Res. Hum. Retroviruses 19(2):133-144 (2003).
Written Opinion for corresponding PCT application PCT/US04/30397 dated Mar. 8, 2005.
Wyatt et al., "Involvement of the V1N2 variable loop structure in the exposure of human immunodeficiency virus type 1 gp120 epitopes induced by receptor binding," J Virol. Sep. 1995;69(9):5723-33.
Wyatt et al., "The antigenic structure of the HIV gp120 envelope glycoprotein," Nature. Jun. 18, 1998;393(6686):705-11.
Ye et al., "Association of structural changes in the V2 and V3 loops of the gp120 envelope glycoprotein with acquisition of neutralization resistance in a simian-human immunodeficiency virus passaged in vivo," J Virol. Dec. 2000;74(24):11955-62.

\* cited by examiner

MRVMGIQRNCQHLWRWGTMILGMLMICSAAAENLWVTVYYGVPVWKEANTTLFCASDAKAYDTEVHNVWAT
HACVPTDPNPQEIVLENVTENFNMWKNNMVEQMHEDIISLWDQSLKPCVKLTPLCVTLNCTNVRNVSSNG
TETDNEEIKNCSFNITTELRDKKQKVYALFYRLDVVPIDDKNSSEISGKNSSEYYRLINCNTSAITQACP
KVSFEPIPIHYCAPAGFAILKCNDKKFNGTGPCKNVSTVQCTHGIKPVVSTQLLLNGSLAEEEIIRSEN
ITNNAKTIIVQLNESVEINCTRPNNNTRKSIHIGPGQAFYATGEIIGDIRQAHCNISRTKWNKTLQQVAK
KLREHFNNKTIIFKPSSGGDLEITTHSFNCGGEFFYCNTSGLFNSTWMFNGTYMFNGTKDNSETITLPCR
IKQIINMWQGVGQAMYAPPIEGKITCKSNITGLLLTRDGGNNSNKNKTETFRPGGGDMRDNWRSELYKYK
VVKIEPLGVAPTKAKRRVVEREKRAVGIGAVFLGFLGAAGSTMGAASITLTVQARQLLSGIVQQSNLLR
AIEAQQHLLQLTVWGIKQLQARVLAVERYLKDQQLLGIWGCSGKLICTTNVPWNSSWSNKSQDEIWDNMT
WMEWEREISNYTDIIYRLIEESQNQEKNEQELLALDKWASLWNWFDITNWLWYIKIFIMIVGGLIGLRI
VFAVLSIVNRVRQGYSPLSFQTLIPNPRGPDRPEGIEEEGEQGRDRSIRLVNGFLALAWDDLRSLCLFS
YHRLRDFLLIAARTVELLGRRSLRGLQKGWEALKYLGNLLQYWGQELKNSAISLLDTTAIAVAEGTDRVI
EIVQRACRAILNIPRRIRQGLERALL

Fig. 1A

Fig. 1B

```
              Cleavage  Fusion
              site      domain   TM
gp160    [_____/////___■■___]
gp140CF  [_____/_____]
gp120    [_____]
```

CON6.env (group M env consensus. This one contain five variable regions in env gene from 98CN006 virus, not in the public domain yet)

```
GCCACCATGCGCGTGATGGGCATCCAGCGCAACTGCCAGCACCTGTGGCGCTGGGGCACCATGATC
CTGGGCATGCTGATGATCTGCTCCGCCGCCGAGAACCTGTGGGTGACCGTGTACTACGGC
GTGCCCGTGTGGAAGGAGGCCAACACCACCCTGTTCTGCGCCTCCGACGCCAAGGCCTAC
GACACCGAGGTGCACAACGTGTGGGCCACCCACGCCTGCGTGCCCACCGACCCCAACCCC
CAGGAGATCGTGCTGGAGAACGTGACCGAGAACTTCAACATGTGGAAGAACAACATGGTG
GAGCAGATGCACGAGGACATCATCTCCCTGTGGGACCAGTCCCTGAAGCCCTGCGTGAAG
CTGACCCCCCTGTGCGTGACCCTGAACTGCACCAACGTGCGCAACGTGTCCTCCAACGGC
ACCGAGACCGACAACGAGGAGATCAAGAACTGCTCCTTCAACATCACCACCGAGCTGCGC
GACAAGAAGCAGAAGGTGTACGCCCTGTTCTACCGCCTGGACGTGGTGCCCATCGACGAC
AAGAACTCCTCCGAGATCTCCGGCAAGAACTCCTCCGAGTACTACCGCCTGATCAACTGC
AACACCTCCGCCATCACCCAGGCCTGCCCCAAGGTGTCCTTCGAGCCCATCCCCATCCAC
TACTGCGCCCCGCCGGCTTCGCCATCCTGAAGTGCAACGACAAGAAGTTCAACGGCACC
GGCCCCTGCAAGAACGTGTCCACCGTGCAGTGCACCCACGGCATCAAGCCCGTGGTGTCC
ACCCAGCTGCTGCTGAACGGCTCCCTGGCCGAGGAGGAGATCATCATCCGCTCCGAGAAC
ATCACCAACAACGCCAAGACCATCATCGTGCAGCTGAACGAGTCCGTGGAGATCAACTGC
ACCCGCCCCAACAACAACACCCGCAAGTCCATCCACATCGGCCCCGGCCAGGCCTTCTAC
GCCACCGGCGAGATCATCGGCGACATCCGCCAGGCCCACTGCAACATCTCCCGCACCAAG
TGGAACAAGACCCTGCAGCAGGTGGCCAAGAAGCTGCGCGAGCACTTCAACAACAAGACC
ATCATCTTCAAGCCCTCCTCCGGCGGCGACCTGGAGATCACCACCCACTCCTTCAACTGC
GGCGGCGAGTTCTTCTACTGCAACACCTCCGGCCTGTTCAACTCCACCTGGATGTTCAAC
GGCACCTACATGTTCAACGGCACCAAGGACAACTCCGAGACCATCACCCTGCCCTGCCGC
ATCAAGCAGATCATCAACATGTGGCAGGGCGTGGGCCAGGCCATGTACGCCCCCCCCATC
GAGGGCAAGATCACCTGCAAGTCCAACATCACCGGCCTGCTGCTGACCCGCGACGGCGGC
AACAACTCCAACAAGAACAAGACCGAGACCTTCCGCCCCGGCGGCGGCGACATGCGCGAC
AACTGGCGCTCCGAGCTGTACAAGTACAAGGTGGTGAAGATCGAGCCCCTGGGCGTGGCC
CCCACCAAGGCCAAGCGCCGCGTGGTGGAGCGCGAGAAGCGCGCCGTGGGCATCGGCGCC
GTGTTCCTGGGCTTCCTGGGCGCCGCCGGCTCCACCATGGGCGCCGCCTCCATCACCCTG
ACCGTGCAGGCCCGCCAGCTGCTGTCCGGCATCGTGCAGCAGCAGTCCAACCTGCTGCGC
GCCATCGAGGCCCAGCAGCACCTGCTGCAGCTGACCGTGTGGGGCATCAAGCAGCTGCAG
GCCCGCGTGCTGGCCGTGGAGCGCTACCTGAAGGACCAGCAGCTGCTGGGCATCTGGGGC
TGCTCCGGCAAGCTGATCTGCACCACCAACGTGCCCTGGAACTCCTCCTGGTCCAACAAG
TCCCAGGACGAGATCTGGGACAACATGACCTGGATGGAGTGGGAGCGCGAGATCTCCAAC
TACACCGACATCATCTACCGCCTGATCGAGGAGTCCCAGAACCAGCAGGAGAAGAACGAG
CAGGAGCTGCTGGCCCTGGACAAGTGGGCCTCCCTGTGGAACTGGTTCGACATCACCAAC
TGGCTGTGGTACATCAAGATCTTCATCATGATCGTGGGCGGCCTGATCGGCCTGCGCATC
GTGTTCGCCGTGCTGTCCATCGTGAACCGCGTGCGCCAGGGCTACTCCCCCCTGTCCTTC
CAGACCCTGATCCCCAACCCCGCGGCCCCGACCGCCCCGAGGGCATCGAGGAGGAGGGC
GGCGAGCAGGGCCGCGACCGCTCCATCCGCCTGGTGAACGGCTTCCTGGCCCTGGCCTGG
GACGACCTGCGCTCCCTGTGCCTGTTCTCCTACCACCGCCTGCGCGACTTCATCCTGATC
GCCGCCCGCACCGTGGAGCTGCTGGGCCGCCGCTCCCTGCGCGGCCTGCAGAAGGGCTGG
GAGGCCCTGAAGTACCTGGGCAACCTGCTGCAGTACTGGGGCCAGGAGCTGAAGAACTCC
GCCATCTCCCTGCTGGACACCACCGCCATCGCCGTGGCCGAGGGCACCGACCGCGTGATC
GAGATCGTGCAGCGCGCCTGCCGCGCCATCCTGAACATCCCCCGCCGCATCCGCCAGGGC
CTGGAGCGCGCCCTGCTGTAA
```

Fig. 6A

C.anc.env (subtype C ancestral env. The amino acid sequence is different from Los Alamos Database August 2002)

GCCGCCATGCGCGTGATGGGCATCCTGCGCAACTGCCAGCAGTGGTGGAT
CTGGGGCATCCTGGGCTTCTGGATGCTGATGATCTGCTCCGTGGTGGGCA
ACCTGTGGGTGACCGTGTACTACGGCGTGCCCGTGTGGAAGGAGGCCAAG
ACCACCCTGTTCTGCGCCTCCGACGCCAAGGCCTACGAGCGCGAGGTGCA
CAACGTGTGGGCCACCCACGCCTGCGTGCCCACCGACCCCAACCCCCAGG
AGATGGTGCTGGAGAACGTGACCGAGAACTTCAACATGTGGAAGAACGAC
ATGGTGGACCAGATGCACGAGGACATCATCTCCCTGTGGGACCAGTCCCT
GAAGCCCTGCGTGAAGCTGACCCCCCTGTGCGTGACCCTGAACTGCACCA
ACGTGACCAACGCCACCAACAACACCTACAACGGCGAGATGAAGAACTGC
TCCTTCAACATCACCACCGAGCTGCGCGACAAGAAGAAGAAGGAGTACGC
CCTGTTCTACCGCCTGGACATCGTGCCCCTGAACGAGAACTCCTCCGAGT
ACCGCCTGATCAACTGCAACACCTCCGCCATCACCCAGGCCTGCCCCAAG
GTGTCCTTCGACCCCATCCCCATCCACTACTGCGCCCCCGCCGGCTACGC
CATCCTGAAGTGCAACAACAAGACCTTCAACGGCACCGGCCCCTGCAACA
ACGTGTCCACCGTGCAGTGCACCCACGGCATCAAGCCCGTGGTGTCCACC
CAGCTGCTGCTGAACGGCTCCCTGGCCGAGGAGGAGATCATCATCCGCTC
CGAGAACCTGACCGACAACGCCAAGACCATCATCGTGCAGCTGAACGAGT
CCGTGGAGATCGTGTGCACCCGCCCCAACAACAACACCCGCAAGTCCATG
CGCATCGGCCCCGGCCAGACCTTCTACGCCACCGGCGACATCATCGGCGA
CATCCGCCAGGCCCACTGCAACATCTCCGAGGACAAGTGGAACAAGACCC
TGCAGCAGGTGGCCGAGAAGCTGGGCAAGCACTTCCCCAACAAGACCATC
ACCTTCGAGCCCTCCTCCGGCGGCGACCTGGAGATCACCACCCACTCCTT
CAACTGCCGCGGCGAGTTCTTCTACTGCAACACCTCCAAGCTGTTCAACT
CCACCTACAACAACAACACCAACTCCAACTCCACCATCACCCTGCCCTGC
CGCATCAAGCAGATCATCAACATGTGGCAGGGCGTGGGCCAGGCCATGTA
CGCCCCCCCCATCGCCGGCAACATCACCTGCAAGTCCAACATCACCGGCC
TGCTGCTGACCCGCGACGGCGGCAAGGAGAACACCACCGAGACCTTCCGC
CCCGGCGGCGGCGACATGCGCGACAACTGGCGCTCCGAGCTGTACAAGTA
CAAGGTGGTGGAGATCAAGCCCCTGGGCGTGGCCCCCACCGAGGCCAAGC
GCCGCGTGGTGGAGCGCGAGAAGCGCGCCGTGGGCCTGGGCGCCGTGTTC
CTGGGCTTCCTGGGCGCCGCCGGCTCCACCATGGGCGCCGCCTCCATCAC
CCTGACCGTGCAGGCCCGCCAGCTGCTGTCCGGCATCGTGCAGCAGCAGT
CCAACCTGCTGCGCGCCATCGAGGCCCAGCAGCACATGCTGCAGCTGACC
GTGTGGGGCATCAAGCAGCTGCAGGCCCGCGTGCTGGCCATGGAGCGCTA
CCTGAAGGACCAGCAGCTGCTGGGCATCTGGGGCTGCTCCGGCAAGCTGA
TCTGCACCACCGCCGTGCCCTGGAACTCCTCCTGGTCCAACAAGTCCCTG
GACGACATCTGGGACAACATGACCTGGATGGAGTGGGACCGCGAGATCTC
CAACTACACCGACACCATCTACCGCCTGCTGGAGGAGTCCCAGAACCAGC
AGGAGAAGAACGAGCAGGACCTGCTGGCCCTGGACTCCTGGGAGAACCTG
TGGAACTGGTTCGACATCACCAACTGGCTGTGGTACATCAAGATCTTCAT
CATGATCGTGGGCGGCCTGATCGGCCTGCGCATCATCTTCGCCGTGCTGT
CCATCGTGAACCGCGTGCGCCAGGGCTACTCCCCCCTGTCCTTCCAGACC
CTGACCCCCAACCCCCGCGGCCCCGACCGCCTGGAGCGCATCGAGGAGGA
GGGCGGCGAGCAGGACCGCGACCGCTCCATCCGCCTGGTGTCCGGCTTCC
TGGCCCTGGCCTGGGACGACCTGCGCTCCCTGTGCCTGTTCTCCTACCAC
CGCCTGCGCGACTTCATCCTGATCGCCGCCCGCACCGTGGAGCTGCTGGG
CCGCTCCTCCCTGCGCGGCCTGCAGCGCGGCTGGGAGGCCCTGAAGTACC
TGGGCTCCCTGGTGCAGTACTGGGGCCAGGAGCTGAAGAAGTCCGCCATC
TCCCTGCTGGACACCATCGCCATCGCCGTGGCCGAGGGCACCGACCGCAT
CATCGAGGTGGTGCAGCGCGCCTGCCGCGCCATCCTGAACATCCCCCGCC
GCATCCGCCAGGGCTTCGAGGCCGCCCTGCTGTAA

Fig. 6B

C.con.env (subtype C consensus env. The amino acid sequence is different from Los Alamos Database August 2002)

```
GCCGCCATGCGCGTGATGGGCATCCTGCGCAACTGCCAGCAGTGGTGGAT
CTGGGGCATCCTGGGCTTCTGGATGCTGATGATCTGCAACGTGGTGGGCA
ACCTGTGGGTGACCGTGTACTACGGCGTGCCCGTGTGGAAGGAGGCCAAG
ACCACCCTGTTCTGCGCCTCCGACGCCAAGGCCTACGAGAAGG AGGTGCA
CAACGTGTGGGCCACCCACGCCTGCGTGCCCACCGACCCCAACCCCCAGG
AGATGGTGCTGGAGAACGTGACCGAGAACTTCAACATGTGGAAGAACGAC
ATGGTGGACCAGATGCACGAGGACATCATCTCCCTGTGGGACCAGTCCCT
GAAGCCCTGCGTGAAGCTGACCCCCCTGTGCGTGACCCTGAACTGCCGCA
ACGTGACCAACGCCACCAACAACACCTACAACGAGGAGATCAAG AACTGC
TCCTTCAACATCACCACCGAGCTGCGCGACAAGAAGAAGAAGGTGTACGC
CCTGTTCTACCGCCTGGACATCGTGCCCCTGAACGAGAACTCCTCCGAGT
ACCGCCTGATCAACTGCAACACCTCCGCCATCACCCAGGCCTGCCCCAAG
GTGTCCTTCGACCCCATCCCCATCCACTACTGCGCCCCGCCGGCTACGC
CATCCTGAAGTGCAACAACAAGACCTTCAACGGCACCGGCCCCTG CAACA
ACGTGTCCACCGTGCAGTGCACCCACGGCATCAAGCCCGTGGTGTCCACC
CAGCTGCTGCTGAACGGCTCCCTGGCCGAGGAGGAGATCATCATCCGCTC
CGAGAACCTGACCAACAACGCCAAGACCATCATCGTGCACCTGAACGAGT
CCGTGGAGATCGTGTGCACCCGCCCCAACAACAACACCCGCAAGTCCATC
CGCATCGGCCCCGGCCAGACCTTCTACGCCACCGGCGACATCATCG GCGA
CATCCGCCAGGCCCACTGCAACATCTCCGAGGACAAGTGGAACAAGACCC
TGCAGCGCGTGTCCAAGAAGCTGAAGGAGCACTTCCCCAACAAGACCATC
AAGTTCGAGCCCTCCTCCGGCGGCGACCTGGAGATCACCACCCACTCCTT
CAACTGCCGCGGCGAGTTCTTCTACTGCAACACCTCCAAGCTGTTCAACT
CCACCTACAACAACAACACCAACTCCAACTCCACCATCACCCTGCCC TGC
CGCATCAAGCAGATCATCAACATGTGGCAGGAGGTGGGCCGCGCCATGTA
CGCCCCCCCCATCGCCGGCAACATCACCTGCAAGTCCAACATCACCGGCC
TGCTGCTGACCCGCGACGGCGGCAAGAAGAACACCACCGAGATCTTCCGC
CCCGGCGGCGGCGACATGCGCGACAACTGGCGCTCCGAGCTGTACAAGTA
CAAGGTGGTGGAGATCAAGCCCCTGGGCGTGGCCCCACCAAGGCCAA GC
GCCGCGTGGTGGAGCGCGAGAAGCGCGCCGTGGGCATCGGCGCCGTGTTC
CTGGGCTTCCTGGGCGCCGCCGGCTCCACCATGGGCGCCGCCTCCATCAC
CCTGACCGTGCAGGCCCGCCAGCTGCTGTCCGGCATCGTGCAGCAGCAGT
CCAACCTGCTGCGCGCCATCGAGGCCCAGCAGCACATGCTGCAGCTGACC
GTGTGGGGCATCAAGCAGCTGCAGACCCGCGTGCTGGCCATCGAGCGCTA
CCTGAAGGACCAGCAGCTGCTGGGCATCTGGGGCTGCTCCGGCAAGCTGA
TCTGCACCACCGCCGTGCCCTGGAACTCCTCCTGGTCCAACAAGTCCCAG
GAGGACATCTGGGACAACATGACCTGGATGCAGTGGGACCGCGAGATCTC
CAACTACACCGACACCATCTACCGCCTGCTGGAGGACTCCCAGAACCAGC
AGGAGAAGAACGAGAAGGACCTGCTGGCCCTGGACTCCTGGAAGAACCTG
TGGAACTGGTTCGACATCACCAACTGGCTGTGGTACATCAAGATCTTCAT
CATGATCGTGGGCGGCCTGATCGGCCTGCGCATCATCTTCGCCGTGCTGT
CCATCGTGAACCGCGTGCGCCAGGGCTACTCCCCCTGTCCTTCCAGACC
CTGACCCCCAACCCCGCGGCCCCGACCGCCTGGGCCGCATCGAGGAGGA
GGGCGGCGAGCAGGACCGCGACCGCTCCATCCGCCTGGTGTCCGGCTTCC
TGGCCCTGGCCTGGGACGACCTGCGCTCCCTGTGCCTGTTCTCCTACCAC
CGCCTGCGCGACTTCATCCTGGTGGCCGCCCGCCGTGGAGCTGCTGGG
CCGCTCCTCCCTGCGCGGCCTGCAGCGCGGCTGGGAGGCCCTGAAGTACC
TGGGCTCCCTGGTGCAGTACTGGGGCCTGGAGCTGAAGAAGTCCGCCATC
TCCCTGCTGGACACCATCGCCATCGCCGTGGCCGAGGGCACCGACCGCAT
CATCGAGCTGATCCAGCGCATCTGCCGCGCCATCCGCAACATCCCCCGCC
GCATCCGCCAGGGCTTCGAGGCCGCCCTGCAGTAA
```

Fig. 6C

C.anc.env (subtype C ancestral env)

MRVMGILRNCQQWWIWGILGFWMLMICSVVGNLWVTVYYGVPVWKEAKTTLFCASDAKAYEREVHNVWAT
HACVPTDPNPQEMVLENVTENFNMKNDMVDQMHEDIISLWDQSLKPCVKLTPLCVTLNCTNVTNATNNT
YNGEMKNCSFNITTELRDKKKKEYALFYRLDIVPLNENSSEYRLINCNTSAITQACPKVSFDPIPIHYCA
PAGYAILKCNNKTFNGTGPCNNVSTVQCTHGIKPVVSTQLLLNGSLAEEEIIRSENLTDNAKTIIVQLN
ESVEIVCTRPNNNTRKSMRIGPGQTFYATGDIIGDIRQAHCNISEDKWNKTLQQVAEKLGKHFPNKTITF
EPSSGGDLEITTHSFNCRGEFFYCNTSKLFNSTYNNNTNSNSTITLPCRIKQIINMWQGVGQAMYAPPIA
GNITCKSNITGLLLTRDGGKENTTETFRPGGGDMRDNWRSELYKYKVVEIKPLGVAPTEAKRRVEREKR
AVGLGAVFLGFLGAAGSTMGAASITLTVQARQLLSGIVQQSNLLRAIEAQQHMLQLTVWGIKQLQARVL
AMERYLKDQQLLGIWGCSGKLICTTAVPWNSSWSNKSLDDIWDNMTWMEWDREISNYTDTIYRLLEESQN
QQEKNEQDLLALDSWENLWNWFDITNWLWYIKIFIMIVGGLIGLRIIFAVLSIVNRVRQGYSPLSFQTLT
PNPRGPDRLERIEEEGGEQDRDRSIRLVSGFLALAWDDLRSLCLFSYHRLRDFILIAARTVELLGRSSLR
GLQRGWEALKYLGSLVQYWGQELKKSAISLLDTIAIAVAEGTDRIIEVVQRACRAILNIPRRIRQGFEAA
LL

Fig. 6D

C.con.env (subtype C consensus env)

MRVRGILRNCQQWWIWGILGFWMLMICNVVGNLWVTVYYGVPVWKEAKTTLFCASDAKAYEKEVHNVWAT
HACVPTDPNPQEMVLENVTENFNMKNDMVDQMHEDIISLWDQSLKPCVKLTPLCVTLNCRNVTNATNNT
YNEEIKNCSFNITTELRDKKKKVYALFYRLDIVPLNENSSEYRLINCNTSAITQACPKVSFDPIPIHYCA
PAGYAILKCNNKTFNGTGPCNNVSTVQCTHGIKPVVSTQLLLNGSLAEEEIIRSENLTNNAKTIIVHLN
ESVEIVCTRPNNNTRKSIRIGPGQTFYATGDIIGDIRQAHCNISEDKWNKTLQRVSKKLKEHFPNKTIKF
EPSSGGDLEITTHSFNCRGEFFYCNTSKLFNSTYNNNTNSNSTITLPCRIKQIINMWQEVGRAMYAPPIA
GNITCKSNITGLLLTRDGGKKNTTEIFRPGGGDMRDNWRSELYKYKVVEIKPLGVAPTKAKRRVEREKR
AVGIGAVFLGFLGAAGSTMGAASITLTVQARQLLSGIVQQSNLLRAIEAQQHMLQLTVWGIKQLQTRVL
AIERYLKDQQLLGIWGCSGKLICTTAVPWNSSWSNKSQEDIWDNMTWMQWDREISNYTDTIYRLLEDSQN
QQEKNEKDLLALDSWKNLWNWFDITNWLWYIKIFIMIVGGLIGLRIIFAVLSIVNRVRQGYSPLSFQTLT
PNPRGPDRLGRIEEEGEQDRDRSIRLVSGFLALAWDDLRSLCFSYHRLRDFILVAARAVELLGRSSLR
GLQRGWEALKYLGSLVQYWGLELKKSAISLLDTIAIAVAEGTDRIIELIQRICRAIRNIPRRIRQGFEAA
LQ

Fig. 6E

Synthesize entire gene in 80-mer fragments overlapping by 20 residues at the 3' end with invariant sequences at the 5' end.

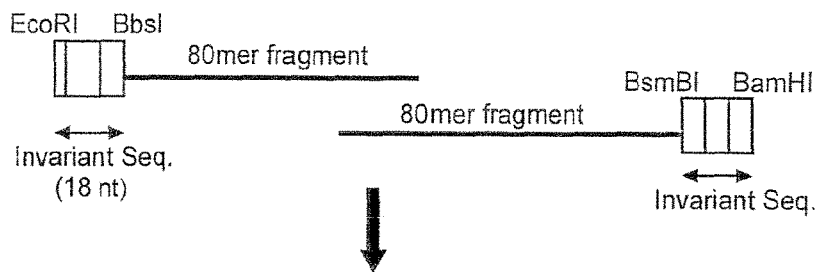

Paired 80mer oligos are connected via PCR in a stepwise manner from 5' to 3' using primers complimentary to the invariant seq.

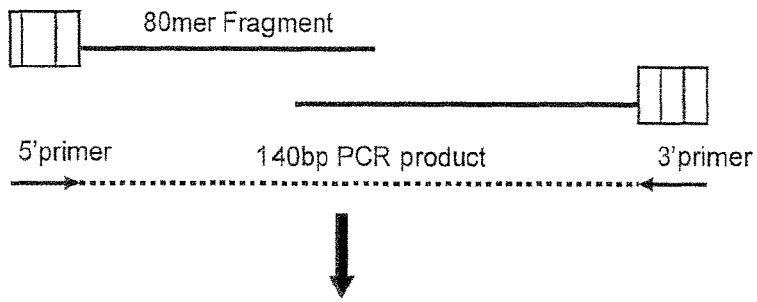

108bp PCR fragments cloned into pGEM-T and sequenced. Clones with the proper sequence will be cut with 2 restriction enzymes. 4 fragments will be ligated together with pcDNA3.1 in a stepwise manner from the 5' to 3' end of gene

| Fragments to be ligated with pcDNA3.1 (1-4 are in order from 5' to 3') | Restriction Enzymes Used to Cleave Fragment |
|---|---|
| Fragment 1 | EcoRI/BsmBI |
| Fragment 2 | BbsI/BsmBI |
| Fragment 3 | BbsI/BsmBI |
| Fragment 4 | BbsI/BamHI |
| pcDNA3.1 | EcoRI/BamHI |

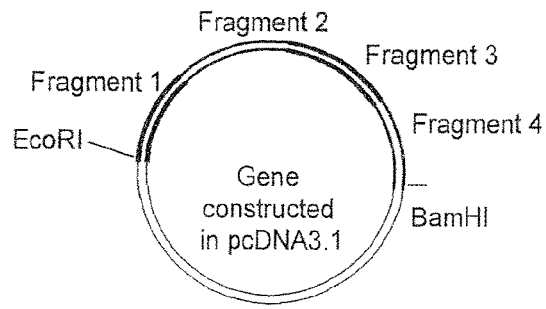

Ligations will be repeated stepwise 5' to 3' until the entire gene has been cloned into pcDNA3.1

Fig. 8

```
MRVMGILRNCQQWWIWGILGFWMLMICNVVGNLWVTVYYGVPVWKEAKTTLFCASDAKAYEREVHNVWATHACVPTDPNPQEMVLENVTENFNMWKNDMVDQMHEDIISLWDQSLKPCVKLTPLC
           +
MRVMGILRNCQQWWIWGILGFWMLMICSVVGNLWVTVYYGVPVWKEAKTTLFCASDAKAYEREVHNVWATHACVPTDPNPQEMVLENVTENFNMWKNDMVDQMHEDIISLWDQSLKPCVKLTPLC
                         V1
VTLNCRNVTNATNNTYNEEIKNCSFNITTELRDKKKVYALFYRLDIVPLNENSSEYRLINCNTSAITQACPKVSFDPIPIHYCAPAGYAILKCNNKTFNGTGPCNNVSTVQCTHGIKPVVSTQL
                   +                                                                                  +
VTLNCTNVTNATNNTYNGEMKNCSFNITTELRDKKKEYALFYRLDIVPLNENSSEYRLINCNTSAITQACPKVSFDPIPIHYCAPAGYAILKCNNKTFNGTGPCNNVSTVQCTHGIKPVVSTQL
                                                         V2
LLNGSLAEEEIIIRSENLTNNAKTIIVHLNESVEIVCTRPNNNTRKSIRIGPGQTFYATGDIIGDIRQAHCNISEDKWNKTLQRVSKKLKEHFPNKTIKFEPSSGGDLEITTHSFNCRGEFFYCN
                                                                                            + ++       +
LLNGSLAEEEIIIRSENLTDNAKTIIVQLNESVEIVCTRPNNNTRKSMRIGPGQTFYATGDIIGDIRQAHCNISEDKWNKTLQQVAEKLGKHFFPNKTITFEPSSGGDLEITTHSFNCRGEFFYCN
       V4                                                     V5
TSKLFNSTYNNNTNSNSTITLPCRIKQIINMWQEVGRAMYAPPIAGNITCKSNITGLLLTRDGGKKNTTEIFRPGGGDMRDNWRSELYKYKVVEIKPLGVAPTKAKRRVVEREKRAVGIAVFLG
                                       +                                                                 +
TSKLFNSTYNNNTNSNSTITLPCRIKQIINMWQGVGQAMYAPPIAGNITCKSNITGLLLTRDGGKENTTETFRPGGGDMRDNWRSELYKYKVVEIKPLGVAPTEAKRRVVEREKRAVGLGAVFLG
                                                                                                       gp120 ↑ gp41
FLGAAGSTMGAASITLTVQARQLLSGIVQQQSNLLRAIEAQQHMLQLTVWGIKQLQTRVLAIERYLKDQQLLGIWGCSGKLICTTAVPWNSSWSNKSQEDIWDNMTWMQWDREISNYTDTIYRLL
                                                                                      +                 +
FLGAAGSTMGAASITLTVQARQLLSGIVQQQSNLLRAIEAQQHMLQLTVWGIKQLQARVLAMERYLKDQQLLGIWGCSGKLICTTAVPWNSSWSNKSLDDIWDNMTWMEWDREISNYTDTIYRLL
EDSQNQQEKNEKDLLALDSWKNLWNWFDITNWLWYIKIFIMIVGGLIGLRIIFAVLSIVNRVRQGYSPLSFQTLTPNRGPDRLGRIEEEGGEQDRDRSIRLVSGFLALAWDDLRSLCLFSYHRL
          +
EESQNQQEKNEQDLLALDSWENLWNWFDITNWLWYIKIFIMIVGGLIGLRIIFAVLSIVNRVRQGYSPLSFQTLTPNRGPDRLERIEEEGGEQDRDRSIRLVSGFLALAWDDLRSLCLFSYHRL
                                                                          gp140 ↑
RDFILVAARAVELLGRSSLRGLQRGWEALKYLGSLVQYWGLELKKSAISLLDTTAIAVAEGTDRIIELIQRICRAIRNIPRRIRQGFEAALQ    843
   +                                                                                      ++
RDFILIAARTVELLGRSSLRGLQRGWEALKYLGSLVQYWGQELKKSAISLLDTIAIAVAEGTDRIIEVVQRACRAILNIPRRIRQGFEAALL    843
```

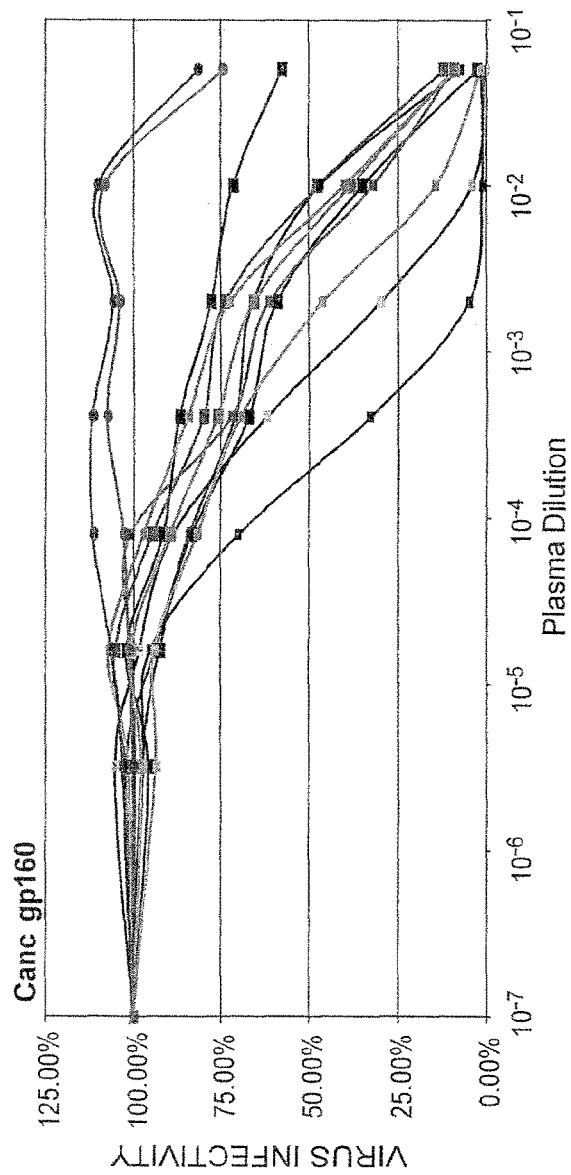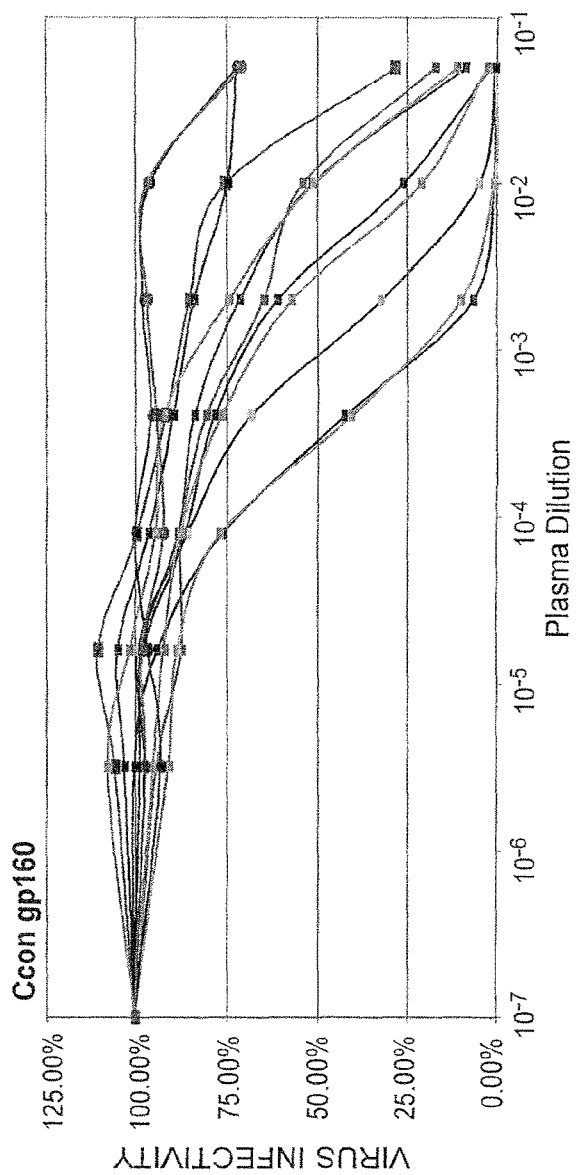

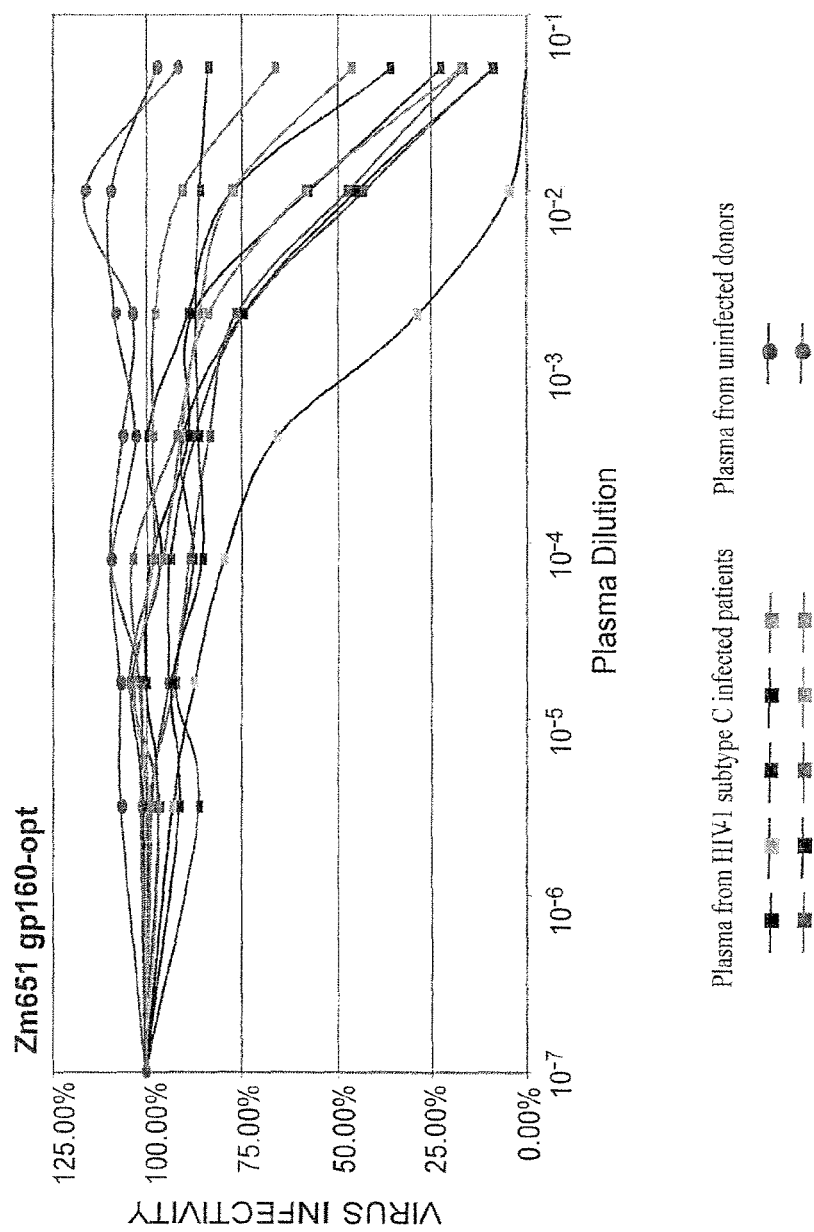

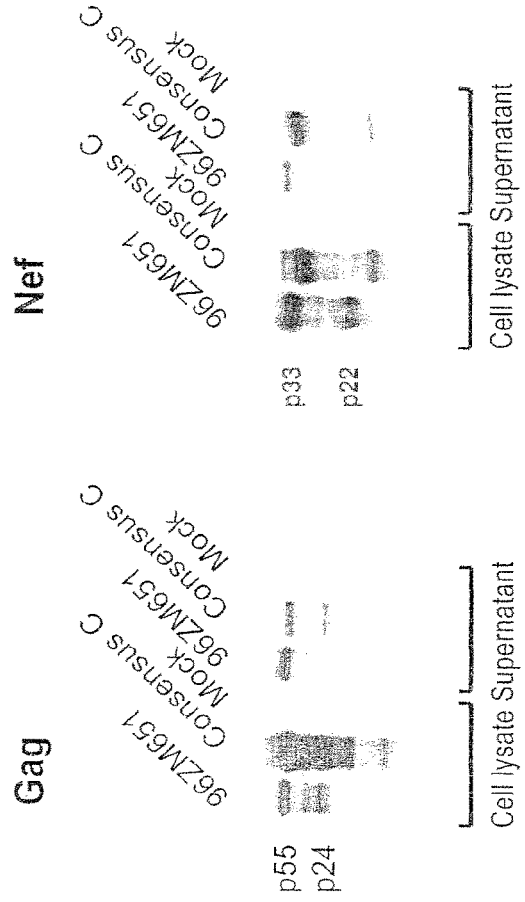

Fig. 13A  Fig. 13B

Fig. 13C C.con.gag (subtype C consensus gag)

MGARASILRGGKLDTWEKIRLRPGGKKRYMIKHLVWASRELERFALNPGLLETSEGCKQIMKQLQPA
LQTGTEELRSLYNTVATLYCVHEKIEVRDTKEALDKIEEEQNKSQQKTQQAEAAADGKVSQNYPI
VQNLQGQMVHQAISPRTLNAWVKVIEEKAFSPEVIPMFTALSEGATPQDLNTMLNTVGGHQAAMQMLKDT
INEEAAEWDRLHPVHAGPIAPGQMREPRGSDIAGTTSTLQEQIAWMTSNPPVPVGDIYKPWIILGLNKIV
RMYSPVSILDIKQGPKEPFRDYVDRFFKTLRAEQATQDVKNWMTDTLLVQNANPDCKTILRALGPGASLE
EMMTACQGVGGPSHKARVLAEAMSQANNTNIMMQRSNFKGPKRIVKCFNCGKEGHIARNCRAPRKKGCWK
CGKEGHQMKDCTERQANFLGKIWPSHKGRPGNFLQSRPEPTAPPAESFRFEETTPA
PKQEPKDREPLTSLKSLFGSDPLSQ

Fig. 13D C.con.nef (subtype C consensus nef)

MGGKWSKSSIVGWPAVRERIRRTEPAAEGVGAASQDLIDKYGALTSSNTATNNADCAWLEAQEEEEFV
GFPVRPQVPLRPMTYKAAFDLSFFLKEKGGLEGLIYSKKKRQEILDLWVYHTQGFFPDWQNYTPGPGVRYP
LTFGWCFKLVPVDPREVEEANEGENNCLLHPMSQHGMEDEDREVLKWKFDSHLARRHMARELHPEYYKDC

C.con.gag (subtype C consensus gag. Not in the public domain)

GCCGCCGCCATGGGCGCCCGCGCCAGCATCCTGCGCGGCGGCCAAGCTGGACACCTGGGAGAAGATCCGCC
TGCGCCCCGGGGGCAAGAAGCGCTACATGATCAAGCACCTGGTGTGGGCCAGCCGCGAGCTGGAGCGCTT
CGCCCTGAACCCCGGCCTGCTGGAGACCAGCGAGGGCTGCAAGCAGATCATGAAGCAGCTGCAGCCCGCC
CTGCAGACCGGCACCGAGGAGCTGCGCAGCCTGTACAACACCGTGGCCACCCTGTACTGCGTGCACGAGA
AGATCGAGGTGCGCGACACCAAGGAGGCCCTGGACAAGATCGAGGAGGAGCAGAACAAGAGCCAGCAGAA
GACCCAGCAGGCCGAGGCCGCCGACGGCAAGGTGAGCCAGAACTACCCCATCGTGCAGAACCTGCAG
GGCCAGATGGTGCACCAGGCCATCAGCCCCCGCACCCTGAACGCCTGGGTGAAGGTGATCGAGGAGAAGG
CCTTCAGCCCCGAGGTGATCCCCATGTTCACCGCCCTGAGCGAGGGCGCCACCCCCCAGGACCTGAACAC
CATGCTGAACACCGTGGGCGGCCACCAGGCCGCCATGCAGATGCTGAAGGACACCATCAACGAGGAGGCC
GCCGAGTGGGACCGCCTGCACCCCGTGCACGCCGGCCCCATCGCCCCCGGCCAGATGCGCGAGCCCCGCG
GCAGCGACATCGCCGGCACCACCAGCACCCTGCAGGAGCAGATCGCCTGGATGACCAGCAACCCCCCCGT
GCCCGTGGGCGACATCTACAAGCGCTGGATCATCCTGGGCCTGAACAAGATCGTGCGCATGTACAGCCCC
GTGAGCATCCTGGACATCAAGCAGGGCCCCAAGGAGCCCTTCCGCGACTACGTGGACCGCTTCTTCAAGA
CCCTGCGCGCCGAGCAGGCCACCCAGGACGTGAAGAACTGGATGACCGACACCCTGCTGGTGCAGAACGC
CAACCCCGACTGCAAGACCATCCTGCGCGCCCTGGGCCCCGGCGCCAGCCTGGAGGAGATGATGACCGCC
TGCCAGGGCGTGGGCGGCCCCAGCCACAAGGCCCGCGTGCTGGCCGAGGCCATGAGCCAGACCAACAACA
CCAACATCATGATGCAGCGCAGCAACTTCAAGGGCCAGCGCAAGATCGTGAAGTGCTTCAACTGCGGCAA
GGAGGGCCACATCGCCCGCAACTGCCGCGCCCCCAGGCCAATTCCTGGCAAGATCTGCCCAGCCACAAGGGCC
CACCAGATGAAGGACTGCACCGAGCGCCAGGCCAATTTCCTGGGCAAGATCTGGCCCAGCCACAAGGGCC
GCCCCGGCAACTTCCTGCAGAGCCGCCCCGAGCCCACCGCCCCCCCCGAGAGCTTCCGCTTCGAGGA
GACCACCCCCGCCCCCAAGCAGGAGCCCAAGGACCGCGAGCCCCTGACCAGCCTGAAGAGCCTGTTCGGC
AGCGACCCCCTGAGCCAGTAA

Fig. 13E

C.con.nef (subtype C consensus nef. Not in the public domain)

GCCGCCCGCCATGGGCGGCAAGTGGAGCAAGAGCAGCATCGTCGGCTGGCCTGCCCGCGAGCGCATCC
GCCGCACCGAGCCCGCCGCCGACGGCGTGGGCGCCGTCCAGGACCTGGACAAGTACGGCGCCCTGAC
CAGCAGCAACACCGCCGCCAACAACGCCGACTGCGCCTGGCTGGAGGCCCAGGAGGAGGAGGAGGTG
GGCTTCCCCGTGCGCCCCCAGGTGCCCCTGAGGGCCTTCTTCAAGGCCTACAAGGCCGCCTTCGACCTGTCT
TCCTGAAGGAGAAGGGCGGCCTGGAGGGCCTGATCTACAGCAAGAAGCGCCAGGAGATCCTGGACCTGTG
GGTGTACCACACCCAGGGCTTCTTCCCCGACTGGCAGAACTACACCCCCGGCCCCGGCGTGCGCTACCCC
CTGACCTTCGGCTGGTGCTTCAAGCTGGTGCCCGTGGAGCCCGACAAGGTCGAGGAGGCCAACGAGGGCG
AGAACAACTGCCTGCTGCACCCCATGAGCCAGCATGGCATGGAGGACGAGGACCGCGAGGTGCTGAAGTG
GAAGTTCGACAGCAGCCTGGCCCGCCGCCACATGGCCCGCGAGCTGCACCCCGAGTACTACAAGGACTGC
TGA

Fig. 13F

Fig. 14A

CONs.env (gorup M consensus env gene. This one contain the consensus sequence for variable regions in env gene)

MRVRGIQRNCQHLWRWGTLILGMLMICSAAENLWVTVYYGVPVWKEANTTLFCASDAKAYDTEVHNV
WATHACVPTDPNPQEIVLENVTENFNMWKNNMVEQMHEDIISLWDQSLKPCVKLTPLCVTLNCTNVNVTN
TTNNTEEKGEIKNCSFNITTEIRDKKQKVYALFYRLDVVPIDDNNNNSSNYRLINCNTSAITQACPKVSF
EPIPIHYCAPAGFAILKCNDKKFNGTGPCKNVSTVQCTHGIKPVVSTQLLLNGSLAEEEIIIRSENITNN
AKTIIVQLNESVEINCTRPNNNTRKSIRIGPGQAFYATGDIIGDIRQAHCNISGTKWNKTLQQVAKKLRE
HFNNKTIIFKPSSGGDLEITTHSFNCRGEFFYCNTSGLFNSTWIGNGTKNNNNTNDTITLPCRIKQIINM
WQGVGQAMYAPPIEGKITCKSNITGLLLTRDGGNNNTNETEIFRPGGGDMRDNWRSELYKYKVVKIEPLG
VAPTKAKRRVVEREKRAVGIGAVFLGFLGAAGSTMGAASITLTVQARQLLSGIVQQQSNLLRAIEAQQHL
LQLTVWGIKQLQARVLAVERYLKDQQLLGIWGCSGKLICTTTVPWNSSWSNKSQDEIWDNMTWMEWEREI
NNYTDIIYSLIEESQNQQEKNEQELLALDKWASLWNWFDITNWLWYIKIFIMIVGGLIGLRIVFAVLSIV
NRVRQGYSPLSFQTLIPNPRGPDRPEGIEEEGGEQDRDRSIRLVNGFLALAWDDLRSLCLFSYHRLRDFI
LIAARTVELLGRKGLRRGWEALKYLWNLLQYWGQELKNSAISLLDTTAIAVAEGTDRVIEVVQRACRAIL
NIPRRIRQGLERALL

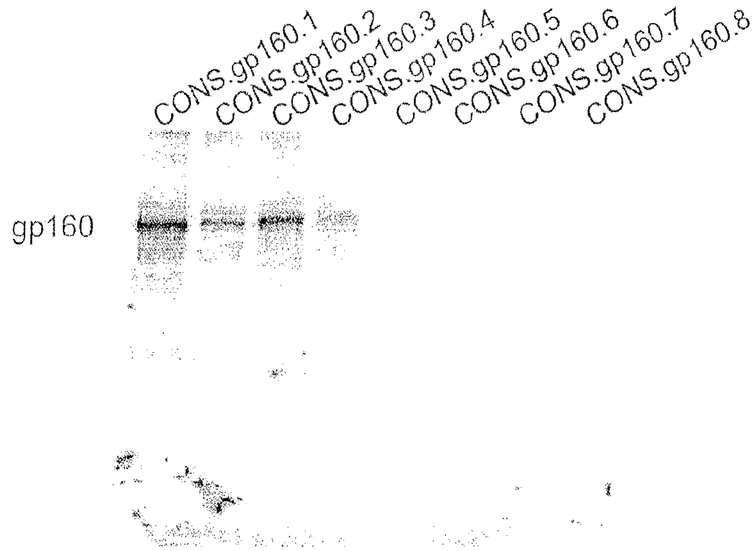

Fig. 14C

Fig. 14B

CONs.env (gorup M consensus env gene. This one contain the consensus sequence for variable regions in env gene. The identical amino acid sequences as in the public domain)

GCCGCCGCCATGCGCGTGCGCGGCATCCAGCGCAACTGCCAGCACCTGTG
GCGCTGGGGCACCCTGATCCTGGGCATGCTGATGATCTGCTCCGCCGCCG
AGAACCTGTGGGTGACCGTGTACTACGGCGTGCCCGTGTGGAAGGAGGCC
AACACCACCCTGTTCTGCGCCTCCGACGCCAAGGCCTACGACACCGAGGT
GCACAACGTGTGGGCCACCCACGCCTGCGTGCCCACCGACCCCAACCCCC
AGGAGATCGTGCTGGAGAACGTGACCGAGAACTTCAACATGTGGAAGAAC
AACATGGTGGAGCAGATGCACGAGGACATCATCTCCCTGTGGGACCAGTC
CCTGAAGCCCTGCGTGAAGCTGACCCCCCTGTGCGTGACCCTGAACTGCA
CCAACGTGAACGTGACCAACACCACCAACAACACCGAGGAGAAGGGCGAG
ATCAAGAACTGCTCCTTCAACATCACCACCGAGATCCGCGACAAGAAGCA
GAAGGTGTACGCCCTGTTCTACCGCCTGGACGTGGTGCCCATCGACGACA
ACAACAACAACTCCTCCAACTACCGCCTGATCAACTGCAACACCTCCGCC
ATCACCCAGGCCTGCCCCAAGGTGTCCTTCGAGCCCATCCCCATCCACTA
CTGCGCCCCCGCCGGCTTCGCCATCCTGAAGTGCAACGACAAGAAGTTCA
ACGGCACCGGCCCCTGCAAGAACGTGTCCACCGTGCAGTGCACCCACGGC
ATCAAGCCCGTGGTGTCCACCCAGCTGCTGCTGAACGGCTCCCTGGCCGA
GGAGGAGATCATCATCCGCTCCGAGAACATCACCAACAACGCCAAGACCA
TCATCGTGCAGCTGAACGAGTCCGTGGAGATCAACTGCACCCGCCCCAAC
AACAACACCCGCAAGTCCATCCGCATCGGCCCCGGCCAGGCCTTCTACGC
CACCGGCGACATCATCGGCGACATCCGCCAGGCCCACTGCAACATCTCCG
GCACCAAGTGGAACAAGACCCTGCAGCAGGTGGCCAAGAAGCTGCGCGAG
CACTTCAACAACAAGACCATCATCTTCAAGCCCTCCTCCGGCGGCGACCT
GGAGATCACCACCCACTCCTTCAACTGCCGCGGCGAGTTCTTCTACTGCA
ACACCTCCGGCCTGTTCAACTCCACCTGGATCGGCAACGGCACCAAGAAC
AACAACAACACCAACGACACCATCACCCTGCCCTGCCGCATCAAGCAGAT
CATCAACATGTGGCAGGGCGTGGGCCAGGCCATGTACGCCCCCCCCATCG
AGGGCAAGATCACCTGCAAGTCCAACATCACCGGCCTGCTGCTGACCCGC
GACGGCGGCAACAACAACACCAACGAGACCGAGATCTTCCGCCCCGGCGG
CGGCGACATGCGCGACAACTGGCGCTCCGAGCTGTACAAGTACAAGGTGG
TGAAGATCGAGCCCCTGGGCGTGGCCCCCACCAAGGCCAAGCGCCGCGTG
GTGGAGCGCGAGAAGCGCGCCGTGGGCATCGGCGCCGTGTTCCTGGGCTT
CCTGGGCGCCGCCGGCTCCACCATGGGCGCCGCCTCCATCACCCTGACCG
TGCAGGCCCGCCAGCTGCTGTCCGGCATCGTGCAGCAGCAGTCCAACCTG
CTGCGCGCCATCGAGGCCCAGCAGCACCTGCTGCAGCTGACCGTGTGGGG
CATCAAGCAGCTGCAGGCCCGCGTGCTGGCCGTGGAGCGCTACCTGAAGG
ACCAGCAGCTGCTGGGCATCTGGGGCTGCTCCGGCAAGCTGATCTGCACC
ACCACCGTGCCCTGGAACTCCTCCTGGTCCAACAAGTCCCAGGACGAGAT
CTGGGACAACATGACCTGGATGGAGTGGGAGCGCGAGATCAACAACTACA
CCGACATCATCTACTCCCTGATCGAGGAGTCCCAGAACCAGCAGGAGAAG
AACGAGCAGGAGCTGCTGGCCCTGGACAAGTGGGCCTCCCTGTGGAACTG
GTTCGACATCACCAACTGGCTGTGGTACATCAAGATCTTCATCATGATCG
TGGGCGGCCTGATCGGCCTGCGCATCGTGTTCGCCGTGCTGTCCATCGTG
AACCGCGTGCGCCAGGGCTACTCCCCCCTGTCCTTCCAGACCCTGATCCC
CAACCCCCGCGGCCCCGACCGCCCCGAGGGCATCGAGGAGGAGGGCGGCG
AGCAGGACCGCGACCGCTCCATCCGCCTGGTGAACGGCTTCCTGGCCCTG
GCCTGGGACGACCTGCGCTCCCTGTGCCTGTTCTCCTACCACCGCCTGCG
CGACTTCATCCTGATCGCCGCCCGCACCGTGGAGCTGCTGGGCCGCAAGG
GCCTGCGCCGCGGCTGGGAGGCCCTGAAGTACCTGTGGAACCTGCTGCAG
TACTGGGGCCAGGAGCTGAAGAACTCCGCCATCTCCCTGCTGGACACCAC
CGCCATCGCCGTGGCCGAGGGCACCGACCGCGTGATCGAGGTGGTGCAGC
GCGCCTGCCGCGCCATCCTGAACATCCCCCGCCGCATCCGCCAGGGCCTG
GAGCGCGCCCTGCTGTAA

Fig. 15A Fig. 15B

M.conS.gp160 / 96ZM651.gp160 / NC / LAVgp120 (50ng)

Cell lysate    Supernatant

Expression of A.con env gene in mammalian cells

Fig. 16A

Infectivity and coreceptor usage of CON6 and CONs env genes (x-axis: CON6, CONs, NL4-3, YU2, No Env; y-axis: Infectious unit (IU/mg p24))

Fig. 16B

Infectivity and coreceptor usage of CON6 and CONs env genes (x-axis: Media, AMD3100, TAK779, Both; y-axis: Infectivity (Percentage); legend: CON6, CONs, NL4-3, YU2)

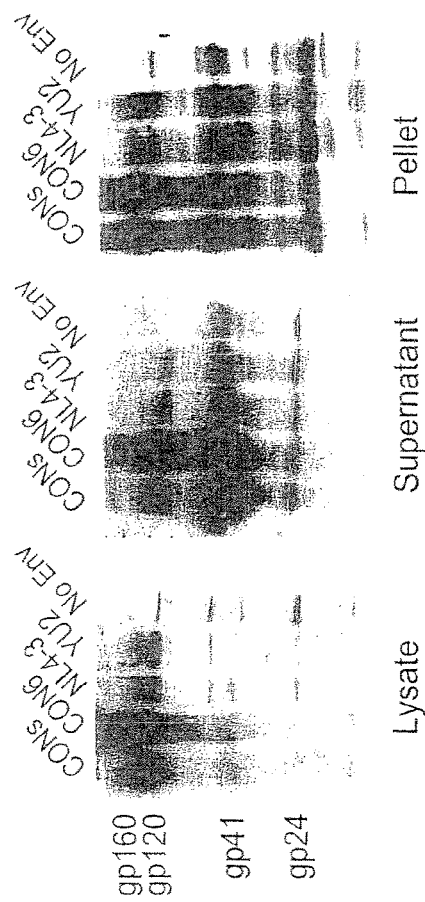

Fig. 17A   Fig. 17B   Fig. 17C

Env protein incorporation in CON6 and CONs Env-pseudovirions

Fig. 17A: Lysate
Fig. 17B: Supernatant
Fig. 17C: Pellet

Fig. 18A

A.con.env (subtype A consensus env)
MRVMGIQRNCQHLWRWGTMILGMIICSAAENLWVTVYYGVPVWKDAETTLFCASDAKAYDTEVHNV
WATHACVPTDPNPQEINLENVTEEFNMKNNMVEQMHTDIISLWDQSLKPCVKLTPLCVTLNCSNVNVTT
NITNITDNMKGEIKNCSFNMTTELRDKKQKVYSLFYKLDVVQINKSNSSSQYRLINCNTSAITQACPKVS
FEPIPIHYCAPAGFAILCKCKDKEFNGTGPCKNVSTVQCTHGIKPVVSTQLLLNGSLAEEVMIRSENITN
NAKNIIVQLTKPVKINCTRPNNNTRKSIRIGPGQAFYATGDIIGDIRQAHCNVSRTEWNETLQKVAKQLR
KYFNNKT

Fig. 18B

A.con.env (subtype A consensus env. Identical amino acid sequence to that in the public domain)

GCCGCCGCCATGCGCGTGATGGGCATCCAGCGCAACTGCCAGCACCTGTG
GCGCTGGGGCACCATGATCCTGGGCATGATCATCATCTGCTCCGCCGCCG
AGAACCTGTGGGTGACCGTGTACTACGGCGTGCCCGTGTGGAAGGACGCC
GAGACCACCCTGTTCTGCGCCTCCGACGCCAAGGCCTACGACACCGAGGT
GCACAACGTGTGGGCCACCCACGCCTGCGTGCCCACCGACCCCAACCCCC
AGGAGATCAACCTGGAGAACGTGACCGAGGAGTTCAACATGTGGAAGAAC
AACATGGTGGAGCAGATGCACACCGACATCATCTCCCTGTGGGACCAGTC
CCTGAAGCCCTGCGTGAAGCTGACCCCCCTGTGCGTGACCCTGAACTGCT
CCAACGTGAACGTGACCACCAACATCACCAACATCACCGACAACATGAAG
GGCGAGATCAAGAACTGCTCCTTCAACATGACCACCGAGCTGCGCGACAA
GAAGCAGAAGGTGTACTCCCTGTTCTACAAGCTGGACGTGGTGCAGATCA
ACAAGTCCAACTCCTCCTCCCAGTACCGCCTGATCAACTGCAACACCTCC
GCCATCACCCAGGCCTGCCCCAAGGTGTCCTTCGAGCCCATCCCCATCCA
CTACTGCGCCCCCGCCGGCTTCGCCATCCTGAAGTGCAAGGACAAGGAGT
TCAACGGCACCGGCCCCTGCAAGAACGTGTCCACCGTGCAGTGCACCCAC
GGCATCAAGCCCGTGGTGTCCACCCAGCTGCTGCTGAACGGCTCCCTGGC
CGAGGAGGAGGTGATGATCCGCTCCGAGAACATCACCAACAACGCCAAGA
ACATCATCGTGCAGCTGACCAAGCCCGTGAAGATCAACTGCACCCGCCCC
AACAACAACACCCGCAAGTCCATCCGCATCGGCCCCGGCCAGGCCTTCTA
CGCCACCGGCGACATCATCGGCGACATCCGCCAGGCCCACTGCAACGTGT
CCCGCACCGAGTGGAACGAGACCCTGCAGAAGGTGGCCAAGCAGCTGCGC
AAGTACTTCAACAACAAGACCATCATCTTCACCAACTCCTCCGGCGGCGA
CCTGGAGATCACCACCCACTCCTTCAACTGCGGCGGCGAGTTCTTCTACT
GCAACACCTCCGGCCTGTTCAACTCCACCTGGAACGGCAACGGCACCAAG
AAGAAGAACTCCACCGAGTCCAACGACACCATCACCCTGCCCTGCCGCAT
CAAGCAGATCATCAACATGTGGCAGCGCGTGGGCCAGGCCATGTACGCCC
CCCCCATCCAGGGCGTGATCCGCTGCGAGTCCAACATCACCGGCCTGCTG
CTGACCCGCGACGGCGGCGACAACAACTCCAAGAACGAGACCTTCCGCCC
CGGCGGCGGCGACATGCGCGACAACTGGCGCTCCGAGCTGTACAAGTACA
AGGTGGTGAAGATCGAGCCCCTGGGCGTGGCCCCCACCAAGGCCAAGCGC
CGCGTGGTGGAGCGCGAGAAGCGCGCCGTGGGCATCGGCGCCGTGTTCCT
GGGCTTCCTGGGCGCCGCCGGCTCCACCATGGGCGCCGCCTCCATCACCC
TGACCGTGCAGGCCCGCCAGCTGCTGTCCGGCATCGTGCAGCAGCAGTCC
AACCTGCTGCGCGCCATCGAGGCCCAGCAGCACCTGCTGAAGCTGACCGT
GTGGGGCATCAAGCAGCTGCAGGCCCGCGTGCTGGCCGTGGAGCGCTACC
TGAAGGACCAGCAGCTGCTGGGCATCTGGGGCTGCTCCGGCAAGCTGATC
TGCACCACCAACGTGCCCTGGAACTCCTCCTGGTCCAACAAGTCCCAGTC
CGAGATCTGGGACAACATGACCTGGCTGCAGTGGGACAAGGAGATCTCCA
ACTACACCGACATCATCTACAACCTGATCGAGGAGTCCCAGAACCAGCAG
GAGAAGAACGAGCAGGACCTGCTGGCCCTGGACAAGTGGGCCAACCTGTG
GAACTGGTTCGACATCTCCAACTGGCTGTGGTACATCAAGATCTTCATCA
TGATCGTGGGCGGCCTGATCGGCCTGCGCATCGTGTTCGCCGTGCTGTCC
GTGATCAACCGCGTGCGCCAGGGCTACTCCCCCCTGTCCTTCCAGACCCA
CACCCCCAACCCCGGCGGCCTGGACCGCCCCGGCCGCATCGAGGAGGAGG
GCGGCGAGCAGGGCCGCGACCGCTCCATCCGCCTGGTGTCCGGCTTCCTG
GCCCTGGCCTGGGACGACCTGCGCTCCCTGTGCCTGTTCTCCTACCACCG
CCTGCGCGACTTCATCCTGATCGCCGCCCGCACCGTGGAGCTGCTGGGCC
ACTCCTCCCTGAAGGGCCTGCGCCTGGGCTGGGAGGGCCTGAAGTACCTG
TGGAACCTGCTGCTGTACTGGGGCCGCGAGCTGAAGATCTCCGCCATCAA
CCTGCTGGACACCATCGCCATCGCCGTGGCCGGCTGGACCGACCGCGTGA
TCGAGATCGGCCAGCGCATCTGCCGCGCCATCCTGAACATCCCCCGCCGC
ATCCGCCAGGGCCTGGAGCGCGCCCTGCTGTAA

Cell lysate    Supernatant
Expression of A.con env gene in mammalian cells

Fig. 19B

M.con.pol.nuc
GCCGCCGCCATGCCCCAGATCACCCTGTGGCAGCGCCCCCTGGTGACCAT
CAAGATCGGCGGCCAGCTGAAGGAGGCCCTGCTGGCCACCGGCGCCGACG
ACACCGTGCTGGAGGAGATCAACCTGCCCGGCAAGTGGAAGCCCAAGATG
ATCGGCGGCATCGGCGGCTTCATCAAGGTGCGCCAGTACGACCAGATCCT
GATCGAGATCTGCGGCAAGAAGGCCATCGGCACCGTGCTGGTGGGCCCCA
CCCCCGTGAACATCATCGGCCGCAACATGCTGACCCAGATCGGCTGCACC
CTGAACTTCCCCATCTCCCCATCGAGACCGTGCCCGTGAAGCTGAAGCC
CGGCATGGACGGCCCCAAGGTGAAGCAGTGGCCCCTGACCGAGGAGAAGA
TCAAGGCCCTGACCGAGATCTGCACCGAGATGGAGAAGGAGGGCAAGATC
TCCAAGATCGGCCCCGAGAACCCCTACAACACCCCCATCTTCGCCATCAA
GAAGAAGGACTCCACCAAGTGGCGCAAGCTGGTGGACTTCCGCGAGCTGA
ACAAGCGCACCCAGGACTTCTGGGAGGTGCAGCTGGGCATCCCCCACCCC
GCCGGCCTGAAGAAGAAGAAGTCCGTGACCGTGCTGGACGTGGGCGACGC
CTACTTCTCCGTGCCCCTGGACGAGGACTTCCGCAAGTACACCGCCTTCA
CCATCCCCTCCATCAACAACGAGACCCCCGGCATCCGCTACCAGTACAAC
GTGCTGCCCCAGGGCTGGAAGGGCTCCCCCGCCATCTTCCAGTCCTCCAT
GACCAAGATCCTGGAGCCCTTCCGCACCCAGAACCCCGAGATCGTGATCT
ACCAGTACATGGACGACCTGTACGTGGGCTCCGACCTGGAGATCGGCCAG
CACCGCGCCAAGATCGAGGAGCTGCGCGAGCACCTGCTGCGCTGGGGCTT
CACCACCCCCGACAAGAAGCACCAGAAGGAGCCCCCCTTCCTGTGGATGG
GCTACGAGCTGCACCCCGACAAGTGGACCGTGCAGCCCATCCAGCTGCCC
GAGAAGGACTCCTGGACCGTGAACGACATCCAGAAGCTGGTGGGCAAGCT
GAACTGGGCCTCCCAGATCTACCCCGGCATCAAGGTGAAGCAGCTGTGCA
AGCTGCTGCGCGGCGCCAAGGCCCTGACCGACATCGTGCCCCTGACCGAG
GAGGCCGAGCTGGAGCTGGCCGAGAACCGCGAGATCCTGAAGGAGCCCGT
GCACGGCGTGTACTACGACCCCTCCAAGGACCTGATCGCCGAGATCCAGA
AGCAGGGCCAGGACCAGTGGACCTACCAGATCTACCAGGAGCCCTTCAAG
AACCTCAAGACCGGCAAGTACGCCAAGATGCGCTCCGCCCACACCAACGA
CGTGAAGCAGCTGACCGAGGCCGTGCAGAAGATCGCCACCGAGTCCATCG
TGATCTGGGGCAAGACCCCCAAGTTCCGCCTGCCCATCCAGAAGGAGACC TGGGAGACCTGGTGGACCGAGTACTGGCAGGCCACCTGGATTCCCGAGTG
GGAGTTCGTGAACACCCCCCCCTGGTGAAGCTGTGGTACCAGCTGGAGA
AGGAGCCCATCGCCGGCGCCGAGACCTTCTACGTGGACGGCGCCGCCAAC
CGCGAGACCAAGCTGGGCAAGGCCGGCTACGTGACCGACCGCGGCCGCCA
GAAGGTGGTGTCCCTGACCGAGACCACCAACCAGAAAACCGAGCTGCAGG
CCATCCACCTGGCCCTGCAGGACTCCGGCTCCGAGGTGAACATCGTGACC
GACTCCCAGTACGCCCTGGGCATCATCCAGGCCCAGCCCGACAAGTCCGA
GTCCGAGCTGGTGAACCAGATCATCGAGCAGCTGATCAAGAAGGAGAAGG
TGTACCTGTCCTGGGTGCCCGCCCACAAGGGCATCGGCGGCAACGAGCAG
GTGGACAAGCTGGTGTCCACCGGCATCCGCAAGGTGCTGTTCCTGGACGG
CATCGACAAGGCCCAGGAGGAGCACGAGAAGTACCACTCCAACTGGCGCG
CCATGGCCTCCGACTTCAACCTGCCCCCCATCGTGGCCAAGGAGATCGTG
GCCTCCTGCGACAAGTGCCAGCTGAAGGGCGAGGCCATGCACGGCCAGGT
GGACTGCTCCCCCGGCATCTGGCAGCTGGACTGCACCCACCTGGAGGGCA
AGATCATCCTGGTGGCCGTGCACGTGGCCTCCGGCTACATCGAGGCCGAG
GTGATCCCCGCCGAGACCGGCCAGGAGACCGCCTACTTCATCCTGAAGCT
GGCCGGCCGCTGGCCCGTGAAGGTGATCCACACCGACAACGGCTCCAACT
TCACCTCCGCCGCCGTGAAGGCCGCCTGCTGGTGGCCGGCATCCAGCAG
GAGTTCGGCATCCCCTACAACCCCCAGTCCCAGGGCGTGGTGGAGTCCAT
GAACAAGGAGCTGAAGAAGATCATCGGCCAGGTGCGCGACCAGGCCGAGC
ACCTCAAGACCGCCGTGCAGATGGCCGTGTTCATCCACAACTTCAAGCGC
AAGGGCGGCATCGGCGGCTACTCCGCCGGCGAGCGCATCATCGACATCAT
CGCCACCGACATCCAGACCAAGGAGCTGCAGAAGCAGATCACCAAGATCC
AGAACTTCCGCGTGTACTACCGCGACTCCCGCGACCCCATCTGGAAGGGC
CCCGCCAAGCTGCTGTGGAAGGGCGAGGGCGCCGTGGTGATCCAGGACAA
CTCCGACATCAAGGTGGTGCCCCGCCGCAAGGCCAAGATCATCCGCGACT
ACGGCAAGCAGATGGCCGGCGACGACTGCGTGGCCGGCCGCCAGGACGAG
GACTAA

Fig. 19C

M.con.nef (group M consensus nef. Identical amino acid sequence to that in the public domain)

GCCGCCGCCATGGGCGGCAAGTGGTCCAAGTCCTCCATCGTGGGCTGGCC
CGCCGTGCGCGAGCGCATCCGCCGCACCCACCCCGCCGCCGAGGGCGTGG
GCGCCGTGTCCCAGGACCTGGACAAGCACGGCGCCATCACCTCCTCCAAC
ACCGCCGCCAACAACCCCGACTGCGCCTGGCTGGAGGCCCAGGAGGAGGA
GGAGGAGGTGGGCTTCCCCGTGCGCCCCCAGGTGCCCCTGCGCCCCATGA
CCTACAAGGCCGCCCTGGACCTGTCCCACTTCCTGAAGGAGAAGGGCGGC
CTGGAGGGCCTGATCTACTCCAAGAAGCGCCAGGAGATCCTGGACCTGTG
GGTGTACCACACCCAGGGCTACTTCCCCGACTGGCAGAACTACACCCCCG
GCCCCGGCATCCGCTACCCCCTGACCTTCGGCTGGTGCTTCAAGCTGGTG
CCCGTGGACCCCGAGGAGGTGGAGGAGGCCAACGAGGGCGAGAACAACTC
CCTGCTGCACCCCATGTGCCAGCACGGCATGGAGGACGAGGAGCGCGAGG
TGCTGATGTGGAAGTTCGACTCCCGCCTGGCCCTGCGCCACATCGCCCGC
GAGCTGCACCCCGAGTACTACAAGGACTGCTAA

Fig. 19D

C.con.pol.nuc

GCCGCCGCCATGCCCCAGATCACCCTGTGGCAGCGCCCCCTGGTGTCCAT
CAAGGTGGGCGGCCAGATCAAGGAGGCCCTGCTGGCCACCGGCGCCGACG
ACACCGTGCTGGAGGAGATCAACCTGCCCGGCAAGTGGAAGCCCAAGATG
ATCGGCGGCATCGGCGGCTTCATCAAGGTGCGCCAGTACGACCAGATCCT
GATCGAGATCTGCGGCAAGAAGGCCATCGGCACCGTGCTGGTGGGCCCCA
CCCCCGTGAACATCATCGGCCGCAACATGCTGACCCAGCTGGGCTGCACC
CTGAACTTCCCCATCTCCCCCATCGAGACCGTGCCCGTGAAGCTGAAGCC
CGGCATGGACGGCCCCAAGGTGAAGCAGTGGCCCCTGACCGAGGAGAAGA
TCAAGGCCCTGACCGCCATCTGCGAGGAGATGGAGAAGGAGGGCAAGATC
ACCAAGATCGGCCCCGAGAACCCCTACAACACCCCCGTGTTCGCCATCAA
GAAGAAGGACTCCACCAAGTGGCGCAAGCTGGTGGACTTCCGCGAGCTGA
ACAAGCGCACCCAGGACTTCTGGGAGGTGCAGCTGGGCATCCCCCACCCC
GCCGGCCTGAAGAAGAAGAAGTCCGTGACCGTGCTGGACGTGGGCGACGC
CTACTTCTCCGTGCCCCTGGACGAGGGCTTCCGCAAGTACACCGCCTTCA
CCATCCCCTCCATCAACAACGAGACCCCCGGCATCCGCTACCAGTACAAC
GTGCTGCCCCAGGGCTGGAAGGGCTCCCCCGCCATCTTCCAGTCCTCCAT
GACCAAGATCCTGGAGCCCTTCCGCGCCCAGAACCCCGAGATCGTGATCT
ACCAGTACATGGACGACCTGTACGTGGGCTCCGACCTGGAGATCGGCCAG
CACCGCGCCAAGATCGAGGAGCTGCGCGAGCACCTGCTGAAGTGGGGCTT
CACCACCCCCGACAAGAAGCACCAGAAGGAGCCCCCCTTCCTGTGGATGG
GCTACGAGCTGCACCCCGACAAGTGGACCGTGCAGCCCATCCAGCTGCCC
GAGAAGGACTCCTGGACCGTGAACGACATCCAGAAGCTGGTGGGCAAGCT
GAACTGGGCCTCCCAGATCTACCCCGGCATCAAGGTGCGCCAGCTGTGCA
AGCTGCTGCGCGGCGCCAAGGCCCTGACCGACATCGTGCCCCTGACCGAG
GAGGCCGAGCTGGAGCTGGCCGAGAACCGCGAGATCCTGAAGGAGCCCGT
GCACGGCGTGTACTACGACCCCTCCAAGGACCTGATCGCCGAGATCCAGA
AGCAGGGCCACGACCAGTGGACCTACCAGATCTACCAGGAGCCCTTCAAG
AACCTCAAGACCGGCAAGTACGCCAAGATGCGCACCGCCCACACCAACGA
CGTGAAGCAGCTGACCGAGGCCGTGCAGAAGATCGCCATGGAGTCCATCG
TGATCTGGGGCAAGACCCCCAAGTTCCGCCTGCCCATCCAGAAGGAGACC
TGGGAGACCTGGTGGACCGACTACTGGCAGGCCACCTGGATTCCCGAGTG
GGAGTTCGTGAACACCCCCCCCCTGGTGAAGCTGTGGTACCAGCTGGAGA
AGGAGCCCATCGCCGGCGCCGAGACCTTCTACGTGGACGGCGCCGCCAAC

Fig. 19D (continued)

```
CGCGAGACCAAGATCCGGCAAGGCCCGGCTACGTGACCGTGACCCGGGCCGCCA
GAAGATCGTGTCCCTGACCGAGACCAACCACCAGAAAACGAGCTGCAGG
CCATCCAGCTGCCCTGCAGGACTCCGGCTCCGAGTGAACATCGTGACC
GACTCCCAGTACGCCCTGGCATCATCGAGCAGCCCAGCCTGACAAGTCCGA
GTCCGAGCTGGTGAACCAGATCCGCCCACAAGGCATGGGCAACGAGCGCG
TGTACCTGTGTCCGGGTGCTCCTCCGCAAGGTGCTGTTCCTGGACGAG
GTGGACAAGCTGGTGTTCCCCAGGAGAGCACGAGAAGTACCACTCCAACTGGCCG
CATCGACAAGCCCGAGTTCAACTGCCAGCTGCCCCCATCGTGGCCAAGGAGATCGTG
GCCTCCTGCGACAAGTGCCAGCTGAAGGGCGAGGCCATGCACCACGCCCAGGT
GGACTGCTCCCCCGCATCTGGCAGCTGGACTGCACCGAGCGCCAGGGCA
AGATCATCCTGGTGCCCGAGACCCGTGCACGTGGCCTCCGGCTACATCATCCTGAAGCT
GTGATCCCCGCGCCTGCCGCCCAGGAGACCGCCTACTTCATCCTGAAGCT
GGCCGGCCGCTGCCCGTGAAGGCCGTGATCCACAAGGCTCCAACT
TCACCCTGCGCCCGCTGCCCCTACAACCCCAGTCGGCCAGTCCGGCATCCAGCAG
GAGTTCGGCATCCCCTACAACCCCAGTCGGCCAGTCGGCCAGGCCGAGC
AACAAGGAGCTGAAGAAGATCATCGCCGTGCGCCCGTGTTCATCCACAACTTCAAGCGC
ACCTCAAGACCCCGTGCAGATGGCCCGTGTTCATCCACAACTTCAAGCGC
AAGGGCGGCATCGGCGGCTACTCCGCGGAGCCGAGAAGCTGACATCAAGATCAT
CGCCACCGACATCCAGAAGGAGCTGCAGAGCTGCAGATCAGGGC
AGAACTCCGCGTGTACTACGACGACTCCCGACCCATCTGGAAGGGC
CCGCCAAGCTGCTGTGGAAGGGCCCCGCCGAGGGCCCGTGGTGATCCAGGACAA
CTCCGACATCAAGGTGGTGCCCCGCCAAGGCCAAGATCATCAAGGACT
ACGGCAAGCAGATGGCCGGGCCCGACTGCGTGGCCGCCGCCAGGACGAG
GACTAA
```

Fig. 19E

M.con.gag (group M consensus gag)

MGARASVLSGGKLDAWEKIRLRPGGKKKYRLKHLVWASRELERFALNPGLLETSEG CKQIIGQLQPA
LQTGSEELRSLYNTVATLYCVHQRIEVKDTKEALEKIEEEQNKSQQKTQQAAADKGNSSKVSQNYPIVQN
LQGQMVHQAISPRTLNAWVKVIEEKAFSPEVIPMFSALSEGATPQDLNTMLNTVGGHQAAMQMLKDTINE
EAAEWDRLHPVHAGPIPPGQMREPRGSDIAGTTSTLQEQIAWMTSNPPIPVGEIYKRWIILGLNKIVRMY
SPVSILDIRQGPKEPFRDYVDRFFKTLRAEQATQDVKNWMTDTLLVQNANPDCKTILKALGPGATLEEMM
TACQGVGGPGHKARVLAEAMSQVTNAAIMMQRGNFKGQRRIIKCFNCGKEGHIARNCRAPRKKGCWKCGK
EGHQMKDCTERQANFLGKIWPSNKGRPGNFLQSRPEPTAPPAESFGFEEITPSPKQEPKDKEPPLTSLK
SLFGNDPLSQ

Fig. 19F

M.con.pol (group M consensus pol)
MPQITLWQRPLVTJKIGGQLKEALLaTGADDTVLEEINLPGKWKPKMIGGIGGFIKVRQYDQILIEICGK
KAIGTVLVGPTPVNIIGRNMLTQIGCTLNFPISPIETVPVKLKPGMDGPKVKQWPLTEEKIKALTEICTE
MEKEGKISKIGPENPYNTPIFAIKKKDSTKWRKLVDFRELNKRTQDFWEVQLGIPHPAGLKKKKSVTVLD
VGDAYFSVPLDEDFRKYTAFTIPSINNETPGIRYQYNVLPQGWKGSPAIFQSSMTKILEPFRTQNPEIVI
YQYMDDLYVGSDLEIGQHRAKIEELREHLLRWGFTTPDKKHQKEPPFLWMGYELHPDKWTVQPIQLPEKD
SWTVNDIQKLVGKLNWASQIYPGIKVKQLCKLLRGAKALTDIVPLTEEAELELAENREILKEPVHGVYYD
PSKDLIAEIQKQGQDQWTYQIYQEPFKNLKTGKYAKMRSAHTNDVKQLTEAVQKIATESIVIWGKTPKFR
LPIQKETWETWWTEYWQATWIPEWEFVNTPPLVKLWYQLEKEPIAGAETFYVDGAANRETKLGKAGYVTD
RGRQKVVSLTETTNQKTELQAIHLALQDSGSEVNIVTDSQYALGIIQAQPDKSESELVNQIIEQLIKKEK
VYLSWVPAHKGIGGNEQVDKLVSTGIRKVLFLDGIDKAQEEHEKYHSNWRAMASDFNLPPIVAKEIVASC
DKCQLKGEAMHGQVDCSPGIWQLDCTHLEGKIILVAVHVASGYIEAEVIPAETGQETAYFILKLAGRWPV
KVIHTDNGSNFTSAAVKAACWWAGIQQEFGIPYNPQSQGVVESMNKELKKIIGQVRDQAEHLKTAVQMAV
FIHNFKRKGGIGGYSAGERIIDIIATDIQTKELQKQITKIQNFRVYYRDSRDPIWKGPAKLLWKGEGAVV
IQDNSDIKVVPRRKAKIIRDYGKQMAGDDCVAGRQDED

Fig. 19G

M.con.nef (group M consensus nef)
MGGKWSKSSIVGWPAVRERIRRTHPAAEGVGAVSQDLDKHGAITSSNTAANNPDCAWLEAQEEEEVGFP
VRPQVPLRPMTYKAALDLSHFLKEKGGLEGLIYSKKRQEILDLWVYHTQGYFPDWQNYTPGPGIRYPLTF
GWCFKLVPVDPEEVEEANEGENNSLLHPMCQHGMEDEEREVLMWKFDSRLALRHIARELHPEYKDC

Fig. 19H

C.con.pol (subtype C consensus pol)
MPQITLWQRPLVTJKIGGQLKEALLaTGADDTVLEEINLPGKWKPKMIGGIGGFIKVRQYDQILIEICGK
KAIGTVLVGPTPVNIIGRNMLTQLGCTLNFPISPIETVPVKLKPGMDGPKVKQWPLTEEKIKALTAICEE
MEKEGKITKIGPENPYNTPVFAIKKKDSTKWRKLVDFRELNKRTQDFWEVQLGIPHPAGLKKKKSVTVLD
VGDAYFSVPLDEGFRKYTAFTIPSINNETPGIRYQYNVLPQGWKGSPAIFQSSMTKILEPFRAQNPEIVI
YQYMDDLYVGSDLEIGQHRAKIEELREHLLKWGFTTPDKKHQKEPPFLWMGYELHPDKWTVQPIQLPEKD
SWTVNDIQKLVGKLNWASQIYPGIKVRQLCKLLRGAKALTDIVPLTEEAELELAENREILKEPVHGVYYD
PSKDLIAEIQKQGHDQWTYQIYQEPFKNLKTGKYAKMRTAHTNDVKQLTEAVQKIAMESIVIWGKTPKFR
LPIQKETWETWWTDYWQATWIPEWEFVNTPPLVKLWYQLEKEPIAGAETFYVDGAANRETKIGKAGYVTD
RGRQKIVSLTETTNQKTELQAIQLALQDSGSEVNIVTDSQYALGIIQAQPDKSESELVNQIIEQLIKKER
VYLSWVPAHKGIGGNEQVDKLVSSGIRKVLFLDGIDKAQEEHEKYHSNWRAMASEFNLPPIVAKEIVASC
DKCQLKGEAMHGQVDCSPGIWQLDCTHLEGKIILVAVHVASGYIEAEVIPAETGQETAYFILKLAGRWPV
KVIHTDNGSNFTSAAVKAACWWAGIQQEFGIPYNPQSQGVVESMNKELKKIIGQVRDQAEHLKTAVQMAV
FIHNFKRKGGIGGYSAGERIIDIIATDIQTKEILQKQIIKIQNFRVYYRDSRDPIWKGPAKLLWKGEGAVV
IQDNSDIKVVPRRKAKIIKDYGKQMAGADCVAGRQDED

Fig. 20A

B.con.gag (subtype B consensus gag. The amino acid sequence is different from Los Alamos Database August 2002)

GCCGCCGCCATGGGCGCCCGCGCCTCCGTGCTGTCCGGCGGCGAGCTGGA
CCGCTGGGAGAAGATCCGCCTGCGCCCCGGCGGCAAGAAGAAGTACAAGC
TGAAGCACATCGTGTGGGCCTCCCGCGAGCTGGAGCGCTTCGCCGTGAAC
CCCGGCCTGCTGGAGACCTCCGAGGGCTGCCGCCAGATCCTGGGCCAGCT
GCAGCCCTCCCTGCAGACCGGCTCCGAGGAGCTGCGCTCCCTGTACAACA
CCGTGGCCACCCTGTACTGCGTGCACCAGCGCATCGAGGTGAAGGACACC
AAGGAGGCCCTGGAGAAGATCGAGGAGGAGCAGAACAAGTCCAAGAAGAA
GGCCCAGCAGGCCGCCGCCGACACCGGCAACTCCTCCCAGGTGTCCCAGA
ACTACCCCATCGTGCAGAACCTGCAGGGCCAGATGGTGCACCAGGCCATC
TCCCCCCGCACCCTGAACGCCTGGGTGAAGGTGGTGGAGGAGAAGGCCTT
CTCCCCCGAGGTGATCCCCATGTTCTCCGCCCTGTCCGAGGGCGCCACCC
CCCAGGACCTGAACACCATGCTGAACACCGTGGGCGGCCACCAGGCCGCC
ATGCAGATGCTGAAGGAGACCATCAACGAGGAGGCCGCCGAGTGGGACCG
CCTGCACCCCGTGCACGCCGGCCCCATCGCCCCGGCCAGATGCGCGAGC
CCCGCGGCTCCGACATCGCCGGCACCACCTCCACCCTGCAGGAGCAGATC
GGCTGGATGACCAACAACCCCCCATCCCCGTGGGCGAGATCTACAAGCG
CTGGATCATCCTGGGCCTGAACAAGATCGTGCGCATGTACTCCCCCACCT
CCATCCTGGACATCCGCCAGGGCCCCAAGGAGCCCTTCCGCGACTACGTG
GACCGCTTCTACAAGACCCTGCGCGCCGAGCAGGCCTCCCAGGAGGTGAA
GAACTGGATGACCGAGACCCTGCTGGTGCAGAACGCCAACCCCGACTGCA
AGACCATCCTGAAGGCCCTGGGCCCCGCCGCCACCCTGGAGGAGATGATG
ACCGCCTGCCAGGGCGTGGGCGGCCCCGGCCACAAGGCCCGCGTGCTGGC
CGAGGCCATGTCCCAGGTGACCAACTCCGCCACCATCATGATGCAGCGCG
GCAACTTCCGCAACCAGCGCAAGACCGTGAAGTGCTTCAACTGCGGCAAG
GAGGGCCACATCGCCAAGAACTGCCGCGCCCCCGCAAGAAGGGCTGCTG
GAAGTGCGGCAAGGAGGGCCACCAGATGAAGGACTGCACCGAGCGCCAGG
CCAACTTCCTGGGCAAGATCTGGCCCTCCACAAGGGCCGCCCCGGCAAC
TTCCTGCAGTCCCGCCCCGAGCCCACCGCCCCCCCGAGGAGTCCTTCCG
CTTCGGCGAGGAGACCACCACCCCCTCCCAGAAGCAGGAGCCCATCGACA
AGGAGCTGTACCCCCTGGCCTCCCTGCGCTCCCTGTTCGGCAACGACCCC
TCCTCCCAGTAA

Fig. 20B

B.con.env (subtype B consensus env. The amino acid sequence is different from Los Alamos Database August 2002)

```
GCCGCCGCCATGCGCGTGAAGGGCATCCGCAAGAACTACCAGCACCTGTG
GCGCTGGGGCACCATGCTGCTGGGCATGCTGATGATCTGCTCCGCCGCCG
AGAAGCTGTGGGTGACCGTGTACTACGGCGTGCCCGTGTGGAAGGAGGCC
ACCACCACCCTGTTCTGCGCCTCCGACGCCAAGGCCTACGACACCGAGGT
GCACAACGTGTGGGCCACCCACGCCTGCGTGCCCACCGACCCCAACCCCC
AGGAGGTGGTGCTGGAGAACGTGACCGAGAACTTCAACATGTGGAAGAAC
AACATGGTGGAGCAGATGCACGAGGACATCATCTCCCTGTGGGACCAGTC
CCTGAAGCCCTGCGTGAAGCTGACCCCCCTGTGCGTGACCCTGAACTGCA
CCGACCTGAAGAACAACCTGCTGAACACCAACTCCTCCTCCGGCGAGAAG
ATGGAGAAGGGCGAGATCAAGAACTGCTCCTTCAACATCACCACCTCCAT
CCGCGACAAGGTGCAGAAGGAGTACGCCCTGTTCTACAAGCTGGACGTGG
TGCCCATCGACAACAACAACAACACCTCCTACCGCCTGATCTCCTGCAAC
ACCTCCGTGATCACCCAGGCCTGCCCCAAGGTGTCCTTCGAGCCCATCCC
CATCCACTACTGCGCCCCCGCCGGCTTCGCCATCCTGAAGTGCAACGACA
AGAAGTTCAACGGCACCGGCCCCTGCACCAACGTGTCCACCGTGCAGTGC
ACCCACGGCATCCGCCCCGTGGTGTCCACCCAGCTGCTGCTGAACGGCTC
CCTGGCCGAGGAGGAGGTGGTGATCCGCTCCGAGAACTTCACCGACAACG
CCAAGACCATCATCGTGCAGCTGAACGAGTCCGTGGAGATCAACTGCACC
CGCCCCAACAACAACACCCGCAAGTCCATCCACATCGGCCCCGGCCGCGC
CTTCTACACCACCGGCGAGATCATCGGCGACATCCGCCAGGCCCACTGCA
ACATCTCCCGCGCCAAGTGGAACAACACCCTGAAGCAGATCGTGAAGAAG
CTGCGCGAGCAGTTCGGCAACAAGACCATCGTGTTCAACCAGTCCTCCGG
CGGCGACCCCGAGATCGTGATGCACTCCTTCAACTGCGGCGGCGAGTTCT
TCTACTGCAACACCACCAGCTGTTCAACTCCACCTGGAACGACAACGGC
ACCTGGAACAACACCAAGGACAAGAACACCATCACCCTGCCCTGCCGCAT
CAAGCAGATCATCAACATGTGGCAGGAGGTGGGCAAGGCCATGTACGCCC
CCCCCATCCGCGGCCAGATCCGCTGCTCCTCCAACATCACCGGCCTGCTG
CTGACCCGCGACGGCGGCAACAACAACAACGACACCGAGATCTTCCGCCC
CGGCGGCGGCGACATGCGCGACAACTGGCGCTCCGAGCTGTACAAGTACA
AGGTGGTGAAGATCGAGCCCCTGGGCGTGGCCCCCACCAAGGCCAAGCGC
CGCGTGGTGCAGCGCGAGAAGCGCGCCGTGGGCATCGGCGCCATGTTCCT
GGGCTTCCTGGGCGCCGCCGGCTCCACCATGGGCGCCGCCTCCATGACCC
TGACCGTGCAGGCCCGCCAGCTGCTGTCCGGCATCGTGCAGCAGCAGAAC
AACCTGCTGCGCGCCATCGAGGCCCAGCAGCACCTGCTGCAGCTGACCGT
GTGGGGCATCAAGCAGCTGCAGGCCCGCGTGCTGGCCGTGGAGCGCTACC
TGAAGGACCAGCAGCTGCTGGGCATCTGGGGCTGCTCCGGCAAGCTGATC
TGCACCACCACCGTGCCCTGGAACGCCTCCTGGTCCAACAAGTCCCTGGA
CGAGATCTGGGACAACATGACCTGGATGGAGTGGGAGCGCGAGATCGACA
ACTACACCTCCCTGATCTACACCCTGATCGAGGAGTCCCAGAACCAGCAG
GAGAAGAACGAGCAGGAGCTGCTGGAGCTGGACAAGTGGGCCTCCCTGTG
GAACTGGTTCGACATCACCAACTGGCTGTGGTACATCAAGATCTTCATCA
TGATCGTGGGCGGCCTGATCGGCCTGCGCATCGTGTTCGCCGTGCTGTCC
ATCGTGAACCGCGTGCGCCAGGGCTACTCCCCCTGTCCTTCCAGACCCG
CCTGCCCGCCCCCCGCGGCCCCGACCGCCCCGAGGGCATCGAGGAGGAGG
GCGGCGAGCGCGACCGCGACCGCTCCGGCCGCCTGGTGGACGGCTTCCTG
GCCCTGATCTGGGACGACCTGCGCTCCCTGTGCCTGTTCTCCTACCACCG
CCTGCGCGACCTGCTGCTGATCGTGACCCGCATCGTGGAGCTGCTGGGCC
GCCGCGGCTGGGAGGTGCTGAAGTACTGGTGGAACCTGCTGCAGTACTGG
TCCCAGGAGCTGAAGAACTCCGCCGTGTCCCTGCTGAACGCCACCGCCAT
CGCCGTGGCCGAGGGCACCGACCGCGTGATCGAGGTGGTGCAGCGCGCCT
GCCGCGCCATCCTGCACATCCCCCGCCGCATCCGCCAGGGCCTGGAGCGC
GCCCTGCTGTAA
```

Fig. 20C

B.con.gag (subtype B consensus gag)

MGARASVLSGGELDRWEKIRLRPGGKKKYKLKHIVWASRELERFAVNPGLLETSEGCRQILGQLQPSLQT
GSEELRSLYNTVATLYCVHQRIEVKDTKEALEKIEEEQNKSKKAQQAAADTGNSSQVSQNYPIVQNLQG
QMVHQAISPRTLNAWVKVVEEKAFSPEVIPMFSALSEGATPQDLNTMLNTVGGHQAAMQMLKETINEEAA
EWDRLHPVHAGPIAPGQMREPRGSDIAGTTSTLQEQIGWMTNNPPIPVGEIYKRWIILGLNKIV RMYSPT
SILDIRQGPKEPFRDYVDRFYKTLRAEQASQEVKNWMTETLLVQNANPDCKTILKALGPAATLEEMMTAC
QGVGGPGHKARVLAEAMSQVTNSATIMMQRGNFRNQRKTVKCFNCGKEGHIAKNCRAPRKKGCWKCGKEG
HQMKDCTERQANFLGKIWPSHKGRPGNFLQSRPEPTAPPEESFRFGEETTTPSQKQEPIDKELYPLASLR
SLFGNDPSSQ

Fig. 20D

B.con.env (subtype B consensus env)

MRVKGIRKNYQHLWRWGTMLLGMLMICSAAEKLWVTV YYGVPVWKEATTTLFCASDAKAYDTEVHNVWAT
HACVPTDPNPQEVVLENVTENFNMWKNNMVEQMHEDIISLWDQSLKPCVKLTPLCVTLNCTDLKNNLLNT
NSSSGEKMEKGEIKNCSFNITTSIRDKVQKEYALFYKLDVVPIDNNNNTSYRLISCNTSVITQACPKVSF
EPIPIHYCAPAGFAILKCNDKKFNGTGPCTNVSTVQCTHGIRPVVSTQLLLNGSLAEEEVVIRSENFTDN
AKTIIVQLNESVEINCTRPNNNTRKSIHIGPGRAFYTTGEIIGDIRQAHCNISRAKWNNTLKQIVKKLRE
QFGNKTIVFNQSSGGDPEIVMHSFNCGGEFFYCNTTQLFNSTWNDNGTWNNTKDKNTITTLPCRIKQIINM
WQEVGKAMYAPPIRGQIRCSSNITGLLLTRDGGNNNNDTEIFRPGGGDMRDNWRSELYKYKVVKIEPLGV
APTKAKRRVVQREKRAVGIGAMFLGFLGAAGSTMGAASMTLTVQARQLLSGIVQQNNLLRAIEAQQHLL
QLTVWGIKQLQARVLAVERYLKDQQLLGIWGCSGKLICTTTVPWNASWSNKSLDEIWDNMTWMEWEREID
NYTSLIYTLIEESQNQQEKNEQELLELDKWASLWNWFDITNWLWYIKIFIMIVGGLIGLRIVFAVLSIVN
RVRQGYSPLSFQTRLPAPRGPDRPEGIEEEGGERDRDRSGRLVDGFLALIWDDLRSLCLFSYHRLRDLLL
IVTRIVELLGRRGWEVLKYWWNLL QYWSQELKNSAVSLLNATAIAVAEGTDRVIEVVQRACRAILHIPRR
IRQGLERALL

Fig. 23A

Trans complementation of env-deficient HIV-1 with codon-optimized subtype B consensus gp160 and gp140 genes.

Fig. 23B

Infectivity of virus particles containing the subtype B concensus envelope.

Neutralization sensitivity of virions containing subtype B concensus gp 160 envelope.

VLP production by co-transfection of subtype B consensus *gag* and *env* genes.

Fig. 26A

Year 2000 Con-S 140CFI.Env

MRVRGIQRNCQHLWRWGTLILGMLMICSAAENLWVTVYYGVPVWKEANTTLFCASDAKAYDTEVH
NVWATHACVPTDPNPQEIVLENVTENFNMWKNNMVEQMHEDIISLWDQSLKPCVKLTPLCVTLNC
TNVNVTNTTNNTEEKGEIKNCSFNITTEIRDKKQKVYALFYRLDVVPIDDNNNNSSNYRLINCNT
SAITQACPKVSFEPIPIHYCAPAGFAILKCNDKKFNGTGPCKNVSTVQCTHGIKPVVSTQLLLNG
SLAEEEIIIRSENITNNAKTIIVQLNESVEINCTRPNNNTRKSIRIGPGQAFYATGDIIGDIRQA
HCNISGTKWNKTLQQVAKKLREHFNNKTIIFKPSSGGDLEITTHSFNCRGEFFYCNTSGLFNSTW
IGNGTKNNNNTNDTITLPCRIKQIINMWQGVGQAMYAPPIEGKITCKSNITGLLLTRDGGNNNTN
ETEIFRPGGGDMRDNWRSELYKYKVVKIEPLGVAPTKAKLTVQARQLLSGIVQQQSNLLRAIEAQ
QHLLQLTVWGIKQLQARVLAVERYLKDQQLEIWDNMTWMEWEREINNYTDIIYSLIEESQNQQEK
NEQELLALDKWASLWNWFDITNWLW

A gp140 CFI is referred to HIV-1 envelope design with the cleavage-site-deleted (C), fusion-site-deleted (F) and gp41 immunodominant region-deleted (I) in addition to the deletion of transmembrane and cytoplasmic domains.

Fig. 26B

Codon-optimized Year 2000 Con-S 140CFI. seq

ATGCGCGTGCGCGGCATCCAGCGCAACTGCCAGCACCTGTGGCGCTGGGGCACCCTGATCCTGGG
CATGCTGATGATCTGCTCCGCCGCCGAGAACCTGTGGGTGACCGTGTACTACGGCGTGCCCGTGT
GGAAGGAGGCCAACACCACCCTGTTCTGCGCCTCCGACGCCAAGGCCTACGACACCGAGGTGCAC
AACGTGTGGGCCACCCACGCCTGCGTGCCCACCGACCCCAACCCCCAGGAGATCGTGCTGGAGAA
CGTGACCGAGAACTTCAACATGTGGAAGAACAACATGGTGGAGCAGATGCACGAGGACATCATCT
CCCTGTGGGACCAGTCCCTGAAGCCCTGCGTGAAGCTGACCCCCCTGTGCGTGACCCTGAACTGC
ACCAACGTGAACGTGACCAACACCACCAACAACACCGAGGAGAAGGGCGAGATCAAGAACTGCTC
CTTCAACATCACCACCGAGATCCGCGACAAGAAGCAGAAGGTGTACGCCCTGTTCTACCGCCTGG
ACGTGGTGCCCATCGACGACAACAACAACAACTCCTCCAACTACCGCCTGATCAACTGCAACACC
TCCGCCATCACCCAGGCCTGCCCCAAGGTGTCCTTCGAGCCCATCCCCATCCACTACTGCGCCCC
CGCCGGCTTCGCCATCCTGAAGTGCAACGACAAGAAGTTCAACGGCACCGGCCCCTGCAAGAACG
TGTCCACCGTGCAGTGCACCCACGGCATCAAGCCCGTGGTGTCCACCCAGCTGCTGCTGAACGGC
TCCCTGGCCGAGGAGGAGATCATCATCCGCTCCGAGAACATCACCAACAACGCCAAGACCATCAT
CGTGCAGCTGAACGAGTCCGTGGAGATCAACTGCACCCGCCCCAACAACAACACCCGCAAGTCCA
TCCGCATCGGCCCCGGCCAGGCCTTCTACGCCACCGGCGACATCATCGGCGACATCCGCCAGGCC
CACTGCAACATCTCCGGCACCAAGTGGAACAAGACCCTGCAGCAGGTGGCCAAGAAGCTGCGCGA
GCACTTCAACAACAAGACCATCATCTTCAAGCCCTCCTCCGGCGGCGACCTGGAGATCACCACCC
ACTCCTTCAACTGCCGCGGCGAGTTCTTCTACTGCAACACCTCCGGCCTGTTCAACTCCACCTGG
ATCGGCAACGGCACCAAGAACAACAACAACACCAACGACACCATCACCCTGCCCTGCCGCATCAA
GCAGATCATCAACATGTGGCAGGGCGTGGGCCAGGCCATGTACGCCCCCCCCATCGAGGGCAAGA
TCACCTGCAAGTCCAACATCACCGGCCTGCTGCTGACCCGCGACGGCGGCAACAACAACAACCAAC
GAGACCGAGATCTTCCGCCCCGGCGGCGGCGACATGCGCGACAACTGGCGCTCCGAGCTGTACAA
GTACAAGGTGGTGAAGATCGAGCCCCTGGGCGTGGCCCCCACCAAGGCCAAGCTTACCGTGCAGG
CCCGCCAGCTGCTGTCCGGCATCGTGCAGCAGCAGTCCAACCTGCTGCGCGCCATCGAGGCCCAG
CAGCACCTGCTGCAGCTGACCGTGTGGGGCATCAAGCAGCTGCAGGCCCGCGTGCTGGCCGTGGA
GCGCTACCTGAAGGACCAGCAGCTCGAGATCTGGGACAACATGACCTGGATGGAGTGGGAGCGCG
AGATCAACAACTACACCGACATCATCTACTCCCTGATCGAGGAGTCCCAGAACCAGCAGGAGAAG
AACGAGCAGGAGCTGCTGGCCCTGGACAAGTGGGCCTCCCTGTGGAACTGGTTCGACATCACCAA
CTGGCTGTGGTGAGGATCC

Fig. 28A

Design of expression-optimized HIV-1 envelope gp140CF

Con-B-2003 Env.pep (841 a.a.)*
MRVKGIRKNYQHLWRWGTMLLGMLMICSAAEKLMVTVYYGVPVWKEATTLFCASDAKAYDTEVHNVWATHACVPTDPNPQEVVL
ENVTENFNMWKNNMVEQMHEDIISLWDQSLKPCVKLTPLCVTLNCTDLMNATNTNTTIYRWRGEIKNCSFNITTSIRDKVQKEY
ALFYKLDVVPIDNDNTSYRLISCNTSVITQACPKVSFEPIPIHYCAPAGFAILKCNDKKFNGTGPCTNVSTVQCTHGIRPVVSTQ
LLLNGSLAEEEVVIRSENFTDNAKTIIVQLNESVEINCTRPNNNTRKSIHIGPGRAFYTTGEIIGDIRQAHCNISRAKWNNTLKQ
IVKKLREQFGNKTIVFNQSSGGDPEIVMHSFNCGGEFFYCNTTQLFNSTWNGTWNNTEGNITLPCRIKQIINMWQEVGKAMYAPP
IRGQIRCSSNITGLLLTRDGGNNETEIFRPGGGDMRDNWRSELYKYKVKIEPLGVAPTKAKRRVVQREKRAVGIGAMFLGFLGA
AGSTMGAASMTLTVQARQLLSGIVQQQNNLLRAIEAQQHLLQLTVWGIKQLQARVLAVERYLKDQQLLGIWGCSGKLICTTAVPW
NASWSNKSLDEIWDNMTWMEWEREIDNYTSLIYTLIEESQNQQEKNEQELLELDKWASLWNWFDITNWLNYIKIFIMIVGGLIVGL
RIVFAVLSIVNRVRQGYSPLSFQTRLPAPRGPDRPEGIEEEGGERDRDRSGRLVDGFLALIWDDLRSLCLFSYHRLRDLLLIVTR
IVELLGRRGWEVLKYWWNLLQYWSQELKNSAVSLLNATAIAVAEGTDRVIEVVQRACRAILHIPRRIRQGLERALL
TVELLGRRGWEVLKYWWNILQYWSQELKNSAVSLLNATAIAVAEGTDRVIEVVQRACRAILHIPRRIRQGLERALL

*Amino acid sequence underlined is the fusion domain that will be deleted in 140CF design and the "W" underlined with red color is the last amino acid at the C terminus, and all the remaining amino acids after the "W" will be deleted in 140CF design.

Fig. 28B

Con-B-140CF.pep (632 a.a.)
Nick name: 002
MRVKGIRKNYQHLWRWGTMLLGMLMICSAAEKLMVTVYYGVPVWKEATTLFCASDAKAYDTEVHNVWATHACVPTDPNPQEVVL
ENVTENFNMWKNNMVEQMHEDIISLWDQSLKPCVKLTPLCVTLNCTDLMNATNTNTTIYRWRGEIKNCSFNITTSIRDKVQKEY
ALFYKLDVVPIDNDNTSYRLISCNTSVITQACPKVSFEPIPIHYCAPAGFAILKCNDKKFNGTGPCTNVSTVQCTHGIRPVVSTQ
LLLNGSLAEEEVVIRSENFTDNAKTIIVQLNESVEINCTRPNNNTRKSIHIGPGRAFYTTGEIIGDIRQAHCNISRAKWNNTLKQ
IVKKLREQFGNKTIVFNQSSGGDPEIVMHSFNCGGEFFYCNTTQLFNSTWNGTWNNTEGNITLPCRIKQIINMWQEVGKAMYAPP
IRGQIRCSSNITGLLLTRDGGNNETEIFRPGGGDMRDNWRSELYKYKVKIEPLGVAPTKAKTLTVQARQLLSGIVQQQNNLLRA
IEAQQHLLQLTVWGIKQLQARVLAVERYLKDQQLLGIWGCSGKLICTTAVPWNASWSNKSLDEIWDNMTWMEWEREIDNYTSLIY
TLIEESQNQQEKNEQELLELDKWASLWNWFDITNWLW*

*Amino acids seen in blue color is for easy identification of the junction of the deleted fusion cleavage site

Fig. 28C

Fig. 28C

Codon-opitmized Con-B 140CF.seq (1927 nt.)
Nick name: 002

TTCAGTCGACGGCCACCATGAGGGTGAAGGGTATTCGGAAAAATTACCAACACCTGTGGCGCTGGGGAACCATGCTCCTTGGTAT
GCTGATGATTTGCAGTGCCGCCGAGAAACTTTGGGTAACTGTGTACTACGGCGTTCCTGTCTGGAAGGAAGCTACAACCACTCTT
TTTTGTGCATCCGACGCTAAAGCTTACGACACAGAAGTGCATAATGTTTGGGCCACCCATGCTTGCGTCCCTACAGATCCCAACC
CCCAGGAAGTCGTCCTTGAGAATGTCACAGAGAATTTTAACATGTGGAAGAATAATATGGTAGAACAAATGCACGAAGACATTAT
TAGCCTGTGGGACCAGTCCTTGAAGCCCTGCGTGAAACTCACTCCACTTTGCGTCACACTTAACTGTACTGATTTGATGAACGCA
ACCAACACAAATACTACTATTATATATCGCTGGAGGGGGGAAATCAAGAACTGCTCTTTCAACATCACCACTTCCATAAGGGATA
AGGTCCAGAAAGAATATGCCCTGTTTTATAAACTTGATGTGGTCCCGATAGACAATGACAACACTAGCTATCGACTGATCTCTTG
TAACACATCCGTGATTACCCAAGCTTGCCCAAAGGTCAGCTTTGAACCAATACCCATTCACTACTGCGCTCCCGCTGGTTTTGCC
ATCCTCAAGTGTAACGACAAAAAATTCAATGGGACCGGACCTTGCACAAACGTGTCCACCGTGCAATGTACTCACGGAATCAGAC
CTGTTGTCAGTACCCAACTCCTCTTGAACGGGTCTCTCGCGGAAGAGGAGGTCGTGATTAGAAGCGAAAACTTTACCGATAACGC
TAAAACAATCATTGTGCAACTTAATGAAAGCGTCGAAATTAACTGCACCAGACCAAACAATAATACCAGAAAATCTATTCACATA
GGGCCCGGCCGCGCATTTTATACAACTGGCGAAATCATTGGTGACATCAGACAAGCTCATTGCAATATCTCCCGCGCGAAATGGA
ACAACACCCTGAAACAGATCGTGAAGAAACTTCGAGAACAATTCGGTAATAAAACAATCGTATTCAACCAAAGCTCCGGAGGCGA
CCCTGAGATAGTTATGCACTCATTCAACTGTGGCGGCGAGTTCTTCTATTGTAACACAACTCAACTTTTTAATAGCACTTGGAAT
GGAACATGGAACAACACAGAAGGGAACATCACTCTGCCTTGTCGGATTAAGCAGATCATTAATATGTGGCAAGAAGTGGGAAAAG
CTATGTACGCCCCGCCTATTCGCGGACAAATAAGATGCTCTAGTAATATTACCGGATTGTTGCTGACACGCGACGGAGGAAATAA
TGAAACAGAGATATTTAGACCTGGCGGAGGCGACATGAGAGATAACTGGAGAAGTGAGCTTTACAAATATAAAGTCGTAAAGATA
GAACCATTGGGGGTAGCACCAACCAAAGCAAAAACCTTGACAGTACAGGCTAGGCAGCTGCTGAGCGGAATCGTGCAACAACAAA
ATAATCTTCTCCGAGCCATAGAAGCACAACAACATCTGTTGCAGCTGACAGTATGGGGAATCAAACAGCTTCAGGCAAGAGTGCT
GGCCGTCGAGAGATACCTCAAAGATCAACAACTGCTGGGCATATGGGGATGTTCCGGTAAACTCATATGCACTACCGCCGTGCCC
TGGAACGCGAGCTGGTCTAATAAATCCCTGGATGAAATTTGGGACAACATGACTTGGATGGAATGGGAACGGGAAATTGACAACT
ATACTAGTTTGATTTATACTCTGATCGAAGAATCTCAGAACCAACAGGAGAAAAACGAACAGGAACTGCTGGAACTGGACAAGTG
GGCATCATTGTGGAACTGGTTTGACATTACTAACTGGCTGTGGTAAAGATCTTACAA

**(For all 140CF design shown here and below, 140CF gene will be flanked with the 5′ sequence of "TTCAGTCGACGGCCACC" that contains a Kozak" sequence (GCCACCATGG/A) and *SalI* site and 3′sequence of TAAAGATCTTACAA containing stop codon and *BglII* site.)**

Fig. 29A

CON OF CON-S-2003 (829 a.a.)

MRVMGIQRNCQHLWRWGILIFGMLIICSAAENLWTVYGVPVWKEANTTLFCASDAKAYDTEVHNVWATHACVPTDPNPQEIVL
ENVTENFNMWKNNMVEQMHEDIISLWDQSLKPCVKLTPLCVTLNCTDVNATNNTTNNEEIKNCSFNITTEIRDKKKVALFYKL
DVVPIDDNNSYRLINCNTSAITQACPKVSFEPIPIHYCAPAGFAILKCNDKKFNGTGPCKNVSTVQCTHGIKPVVSTQLLLNGSL
AEEEIIRSENITNNAKTIIVQLNESVEINCTRPNNNTRKSIRIGPGQAFYATGDIIGDIRQAHCNISRTKWNKTLQQVAKKLRE
HFNKTIIFNPSSGDLEITTHSFNCGGEFFYCNTSELFNSTWNGTNNTITLPCRIKQIINMWQGVGQAMYAPPIEGKIRCTSNIT
GLLLTRDGGNNNTETFRPGGGDMRDNWRSELYKYKVKIEPLGVAPTKAKRRVVEREKRAVGIGAVFLGFLGAAGSTMGAASITL
TVQARQLLSGIVQQQSNLLRAIEAQQHLLQLTVWGIKQLQARVLAVERYLKDQQLLGIWGCSGKLICTTNVPWNSSWSNKSQDEI
WDNMTWMEWDKEINNYTDIIYSLIEESQNQQEKNEQELLALDKWASLWNWFDITNWLWYIKIFIMIVGGLIGLRIVFAVLSIVNR
VRQGYSPLSFQTLIPNPRGPDRPEGIEEEGGEQDRDRSIRLVNGFLALAWDDLRSLCLFSYHRLRDLLLIAARTVELLGRRGWEA
LKYLWNLLQYWGQELKNSAISLLDTTAIAVAEGTDRVIEVVQRVCRAILNIPRRIRQGFERALL

*Amino acid sequence underlined is the fusion domain that will be deleted in 140CF design and

*Fig. 29C*

```
CODON-OPTIMIZED CON-S-2003 140CF.seq (1891 nt
Nick name :006

TTCAGTCGACAGCCACCATGCGGGTCATGGGAGATACAGAGGAATTGCCAGCACTTTGTGGAGGTGGGGAATTTTGATATATTCGGGAT
GCTCATAATCTGCTCTGCCGCTGAGAGAATACAGGAACCTGTGGGCTCACTGTGTATTACGGCGTTCCCGTCTGAGAAAGAAGCTAATACTACCCTG
TTTTGTGCAAGCGACGCCAAAGCATACGACGAAGTCCACACCGAAGTCTGGGCTACCCACGCCTGTGTACCTACTGATCCAAATC
CCCAGGAAATTGTTCTTGAAAACGTAACGGAAAACTTTAACATGTGGAAGAATAATATGGTGGAGCAAATGCACGAGGATATAAT
CAGCCTGTGGGACCAGTCCCCTCAAACCATGGAGGAGATAAAGAATTGTTGTTCATTTAATATAACCACTGAGATACGGGATATAAGAAAAAAGGTTTATG
AATAATACAACAACAATGAGGAGATAAAGAATTGTTGTTCATTTAATATAACCACTGAGATACGGGATATAAGAAAAAAGGTTTATG
CACTCTTTTACAAGCTCGACGTGGTGCCCATAGACGACGATAAATAGCTACCGACTCATTAATTGCAATACTAGCGCTATAACCCA
GGCATGCCCCAAAGTTTCCTTGCGAGCCCTGTAAGAACGTAAGCACTGTTCAATGTACACAGCTACCGTGTAGTGTCAACGCAGCTCC
AAGTTCAACGGCACCGACCCCTTGCAGAAGAAGAGATCATTATCAGGTCAGAAATATCACAAGAAAGTCAATTAGGATCGAATGCAGCTCC
TCCTCAACGGAAGCCTTGCAGAAGAAGAGATCATTATCAGGTCAGAAATATCACAAGAAAGTCAATTAGGATCGAATGCAGGTAG
GAATGAGTCTGTAGAAATCAATTGTACCCGCCTAATAATAACACAAGCCCCACTGCAACATTTCTAGAACTAAGTGAATAAAAACTTTGCAGCAGGTAG
GCAACCGGAGATATCATCGGGATATACGAGACAGGCCACAATCATCTTCAAGTAGCGAGGGGACCTGGAAATCACTACACATTCCTT
CCAAGAAACTGCCGGGAACATTTTAATAAGACAATCATCTTCAAGTAGCGAGGGGACCTGGAAATCACTACACATTCCTT
TAACTGTGGGGGGCGAGTTTTTCTACTGTAATACCCTGTTCAACTCAACATGTTGGGGCAAGCAATGTATGCACCACCAATCGAAGGCAAAATAAGAT
CCTTGCAGATAAAACAGATTATCAACATGTGGGGCAAGCAATGTATGCACCACCAATCGAAGGCAAAATAAGAT
GCACCTCCAATATTACCGGACTCCTCCTGATAAATACAAAAGTCGTTAAGATCGACCAATCTAATCTTTTGAGAGCAGCCATTGAGGCTCAGCAGCACC
GAGAGATAACTGGCGCTCCGAGCTTGCTTGTCAGCAGCCAGTTGTGCAGGTATCGTACAGCACGGAACTCTAATCTTTTGAGAGCAGCCATTGAGGCTCAGCAGCACC
TTGACCGTGCAAGCCAGCAGTTGTCAGCAGCCAGTTGTGCAGGTATCGTACAGCACGTCCAAATGTGCCTTGGAACAAATGTGAAAGACCAACACTTCT
CGGGATCTGGGGGTGTTCTGGAAATGGAATGGGATAAAGAAATTGATCTGCACGCACAAATGTGCCTTGGAACAAATGTGAAAGACCAACACTTCT
ATATGGGATAACATGGACGATGGAATGGGATAAAGAAATTGATCTGAATGGGATAAAGAAATTACTCTTATGGAGGAATCAC
AAAATCAACAGGAAAAAAATGAACAGGAACTCTTGGCTCTGGACAAAATTAATAATTACACTGACATTATTACTCTTATGGAGGAATCAC
GCTCTGGTAAAGATCTTACAA
```

Fig. 30A

CONSENSUS_A1-2003(845 a.a.)

MRVMGIQRNCQHLLRWGTMILGMIICSAAENLWTVYYGVPVWKDAETTLFCASDAKAYETEMHNVWATHACVPTDPNPQEIHL
ENVTEEFNMWKNNMVEQMHTDIISLWDQSLKPCVKLTPLCVTLNCSNVNVTNNTTNTHEEEIKNCSFNMTTELRDKKQKVYSLFY
RLDVVQINENNSNSSYRLINCNTSAITQACPKVSFEPIPIHYCAPAGFAILKCKDKEFNGTGPCKNVSTVQCTHGIKPVVSTQLL
LNGSLAEEEVIIRSENITNNAKTIIVQLTKPVKINCTRPNNNTRKSIRIGPGQAFYATGDIIGDIRQAHCNVSRSEWNKTLQKVA
KQLRKYFKNKTIIFTNSSGGDLEITTHSFNCGGEFFYCNTSGLFNSTWNNGTMKNTITLPCRIKQIINMWQRAGQAMYAPPIQGV
IRCESNITGLLLTRDGGNNNTNETFRPGGGDMRDNWRSELYKYKVVKIEPLGVAPTRAKRRVVEREKRAVGIGAVFLGFLGAAGS
TMGAASITLTVQARQLLSGIVQQQSNLLRAIEAQQHLLKLTVWGIKQLQARVLAVERYLKDQQLLGIWGCSGKLICTTNVPWNSS
WSNKSQNEIWDNMTWLQWDKEISNYTHIIYNLIEESQNQQEKNEQDLLALDKWANLWNWFDISNWLWYIKIFIMIVGGLIGLRIV
FAVLSVINRVRQGYSPLSFQTHTPNPRGLDRPGRIEEGGEQGRDRSIRLVSGFLALAWDDLRSLCLFSYHRLRDFILIAARTVE
LLGHSSLKGLRLGWEGLIKYLWNLLLYWGRELKTSAINLVDTIAIAVAGWTDRVIEIGQRIGRAIIHIPRRIRQGLERALL

*Amino acid sequence underlined is the fusion domain that will be deleted in 140CF design and the "W" underlined with red color is the last amino acid at the C terminus, and all the remaining amino acids after the "W" will be deleted in 140CF design.

Fig. 30B

Con-A1-2003 140CF.pep (629 a.a.)

Nick name: 001

MRVMGIQRNCQHLLRWGTMILGMIIICSAAENLWVTVYYGVPVWKDAETTLFCASDAKAYETEMHNVWATHACVPTDPNPQEIHL
ENVTEEFNMWKNNMVEQMHTDIISLWDQSLKPCVKLTPLCVTLNCSNVNVTNNTTNTHEEEIKNCSFNMTTELRDKKQKVYSLFY
RLDVVQINENNSNSSYRLINCNTSAITQACPKVSFEPIPIHYCAPAGFAILKCKDKEFNGTGPCKNVSTVQCTHGIKPVVSTQLL
LNGSLAEEEVIIRSENITNNAKTIIVQLTKPVKINCTRPNNNTRKSIRIGPGQAFYATGDIIGDIRQAHCNVSRSEWNKTLQKVA
KQLRKYFKNKTIIFTNSSGGDLEITTHSFNCGGEFFYCNTSGLFNSTWNNGTMKNTITLPCRIKQIINMWQRAGQAMYAPPIQGV
IRCESNITGLLLTRDGGNNNTNETFRPGGGDMRDNWRSELYKYKVVKIEPLGVAPTRAKTLTVQARQLLSGIVQQQSNLLRAIEA
QQHLLKLTVWGIKQLQARVLAVERYLKDQQLLGIWGCSGKLICTTNVPWNSSWSNKSQNEIWDNMTWLQWDKEISNYTHIIYNLI
EESQNQQEKNEQDLLALDKWANLWNWFDISNWLW*

*Amino acids seen in blue color is for easy identification of the junction of the deleted fusion cleavage site.

*Fig. 30C*

CODON-OPTIMIZED Con-A1-2003.seq
Nick name: 001 (1918 nt)

```
TTCAGTCGACAGCCACCATGAGGGTGATGGGAATCCAACGGAACTGCCAGCATCTTCTCCGTGGGGAACGATGATACTGGAAT
GATAATAATCTGCTCTGCCGCTGAAAACCTCTGGGTCACAGTGTACTACGGAGTGCCTGTTATGGAAGGACGCTGAAACCACTCTC
TTTTGTGCTTCCGATGCTAAAGCCTACGAAACCGAGATGTTTGGGCCACCACGCCTGCGTGCCAACTGATCCTAATC
CACAAGAATACATCTGGAGAATGTTACTGAGGAATTTAACATGTGGAAAAATAATATGGTAGAGCAAATGCACACTGACATCAT
TTCACTCTGGGACCAATCACTCAAACCCTGCGTTAAACTTAAAATTGCTCTTTAATATGACCACTGAACTTCGCGACAAAAACAAAAG
AATAATACAACCAACACTCACGGAGGAAGAAATTAAAAATTCAACGAGTCGTCCAAATCAACGAGAACAATTCTAACACTAGTAGCTATCGACTTATCGACTTACTGTCCCAGCTGATTCGCAATTCTG
TCTATTCACTGTTTTACCCAAGCTTGTCCTAAAGTCTCTTTTGAACAATTGGCCCTTGCCGAAGAAGAGAGGTTGATTATCGAAGCGAGATCGTATGAAGCGAGAACATAAACTCATCAGAATTGGCCCC
AAGTGCAAGGATAAGGAATTCAACGGAACTGGCTCCTGAATGGCTCACTCGCCGAAGAGAAGAGAGGTGATTATCGAAGCGAGAACATAAACTATCAGAATTGGCCCC
TCAGCACTCAACTGCCTCCTGAATGGCTCACTCGCCGAAGAGAAGAGAGGTGATTATCGAAGCGAGAACATAAACTATCAGAATTGGCCCC
AATAATTGTTCAATTGACGAAACAGGAGATATCATAGGTGACATCAGAACAAGTCGACTTTGACGACACAAGCCCATTGCAACGTTTCAAGAAGCGAGTGGAATAAA
GACAAGCCTTCTACGCAACAGGACAGCAGTAGCTAGACAACAAGACAATCATATTTACTAACTCCTCCGAGGTGATCTCGA
CACTCCAGAAGTGGCAAAGCAGCTGAGAAATACTTTAAGAACAAGACAATCATATTTACTAACTCCTCCGAGGTGATCTCGA
AATAACCACTCATAGCTTTAATTGTGGGGGCGAATTCTTCTACTGTAACACATCTGGCCTCTTTAATTCTACCTGGAATAACGGC
ACCATGAAAAATACTATCACCCCTCCCTTTGCAGAATTAAGCAAATCATTAACATGTGGCAGAGAGCAGGACAGGCCATGTATGCCC
CTCCCATTCAAGGTGTGATTGAAAGCAACAATTACTGGACTTCTTCTGACTTGGAAGTGAACAAGTAGTTATAAATACAAATGA
GACATTCAGACCCGGCGCGCTAGAGCAAAAACATTGGCGAAGTGAACTTTATAAATACAAAGTAGTTAAGATTGAGCCCTT
GGAGTTGCCCCTACTAGAGCACAACAGCAGCTGACCGTTCAGGCCAGCTATGGGAATGACCGTATGGCTCTGGGATGCTCTGGGAATGACCGTATGGCTCTGGGATGCTCTGGGAATCTGGGATGCTCTGGGAAGTAACCTCC
TCCGAGCTATCGAGGCACAACAGCAGCTGACCGTTCAGGCCAGCTATGGGAATGACCGTATGGCTCTGGGATGCTCTGGGAATGACCGTATGGCTCTGGGAAATGACCGCCAGTGCTCTGGACCTGGCAGTGCTCTGGGACCTGGCAGTGCTCTGGACCTGGCAGTGCTCTGTGGA
ACGCTATCCAAGGATAAAGCCAGAATCGAAGAATCACAGAACCAGCAGGAAAGAATGAGCAAGAACCTTCTGCCTTGGACAAGTGGGCTAACTT
TCATATACAATCTGATCGAAGAATCACAGAACCAGCAGGAAAGAATGAGCAAGAACCTTCTGCCTTGGACAAGTGGGCTAACTT
GTGGAACTGGTTTGACATTAGCAACTGGTAAAGATCTTACAA
```

Fig. 31A

CONSENSUS_C-2003 (835 a.a)

MRVRGILRNCQQWWIWGILGFWMLMICNVVGNLWVTVYYGVPVWKEAKTTLFCASDAKAYEKEVHNVWATHACVPTDPNPQEIVL
ENVTENFNMWKNDMVDQMHEDIISLWDQSLKPCVKLTPLCVTLNCTNATNATNTMGEIKNCSFNITTELRDKKQKVYALFYRLDI
VPLNENNSYRLINCNTSAITQACPKVSFDPIPIHYCAPAGYAILKCNNKTFNGTGPCNNVSTVQCTHGIKPVVSTQLLLNGSLAE
EEIIIRSENLTNNAKTIIVHLNESVEIVCTRPNNNTRKSIRIGPGQTFYATGDIIGDIRQAHCNISEDKWNKTLQKVSKKLKEHF
PNKTIKFEPSSGGDLEITTHSFNCRGEFFYCNTSKLFNSTYNSTNSTITLPCRIKQIINMWQEVGRAMYAPPIAGNITCKSNITG
LLLTRDGGKNNTETFRPGGGDMRDNWRSELYKYKVVEIKPLGIAPTKAKRRVVEREKRAVGIGAVFLGFLGAAGSTMGAASITLT
VQARQLLSGIVQQQSNLLRAIEAQQHMLQLTVWGIKQLQTRVLAIERYLKDQQLLGIWGCSGKLICTTAVPWNSSWSNKSQEDIW
DNMTWMQWDREISNYTDTIYRLLEDSQNQQEKNEKDLLALDSWKNLWNWFDITNWLWYIKIFIMIVGGLIGLRIIFAVLSIVNRV
RQGYSPLSFQTLTPNPRGPDRLGRIEEEGGEQDRDRSIRLVSGFLALAWDDLRSLCLFSYHRLRDFILIAARAVELLGRSSLRGL
QRGWEALKYLGSLVQYWGLELKKSAISLLDTIAIAVAEGTDRIIELIQRICRAIRNIPRRIRQGFEAALQ

*Amino acid sequence underlined is the fusion domain that will be deleted in 140CF design and the "W" underlined with red color is the last amino acid at the C terminus, and all the remaining amino acids after the "W" will be deleted in 140CF design..

Fig. 31B

Con-C 2003 140CF.pep (619 a.a.)

Nick name: 003

MRVRGILRNCQQWWIWGILGFWMLMICNVVGNLWVTVYYGVPVWKEAKTTLFCASDAKAYEKEVHNVWATHACVPTDPNPQEIVL
ENVTENFNMWKNDMVDQMHEDIISLWDQSLKPCVKLTPLCVTLNCTNATNATNTMGEIKNCSFNITTELRDKKQKVYALFYRLDI
VPLNENNSYRLINCNTSAITQACPKVSFDPIPIHYCAPAGYAILKCNNKTFNGTGPCNNVSTVQCTHGIKPVVSTQLLLNGSLAE
EEIIIRSENLTNNAKTIIVHLNESVEIVCTRPNNNTRKSIRIGPGQTFYATGDIIGDIRQAHCNISEDKWNKTLQKVSKKLKEHF
PNKTIKFEPSSGGDLEITTHSFNCRGEFFYCNTSKLFNSTYNSTNSTITLPCRIKQIINMWQEVGRAMYAPPIAGNITCKSNITG
LLLTRDGGKNNTETFRPGGGDMRDNWRSELYKYKVVEIKPLGIAPTKAKTLTVQARQLLSGIVQQQSNLLRAIEAQQHMLQLTVW
GIKQLQTRVLAIERYLKDQQLLGIWGCSGKLICTTAVPWNSSWSNKSQEDIWDNMTWMQWDREISNYTDTIYRLLEDSQNQQEKN
EKDLLALDSWKNLWNWFDITNWLW*

*Amino acids seen in blue color is for easy identification of the junction of the deleted fusion cleavage site.

Fig. 31C

CODON-OPTIMIZED Con-C-2003 140CF (1,888 nt.)
Nick name:003

TTCAGTCGACAGCCACCATGCGAGTGAGAGGCATTCTGCGGAATTGTCAGCAATGTGATCTCGGGCATACTCGGATTCTGGAT
GCTTATGATATGCAATGTTGTGGGGAACCTGTGGGTTACCGTATACTAGGGTTCCAGTCGAAGGAGGCTAAAACAACGCTG
TTCTGTGCAAGTGACGCCAAAGCCTACGAGAAAGAAGTGCACAAGTCTGGCTACCCACGCTTGTGTTCCAACGATCCAAACC
CCCAGGAAATCGTCCTCGAGAACGTGACTGAACCATGGAAGAATGATATGTAGATCAGATGCACGAAGATATCAT
TTCATTGTGGGACCAATCATTGAAACCATGCGTAAAACTGACCCCCTGCGTAACACTTAACTGCACCAATGCAACTAATGCC
ACCAATACTATGGCGAAATAAAAAACTGTAGCTTTAACATTATTACCGGATAAGAAACAAAAGTTCTACGCGCTCT
TTTACCGACTCGATATCGTCCCACTTAAACGAGAATAATAGTTACCGCCTGATTAACTGTAACATGTAACATCAGCCATTACGCAAGCTTG
CCCCAAAGTTTCTTTCGACCCCATCCACTATTGTGCCCCCCGTGGATACGCTATACTTAAATGCAACAATAAAACATTT
AATGGAACCGACCATGTGGCGAGGAAGAATTATTATCAGATCAGAAAACTTGACCAACAATGCCAAAACCATCGTGCACCTCAATGA
ACGGCTCATTGCCGAGGAAGAATTATTATCAGATAACAATAACCCGGAAATCAGGATTGGGAATAAGACCTTCCACTAATAGTACCATCACACTCCCC
ATCCGTGGAAATCGTGTGCCGATATTAGACAAGCCATTAAGTTCGAGGAGACTCTGAGATCACAACACACTCTTTTAA
GGTGATAATAATTGGCCATTTCCCAATAAAACGATTAAGTTCGAGGAGACTCTGAGATCACAACACACTCTTTTAA
AGCTGAAGGAACACTTTCCAATAAAACGATTAAGTTCGAGGAGACCTTGAGATCACAACACACTCTTTTAA
TTGTAGAGGGAGTTCTTCTATTGTAATACATCAAAGCTCTTTAACAGTACCTACACTCCCATAGTACCATCACACTCCCC
TGCAGAATAAAGCAAATAACATGTGGCCAAGAAGTCGTTGGAACAAGTCGTTGGCAACACGAGTGCTGCCGTGAACTGGAGTAACAGCCAAGAGATATA
AATCCAATAATTGGCCCTTTTGCTGACACGTATAAAGTCGTTGGCAACACGAGTGCTGCCGTGAACTGGAGTAACAGCCAAGAGATATA
CGATAATTGGCCGGAGCGAGCTTCTACAAGTATAAAGTCGTTGGCAACACGAGTGCTGCCGTGAACTGGAGTAACAGCCAAGAGATATA
ACTGTTCAGGCTAGACAGCTGCTCTCCGGAATCAAACATTGCAAACACGAGTGCTGCCGTGAACTATACAGATACATTTATCGGCTCCTGAGGACTCACAGA
TCCAGCTTACCGTCTGGGGAATCAAACATTGCAAACACGAGTGCTGCCGTGAACTATACAGATACATTTATCGGCTCCTGAGGACTCACAGA
GATTTGGGCGCTGTTCAGGTAAGCTCATCTGTACAAGCTCAAGCTGGAGTAACAAAAAGCCAAGAGATATA
TGGGACAACATGACTTGGATGCAGTGAGATGCAGGAACAACTATAAAGCCAAGAGATATA
ACCAGCAGCAGAAAATGAGAAAGATTTGCTTCGCGCTTGACAGTTTGCTGAAGAATTTGTGAATTGGTTCGACATTACAAACTGGCT
CTGGTAAAGATCTTACAA

Fig. 32A

CONSENSUS_G-2003 (842 a.a.)

MRVKGIQRNWQHLWKWGTLILGLVIICSASNNLWVTVYYGVPVWEDADTTLFCASDAKAYSTERHNVWATHACVPTDPNPQEITL
ENVTENFNMWKNNMVEQMHEDIISLWDESLKPCVKLTPLCVTLNCTDVNVTNNNTNNTKKEIKNCSFNITTEIRDKKKKEYALFY
RLDVVPINDNGNSSIYRLINCNVSTIKQACPKVTFDPIPIHYCAPAGFAILKCRDKKFNGTGPCKNVSTVQCTHGIKPVVSTQLL
LNGSLAEEEIIIRSENITDNTKVIIVQLNETIEINCTRPNNNTRKSIRIGPGQAFYATGDIIGDIRQAHCNVSRTKWNEMLQKVK
AQLKKIFNKSITFNSSSGGDLEITTHSFNCRGEFFYCNTSGLFNNSLLNSTNSTITLPCKIKQIVRMWQRVGQAMYAPPIAGNIT
CRSNITGLLLTRDGGNNNTETFRPGGGDMRDNWRSELYKYKIVKIKPLGVAPTRARRRVVEREKRAVGLGAVLLGFLGAAGSTMG
AASITLTVQVRQLLSGIVQQQSNLLRAIEAQQHLLQLTVWGIKQLQARVLAVERYLKDQQLLGIWGCSGKLICTTNVPWNTSWSN
KSYNEIWDNMTWIEWEREISNYTQQIYSLIEESQNQQEKNEQDLLALDKWASLWNWFDITKWLWYIKIFIMIVGGLIGLRIVFAV
LSIVNRVRQGYSPLSFQTLTHHQREPDRPERIEEGGGEQDKDRSIRLVSGFLALAWDDLRSLCLFSYHRLRDFILIAARTVELLG
RSSLKGLRLGWEGLKYLWNLLLYWGQELKNSAINLLDTIAIAVANWTDRVIEVAQRACRAILNIPRRIRQGLERALL

*Amino acid sequence underlined is the fusion domain that will be deleted in 140CF design and the "W" underlined with red color is the last amino acid at the C terminus, and all the remaining amino acids after the "W" will be deleted in 140CF design

Fig. 32B

Con-G-2003 140CF (626 a.a.)

Nick name: 007

MRVKGIQRNWQHLWKWGTLILGLVIICSASNNLWVTVYYGVPVWEDADTTLFCASDAKAYSTERHNVWATHACVPTDPNPQEITL
ENVTENFNMWKNNMVEQMHEDIISLWDESLKPCVKLTPLCVTLNCTDVNVTNNNTNNTKKEIKNCSFNITTEIRDKKKKEYALFY
RLDVVPINDNGNSSIYRLINCNVSTIKQACPKVTFDPIPIHYCAPAGFAILKCRDKKFNGTGPCKNVSTVQCTHGIKPVVSTQLL
LNGSLAEEEIIIRSENITDNTKVIIVQLNETIEINCTRPNNNTRKSIRIGPGQAFYATGDIIGDIRQAHCNVSRTKWNEMLQKVK
AQLKKIFNKSITFNSSSGGDLEITTHSFNCRGEFFYCNTSGLFNNSLLNSTNSTITLPCKIKQIVRMWQRVGQAMYAPPIAGNIT
CRSNITGLLLTRDGGNNNTETFRPGGGDMRDNWRSELYKYKIVKIKPLGVAPTRARTLTVQVRQLLSGIVQQQSNLLRAIEAQQH
LLQLTVWGIKQLQARVLAVERYLKDQQLLGIWGCSGKLICTTNVPWNTSWSNKSYNEIWDNMTWIEWEREISNYTQQIYSLIEES
QNQQEKNEQDLLALDKWASLWNWFDITKWLW*

*Amino acids seen in blue color is for easy identification of the junction of the deleted fusion cleavage site

Fig. 32C

CODON-OPTIMIZED Con-G-2003 140CF.seq

Nick name:007

TTCAGTCGACAGCCACCATGCGAGTGAAGGGAATCCAGAGAAATTGGCAGCACCTTTGGAAGTGGGGCACACTCATCCTCGGCCT
TGTGATCATATGCTCTGCCTCAAATAACCTTTGGGTCACAGTTTATTACGGCGTGCCCGTTTGGGAGGACGCAGACACAACTCTT
TTTTGTGCCAGCGACGCTAAGGCTTATTCAACAGAGAGGCATAACGTTTGGGCTACACATGCATGCGTGCCGACCGATCCTAATC
CCCAGGAAATCACTCTTGAGAATGTTACAGAGAATTTTAATATGTGGAAGAACAACATGGTTGAACAGATGCATGAAGACATAAT
TTCTCTCTGGGATGAATCTCTGAAACCTTGCGTGAAGCTTACACCACTGTGCGTTACCCTGAATTGCACTGACGTCAATGTCACA
AATAATAATACCAACAATACAAAAAAAGAAATCAAAAATTGTTCTTTCAACATAACCACCGAGATACGCGATAAAAAAAAGAAAG
AATACGCCCTGTTCTACAGACTCGATGTGGTCCCAATTAATGACAACGGAAATTCTTCCATCTACCGACTTATCAATTGTAACGT
GTCTACAATCAAACAGGCCTGTCCTAAAGTCACATTTGACCCTATTCCCATTCATTACTGTGCCCCCGCTGGCTTCGCTATTCTT
AAATGCCGAGACAAAAAATTTAACGGAACAGGACCATGCAAGAATGTCTCAACAGTTCAATGCACTCATGGAATTAAACCAGTCG
TTTCTACTCAACTCCTTCTCAATGGAAGCCTGGCAGAAGAGGAAATCATAATCCGCAGCGAAAACATAACCGACAACACAAAAGT
AATCATCGTACAGCTGAACGAGACCATTGAAATAAATTGTACGAGACCTAATAATAACACAAGAAAAAGCATACGCATCGGCCCC
GGACAGGCTTTCTACGCCACAGGAGACATTATCGGAGATATCCGCCAGGCTCACTGTAATGTGTCTAGAACAAAATGGAACGAAA
TGCTTCAGAAGGTCAAAGCTCAGCTCAAGAAAATATTCAACAAATCTATTACATTCAACTCATCATCAGGCGGCGATCTGGAGAT
AACAACTCATTCCTTCAACTGTCGGGGAGAATTTTTTTACTGTAACACGTCCGGCCTGTTCAACAATTCACTCCTGAATAGCACT
AACTCCACCATCACTCTCCCATGTAAGATCAAACAAATCGTCAGAATGTGGCAGCGAGTCGGTCAAGCTATGTACGCCCCTCCAA
TCGCCGGTAATATCACATGTAGAAGCAATATCACAGGGCTCTTGCTTACAAGGGACGGCGGGAACAACAACACCGAAACCTTCAG
ACCAGGAGGAGGAGACATGCGAGACAATTGGCGGAGCGAGCTGTATAAATATAAGATCGTAAAAATCAAACCATTGGGTGTAGCG
CCAACTAGAGCCCGAACACTGACCGTGCAGGTGAGGCAACTGCTGAGCGGCATTGTCCAACAACAATCCAATCTTCTTAGAGCAA
TCGAGGCCCAGCAGCATCTGCTCCAGCTTACTGTATGGGGAATCAAACAACTGCAAGCAAGAGTATTGGCAGTGGAGAGGTATCT
CAAGGACCAGCAGCTTCTGGGAATTTGGGGTTGCAGCGGAAAGCTCATATGTACAACCAATGTGCCCTGGAACACTAGTTGGAGT
AATAAGAGTTACAATGAAATCTGGGACAATATGACATGGATCGAATGGGAGCGCGAAATATCCAACTATACTCAGCAAATCTATT
CCCTCATTGAAGAGAGTCAGAACCAGCAGGAAAAGAATGAGCAAGACCTCCTCGCCCTGGATAAATGGGCATCTCTGTGGAACTG
GTTTGACATAACTAAATGGTTGTGGTAAAGATCTTACAA

Fig. 33A

CONSENSUS_01_AE-2003 (854 a.a.)

MRVKETQMNWPNLWKWGTLILGLVIICSASDNLWVTVYYGVPVWRDADTTLFCASDAKAHETEVHNVWATHACVPTDPNPQEIHL
ENVTENFNMWKNNMVEQMQEDVISLWDQSLKPCVKLTPLCVTLNCTNANLTNVNNITNVSNIIGNITNEVRNCSFNMTTELRDKK
QKVHALFYKLDIVQIEDNNSYRLINCNTSVIKQACPKISFDPIPIHYCTPAGYAILKCNDKNFNGTGPCKNVSSVQCTHGIKPVV
STQLLLNGSLAEEEIIIRSENLTNNAKTIIVHLNKSVEINCTRPSNNTRTSITIGPGQVFYRTGDIIGDIRKAYCEINGTKWNEV
LKQVTEKLKEHFNNKTIIFQPPSGGDLEITMHHFNCRGEFFYCNTTKLFNNTCIGNETMEGCNGTIILPCKIKQIINMWQGAGQA
MYAPPISGRINCVSNITGILLTRDGGANNTNETFRPGGGNIKDNWRSELYKYKVVQIEPLGIAPTRAKRRVVEREKRAVGIGAMI
FGFLGAAGSTMGAASITLTVQARQLLSGIVQQQSNLLRAIEAQQHLLQLTVWGIKQLQARVLAVERYLKDQKFLGLWGCSGKIIC
TTAVPWNSTWSNRSFEEIWNNMTWIEWEREISNYTNQIYEILTESQNQQDRNEKDLLELDKWASLWNWFDITNWLWYIKIFIMIV
GGLIGLRIIFAVLSIVNRVRQGYSPLSFQTPTHHQREPDRPERIEEGGGEQGRDRSVRLVSGFLALAWDDLRSLCLFSYHRLRDF
ILIAARTVELLGHSSLKGLRRGWEGLKYLGNLLLYWGQELKISAISLLDATAIAVAGWTDRVIEVAQGAWRAILHIPRRIRQGLE
RALL

*Amino acid sequence underlined is the fusion domain that will be deleted in 140CF design and the "W" underlined with red color is the last amino acid at the C terminus, and all the remaining amino acids after the "W" will be deleted as 140CF.

Fig. 33B

Con-AE01-2003 140CF.pep (638 a.a.)
Nick name: 008

MRVKETQMNWPNLWKWGTLILGLVIICSASDNLWVTVYYGVPVWRDADTTLFCASDAKAHETEVHNVWATHACVPTDPNPQEIHL
ENVTENFNMWKNNMVEQMQEDVISLWDQSLKPCVKLTPLCVTLNCTNANLTNVNNITNVSNIIGNITNEVRNCSFNMTTELRDKK
QKVHALFYKLDIVQIEDNNSYRLINCNTSVIKQACPKISFDPIPIHYCTPAGYAILKCNDKNFNGTGPCKNVSSVQCTHGIKPVV
STQLLLNGSLAEEEIIIRSENLTNNAKTIIVHLNKSVEINCTRPSNNTRTSITIGPGQVFYRTGDIIGDIRKAYCEINGTKWNEV
LKQVTEKLKEHFNNKTIIFQPPSGGDLEITMHHFNCRGEFFYCNTTKLFNNTCIGNETMEGCNGTIILPCKIKQIINMWQGAGQA
MYAPPISGRINCVSNITGILLTRDGGANNTNETFRPGGGNIKDNWRSELYKYKVVQIEPLGIAPTRAKTLTVQARQLLSGIVQQQ
SNLLRAIEAQQHLLQLTVWGIKQLQARVLAVERYLKDQKFLGLWGCSGKIICTTAVPWNSTWSNRSFEEIWNNMTWIEWEREISN
YTNQIYEILTESQNQQDRNEKDLLELDKWASLWNWFDITNWLW*

*Amino acids seen in blue color is for easy identification of the junction of the deleted fusion cleavage site.

Fig. 33C

CODON-OPTIMIZED Con-AE01-2003 140CF.seq (1945 nt.)

Nick name: 008

```
ttcagtcgacagccaccATGCGAGTCAAGGAAACACAAATGAACTGGCCTAATCTGTGGAAGTGGGGCACCCTGATCCTGGGTTT
GGTCATTATTTGCTCTGCGAGCGACAATCTCTGGGTTACTGTCTATTACGGAGTCCCCGTTTGGAGAGATGCCGACACTACACTG
TTCTGCGCCTCAGATGCCAAAGCTCATGAAACTGAAGTGCATAATGTTTGGGCAACCCACGCCTGTGTTCCTACCGACCCAAACC
CCCAAGAAATACACCTGGAAAACGTGACCGAGAACTTTAATATGTGGAAGAATAACATGGTTGAACAGATGCAAGAAGACGTAAT
CAGCCTGTGGGATCAAAGTCTGAAACCTTGCGTAAAACTGACTCCACTTTGCGTAACACTTAATTGCACCAACGCGAACCTGACA
AACGTTAACAACATCACTAACGTCTCCAACATCATCGGCAACATAACGAACGAAGTGAGAAATTGCAGTTTCAATATGACTACAG
AGCTCCGGGACAAGAAACAGAAGGTCCATGCTCTCTTTTACAAACTCGACATCGTCCAGATCGAAGACAATAACAGCTACAGACT
TATAAATTGTAATACATCCGTGATTAAACAAGCATGCCCCAAAATAAGCTTCGATCCTATTCCTATCCACTACTGTACTCCTGCC
GGCTATGCTATCTTGAAATGCAATGATAAGAACTTCAATGGGACCGGACCTTGTAAGAACGTGTCTAGTGTGCAATGCACTCACG
GCATTAAACCAGTGGTAAGCACCCAGCTGCTCCTGAACGGCTCTCTGGCAGAGGAAGAGATTATTATTCGAAGTGAGAACCTCAC
CAACAACGCTAAGACTATCATCGTACATCTCAATAAATCAGTCGAAATTAATTGCACCAGACCCTCCAATAATACTAGAACTTCA
ATCACTATCGGCCCAGGACAAGTCTTTTATAGAACAGGAGATATCATAGGAGATATCAGAAAGGCATATTGCGAGATAAACGGGA
CAAAATGGAACGAAGTACTCAAACAAGTCACAGAGAAGCTTAAGGAACATTTCAACAATAAAACCATTATTTTTCAACCCCCAAG
TGGCGGAGACCTCGAAATCACTATGCACCACTTCAACTGCCGCGGCGAATTTTTTTATTGCAATACCACTAAACTTTTCAACAAT
ACGTGCATCGGAAATGAGACCATGGAGGGCTGCAATGGAACAATCATACTCCCATGCAAGATAAAACAAATCATTAACATGTGGC
AAGGTGCTGGACAAGCTATGTATGCACCCCCAATATCCGGTAGAATTAATTGCGTCAGCAACATCACTGGCATACTGCTCACTAG
AGACGGAGGAGCAAATAATACAAATGAAACATTCCGACCAGGCGGCGGCAACATTAAGGACAACTGGCGGTCCGAACTCTATAAG
TACAAAGTCGTACAGATCGAACCTCTTGGAATAGCACCGACTCGCGCTAAGACACTCACAGTACAGGCCCGACAACTTCTTTCTG
GAATCGTACAGCAGCAATCCAACCTCCTCCGCGCAATCGAGGCCCAACAACATCTGCTTCAGCTCACAGTTTGGGGAATCAAGCA
GCTCCAGGCACGCGTGCTCGCAGTGGAAAGATACCTGAAGGATCAGAAATTCCTTGGTCTCTGGGGATGTTCTGGCAAAATAATC
TGCACTACCGCGGTTCCCTGGAATTCAACATGGAGCAACCGGAGTTTTGAAGAGATATGGAACAATATGACATGGATAGAGTGGG
AAAGGGAAATTAGTAACTATACGAACCAGATATACGAAATCCTCACCGAAAGCCAAAATCAGCAGGATCGCAACGAAAAAGACCT
CCTCGAGCTTGATAAGTGGGCATCCCTTTGGAACTGGTTCGACATCACAAATTGGCTCTGGtaaagatcttacaa
```

Fig. 34A

Wild-type subtype A Env

OOKE_MSA4076-A (Subtype A, 891 a.a)

MGAMGIQMNWQNLWRWGTMILGMLIICSVAEKSWVTVYYGVPVWRDAETTLFCASDAKAHDKEVHNVWATHACVPTDPNPQEMIL
ENVTEDFNMWKNSMVEQMHTDIISLWDQSLKPCVKLTPLCVTLNCSDSNITSNSTSNSTKDSATLDMKSEIQNCSFNMTTELRDK
KQKVYSLFYRLDVVQINENSSDYRLINCNTSAITQACPKVTFEPIPIHYCAPAGFAILKCNDKKFNGTGPCTNVSTVQCTHGIKP
VVTTQLLLNGSLAEEEVMIRSENITENAKNIIVQFKEPVQIICIRPGNNTRKSVHIGPGQAFYATGDIIGDIRQAHCNVSRELWN
KTLQEVATQLRKHFRNNTKIIFTNSSGGDVEITTHSFNCGGEFFYCDTSGLFNSSWTASNDSMQEAHSTESNITLQCRIKQIINM
WQRAGQAMYAPPIPGIIRCESNITGLILTRDGGEGNNSTNETFRPVGGNMRDNWRSELYKYKVVKVEPLGVAPTKSRRRVVEREK
RAVGLGAVFIGFLGAAGSTMGAASMTLTVQARQLLSGIVQQQSNLLRAIEAQQHLLKLTVWGIKQLQARVLAVERYLRDQQLLGI
WGCSGKLICTTNVPWNSSWSNKSLDEIWENMTWMQWDKEVSNYTQMIYNLLEESQNQQEKNEQELLALDKWANLWNWFNISNWLW
YIKIFIMIVGGLIGLRIVFAVLSVINRVRQGYSPLSFQTHTPNPRGLDRPGRIEEEGGEQDRDRSIRLVSGFLALAWDDLRSLCL
FSYHRLRDFILIAARTLELLGHNSLKGLRLGWEGLKYLWNLLAYWGRELKISAISLVDSIAIAVAGWTDRIIEIVQAIGRAILHI
PRRIRQGLERALI

*Amino acid sequence underlined is the fusion domain that will be deleted in 140CF design and the "W" underlined with red color is the last amino acid at the C terminus, and all the remaining amino acids after the "W" will be deleted in 140CF design.

Fig. 34B

OOKE_MSA4076-A 140CF.pep (647 a.a)

Nick name: 011

MGAMGIQMNWQNLWRWGTMILGMLIICSVAEKSWVTVYYGVPVWRDAETTLFCASDAKAHDKEVHNVWATHACVPTDPNPQEMIL
ENVTEDFNMWKNSMVEQMHTDIISLWDQSLKPCVKLTPLCVTLNCSDSNITSNSTSNSTKDSATLDMKSEIQNCSFNMTTELRDK
KQKVYSLFYRLDVVQINENSSDYRLINCNTSAITQACPKVTFEPIPIHYCAPAGFAILKCNDKKFNGTGPCTNVSTVQCTHGIKP
VVTTQLLLNGSLAEEEVMIRSENITENAKNIIVQFKEPVQIICIRPGNNTRKSVHIGPGQAFYATGDIIGDIRQAHCNVSRELWN
KTLQEVATQLRKHFRNNTKIIFTNSSGGDVEITTHSFNCGGEFFYCDTSGLFNSSWTASNDSMQEAHSTESNITLQCRIKQIINM
WQRAGQAMYAPPIPGIIRCESNITGLILTRDGGEGNNSTNETFRPVGGNMRDNWRSELYKYKVVKVEPLGVAPTKSRTLTVQARQ
LLSGIVQQQSNLLRAIEAQQHLLKLTVWGIKQLQARVLAVERYLRDQQLLGIWGCSGKLICTTNVPWNSSWSNKSLDEIWENMTW
MQWDKEVSNYTQMIYNLLEESQNQQEKNEQELLALDKWANLWNWFNISNWLW*

*Amino acids seen in blue color is for easy identification of the junction of the deleted fusion cleavage site.

Fig. 34C

CODON-OPTIMIZED OOKE_MSA4076-A 140CF.seq (1972 nt.)
Nick name: 011 ttcagtcgacagccaccATGGGGCAATGGGAATCCAGATGAACTGGCAGAACCTCTGGCGATGGGCACAATGATCCTGGTAT
GCTCATCATCTGCTCTGTTGCAGAAAAGTCATGGTAACAGTCTACTACGGCGTACCAGTGTGGCGGACGCCGAAACCACTCTC
TTCTGCGCCTCCGATGCGCCAAAGCACACGATAAAGAAGAAGTCCACATGTTTGGGCTACCCATGCGTGCGTGCCAACCGATCCTAACC
CACAAGAAATGATACTCGAAAACGTTACTGAAGACTTCAACATGTGGAAAAATTCTATGTTGAACAGATGCACACCGACATAAT
ATCACTGTGGGATCAGTCTCTCAAACCCTGTGTCAAATTGACCCCCTGCGTTACACTGAACTGTTCCGACTCAAATATCACT
TCTAATTCAACGAGCAATAGTACGAAAGACTCCGCAACCCTTGATATGAAAAGCGAAATACAGAACTGTTCATTTAATATGACCA
CCGAACTGAGAGATAAAAAGCAGAAGGTTTATTCTCTGTTCATCGATTGGACGTGGTTCAGATTAACGAAATAGCAGCGATTA
CCGACTCATTAACTGCAATACATCGAAATGCAATAATCACACAGCCTTGCCCAAAGGTAACATTTGAGCCACCACCGTGCAATGCGCC
CCTGCAGGATTTGCCATCCATCGAAATGCAACACCACAACCTGTGTTACCACACAAGATAAGAAGTTTAATGGGACACGGACCCTGCTGAAGAGAAGTCACTTCGGTCTGAAAA
CACGGCATAAAACCTGTTGTTACCACACAACCTGTTCAGTTCAAAGAACCCGTCAGATCATTGCATTGCCCTGGTAACAACACTCGC
AGTCAGTGCACATTGGGCCCGGCCAGGCTTTCTATGCAAGAAGTTGCTACTCAGGAAGTTGCTACTCAGGAACAATACAAAGATTATTTCAC
GCCGGAATTGTGAACAAAACTTTGCAGGAACAAACTTTGCAGGAATTCTTCTATTGCGATACCTCTGGCTC
TAATTCATCAGGCGGTGACCTGGACTGCATGGACTGCTAGCAACGATTCAATGCAAGAAGCACATTCCACAGAAAGTAATATCACACTGCCAGTGCCGAATTA
TTTAATTCCCTCATGGACTGCTAGCAACGATTCAATGCAAGAAGCACATTCCACAGAAAGTAATATCACACTGCCAGTGCCGAATTA
AACAAATCATCAATATGTGACGCAGCGGGCCGGTCAAGCAATGTACGCACCTCCCATCCCGAGACTTTCAGACCCGTAGGAGGCAATATGCGA
CACTGGCCCTCATTCTGACCCGAGACGTGGCGAAAGCAATGTATAAATATAAAGTGGTGAAGGTAGAACCTCTTGAGTGGCACCAACCGAACAAACAGACCCTGA
GACAATTGGCGATCCGACCGCCAACTTCTGAGAATAGTCCAACAGCAATGTCCAACAGAGTGCTGGCAGCGATACTTGAGAGACCAACAACTCCTGGGA
CTGTGCAGGCACGCACCAACTTCTGAGAACGATATTGCAGGCAAATTGCAGGCAAGAGTGCTGGCAGCGATACTTGAGAGACCAACAACTCCTGGGA
TAAACTTACGGTGTGGGAATCAACAATTGCAGGCAAGAAGTTAGCAACTATACACAGATGATCTACAACCTCCTGTCAAACAAGAGTCTGACGAAATAT
ATCTGGGGATGTTCCGGTAAGTTGATTTGCACGACAAGAAGTTAGCAACTATACACAGATGATCTACAACCTCCTGTCAAACAAGAGTCTGACGAAATAT
GGGAAATATGACATGAAAAACGAACAAGAACTGCTCGCCCTCGATAAGTGGGCTAACCTCTGAACCTCTGAAGAATTCAGAA
TCAACAGGAAAAAAACGAACAAGAACTGCTCGCCCTCGATAAGTGGGCTAACCTCTGAACCTCTGAAGAATTCAGAA
TGGtaaagatcttacaa

Fig. 35A

Wild-type subtype B
QH0515.1g gp160 (861a.a)
MRVKEIRRNCQRLRRWGTMLLGMLMICSATEQLWVTVYYGVPVWKEATTTLFCASDAKAYVTEKHNVWATHACVPTDPNPQEVVL
ENVTENFNMWKNNMVEQMHEDIISLWEQSLKPCVKLTPLCVTLNCTDKLRNDTSGTNSSSWEKVQKGEIKNCSFNITTGIRGRVQ
EYSLFYKLDVIPIDSRNNSNNSTEFSSYRLISCNTSVITQACPKISFEPIPIHYCAPAGFAILKCNDKKFNGTGPCKNVSTVQCT
HGIKPVVSTQLLLNGSLAEEEVVIRSENFTNNVKSIIVQLNKSVVINCTRPNNNTRKSIHIGAGKALYTGEIIGDIRQAHCNLSR
AQWNNTLKQIVIKLREQFGNKTIVFNQSSGGDVEIVMHSFNCGGEFFYCNSTQLFNSTWNGNDTWKDTTNDNITLPCRIKQ
IVNMWQKVGKAMYAPPIRGQIRCSSKITGLILTRDGGTNGTNETETFRPGGGNMKDNWRSELYKYKVVKIEPLGIAPTKAKRRVV
QREKRAVGTIGAMFLGFLGAAGSTMGAASLTLTVQARLLLSGIVQQQNNLLRAIEAQQHLLQLTVWGIKQLQARVLAVERYLRDQ
QLLGIWGCSGRLICTTNVPWNTSWSNRSLNYIWDNMTWMQWDREINNYTDYIYTLLEDAQNQQEKNEQELLELDKWASLWNWFDI
TNWLWYIKIFIMIVGGLIGLRIVFAVLSIVNRVRQGYSPLSLQTHLPARRGPDRPEGIEEGGERDRDSVRLVHGFLALVWEDL
RSLCLFSYHRLRDLLLIVARTVELLGQRGWEALKYWNNLLIYWSLELKNSAVSLVDTIAIAVAEGTDRIIEIARRIFRAFLHIPT
RIRQGLERALL

*Amino acid sequence underlined is the fusion domain that will be deleted in 140CF design and the "W" underlined with red

Fig. 35C

CODON-OPTIMIZED QH0515.1g 140CF.seq (1984 nt.)
Nick name:012 ttcagtcgacagcagccaccATGGAGTCGACAGCAGCCACCATGGAGTCAGTAAAAGAGAATCAGACGCAACTGTCAGAGGTTCAGGAGGATGGGGAACGATGCTCCTGGCAT
GCTGATGATTTGCAGTGCCACCGACGTGCCACCGACGTGCCACCGACGTGCCAATCAGCTTTGGGTAACCGTGTACTATGTGTACCTGTATGGAAGAGCCACTACAACCCTG
TTTTGCGCGTCCGACGCAAAAGCCTACGTAACAGAAAAGCACAACGTGTGGGCCACACATGCGTGCCAACATGCATGCGTGCCAACAGATCCAAATC
CTCAGGAAGTCGTTCGTTCTGGAAATGTAACAGAAATGTTAATATGTGGAAAAACAATATGGTAGAGCAGATGCATGAAGATATCAT
CTCACTGTGGGAACAATCCTTGTGTCAAACTTTGCGTAACACTTAACTGTACTTAACTGTACTTAACATCACTACCGTA
GATACGTCCGGAACAAATTCAAGCAGCTGGGAAAAAGTGCAAAAGGGCGAAATCAAAAATGTTCATTTAACATCACTACCGTA
TCAGAGGGGGGTACAGGAATATTCTCTTTTCTACAAACTCGACGTGATTACGACACCAGCGTGCCCTAAAATCTCTTTTGAGCCCATTCCT
AGAATTTAGTAGTTATCGCCACCAGCGCTTCGCCATCCTCAAATGTAACGACAAGAAATTTAACGAACCGGACCCTGTAAGAATGTGT
ATTCACTACTGCGCACCAGCGCTTCGCCATCCTCAAATGTAACGACAAGAAATTTAACGAACCGGACCCTGTAAGAATGTGT
CCACCGTTCAATGCACTCATGGAATCAAGCACGTCAAGCACGTCAAGCACGTCAAGCACGTCAAGCACGTCAAGCACGTCAAGCACGTCAAGCACGTCAAGCACGTCAAGCACG
GATTCGCTCCGAAATTTACAAACAACCATTCACATGGAAATCCAGCTTCGTCTATACCGGGAAATTATTGGAGACATCAGACAAGCAC
AACAATAACACCAGAAATCCATTCACATGGAACAACAGATCGTGATCAAGCTCGTGATCAAGAGCAGTTCGGGAATAAGACTAT
ACTGTAACTTGAGTCGCGCCAGTGGAACAACAGATCGTGATCAAGCTCGTGATCAAGAGCAGTTCGGGAATAAGACTAT
CGTGTTTAATCAGAGCTCCGGCGGTGATGTCGAAATCGTAATGCACTCGTCTTTTAATTGTGGGGTGAATTTTTTACTGCAATTCT
ACACAACTTGTTTAACGACACCTGGAATCGTAAATCGTAAATGACACTCTGAAAGATACGACCTGGAAAGATAACAAATGATAATATTACTCTTC
CGTTGCAGAATAAAGCAATCGTAAATATGTGGCAAGGCCATGTAAGCGAAACGGACCCTGGCGACCTTCCGACCAGGAGGC
TTCTTCCAAGATCACAGGTCTGATACTCCAAGACGAGTCAAGGAAGTGTCCAAGATAAGTCAAAGATAAGACCTCGGTATCGCCCCTACTAAGG
GGCAACATGAAGACGACGGATAACTGAGAAGTTACAAGTAGAACTTTCAAGGATAGCGAACTTTCAAGGATAGTCAAGAACAACAACTTCTTGAACGGTATCTCTAGAGATCAG
CTAAACACTCACCGTGCAGTTGACAGTGTGGGGGAATTAAACAGTTGCAGGCCCGGGTTCAAAGTAACCTCATGGAGTAACAGGTCTC
TTAATTATATTTGGGACAATATGACATGGACAATGGACAATGAGAATTAATATTAATAACTACACCGATACTACCACTTCTGA
GGACGCCAGAATCAGCAGCAGGAGAACGACCAGGAACTCCTCGAATTGGATAAGTGGGCATCACTGTGATAAGTTGGATAAGTTCGATATATA
ACTAATTGGCTTTGGtaaagatcttacaa

Fig. 36A

Wild-type subtype C
DU123.6 gp160(854 a.a)

MRVKGIQRNWPQWWIWGILGFWMIIICRVVGNLWVTVYYGVPVWTEAKTTLFCASDAKAYEREVHNVWATHACVPTDPNPQEIVL
GNVTENFNMWKNDMVDQMHEDIISIWDQSLKPCVKLTPLCVTLNCTDVKVNATSNGTTTYNNSIDSMNGEIKNCSFNITTEIRDK
KQKVYALFYRPDVVPLNENSSSYILNCNTSTTQACPKVSFDPIPIHYCAPAGYAILKCNNKTFNGTGPCHNVSTVQCTHGIKP
VVSTQLLLNGSLAEEEIIIRSENLTNNAKTIIVHLNESIEIVCTRPNNNTRKSIRIGPGQTVYATNDIIGDIRQAHCNISKTKWN
TTLEKVKEKLKEHFPSKAITFQPHSGGDLEVTTHSFNCRGEFFYCDTTKLFNESNLNTTNTTLTLPCRIKQIVNMWQGVGRAMY
APPVEGNITCNSSITGLLLVRDGGNTSNSTPEIFRPGGGNMKDNWRSELYKYKVVEIKPLGVAPTKAKRRVVEREKRAVGIGAVL
FGFLGAAGSTMGAASITLTVQARQLLSGIVQQQSNLLRAIEAQQHMLQLTVWGIKQLQARVLAIERYLKDQQLLGLWGCSGKLIC
PTTVPWNSSWSNKSQTDIWDNMTWMQWDREISNYTGTIYKLLEESQNQQEKNEKDLLALDSWKNLWSWFDITNWLWYIKIFIMIV
GGLIGLRIIFGVLSIVKRVRQGYSPLSFQTLTPNPRGLDRLGRIEEEGGEQDKDRSIRLVNGFLALAWDDLRSLCLFSYHRLRDF
ILVAARAVELLGRSSLRGLQRGWEALKYLGNLVQYGGLELKRRAISLFDTIAIAVAEGTDRILEVILRIIRAIRNIPTRIRQGFE
AALL

Fig. 36B

DU123.6 140CF (638 a.a)
Nick name: 013

MRVKGIQRNWPQWWIWGILGFWMIIICRVVGNLWVTVYYGVPVWTEAKTTLFCASDAKAYEREVHNVWATHACVPTDPNPQEIVL
GNVTENFNMWKNDMVDQMHEDIISIWDQSLKPCVKLTPLCVTLNCTDVKVNATSNGTTTYNNSIDSMNGEIKNCSFNITTEIRDK
KQKVYALFYRPDVVPLNENSSSYILNCNTSTTQACPKVSFDPIPIHYCAPAGYAILKCNNKTFNGTGPCHNVSTVQCTHGIKP
VVSTQLLLNGSLAEEEIIIRSENLTNNAKTIIVHLNESIEIVCTRPNNNTRKSIRIGPGQTVYATNDIIGDIRQAHCNISKTKWN
TTLEKVKEKLKEHFPSKAITFQPHSGGDLEVTTHSFNCRGEFFYCDTTKLFNESNLNTTNTTLTLPCRIKQIVNMWQGVGRAMY
APPVEGNITCNSSITGLLLVRDGGNTSNSTPEIFRPGGGNMKDNWRSELYKYKVVEIKPLGVAPTKAKTLTVQARQLLSGIVQQQ
SNLLRAIEAQQHMLQLTVWGIKQLQARVLAIERYLKDQQLLGLWGCSGKLICPTTVPWNSSWSNKSQTDIWDNMTWMQWDREISN
YTGTIYKLLEESQNQQEKNEKDLLALDSWKNLWSWFDITNWLW*

*Amino acids seen in blue color is for easy identification of the junction of the deleted fusion cleavage site.

Fig. 36C

CODON-OPTIMIZED DU123.6 140CF.seq (1945 nt.)
Nick name: 013 ttcagtcgacagcagccaccATGGCGCGTGTAAAGGGGATTCAAAGAAATTGGCCGCAATGGTGGATTTGGGGAATTCTCGGCTTTTGGAT
GATAATTATATGCCGCGTGTCGGAAATTTGTGGGTGACTGTGTACTACGGGGTGCCCGTGTGGACTGAGGCAAAGACCACCCTG
TTCTGTGCTAGCGATGCCAAAGCCTATGAACGCGAAAGTGCACAATGTTTGGGCTACTCATGCCTGTGTCCCTACCGACCCAAACC
CTCAGGAAATAGTGCTCGGCAATGTAACGGAAAAACTTCAACATGTGGAAAAATGATATGGTGGATCAGATGCACGAAGACATTAT
CTCAATCTGGGACCAAAGCCTGAAACCCTGCGTTAAACAATTGACTCTGCGTCTATGAACGGGGAAATCAAAAATTGTTCCTTTAACATCACCA
GCCACCTCAAACGTACGACAACTTACAACAATTCTATTGACTCTATGAACGGGAAATCAAAAATTGTTCCTTTAACATCACCA
CCGAGATACGCGACAAAAGCAGAAGTCTATGCCCTTTTTACCGCCCGAAAGTTAGCTTTGATCCAATTCCTATACATTACTGCGCC
CATCCTCATCAACTGCTATATACCACACAAGCATGCAATAATAAGACTTTTAAGGGACCGGCCATGTCACACCGTGCAATGCA
CCCGCGGCTACGCTCAAGCCCGTGGTGTCAGATTATCGTGCACCTTAATCAATGAATCAATAGAAATCGTGTACTCGGCCACAATAATACTAGA
TCTTACTAACAATGCAAAAACGATTATCGTGCCAGACAGTTTACGCAATGAAAAACTTAAAGAACATCATCGGGGACATCCGACACGCCATTGCAACATTT
AAAGCATTCGCATGGAATGAATACAACCCTGGAATAAGTAAAGGAAAAAGTAAAGAACATTTTCCCTCTAAGGCGATCACGTTTCAACC
CTAAAACCAAGTGGCGGAGACTTGGAAGTCACAACACATTCTTTTAACTGCCGCGGAGAATTTTTTTATTGTGATACAACAAAACTTTTT
AATGAATCAAATCTCAACACCACAAATACAACCACTGACCCTCCCCCTGTAGAATCAAACAAATCGTAAACATGTGGCAAGGGG
TTGGAAGGGCTATGTGACGCTCCCCCCCGTCGAAGGAAATATAACGTGTAACAGCATCACTGGCTTCTTGTCGGAGACGG
AGGCAATACTTCTAATTCAACTCCTGAAATTTTTAGGCCTGGCGGTGGCAATATGAAAGATAACACTCACAGTGCGCTGTACAAA
TACAAAGTTGTTGAACAATTAAGCCCTGGGAGTCGCTCCAACCAAAGTCTAAAACACTCACAGTGCTCCAACAGCAGCTCCTTTCAG
GCATCGTCCAGCAACAGTGCTTGCCTATCTTAAAGACGCTATCTTAAAGAATCTTAAAGACACCGATATTTGGGCCTCTGGGGATTAAACA
GCTTCAAGCCCGCGTGCTCCTTGGAATAGTTCTTGGCACAATCTACAAACTCTTGGAAGAAAGTCAAATCAGCAACATGACCTGATGCAATGGG
ATAGGGAAATTTCTAATTATACTGGCACATAACTAATTGGAGCTGGTTCGACATAACTAATTGGCTGTGGtaaagatcttacaa
CCTCGCCCTGACTCCTGGAAGAATCTTTGGAGCTGGTTCGACATAACTAATTGGCTGTGGtaaagatcttacaa

Fig. 37A

Wild-type subtype CRF01_AE
97CNGX2F-AE (854 a.a.)

MRVKETQMNWPNLWKWGTLILGLVIICSASDNLWVTVYYGVPVWRDADTTLFCASDAKAHETEVHNVWATHACVPTDPNPQEIHL
ENVTENFNMWRNNMVEQMQEDVISLWDQSLKPCVKLTPLCVTLNCTNANWTNSNNTTNGPNKIGNITDEVKNCTFNMTTELKDKK
QKVHALFYKLDIVQINSSEYRLINCNTSVIKQACPKISFDPIPIHYCTPAGYAILKCNDKNFNGTGPCKNVSSVQCTHGIKPVVS
TQLLLNGSLAEEEIIIRSENLTNNAKTIIVHLNKSVEINCTRPSNNTRTSITMGPGQVFYRTGDIIGDIRKAYCEINGIKWNEVL
VQVTGKLKEHFNKTIIFQPPSGGDLEITTHHFSCRGEFFYCNTTKLFNNTCIGNTSMEGCNNTIILPCKIKQIINMWQGVGQAMY
APPISGRINCVSNITGILLTRDGGADNTTNETFRPGGGNIKDNWRSELYKYKVVEIEPLGIAPTRAKRRVVEREKRAVGIGAMI
FGFLGAAGSTMGAASITLTVQARQLLSGIVQQQSNLLRAIEAQQHLLQLTVWGIKQLQARVLAVERYLKDQKFLGLWGCSGKIIC
TTAVPWNSSWSNKSFEEIWDNMTWIEWEREISNYTSQIYEILTESQNQQDRNEKDLLELDKWASLWNWEDITNWLWYIKIFIIIV
GSLIGLRIIFAVLSIVNRVRQGYSPLSFQTPTHHQREPDRPEEIEGGGEQSKDRSVRLVSGFLALAWDDLRSLCLFSYHLLRDF
ILIAARTVELLGHSSLKGLRRGWEGLKYLGNLLLYWGQEIKISAISLLNATAIAVAGWTDRVIEVAQRAWRALLHIPRRIRQGLE
RALL

*Amino acid sequence underlined is the fusion domain that will be deleted in 140CF design and the "W" underlined with red color is the last amino acid at the C terminus, and all the remaining amino acids after the "W" will be deleted in 140CF design.

Fig. 37B

97CNGX2F-AE 140CF.pep (629 a.a.)
Nick name: 018

MRVKETQMNWPNLWKWGTLILGLVIICSASDNLWVTVYYGVPVWRDADTTLFCASDAKAHETEVHNVWATHACVPTDPNPQEIHL
ENVTENFNMWRNNMVEQMQEDVISLWDQSLKPCVKLTPLCVTLNCTNANWTNSNNTTNGPNKIGNITDEVKNCTFNMTTELKDKK
QKVHALFYKLDIVQINSSEYRLINCNTSVIKQACPKISFDPIPIHYCTPAGYAILKCNDKNFNGTGPCKNVSSVQCTHGIKPVVS
TQLLLNGSLAEEEIIIRSENLTNNAKTIIVHLNKSVEINCTRPSNNTRTSITMGPGQVFYRTGDIIGDIRKAYCEINGIKWNEVL
VQVTGKLKEHFNKTIIFQPPSGGDLEIITHHFSCRGEFFYCNTTKLFNNTCIGNTSMEGCNNTIILPCKIKQIINMWQGVGQAMY
APPISGRINCVSNITGILLTRDGGADNNTTNETFRPGGGNIKDNWRSELYKYKVVEIEPLGIAPTRARTLTVQARQLLSGIVQQQ
SNLLRAIEAQQHLLQLTVWGIKQLQARVLAVERYLKDQKFLGLWGCSGKIICTTAVPWNSSWSNKSFEEIWDNMTWIEWEREISN
YTSQIYEILTESQNQQDRNEKDLLELDKWASLWNW*

*Amino acids seen in blue color is for easy identification of the junction of the deleted fusion cleavage site.

Fig. 37C

CODON-OPTIMIZED 97CNGX2F-AE 140CF.seq (1921 nt.)

Nick name: 018

```
ttcagtcgacagccaccATGGCGAGTCAGTAAAAGAGACACAAATGAATTGGCCCAATTTGTGAAGTGGGAACATTGATCCTGGGACT
GGTGATAATCTGTAGTGCATCCGACAATCTCTGGGTGACCGTTTACTATGGTGTACCAGTTTGGAGAGACGCTGATACCACCCTC
TTCTGTGCAAGCGACGCCAAAGCCCACGAAGTCAATGTATGGGCCACCACGCGTGCTACCAACGACCCTAATC
CCCAAGAGAGATCCACCTTGAGAATGTAACCTTTAAACCTTGTGTCAAATTGACTCCCCTGTGTGACTCTCAATTGTACAAACGCAAATTGGACC
TTCCTTGTGGGACCAGAGCCTTAAACGCCCTAACAAAATTGGCAATATTACTGATGAGTCAAGAACTGCACTTTTAACATGACAACAG
AACTGAAGGATAAGAAACAGAAAGTCCATGCTCTGTTCTATAAGCTCGACATAGTACAAATTAAATAGCTCAGAATATAGACTGAT
AAACTGCAATACTTCCGTTATCAACAGGCCTGTCAAACAGGCCTATCAACGATAAGAATTTAACGGCACAGTTCCATCTGCACACCAGCCGT
TACGCTATCCTGAAATGCAACGATATCAACACAGTCGATCCCTGTCCAAAGAGAGAGCTTCCCTGCCGAAGAAGAGATCATCATTAGAAGTTGAGAACCTGACGAA
TCAAGCCTATCCTGTAGTATCAACAGCTCTGTAGCACCTCAATAATCTGTAGAAATAATCAACCTGTACCCGACATCGAAGGCATATTGCGAGATCAATGGCATCA
CAACGCCAAGACTATAGTGCACCTCAATAATCTGTAGAAATAATCAACCTGTACCCGACATCGAAGGCATATTGCGAGATCAATGGCATCA
ACAATGGGCCCTGGCCAAGTTTTTTACCGGACCGGCGATCCGGCGACATAATAGCGACGACATAATAAGAACATTTTAATAAGAACATTTTTACTGTAACACGACCAAGCTCTTCAATAACACGTGC
AGTGGAACGAAGTACTGGTTCAAGTAACTGGAAACTCAAGAGAACATTTTAATAAGAACATTTTTACTGTAACACGACCAAGCTCTTCAATAACACGTGC
CGACCTCGAGATTATCACCCATCACTTTCTTGTAGAGGCGAATTTTTACTGTAACACGACCAAGCTCTTCAATAACACGTGC
ATCGGGAACACTTCTATGGAAGGATGTAATAATACCATTATACTGCCCTGTAAGATCAAGCAGATTATCAACATGTGGCAGGGAG
TAGGTCAGGCAATGTACGCACCACTAACGAGACATTCAGGACGATCAATTGCGTATCAAATATCACCGGCATTCTGCTGACCCGGACCG
AGGCGCGAACAACAATACCACTAACGAGACATTAGACCTGGAGGCGGCAATATAAAGGATAATTGGAGAAGTGAGCTGTATAAA
TACAAAGTCGTAGAGATCGAACCTCAACGAGTCAAACCTCCTCCCGGACTCTCACCAACCTGCTCCAGCTGACTGTGTGGGAATCAAACA
GCATAGTCCAACGACAGCAGTCAAACCTCCTCCCGCTATTGAAGCACACAAGATCAGAAATTTCTTGGACTTTGGGCTGACTGTGTGCAGCGGCCAAAATTATT
ATTGCAAGCAAGAGTGCTCGCCGTGAACCTCATCCTGGAGTAATAAAAGCTTGAAGAAATCTGGGACAATATGACATTGAGTGGG
TGTACAACAGCCGGTGCTTGAACTATACAAGCCAAATTTACGAAATATCGACAGAAGTCAAAACCAGCAGGACAATATTCAAACCAGCAGGACCAGAGAAGACCT
AGAGAGAGATTTCAAATATACAAGCCAAATTTACGAAATATCGACAGAAGTCAAAACCAGCAGGACAATATTCAAACCAGCAGGACCAGAGAAGACCT
GCTCGAACTGGATAAGTGGCCTCTTTGTGAACTGGtaaagatcttacaa
```

Fig. 38A

Wild-type DRCBL-G (854 a.a.)

MRVKGIQRNWQHLWNWGILILGLVIICSAEKLWVTVYYGVPVWEDANAPLFCASDAKAHSTESHNIWATHACVPTDPSPQEINMR
NVTENFNMWKNNMVEQMHEDIISLWDESLKPCVKLTPLCVTLNCTEINNNSTRNITEEYRMTNCSFNMTTELRDKKAEYALFYR
TDVPINEMNNENNGTNSTWYRLTNCNVSTIKQACPKVTFEPIPIHYCAPAGFAILKCVDKKFNGTGTCNNVSTVQCTHGIKPVV
STQLLLNGSIAEKDIIISSENISDNAKVIIVHLNRSVEINCTRPNNNTRRSVAIGPGQAFYTTGEVIGDIRKAHCNVSWTKWNET
LRDVQAKLQEYFINKSIEFNSSSGGDLEITTHSFNCGGEFFYCNTSGLFNNSILKSNISENNDTITLNCKIKQIVRMWQRVGQAM
YAPPIAGNITCRSNITGLILTRDGGDNNSTSEIFRPGGGDMKNNWRSELYKYKTVKIKSLGIAPTRARRRVVEREKRAVGVGAIF
LGFLGTAGSTMGAASITLTVQVRQLLSGIVQQQSNLLRAIEAQQHLLQLTVWGIKQLRARVLALERYLKDQQLLGIWGCSGKLIC
TTNVPWNTSWSNKSYNEIWENMTWIEWEREIDNYTYHIYSLIEQSIQQEKNEQDLLALDQWASLMWFSISNWLWYIRIFVMIV
GGLIGLRIVFAVLSIVNRVRQGYSPLSFQTLLHHQREPDRPAGIEEGGGEQDRDRSIRLVSGFLALAWDDLRSLCLFSYHRLRDF
ILIAARTVELLGRNSLKGLRLGWEALKYLWNLLLYWARELKNSAINLLDTIAIAVANWTDRVIEVAQRAGRAVLNIPRRIRQGLE
RALL

*Amino acid sequence underlined is the fusion domain that will be deleted in 140CF design and the "W" underlined with red color is the last amino acid at the C terminus, and all the remaining amino acids after the "W" will be deleted in 140CF design.

Fig. 38B

DRCBL-G 140CF.

Fig. 38C

CODON-OPTIMIZED DRCBL-G 140CF.seq (1921 nt.)

Nick name: 017 ttcagtcgacagccaccATGAGAGTTAAAGGAATCCAACGCAATTGGCAACACCTTTGGAACTGGGGCATATTGATTCTTGGACT
GGTGATAATTTGTAGCGCTGAAAAACTCTGGGTAACTGTCTATTACGGCGTGCCTGTCTGGGAGGATGCCAACGCCCCCCTGTTC
TGCGCAAGTGATGCAAAGGCTCACAGCACTGAATCTCACAACATTTGGGCCACCCACGCCTGTGTGCCAACCGACCCTAGTCCTC
AGGAGATCAACATGAGAAACGTTACCGAAAATTTTAATATGTGGAAGAATAATATGGTGGAGCAAATGCACGAAGACATAATTTC
ACTCTGGGACGAGTCTCTGAAACCATGTGTGAAACTTACCCCCCTGTGCGTCACCCTGAACTGTACCGAAATCAACAATAACTCA
ACGAGAAATATCACAGAAGAATACCGAATGACTAACTGTTCCTTTAATATGACAACCGAACTGCGAGACAAAAAGAAGGCTGAAT
ACGCACTTTTCTACCGAACAGATGTTGTACCAATCAACGAGATGAACAATGAAAACAATGGAACGAACTCTACCTGGTATAGACT
GACAAACTGTAACGTTAGCACAATCAAGCAGGCCTGCCCTAAAGTCACATTCGAACCAATACCAATTCACTACTGCGCACCCGCC
GGATTCGCTATTCTTAAGTGCGTGGATAAGAAGTTTAACGGAACTGGAACCTGCAATAATGTATCTACAGTACAATGCACGCATG
GAATTAAGCCTGTCGTTTCAACCCAGTTGCTGCTGAATGGATCACTCGCAGAAAAGGATATTATTATCTCAAGCGAAAACATATC
TGATAATGCAAAGGTCATCATCGTCCACCTCAACCGCTCAGTTGAAATAAACTGCACTCGGCCTAATAATAACACAAGACGCTCT
GTCGCAATCGGCCCAGGACAAGCTTTTTACACTACCGGGGAAGTTATCGGCGACATACGGAAAGCCCACTGCAACGTTAGCTGGA
CCAAGTGGAATGAAACACTGCGCGATGTTCAAGCCAAACTTCAAGAATACTTCATAAACAAATCAATTGAGTTCAATTCTAGCTC
TGGCGGCGACCTCGAGATTACAACTCACTCCTTTAACTGCGGCGGCGAATTCTTTTATTGTAATACCTCCGGTCTCTTCAACAAC
TCTATCCTCAAAAGTAACATTTCTGAAAATAATGACACAATCACACTGAATTGCAAGATCAAGCAGATTGTTAGGATGTGGCAAC
GAGTCGGACAAGCTATGTACGCCCCACCCATCGCCGGAAATATAACGTGTCGATCAAATATCACTGGCCTCATCCTTACTAGAGA
TGGCGGAGACAATAATAGCACCAGCGAGATATTCAGACCAGGCGGAGGCGATATGAAAAACAACTGGAGGTCAGAGCTCTACAAG
TACAAAACAGTCAAAATTAAAAGCCTGGGCATTGCTCCCACTCGGGCCCGCACACTGACTGTCCAAGTCCGACAGCTCCTGTCCG
GAATCGTCCAACAACAGTCCAACTTGCTGCGCGCTATAGAGGCTCAACAACATCTCCTTCAACTGACTGTGTGGGGTATCAAACA
ATTGAGAGCAAGAGTGCTGGCGCTGGAACGGTATCTTAAGGACCAACAACTCCTGGGCATATGGGGGTGTTCCGGCAAACTGATC
TGCACAACAAATGTACCCTGGAACACCAGCTGGTCAAATAAAAGTTATAATGAGATATGGGAAAACATGACATGGATTGAATGGG
AAAGGGAAATTGACAATTATACATACCATATATACTCTCTCATCGAACAATCTCAGATACAACAGGAAAAGAATGAACAAGATTT
GTTGGCTCTTGACCAATGGGCTTCTTTGTGGAGTTGGtaaagatcttacaa 2003 Centralized HIV-1 Envelope Proteins and the Codon-Optimized Gene sequences

Fig. 39A

2003 Cons Env

MRVMGIQRNCQHLWRWGILIFGMLIICSAAENLWVTVYYGVPVWKEANTTLFCASDAKAYDTEVHNVWATHACVPTDPNPQEIVLENVTENF
NMWKNNMVEQMHEDIISLWDQSLKPCVKLTPLCVTLNCTDVNATNNTTNNEEIKNCSFNITTEIRDKKKKVYALFYKLDVVPIDDNNSYRLI
NCNTSAITQACPKVSFEPIPIHYCAPAGFAILKCNDKKFNGTGPCKNVSTVQCTHGIKPVVSTQLLLNGSLAEEEIIIRSENITNNAKTIIV
QLNESVEINCTRPNNNTRKSIRIGPGQAFYATGDIIGDIRQAHCNISRTKWNKTLQQVAKKLREHFNKTIIFNPSSGGDLEITTHSFNCGGE
FFYCNTSELFNSTWNGTNNTITLPCRIKQIINMWQGVGQAMYAPPIEGKIRCTSNITGLLLTRDGGNNNTETFRPGGGDMRDNWRSELYKYK
VVKIEPLGVAPTKAKRRVVEREKRAVGIGAVFLGFLGAAGSTMGAASITLTVQARQLLSGIVQQQSNLLRAIEAQQHLLQLTVWGIKQLQAR
VLAVERYLKDQQLLGIWGCSGKLICTTNVPWNSSWSNKSQDEIWDNMTWMEWDKEINNYTDIIYSLIEESQNQQEKNEQELLALDKWASLWN
WFDITNWLWYIKIFIMIVGGLIGLRIVFAVLSIVNRVRQGYSPLSFQTLIPNPRGPDRPEGIEEEGGEQDRDRSIRLVNGFLALAWDDLRSL
CLFSYHRLRDLILIAARTVELLGRRGWEALKYLWNLLQYWGQELKNSAISLLDTTAIAVAEGTDRVIEVVQRVCRAILNIPRRIRQGFERAL
L$

Fig. 40A

2003 M. Group.AnC Env

MRVMGIQRNCQHLWRWGILIFGMLMICSAAENLWVTVYYGVPVWKEANTTLFCASDAKAYDTEVHNVWATHACVPTDPNPQEIVLENVTENF
NMWKNNMVEQMHEDIISLWDQSLKPCVKLTPLCVTLNCTDVNATNNSTNMGEIKNCSFNITTEIRDKKQKVYALFYRLDVVPINDNNSYRLI
NCNTSAITQACPKVSFEPIPIHYCAPAGFAILKCNDKKFNGTGPCKNVSTVQCTHGIKPVVSTQLLLNGSLAEEEIIIRSENITDNAKTIIV
QLNESVEINCTRPNNNTRKSIRIGPGQAFYATGDIIGDIRQAHCNISGAEWNKTLQQVAAKLREHFNNKTIIFKPSSGGDLEITTHSFNCGG
EFFYCNTSGLFNSTWNGTNETITLPCRIKQIVNMWQRVGQAMYAPPIAGNITCKSNITGLLLTRDGGTNNTETFRPGGGDMRDNWRSELYKY
KVVKIEPLGVAPTKAKRRVVEREKRAVGIGAVFLGFLGAAGSTMGAASITLTVQARQLLSGIVQQQSNLLRAIEAQQHLLQLTVWGIKQLQA
RVLAVERYLKDQQLLGIWGCSGKLICTTNVPWNSSWSNKSQDEIWDNMTWMQWEREISNYTDIIYSLIEESQNQQEKNEQDLLALDKWASLW
NWFDITNWLWYIKIFIMIVGGLIGLRIVFAVLSIVNRVRQGYSPLSFQTLIPNPRGPDRPGGIEEEGGEQDRDRSIRLVSGFLALAWDDLRS
LCLFSYHRLRDFILIAARTVELLGRRGWEALKYLWNLLQYWGQELKNSAISLLDTTAIAVAEGTDRVIEVVQRACRAILHIPRRIRQGFERA
LL$

Fig. 39B

2003 CON-S Env.seq.opt

ATGCGCGTGATGGGCATCCAGCGCAACTGCCAGCACCTGTGGCGCTGGGGCATCCTGATCTTCGGCATGCTGATCATCTGCTCCGCCGCCGA
GAACCTGTGGGTGACCGTGTACTACGGCGTGCCCGTGTGGAAGGAGGCCAACACCACCCTGTTCTGCGCCTCCGACGCCAAGGCCTACGACA
CCGAGGTGCACAACGTGTGGGCCACCCACGCCTGCGTGCCCACCGACCCCAACCCCCAGGAGATCGTGCTGGAGAACGTGACCGAGAACTTC
AACATGTGGAAGAACAACATGGTGGAGCAGATGCACGAGGACATCATCTCCCTGTGGGACCAGTCCCTGAAGCCCTGCGTGAAGCTGACCCC
CCTGTGCGTGACCCTGAACTGCACCGACGTGAACGCCACCAACAACACCACCAACAACGAGGAGATCAAGAACTGCTCCTTCAACATCACCA
CCGAGATCCGCGACAAGAAGAAGAAGGTGTACGCCCTGTTCTACAAGCTGGACGTGGTGCCCATCGACGACAACAACTCCTACCGCCTGATC
AACTGCAACACCTCCGCCATCACCCAGGCCTGCCCCAAGGTGTCCTTCGAGCCCATCCCCATCCACTACTGCGCCCCCGCCGGCTTCGCCAT
CCTGAAGTGCAACGACAAGAAGTTCAACGGCACCGGCCCCTGCAAGAACGTGTCCACCGTGCAGTGCACCCACGGCATCAAGCCCGTGGTGT
CCACCCAGCTGCTGCTGAACGGCTCCCTGGCCGAGGAGGAGATCATCATCCGCTCCGAGAACATCACCAACAACGCCAAGACCATCATCGTG
CAGCTGAACGAGTCCGTGGAGATCAACTGCACCCGCCCCAACAACAACACCCGCAAGTCCATCCGCATCGGCCCCGGCCAGGCCTTCTACGC
CACCGGCGACATCATCGGCGACATCCGCCAGGCCCACTGCAACATCTCCCGCACCAAGTGGAACAAGACCCTGCAGCAGGTGGCCAAGAAGC
TGCGCGAGCACTTCAACAAGACCATCATCTTCAACCCCTCCTCCGGCGGCGACCTGGAGATCACCACCCACTCCTTCAACTGCGGCGGCGAG
TTCTTCTACTGCAACACCTCCGAGCTGTTCAACTCCACCTGGAACGGCACCAACAACACCATCACCCTGCCCTGCCGCATCAAGCAGATCAT
CAACATGTGGCAGGGCGTGGGCCAGGCCATGTACGCCCCCCCCATCGAGGGCAAGATCCGCTGCACCTCCAACATCACCGGCCTGCTGCTGA
CCCGCGACGGCGGCAACAACAACACCGAGACCTTCCGCCCCGGCGGCGGCGACATGCGCGACAACTGGCGCTCCGAGCTGTACAAGTACAAC
GTGGTGAAGATCGAGCCCCTGGGCGTGGCCCCCACCAAGGCCAAGCGCCGCGTGGTGGAGCGCGAGAAGCGCGCCGTGGGCATCGGCGCCGT
GTTCCTGGGCTTCCTGGGCGCCGCCGGCTCCACCATGGGCGCCGCCTCCATCACCCTGACCGTGCAGGCCCGCCAGCTGCTGTCCGGCATCC
TGCAGCAGCAGTCCAACCTGCTGCGCGCCATCGAGGCCCAGCAGCACCTGCTGCAGCTGACCGTGTGGGGCATCAAGCAGCTGCAGGCCCGC
GTGCTGGCCGTGGAGCGCTACCTGAAGGACCAGCAGCTGCTGGGCATCTGGGGCTGCTCCGGCAAGCTGATCTGCACCACCAACGTGCCCTG
GAACTCCTCCTGGTCCAACAAGTCCCAGGACGAGATCTGGGACAACATGACCTGGATGGAGTGGGACAAGGAGATCAACAACTACACCGACA
TCATCTACTCCCTGATCGAGGAGTCCCAGAACCAGCAGGAGAAGAACGAGCAGGAGCTGCTGGCCCTGGACAAGTGGGCCTCCCTGTGGAAC
TGGTTCGACATCACCAACTGGCTGTGGTACATCAAGATCTTCATCATGATCGTGGGCGGCCTGATCGGCCTGCGCATCGTGTTCGCCGTGCT
GTCCATCGTGAACCGCGTGCGCCAGGGCTACTCCCCCCTGTCCTTCCAGACCCTGATCCCCAACCCCCGCGGCCCCGACCGCCCCGAGGGCA
TCGAGGAGGAGGGCGGCGAGCAGGACCGCGACCGCTCCATCCGCCTGGTGAACGGCTTCCTGGCCCTGGCCTGGGACGACCTGCGCTCCCTG
TGCCTGTTCTCCTACCACCGCCTGCGCGACCTGATCCTGATCGCCGCCCGCACCGTGGAGCTGCTGGGCCGCCGCGGCTGGGAGGCCCTGAA
GTACCTGTGGAACCTGCTGCAGTACTGGGGCCAGGAGCTGAAGAACTCCGCCATCTCCCTGCTGGACACCACCGCCATCGCCGTGGCCGAGG
GCACCGACCGCGTGATCGAGGTGGTGCAGCGCGTGTGCCGCGCCATCCTGAACATCCCCCGCCGCATCCGCCAGGGCTTCGAGCGCGCCCTG
CTGTAA

Fig. 40B

```
2003 M. Group.anc Env.seq.opt
ATGGCGGTGATGGGCATCCAGCGGCAACTGCCAGCACCTGTGGGCGCTGGGCATCCTGATCTTCGGCATGCTGATGATCTGCTCCGCCGGA
GAACCTGTGGGTGACCGTGTACTACGGCGTGCCCGTGCCTGTGCTGCCCACCCCAACCCCTGTTCTGCGCCAAGGCCTACGACA
CCGAGGTGCACAACGTGTGGGCCACACGTGTGCTGCTGCCCTGCTGCGTGCCTGTCCTGTGCGGAGATCGTCGTGCCTGGAGAACGTGACCGAGAACTTC
AACATGTGGAAGAACATGGTGGAGCAGATGCACGAGGACATCATCTCCCTGTGGGACCAGAGCCTGAAGCCCTGCGTGCAGCTGACCCC
CCTGTGCGTGACCCTGAACTGCACCGACGTGAACGCC

Fig. 41A

2003 CON_A1 Env

MRVMGIQRNCQHLLRWGTMILGMIIICSAAENLWVTVYYGVPVWKDAETTLFCASDAKAYETEMHNVWATHACVPTDPNPQEIHLENVTEEF
NMWKNNMVEQMHTDIISLWDQSLKPCVKLTPLCVTLNCSNVNVTNNTTNTHEEEIKNCSFNMTTELRDKKQKVYSLFYRLDVVQINENNSNS
SYRLINCNTSAITQACPKVSFEPIPIHYCAPAGFAILKCKDKEFNGTGPCKNVSTVQCTHGIKPVVSTQLLLNGSLAEEEVIIRSENITNNA
KTIIVQLTKPVKINCTRPNNNTRKSIRIGPGQAFYATGDIIGDIRQAHCNVSRSEWNKTLQKVAKQLRKYFKNKTIIFTNSSGGDLEITTHS
FNCGGEFFYCNTSGLFNSTWNNGTMKNTITLPCRIKQIINMWQRAGQAMYAPPIQGVIRCESNITGLLLTRDGGNNNTNETFRPGGGDMRDN
WRSELYKYKVVKIEPLGVAPTRAKRRVVEREKRAVGIGAVFLGFLGAAGSTMGAASITLTVQARQLLSGIVQQQSNLLRAIEAQQHLLKLTV
WGIKQLQARVLAVERYLKDQQLLGIWGCSGKLICTTNVPWNSSWSNKSQNEIWDNMTWLQWDKEISNYTHIIYNLIEESQNQQEKNEQDLLA
LDKWANLWNWFDISNWLWYIKIFIMIVGGLIGLRIVFAVLSVINRVRQGYSPLSFQTHTPNPRGLDRPGRIEEEGGEQGRDRSIRLVSGFLA
LAWDDLRSLCLFSYHRLRDFILIAARTVELLGHSSLKGLRLGWEGLKYLWNLLLYWGRELKISAINLVDTIAIAVAGWTDRVIEIGQRIGRA
ILHIPRRIRQGLERALL$

Fig. 42A

2003 A1.AnC Env

MRVMGIQRNCQHLWRWGTMIFGMIIICSAAENLWVTVYYGVPVWKDAETTLFCASDAKAYDTEVHNVWATHACVPTDPNPQEIDLENVTEEF
NMWKNNMVEQMHADIISLWDQSLKPCVKLTPLCVTLNCSNVNVTNNTTNTHEEEIKNCSFNMTTELRDKKQKVYSLFYRLDVVPINENNSNS
SYRLINCNTSAITQACPKVSFEPIPIHYCAPAGFAILKCKDKEFNGTGPCKNVSTVQCTHGIKPVVSTQLLLNGSLAEEEVMIRSENITDNA
KTIIVQLTEPVKINCTRPNNNTRKSIRIGPGQAFYATGDIIGDIRQAHCNVSRTEWNKTLQKVAAQLRKHFNNKTIIFNSSSGGDLEITTHS
FNCGGEFFYCNTSGLFNSTWNNGTMKDTITLPCRIKQIINMWQRVGQAMYAPPIQGVIRCESNITGLLLTRDGGNNNTNETFRPGGGDMRDN
WRSELYKYKVVKIEPLGVAPTRAKRRVVEREKRAVGLGAVFLGFLGAAGSTMGAASITLTVQARQLLSGIVQQQSNLLRAIEAQQHLLKLTV
WGIKQLQARVLAVERYLKDQQLLGIWGCSGKLICTTNVPWNSSWSNKSQDEIWDNMTWLQWDKEISNYTDIIYNLIEESQNQQEKNEQDLLA
LDKWANLWNWFDISNWLWYIKIFIMIVGGLIGLRIVFAVLSVINRVRQGYSPLSFQTLTPNPEGPDRPGRIEEEGGEQGRDRSIRLVSGFLA
LAWDDLRSLCLFSYHRLRDFILIAARTVELLGRSSLKGLRLGWEGLKYLWNLLLYWGRELKISAINLLDTIAIAVAGWTDRVIEIGQRICRA
ILNIPRRIRQGLERALL$

Fig. 41B

2003_CON_A1 Env.seq.opt
ATGCGCGTGATGGGCATCCAGCGGCAACTGCCAGCACCTGCTGCTGGGCTGGGGCATGATCATCCTGTTCTGCTCCGCCGCCGA
GAACCTGTGGGTGACCGTGTACTACGGCGTGCCCGTGTGGAAGGACGCCGAGACCACCCTGTTCTGCGCCAGCGATGCCGAGATC
CCGAGATGCACAACGTGTGGGCCACCCACGCCTGCGTGCCCACCGACCCCAACCCCCAGGAGATCCACCTGGAGAACGTGACCGAGTTC
AACATGTGGAAGAACAACATGGTGGAGCAGATGCACGAGGACATCATCTCCCTGTGGGACCAGAGCCTGAAGCCCTGCGTGAAGCTGACCCC
CCTGTGCGTGACCCTGAACTGCTCCAACGTGAACGTGACAGAAGTGTACTCCCGCCATCAACGAGAGAGATCAACGAGAACAACTCCAACTCC
TGACCACCGAGCTGCCGCAAGAAGAGCAGAACACCTCCGCCATCAACCGCGACCTGGACGTGGTGCAGATCCCATCCACTGCGCCCCC
TCCTACCGCCTGATCAACTGCAACACCTCCGCCATCACCCAGGCCTGTCCTTCAAGCCGTCCTTCGAGCCCATCCACTACTGCGCCCCC
CGCCGGCTTCGCCATCCTGAAGTGTCGTCCACCCAGCTGCTGCTGAACGGCTCCCTGGCCGAGGAGTTCAACGAGTGATCATCGCGAGCTCCGAGATCATCGCGCCCACGGCA
TCAAGCCCGTGGTGTCCACCCAGCTGCTCAACGGCTCCCTGGCCGAGGAGTTCAACGAGGTGATCATCCGCTCCGAGAACATCACCAACAACGCC
AAGACCATCATCGTGCAGCTGAACGAGTCCGTGCAGATCAATCTGCGCCAAGCCCCCCGTCCGGATGGAACAAGAGACCGCCGCCTGCAGA
CCAGGCCTTCTACGCCACCGGCGACATCATCGGCGACATCAAGAGACCTACTTCAAGAACAGTGCCCCGCCAACATCACCACCTCC
AGGTGGCCAAGCTGGCAGCGAGTTCTTCTACTGCAACATGACCGGGCCTGTTCAACTGCAACATCGGCCACCATGAAGAACACCATCACCCT
TTCAACTGCGGCGGCGAGTTCTTCTACTGCAACATGACCGGGCCTGTTCAACTGCAACATGGGCGCCAATCCAGGCGTGATCCGCTGCGAGT
GCCTCCGGCCATCAAGCAGATCATCAACATGTGGCAGCAGGTCCCAAGCCCGGCCAACAACACCAACAACGAGACCTTCCGCCCGGACAAC
CAACATCACCGGCCTGCTGCTGACCCGGGACGGCGGCAACAACAACACCAACGAGACCTTCCGCCCCGGCGGCGGCGACATGCGCGACAAC
TGGCGCTCCGAGCTGTACAAGTACAAGGTGGTGAAGATCGAGCCCCTGGGCGTGGCCCCCACCCGGGCCAAGCGCCGCGTGGTGGAGCGCGA
GAAGCGCGCCGTGGGCATCGGCGCCGTGTTCCTGGGCTTCCTGGGCGCAGCAGTCCGTGCCGAGTCCAACCTGACAGTGACAGCCAGGCCCCTGACCCTGA
AGGCCCAGCAAGCACGTGCTGTCAGGCATCGTGCAGCAGCAGAACAACCTGCTGCGGGCCATCGAGGCCCAGCAGCACCTGCTGAAGCTGACCGTG
TGGGGCATCAAGCAGCTGCAGGCCCGGGTGCTGGCCGTGGAGCGCTACCTGCGGGACCAGCAGCTGCTGGGCATCTGGGGCTGCAGTGGG
GCTGATCTGCACCACCGCCGTGCCCTGGAACACCTCCTGGTCCAACAAGTCCCCAAACCAGATCTGGGACAACATGACCTGGATGCAGT
ACAAGGAGATCTCCAACTACACCGACCACATCTACAACCTGATCGAGGAGTCCCAGAACCAGCAGGAGAAGAACGAGCAGGACCTGCTGGCC
CTGGACAAGTGGGCCAACCTGTGGAACTGGTTCGACATCTCCAACTGGCTGTGGTACATCAAGATCTTCATCATGATCGTGGGCGGCCTGAT
CGGCCTGCGCATCGTGTTCGCCGTGCTGAGCATCGTGAACAGGGTGCGCCAGGGCTACTCCCCGCTCCTCCCCGCCTCCGGCTTCCTGGCC
CCCGGCCTGGGACCGGCGAGGGCACCGAGGAGGACGGCGAGCAGCCCGGCGGGCGAGGCACCGGCGGCGCAGGGCTGCCCCAGGACACCAGAACAACACCCCGTGTCCCGCCACCGTGTCTCCGAGCTGCT
CTGGCCCTGGGACGACCTGGACTCTCTGCTGTTCTCTCCTGGCGGCCTGCGCCCTGATCGCCGCCCGCACCGTCCGTGCGCGAGCTGCT
GGGCCACTCCCCGATCAACCGGTGACAACATCCGCGCCATCGCCCTGGCTGGGGCCGTGGCCACCGGCCCAGTACTGGAACCGCTGAAGA
TCTCCGCCATCAACCCCCCGCCCGCCGCCATCCCCGCCAGGGCCTGGAGCGCGCCCTGCTGTAA
ATCCTGCACATCCCCCGCCATCGCCGCCAGGGCCTGGAGCGCGCCCTGCTGTAA

Fig. 42B

2003 A1.anc Env.seq.opt
ATGGCGGTGATGGGCATCCAGCGCAACTGCCAGCACCTGTGGCGCTGGGGCACCATGATCATCTTCGGCATGATCATCTGCTCCGCCCGA
GAACCTGTGGGTGACCGTGTACTACGGCGTGTGTGGCCCTGTGCGTGTGCCCGAGACCACCCTGTTCTGCGCCTCTGACGAGGCCTACGACA
CCGAGGTGCACAACGTGGTGTGGGCCACCCACGCCTGCGTGCCCACCGACCCTAACCCCCAGGAGATCATCCTGGAGAACGTGACCGAGTTC
AACATGTGGAAGAACAACATGGTGGAGCAGATGCACGAGGACATCATCTCCCTGTGGGACCAGTCCCTGAAGCCCTGCGTGAAGCTGACCCC
CCTGTGCGTGACCCTGAACTGCGCCGACGTGAACAGCAGCAGAAGCAGAGCCGCCATCAACGAGGAGATCAAGAACTGCTCCTTCAACA
TGACCACCGAGCTGCGCGATCAACTGCCACAAGAGCAGAAGGTGTACTCCCTGCCCATCACCGCCCCCCTGCGCCCATCAACCCTGCCCACCTCC
CGCCGGCTTCGCCCATCCTGCCACCGCCAAGGACAAGGAGTTCAACGCCTGTCCCCAGCTGCTGAAGGACAACATCGCCCACCTACTGCGCCCC
TCAAGCCCGTGTCCACCCAGCTGCTGATCAACGGCAGCCTGGCCGAGGAGGTGATGATCCGCTCCGAGAACATCACCGACAACGCC
AAGACCATCATCGTGCAGCTGAACGAGCCCGTGAAGATCAACTGCCG

Fig. 43A

2003 CON_A2 Env

MRVMGTQRNYQHLWRWGILILGMLIMCKATDLWVTVYYGVPVWKDADTTLFCASDAKAYDTEVHNVWATHACVPTDPNPQEVNLENVTEDFN
MWKNNMVEQMHEDIISLWDQSLKPCVKLTPLCVTLNCSNANTTNNSTMEEIKNCSYNITTELRDKTQKVYSLFYKLDVVQLDESNKSEYYYR
LINCNTSAITQACPKVSFEPIPIHYCAPAGFAILKCKDPRFNGTGSCNNVSSVQCTHGIKPVASTQLLLNGSLAEGKVMIRSENITNNAKNI
IVQFNKPVPITCIRPNNNTRKSIRFGPGQAFYTNDIIGDIRQAHCNINKTKWNATLQKVAEQLREHFPNKTIIFTNSSGGDLEITTHSFNCG
GEFFYCNTTGLFNSTWKNGTTNNTEQMITLPCRIKQIINMWQRVGRAMYAPPIAGVIKCTSNITGIILTRDGGNNETETFRPGGGDMRDNWR
SELYKYKVVKIEPLGVAPTRAKRRVVEREKRAVGMGAVFLGFLGAAGSTMGAASITLTVQARQLLSGIVQQQSNLLKAIEAQQHLLKLTVWG
IKQLQARVLALERYLQDQQLLGIWGCSGKLICATTVPWNSSWSNKTQEEIWNNMTWLQWDKEISNYTNIIYKLLEESQNQQEKNEQDLLALD
KWANLWNWFNITNWLWYIRIFIMIVGGLIGLRIVIAIISVVNRVRQGYSPLSFQIPTPNPEGLDRPGRIEEGGGEQGRDRSIRLVSGFLALA
WDDLRSLCLFSYHRLRDCILIAARTVELLGHSSLKGLRLGWEGLKYLWNLLLYWGRELKNSAISLLDTIAVAVAEWTDRVIEIGQRACRAIL
NIPRRIRQGFERALL$

Fig. 44A

2003 CON_B Env

MRVKGIRKNYQHLWRWGTMLLGMLMICSAAEKLWVTVYYGVPVWKEATTTLFCASDAKAYDTEVHNVWATHACVPTDPNPQEVVLENVTENF
NMWKNNMVEQMHEDIISLWDQSLKPCVKLTPLCVTLNCTDLMNATNTNTTIIYRWRGEIKNCSFNITTSIRDKVQKEYALFYKLDVVPIDND
NTSYRLISCNTSVITQACPKVSFEPIPIHYCAPAGFAILKCNDKKFNGTGPCTNVSTVQCTHGIRPVVSTQLLLNGSLAEEEVVIRSENFTD
NAKTIIVQLNESVEINCTRPNNNTRKSIHIGPGRAFYTTGEIIGDIRQAHCNISRAKWNNTLKQIVKKLREQFGNKTIVFNQSSGGDPEIVM
HSFNCGGEFFYCNTTQLFNSTWNGTWNNTEGNITLPCRIKQIINMWQEVGKAMYAPPIRGQIRCSSNITGLLLTRDGGNNETEIFRPGGGDM
RDNWRSELYKYKVVKIEPLGVAPTKAKRRVVQREKRAVGIGAMFLGFLGAAGSTMGAASMTLTVQARQLLSGIVQQQNNLLRAIEAQQHLLQ
LTVWGIKQLQARVLAVERYLKDQQLLGIWGCSGKLICTTAVPWNASWSNKSLDEIWDNMTWMEWEREIDNYTSLIYTLIEESQNQQEKNEQE
LLELDKWASLWNWFDITNWLWYIKIFIMIVGGLVGLRIVFAVLSIVNRVRQGYSPLSFQTRLPAPRGPDRPEGIEEEGGERDRDRSGRLVDG
FLALIWDDLRSLCLFSYHRLRDLLLIVTRIVELLGRRGWEVLKYWWNLLQYWSQELKNSAVSLLNATAIAVAEGTDRVIEVVQRACRAILHI
PRRIRQGLERALL$

Fig. 43B

2003 CON_A2 Env.seq.opt

ATGCGCGTGATGGGCACCCAGCGCAACTACCAGCACCTGTGGCGCTGGGGCATCCTGATCCTGGGCATGCTGATCATGTGCAAGGCCACCGA
CCTGTGGGTGACCGTGTACTACGGCGTGCCCGTGTGGAAGGACGCCGACACCACCCTGTTCTGCGCCTCCGACGCCAAGGCCTACGACACCG
AGGTGCACAACGTGTGGGCCACCCACGCCTGCGTGCCCACCGACCCCAACCCCCAGGAGGTGAACCTGGAGAACGTGACCGAGGACTTCAAC
ATGTGGAAGAACAACATGGTGGAGCAGATGCACGAGGACATCATCTCCCTGTGGGACCAGTCCCTGAAGCCCTGCGTGAAGCTGACCCCCCT
GTGCGTGACCCTGAACTGCTCCAACGCCAACACCACCAACAACTCCACCATGGAGGAGATCAAGAACTGCTCCTACAACATCACCACCGAGC
TGCGCGACAAGACCCAGAAGGTGTACTCCCTGTTCTACAAGCTGGACGTGGTGCAGCTGGACGAGTCCAACAAGTCCGAGTACTACTACCGC
CTGATCAACTGCAACACCTCCGCCATCACCCAGGCCTGCCCCAAGGTGTCCTTCGAGCCCATCCCCATCCACTACTGCGCCCCCGCCGGCTT
CGCCATCCTGAAGTGCAAGGACCCCCGCTTCAACGGCACCGGCTCCTGCAACAACGTGTCCTCCGTGCAGTGCACCCACGGCATCAAGCCCG
TGGCCTCCACCCAGCTGCTGCTGAACGGCTCCCTGGCCGAGGGCAAGGTGATGATCCGCTCCGAGAACATCACCAACAACGCCAAGAACATC
ATCGTGCAGTTCAACAAGCCCGTGCCCATCACCTGCATCCGCCCCAACAACAACACCCGCAAGTCCATCCGCTTCGGCCCCGGCCAGGCCTT
CTACACCAACGACATCATCGGCGACATCCGCCAGGCCCACTGCAACATCAACAAGACCAAGTGGAACGCCACCCTGCAGAAGGTGGCCGAGC
AGCTGCGCGAGCACTTCCCCAACAAGACCATCATCTTCACCAACTCCTCCGGCGGCGACCTGGAGATCACCACCCACTCCTTCAACTGCGGC
GGCGAGTTCTTCTACTGCAACACCACCGGCCTGTTCAACTCCACCTGGAAGAACGGCACCACCAACAACACCGAGCAGATGATCACCCTGCC
CTGCCGCATCAAGCAGATCATCAACATGTGGCAGCGCGTGGGCCGCGCCATGTACGCCCCCCCCATCGCCGGCGTGATCAAGTGCACCTCCA
ACATCACCGGCATCATCCTGACCCGCGACGGCGGCAACAACGAGACCGAGACCTTCCGCCCCGGCGGCGGCGACATGCGCGACAACTGGCGC
TCCGAGCTGTACAAGTACAAGGTGGTGAAGATCGAGCCCCTGGGCGTGGCCCCCACCCGCGCCAAGCGCCGCGTGGTGGAGCGCGAGAAGCG
CGCCGTGGGCATGGGCGCCGTGTTCCTGGGCTTCCTGGGCGCCGCCGGCTCCACCATGGGCGCCGCCTCCATCACCCTGACCGTGCAGGCCC
GCCAGCTGCTGTCCGGCATCGTGCAGCAGCAGTCCAACCTGCTGAAGGCCATCGAGGCCCAGCAGCACCTGCTGAAGCTGACCGTGTGGGGC
ATCAAGCAGCTGCAGGCCCGCGTGCTGGCCCTGGAGCGCTACCTGCAGGACCAGCAGCTGCTGGGCATCTGGGGCTGCTCCGGCAAGCTGAT
CTGCGCCACCACCGTGCCCTGGAACTCCTCCTGGTCCAACAAGACCCAGGAGGAGATCTGGAACAACATGACCTGGCTGCAGTGGGACAAGG
AGATCTCCAACTACACCAACATCATCTACAAGCTGCTGGAGGAGTCCCAGAACCAGCAGGAGAAGAACGAGCAGGACCTGCTGGCCCTGGAC
AAGTGGGCCAACCTGTGGAACTGGTTCAACATCACCAACTGGCTGTGGTACATCCGCATCTTCATCATGATCGTGGGCGGCCTGATCGGCCT
GCGCATCGTGATCGCCATCATCTCCGTGGTGAACCGCGTGCGCCAGGGCTACTCCCCCCTGTCCTTCCAGATCCCCACCCCCAACCCCGAGG
GCCTGGACCGCCCCGGCCGCATCGAGGAGGGCGGCGGCGAGCAGGGCCGCGACCGCTCCATCCGCCTGGTGTCCGGCTTCCTGGCCCTGGCC
TGGGACGACCTGCGCTCCCTGTGCCTGTTCTCCTACCACCGCCTGCGCGACTGCATCCTGATCGCCGCCCGCACCGTGGAGCTGCTGGGCCA
CTCCTCCCTGAAGGGCCTGCGCCTGGGCTGGGAGGGCCTGAAGTACCTGTGGAACCTGCTGCTGTACTGGGGCCGCGAGCTGAAGAACTCCG
CCATCTCCCTGCTGGACACCATCGCCGTGGCCGTGGCCGAGTGGACCGACCGCGTGATCGAGATCGGCCAGCGCGCCTGCCGCGCCATCCTG
AACATCCCCCGCCGCATCCGCCAGGGCTTCGAGCGCGCCCTGCTGTAA

Fig. 44B

2003 CON_B Env.seq.opt

ATGCGCGTGAAGGGCATCCGCAAGAACTACCAGCACCTGTGGCGCTGGGGCACCATGCTGCTGGGCATGCTGATGATCTGCTCCGCCGCCGA
GAAGCTGTGGGTGACCGTGTACTACGGCGTGCCCGTGTGGAAGGAGGCCACCACCACCCTGTTCTGCGCCTCCGACGCCAAGGCCTACGACA
CCGAGGTGCACAACGTGTGGGCCACCCACGCCTGCGTGCCCACCGACCCCAACCCCCAGGAGGTGGTGCTGGAGAACGTGACCGAGAACTTC
AACATGTGGAAGAACAACATGGTGGAGCAGATGCACGAGGACATCATCTCCCTGTGGGACCAGTCCCTGAAGCCCTGCGTGAAGCTGACCCC
CCTGTGCGTGACCCTGAACTGCACCGACCTGATGAACGCCACCAACACCAACACCACCATCATCTACCGCTGGCGCGGCGAGATCAAGAACT
GCTCCTTCAACATCACCACCTCCATCCGCGACAAGGTGCAGAAGGAGTACGCCCTGTTCTACAAGCTGGACGTGGTGCCCATCGACAACGAC
AACACCTCCTACCGCCTGATCTCCTGCAACACCTCCGTGATCACCCAGGCCTGCCCCAAGGTGTCCTTCGAGCCCATCCCCATCCACTACTG
CGCCCCCGCCGGCTTCGCCATCCTGAAGTGCAACGACAAGAAGTTCAACGGCACCGGCCCCTGCACCAACGTGTCCACCGTGCAGTGCACCC
ACGGCATCCGCCCCGTGGTGTCCACCCAGCTGCTGCTGAACGGCTCCCTGGCCGAGGAGGAGGTGGTGATCCGCTCCGAGAACTTCACCGAC
AACGCCAAGACCATCATCGTGCAGCTGAACGAGTCCGTGGAGATCAACTGCACCCGCCCCAACAACAACACCCGCAAGTCCATCCACATCGG
CCCCGGCCGCGCCTTCTACACCACCGGCGAGATCATCGGCGACATCCGCCAGGCCCACTGCAACATCTCCCGCGCCAAGTGGAACAACACCC
TGAAGCAGATCGTGAAGAAGCTGCGCGAGCAGTTCGGCAACAAGACCATCGTGTTCAACCAGTCCTCCGGCGGCGACCCCGAGATCGTGATG
CACTCCTTCAACTGCGGCGGCGAGTTCTTCTACTGCAACACCACCCAGCTGTTCAACTCCACCTGGAACGGCACCTGGAACAACACCGAGGG
CAACATCACCCTGCCCTGCCGCATCAAGCAGATCATCAACATGTGGCAGGAGGTGGGCAAGGCCATGTACGCCCCCCCCATCCGCGGCCAGA
TCCGCTGCTCCTCCAACATCACCGGCCTGCTGCTGACCCGCGACGGCGGCAACAACGAGACCGAGATCTTCCGCCCCGGCGGCGGCGACATG
CGCGACAACTGGCGCTCCGAGCTGTACAAGTACAAGGTGGTGAAGATCGAGCCCCTGGGCGTGGCCCCCACCAAGGCCAAGCGCCGCGTGGT
GCAGCGCGAGAAGCGCGCCGTGGGCATCGGCGCCATGTTCCTGGGCTTCCTGGGCGCCGCCGGCTCCACCATGGGCGCCGCCTCCATGACCC
TGACCGTGCAGGCCCGCCAGCTGCTGTCCGGCATCGTGCAGCAGCAGAACAACCTGCTGCGCGCCATCGAGGCCCAGCAGCACCTGCTGCAG
CTGACCGTGTGGGGCATCAAGCAGCTGCAGGCCCGCGTGCTGGCCGTGGAGCGCTACCTGAAGGACCAGCAGCTGCTGGGCATCTGGGGCTG
CTCCGGCAAGCTGATCTGCACCACCGCCGTGCCCTGGAACGCCTCCTGGTCCAACAAGTCCCTGGACGAGATCTGGGACAACATGACCTGGA
TGGAGTGGGAGCGCGAGATCGACAACTACACCTCCCTGATCTACACCCTGATCGAGGAGTCCCAGAACCAGCAGGAGAAGAACGAGCAGGAG
CTGCTGGAGCTGGACAAGTGGGCCTCCCTGTGGAACTGGTTCGACATCACCAACTGGCTGTGGTACATCAAGATCTTCATCATGATCGTGGG
CGGCCTGGTGGGCCTGCGCATCGTGTTCGCCGTGCTGTCCATCGTGAACCGCGTGCGCCAGGGCTACTCCCCCCTGTCCTTCCAGACCCGCC
TGCCCGCCCCCCGCGGCCCCGACCGCCCCGAGGGCATCGAGGAGGAGGGCGGCGAGCGCGACCGCGACCGCTCCGGCCGCCTGGTGGACGGC
TTCCTGGCCCTGATCTGGGACGACCTGCGCTCCCTGTGCCTGTTCTCCTACCACCGCCTGCGCGACCTGCTGCTGATCGTGACCCGCATCGT
GGAGCTGCTGGGCCGCCGCGGCTGGGAGGTGCTGAAGTACTGGTGGAACCTGCTGCAGTACTGGTCCCAGGAGCTGAAGAACTCCGCCGTGT
CCCTGCTGAACGCCACCGCCATCGCCGTGGCCGAGGGCACCGACCGCGTGATCGAGGTGGTGCAGCGCGCCTGCCGCGCCATCCTGCACATC
CCCCGCCGCATCCGCCAGGGCCTGGAGCGCGCCCTGCTGTAA

Fig. 45A

2003 B.anc Env

MRVKGIRKNCQHLWRWGTMLLGMLMICSAAENLWVTVYYGVPVWKEATTTLFCASDAKAYETEVHNVWATHACVPTDPNPQEVVLENVTENF
NMWKNNMVEQMHEDIISLWDQSLKPCVKLTPLCVTLNCTDLLNATNTNSTNMYRWRGEIKNCSFNITTSIRDKMQKEYALFYKLDVVPIDNN
TSYRLINCNTSVITQACPKVSFEPIPIHYCTPAGFAILKCNDKKFNGTGPCKNVSTVQCTHGIRPVVSTQLLLNGSLAEEEVVIRSENFTDN
AKTIIVQLNESVEINCTRPNNNTRKSIHIGPGRAFYATGEIIGDIRQAHCNLSRAKWNNTLKQVVTKLREQFDNKTIVFNPSSGGDPEIVMH
SFNCGGEFFYCNTTQLFNSTWNGTWNNTEGNITLPCRIKQIINMWQEVGKAMYAPPIRGQIRCSSNITGLLLTRDGGNNETEIFRPGGGDMR
DNWRSELYKYKVVKIEPLGVAPTKAKRRVVQREKRAVGIGAMFLGFLGAAGSTMGAASMTLTVQARQLLSGIVQQQNNLLRAIEAQQHLLQL
TVWGIKQLQARVLAVERYLRDQQLLGIWGCSGKLICTTTVPWNASWSNKSLDEIWNNMTWMEWEREIDNYTGLIYTLIEESQNQQEKNEQEL
LELDKWASLWNWFDITNWLWYIKIFIMIVGGLVGLRIVFAVLSIVNRVRQGYSPLSFQTRLPAPRGPDRPEGIEEEGGERDRDRSGRLVNGF
LALIWDDLRSLCLFSYHRLRDLLLIVARIVELLGRRGWEALKYWWNLLQYWSQELKNSAVSLLNATAIAVAEGTDRVIEVVQRACRAILHIP
RRIRQGLERALL$

Fig. 46A

2003 CON_C Env

MRVRGILRNCQQWWIWGILGFWMLMICNVVGNLWVTVYYGVPVWKEAKTTLFCASDAKAYEKEVHNVWATHACVPTDPNPQEIVLENVTENF
NMWKNDMVDQMHEDIISLWDQSLKPCVKLTPLCVTLNCTNATNATNTMGEIKNCSFNITTELRDKKQKVYALFYRLDIVPLNENNSYRLINC
NTSAITQACPKVSFDPIPIHYCAPAGYAILKCNNKTFNGTGPCNNVSTVQCTHGIKPVVSTQLLLNGSLAEEEIIIRSENLTNNAKTIIVHL
NESVEIVCTRPNNNTRKSIRIGPGQTFYATGDIIGDIRQAHCNISEDKWNKTLQKVSKKLKEHFPNKTIKFEPSSGGDLEITTHSFNCRGEF
FYCNTSKLFNSTYNSTNSTITLPCRIKQIINMWQEVGRAMYAPPIAGNITCKSNITGLLLTRDGGKNNTETFRPGGGDMRDNWRSELYKYKV
VEIKPLGIAPTKAKRRVVEREKRAVGIGAVFLGFLGAAGSTMGAASITLTVQARQLLSGIVQQQSNLLRAIEAQQHMLQLTVWGIKQLQTRV
LAIERYLKDQQLLGIWGCSGKLICTTAVPWNSSWSNKSQEDIWDNMTWMQWDREISNYTDTIYRLLEDSQNQQEKNEKDLLALDSWKNLWNW
FDITNWLWYIKIFIMIVGGLIGLRIIFAVLSIVNRVRQGYSPLSFQTLTPNPRGPDRLGRIEEEGGEQDRDRSIRLVSGFLALAWDDLRSLC
LFSYHRLRDFILIAARAVELLGRSSLRGLQRGWEALKYLGSLVQYWGLELKKSAISLLDTIAIAVAEGTDRIIELIQRICRAIRNIPRRIRQ
GFEAALQ$

Fig. 45B

```
2003 B.anc Env.seq.opt
ATGGCGCGTGAAGGCATCCGCAAGAACTGCCAGCACCTGTGGCGCTGGGCACCATGCTGCTGCTGCTGATGATCTGCTCCGCCGCCGA
GAACCTGTGGGTGACCGTGTACTACGGCGTGCCCGTGTGGAAGGAGGCCACCACCACCCTGTTCTGCGCCAGCGACGCCAAGGCCTACGAGA
CCGAGGTGCACAACGTGTGGGCCACCCACGCCTGCGTGCCCACCGACCCCAACCCCCAGGAGGTGGTGCTGGAGAACGTGACCGAGAACTTC
AACATGTGGAAGAACAACATGGTGGAGCAGATGCACGAGGACAT

Fig. 46B

2003 CON_C Env.seq.opt
ATGCGCGTGCGCGGCATCCTGCGCAACTGCCAGCAGTGGTGGAAGTGGCCGCCGCTTCTGGGCTTCTGGGGCATCCTGGGCATCTGCAACGTGGTGGGG
CAACCTGTGGGTGACCGTGTACTACGGCGTGCCCGTGCTGCCGCTGCTGCCCTGTTTCTGCGCCTGGAGAGATCGTGGAGAACGTGACCGAGAACTTC
AGGAGGTGCACAACGTGTGTGGGCACCGCGCTGCGCCTGCCCTGTGTCTGAAGGAGATCGTCCGGAGAGATCGTGGAGAACGTGACCGAGAACTTC
AACATGTGGAAGAACGACATGGTGGACCAGATGCACGAGGACATCATCCGTGTGGGACCAGTGCCCGAGATCAAGAACTGTCTCTTCAACATCACCACCGAGC
CCTGTGCGCTGAACCTGACCCTGAACCTGAACAAGCAGAAGGTGCAGGCCCTGTTCTACGCCCTGGACATCGTGCCCCTGAACGAGAACAACTCCTACCGCCTGATCAACTGC
TGCGCGACAAGAACAGAAGGTGTACGCCCTGTTCTACCGGCCCCTGTGCCCCCTGATCCCCATCTCCGCCTACGCCCATCGTGGGGAGTTC
AACACCTCCGCCAT

Fig. 47A

2003 C.anc Env

MRVMGILRNCQQWWIWGILGFWMLMICNVVGNLWVTVYYGVPVWKEAKTTLFCASDAKAYEREVHNVWATHACVPTDPNPQEMVLENVTENF
NMWKNDMVDQMHEDIISLWDQSLKPCVKLTPLCVTLNCTNATNATNTMGEMKNCSFNITTELRDKKQKVYALFYRLDIVPLNDNNSYRLINC
NTSAITQACPKVSFDPIPIHYCAPAGYAILKCNNKTFNGTGPCNNVSTVQCTHGIKPVVSTQLLLNGSLAEEEIIIRSENLTDNAKTIIVHL
NESVEIVCTRPNNNTRKSIRIGPGQTFYATGDIIGDIRQAHCNISEEKWNKTLQRVGEKLKEHFPNKTIKFAPSSGGDLEITTHSFNCRGEF
FYCNTSRLFNSTYNSKNSTITLPCRIKQIINMWQGVGRAMYAPPIAGNITCKSNITGLLLTRDGGKNNTETFRPGGGDMRDNWRSELYKYKV
VEIKPLGIAPTEAKRRVVEREKRAVGIGAVFLGFLGAAGSTMGAASITLTVQARQLLSGIVQQQSNLLRAIEAQQHMLQLTVWGIKQLQTRV
LAIERYLKDQQLLGIWGCSGKLICTTAVPWNSSWSNKSQEEIWDNMTWMQWDREISNYTDTIYRLLEDSQNQQEKNEQDLLALDSWENLWNW
FDITNWLWYIKIFIMIVGGLIGLRIIFAVLSIVNRVRQGYSPLSFQTLTPNPRGPDRLGRIEEEGGEQDRDRSIRLVSGFLALAWDDLRSLC
LFSYHRLRDFILIAARAVELLGRSSLRGLQRGWEALKYLGSLVQYWGLELKKSAISLLDTIAIAVAEGTDRIIELIQRICRAIRNIPRRIRQ
GFEAALL$

Fig. 48A

2003 CON_D Env

MRVRGIQRNYQHLWRWGIMLLGMLMICSVAENLWVTVYYGVPVWKEATTTLFCASDAKSYKTEAHNIWATHACVPTDPNPQEIELENVTENF
NMWKNNMVEQMHEDIISLWDQSLKPCVKLTPLCVTLNCTDVKRNNTSNDTNEGEMKNCSFNITTEIRDKKKQVHALFYKLDVVPIDDNNSNT
SYRLINCNTSAITQACPKVTFEPIPIHYCAPAGFAILKCKDKKFNGTGPCKNVSTVQCTHGIRPVVSTQLLLNGSLAEEEIIIRSENLTNNA
KIIIVQLNESVTINCTRPYNNTRQRTPIGPGQALYTTRIKGDIRQAHCNISRAEWNKTLQQVAKKLGDLLNKTTIIFKPSSGGDPEITTHSF
NCGGEFFYCNTSRLFNSTWNNTKWNSTGKITLPCRIKQIINMWQGVGKAMYAPPIEGLIKCSSNITGLLLTRDGGANNSHNETFRPGGGDMR
DNWRSELYKYKVVKIEPLGVAPTRAKRRVVEREKRAIGLGAMFLGFLGAAGSTMGAASMTLTVQARQLLSGIVQQQNNLLRAIEAQQHLLQL
TVWGIKQLQARILAVERYLKDQQLLGIWGCSGKHICTTTVPWNSSWSNKSLDEIWNNMTWMEWEREIDNYTGLIYSLIEESQNQQEKNEQEL
LELDKWASLWNWFSITQWLWYIKIFIMIVGGLIGLRIVFAVLSLVNRVRQGYSPLSFQTLLPAPRGPDRPEGIEEEGGEQGRGRSIRLVNGF
SALIWDDLRNLCLFSYHRLRDLILIAARIVELLGRRGWEALKYLWNLLQYWIQELKNSAISLFDTTAIAVAEGTDRVIEIVQRACRAILNIP
TRIRQGLERALL$

Fig. 47B

```
2003 C.anc Env.seq.opt
ATGCGCGTGATGGGCATCCTGCGCAACTGCCAGCAGTGGTGGATCTGGGGCATCCTGGGCTTCTGGATGCTGATGATCTGCAACGTGGTGGG
CAACCTGTGGGTGACCGTGTACTACGGCGTGCCCGTGTGGAAGGAGGCCACCACCACCCTGTTCTGCGCCTCCGACGCCAAGGCCTACGAGC
GCGAGGTGCACAACGTGTGGGCCACCCACGCCTGCGTGCCCACCGACCCCAACCCCCAGGAGATGGTGCTGGAGAACGTGACCGAGAACTTC
AACATGTGGAAGAACGACATGGTGGACCAGATGCACGAGGACATCATCTCCCTGTGGGACCAGTCCCTGAAGCCCTGTGTGAAGCTGACCCC
CCTGTGCGTGACCCTGAACTGCACCAACGTGAACGCCACCATGGGCGAGATGAAGAACTGCTCCTTCAACATCACCACCGAGC
TGCGCGACAAGAAGCAGAAGGTGTACGCCCTGTTCTACCGCCTGGACGTGGTGCCCCTGGACGAGAACAACAGCAGCTCCGCCATGCTGAAC
AACACCTCCGCCATCAAGAGACCTTCAACGGCACCGGCCCTGCCCAAGGTGTCCTTCGACCCCATCCCCATCCACTACTGCGCCCCCGCCGGC
GTGCAACAAGACCTTCAACGGCACCGGCCCTGCCCAAGGTGTCCTTCGACCCCATCCCCATCCACTACTGCGCACCCGCTGGTGTCCACCCC
AGCTGCTGCTGAACGGCTCCCTGGCCGAGGCCGGCCAAGGAGATCATCATCCGCTCCGAGAACCTGACCGACAACGCCAAGACCATCATCGTG
AACGAGTCCGTGGAGATCGTGTGCACCCGCCCCAACAACAACACCCGCAAGTCCATCCGCATCGGCCCCAGACCTTCTACGCCACCGG
CGACATCATCGGCGACATCCGCCAGGCCCACTGCAACATCTCCGAGAGAAGTGGAACAAGACCCTCCAGAGATCCTGAAGCTGGGCGAGTTC
AGCAACCTCCCCAACAAGACCATCAAGTTCGCCCCCTCCAGCGGCGGCGACCTGGAGATCCTGACCCTGCAAGTCCAACATCACCTGCAAGCCGCTGCTGACCC
CATGTGGCAGCGGTGGGCCGTGGCCCCATGTACGCCCCCCCCATCCGCGGCCAAGCCCGGCGCGCCGAGGGCGCCAAGCCGCGTGGCGCGCCGTGTT
GCGACGGGCAAGAACAACACCGAGACCTTCCGCCCCGGCGGCGGCGACATGCGCGACAACTGGCGCTCCGAGCTGTACAAGTACAAGGTG
GTGGAGATCAAGCCCCTGGGCATCGCCCCCACCAGGGCCAAGCGCCGAGCGCCAAGCGCGCAAGCCCGCCAGTGCCTGTCCGCCATGCGTGC
CCTGGGCTTCCTGGGCGCCGCCGGCTCCACCATGGGCGCCGCCAGCATGACCCTGACCGTGCAGGCCCGCCAGCTGCTGTCCGGCATCGTGC
AGCAGCAGAACAACCTGCTGCGCGCCATCGAGGCCCAGCAGCACCTGCTGCAGCTGACCGTGTGGGGCATCAAGCAGCTGCAGACCCGCGTG
CTGGCCATCGAGCGCTACCTGAAGGACCAGCAGCTGCTGGGCATCTGGGGCTGCTCCGGCAAGCTGATCTGCACCACCGCCGTGCCCTGGAA
CTCCTCCTGGTCCAACAAGTCCCAAGAGACTCCAGGAGGAAGAACCAGGAGGAGAACCAGATCTGGGACAACCTGTGGAACTGG
TTCGACATCACCAACTGGCTGTGGTACATCAAGATCTTCATCATGATCGTGGGCGGCCTGATCGGCCTGCGCATCATCTTCGCCGTGCTGTC
CATCGTGAACCGCGTGCGCCAGGGCTACTCCCCCCTGTCCTTCCAGACCCGCCTGCCCTCGGTGCCCGACCGCCTGGCCGCCGCCCCGTGC
AGGAGAGGGCAGCGAGCAGGACCGCGACCGCTCCATCCGCCTGGTGAACGGCTCCCTGGCCCTGGCCTGGGACGATCCTGCCCGCCGCCCCGG
CTGTTCTCCTACCACCGCCTGCGCGATCTGATCCTGGTCGCCCTGGCGCCCTGAAGTACCTGGGCAACCTGCTGCTGACCTGGGCCGCAGCG
CGGCTGGGGAGCCGTGAAGTACCTGGGCAACCTGCTGCTGTACTGGTCCCAGGAACTGAAGAAGTCCGCCATCAACCTGCTGGACACCATCGC
CATCGCCGTGGCCGAGGGCACCGACCGCGTGATCGAGCTGATCCAGCGCCATCGGGCGCGCGCCATCCGCCAACATCCCCCGCGCGCATCCGCCAG
GGCTTCGAGCGCGCCCTGCTGTAA
```

Fig. 48B

2003 CON_D Env.seq.opt

ATGCGCGTGCGCGGCATCCAGCGCAACTACCAGCACCTGTGGCGCTGGGGCATCATGCTGCTGGGCATGCTGATGATCTGCTCCGTGGCCGA
GAACCTGTGGGTGACCGTGTACTACGGCGTGCCCGTGTGGAAGGAGGCCACCACCACCCTGTTCTGCGCCTCCGACGCCAAGTCCTACAAGA
CCGAGGCCCACAACATCTGGGCCACCCACGCCTGCGTGCCCACCGACCCCAACCCCCAGGAGATCGAGCTGGAGAACGTGACCGAGAACTTC
AACATGTGGAAGAACAACATGGTGGAGCAGATGCACGAGGACATCATCTCCCTGTGGGACCAGTCCCTGAAGCCCTGCGTGAAGCTGACCCC
CCTGTGCGTGACCCTGAACTGCACCGACGTGAAGCGCAACAACACCTCCAACGACACCAACGAGGGCGAGATGAAGAACTGCTCCTTCAACA
TCACCACCGAGATCCGCGACAAGAAGAAGCAGGTGCACGCCCTGTTCTACAAGCTGGACGTGGTGCCCATCGACGACAACAACTCCAACACC
TCCTACCGCCTGATCAACTGCAACACCTCCGCCATCACCCAGGCCTGCCCCAAGGTGACCTTCGAGCCCATCCCCATCCACTACTGCGCCCC
CGCCGGCTTCGCCATCCTGAAGTGCAAGGACAAGAAGTTCAACGGCACCGGCCCCTGCAAGAACGTGTCCACCGTGCAGTGCACCCACGGCA
TCCGCCCCGTGGTGTCCACCCAGCTGCTGCTGAACGGCTCCCTGGCCGAGGAGGAGATCATCATCCGCTCCGAGAACCTGACCAACAACGCC
AAGATCATCATCGTGCAGCTGAACGAGTCCGTGACCATCAACTGCACCCGCCCCTACAACAACACCCGCCAGCGCACCCCCATCGGCCCCGG
CCAGGCCCTGTACACCACCCGCATCAAGGGCGACATCCGCCAGGCCCACTGCAACATCTCCCGCGCCGAGTGGAACAAGACCCTGCAGCAGG
TGGCCAAGAAGCTGGGCGACCTGCTGAACAAGACCACCATCATCTTCAAGCCCTCCTCCGGCGGCGACCCCGAGATCACCACCCACTCCTTC
AACTGCGGCGGCGAGTTCTTCTACTGCAACACCTCCCGCCTGTTCAACTCCACCTGGAACAACACCAAGTGGAACTCCACCGGCAAGATCAC
CCTGCCCTGCCGCATCAAGCAGATCATCAACATGTGGCAGGGCGTGGGCAAGGCCATGTACGCCCCCCCCATCGAGGGCCTGATCAAGTGCT
CCTCCAACATCACCGGCCTGCTGCTGACCCGCGACGGCGGCGCCAACAACTCCCACAACGAGACCTTCCGCCCCGGCGGCGGCGACATGCGC
GACAACTGGCGCTCCGAGCTGTACAAGTACAAGGTGGTGAAGATCGAGCCCCTGGGCGTGGCCCCCACCCGCGCCAAGCGCCGCGTGGTGGA
GCGCGAGAAGCGCGCCATCGGCCTGGGCGCCATGTTCCTGGGCTTCCTGGGCGCCGCCGGCTCCACCATGGGCGCCGCCTCCATGACCCTGA
CCGTGCAGGCCCGCCAGCTGCTGTCCGGCATCGTGCAGCAGCAGAACAACCTGCTGCGCGCCATCGAGGCCCAGCAGCACCTGCTGCAGCTG
ACCGTGTGGGGCATCAAGCAGCTGCAGGCCCGCATCCTGGCCGTGGAGCGCTACCTGAAGGACCAGCAGCTGCTGGGCATCTGGGGCTGCTC
CGGCAAGCACATCTGCACCACCACCGTGCCCTGGAACTCCTCCTGGTCCAACAAGTCCCTGGACGAGATCTGGAACAACATGACCTGGATGG
AGTGGGAGCGCGAGATCGACAACTACACCGGCCTGATCTACTCCCTGATCGAGGAGTCCCAGAACCAGCAGGAGAAGAACGAGCAGGAGCTG
CTGGAGCTGGACAAGTGGGCCTCCCTGTGGAACTGGTTCTCCATCACCCAGTGGCTGTGGTACATCAAGATCTTCATCATGATCGTGGGCGG
CCTGATCGGCCTGCGCATCGTGTTCGCCGTGCTGTCCCTGGTGAACCGCGTGCGCCAGGGCTACTCCCCCCTGTCCTTCCAGACCCTGCTGC
CCGCCCCCCGCGGCCCCGACCGCCCCGAGGGCATCGAGGAGGAGGGCGGCGAGCAGGGCCGCGGCCGCTCCATCCGCCTGGTGAACGGCTTC
TCCGCCCTGATCTGGGACGACCTGCGCAACCTGTGCCTGTTCTCCTACCACCGCCTGCGCGACCTGATCCTGATCGCCGCCCGCATCGTGGA
GCTGCTGGGCCGCCGCGGCTGGGAGGCCCTGAAGTACCTGTGGAACCTGCTGCAGTACTGGATCCAGGAGCTGAAGAACTCCGCCATCTCCC
TGTTCGACACCACCGCCATCGCCGTGGCCGAGGGCACCGACCGCGTGATCGAGATCGTGCAGCGCGCCTGCCGCGCCATCCTGAACATCCCC
ACCCGCATCCGCCAGGGCCTGGAGCGCGCCCTGCTGTAA

Fig. 49A

2003_CON_F1 Env

MRVRGMQRNWQHLGKWGLLFLGILIIICNAAENLWVTVYYGVPVWKEATTLFCASDAKSYEKEVHNVWATHACVPTDPNPQEVVLENVTENF
DMWKNNMVEQMHTDIISLWDQSLKPCVKLTPLCVTLNCTDVNATNNDTNDNKTGAIQNCSFNMTTEVRDKKLKVHALFYKLDIVPLSNNNSK
YRLINCNTSTITQACPKVSWDPIPIHYCAPAGYAILKCNDKRFNGTGPCKNVSTVQCTHGIKPVVSTQLLLNGSLAEEDIIIRSQNISDNAK
TIIVHLNESVQINCTRPNNNTRKSIHLGPGQAFYATGEIIGDIRKAHCNISGTQWNKTLEQVKAKLKSHFPNKTIKFENSSSGGDLEITMHSF
NCRGEFFYCNTSGLFNDTGSNGTITLPCRIKQIVNMWQEVGRAMYAAPIAGNITCNSNITGLLLTRDGGQNNTETFRPGGGNMKDNWRSELY
KYKVVEIEPLGVAPTKAKRQVVKRERRAVGIGAVFLGFLGAAGSTMGAASITLTVQARQLLSGIVQQQNLLRAIEAQQHLLQLTVWGIKQL
QARVLAVERYLKDQQLLGLWGCSGKLICTTNVPWNSSWSNKSQDEIWNNMTWMEWEKEISNYSNIIYRLIEESQNQQEKNEQELLALDKWAS
LWNWFDISNWLWYIKIFIMIVGGLIGLRIVFAVLSIVNRVRKGYSPLSLQTLIPSPREPDRPEGIEEGGEQGKDRSVRLVNGFLALVWDDL
RNLCLFSYRHLRDFLLIAARIVDRGLRRGWEALKYLGNLTQYWSQELKNSAISLLNTTAIVVAEGTDRVIEALQRAGRAVLNIPRRIRQGLE
RALLS

Fig. 50A

2003_CON_F2 Env

MRVREMQRNWQHLGKWGLLFLGILIIICNAADNLWVTVYYGVPVWKEATTLFCASDAKAYEREVHNVWATYACVPTDPSPQELVLGNVTENF
NMWKNNMVDQMHEDIISLWDQSLKPCVKLTPLCVTLNCTDVNVTINTTNVTLGEIKNCSFNITTEIKDKKKEYALFYRLDVVPINNSIVYR
LISCNTSTVTQACPKVSFEPIPIHYCAPAGFAILKCNDKKFNGTGLCRNVSTVQCTHGIRPVVSTQLLLNGSLAEEDIIIRSENISDNTKTI
IVQFNRSVEINCTRPNNNTRKSIRIGPGRAFYATGDIIGDIRKAYCNINRTLWNETLKKVAEEFKNHFNITVTFNPSSGGDLEITTHSFNCR
GEFFYCNTSDLFNNTEVNNTKTITLPCRIRQFVNMWQRVGRAMYAPPIAGQIQCNSNITGLLLTRDGGKNGSETLRPGGGDMRDNWRSELYK
YKVVKIEPLGVAPTKAKRQVVQREKRAVGIGAVLLGFLGAAGSTMGAASITLTVQARQLLSGIVQQQSNLLKAIEAQQHLLQLTVWGIKQLQ
ARILAVERYLKDQQLLGIWGCSGKLICTTNVPWNSSWSNRVRQGYSPLSLQTLIPNPRGPERPGGIEEEGEQDRDRSIRLVSGFLALAWDDLR
WSWFTITNWLWYITNWLWNLPQYWGQELKNSAISLLDTTAIAVAEGTDRIIEVLQRAGRAVLHIPRRIRQGFER
ALLS

Fig. 49B

```
2003_CON_F1_Env.seq.opt
ATGGCGGTGCGCGGCATGCAGCAGCAACTGGCAGCACCTGGGCAAGTGGGCCTGCTGTTCCTGGCATCCTGATCATCTGCTGCAAGCGCCGCCGA
GAACCTGTGGGTGACCGTGTACTACGGCGTGCCGCGTGCCCGGCCGTGCCACCACCCCAACCCTGTTCTGCGCCAAGTCCTACGAGA
AGGAGGTGCACAACGTGTGGGCCACCCACGCCTGCGTGCCCACCGACCCTGTGGGACCAGTCCCTGTGGGACCAACAGGACCAACAAGACCGGAACGTGACCGAGAACTTC
GACATGTGGAAGAACATGGTGGAGCAGATGCACGAGGACATCATCCTGTGGGACCAGTCCCTGAAGCCCTGCGTGAAGCTGACCCC
CCTGTGCGTGACCCTGAACTGCACCGACGTGAAGGTGCACCAGAAGAGCTGACCATCCACCATCCCCCATCCCAATCCCCATCCCACCAAGTCTGCTCCTTCA
ACATGACCACCGAGGTGCGCGACAAGAAGCAGCTGCAAGAACTGCCCCATCGGCGACATCGTGCCCATCCCATCCCATCCACCTGCGCCCCCAAG
TACCGCCTGATCAACTGCAACACGCCTCCACCACTGCAAGGTGCACCGGCCCTGCCCCGGCTTCAACGGCACAAGCGCTTCAAGGACACACCGTGTCCCCTGCAAGAACGTGTCCCTGCTGCACCCACCGGCATCA
CGGCTACCGCCATCCTGAAGTGCAACCAGAGCGCCTTCAACGGCTTCAACAGCGGCGACATCATCAACATCCGCCAAGTCCATCGGGCCCCCCGCCA
AGCCCGTGGTGTCCACCCAGCTGCTGCTGAACGGCAGCCTGGCGAAGTCCGTGCAGATCATCCGCGACATCGGCGACATCATCAACATCATCCCCAAGTCCATCCTGAACGACCCTGGAGCAGG
GCCTTTCTACGCCACCCGGCGAGTGAAGTCCACTGCCCCATCAAGACAATCAAGTTCAACGGCCCCCCCGGCCAGCTGCGGCAACAACCATCCCCCAACCTGGGCGTCCGAGCTGTAC
TGAAGGCCAAGCTGAACACTGCGGACCCTTCCCGCCGCCAGAGAACCCGGCCCAATGAAGGGACCTCCAAGCGCCTTCCCATCCCGAGCTCCTCTG
AACTGCGCGGCAGAGTTCTTCTACTGCAACACCCTCCGGCTGTTCAACGACACCATCACCCTGCCGCATCAA
GCAGATCGTGAACATGTGGCAGGAGGTTGGGCAGGAGATCATCACCGGCCCCCCCGGCCAACATGAACGGCAACATGAACATGAAGGACAACTGGGCGCTCCGAGCTGTAC
TGCTGCGTGACCCGGCGACGGCCAGAACCAGAACACCTTCCGCCCCGGCGGCCAACATGAAGGACAACATGAACATGACCCCTTCTGCGGGCTGTCCGGGAGCTGTCC
AAGTACAAGGTGGTGAAGATCGAGCCTTCCTGGGCCTGTGTTCCTGCAGCAGAACCAACTGGGCCCTTCAGGCGCCGAGGCGCCGCCGCCAGCTGCTGT
CGGCGCCGTGTTCCTGGCCTTCTTCCTGGGCCTGTCCCGCATCAAGAACATGAACATGACCCTGCACCCTGCACCCTGCAGGCCGTGCAGGCCGTGCAGGCCGTCAAGCACTGCGCCAGCTGCAAGCGACTG
CCGGCATCGAGCACCCTGGCCCTGCAAGTCCGAGGAGTGCCTGCCAGCGAGAGCTTGGCCCTGGCCTGCGACCCTGCGACCAGCAAGGTCGTGCCGGCGACCCGCCCGTGCACCACCAA
CAGGCCCGCCGGCCCCTGGCCCGGCCACCAAGTCCCAAGGAGTCCTGCTGAGGACGAGCTGCGAGAGAAGCCCCAAGCCAAGATCCGAGCCCGGCCCCTCCGACACCAA
CGTGCCCCTGGAACATCATCTACCGCCTGTTCGACATCTCCAACTGGCGTCGCCAAGCGCGTGCCGAGTGCTGCTGCTGGCATGACATCCCCTCCCCCCCAACT
CTGTGGAACTGGTTCGACATCTCCAACTGGCTGTGGTACATCAAGATCTTCATCATGATCGTGGCCGGCCTGATCGGCCTGCGCCATCGTGTCT
CGCCGTGTCGTGTTCCATCGTGAACCGCGGGCGGCAGCGCCCTGGGCCGAGCTACCTGCCCAAGCCCCGGTCGCCGATCCCCCGAACCAGCGCCCTGCCCCGCCGAGCCCGACCGCC
CCGAGGGCATCGAGGAGGGCCGGGGCCGCCTACCGCCGACTTCATCGCCGACCTGTCCCCCGCCCCCATCGTGCCGCCCGCCCGGCCTGGGA
CGCAACCTGTGCCTGTTCTCCTATCACCCGCTCAGGAGCTGAAGAACTCCCTGCTGAAGACTGCTCCCCTGATCCCTGCGCCATCGTGCCGGCCATCGTGGA
GGCCCCTGACCCTGGGCAACCTGAACCTGACCTGAACCTGACCCTGACCCTGAACGACCCCGCCGCCCTGCTGAACATCCCCCGCCCCCAGGCCCTGGAG
CGCGCCCTGCTGTAA
```

Fig. 50B

```
2003_CON_F2_Env.seq.opt
ATGCGCGTGCGCGAGATGCAGCGCAACTGGCAGCACCTGGGCAAGTGGGGCCTGCTGTTCCTGGGCATCCTGATCATCTGCAACGCCGCCGA
CAACCTGTGGGGTGACCGTGTACTACGGCGTGCCCGTGTGGGAAGGAGGCCACCACCCCTGTTCTGCGCCTGGCAACGTGGTGCTGACCGAGAACTTC
GCGAGGTGCACAACGTGTGGGCCACCCACGCCTGCGTGCCCACCGACCCCTCCCAGGAGGTGGTCCTGTGGGACCCAGCCCTGCGTGAAGCTGACCCC
AACATGTGGAAGAACAACATGGTGGACCAGATGCACGAGGACATCATCTCCCTGTGGGACCAGAGCCTGAAGCCCTGTGTGAAGCTGACCCC
CCTGTGCGTGACCCTGAACTGCACCGACGTGAACGTGACCGGCGAGATCAAGAACTGCTCCTTCAACA
TCACCACCGAGATCAAGGACAAGAAGAAGAAGGAGTACGCCCTGTTCTACCGCCTGGACGTGGTGCCCATCAACAACTACTGCGCCATCCGC
CTGATCCTGCAAGTGCAACGACAAGAAGTTCAACGGACACCTCCACCGGCACCTGCCCCAAGGTGTCCTTCGAGCCCATCCCCATCCACTACTGCGCCCCGGCTT
CGCCATCCTGAAGTGCAACGACAAGAAGTTCAACGGCACCGGCCCGTGCCAACAACGTGTCCACCGTGCAGTGCACCCACGGCATCCGCCCCG
TGGTGTCCACCCAGCTGCTGCTGAACGGCTCCCTGGCGGAGGACATCATCATCCGCTCCGAGAACATCTCCGACAACACCCGCAACATCATCGTGCAACGCCAT
ATCCGTCAGTTCAACGCCACGCTGTCCGTGGAGATCAACCACCGGCGACATCATCGGCGACATCCGCAAGGCCTTCAACATGTACGCCCCTGAAGAGACCCCCATC
CTACGCCACCGGCGACATCATCGGCGACATCCGCAAGGCCTTCAACATGTACGCCCCTGAAGAGACCCCCCACTCCTTCCCTGCCCATCCGCC
AGGAGTTCAAGAACCACTTCAACATCACCGTGACCTTGTTCAACAACACCCTCCGAGGTGAACAACAACCGCCATCGCCCCCATCGCCCA
GGCGAGTTCTTCTACTGCAACACCACCGAGCTGCCCCTGAACAACTCCAATCACCCGGCCGCCAAGTCCAATCACCCGGCCGCCA
GTTCGTGAACATGTGGCAGGGCGTGGGCAGGGCCATGTACGCCCCCCATCGCCCGACATCAAGCCGCGATTCAACCCCCGCGCGAACATCATCACCGGCCTGC
TGCTGACCCGCGACGGCGGCAAGAACGGCAATGAGGCCCCAGGTGCGTGGCAGCCCGTGCCAGCTGCTGTCCG
TACAAGGTGGTGAAGATCGAGCCGCTTCCTGGGGCTACCACCATGGCAAGCGCGAGAAGCGCGCCGTGGGCATCGG
CGCCCTGTGGCTGGGCAGCAGTGCAGCATCCTGCTGAAGCCAACCTGCTGAAGGCCATCGAGGCCCAGCAGCACCTGCTGCAGCTGACC
GCCATCGTCCAGGCCATCGAGCGCCGCCCTGCGCTGCTGAAGGAGTACCCAACAGTCCCAACAGCCGAGATCCCAACTACA
GCCCTGATCCCTGGTCCAACAAGCTCCCCGTGATCTGAGCCCCAGGCCGAAGTCGGGCCCGCCAGCAGCTGCTGCTGACAGCCCGCCA
CCGACACCATCTACCGCCTGCTGGAGGACGAACCAACTGGCTGTGTGCCCCAGGGCACCAAGTGGGACAACCTG
TGGTCCTGGTTCAACATCAGCAACTGGGCTGTACACCATCAAGATCTTCATCATCATGATCGTGGGCCCCTGCGCCTGCGCATCGTGTTCGC
CGTGCTGTCCGTGGTGAACAGAGCGGCCAGGGCTACAGCCCCTTGTCCTGCCCCACCCCCAACCCCCCCCCGACCCCCCGGAGCCCCGACCGGAGCCCCGACCCCG
GCGGCATCGAGGAGGAGGGCGGCGAGCAGGACAGGGACCGCTCCATCCGCCTGGTCAACGGCTCCATCGTGGAGGGCCGGGACCGCCTGCCTGCGC
TCCCTGTGCCTGTTCTCCTACCACCGCCTGCGGGACTTCATCCTGATCGCCGCCAGGACCGTGGAGCTGCTCGGGCACCGCAGCCTGAAGGGCCTGCGCCGGGCTTGGGGAGCC
CCTGAAGTACCTGTGGAACCTGCTGCAGTACTGGGGCCAGGAGCTGAAGAACTCCGCCATCTCCCTGCTGGACACCATCGCCATCGCCGTGG
CCGAGGGCACCGACCGCATCATCGAGGTGCTGCAGCGCCTCGCCCGGGCCATCCTGCACATCCCCCGCCGCATCCGCCAGGGCCTTCGAGCGC
GCCCTGCTGTAA
```

Fig. 51A

2003 CON_G Env

MRVKGIQRNWQHLWKWGTLILGLVIICSASNNLWVTVYYGVPVWEDADTTLFCASDAKAYSTERHNVWATHACVPTDPNPQEITLENVTENF
NMWKNNMVEQMHEDIISLMDESLKPCVKLTPLCVTLNCTDVNVTNNNTNNTKKEIKNCSFNITTEIRDKKKEYALFYRLDVVPINDNGNSS
IYRLINCNVSTIKQACPKVTFDPIPIHYCAPAGFAILKCRDKKFNGTGPCKNVSTVQCTHGIKPVVSTQLLLNGSLAEEEIIRSENITDNT
KVIIVQLNETIEINCTRPNNNTRKSIRIGPGQAFYATGDIIGDIRQAHCNVSRTKWNEMLQKVKAQLKKIFNKSITFNSSSGGDLEITTHSF
NCRGEFFYCNTSGLFNNSLLNSTNSTITLPCKIKQIVRMWQRVGQAMYAPPIAGNITCRSNITGLLLTRDGGNNNTETFRPGGGDMRDNWRS
ELYKYKIVKIKPLGVAPTRARRRVEREKRAVGLGAVLLGFLGAAGSTMGAASITLTVQVRQLLSGIVQQQSNLLRAIEAQQHLLQLTVWGI
KQLQARVLAVERYLKDQQLLGIWGCSGKLICTTNVPWNTSWSNKSYNEIWDNMTWIEWEREISNYTQQIYSLIEESQNQQEKNEQDLLALDK
WASLWNWFDITKWLWYIKIFIMIVGGLIGLRIVFAVLSIVNRVRQGYSPLSFQTLTHHQREPDRPERIEEGGEQDKDRSIRLVSGFLALAW
DDLRSLCLFSYHRLRDFLLIAARTVELLGRSSLKGLRLGWEGLKYLWNLLLYWGQELKNSAINLLDTIAIAVANWTDRVIEVAQRACRAILN
IPRRIRQGLERALLS

Fig. 52A

2003 CON_H Env

TRVMETQRNYPSLWRWGTLILGMLLICSAAGNLWVTVYYGVPVWKEAKTTLFCASDAKAYETEKHNVWATHACVPTDPNPQEMVLENVTENF
NMWENDMVEQMHTDIISLWDQSLKPCVKLTPLCVTLDCSNVNTTNATNSRFNMQEELTNCSFNVTTVIRDKQQKVHALFYRLDVVPIDDNNS
YQYRLINCNTSVITQACPKVSFEPIPIHYCAPAGFAILKCNNKTFNGTGPCTNVSTVQCTHGIRPVVSTQLLLNGSLAEEQVIIRSKNISDN
TKNIIVQLNKPVEITCTRPNNNTRKSIHLGPGQAFYATGDIIGDIRQAHCNISGKKWNKTLHQVVTQLGKYFDNRTIIFKPHSGGDMEVTTH
SFNCRGEFFYCNTSGLIFNSSWTNSTNDTKNIITLPCRIKQIVNMWQRVGQAMYAPPIKGNITCVSNITGLILTFDEGNNTVTFRPGGGDMRD
NWRSELYKYKVVKIEPLGVAPTEARRRVEREKRAVGMGAFLGFLGAAGSTMGAASITLTVQARQLLSGIVQQQSNLLRAIQAQQHMLQLT
VWGIKQLQARVLAVERYLKDQQLLGIWGCSGKLICTTNVPWNSSWSNKSLDEIWDNMTWMEWDKQINNYTEEIYRLLEVSQTQQEKNEQDLL
ALDKWASLWNWFSITNWLWYIKIFIMIVGGLIGLRIIFAVLSIVNRVRQGYSPLSFQTLIPNPRGPDRPEGIEEEGGEQDRDRSVRLVNGFL
PLVWDDLRSLCLFSYRLLRDLLLIVVRTVELLGRRGREALKYLWNLLQYWGQELKNSAINLLNTTAIAVAEGTDRIIEIVQRAMRAILHIPR
RIRQGFERTLLS

Fig. 51B

2003 CON_G Env.seq.opt

ATGCGCGTGAAGGGCATCCAGCGCAACTGGCAGCACCTGTGGAAGTGGGGCACCCTGATCCTGGGCCTGGTGATCATCTGCTCCGCCTCCAA
CAACCTGTGGGTGACCGTGTACTACGGCGTGCCCGTGTGGGAGGACGCCGACACCACCCTGTTCTGCGCCTCCGACGCCAAGGCCTACTCCA
CCGAGCGCCACAACGTGTGGGCCACCCACGCCTGCGTGCCCACCGACCCCAACCCCCAGGAGATCACCCTGGAGAACGTGACCGAGAACTTC
AACATGTGGAAGAACAACATGGTGGAGCAGATGCACGAGGACATCATCTCCCTGTGGGACGAGTCCCTGAAGCCCTGCGTGAAGCTGACCCC
CCTGTGCGTGACCCTGAACTGCACCGACGTGAACGTGACCAACAACAACACCAACAACACCAAGAAGGAGATCAAGAACTGCTCCTTCAACA
TCACCACCGAGATCCGCGACAAGAAGAAGAAGGAGTACGCCCTGTTCTACCGCCTGGACGTGGTGCCCATCAACGACAACGGCAACTCCTCC
ATCTACCGCCTGATCAACTGCAACGTGTCCACCATCAAGCAGGCCTGCCCCAAGGTGACCTTCGACCCCATCCCCATCCACTACTGCGCCCC
CGCCGGCTTCGCCATCCTGAAGTGCCGCGACAAGAAGTTCAACGGCACCGGCCCCTGCAAGAACGTGTCCACCGTGCAGTGCACCCACGGCA
TCAAGCCCGTGGTGTCCACCCAGCTGCTGCTGAACGGCTCCCTGGCCGAGGAGGAGATCATCATCCGCTCCGAGAACATCACCGACAACACC
AAGGTGATCATCGTGCAGCTGAACGAGACCATCGAGATCAACTGCACCCGCCCCAACAACAACACCCGCAAGTCCATCCGCATCGGCCCCGG
CCAGGCCTTCTACGCCACCGGCGACATCATCGGCGACATCCGCCAGGCCCACTGCAACGTGTCCCGCACCAAGTGGAACGAGATGCTGCAGA
AGGTGAAGGCCCAGCTGAAGAAGATCTTCAACAAGTCCATCACCTTCAACTCCTCCTCCGGCGGCGACCTGGAGATCACCACCCACTCCTTC
AACTGCCGCGGCGAGTTCTTCTACTGCAACACCTCCGGCCTGTTCAACAACTCCCTGCTGAACTCCACCAACTCCACCATCACCCTGCCCTG
CAAGATCAAGCAGATCGTGCGCATGTGGCAGCGCGTGGGCCAGGCCATGTACGCCCCCCCCATCGCCGGCAACATCACCTGCCGCTCCAACA
TCACCGGCCTGCTGCTGACCCGCGACGGCGGCAACAACAACACCGAGACCTTCCGCCCCGGCGGCGGCGACATGCGCGACAACTGGCGCTCC
GAGCTGTACAAGTACAAGATCGTGAAGATCAAGCCCCTGGGCGTGGCCCCCACCCGCGCCCGCCGCCGCGTGGTGGAGCGCGAGAAGCGCGC
CGTGGGCCTGGGCGCCGTGCTGCTGGGCTTCCTGGGCGCCGCCGGCTCCACCATGGGCGCCGCCTCCATCACCCTGACCGTGCAGGTGCGCC
AGCTGCTGTCCGGCATCGTGCAGCAGCAGTCCAACCTGCTGCGCGCCATCGAGGCCCAGCAGCACCTGCTGCAGCTGACCGTGTGGGGCATC
AAGCAGCTGCAGGCCCGCGTGCTGGCCGTGGAGCGCTACCTGAAGGACCAGCAGCTGCTGGGCATCTGGGGCTGCTCCGGCAAGCTGATCTG
CACCACCAACGTGCCCTGGAACACCTCCTGGTCCAACAAGTCCTACAACGAGATCTGGGACAACATGACCTGGATCGAGTGGGAGCGCGAGA
TCTCCAACTACACCCAGCAGATCTACTCCCTGATCGAGGAGTCCCAGAACCAGCAGGAGAAGAACGAGCAGGACCTGCTGGCCCTGGACAAG
TGGGCCTCCCTGTGGAACTGGTTCGACATCACCAAGTGGCTGTGGTACATCAAGATCTTCATCATGATCGTGGGCGGCCTGATCGGCCTGCG
CATCGTGTTCGCCGTGCTGTCCATCGTGAACCGCGTGCGCCAGGGCTACTCCCCCCTGTCCTTCCAGACCCTGACCCACCACCAGCGCGAGC
CCGACCGCCCCGAGCGCATCGAGGAGGGCGGCGGCGAGCAGGACAAGGACCGCTCCATCCGCCTGGTGTCCGGCTTCCTGGCCCTGGCCTGG
GACGACCTGCGCTCCCTGTGCCTGTTCTCCTACCACCGCCTGCGCGACTTCATCCTGATCGCCGCCCGCACCGTGGAGCTGCTGGGCCGCTC
CTCCCTGAAGGGCCTGCGCCTGGGCTGGGAGGGCCTGAAGTACCTGTGGAACCTGCTGCTGTACTGGGGCCAGGAGCTGAAGAACTCCGCCA
TCAACCTGCTGGACACCATCGCCATCGCCGTGGCCAACTGGACCGACCGCGTGATCGAGGTGGCCCAGCGCGCCTGCCGCGCCATCCTGAAC
ATCCCCCGCCGCATCCGCCAGGGCCTGGAGCGCGCCCTGCTGTAA

Fig. 52B

```
2003 CON_H Env.seq.opt
ACCCGCGTGATGGAGAGACCAGCCAACTACCCCTCCCTGTGGGCTGGGCACCCTGATCCTGGGCATGCTGCTGATCTGCTCCGCCGCGG
CAACCTGTGCGGTGACCGTGACTACGGCGTGCCCGTGTGGAAGGAGGCCAAGACCACCCTGTTCTGCGCCTCCGACGCCAAGGCCTACGAGA
CCGAGAAGCACAACGTGTGGGCCACCCACGCCTGCGTGCCCACCGATCCCAACCCACAGGAGATGGTGCTCGAGAACGTGACCGAGAACTTC
AACATGTGGGAGAACGACATGGTGGAGCAGATGCACGAGGACATCATCTCCCTGTGGGACCAGAGCCTGAAGCCCTGCGTGAAGCTGACCCC
CCTGTGCGTGACCCTGAACTGCACCAACGTGAACGCCACCAACAACGCCACCAACGCCACCAACGCCCTTCAACATGCAGGAGGAGGCCCATCCCCATCGGCGACGACAACTCC
TCAACGTGACCACCGTGATCCGCGACAAGAAGCAGCAGAAGGTGCACGCCCTGTTCTACCGCCTGGACGTGGTGCCCATCGACGACAACAACTCC
TACCAGTACCGCCTGATCAACTGCAACACCTCCGTGATCACCCAGGCCTGCCCCAAGGTGTCCTTCGAGCCCATCCCCATCCACTACTGCGC
CCCCGCCGGCTTCGCCATCCTGAAGTGCAACGACAAGAAGTTCAACGGCACCGGCCCCTGCCACAACGTGTCCACCGTGCAGTGCACCCACG
GCATCCGCCCCGTGGTGTCCACCCAGCTGCTGCTGAACGGCAGCCTGGCCGAGGAGGAGGTCGTGATCCGCTCCGAGAACATCACCGACAAC
ACCAAGAACATCATCGTGCAGCTGAACGCCCCCGTGGAGATCAACTGCACCCGCCCTAACAACAACACCCCGCAAGTCCATCCACCTGGGCCC
CGGCCAGGCCTTCTACGCCACCGGCGACATCATCGGCGACATCCGCCAGGCCCACTGCAACATCTTCAAGTCCAACTGGACCGAGACCCTGC
ACCAGGTGGTGACCCAGCTGGGCGAGTTCTTCTACCACCCCGCGCCCAACCAACACCTCCGACCAACCTCCGAAGTCCACCAAGGTGACCTCCGAGCG
TCCTTCAACTGCCGCGGCGAGTTCTTCTACTGCAACGCCACCAACCTCCTGTTCAACCCGCCCAGGCCATGTGGCAGCGCACCGAGGCGGCGCG
CATCACCCTGCCCTGCCGCATCAAGCAGATCGTGAACATGTGGCAGCGCGTGGGCCAGGCCATGTACGCCCCCCCATCAAGGCCAACATCA
CGGCGTGTCCAACATCACCGGCCTGATCCTGACCCGCGACGGCGGCAACAACACCGGCACCAACGAGACCTTCCGCCCCGGCGGCGGCGAC
AACTGGCGCTCCGAGCTGTACAAGTACAAGGTGGTGAAGATCGAGCCCCTGGGCGTGGCCCCCACCCGCGCGCCAAGCGCCGCGTGGTGGAGCG
CGAGAAGCGCGCCGTGGGCATGGGCGCCCTGTTCCTGGGCTTCCTGGGCGCGCTGGGCTGGCGCGGCAGCAGCATGGGCGCCGCGTCCATGACCCTGACCG
TGCAGGCCCGCCAGCTGCTGCTGTCTGGCATCGTGCAGCAGCAGAACAACCTGCTGCGCGCCATCGAGGCCCAGCAGCACCTGCTGCAGCTGACCGTGTGGGGCATCAAGCAGCTGCAG
GCCAGGGTGCTGGCCGTGGAGCGCTACCTGCGCCGACCAGCAGCTGCTGGGCATCTGGGGCCTGCAGCCTGTGGGGCATCAAGCAGCTGCTGG
GTGTGGGGCATCAAGCAGCTGCAGACGCGCGTGCTGGCCGTGGAGCGCTACCTGCGCGACCAGCAGCTGCTGGGCATCTGGGGCTGCTCCGG
CAAGCTGATCTGCACCACCGCCGTGCCCTGGAACGCCTCCTGGTCCAACAAGTCCCTGGACGAGATCTGGGACAACATGACCTGGATGGAGT
GGGAGCGCGAGATCAACAACTACACCGACATCATCTACTCCCTGATCGAGGAATCGTTCTCCATCACCAACCGCGTGCTGTCCCAGGATCGCTG
GCCCTGGACAAGTGGCCCTCCATCATCTTCGCCCCCCGTGTTCATCGTGATGATGATCATGCTACCATCAACCCGCGTGCTGCGCCGTGCGCCCCCAGGGCTGGCCT
GATCGGCTGCCTGCGCATCATCCGCGCCCATCCTGCGCCTGCGTGCGCGAGCCCGACCGCGTGCGCCCGCCTCGTGTGCCTCCGTGGCCTTCCTG
ACCCCCTGGTGTGGAACGACCTGCGCTCCCTGTGCCTGTTCTCCTACCACCGCCTGCGCGACTTCCTCCTGATCGTGGCCCGCACCGTGGAGCTT
GCTGGGCCGCCGCGGCTGGGAGGCCCTGAAGTACTGGTGGAACCTGCTGCAGTACTGGTCCCAGGAACTGAAGAACTCCGCCATCAACCTGC
TGAACACCACCGCCATCGCCGTGGCCGAGGGCACCGACCGCATCATCGAGATCATCGAGCACCGCCATCCGCGCCATCGCGCGCCATCCCCAGGGCGC
CGCATCCGCCAGGGCCTTCGAGCGCGCCCTGCTGCTGTAA
```

Fig. 53A

2003 CON 01 AE Env
MRVKETQMNWPNLWKWGTLILGLVIICSASDNLWVTVYYGVPVWRDADTTLFCASDAKAHETEVHNVWATHACVPTDPNPQEIHLENVTENF
NMWKNNMVEQMQEDVISLWDQSLKPCVKLTPLCVTLNCTNANLTNVNNITNVSNIIGNITNEVRNCSFNMTTELRDKKQKVHALFYKLDIVQ
IEDNNSYRLINCNTSVIKQACPKISFDPIPIHYCTPAGYAILKCNDKNFNGTGPCKNVSSVQCTHGIKPVVSTQLLLNGSLAEEEIIRSEN
LTNNAKTIIVHLNKSVEINCTRPSNNTRTSITIGPGQVFYRTGDIIGDIRKAYCEINGTKWNEVLKQVTEKLKEHFNNKTIIFQPPSGGDLE
ITMHHFNCRGEFFYCNTTKLFNNTCIGNETMEGCNGTIILPCKIKQIINMWQGAGQAMYAPPISGRINCVSNITGILLTRDGGANNTNETFR
PGGGNIKDNWRSELYKYKVVQIEPLGIAPTRAKRRVVEREKRAVGIGAMIFGFLGAAGSTMGAASITLTVQARQLLSGIVQQQSNLLRAIEA
QQHLLQLTVWGIKQLQARVLAVERYLKDQKELGLWGCSGKIICTTAVPWNSTWSNRSFEEIWNNMTWIEWEREISNYTNQIYEILTESQNQQ
DRNEKDLLELDKWASLWNWFDITNWLWYIKIFIMIVGGLIGLRIIFAVLSIVNRVRQGYSPLSFQTPTHHQREPDRPERIEEGGEQGRDRS
VRLVSGFLALAWDDLRSLCLFSYHRLRDFILIAARTVELLGHSSLKGLRRGWEGLKYLGNLLLYWGQELKISAISLLDATAIAVAGWTDRVI
EVAQGAWRAILHIPRRIRQGLERALL$

Fig. 54A

2003 CON 02 AG Env
MRVMGIQKNYPLLRWGMIIFWIMIICNAENLWVTVYYGVPVWRDAETTLFCASDAKAYDTEVHNVWATHACVPTDPNPQEIHLENVTENFN
MWKNNMVEQMHEDIISLWDQSLKPCVKLTPLCVTLDCHNNITNSNTTNNNAGEIKNCSFNMTTELRDKKQKVYALFYRLDVVQINKNNSQYR
LINCNTSAITQACPKVSFEPIPIHYCAPAGFAILKCNDKEFNGTGPCKNVSTVQCTHGIKPVVSTQLLLNGSLAEEEIVIRSENITNNAKTI
IVQLVKPVKINCTRPNNNTRKSVRIGPGQTFYATGDIIRQAHCNVSRTKWNNTLQQVATQLRKYFNKTIIFANPSGGDLEITTHSFNCG
GEFFYCNTSELFNSTWNSTWNNTEKCITLQCRIKQIVNMWQKVGQAMYAPPIQGVIRCESNITGLLLTRDGGNNNSTNETFRPGGGDMRDNW
RSELYKYKVVKIEPLGVAPTRAKRRVVEREKRAVGLGAVFLGFLGAAGSTMGAASITLTVQARQLLSGIVQQQSNLLRAIEAQQHLLKLTVW
GIKQLQARVLALERYLKDQQLLGIWGCSGKLICTTTVPWNSSWSNKTYNDIWDNMTWLQWDKEISNYTDIIYNLIEESQNQQEKNEQDLLAL
DKWASLWNWFDITNWLWYIKIFIMIVGGLIGLRIVFAVLTIINRVRQGYSPLSFQTLTHHQREPDRPERIEEGGEQDRDRSVRLVSGFLAL
AWDDLRSLCLFSYHRLRDFVLIAARTVELLGHSSLKGLRLGWEALKYLGNLLSYWGQELKNSAINLLDTIAIAVANWTDRVIEIGQRAGRAI
LNIPRRIRQGLERALL$

Fig. 53B

2003_CON_01_AE_Env.seq.opt
ATGCGCGTGAAGGAGACCCAGATGAACTGGCCCCAACCTGTGTGGAAGTGGGCACCCTGATCCTGGGCCTGGTGATCATCTGCTCCGCCTCCGA
CAACCTGTGGGTGACCGTGTACTACGGCGTGCCCGTGTGGCGCGACGCCGACACCACCCTGTTCTGCGCCAGCGACGCCAAGGCCCACGAGA
CCGAGGTGCACAACGTGTGGGCCACCCACGCCTGCGTGCCCACCGACCCCAACCCCCAGGAGATCCACCTGGAGAACGTGACCGAGAACTTC
AACATGTGGAAGAACAACATGGTGGAGCAGATGCAGGAGGACATCATCTCCCTGTGGGACCAGAGCCTGAAGCCCTGCGTGAAGCTGACCCC
CCTGTGCGTGACCCTGAACTGCACCAACGCCAACCTGACCAACGTGAACAACATCACCAACGTGTCCAACATCATCGGCAACATCACCGACG
AGGTGCGCAACTGCTCCTTCAACATGACCACCGAGCTGCGCGACAAGAAGCAGAAGGTGCACGCCCTGTTCTACAAGCTGGACATCGTGCAG
ATCGAGGACAACAACTCCTCCGAGTACCGCCTGATCAACTGCAACACCTCCGTGATCAAGCAGGCCTGCCCCAAGATCTCTTTCGACCCCCAT
CCACTACTGCACCCCCGGCTACGCCATCCTGAAGTGCAACGACAAGAACTTCAACGGCTCTGCCACCTGCAAGAACGTGTCCTCCGTGCAG
AGTGCACCCACGGCATCAAGCCCGTGGTGTCCACCCAGCTGCTGCTGAACGGCTCTCTGGCCGAGGAGGAGATCATCATCCGCTCCGAGAAC
CTGACCAACAACGCCAAGACCATCATCGTGCACCTGAACAAGTCCGTGGAGATCAACTGCACCCGCCCCAGCAACAACACCCGCACCTCCAT
CACCATCGGCCCCGGCCAGGTGTTCTACCGCACCGGCGACATCATCGGCGACATCAGAAAGGCCTACTGCGAGATCAACGGCACCAAGTGGA
ACGAGGTGCTGAAGCAGGTGACCGAGAAGCTGAAGGAGCACTTCAACAACAAGACCATCATCTTCCAGCCCCCCTCCGGCGGCGACCTGGAG
ATCACCATGCACCACTTCAACTGCCGCGGCGAGTTCTTCTACTGCAACACCAGCAAGCTGTTCAACAGCACCTGGATCGGCAACGAGACCAT
GGAGGGCTGCAACGGCACCATCATCCTGCCCTGCAAGATCAAGCAGATCATCAACATGTGGCAGGGCGCCGGCCAGGCCATGTACGCCCCCC
CCATCTCCGGCCGCATCAACTGCGTGTCCAACATCACCGGCATCCTGCTGACCCGCGACGGCGGCAACAACACCGAGAACGAGACCTTCCGC
CCCGGCGGCGGCAACATCAAGGACAACTGGCGCTCCGAGCTGTACAAGTACAAGGTGGTGCAGATCGAGCCCCTGGGCATCGCCCCCACCCG
GCCAAGCGCCGCGTGGTGGAGCGCGAGAAGCGCGCCCGTGGGCATCGGCGCCATGATCTTCGGCTTCCTGGGCGCCGCCGGCTCCACCATGG
GCGCCGCCTCCATCACCCTGACCGTGCAGGCCCGCCAGCTGCTGAGCGGCATCGTGCAGCAGCAGAGCAACCTGCTGCGCGCCATCGAGGCC
CAGCAGCACCTGCTGCAGCTGACCGTCTGGGGCATCAAGCAGCTGCAGGCCCGCGTGCTGGCCGTGGAACGCTACCTGCGCGACCAGAAGTT
CCTGGGCCTGTGGGGCTGCTCCGGCAAGATCATCTGCACCACCGCCGTGCCCTGGAACTCCAGCTGGTCCAACAAGTCCTACGAGGAGATCT
GGAACAACATGACCTGGATCGAGTGGGAGCGCGAGATCAGCAACTACACCAACCAGATCTACGAGATCCTGACCGAGTCCCAGAACCAGCAG
GACCGCAACGAGAAGGACCTGCTGGAGCTGGACAAGTGGGCCTCCCTGTGGAACTGGTTCGACATCACCAACTGGCTGTGGTACATCAAGAT
CTTCATCATGATCGTGGGCGGCCTGATCGGCCTGCGCATCATCTTCGCCGTGCTGTCCATCGTGAACCGCGTGCGCCAGGGCTACTCCCCCC
TGTCCTTCCAGACCCCCACCCACCACCAGCGCGAGCCCCCGACCGCCCCTCCCCCGTCCCCTTCCTGCAGCAGCTGCTGCTTCAGCCGTTC
GTGCCCCTGGGTGGCTGCAGGCTTCCTGGCCCTGCGCCTCCTACACCGCCTCCTGCGCCGACTTCATCCT
GATCGCCGTGCGCACCGTGGAGCTGCTGGGCCACTCCTCCCTGAAGGGCCTGCGCCTGGGCTGGGAGGCCTGAAGTACCTGGGCAACCTGC
TGCTGTACTGGGGCCAGGAGCTGAAGATCTCCGCCATCAGCCTGCTGGACACCATCGCCATCGCCGTGGCCGGCTGGACCGACCGCGTGATC
GAGGTGGCCCAGGGCGCCTGGCGCGCCATCCCCGCCCAGGGCCTGGAGCGCGCCCTGCTGTAA

Fig. 54B

2003_CON_02_AG_Env.seq.opt
ATGCGCGTGATGGGCATCCAGAAGAACTACCCCCTGCTGTGGGCTGTGGGCGACGCCGAGAACTACCCCCGTGTGGGCGACGCCGAGAACCCCCAACCTGCCTGTGGCCGCCCACCCCGACGCCTACGACCG
CCTGTGGGTGACCGTGTACTACGGCGTGCCCGTGCCCGTGCCTGCTGCCCACCGACATCATCAACAACATCCAACCCCCAGAGAGATCCATCTTCTGCGCCTCCGACGCCAAGGCCTACGACACCG
AGGTGCACAACGTGTGGGCCACCCACGCCTGCGTGCCCACCGACCCCAACCCCCAGGAGAACGTCCTGGAGAACGTGACCGAGAACTTCAAC
ATGTGGAAGAACAACATGGTGGAGCAGATGCACGAGGACATCATCTCCCTGTGGGACGAGTCCCTGAAGCCCTGCGTGAAGCTGACCCCCT
GTGCGTGACCCTGAACTGCCGACAAGAAGCAGAAGTGTACGCCGCCATCAACAACAACAAGCCCGGAGATCAAGAACTGCTCCTTCAACATGA
CCACCGAGCTGCGCGACAAGACCCTCCGCCATCCGCTGAAGGCCCTGCCCATCCGAGCCTGGTGCAGATCAACAAGAACACTCCGCCCCCGGCTT
CTGATCAACTGCAACAACACCAGCGAGATCCCCTGCACCGTGTCTTCGAGCCCATCCCCATCCACTACTGCGCCCCACCGGCATCAAGCCCG
CGCCATCATCCTGAAGTGCAACGACAAGGAGTTCAACGGCACCGGCCCCTGCTGCAACGTGTCCACCGTCCAACCAACAACGCCAAGACCATC
TGGTGTGCCAGTGCTGTGAAGCCCGTGAAGATCGGCGACATGCGGCAGGAGATCGTGATCCGCTCCGAGAACATCACCGACAACGCCAAGACCATC
ATCGTGCAGCTGGTGGAGCCCGTGAAGATCAACGGCACCGGCGACATCAGATCCGCCAGGCCGACATGGAAACACACCGAGAAGTCCGTGCCCATCGGCCCCGGCCAGGTGGCCA
CTACGCCACCGGCGACATCATCGGCGACATCCGGCAGGCGACATCAACCCCTGCAACGTGTCCCGGCGACGACCCTGGAAACACACCCAGAAGTCCGTGCCCATCGGCCCCGGCCAGGTGGCCA
CCCAGCTGCGCAAGCTGTCCTGCTGCAACAAGACCATCATCTTCCGCCCCCAGCCCAGCCCTGGGCCTGGGCCCGGCCAAGCCCGCCCTCCATCCGCCGCCCTGCAGCCGCCAGGTGGAGCGCGAGAA
GGCGAGTCTTCTACTGCAACATCCGAGCTGTGTTCAACTGCCAGAAGCTGGAGCAGGAATGGAATCAGCCCGGCCTCCATCAGCCCATCTCGACCTCATCCCCATCAGCCCTCCAAAGCTGCAGGCCTGCAGG
CCGATCAAGCAGCAGATCGTGAAACGACAGGCCGGCCAACCTGGCCCCGGCGCACAGTCGCGTGCCCCTGCCCCTGCCCTGTTCCTGGGCTTCCTGGGCCCGGGCCCGATCGCGACCGTGTGG
GGCATCAAGCAGCAGCTGCTGCTGAACCGCGTGCCCCTGCGGCCTGGCCCTGGCCCCCTGGCCCCTGGCCCCAGCCCCCGCCCTCCGGCCCAGCCCCGCCAGCCCCGCAAACGCCCCCGCAAGGACACCTGAACTGCAAGAAGGCCCCCGCCCCCGCAAACCTGGACGCCGAATGATACTGCAACAAGCCCCCCCTGGGCCCCTGGGGACA
GATCTCCAACATGACCGGCGCCCTGCCTGTCCTGAACTCCTGGGTCAACGAGGAGGTGCGGAACTACACCAACGACATCTGGGACAACATGACCGGCACCAAGATGACCAATGGGACCTGCAGTGGGACA
AGGAGATCCAACCTGTACAACCTGATCGAGGAGAGTCCCAGGAATCCGTGAACCTGGTGCAAGATCTTCATCATGATCGTGGGCCTGATCGG
GACAAGTGGCCCCATGTTCCGTGATCTGCTTGACCAATCATCAACAACCGCGTGCGCCAGGGCTACTCCCCCCTGTCCTTCCAGACCCCTGACCCACCAGC
CCTGCGCATGCCGCGCCCCTGAGCCCGCCCGAGCCGGCACGGAGGGCGGCGAGGCTGGCGACCACCAGGACCAGCCGAGGCCCTGCGCTGGGAGATCCTGCAGCAGAACAGCAGCAGCAGCAGCAGCAGAGCAGACTGC
GCGACTGGGACCCCCTGAGGGTCCTTGTCCCTGCGCTACCTGGGCCGCCACCGCCACCGCCGCCAGCGTGCTGAGCTGCTGGG
GCCTGGAGACGACTGCTGAAGTACTGGCCTGGCCGCCCCCTGCTCCCGCCCGCCCCCTGACCCGAGCCCCGTGATCCCGCCCTGAGTCCGCCATCGTGCTGAAGGCCCTGCAACTGGAGATCGACAACTGGAAGAACT
CGGCCCTCAACATCCCGCCAGGCCCATCGCCGAGGCGCGCCAGGCCCAGGGCCAGCCCAGGCCCCGCCCAGCCCCATC
CTGAAACATCCCCCGCCAGGGCCTGGAGCCGGCGCCCCTGCTGTAA

Fig. 55A

2003 CON 03 AB Env
MRVKEIRKHLWRWGTLFLGMLMICSATENLWVTVYYGVPVWKEATTLFCASDAKAYSKEVHNVWATYACVPTDPSPQEIPLENVTENFNMG
KNNMVEQMHEDIISLWDQSLKPCVKLTPLCVTLNCTDLKKNVTSTNTSSIKMMEMKNCSFNITTDLRDKVKKEYALFYKLDVVQIDNDSYRL
ISCNTSVVTQACPKISFEPIPIHYCAPAGFAILKCNDKKFNGTGPCTNVSTVQCTHGIKPVVSTQLLLNGSLAEEEVVIRSVNFTDNTKTII
VQLKEPVEINCTRPNNNTRKGIHIGPGRAFYATGDIIGDIRQAHCNISITKWNNTLKQIVIKLRKQFGNKTIVFNQSSGGDPEIVMHSFNCG
GEFFYCNTTKLFNSTWNGTEELNNTEGDIVTLPCRIKQIINMWQEVGKAMYAPPIAGQIRCSSNITGLLLTRDGGNQSNVTEIFRPGGGDMR
DNWRSELYKYKVVKIEPLGVAPTKAKRRVVQREKRAVGIGAVFLGFLGAAGSTMGAASITLTVQARQLLSGIVQQQNNLLRAIEAQQHLLQL
TVWGIKQLQARVLAVERYLKDQQLLGIWGCSGKLICTTAVPWNTSWSNKSLDEIWNNMTWMEWEREINNYTGLIYNLIEESQNQQEKNEQEI
LALDKWASLWNWFDISKWLWYIKIFIMIVGGLVGLRIIFAVLSIVNRVRQGYSPLSFQTRLPTQRGPDRPEGIEEGGERDRDTSIRLVNGF
LALIWDDLRSLCLFIYHHLRDLLLIAARIVELLGRRGWEALKYWWNLLQYWIQELKKSSAINLIDTIAIAVAGWTDRVIEIGQRFCRAIRNIP
RRIRQGAEKALQ$

Fig. 56A

2003 CON 04 CPX Env
MRVMGIQRNYPHLWEGTLILGLVIICSASKNLMVTVYYGVPVWRDAETTPFCASDAKAYDKEVHNIMATHACVPTDPNPQEIALKNVTENF
NMWKNNMVEQMHEDIISLWDEGLKPCVKLTPLCVALNCSNATINNSTKTNSTEEIKNCSFNITTEIRDKKKKEYALFYRLDIVPINDSANNN
SINSEYMLINCNASTIKQACPKVTFEPIPIHYCAPAGFAILKCNDKNFTGLGPCTNVSSVQCTHGIKPVVSTQLLLNGSLATEGVVIRSKNF
TDNTKNIIVQLAKAVKINCTRPNNNTRKSVHIGPGQTWYATGEIIGDIRQAHCNISGNDWNETLQKIVEELRKHFPNKTIIFAPSAGGDLEI
TTHSFNCGGEFFYCNTSELFNSTYMNSTTINKTITLPCRIKQIVSMWQEVGQAMYAPPIAGSINCSSDITGILLTRDGGNNTNNETFR
PGGGDMRDNWRSELYKYKVVKIEPVGVAPTRARRRVVQREKRAVGIGAVFLGFLGAAGSTMGAASITLTVQARQLLSGIVQQQSNLLRAIEA
QQHLLRLTVWGIKQLQARVLALESYLKDQQLLGIWGCSGKLICTTNVPWNSSWSNKSYNDIWDNMTWLQWDKEINNYTQIIYELLEESQNQQ
EKNEQDLLALDKWANLWNWFNISNWLWYIKIFIMIVGGLIGLRIIFAVLSIVNRVRQGYSPLSLQTLIPTTQRGPDREPEGTEEEGEQDRSR
SIRLVNGFLPLIWDDLRNLCLFSYRHLRNLLLIVARTVELLGRGWEALKYLWNLLLYWGQELRNSAINLLDTTAIAVAEGTDRIIEAVQRA
CRAIRNIPRRIRQGLERALLS$

Fig. 55B

2003_CON_03_AB_Env.seq.opt
ATGGCGGTGAAGGAGATCCGCAAGCACCTGTGGCGCTGGGGCACCCTGTTCCTGGGCATGCTGATGATCTGCTCCGCCACCGAGAACCTGTG
GGTGACCGTGTACTACGGCGTGCCCGTGTGGAAGGAGGCCACCACCACCCTGTTCTGCGCCTCCGACGCCAAGGCCTACTCCAAGGAGGTGC
ACAACGTGTGGGCCACCCACGCCTGCGTGCCTACCGACCCCAACCCCCAGGAGATCCATCTCCCTGGAGAACGTGACCGAGAACTTCAACATGGGC
AAGAACAACATGGTGGAGCAGATGCACGAGGACATCATCTCCCTGTGGGACCAGTCCCTGAAGCCCTGCGTGAAGCTGACCCCCCTGTGCGT
GACCCTGAACTGCACCGACCTGCGCAACGACACCAACACCAACAGCAGCAGCAGCGGCGAGCCGATGATGGAGAGATGATGGAGAAGGGCGAGATCAAGAACTGCTCCTTCAACA
TCACCACCGAGCTGCGCGACAAGGTGAAGAAGGTGTACGCCCTGTTCTACAAGCTGGACATCGTGCCCATCGACAACAACAACCAACAGCACCGGCGAGATCCGGCCAGAAGATGTACCGCCTGATCAACTGCAACACCTCCGCCATCACTCCTACCGCCCGCCTTCGC
ATCTCCTGAAGTGCAACGACAAGAAGTTCAACGGCACCGGCCCCTGCAACGAACCAACGTGTCCACCGTGCAGTGCACCCACGGCATCAAGACCATCATC
TGTCCAGCTGCTGGAGGCCCTGAAGTGGTGTGAACAACAACATCTCCACCCCGCAAGGGCATCACCATCGGCCCTGCCCCGCCTTCTA
GTGCAGCACCGGCCAAGCAGTTCGGCAACAGCAGTTCGGCGACATCGTGTTCAACCAGCAGCATCCGGCCAACAACCTGAAGCGACACTCTTCCTGAAGGCTGATCA
CGGCCACCGGCCAAGCAGTTCGGCAACAAGCAGTTCGGCGACATCGTGTTCAACCAGCATCCGGGCCAACAACCTGAAGCGACACTCTTCCTGAAGATCGCGGC
AGCTGCGCCAAGTTCTTCTACTGCAACACCACCAGATTGCAACATGGCCAAGCCCATGTGAACAACGGCCAAGGCCCATGTGACCCGGGGCCGACATCGCTGAC
GGCGAGTTCTTCTACTGCAACACCACCAGATTGCAACATGGCCAAGCCCATGTGAACAACGGCCAAGGCCCATGTGACCCGGGCCGACATGCGC
CCTGCCCTGCCGCCATCAAGCCCCTGCTGCGTGACCAGTCCAACAGTCGAGCGCCTCCTGGGCTTCCTGGGCGCAGCAGCAGCTGCTGCACCCTGA
GACAACTGGGGCTTCCGAGCTGTACAAGTGGTGGGCTGGCGCCTCTGCCACATCGGCCCGTCCGGGCCCAGCAGCGACGCGCCATGGGCCA
CGCGAGAAGCGCGCCCGCCGCCCCAGCAGCTGCTGCTGCTTCCGGCACAGAACAACCTGCTGCGCTCGGGGCCCGTCCTGCAGCTG
CCGGTGTGGCATCAAGCAGCTGCAGCCGCCGCCGGCGACGCACCCGGCTCTGGTCCGTGGAGAGATCCCTGGCTGAAGAAATCAGAGAGATCAGAGAGATCGAAGAGATGATGGG
ACCGTGTGGGGCATCAAGCAGCTGCAGCCGCCGCCACCGTGCCGTCCCTGCCGCCGCCGGCCGCCGGAGATCAGCCAGAGATCGGAGATGATCG
CGGCAAGCTGATCGCCGAGATCGCGCGAGCACAACCACCGCCTCGCCGCCCTGCCTGCTGGAACACCTGTACAACGTGTCCCAGAGATCCCTGATCAACGGCC
AGTGGGAGCGCGGAGATCGCGCGAGCACAACCACCGCCTCGCCGCCCTGCCTGCTGGAACACCTGTACAACGTGTCCCAGAGATCCCTGATCAACGGCCAGGAGATCG
CTGGCCCTTGACAAGTGGGGCCCTGCCATCATCTTCGCCCGTGTGCGCGCTGTGAACTGGTTCGACATCTCCAAGTGGCTGTGGTACATCAAGATCTTCATCATGATCGTGGGCGG
CCTGGTGGGCCTGCGCATCGTGTTCGCCGTGCTGTCCATCGTGAACCGGGTGCGCCAGGGCTACTCCCCTGCCCCACCTCCCTGGTGCCCCGCCATCGTGAAT
CCACCCAGCGCGCCCCCCGAGCTGCTGCGCCCGACGACAGCATCGGAGAGGGCATCGTGCTGCCGCTGTTCATCTACCACCGCCCTGCGCTACTCCCCGAT
CTGGCCCTGATCGTGGAGCGACTGGGCCGCCCTGCGCGTGTGGAAGATCCTGCGAGATACCTGCAGTACTGGGACCAGGAGCTGAAGAACTCC
GCTGTGAGCCTGAGCTGGGACCCCGAGGGGCCCGTGGGCCCGTGGGCCGAGAAGGCCCCGAGAAGGCCCCGAGAAGGG
CGCCCATCCGGCCAGGGGCCCGAGAAGGGCCCCGAGTAA

Fig. 56B

2003 CON_04_CPX Env.seq.opt

ATGCGCGTGATGGGCATCCAGCGCAACTACCCCCACCTGTGGAGTGGGGCACCCTGATCCTGGGCCTGGTGATCATCTGCTCCGCCTCCAA
GAACCTGTGGGTGACCGTGTACTACGGCGTGCCCGTGTGGCGCGACGCCGAGACCACCCCCTTCTGCGCCTCCGACGCCAAGGCCTACGACA
AGGAGGTGCACAACATCTGGGCCACCCACGCCTGCGTGCCCACCGACCCCAACCCCCAGGAGATCGCCCTGAAGAACGTGACCGAGAACTTC
AACATGTGGAAGAACAACATGGTGGAGCAGATGCACGAGGACATCATCTCCCTGTGGGACGAGGGCCTGAAGCCCTGCGTGAAGCTGACCCC
CCTGTGCGTGGCCCTGAACTGCTCCAACGCCACCATCAACAACTCCACCAAGACCAACTCCACCGAGGAGATCAAGAACTGCTCCTTCAACA
TCACCACCGAGATCCGCGACAAGAAGAAGAAGGAGTACGCCCTGTTCTACCGCCTGGACATCGTGCCCATCAACGACTCCGCCAACAACAAC
TCCATCAACTCCGAGTACATGCTGATCAACTGCAACGCCTCCACCATCAAGCAGGCCTGCCCCAAGGTGACCTTCGAGCCCATCCCCATCCA
CTACTGCGCCCCCGCCGGCTTCGCCATCCTGAAGTGCAACGACAAGAACTTCACCGGCCTGGGCCCCTGCACCAACGTGTCCTCCGTGCAGT
GCACCCACGGCATCAAGCCCGTGGTGTCCACCCAGCTGCTGCTGAACGGCTCCCTGGCCACCGAGGGCGTGGTGATCCGCTCCAAGAACTTC
ACCGACAACACCAAGAACATCATCGTGCAGCTGGCCAAGGCCGTGAAGATCAACTGCACCCGCCCCAACAACAACACCCGCAAGTCCGTGCA
CATCGGCCCCGGCCAGACCTGGTACGCCACCGGCGAGATCATCGGCGACATCCGCCAGGCCCACTGCAACATCTCCGGCAACGACTGGAACG
AGACCCTGCAGAAGATCGTGGAGGAGCTGCGCAAGCACTTCCCCAACAAGACCATCATCTTCGCCCCCTCCGCCGGCGGCGACCTGGAGATC
ACCACCCACTCCTTCAACTGCGGCGGCGAGTTCTTCTACTGCAACACCTCCGAGCTGTTCAACTCCACCTACATGAACTCCACCAACTCCAC
CACCATCAACAAGACCATCACCCTGCCCTGCCGCATCAAGCAGATCGTGTCCATGTGGCAGGAGGTGGGCCAGGCCATGTACGCCCCCCCCA
TCGCCGGCTCCATCAACTGCTCCTCCGACATCACCGGCATCATCCTGACCCGCGACGGCGGCAACAACAACACCAACAACGAGACCTTCCGC
CCCGGCGGCGGCGACATGCGCGACAACTGGCGCTCCGAGCTGTACAAGTACAAGGTGGTGAAGATCGAGCCCGTGGGCGTGGCCCCCACCCG
CGCCCGCCGCCGCGTGGTGCAGCGCGAGAAGCGCGCCGTGGGCATCGGCGCCGTGTTCCTGGGCTTCCTGGGCGCCGCCGGCTCCACCATGG
GCGCCGCCTCCATCACCCTGACCGTGCAGGCCCGCCAGCTGCTGTCCGGCATCGTGCAGCAGCAGTCCAACCTGCTGCGCGCCATCGAGGCC
CAGCAGCACCTGCTGCGCCTGACCGTGTGGGGCATCAAGCAGCTGCAGGCCCGCGTGCTGGCCCTGGAGTCCTACCTGAAGGACCAGCAGCT
GCTGGGCATCTGGGGCTGCTCCGGCAAGCTGATCTGCACCACCAACGTGCCCTGGAACTCCTCCTGGTCCAACAAGTCCTACAACGACATCT
GGGACAACATGACCTGGCTGCAGTGGGACAAGGAGATCAACAACTACACCCAGATCATCTACGAGCTGCTGGAGGAGTCCCAGAACCAGCAG
GAGAAGAACGAGCAGGACCTGCTGGCCCTGGACAAGTGGGCCAACCTGTGGAACTGGTTCAACATCTCCAACTGGCTGTGGTACATCAAGAT
CTTCATCATGATCGTGGGCGGCCTGATCGGCCTGCGCATCATCTTCGCCGTGCTGTCCATCGTGAACCGCGTGCGCCAGGGCTACTCCCCCC
TGTCCCTGCAGACCCTGATCCCCACCACCCAGCGCGGCCCCGACCGCCCCGAGGGCACCGAGGAGGAGGGCGGCGAGCAGGACCGCTCCCGC
TCCATCCGCCTGGTGAACGGCTTCCTGCCCCTGATCTGGGACGACCTGCGCAACCTGTGCCTGTTCTCCTACCGCCACCTGCGCAACCTGCT
GCTGATCGTGGCCCGCACCGTGGAGCTGCTGGGCATCCGCGGCTGGGAGGCCCTGAAGTACCTGTGGAACCTGCTGCTGTACTGGGGCCAGG
AGCTGCGCAACTCCGCCATCAACCTGCTGGACACCACCGCCATCGCCGTGGCCGAGGGCACCGACCGCATCATCGAGGCCGTGCAGCGCGCC
TGCCGCGCCATCCGCAACATCCCCCGCCGCATCCGCCAGGGCCTGGAGCGCGCCCTGCTGTAA

Fig. 57A

2003 CON_06_CPX Env

MRVKGIQKNWQHLWKWGTLILGLVIICSASNNMWVTVYYGVPAWEDADTILFCASDAKAYSAEKHNVWATHACVPTDPNPQEIALENVTENF
NMWKNHMVEQMHEDIISLWDESLKPCVKLTPLCVTLNCTNVTKNNNTKIMGREEIKNCSFNVTTEIRDKKKKEYALFYRLDVVPIDDNNNSY
RLINCNASTIKQACPKVSFEPIPIHYCAPAGFAILKCRDKNFNGTGPCKNVSTVQCTHGIKPVVSTQLLLNGSLAEEEIIIKSENLTDNTKT
IIVQLNKSVEIRCTRPNNNTRKSISFGPGQAFYATGDIIGDIRQAHCNVSRTDWNNMLQNVTAKLKELFNKNITFNSSAGGDLEITTHSFNC
GGEFFYCNTSQLFNSTRPNETNTITLPCKIKQIVRMWQRVGQAMYAPPIAGNITCTSNITGLLLTRDGNNNDSETFRPGGGDMRDNWRSELY
KYKVVKIKPLGIAPTRARRRVVGREKRAVGLGAVFLGFLGTAGSTMGAASITLTVQVRQLLSGIVQQQSNLLRAIEAQQHLLQLTVWGIKQL
QARVLAVERYLKDQQLLGIWGCSGKLICPTNVPWNASWSNKTYNEIWDNMTWIEWDREINNYTQQIYSLIEESQNQQEKNEQDLLALDKWAS
LWSWFDISNWLWYIKIFIMIVGGLIGLRIVFAVLSIVNRVRQGYSPLSLQTLIPNPTGADRPGEIEEGGGEQGRTRSIRLVNGFLALAWDDL
RSLCLFSYHRLRDFVLIAARTVETLGHRGWEILKYLGNLVCYWGQELKNSAISLLDTTAIAVANWTDRVIEVVQRVFRAFLNIPRRIRQGFE
RALL$

Fig. 58A

2003 CON_08_BC Env

MRVRGTRRNYQQWWIWGVLGFWMLMICNVEGNLWVTVYYGVPVWKEAKTTLFCASDAKAYETEVHNVWATHACVPTDPNPQEIVMENVTENF
NMWNNDMVNQMHEDVISLWDQSLKPCVKLTPLCVTLECTNVSSNGNGTYNETYNESVKEIKNCSFNATTLLRDRKKTVYALFYRLDIVPLND
ENSGKNSSEYYRLINCNTSAITQACPKVTFDPIPIHYCTPAGYAILKCNDKKFNGTGQCHNVSTVQCTHGIKPVVSTQLLLNGSLAEREIII
RSENLTNNVKTIIVHLNQSVEIVCTRPNNNTRKSIRIGPGQTFYATGDIIGDIRQAHCNISKDKWYETLQRVSKKLAEHFPNKTIKFASSSG
GDLEITTHSFNCRGEFFYCNTSGLFNGTYMNGTNNSSSIITIPCRIKQIINMWQEVGRAMYAPPIEGNITCKSNITGLLLVRDGGRTESNNT
EIFRPGGGDMRNNWRNELYKYKVVEIKPLGVAPTAAKRRVVEREKRAVGLGAVFLGFLGAAGSTMGAASITLTVQARQLLSGIVQQQSNLLR
AIEAQQHMLQLTVWGIKQLQTRVLAIERYLKDQQLLGIWGCSGKLICTTAVPWNSSWSNKSQQEIWDNMTWMQWDKEISNYTNTIYRLLEDS
QNQQERNEKDLLALDSWKNLWSWFDITNWLWYIKIFIMIVGGLIGLRIIFAVLSIVNRVRQGYSPLSFQILTPNPGGPGRLGRIEEEGGEQD
KTRSIRLVNGFLALAWDDLRNLCLFSYHRLRDFILLTARGVELLGRNSLRGLQRGWEALKYLGSLVQYWGLELKKSTISLVDTIAIAVAEGT
DRIINIVQGICRAIHNIPRRIRQGFEAALQ$

Fig. 57B

2003 CON_06_CPX Env.seq.opt

ATGCGCGTGAAGGGCATCCAGAAGAACTGGCAGCACCTGTGGAAGTGGGGCACCCTGATCCTGGGCCTGGTGATCATCTGCTCCGCCTCCAA
CAACATGTGGGTGACCGTGTACTACGGCGTGCCCGCCTGGGAGGACGCCGACACCATCCTGTTCTGCGCCTCCGACGCCAAGGCCTACTCCG
CCGAGAAGCACAACGTGTGGGCCACCCACGCCTGCGTGCCCACCGACCCCAACCCCCAGGAGATCGCCCTGGAGAACGTGACCGAGAACTTC
AACATGTGGAAGAACCACATGGTGGAGCAGATGCACGAGGACATCATCTCCCTGTGGGACGAGTCCCTGAAGCCCTGCGTGAAGCTGACCCC
CCTGTGCGTGACCCTGAACTGCACCAACGTGACCAAGAACAACAACACCAAGATCATGGGCCGCGAGGAGATCAAGAACTGCTCCTTCAACG
TGACCACCGAGATCCGCGACAAGAAGAAGAAGGAGTACGCCCTGTTCTACCGCCTGGACGTGGTGCCCATCGACGACAACAACAACTCCTAC
CGCCTGATCAACTGCAACGCCTCCACCATCAAGCAGGCCTGCCCCAAGGTGTCCTTCGAGCCCATCCCCATCCACTACTGCGCCCCCGCCGG
CTTCGCCATCCTGAAGTGCCGCGACAAGAACTTCAACGGCACCGGCCCCTGCAAGAACGTGTCCACCGTGCAGTGCACCCACGGCATCAAGC
CCGTGGTGTCCACCCAGCTGCTGCTGAACGGCTCCCTGGCCGAGGAGGAGATCATCATCAAGTCCGAGAACCTGACCGACAACACCAAGACC
ATCATCGTGCAGCTGAACAAGTCCGTGGAGATCCGCTGCACCCGCCCCAACAACAACACCCGCAAGTCCATCTCCTTCGGCCCCGGCCAGGC
CTTCTACGCCACCGGCGACATCATCGGCGACATCCGCCAGGCCCACTGCAACGTGTCCCGCACCGACTGGAACAACATGCTGCAGAACGTGA
CCGCCAAGCTGAAGGAGCTGTTCAACAAGAACATCACCTTCAACTCCTCCGCCGGCGGCGACCTGGAGATCACCACCCACTCCTTCAACTGC
GGCGGCGAGTTCTTCTACTGCAACACCTCCCAGCTGTTCAACTCCACCCGCCCCAACGAGACCAACACCATCACCCTGCCCTGCAAGATCAA
GCAGATCGTGCGCATGTGGCAGCGCGTGGGCCAGGCCATGTACGCCCCCCCCATCGCCGGCAACATCACCTGCACCTCCAACATCACCGGCC
TGCTGCTGACCCGCGACGGCAACAACAACGACTCCGAGACCTTCCGCCCCGGCGGCGGCGACATGCGCGACAACTGGCGCTCCGAGCTGTAC
AAGTACAAGGTGGTGAAGATCAAGCCCCTGGGCATCGCCCCCACCCGCGCCCGCCGCCGCGTGGTGGGCCGCGAGAAGCGCGCCGTGGGCCT
GGGCGCCGTGTTCCTGGGCTTCCTGGGCACCGCCGGCTCCACCATGGGCGCCGCCTCCATCACCCTGACCGTGCAGGTGCGCCAGCTGCTGT
CCGGCATCGTGCAGCAGCAGTCCAACCTGCTGCGCGCCATCGAGGCCCAGCAGCACCTGCTGCAGCTGACCGTGTGGGGCATCAAGCAGCTG
CAGGCCCGCGTGCTGGCCGTGGAGCGCTACCTGAAGGACCAGCAGCTGCTGGGCATCTGGGGCTGCTCCGGCAAGCTGATCTGCCCCACCAA
CGTGCCCTGGAACGCCTCCTGGTCCAACAAGACCTACAACGAGATCTGGGACAACATGACCTGGATCGAGTGGGACCGCGAGATCAACAACT
ACACCCAGCAGATCTACTCCCTGATCGAGGAGTCCCAGAACCAGCAGGAGAAGAACGAGCAGGACCTGCTGGCCCTGGACAAGTGGGCCTCC
CTGTGGTCCTGGTTCGACATCTCCAACTGGCTGTGGTACATCAAGATCTTCATCATGATCGTGGGCGGCCTGATCGGCCTGCGCATCGTGTT
CGCCGTGCTGTCCATCGTGAACCGCGTGCGCCAGGGCTACTCCCCCCTGTCCCTGCAGACCCTGATCCCCAACCCCACCGGCGCCGACCGCC
CCGGCGAGATCGAGGAGGGCGGCGGCGAGCAGGGCCGCACCCGCTCCATCCGCCTGGTGAACGGCTTCCTGGCCCTGGCCTGGGACGACCTG
CGCTCCCTGTGCCTGTTCTCCTACCACCGCCTGCGCGACTTCGTGCTGATCGCCGCCCGCACCGTGGAGACCCTGGGCCACCGCGGCTGGGA
GATCCTGAAGTACCTGGGCAACCTGGTGTGCTACTGGGGCCAGGAGCTGAAGAACTCCGCCATCTCCCTGCTGGACACCACCGCCATCGCCG
TGGCCAACTGGACCGACCGCGTGATCGAGGTGGTGCAGCGCGTGTTCCGCGCCTTCCTGAACATCCCCCGCCGCATCCGCCAGGGCTTCGAG
CGCGCCCTGCTGTAA

Fig. 58B

```
2003_CON_08_BC Env seq.opt
ATGGCGGTGCGCGGCACCCGCGGCAACTACCAGCAGTGGTGTGGATCTGGGGCGTGCTGGGCTTCTGGATGCTGTGCTCTGGTGCAACGTGGAGGG
CAACCTGTGGGTGACCGTGTACTACGGCGTGCCCGTGTGGAAGGAGGCCAAGACCACCCTGTTCTGCGCCTCCGACGCCAAGGCCTACGAGA
CCGAGGTGCACAACGTGTGGGCCACCCACGCCTGCGTGCCCACCGACCCCAACCCCCAGGAGATCGTCCTGGAGAACGTGACCGAGAACTTC
AACATGTGGAACAACGACATGGTGGACCAGATGCACGAGGACGTGATCTCCCTGTGGGACCAGAGCCTGAAGCCCTGCGTGAAGCTGACCCC
CCTGTGCGTGACCCTGAACTGCACCACCGCCACTGTCCTGGCGACGACCGACCGTGTTCTACCGCCTGGACATCGTGCCCCTGAAGGAGATCAAGA
ACTGCTCCTTCAACGCCACCACTGAGATCCGCGACAAGAAGCAGAAAGACCGTGTACGCCCTGTTCTACACCCCGCCTCGGACATCGTGCCCCTGAACGAC
GAGAACTCCGGCAAGAACTCCCTGGAGTACAGGCTGATCAACTGCAACACCCAGCCGCCTCCATTGCGACAAGGTTGACCTGTCGA
CCCCATCCCATTGCCACCCAGCTACTGCGCACCCCGGCTACGCCATCCTGAAGTGCAACGACAAGAAGTTCAACGGCACCGGCGGAGAATCATCATC
TGTCCACCGTGCAGTGCACCCACGGCATCAAGCCCGTGGTGTCCACCCCAGCTGCTGCTGAACGGCCCTGGAGATCGTGTGCCACCCGCACAACAC
CGCTCCGAGAACCTGACCGACAACGTGAAGAACCTGACCCTGCATCGTGAAGGCCCAGACCAGCATCATCCGGCCAGATCGTGTTCAACGGCCACCCTACGAA
CCGCAAGTCCATCCGCATCGGCCCCAGGAGACCCTTCCTACGCCGACACTCATTCCCCAACAACAACACCCTCCGGCTTGTTCAACGGCACCTACACCC
AGGACAAGTGGTACGAGATCACCACCCTCCTCAACTGCCGGGCGTTCTTCTACTGCAATCAAGCAGATCATCAAGCAGTGGGCGCGAGGTTGGGCCGTCG
GGCGACCTGGAGATCACCACCCTCCTCAACTGGCGACATCCCGCGAGTTCTTCAACGGCCAAGAGCGCCCTCCATCCCCCGAGTGCCCACCGAGTCCAACACACC
CGGCACCACCATCACCCTCCCATCATCGGCCGGGCAACATGCGGGACATCCTGGGCAACATGTGGCAGGAGGTCGGCCGGGCCATGTACGCCCCGCCAGATCAAGCCCCTGGGCGT
CCCCCCCAATCGAGGGCCGCCAAGCCGCCAAGCCCCCTGACCGTGCCGGCTTCCTGCTGTACGCCCCCCTGTTCCTGCAGCAGCCAGCAGTCCAACCTGCTGCGC
GCTCACCATGGGCGCCCTCCATCGAGTGCTGCACCATCCCCGCGTCCAAGTCCAACATCAGCCATGCTCCCGCTGGCCATCTGCGGGGCCATCTGCGGGCCATCTGCGAACCTGCTGCGACCTGAA
GCCATCAAGGCCGAGATCTGGGACAACATGACCTGGATGCAGTGGGAACAAGGAGGACTGGGCCCCTGTGACCAAGGCCATCCCTGGGTCCAACAAAGTCCC
GGACCAGCAGCTGCTGGGCTGGCATCGAC

Fig. 59A

2003 CON 10 CD Env
MRVMGIQRNCQQWIWGILGFWMLMICNATGNLWVTVYYGVPVWKETTTTLFCASDAKAYKAEAHNIWATHACVPTDENPQEIVLENVTENF
NMWKNGMVDQMHEDIISIWDQGLKPCVKLTPLCVTLNCSDVNATNSATNTVVAGMKNCSFNITTEIRDKKKQEYALFYKLDVVQIDGSNTSY
RLINCNTSAITQACPKVTFEPIPIHYCAPAGFAILKCNDKKFNGTGPCKNVSTVQCTHGIKPVVSTQLLLNGSLAEEEIIIRSENLTDNAKT
IIVQLNESVTINCTRPNNNTRKSIRIGPGQTFYATGDIIGNIRQAYCNISGTEWNKTLQQVAKKLGDLLNKTTIIFKPSSGDPEITTHTFN
CGGEFFYCNTSKLFNSSWTSNNTGNTSTITLPCRIKQIINMWQGVGKAIYAPPIAGLINCSSNITGLLLTRDGGANNSETFRPGGGDMRDNW
RSELYKYKVVKIEPLGLAPTKAKRRVVEREKRAIGLGAVFLGFLGAAGSTMGAASLTLTVQARQLLSGIVQQNNLLRAIEAQQHLLQLTVW
GIKQLQARVLAVESYLKDQQLLGIWGCSGKHICTTNVPWNSSWSNKSLEEIWDNMTWMEWEREIDNYTGLIYSLIEESQNQEKNEQELLQL
DKWASLWNWFSITNWLWYIKIFIMIVGGLIGLRIVFAVLSLVNRVRQGYSPLSFQTLLPAPRGPDRPEGIEEGGGEQGRSIRLVNGFSAL
IWDDLRNLCLFSYHRLRDLILIATRIVELLGRRGWEAIKYLWNLLQYWIQELKNSAISLLDTTAIAVAEGTDRAIEIVQRAVRAVLNIPTRI
RQGLERALL$

Fig. 60A

2003 CON 11 CPX Env
MRVKETQRNWHNLWRWGLMIFGMLMICNATENLWVTVYYGVPVWKDADTTLFCASDAKAYSTEKHNVWATHACVPTDENPQEIPLENVTENF
NMWKNNMVEQMHEDIISLWDESLKPCVKLTPLCVTLNCTDVKNATNTTVEAAEIKNCSFNITTEIKDKKKKEYALFYKLDVVPINDNNNSIY
RLINCNVSTVKQACPKVTFEPIPIHYCAPAGFAILKCNDKKFNGTGPCKNVSTVQCTHGIKPVVSTQLLLNGSLAEGEVRIRSENFTNNAKT
IIVQLNSSVRINCTRPNNNTRKSIHIGPGQAFYATGDIIGDIRQAHCNISRAEWNNTLQQVAKQLRENFNKTIIFNNPSGGDLEITTHSFNC
GGEFFYCNTSRLFNSTWNNDTRNDTKQMHITLPCRIKQIVNMWQRVGQAMYAPPIQGKIRCNSNITGLLLTRDGGNNNTNETFRPTGGDMRD
NWRSELYKYKVVEIKPLGVAPTRAKRRVVEREKRAVGIGAVLLGFLGAAGSTMGAASITLTVQARQLLSGIVQQQSNLLKAIEAQQHLLKLT
VWGIKQLQARVLAVERYLKDQQLLGIWGCSGKLICTTNVPWNFSWSNKSYDEIWDNMTWIEWEREINNYTQTIYTLLEESQNQQEKNEQDLL
ALDKWASLWNWFDISNWLWYIKIFIMIVGGLIGLRIIFAVLSIVNRCRQGYSPLSFQTLTPNHKEADRPGGIEEGGGEQDRTRSIRLVSGFL
ALAWDDLRNLCLFSYHRLRDFILIAARIVETLGRRGWEILKYLGNLAQYWGQELKNSAISLLNATAIAVAEGTDRIIEVVHRVLRAILHIPR
RIRQGFERALL$

Fig. 59B

```
2003_CON_10_CD_Env.seq.opt
ATGCGCGTGATGGGCATCCAGCGACTGCCAGCACTGGTCGGGCATCCTGGGCTTCTGGATGCTGATGATCTGCAACGGCCACCGG
CAACCTGTGGGTGACCGTGTACTACGGCGTGCCCGTGCCCTGCGTGCCCGTGCTGTTCTGCGCCACCACCCTGGACCCTACAAGG
CCGAGGCCCACAACATCTGGGCCACACCCTGGACCCTGCTGGAGAAGATCGTCGTGACCGAGAACTTC
AACATGTGGAAGAACGGGATGGTGACCAGATGCACGAGGACATCATCTCCCTGTGGGACCAGGCCCTGAAGCCCTGCGTGAAGCTGACCCC
CCTGTGCGTGACCCTGAACTGCTCCGACAAGAAGCAGGAGTACGCCGCCATCCCGTGCACCCTGAAGAACTGCTCCTTCAACA
TCACCACCGAGATCCGCGACAAGAAGCAGAAGGTGACCGCCCTGCAACGTGGACGTGACGTGCCCATCCTGATCCCCCGCGG
CGCCTGATCAACTGCAACACCTCCGCCATCACCCAGGCCTGCCCCAAGGTGACCTTCGAGCCCATCCCGATCGGCCATCAAGC
CTTCGCCATCCTGAAGTGCAACGACAAGAAGTTCAACGGCACCGGGACCATCATCGTGCACCTGAACGAGCCCGTGCAGATCAACTGCACCCGG
CCGTGGTGTCCACCCAGCTGCTGCTGAACGGCAGTCCGTGAACGAGGAGATCATCATCCGAGAAACCGCGAGAACCTGACCGACAACGCCAAGACC
ATCATCGTGCAGCTGACCGAGTCCGTGACCATCAACTGCACACCCCGGCCTACTGCAACATCTCCGGCACCAAGTCCGAGTGGAACAAGACCCTGCAGCAGGTGG
CTTCTACCGCCACCGGCGACATCATCGGCAACAAGACCACCATCCTCCAAGCTGTGTTCAACTCCTCCTCCGGACCTCTCCGAGATCATCCACACCTTCAAC
CAAGAAGCTGGGCGCGGAGTTCTTCTACTGCAACAAGACACCTCCAAGCTGTCTTCAACTGCCGCGGCGAATCCGCAACACCGGCATCCAACATCAACCTCCACATAACTGCTCCT
GCCCCCGCGGCCATCATCCAGCAGATCCATCATCAACATGTGGCAGGGCGTGGGCCAAACACTGCGCGCAACATGCGCGACATCGCCGACAACTGG
CGCTCCGAGCTGTGTACAAGTACAAGGTGGTGAAGATCGAGCCCCTGGGCTTCCTGGGCGCCGCCGTGTTCCTGCAGCAGAACATGCGCCGAGAA
GCGCGCCATCGGGGCGCCCGTGTTCCTGCAGCAGAACATCGAGGCCGCCAAGCGGGCCCCGCCCTGCCCCACAACCTGCTGCAGCCGTGCAGG
CCCGCCAGCAGCTGCTGTTCCGGCATCGAGCAGAACCTGCCTACCTGAGTCCCAACAGATCCCTGGACAACATGACCTGGATGGAGTGGGAGC
GGCATCAAGCACCACCGCCAACGTGCCCTGGAACTCCTCCTGGAGCAACTGGGACAACATGACCTGGATGGAGTGGGAGAGC
CATCTGCCACCAGCTGACAGAACGTGCCCTGGAACTCCTCCTGGAGCAACTGGGACAACATGACCTGGATGGAGTGGGAGAGC
GCGAGATCGACAACTACACCCTGTCCAACGCCCTGAAGCTGGTCTCCATCACCAACGGCCTGTGTATCCTGGCGGCCCTGATCGG
GACAAGTGGCCTCCCTGTGCCAGTTCAGATCAATGCCTGCTGCTCAGATCTTCATCATGATCGTGGGCGCGCCTCGTCGG
CCTGCGCATCGTGTTCGCCGTGCTGTCCATCGTGAACCGGGTGCGCCAGGGCTACTCCCCGCTGTCCTTCCAGATCCCGACCCCCCACCCCCGGG
GCGCCCCCGACGCCCTGGGAGGGCACCGAGGAGGGGGCCGAGACCCTGGCCCTGCGGCCTTCTCCGCCCTG
ATCTGGACGACCTGCGCTCCCTGTGCCTGTTCTCCTACCACCGCCTGCGGGACCCTGATCCTGGAACGGCCTGGTGCTGGG
CCGGCGGGGCCTGGAGCGCCTGGGCCGAGGGACCACCAAGCTGCCGGGTAACCGGAGGGCCCGCGTGCAGCGGGACATCCGGAACATCCCCACCGGACA
CGCCAGGGCCTGGAGCGCCTGGGCGCCCTGCTGTAA
```

Fig. 60B

```
2003_CON_11_CPX Env.seq.opt
ATGCGCGTGAAGGAGACCCAGCCAACTGGCACAACCTGTGGCGCTGGGCCTGATGATCTTCGGCATGCTGCTGATCTGCAACGCCACCGA
GAACCTGTGGGTGACCGTGTACTACGGCGTGCCCGTGTGGAAGGACGCCGACACCACCCTGTTCTGCGCCAGCGATGCCCAAGCCTACTCCA
CCGAGAAGCACAACGTGTGTGGCCACGCCCTGCTGCGTGACCCCAACGAGATCATCCCCAGGAGAATCCCTGGGACGAGTCCCTGAAGCCCTGACCCC
AACATGTGGAAGAACAACATGGTGGAGCAGATGCACGAGGACATCATCTCCCTGTGGGACGAGTCCGCCGTGAAGCTGACCCCTGAGCTGAC
CCTGTGCCGTGACCCTGAACTGCAAGGACGTGAAGAACAGCGAGTACAGAGGAGACGGAGACGTGGACCTTGCCCATCAACGACATCCATCTAC
CGCCTGATCAACTGCAACTGTCCAAGCTGTCCAACGACGAGAAGTTCAACGCGACAAGAAGTTCAACGGCACACGACAACGCCAAGACC
CGGTGGTGCCAGCTGCGAACTCCCTCCGTGCGCATCAACGACACCGCCAAGTCCATCCACATCACCCCCGGACGAGTGCAGGC
ATCATCGTGCAGCTGAACTCCCTCCGTGCGCATCAACTGCACACCGCCAAGTCCATCCACATCACCCCGGACGAGTGCAGGC
CTTCTACGCCACCGGCGACGTCATCGGCGAAACATTCAACAAGACCATCGCCCCGCCGACCTGGAACACACCACCCACTCCTTCAACTGC
CAAGCAGCTGCGCGAGATCTTCTACTGCAAGACCGGCGCCACAGAGATCAACAAGCAAGACACCACCCCTGCCCATCAGCAGCAAGAGATCACAC
GGCGGCGAGTTCTTCTACTGCAACCACACACCCGGGAACACGCCAAGACCATATCCCCTGCAAGAACCGGCATCAACGACATGTGCACATCAC
CTGCCCTGCCTGTGCTGACCCGGCAACGAGCAGATGTCGTGAACGCGCGTGGACGGGCCAACCACATCCGCCCCATCCCACCCGGCGGCACATGCCGAC
ACTGAACATCACCGGCCTGCTGACCCGCGCAACGGCCAACCAACCACAAGGCCCCTCGGCCGTGGGAGCG
AACTGGCGCTCCGAGCTGTACAAGGTGGTGCTGCTGGAGATCAAGCCCTTCCTGGCCGTCCCCGCCACCCGTGGGCCCCTGACCG
CGAGAAGCGCGACCTGGGCATCCGGGCGTCGCCAGCTGCTCGTGCAGCAGCTGGCCGTGCGTGAGCGCCGCCAGCTGAAGGCCACCTGAAGCTGACC
TGCAGGCTGACCAAGCAGCACAGGCCGCCATCAAGCAGCTGCAGCTGCGGTCCGTGCAGCTGGAGCGCTACCTGAAGGACCAGCAGCTGCTGGGCATCTGGGGCTGCTCCGG
GTGTGGGGCATCAAGCAGCTGCAGCACCAAGTCCTGGAACTTCGCCTGGTCCAACAAGAGCCTCCTCAACCAAGTTGGCCCCGACAAAGCTGGATCGAGT
CAAGCTGATCTGCACCACCAAGGTGCACCACCCAGAACTACCAAGTCCCTGGTCCTGGTCGGTGGTGCTGGAAGAACAAGGCGGCCACCAGCAGAACAATGAGCAGCAGGACCTGCTG
GGGAGCGCGAGATCAAGGAATCAACAACTACACCCAGGAAACTGGTCCAACATCTCCAACTGGCTGTGTTCCAACATCAAGATCTTTCATCATGATCGTGGGGCGCT
GCCCTGCCTGCGATCATCTGGCCCTGTGCCGTGCATCCGGAAGCCTGTGTCCGTGCATCATCATCATCCGCTGCCTGGTTCCGCTTCCTG
GATCGGCCTGCGCATCATCCCCGGCCACCTGCCCTGCGGCATCGAAGGCGGCAACATCATCGACGATCATCCTGATCGTGGAGAC
ACCACAAGGAGCGCGGCTGGGACCTGCGCAACGTGTTCCTCTACCACCGGCGGCAGTTCATCCTGATCGCCGCCATGCGCATCCCCTG
GCCCTGGCCTGGAGCGCGCCTCGGGCGATCGAGTGTCCCAACCGGACCGCCAACCTGGGCATCATCGACACGGCAACATCCCCCTG
GAACGGCACCGCCACCCCGGGCGCCACCGGACGAGCGCCATCGAAGGGCGGGGCACCGGCCTGGAAGAACTCCGCCATCTCCCTG
CGCATCCCGCCAGGGCTTCGAGCGCGCCCCTGCTGTAA
```

Fig. 61A

2003_CON_12_BF_Env

MRVRGMQRNWQHLGKWGLLFLGILIICNATENLWVTVYYGVPVWKEATTLFCASDAKSYEREVHNVWATHACVPTDPNPQEVDLENVTENF
DMWKNNMVEQMHTDIISLWDQSLKPCVKLTPLCVTLNCTDANATANATKEHPEGRAGAIQNCSFNMTTEVRDKQMKVQALFYRLDIVPISDN
NSNEYRLINCNTSTITQACPKVSWDPIPIHYCAPAGYAILKCNDKKFNGTGPCKNVSTVQCTHGIKPVVSTQLLLNGSLAEEEIIIRSQNIS
DNAKTIIVHLNESVQINCTRPNNNTRKSIHIGPGRAFYATGDIIGDIRKAHCNVSGTQWNKTLEQVKKKLRSYFNTTIKFNSSGDPEITM
HSFNCRGEFFYCNTSKLFNDTVSNDTIILPCRIKQIVNMWQEVGRAMYAAPIAGNITCTSNITGLLLTRDGGHNETNKTETFRPGGGNMKDN
WRSELYKYKVVEIEPLGVAPTRAKRQVVKREKRAVGIALFLGFLGAAGSTMGAASITLTVQARQLLSGIVQQQSNLLRAIEAQQHLLQLTV
WGIKQLQARVLAVERYLKDQQLLGLWGCSGKLICTTNVPWNSSWSNKSQEEIWENMTWMEWEKEINNYSNEIYRLIEESQNQQEKNEQELLA
LDKWASLWNWFDISNWLWYIRIFIMIVGGLIGLRIVFAVLSIVNRVRKGYSPLSLQTHIPSPREPDRPEGIEEGGEQGKDRSVRLVNGFLA
LIWDDLRSLCLFSYHRLRDLLLIVTRIVELLGRRGWEVLKYWWNLLQYWSQELKNSAISLLNTTAIVVAEGTDRVIEALQRVGRAILNIPRR
IRQGLERALL$

Fig. 62A

2003_CON_14_BG_Env

MKAKGTQRNWQSLWKWGTLILGLVIICSASNDLWVTVYYGVPVWKEATTLFCASDAKAYDAEVHNVWATHACVPTDPNPQEVALENVTENF
NMWENNMVDQMQEDIISLWDQSLKPCVELTPLCVTLNCTDFNNTTNNTRNDGEGEIKNCSFNITTSLRDKIKKEYALFYNLDVVQMDND
NSSYRLITSCNTSIITQACPKVSFTPIPIHYCAPAGFVILKCNNKTFNGTGPCTNVSTVQCTHGIRPVVSTQLLLNGSLAEEEIVIRSKNFTD
NAKTIIVQLKDPIEINCTRPNNNTRKRITMGPGRVLYTTGQIIGDIRKAHCNISKTKWNNTLGQIVKKLREQFMNKTIVFQRSSGDPEIVM
HSFNCGGEFFYCNTTQLFNSTWRSNSTWNDTTETNNTDLIITLPCRIKQIVNMWQKVGKAMYAPPISGQIRCSSNITGLLLIRDGGSNNTEFE
RPGGGNMKDNWRSELYKYKVVKIEPLGVAPTRAKRRVQREKRAVGIGALLFGFLGAAGSTMGAASMTLTVQARQLLSGIVQQQNNLLRAIE
AQQHMLQLTVWGIKQLQARVLAVERYLKDQQLLGIWGCSGKLICTTTVPWNASWSNKSLDDIWNNMTWMEWEREIDNYTGLIYTLIEQSQNQ
QERNEQELLELDKWASLWNWFNITNWLWYIKIFIMIIGGLIGLRIVFAVLSIINRVRKGYSPLSFQTLTHHQREPDRPGRIEEGGEQDKDR
SIRLVSGFLALAWDDLRSLCLFSYHRLRDFILIAARTVELLGRSSLKGLRLGWEGLKYLWNLLLYWGRELKNSAINLLDTVAIAVANWTDRA
IEVVQRVGRAVLNIPVRIRQGLERALL$

Fig. 61B

2003_CON_12_BF_Env.seq.opt
ATGGCCGTGCGCGGCAATGCAGCAGCCAACTGGCAGCACCTGGGCAAGTGGGGCCTGCTGTTCCTGGGCATCCTGATCATCTGCAACGCCACCGA
GAACCTGTGGGTGACCGTGTACTACGGCGTGCCCGTGTGCGAAGGAGGCCACCACCGTGTTCTGCGCCAGTGCCTACGAGC
GCGAGGTGCACAACGTGTGGGCCACCCACGCCTGCGTGCCCACCGACCCCAACCCCCAGGAGGTGACGTGACCGAGAACTTC
GACATGTGGAAGAACAACATGGTGGAGCAGATGCACACCGACATCATCTCCCTGTGGGACCAGAGCCTGAAGCCCTGCGTGAAGCTGACCCC
CCTGTGCGTGACCCTGAACTGCACCGACGTGCGCAACGCCACCAACGCCACCAAGGAGCAGATGAAGGTGCAGGCCCTGTTCTACCGCCTGGACATCGTGCCCATCCGACAAC
ACTCCAACGAGTACCGCCTGATCAACTGCAACACCTCCACCATCAAGAAGTTGCACGGCACCCAAGGTGTCCTGGACGCCCTGTTCTACCGCCTGGACATCGTGCCCATCCGACAAC
CTGCCCCCCCGGCATCAAGCCCGTGGTGTCCACCCAGCTGCTGCTGAACGGCAGCCTGCTGAACGAGTCCGTGCAGATCAACTGCACCCGCCCCAACAACAACACCCGCAAGTCCATCCACAT
CGGCCCCGGCCGCGCCTTCTACGCCACCGGCGACATCATCGGCGACATCCGGCAGGCCCACTGCAACATCAGCAGCTCCCAGTGGAACGAGACC
CTGGAGCAGGTGAAGAAGAAGCTGCGCGAGTTGCCCGGCAAAGATCAAACGCCGTGGCTGCGCCGCACATGCCCAAGGGCCCAGCGCTGCTCGCCGCCTGGGCGCCGCAAGCATGGTGTGAAGCGCGAA
TCAACCGGCTGCTGCTGACCCGACGAAGTACAAGTTGCGGCGCATCCGCGGCCAGTTCTTCTACTGCAACACCTCCCGCCTGTTCAACCGGAACCTTCCGCCCGCAACCATGAGGGCCACCAGCAAACGAGAGCTGAGCGCCCCCCCCACCATCGAGGCCAACAATGGTGGAAGGACAAC
AGGGCCCCAGCAGCTGCCTGGCCATCCGGCGCCTGCGTGTTCGCGCCGCCAGCCGTGCTGGCCAAGTCGATCTACCGCCCTTCCTGGTCCTGATCGAGAGAAGAACCAGCAGGAGGAGAACAATGAGCAGCAAGCACCATCATGATCGTGGGCGGCCTGATCGGGCCCGCTGGGCC
CTGATCTGCACCAGCAAGGCCAAGCGCCGCCTGGTCTAGCCGTGGCCCCGTCTTAAATAAT
CGGCCTGCGCATCGTGTTCGCCGTGCTGTCCATCGTGAACCGTGTGCGCGAGGGGCGGCCGCAAGAGGGCTACTCCCCCCTGTCCCTGCAGACCCACATCCCCCTCCCC
CCCGCGAGCCCGACCTGGAGCGTGCTCCTCCTGCCCGCCGCGCCTACCACCGCAAGGAGCCCTGGGACCTGGTGCGCATCGTGAAGCGCTTCCTGCTCCCTGCCCTGCCGCCCCGCGCCTCCTGCC
CTGATCTGGGACGACCTGCGCAGCCTGTGCCGCTTCTCCCGCCCTGTTCCTGGAACTGCTGAAGTACTGGTCCCAGGAGCTGAAGAACAGCGCCGTCAGTCTGCTGGACGCCACCGCCATCTCCGTGGCCGAGGGCGTGCTGCT
GGGCGCCGCCATCGCCCCCGCCCTGGAGAGGTGGCC

Fig. 62B

2003 CON_14_BG Env.seq.opt

ATGAAGGCCAAGGGCACCCAGCGCAACTGGCAGTCCCTGTGGAAGTGGGGCACCCTGATCCTGGGCCTGGTGATCATCTGCTCCGCCTCCAA
CGACCTGTGGGTGACCGTGTACTACGGCGTGCCCGTGTGGAAGGAGGCCACCACCACCCTGTTCTGCGCCTCCGACGCCAAGGCCTACGACG
CCGAGGTGCACAACGTGTGGGCCACCCACGCCTGCGTGCCCACCGACCCCAACCCCCAGGAGGTGGCCCTGGAGAACGTGACCGAGAACTTC
AACATGTGGGAGAACAACATGGTGGACCAGATGCAGGAGGACATCATCTCCCTGTGGGACCAGTCCCTGAAGCCCTGCGTGGAGCTGACCCC
CCTGTGCGTGACCCTGAACTGCACCGACTTCAACAACACCACCAACAACACCACCAACACCCGCAACGACGGCGAGGGCGAGATCAAGAACT
GCTCCTTCAACATCACCACCTCCCTGCGCGACAAGATCAAGAAGGAGTACGCCCTGTTCTACAACCTGGACGTGGTGCAGATGGACAACGAC
AACTCCTCCTACCGCCTGACCTCCTGCAACACCTCCATCATCACCCAGGCCTGCCCCAAGGTGTCCTTCACCCCCATCCCCATCCACTACTG
CGCCCCCGCCGGCTTCGTGATCCTGAAGTGCAACAACAAGACCTTCAACGGCACCGGCCCCTGCACCAACGTGTCCACCGTGCAGTGCACCC
ACGGCATCCGCCCCGTGGTGTCCACCCAGCTGCTGCTGAACGGCTCCCTGGCCGAGGAGGAGATCGTGATCCGCTCCAAGAACTTCACCGAC
AACGCCAAGACCATCATCGTGCAGCTGAAGGACCCCATCGAGATCAACTGCACCCGCCCCAACAACAACACCCGCAAGCGCATCACCATGGG
CCCCGGCCGCGTGCTGTACACCACCGGCCAGATCATCGGCGACATCCGCAAGGCCCACTGCAACATCTCCAAGACCAAGTGGAACAACACCC
TGGGCCAGATCGTGAAGAAGCTGCGCGAGCAGTTCATGAACAAGACCATCGTGTTCCAGCGCTCCTCCGGCGGCGACCCCGAGATCGTGATG
CACTCCTTCAACTGCGGCGGCGAGTTCTTCTACTGCAACACCACCCAGCTGTTCAACTCCACCTGGCGCTCCAACTCCACCTGGAACGACAC
CACCGAGACCAACAACACCGACCTGATCACCCTGCCCTGCCGCATCAAGCAGATCGTGAACATGTGGCAGAAGGTGGGCAAGGCCATGTACG
CCCCCCCCATCTCCGGCCAGATCCGCTGCTCCTCCAACATCACCGGCCTGCTGCTGATCCGCGACGGCGGCTCCAACAACACCGAGACCTTC
CGCCCCGGCGGCGGCAACATGAAGGACAACTGGCGCTCCGAGCTGTACAAGTACAAGGTGGTGAAGATCGAGCCCCTGGGCGTGGCCCCCAC
CCGCGCCAAGCGCCGCGTGGTGCAGCGCGAGAAGCGCGCCGTGGGCATCGGCGCCCTGCTGTTCGGCTTCCTGGGCGCCGCCGGCTCCACCA
TGGGCGCCGCCTCCATGACCCTGACCGTGCAGGCCCGCCAGCTGCTGTCCGGCATCGTGCAGCAGCAGAACAACCTGCTGCGCGCCATCGAG
GCCCAGCAGCACATGCTGCAGCTGACCGTGTGGGGCATCAAGCAGCTGCAGGCCCGCGTGCTGGCCGTGGAGCGCTACCTGAAGGACCAGCA
GCTGCTGGGCATCTGGGGCTGCTCCGGCAAGCTGATCTGCACCACCACCGTGCCCTGGAACGCCTCCTGGTCCAACAAGTCCCTGGACGACA
TCTGGAACAACATGACCTGGATGGAGTGGGAGCGCGAGATCGACAACTACACCGGCCTGATCTACACCCTGATCGAGCAGTCCCAGAACCAG
CAGGAGCGCAACGAGCAGGAGCTGCTGGAGCTGGACAAGTGGGCCTCCCTGTGGAACTGGTTCAACATCACCAACTGGCTGTGGTACATCAA
GATCTTCATCATGATCATCGGCGGCCTGATCGGCCTGCGCATCGTGTTCGCCGTGCTGTCCATCATCAACCGCGTGCGCAAGGGCTACTCCC
CCCTGTCCTTCCAGACCCTGACCCACCACCAGCGCGAGCCCGACCGCCCCGGCCGCATCGAGGAGGAGGGCGGCGAGCAGGACAAGGACCGC
TCCATCCGCCTGGTGTCCGGCTTCCTGGCCCTGGCCTGGGACGACCTGCGCTCCCTGTGCCTGTTCTCCTACCACCGCCTGCGCGACTTCAT
CCTGATCGCCGCCCGCACCGTGGAGCTGCTGGGCCGCTCCTCCCTGAAGGGCCTGCGCCTGGGCTGGGAGGGCCTGAAGTACCTGTGGAACC
TGCTGCTGTACTGGGGCCGCGAGCTGAAGAACTCCGCCATCAACCTGCTGGACACCGTGGCCATCGCCGTGGCCAACTGGACCGACCGCGCC
ATCGAGGTGGTGCAGCGCGTGGGCCGCGCCGTGCTGAACATCCCCGTGCGCATCCGCCAGGGCCTGGAGCGCGCCCTGCTGTAA

Centralized HIV-1 gag/nef/pol Protein and the Codon-optimized Gene Sequences

Fig. 63A 1. 2003_CON_S_gag.PEP

MGARASVLSGGKLDAWEKIRLRPGGKKKYRLKHLVWASRELERFALNPGLLETSEGCQQIIEQLQPALQTGSEELRSLYNTVATLYCVHQRI
EVKDTKEALDKIEEEQNKSKQKTQQAAADTGNSSKVSQNYPIVQNLQGQMVHQAISPRTLNAWVKVVEEKAFSPEVIPMFSALSEGATPQDL
NTMLNTVGGHQAAMQMLKDTINEEAAEWDRLHPVHAGPIPPGQMREPRGSDIAGTTSTLQEQIGWMTSNPPIPVGEIYKRWIILGLNKIVRM
YSPVSILDIRQGPKEPFRDYVDRFFKTLRAEQATQDVKNWMTDTLLVQNANPDCKTILKALGPGATLEEMMTACQGVGGPSHKARVLAEAMS
QVTNTTIMMQRGNFKGQKRIIKCFNCGKEGHIARNCRAPRKKGCWKCGKEGHQMKDCTERQANFLGKIWPSNKGRPGNFLQSRPEPTAPPAE
SFGFGEEITPSPKQEPKDKELYPLASLKSLFGNDPLSQ$

Fig. 63B

2003_CON_S gag.OPT

ATGGGCGCCCGCGCCTCCGTGCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCTCCGAGGGCTGCCAGCAGATCATCG
AGCAGCTGCAGCCCGCCCTGCAGACCGGCTCCGAGGAGCTGCGCTCCCTGTACAACACCGTGGCCACCCTGTACTGCGTGCACCAGCGCATC
GAGGTGAAGGACACCAAGGAGGCCCTGGACAAGATCGAGGAGGAGCAGAACAAGTCCAAGCAGAAGACCCAGCAGGCCGCCGCCGACACCGG
CAACTCCTCCAAGGTGTCCCAGAACTACCCCATCGTGCAGAACCTGCAGGGCCAGATGGTGCACCAGGCCATCTCCCCCCGCACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGACACCATCAACGAGGAGGCCGCCGAGTGGGACCGCCT
GCACCCCGTGCACGCCGGCCCCATCCCCCCCGGCCAGATGCGCGAGCCCCGCGGCTCCGACATCGCCGGCACCACCTCCACCCTGCAGGAGC
AGATCGGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGACGTGAAGAACTGGATGACCGACACCCTGCTGGTGCAGAACGCCAACCCCGACTGCAAGACCATCCTGAAGGCCCTGG
GCCCCGGCGCCACCCTGGAGGAGATGATGACCGCCTGCCAGGGCGTGGGCGGCCCCTCCCACAAGGCCCGCGTGCTGGCCGAGGCCATGTCC
CAGGTGACCAACACCACCATCATGATGCAGCGCGGCAACTTCAAGGGCCAGAAGCGCATCATCAAGTGCTTCAACTGCGGCAAGGAGGGCCA
CATCGCCCGCAACTGCCGCGCCCCCCGCAAGAAGGGCTGCTGGAAGTGCGGCAAGGAGGGCCACCAGATGAAGGACTGCACCGAGCGCCAGG
CCAACTTCCTGGGCAAGATCTGGCCCTCCAACAAGGGCCGCCCCGGCAACTTCCTGCAGTCCCGCCCCGAGCCCACCGCCCCCCCCGCCGAG
TCCTTCGGCTTCGGCGAGGAGATCACCCCCTCCCCCAAGCAGGAGCCCAAGGACAAGGAGCTGTACCCCCTGGCCTCCCTGAAGTCCCTGTT
CGGCAACGACCCCCTGTCCCAGTAA

Fig. 64A 2. 2003_M.GROUP.anc_gag.PEP

MGARASVLSGGKLDAWEKIRLRPGGKKKYRLKHLVWASRELERFALNPGLLETAEGCQQIMGQLQPALQTGTEELRSLYNTVATLYCVHQRI
EVKDTKEALDKIEEEQNKSQKTQQAAADKGDSSQVSQNYPIVQNLQGQMVHQAISPRTLNAWVKVVEEKAFSPEVIPMFSALSEGATPQDL
NTMLNTVGGHQAAMQMLKDTINEEAAEWDRLHPVHAGPIPPGQMREPRGSDIAGTTSTLQEQIGWMTSNPPIPVGEIYKRWIILGLNKIVRM
YSPVSILDIRQGPKEPFRDYVDRFFKTLRAEQATQDVKNWMTDTLLVQNANPDCKTILKALGPGATLEEMMTACQGVGGPGHKARVLAEAMS
QVTNANIMMQRGNFKGPRRIVKCFNCGKEGHIARNCRAPRKKGCWKCGKEGHQMKDCTERQANFLGKIWPSNKGRPGNFLQSRPEPTAPPAE
SFGFGEEITPSPKQEPKDKELYPLASLKSLFGSDPLSQ$

Fig. 64B

2003_M.GROUP.anc_gag.OPT

ATGGGCGCCCGCGCCTCCGTCCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCGCCGAGGGCTGCCAGCAGATCATGG
GCCAGCTGCAGCCCGCCCTGCAGACCGGCACCGAGGAGCTGCGCTCCCTGTACAACACCGTGGCCACCCTGTACTGCGTGCACCAGCGCATC
GAGGTGAAGGACACCAAGGAGGCCCTGGACAAGATCGAGGAGGAGCAGAACAAGTCCCAGAAGACCCAGCAGGCCGCCGCCGACAAGGG
CGACTCCTCCCAGGTGTCCCAGAACTACCCCATCGTGCAGAACCTGCAGGGCCAGATGGTGCACCAGGCCATCTCCCCGCGACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCATCAAGCCGCCATGCAGATGCTGAAGGACACCATCAACGAGGAGGCCGCCGAGTGGGACCGCCT
GCACCCCGTGCACGCCGGCCCCATCCCCCCGGCCAGATGCGCGAGCCCCGCGGCTCCGACATCGCCGGCACCACCTCCACCCTGCAGGAGC
AGATCGGCTGGATGACCTCCAACCCCCCGATCCCCGTGGGCGAGATCTACAAGCGCTGGATCATCCTGGGCCTGAACAAGATCGTGCGCAT
GTACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGACGTGAAGAACTGGATGACCGACACCCTGCTGGTGCAGAACGCCAACCCCGACTGCAAGACCATCCTGAAGGCCCTGG
GCCCCGGCGCCACCCTGGAGGAGATGATGACCGCCTGCCAGGGCGTGGGCGGCCCCGGCCACAAGGCCCGCGTGCTTGCCGAGGCCATGTCC
CAGGTGACCAACGCCAACATCATGATGCAGCGCGGCAACTTCAAGGGCCCCCGCCGCATCGTGAAGTGCTTCAACTGCGGCAAGGAGGGCCA
CATCGCCCGCAACTGCCGCGCCCCCCGCAAGAAGGGCTGCTGGAAGTGCGGCAAGGAGGGCCACCAGATGAAGGACTGCACCGAGCGCCAGG
CCAACTTCCTGGGCAAGATCTGGCCCTCCAACAAGGGCCGCCCCGGCAACTTCCTGCAGTCCCGCCCCGAGCCCACCGCCCCCCCGAG
TCCTTCGGCTTCGGCGAGGAGATCACCCCCTCCCCCAAGCAGGAGCCCAAGGACAAGGAGCTGTACCCCCTGGCCTCCCTGAAGTCCCTGTT
CGGCTCCGACCCCCTGTCCCAGTAA

Fig. 65A 3. 2003_CON_A1_gag.PEP

MGARASVLSGGKLDAWEKIRLRPGGKKKYRLKHLVWASRELERFALNPSLLETTEGCQQIMEQLQPALKTGTEELRSLYNTVATLYCVHQRI
DVKDTKEALDKIEEIQNKSKQKTQQAAADTGNSSKVSQNYPIVQNAQGQMVHQSLSPRTLNAWVKVIEEKAFSPEVIPMFSALSEGATPQDL
NMMLNIVGGHQAAMQMLKDTINEEAAEWDRLHPVHAGPIPPGQMREPRGSDIAGTTSTPQEQIGWMTGNPIPVGDIYKRWIILGLNKIVRM
YSPVSILDIKQGPKEPFRDYVDRFFKTLRAEQATQEVKNWMTETLLVQNANPDCKSILRALGPGATLEEMMTACQGVGGPGHKARVLAEAMS
QVQHTNIMMQRGNFRGQKRIKCFNCGKEGHLARNCRAPRKKGCWKCGKEGHQMKDCTERQANFLGKIWPSSKGRPGNFPQSRPEPTAPPAEI
FGMGEEITSPPKQEQKDREQDPPLVSLKSLFGNDPLSQ$

Fig. 65B 3. 2003_CON_A1_gag.OPT

ATGGGCGCCCGCGCCTCCGTGCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCTCCCTGCTGGAGACCACCGAGGGCTGCCAGCAGATCATGG
AGCAGCTGCAGCCCGCCCTGAAGACCGGCACCGAGGAGCTGCGCTCCCTGTACAACGTGGCCACCCTGTACTGCGTGCACCAGCGCATC
GACGTGAAGGACACCAAGGAGGCCCTGGACAAGATCGAGGAGATCCAGAACAAGTCCAAGCAGAAGACCCAGCAGGCCGCCGCCGACGG
CAACTCCTCCAAGGTGTCCCAGAACTACCCCATCGTGCAGAACGCCCAGGGCCAGATGGTGCACCAGTCCCTGTCCCCCCGCACCCTGAACG
CCTGGGTGAAGGTGATCGAGGAGAAGGCCTTCTCCCCCGAGGTGATCCCCATGTTCTCCGCCCTGTCCGAGGGCGCCACCCCCCAGGACCTG
AACATGATGCTGAACATCGTGGGCGGCCACCAGGCCGCCATGCAGATGCTGAAGGACACCATCAACGAGGAGGCCGCCGAGTGGGACCGCCT
GCACCCCGTGCACGCCGGCCCCATCCCCCCCGGCCAACTGCGCGAGCCCCGCGGCTCCGACATCGCCGGCACCACCTCCACCCCCCAGGAGC
AGATCGGCTGGATGACCGGCAACCCCATCCCCGTGGGCGACATCTACAAGCGCTGGATCATCCTGGGCCTGAACAAGATCGTGCGCATG
TACTCCCCCGTGTCCATCCTGGACATCAAGCAGGGCCCCAAGGAGCCCTTCCGCGACTACGTGGACCGCTTCTTCAAGACCCTGCGCGCCGA
GCAGGCCACCCAGGAGGTGAAGAACTGGATGACCGAGACCCTGCTGGTGCAGAACGCCAACCCCGACTGCAAGTCCATCCTGCGCGCCCTGG
GCCCCGGCGCCACCCTGGAGGAGATGATGACCGCCTGCCAGGGCGTGGGCGGCCCAGGCCACAAGGCCCGCGTGCTGGCCGAGGCCATGTCC
CAGGTGCAGCACACCAACATCATGATGCAGCGCGGCAACTTCCGCGGCCAGAAGCGCATCAAGTGCTTCAACTGCGGCAAGGAGGGCCACCT
GGCCCGCAACTGCCGCGCCCCCCGCAAGAAGGGCTGCTGGAAGTGCGGCAAGGAGGGCCACCAGATGAAGGACTGCACCGAGCGCCAGGCCA
ACTTCCTGGGCAAGATCTGGCCCTCCTCCAAGGGCCGCCCCGGCAACTTCCCCCAGTCCCGCCCCGAGCCCACCGCCCCCCCCGCCGAGATC
TTCGGCATGGGCGAGGAGATCACCTCCCCCCCCAAGCAGGAGCAGAAGGACCGCGAGCAGGACCCCCCCCTGGTGTCCCTGAAGTCCCTGTT
CGGCAACGACCCCCTGTCCCAGTAA

Figure 4:
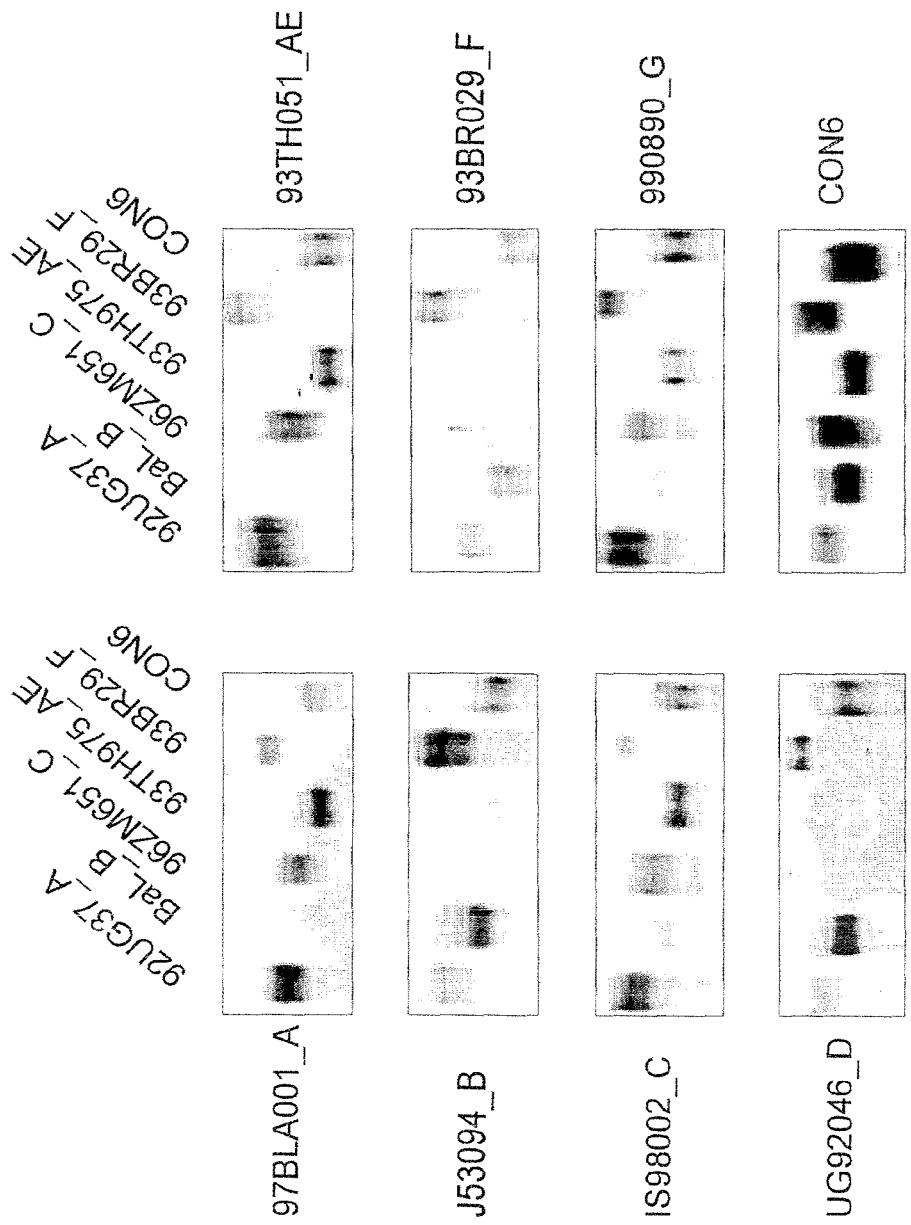

Fig. 65C 4. 2003_A1.anc_gag.PEP

MGARASVLSGGKLDAWEKIRLRPGGKKKYRLKHLVWASRELERFALNPGLLETAEGCQQIMGQLQPALKTGTEELRSLYNTVATLYCVHQRI
EVKDTKEALDKIEEIQNKSKQKTQQAAADTGNSSKVSQNYPIVQNAQGQMVHQSLSPRTLNAWVKVIEEKAFSPEVIPMFSALSEGATPQDL
NMMLNIVGGHQAAMQMLKDTINEEAAEWDRLHPVHAGPIPPGQMREPRGSDIAGTTSTLQEQIGWMTGNPPIPVGDIYKRWIILGLNKIVRM
YSPVSILDIRQGPKEPFRDYVDRFFKTLRAEQATQEVKNWMTETLLVQNANPDCKSILRALGPGATLEEMMTACQGVGGPGHKARVLAEAMS
QVQNTDIMMQRGNFRGPKRIKCFNCGKEGHLARNCRAPRKKGCWKCGKEGHQMKDCTERQANFLGKIWPSSKGRPGNFPQSRPEPTAPPAEN
FGMGEEMISSPKQEQKDREQYPPLVSLKSLFGNDPLSQ$

Fig. 65D

2003_A1.anc_gag.OPT

ATGGGCGCCCGCGCCTCCGTGCTGTCCGGCGGCAAGCTGGACGCTGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCGCCGAGGGCTGCCAGCAGATCATGG
GCCAGCTGCAGCCCGCCCTGAAGACCGGCACCGAAGAGCTGCGGAGCCTGTACAACGTGGCCACCCTGTACTGCGTGCACCAGCGCATC
GAGGTGAAGGACACCAAGGAGGCCCTGGACAAGATCGAGGAGATCCAGAACAAGTCCAGCAAGCAGAAGACCCAGCAGGCCGCCGACGG
CAACTCCTCCAAGGTGTCCCAGAACTACCCCATCGTGCAGAACGCCCAGGGCCAGATGGTGCACCAGTCCCTGTCCCCGAGGACCCTGAACG
CCTGGGTGAAGGTGATCGAGGAGAAGGCCTTCAGCCCCGAGGTGATCCCCATGTTCTCCGCCCTGTCCGAGGGCGCCACCCCCCAGGACCTG
AACATGATGCTGAACATCGTGGGCGGCCACCAGGCCGCCATGCAGATGCTGAAGGACACCATCAACGAGGAGGCCGCCGAGTGGGACCGCCT
GCACCCCGTGCACGCCGGCCCCATCCCGCCCAGGGCCAGATGAGGGAGCCCCGGGGCTCCGACATCGCCGGCACCACCTCCACCCTGCAGGAGC
AGATCGGCTGGATGACCGGCAACCCCCCCATCCCCGTGGGCGACATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGAGGTGAAGAACTGGATGACCGAGACCCTGCTGGTGCAGAACGCCAACCCCGACTGCAAGTCCATCCTGCGCGCCCTGG
GCCCCGGCGCCACCCTGGAGGAGATGATGACCGCCTGCCAGGGCGTGGGCGGCCCCGGCCACAAGGCCCGCGTGCTGGCCGAGGCCATGTCC
CAGGTGCAGAACACCGACATCATGATGCAGCGCGGCAACTTCCGCGGCCCCAAGCGCATCAAGTGCTTCAACTGCGGCAAGGAGGGCCACCT
GGCCCGCAACTGCCGCGCCCCCAGAAAGAAGGGCTGCTGGAAGTGCGGCAAGGAGGGCCACCAGATGAAGGACTGCACCGAGCGCCAGGCCA
ACTTCCTGGGCAAGATCTGGCCCTCCTCCAAGGGCCGCCCCGGCAACTTCCCCCAGTCCCGCCCCGAGCCCACCGCCCCCGCCGAGAAC
TTCGGCATGGGCGAGGAGATGATCTCCTCCCCCAAGCAGGAGCAGAAGGACCGCGAGCAGTACCCCCCCCTGGTGTCCCTGAAGTCCCTGTT
CGGCAACGACCCCCTGTCCCAGTAA

Figure 5:
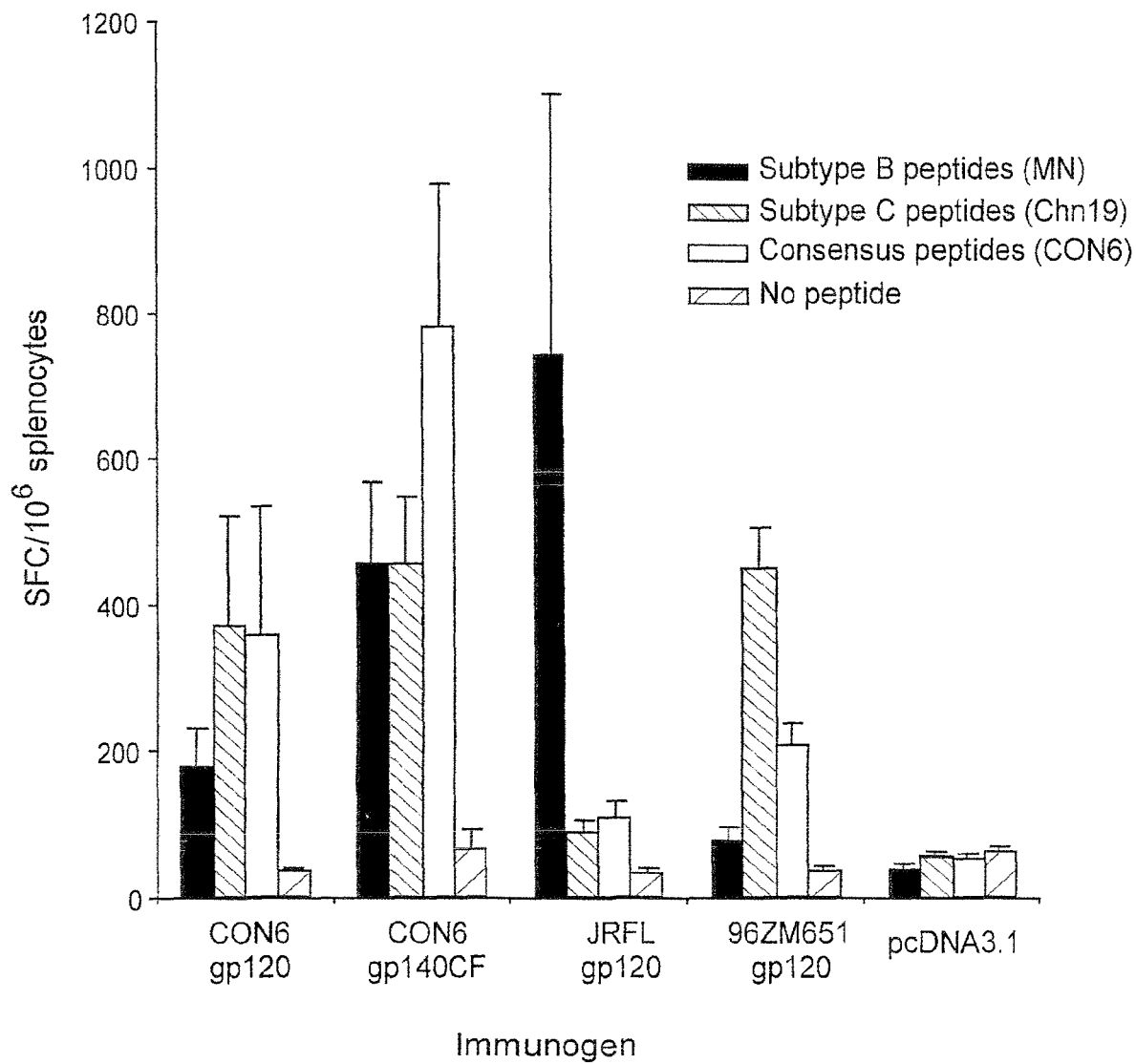

Fig. 66A 5. 2003_CON_A2_gag.PEP

MGARASILSGGKLDAWEKIRLRPGGKKKYRLKHLVWASRELEKFSINPSLLETSEGCRQIIRQLQPALQTGTEELKSLYNTVAVLYCVHQRI
DVKDTKEALDKIEEEQNKCKQKTQHAAADTGNSSSSSQNYPIVQNAQGQMVHQAISPRTLNAWVKVVEEKAFSPEVIPMFTALSEGATPQDL
NTMLNTVGGHQAAMQMLKDTINEEAAEWDRLHPVHAGPIPPGQMREPRGSDIAGTTSTLQEQIGWMTSNPPIPVGEIYKRWIILGLNKIVRM
YSPVSILDIRQGPKEPFRDYVDRFFKTLRAEQATQEVKNWMTDTLLVQNANPDCKSILRALGPGATLEEMMTACQVGGPSHKARVLAEAMS
QVQNTNIMMQRGNFRGQKRIKCFNCGKEGHLARNCRAPRKKGCWKCGKEGHQMKDCTERQANFLGKIWPSNKGRPGNFPQSRTEPTAPPA
ENLRMGEEITSSLKQELKTREPYNPAISLKSLFGNDPLSQ$

Fig. 66B

2003_CON_A2_gag.OPT

ATGGGCGCCCGGGCCTCCATCCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGAAGTTCTCCATCAACCCCTCCCTGCTGGAGACCTCCGAGGGCTGCCGCCAGATCATCC
GCCAGCTGCAGCCCGCCCTGCAGACCGGCACCGAGGAGCTGAAGTCCCTGTACAACACCGTGGCCGTGCTGTACTGCGTGCACCAGCGCATC
GACGTGAAGGACACCAAGGAGGCCCTGGACAAGATCGAGGAGGAGCAGAACAAGTGCAAGCAGAAGACCCAGCACGCCGCCGCCGACACCGG
CAACTCCTCCTCCTCCCAGAACTACCCCATCGTGCAGAACGCCCAGGGCCAGATGGTGCACCAGGCCATCTCCCCCCGCACCCTGAACG
CCTGGGTGAAGGTGGTGGAAGAGAAGGCCTTCAGCCCCGAGGTGATCCCCATGTTCACCGCCCTGTCCGAGGGCGCCACCCCCCAGGACCTG
AACACCATGCTGAACACCGTGGGCGGCCACCAGGCCGCCATGCAGATGCTGAAGGACACCATCAACGAGGAGGCCGCCGAGTGGGACCGCCT
GCACCCCGTGCACGCCGGCCCCATCCCCCCCGGCCAGATGCGCGAGCCCCGCGGCTCCGACATCGCCGGCACCACCTCCACCCTGCAGGAGC
AGATCGGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGAGGTGAAGAACTGGATGACCGACACCCTGCTGGTGCAGAACGCCAACCCCGACTGCAAGTCCATCCTGCGCGCCCTGG
GCCCCGGCGCCACCCTGGAGGAGATGATGACCTGCCAGGTGGGCGGCCCCTCCCACAAGGCCCGCGTGCTGGCCGAGGCCATGTCC
CAGGTGCAGAACACCAACATCATGATGCAGCGCGGCAACTTCCGCGGCCAGAAGCGCATCAAGTGCTTCAACTGCGGCAAGGAGGG
CCACCTGGCCCGCAACTGCCGCGCCCCCCGCAAGAAGGGCTGCTGGAAGTGCGGCAAGGAGGGCCACCAGATGAAGGACTGCACCGAGCGCC
AGGCCAACTTCCTGGGCAAGATCTGGCCCTCCAACAAGGGCCGCCCCGGCAACTTCCCCCAGTCCCGCACCGAGCCCACCGCCCCCCCGCC
GAGAACCTGCGCATGGGCGAGGAGATCACCTCCTCCCTGAAGCAGGAGCTGAAGACCCGCGAGCCCTACAACCCCGCCATCTCCCTGAAGTC
CCTGTTCGGCAACGACCCCCTGTCCCAGTAA

Fig. 67A 6. 2003_CON_B_gag.PEP

MGARASVLSGGELDRWEKIRLRPGGKKKYKLKHIVWASRELERFAVNPGLLETSEGCRQILGQLQPSLQTGSEELRSLYNTVATLYCVHQRI
EVKDTKEALEKIEEEQNKSKKKAQQAAADTGNSSQVSQNYPIVQNLQGQMVHQAISPRTLNAWVKVVEEKAFSPEVIPMFSALSEGATPQDL
NTMLNTVGGHQAAMQMLKETINEEAAEWDRLHPVHAGPIAPGQMREPRGSDIAGTTSTLQEQIGWMTNNPPIPVGEIYKRWIILGLNKIVRM
YSPTSILDIRQGPKEPFRDYVDRFYKTLRAEQASQEVKNWMTETLLVQNANPDCKTILKALGPAATLEEMMTACQGVGGPGHKARVLAEAMS
QVTNSATIMMQRGNFRNQRKTVKCFNCGKEGHIAKNCRAPRKKGCWKCGKEGHQMKDCTERQANFLGKIWPSHKGRPGNFLQSRPEPTAPPE
ESFRFGEETTTPSQKQEPIDKELYPLAS$

Fig. 67B

2003_CON_B_gag.OPT

ATGGGCGCCCGCGCCTCCGTGCTGTCCGGCGGCGAGCTGGACCGCTGGGAGAAGATCCGCCTGCGCCCCGGCGGCAAGAAGAAGTACAAGCT
GAAGCACATCGTGTGGGCCTCCCGCGAGCTGGAGCGCTTCGCCGTGAACCCCGGCCTGCTGGAGACCTCCGAGGGCTGCCGCCAGATCCTGG
GCCAGCTGCAGCCCTCCCTGCAGACCGGCTCCGAGGAGCTGCGCTCCCTGTACAACACCGTGGCCACCCTGTACTGCGTGCACCAGCGCATC
GAGGTGAAGGACACCAAGGAGGCCCTGGAGAAGATCGAGGAGGAGCAGAACAAGTCCAAGAAGAAGGCCCAGCAGGCCGCCGCCGACACCGG
CAACTCCTCCCAGGTGTCCCAGAACTACCCCATCGTGCAGAACCTGCAGGGCCAGATGGTGCACCAGGCCATCTCCCCCCGCACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGAGACCATCAACGAGGAGGCCGCCGAGTGGGACCGCCT
GCACCCCGTGCACGCCGGCCCCATCGCCCCCGGCCAGATGCGCGAGCCCCGCGGCTCCGACATCGCCGGCACCACCTCCACCCTGCAGGAGC
AGATCGGCTGGATGACCAACAACCCCCCCATCCCCGTGGGCGAGATCTACAAGCGCTGGATCATCCTGGGCCTGAACAAGATCGTGCGCATG
TACTCCCCCACCTCCATCCTGGACATCCGCCAGGGCCCCAAGGAGCCCTTCCGCGACTACGTGGACCGCTTCTACAAGACCCTGCGCGCCGA
GCAGGCCTCCCAGGAGGTGAAGAACTGGATGACCGAGACCCTGCTGGTGCAGAACGCCAACCCCGACTGCAAGACCATCCTGAAGGCCCTGG
GCCCCGCCGCCACCCTGGAGGAGATGATGACCGCCTGCCAGGGCGTGGGCGGCCCCGGCCACAAGGCCCGCGTGCTGGCCGAGGCCATGTCC
CAGGTGACCAACTCCGCCACCATCATGATGCAGCGCGGCAACTTCCGCAACCAGCGCAAGACCGTGAAGTGCTTCAACTGCGGCAAGGAGGG
CCACATCGCCAAGAACTGCCGCGCCCCCCGCAAGAAGGGCTGCTGGAAGTGCGGCAAGGAGGGCCACCAGATGAAGGACTGCACCGAGCGCC
AGGCCAACTTCCTGGGCAAGATCTGGCCCTCCCACAAGGGCCGCCCCGGCAACTTCCTGCAGTCCCGCCCCGAGCCCACCGCCCCCCCCGAG
GAGTCCTTCCGCTTCGGCGAGGAGACCACCACCCCCTCCCAGAAGCAGGAGCCCATCGACAAGGAGCTGTACCCCCTGGCCTCCTAA

Figure 7:
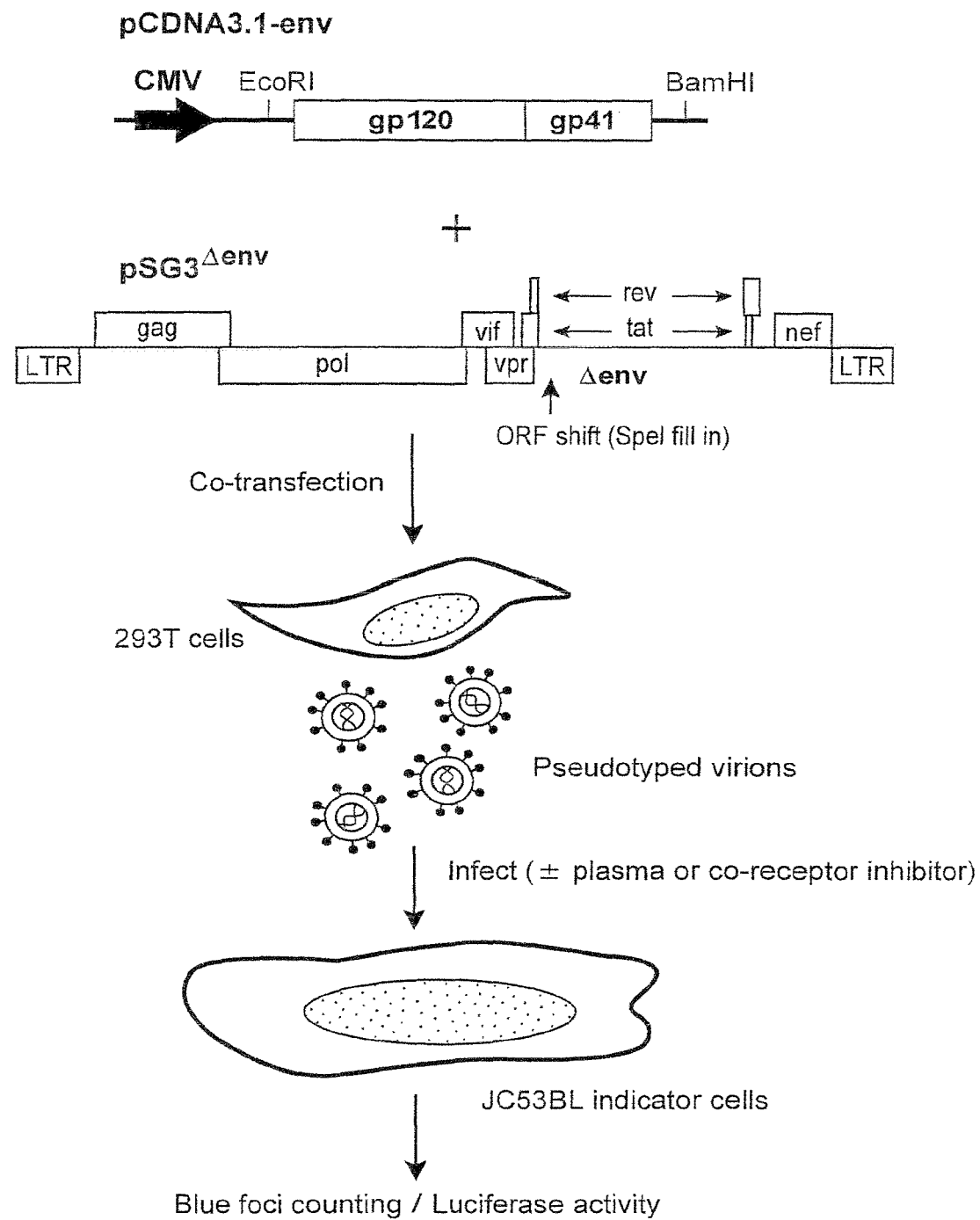

Fig. 67C 7. 2003_B.anc_gag.PEP

MGARASVLSGGKLDKWEKIRLRPGGKKKYKLKHIVWASRELERFAVNPGLLETSEGCRQILGQLQPALQTGSEELRSLYNTVATLYCVHQRI
EVKDTKEALDKIEEEQNKSKKAQQAAADTGNSSQVSQNYPIVQNLQGQMVHQAISPRTLNAWVKVVEEKAFSPEVIPMFSALSEGATPQDL
NTMLNTVGGHQAAMQMLKETINEEAAEWDRLHPVHAGPIAPGQMREPRGSDIAGTTSTLQEQIGWMTNNPPIPVGEIYKRWIILGLNKIVRM
YSPISILDIRQGPKEPFRDYVDRFYKTLRAEQASQDVKNWMTETLLVQNANPDCKTILKALGPAATLEEMMTACQGVGGPGHKARVLAEAMS
QVTNSTTIMMQRGNFRDQRKIVKCFNCGKEGHIARNCRAPRKKGCWKCGKEGHQMKDCTERQANFLGKIWPSHKGRPGNFLQSRPEPTAPPE
ESFRFGEETTTPSQKQEPIDKELYPLASLKSLFGNDPSSQ$

Fig. 67D

2003_B.anc_gag.OPT

ATGGGCGCCCGCGCCTCCGTGCTGTCCGGCGGCAAGCTGGACAAGTGGGAGAAGATCCGCCTGCGCCCCGGCGGCAAGAAGAAGTACAAGCT
GAAGCACATCGTGTGGGCCTCCCGCGAGCTGGAGCGCTTCGCCGTGAACCCCGGCCTGCTGGAGACCTCCGAGGGCTGCCGCCAGATCCTGG
GCCAGCTGCAGCCCGCCCTGCAGACCGGCTCCGAGGAGCTGCGCTCCCTGTACAACGTGGCCACCCTGTACTGCGTGCACCAGCGCATC
GAGGTGAAGGACACCAAGGAGGCCCTGGACAAGATCGAGGAGGAGCAGAACTCCAAGAAGGCCCAGCAGGCCGCCGCCGACACCGG
CAACTCCTCCCAGGTGTCCCAGAACTACCCCATCGTGCAGAACCTGCAGGGCCAGATGGTGCACCAGGCCATCTCCCCGCGCACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGAGACCATCAACGAGGAGGCCGCCGAGTGGGACCGCCT
GCACCCCGTGCACGCCGGCCCCATCGCCCCCGGCCAGATGCGCGAGCCCCGCGGCTCCGACATCGCCGGCACCACCTCCACCCTGCAGGAGC
AGATCGGCTGGATGACCAACAACCCCCCCATCCCCGTGGGCGAGATCTACAAGCGCTGGATCATCCTGGGCCTGAACAAGATCGTGCGCATG
TACTCCCCCATCTCCATCCTGGACATCCGCCAGGGCCCCAAGGAGCCCTTCCGCGACTACGTGGACCGCTTCTACAAGACCCTGCGCGCCGA
GCAGGCCTCCCAGGACGTGAAGAACTGGATGACCGAGACCCTGCTGGTGCAGAACGCCAACCCCGACTGCAAGACCATCCTGAAGGCCCTGG
GCCCCGCCGCCACCCTGGAGGAGATGATGACCGCCTGCCAGGGCGTGGGCGGCCCCGGCCACAAGGCCCGCGTGCTGGCCGAGGCCATGTCC
CAGGTGACCAACTCCACCACCATCATGATGCAGCGCGGCAACTTCCGCGACCAGCGCAAGATCGTGAAGTGCTTCAACTGCGGCAAGGAGGG
CCACATCGCCCGCAACTGCCGCGCCCCCAGAAAGAAGGGCTGCTGGAAGTGCGGCAAGGAAGGCCACCAGATGAAGGACTGCACCGAGCGCC
AGGCCAACTTCCTGGGCAAGATCTGGCCTCCCACAAGGGCCGCCCCGGCAACTTCCTGCAGTCCCGCCCCGAGCCCACCGCCCCCCCCGAG
GAGTCCTTCCGCTTCGGCGAGGAGACCACCACCCCCTCCCAGAAGCAGGAGCCCATCGACAAGGAGCTGTACCCCCTGGCCTCCCTGAAGTC
CCTGTTCGGCAACGACCCCTCCTCCCAGTAA

Fig. 68A

8. 2003_CON_C_gag.PEP

MGARASILRGGKLDKWEKIRLRPGGKKHYMLKHLVWASRELERFALNPGLLETSEGCKQIIKQLQPALQTGTEELRSLYNTVATLYCVHEKI
EVRDTKEALDKIEEQNKSQQKTQQAKAADGKVSQNYPIVQNLQGQMVHQAISPRTLNAWVKVIEEKAFSPEVIPMFTALSEGATPQDLNTM
LNTVGGHQAAMQMLKDTINEEAAEWDRLHPVHAGPIAPGQMREPRGSDIAGTTSTLQEQIAWMTSNPPIPVGDIYKRWIILGLNKIVRMYSP
VSILDIKQGPKEPFRDYVDRFFKTLRAEQATQDVKNWMTDTLLVQNANPDCKTILRALGPGATLEEMMTACQGVGGPSHKARVLAEAMSQAN
NTNIMMQRSNFKGPKRIVKCFNCGKEGHIARNCRAPRKKGCWKCGKEGHQMKDCTERQANFLGKIWPSHKGRPGNFLQNRPEPTAPPAESFR
FEETTPAPKQEPKDREPLTSLKSLFGSDPLSQ$

Fig. 68B

2003_CON_C_gag.OPT

ATGGGCGCCCGCGCCTCCATCCTGCGCGGCGGCAAGCTGGACAAGTGGGAGAAGATCCGCCTGCGCCCCGGCGGCAAGAAGCACTACATGCT
GAAGCACCTGGTGTGGGCCTCCCGCGAGCTGGAGCGCTTCGCCCTGAACCCCGGCCTGCTGGAGACCTCCGAGGGCTGCAAGCAGATCATCA
AGCAGCTGCAGCCCGCCCTGCAGACCGGCACCGAGGAGCTGCGCTCCCTGTACAACACCGTGGCCACCCTGTACTGCGTGCACGAGAAGATC
GAGGTGCGCGACACCAAGGAGGCCCTGGACAAGATCGAGGAGCAGAACAAGTCCCAGCAGAAGACCCAGCAGGCCAAGGCCGCCGACGG
CAAGGTGTCCCAGAACTACCCCATCGTGCAGAACCTGCAGGGCCAGATGGTGCACCAGGCCATCTCCCCCCGCACCCTGAACGCCTGGGTGA
AGGTGATCGAGGAGAAGGCCTTCTCCCCCGAGGTGATCCCCATGTTCACCGCCCTGTCCGAGGGCGCCACCCCCCAGGACCTGAACACCATG
CTGAACACCGTGGGCGGCCACCAGGCCGCCATGCAGATGCTGAAGGACACCATCAACGAGGAGGCCGCCGAGTGGGACCGCCTGCACCCCGT
GCACGCCGGCCCCATCGCCCCCGGCCAGATGCGCGAGCCCCGCGGCTCCGACATCGCCGGCACCACCTCCACCCTGCAGGAGCAGATCGCCT
GGATGACCTCCAACCCCCCCATCCCCGTGGGCGACATCTACAAGCGCTGGATCATCCTGGGCCTGAACAAGATCGTGCGCATGTACTCCCCC
GTGTCCATCCTGGACATCAAGCAGGGCCCCAAGGAGCCCTTCCGCGACTACGTGGACCGCTTCTTCAAGACCCTGCGCGCCGAGCAGGCCAC
CCAGGACGTGAAGAACTGGATGACCGACACCCTGCTGGTGCAGAACGCCAACCCCGACTGCAAGACCATCCTGCGCGCCCTGGGCCCCGGCG
CCACCCTGGAGGAGATGATGACCGCCTGCCAGGGCGTGGGCGGCCCCAGCCACAAGGCCCGCGTGCTGGCCGAGGCCATGTCCCAGGCCAAC
AACACCAACATCATGATGCAGCGCTCCAACTTCAAGGGCCCCAAGAGGATCGTGAAGTGCTTCAACTGCGGCAAGGAGGGCCACATCGCCCG
CAACTGCCGCGCCCCCCGCAAGAAGGGCTGCTGGAAGTGCGGCAAGGAGGGCCACCAGATGAAGGACTGCACCGAGCGCCAGGCCAACTTCC
TGGGCAAGATCTGGCCCTCCCACAAGGGCCGCCCCGGCAACTTCCTGCAGAACCGCCCCGAGCCCACCGCCCCCCCCGAGTCTTCCGC
TTCGAGGAGACCACCCCCGCCCCCAAGCAGGAGCCCAAGGACCGCGAGCCCCTGACCTCCCTGAAGTCCCTGTTCGGCTCCGACCCCCTGTC
CCAGTAA

Figure 9:
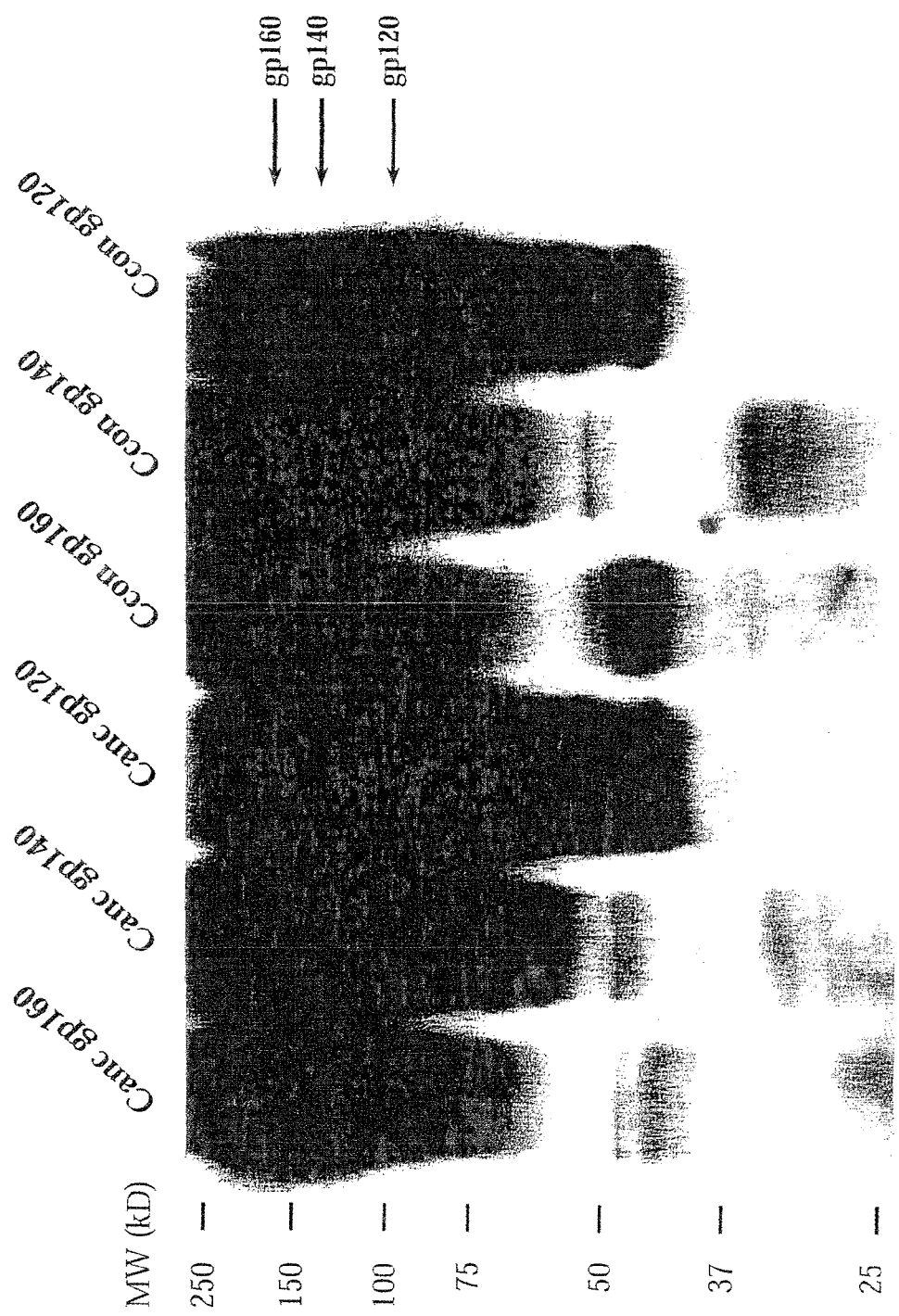

Fig. 68C 9. 2003_C.anc.gag.PEP
MGARASILRGGKLDTWEKIRLRPGGKKHYMIKHLVWASRELERFALNPGLLETSEGCKQIMKQLQPALQTGTEELRSLYNTVATLYCVHERI
EVRDTKEALDKIEEEQNKSQKTQQAEAADGDNGKVSQNYPIVQNLQGQMVHQAISPRTLNAWVKVVEEKAFSPEVIPMFTALSEGATPQDL
NTMLNTVGGHQAAMQMLKDTINEEAAEWDRLHPVHAGPVAPGQMREPRGSDIAGTTSTLQEQIAWMTSNPPIPVGDIYKRWIILGLNKIVRM
YSPVSILDIKQGPKEPFRDYVDRFFKTLRAEQATQDVKNWMTDTLLVQNANPDCKTILRALGPGATLEEMMTACQVGGPGHKARVLAEAMS
QANNTNIMMQRSNFKGPKRIVKCFNCGKEGHIARNCRAPRKKGCWKCGKEGHQMKDCTERQANFLGKIWPSHKGRPGNFLQSRPEPTAPPAE
SFRFEETTPAPKQEPKDREPLTSLKSLFGSDPLSQ$

Fig. 68D

2003_C.anc.gag.OPT
ATGGGCGCCCGCGCCTCCATCCTGCGCGGCAAGCTGGACACCTGGGAGAAGATCCGCCTGCGCCCGGGCGGCAAGAAGCACTACATGAT
CAAGCACCTGGTGTGGGCCTCCCGCGAGCTGGAGCGCTTCGCCCTGAACCCCGGCCTGCTGGAGACCTCCGAGGGCTGCAAGCAGATCATGA
AGCAGCTGCAGCCCGCTCTGCAGACCGGCACCGAGGAGCTGCGCTCCCTGTACAACACCGTGGCCACCCTGTACTGCGTGCACGAGCGCATC
GAGGTGCGCGACACCAAGGAGGCCCTGGACAAGATCGAGGAGGAGCAGAACAAGTCCCAGAAGACCCAGCAGGCCGAAGCCGCCGACGG
CGACAACGGCAAGGTGTCCCAGAACTACCCCATCGTGCAGAACCTGCAGGGCCAGATGGTGCACCAGGCCATCTCCCCCCGCACCCTGAACG
CCTGGGTGAAGGTGGTGGAGGAGAAGGCCTTCTCCCCCGAGGTGATCCCCATGTTCACCGCCCTGTCCGAGGGCGCCACCCCCCAGGACCTG
AACACCATGCTGAACACCGTGGGCGGCCACCAGGCCGCCATGCAGATGCTGAAGGACACCATCAACGAGGAGGCCGCCGAGTGGGACCGCCT
GCACCCCGTGCACGCCGGCCCCGTGGCCCCCGGCCAGATGCGCGAGCCCCGCGGCTCCGACATCGCCGGCACCACCTCCACCCTGCAGGAGC
AGATCGCCTGGATGACCTCCAACCCCCCCATCCCCGTGGGCGACATCTACAAGCGCTGGATCATCCTGGGCCTGAACAAGATCGTGCGCATG
TACTCCCCCGTGTCCATCCTGGACATCAAGCAGGGCCCCAAGGAGCCCTTCCGCGACTACGTGGACCGCTTCTTCAAGACCCTGCGCGCCGA
GCAGGCCACCCAGGACGTGAAGAACTGGATGACCGACACCCTGCTGGTGCAGAACGCCAACCCCGACTGCAAGACCATCCTGCGCGCCCTGG
GCCCCGGCGCCACCCTGGAGGAGATGATGACCGCCTGCCAGGTGGGCGGCCCCGGCCACAAGGCCCGCGTGCTGGCCGAGGCCATGTCC
CAGGCCAACAACACCAACATCATGATGCAGCGCTCCAACTTCAAGGGCCCCAAGCGCATCGTGAAGTGCTTCAACTGCGGCAAGGAGGGCCA
CATCGCCCGCAACTGCCGCGCCCCCCGCAAGAAGGGCTGCTGGAAGTGCGGCAAGGAGGGCCACCAGATGAAGGACTGCACCGAGCGCCAGG
CCAACTTCCTGGGCAAGATCTGGCCCTCCCACAAGGGCCGCCCCGGCAACTTCCTGCAGTCCCGCCCCGAGCCCACCGCCCCCCCGGCCGAG
TCCTTCCGCTTCGAGGAGACCACCCCCGCCCCCAAGCAGGAGCCCAAGGACCGCGAGCCCCTGACCTCCCTGAAGTCCCTGTTCGGCTCCGA
CCCCCTGTCCCAGTAA

Fig. 69A

10. 2003_CON_D_gag.PEP

MGARASVLSGGKLDAWEKIRLRPGGKKKYRLKHIVWASRELERFALNPGLLETSEGCKQIIGQLQPAIQTGSEELRSLYNTVATLYCVHERI
EVKDTKEALEKIEEEQNKSKKKAQQAAADTGNSSQVSQNYPIVQNLQGQMVHQAISPRTLNAWVKVIEEKAFSPEVIPMFSALSEGATPQDL
NTMLNTVGGHQAAMQMLKETINEEAAEWDRLHPVHAGPVAPGQMREPRGSDIAGTTSTLQEQIGWMTSNPPIPVGEIYKRWIILGLNKIVRM
YSPVSILDIRQGPKEPFRDYVDRFYKTLRAEQASQDVKNWMTETLLVQNANPDCKTILKALGPEATLEEMMTACQGVGGPSHKARVLAEAMS
QATNSAAVMMQRGNFKGPRKIIKCFNCGKEGHIAKNCRAPRKKGCWKCGKEGHQMKDCTERQANFLGKIWPSHKGRPGNFLQSRPEPTAPPA
ESFGFGEEITPSQKQEQKDKELYPLTSLKSLFGNDPLSQ$

Fig. 69B

2003_CON_D_gag.OPT

ATGGGCGCCCGGGCCTCCGTGCTGTCCGGCGGCAAGCTGGACGCCTGGGAGAAGATCCGCCTGCGCCCGGGCGGCAAGAAGAAGTACCGCCT
GAAGCACATCGTGTGGGCCTCCCGCGAGCTGGAGCGCTTCGCCCTGAACCCTGGCCTGCTGGAGACCTCCGAGGGCTGCAAGCAGATCATCG
GCCAGCTGCAGCCCGCCATCCAGACCGGCTCCGAGGAGCTGCGCTCCCTGTACAACACCGTGGCCACCCTGTACTGCGTGCACGAGCGCATC
GAGGTGAAGGACACCAAGGAGGCCCTGGAGAAGATCGAGGAGGAGCAGAACTCGTGCAGGGCCAGATGGTGCACCAGGCCATCTCCCCGCAC
CAACTCCTCCCAGGTGTCCCAGAACTACCCCATCGTGCAGAACCTGCAGGGCCAGATGGTGCACCAGGCCATCTCCCCGCGCACCCTGAACG
CCTGGGTGAAGGTGATCGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGAGACCATCAACGAGGAGGCCGCCGAGTGGGACCGCCT
GCACCCCGTGCACGCCGGCCCTGTGGCCCCCGGCCAGATGCGCGAGCCCCGCGGCTCCGACATCGCCGGCACCACCTCCACCCTGCAGGAGC
AGATCGGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTACAAGACCCTGCGCGCCGA
GCAGGCCTCCCAGGACGTGAAGAACTGGATGACCGAGACCCTGCTGGTGCAGAACGCCAACCCCGACTGCAAGACCATCCTGAAGGCCCTGG
GCCCCGAGGCCACCCTGGAGGAGATGATGACCGCCTGCCAGGGCGTGGGCGGCCCCTCCCACAAGGCCCGCGTGCTGGCCGAGGCCATGTCC
CAGGCCACCAACTCCGCCGCCGTGATGATGCAGCGCGGCAACTTCAAGGGCCCGCGCAAGATCATCAAGTGCTTCAACTGCGGCAAGGAGGG
CCACATCGCCAAGAACTGCCGCGCCCCCCGCAAGAAGGGCTGCTGGAAGTGCGGCAAGGAGGGCCACCAGATGAAGGACTGCACCGAGCGCC
AGGCCAACTTCCTGGGCAAGATCTGGCCCTCCCACAAGGGCCGCCCCGGCAACTTCCTGCAGTCCCGCCCCGAGCCCACCGCCCCCCCGCC
GAGTCCTTCGGCTTCGGCGAGGAGATCACCCCCTCCCAGAAGCAGGAGCAGAAGGACAAGGAGCTGTACCCCCTGACCTCCCTGAAGTCCCT
GTTCGGCAACGACCCCCTGTCCCAGTAA

Figure 11:
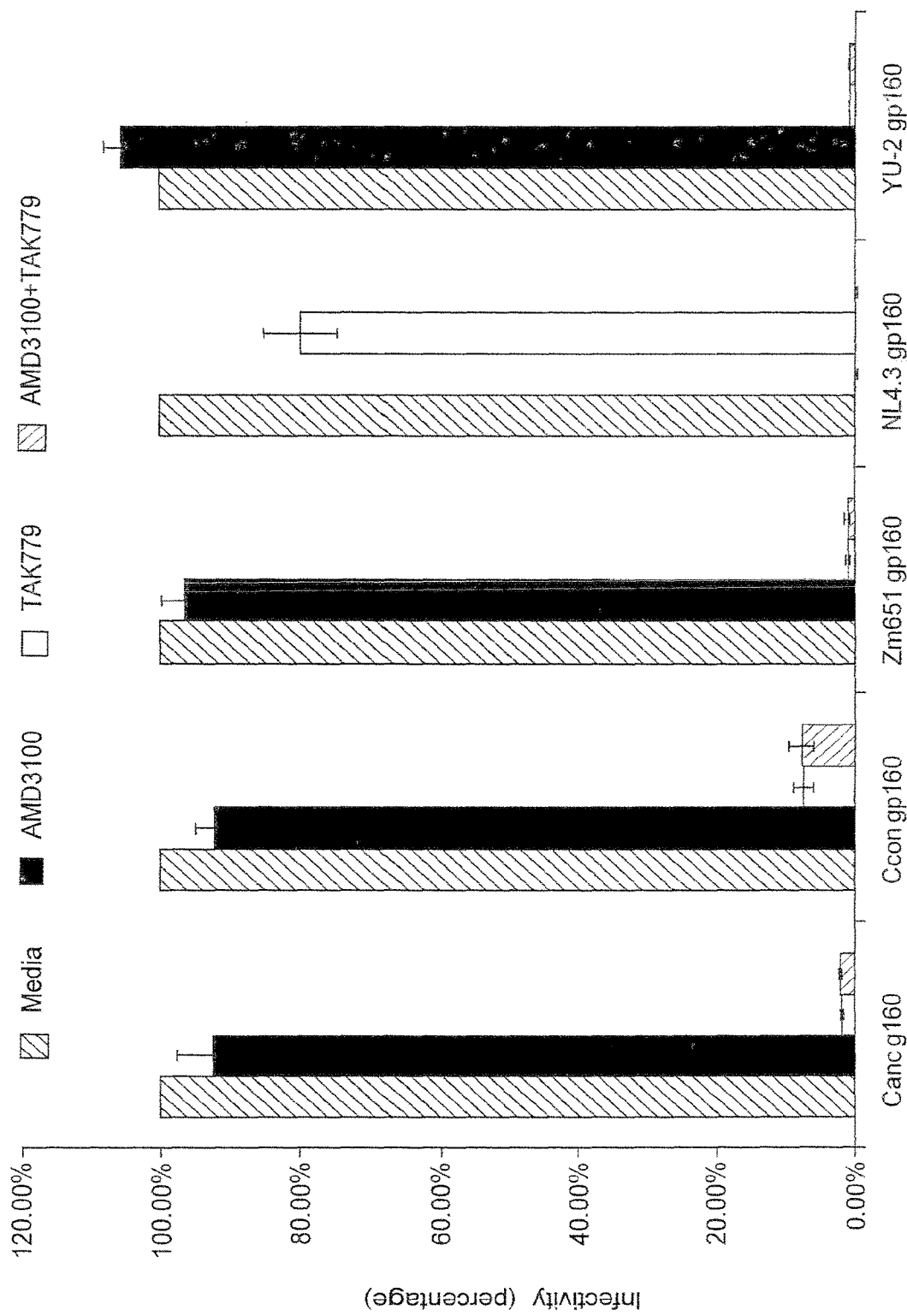

Fig. 70A 11. 2003_CON_F_gag.PEP
MGARASVLSGGKLDAWEKIRLRPGGKKKYRMKHLVWASRELERFALDPGLLETSEGCQKIIGQLQPSLQTGSEELRSLYNTVAVLYCVHQKV
EVKDTKEALEKLEEQNKSQQKTQQAAADKGVSQNYPIVQNLQGQMVHQAISPRTLNAWVKVIEEKAFSPEVIPMFSALSEGATPQDLNTML
NTVGGHQAAMQMLKDTINEEAAEWDRLHPVHAGPIPPGQMREPRGSDIAGTTSTLQEQIQWMTSNPPVPVGDIYKRWIILGLNKIVRMYSPV
SILDIRQGPKEPFRDYVDRFFKTLRAEQATQEVKGWMTDTLLVQNANPDCKTILKALGPGATLEEMMTACQGVGGPGHKARVLAEAMSQATN
TAIMMQKSNFKGQRRIVKCFNCGKEGHIAKNCRAPRKKGCWKCGREGHQMKDCTERQANFLGKIWPSNKGRPGNFLQSRPEPTAPPAESFGF
REEITPSPKQEQKDEGLYPPLASLKSLFGNDP$

Fig. 70B

2003_CON_F_gag.OPT
ATGGGCGCCCGCGCCTCCGTGCTGTCCGGCGGCAAGCTGGACGCCTGGGAGAAGATCCGCCTGCGCCCCGGCGGCAAGAAGAAGTACCGCAT
GAAGCACCTGGTGTGGGCCTCCCGCGAGCTGGAGCGCTTCGCCCTGGACCCCGGCCTGCTGGAGACCTCCGAGGGCTGCCAGAAGATCATCG
GCCAGCTGCAGCCCTCCCTGCAGACCGGCTCCGAGGAGCTGCGCTCCCTGTACAACACCGTGGCCGTGCTGTACTGCGTGCACCAGAAGGTG
GAGGTGAAGGACACCAAGGAGGCCCTGGAGAAGCTGGAGGAGCAGAACAAGTCCCAGCAGAAGACCCAGCAGGCCGCCGCCGACAAGGG
CGTGTCCCAGAACTACCCCATCGTGCAGAACCTGCAGGGCCAGATGGTGCACCAGGCCATCTCCCCCCGCACCCTGAACGCCTGGGTGAAGG
TGATCGAGGAGAAGGCCTTCTCCCCCGAGGTGATCCCCATGTTCTCCGCCCTGTCCGAGGGCGCCACCCCCCAGGACCTGAACACCATGCTG
AACACCGTGGGCGGCCACCAGGCCGCCATGCAGATGCTGAAGGACACCATCAACGAGGAGGCCGCCGAGTGGGACCGCCTGCACCCCGTGCA
CGCCGGCCCCATCCCCCCGGCCAGATGCGCGAGCCCCGCGGCTCCGACATCGCCGGCACCACCTCCACCCTGCAAGAGCAGATCCAGTGGA
TGACCTCCAACCCCCCCGTGCCCGTGGGCGACATCTACAAGCGCTGGATCATCCTGGGCCTGAACAAGATCGTGCGCATGTACTCCCCCGTG
TCCATCCTGGACATCCGCCAGGGCCCCAAGGAGCCCTTCCGCGACTACGTGGACCGCTTCTTCAAGACCCTGCGCGCCGAGCAGGCCACCCA
GGAGGTGAAGGGCTGGATGACCGACACCCTGCTGGTGCAGAACGCCAACCCCGACTGCAAGACCATCCTGAAGGCCCTGGGCCCCGGCGCCA
CCCTGGAGGAGATGATGGCCTGCCAGGGCGTGGGCGGCCCCGGCCATAAGGCCCGCGTGCTTGCCGAGGCCATGTCCCAGGCCACCAACA
CCGCCATCATGATGCAGAAGTCCAACTTCAAGGGCCAGCGCCGCATCGTGAAGTGCTTCAACTGCGGCAAGGAGGGCCACATCGCCAAGAA
CTGCCGCGCCCCCCGCAAGAAGGGCTGCTGGAAGTGCGGCCGCGAGGGCCACCAGATGAAGGACTGCACCGAGCGCCAGGCCAACTTCCTGG
GCAAGATCTGGCCCTCCAACAAGGGCCGCCCCGGCAACTTCCTGCAGTCCCGCCCCGAGCCCACCGCCCCCCCGCCGAGTCCTTCGGCTTC
CGCGAGGAGATCACCCCCTCCCCCAAGCAGGAGCAGAAGGACGAGGGCCTGTACCCCCCGCTGGCCTCCCTGAAGTCCCTGTTCGGCAACGA
CCCCTAA

Fig. 71A 12. 2003_CON_G_gag.PEP

MGARASVLSGGKLDAWEKIRLRPGGKKKYRMKHLVWASRELERFALNPDLLETAEGCQQIMGQLQPALQTGTEELRSLFNTVATLYCVHQRI
EVKDTKEALEEVEKIQKKSQQKTQQAAMDEGNSSQVSQNYPIVQNAQGQMVHQAISPRTLNAWVKVVEEKAFSPEVIPMFSALSEGATPQDL
NTMLNTVGGHQAAMQMLKDTINEEAAEWDRMHPQQAGPIPPGQIREPRGSDIAGTTSTLQEQIRWMTSNPPIPVGEIYKRWIILGLNKIVRM
YSPVSILDIRQGPKEPFRDYVDRFFKTLRAEQATQEVKGWMTDTLLVQNANPDCKTILRALGPGATLEEMMTACQGVGGPSHKARVLAEAMS
QASGAAAIMMQKSNFKGPRRTIKCFNCGKEGHLARNCRAPRKKGCWKCGKEGHQMKDCTERQANFLGKIWPSNKGRPGNFLQNRPEPTAPP
AESFGFGEEIAPSPKQEQKEKELYPLASLKSLFGSDP$

Fig. 71B

2003_CON_G_gag.OPT

ATGGGCGCCCGCGCCTCCGTGCTGTCCGGCGGCAAGCTGGACGCCTGGGAGAAGATCCGCCTGCGGCCCGGCGGCAAGAAGAAGTACCGCAT
GAAGCACCTGGTGTGGGCCTCCCGCGAGCTGGAGCGCTTCGCCCTGAACCCCGACCTGCTGGAGACCGCCGAGGGCTGCCAGCAGATCATGG
GCCAGCTGCAGCCCGCCCTGCAGACCGGCACCGAGGAGCTGCGGTCCCTGTTCAACACCGTGGCCACCCTGTACTGCGTGCACCAGCGCATC
GAGGTGAAGGACACCAAGGAGGCCCTGGAGGAGGTGGAGAAGATCCAGAAGAAGTCCCAGCAGAAGACCCAGCAGGCCGCCATGGACGAGGG
CAACTCCTCCCAGGTGTCCCAGAACTACCCCATCGTGCAGAACGCCCAGGGCCAGATGGTGCACCAGGCCATCTCCCCCCGCACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGACACCATCAACGAGGAGGCCGCCGAGTGGGACCGCAT
GCACCCCCAGCAGGCCGGCCCCATCCCCCCCGGCCAGATCCGCGAGCCCCGTGGGCTCCGACATCGCTGGCACCACCTCCACCCTGCAGGAGC
AGATCCGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGAGGTGAAGGGCTGGATGACCGACACCCTGCTGGTGCAGAACGCCAACCCCGACTGCAAGACCATCCTGCGCGCCCTGG
GCCCCGGCGCCACCCTGGAGGAGATGATGACCGCCTGCCAGGGCGTGGGCGGCCCCTCCCACAAGGCCCGCGTGCTGGCCGAGGCCATGTCC
CAGGCCTCCGGCGCCGCCGCCATCATGATGCAGAAGTCCAACTTCAAGGGCCCCCGCCGCACCATCAAGTGCTTCAACTGCGGCAAGGA
GGGCCACCTGGCCCGCAACTGCCGCGCCCCCCGCAAGAAGGGCTGCTGGAAGTGCGGCAAGGAGGGCCACCAGATGAAGGACTGCACCGAGC
GCCAGGCCAACTTCCTGGGCAAGATCTGGCCCTCCAACAAGGGCCGCCCCGGCAACTTCCTGCAGAACCGCCCCGAGCCCACCGCCCCCCCC
GCCGAGTCCTTCGGCTTCGGCGAGGAGATCGCCCCCTCCCCCAAGCAGGAGCAGAAGGAGAAGGAGCTGTACCCCCTGGCCTCCCTGAAGTC
CCTGTTCGGCTCCGACCCCTAA

Fig. 72A 13. 2003_CON_H_gag.PEP

MGARASVLSGGKLDAWEKIRLRPGGKKKYRLKHLVWASRELERFALNPGLLETAEGCLQIIEQLQSLFNTVAVLYCVHQRI
DVKDTKEALGKIEEIQNKSQQKTQQAAADKEKDNKVSQNYPIVQNAQGMVHQAISPRTLNAWVKVVEEKAFSPEVIPMFSALSEGATPQDL
NAMLNTVGGHQAAMQMLKDTINEEAAEWDRLHPVHAGPIPPGQMREPRGSDIAGTTSTLQEQIAWMTGNPPIPVGDIYKRWIILGLNKIVRM
YSPVSILDIKQGPKEPFRDYVDRFFKTLRAEQATQDVKNWMTDTLLVQNANPDCKTILRALGQGASIEEMMTACQGVGGPSHKARVLAEAMS
QVTNANAAIMMQKGNFKGPRKIVKCFNCGKEGHIARNCRAPRKKGCWKCGREGHQMKDCTERQANFLGKIWPSSKGRPGNFLQSRPEPTAPP
AESFGFGEEMTPSPKQELKDKEPPLASLRSLFGNDPLSQ$

Fig. 72B

2003_CON_H_gag.OPT
ATGGGCGCCCGCGCCTCCGTGCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCGCCGAGGGCTGCCTGCAGATCATCG
AGCAGCTGCAGTCCCTGTTCAACACCGTGGCCGTGCTGTACTGCGTGCACCAGCGCATC
GACGTGAAGGACACCAAGGAGGCCCTGGGCAAGATCGAGGAGATCCAGAACAAGTCCCAGCAGAAGACCCAGCAGGCCGCCGCCGACAAGGA
GAAGGACAACAAGGTGTCCCAGAACTACCCCATCGTGCAGAACGCCCAGATGGTGCACCAGGCCATCTCCCCCCGCACCCTGAACG
CCTGGGTGAAGGTGGTGGAGGAGAAGGCCTTCTCCCCCGAGGTGATCCCCATGTTCTCCGCCCTGTCCGAGGGCGCCACCCCCCAGGACCTG
AACGCCATGCTGAACACCGTGGGCGGCCATCAGGCCGCCATGCAGATGCTGAAGGACACCATCAACGAGGAGGCCGCCGAGTGGGACCGCCT
GCACCCCGTGCACGCCGGCCCCATCCCCCCCGGCCAGATGCGCGAGCCCCGCGGCTCCGACATCGCCGGCACCACCTCCACCCTGCAGGAGC
AGATCGCCTGGATGACCGGCAACCCGCCCATCCCCGTGGGCGACATCTACAAGCGCTGGATCATCCTGGGCCTGAACAAGATCGTGCGCATG
TACTCCCCCGTGTCCATCCTGGACATCAAGCAGGGCCCCAAGGAGCCCTTCCGCGACTACGTGGACCGCTTCTTCAAGACCCTGCGCGCCGA
GCAGGCCACCCAGGACGTGAAGAACTGGATGACCGACACCCTGCTGGTGCAGAACGCCAACCCCGACTGCAAGACCATCCTGCGCGCCCTGG
GCCAGGGCGCCTCCATCGAGGAGATGATGACCGCCTGCCAGGGCGTGGGCGGCCCCTCCCACAAGGCCCGCGTGCTGGCCGAGGCCATGTCC
CAGGTGACCAACGCCAACGCCGCCATCATGATGCAGAAGGGCAACTTCAAGGGCCCGCGCAAGATCGTGAAGTGCTTCAACTGCGGCAAGGA
GGGCCACATCGCCCGCAACTGCCGCGCCCCCCGCAAGAAGGGCTGCTGGAAGTGCGGCCGCGAGGGCCACCAGATGAAGGACTGCACCGAGC
GCCAGGCCAACTTCCTGGGCAAGATCTGGCCCTCCTCCAAGGGCCGCCCCGGCAACTTCCTGCAGTCCCGCCCCGAGCCCACCGCCCCCGCC
GAGTCCTTCGGCTTCGGCGAGGAGATGACCCCCTCCCCCAAGCAGGAGCTGAAGGACAAGGAGCCCCCCCTGGCCTCCCTGCGCTCCCT
GTTCGGCAACGACCCCCTGTCCCAGTAA

Fig. 73A

14. 2003_CON_K_gag.PEP
MGARASVLSGGKLDTWEKIRLRPGGKKKYRLKHLVWASRELERFALNPSLLETTEGCRQIIRQLQPSLQTGSEELKSLFNTVATLYCVHQRI
EVRDTKEALDKLEEQNKSQQKTQQETADKGVSQNYPIVQNLQGQMVHQAISPRTLNAWVKVIEEKAFSPEVIPMFSALSEGATPQDLNTML
NTVGGHQAAMQMLKDTINEEAAEWDRLHPVHAGPIPPGQMREPRGSDIAGTTSTLQEQITWMTSNPPVPVGEIYKRWIILGLNKIVRMYSPV
SILDIRQGPKEPFRDYVDRFFKTLRAEQATQEVKNWMTDTLLVQNANPDCKTILKALGPGASLEEMMTACQGVGGPGHKARILAEAMSQVTN
TAVMMQRGNFKGQRKIIKCFNCGKEGHIARNCRAPRKKGCWKCGKEGHQMKDCTERQANFLGKIWPSNKGRPGNFLQSRPEPTAPPAESFGF
GEEITPSPRQETKDKEQGPPLTSLKSLFGNDPLSQS

Fig. 73B

2003_CON_K_gag.OPT
ATGGGCGCCCGCGCCTCCGTGCTGTCCGGCGGCAAGCTGGACACCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCTCCCTGCTGGAGACCACCGAGGGCTGCCGCCAGATCATCC
GCCAGCTGCAGCCCTCCCTGCAGACCGGCTCCGAGGAGCTGAAGTCCCTGTTCAACACCGTGGCCACCCTGTACTGCGTGCACCAGCGCATC
GAGGTGCGCGACACCAAGGAGGCCCTGGACAAGCTGGAGGAGCAGAACAAGTCCCAGCAGAAGACCCAGCAGGAGACCGCCGACAAGGG
CGTGTCCCAGAACTACCCCATCGTGCAGAACCTGCAGGGCCAGATGGTGCACCAGGCCATGTCTCCGCGCACCCTGAACGCCTGGGTGAAGG
TGATCGAGGAGAAGGCCTTCTCCCCCGAGGTGATCCCCATGTTCTCCGCCCTGTCCGAGGGCGCCACCCCCCAGGACCTGAACACCATGCTG
AACACCGTGGGCGGCCACCAGGCCGCCATGCAGATGCTGAAGGACACCATCAACGAGGAGGCCGCCGAGTGGGACCGCCTGCACCCCGTGCA
CGCCGGCCCCATCCCCCCCGGCCAGATGCGCGAGCCCCGCGGCTCCGACATCGCTGGCACTACGTCCACCCTGCAGGAGCAGATCACCTGGA
TGACCTCCAACCCCCCCGTGCCCGTGGGCGAGATCTACAAGCGCTGGATCATCCTGGGCCTGAACAAGATCGTGCGCATGTACTCCCCCGTG
TCCATCCTGGACATCCGCCAGGGCCCCAAGGAGCCCTTCCGCGACTACGTGGACCGCTTCTTCAAGACCCTCCGCGCCGAGCAGGCCACCCA
GGAGGTGAAGAACTGGATGACCGACACCCTGCTGGTGCAGAACGCCAACCCCGACTGCAAGACCATCCTGAAGGCCCTGGGCCCCGGCGCCT
CCCTGGAGGAGATGATGACCGCCTGCCAGGGCGTGGGCGGCCCCGGCCACAAGGCCCGCATCCTGGCCGAGGCCATGTCCCAGGTGACCAAC
ACCGCCGTGATGATGCAGCGCGGCAACTTCAAGGGCCAGCGCAAGATCATCAAGTGCTTCAACTGCGGCAAGGAGGGCCACATCGCCCGCAA
CTGCCGCGCCCCCCGCAAGAAGGGCTGCTGGAAGTGCGGCAAGGAGGGCCACCAGATGAAGGACTGCACCGAGCGCCAGGCCAACTTCCTGG
GCAAGATCTGGCCCTCCAACAAGGGCCGCCCCGGCAACTTCCTGCAGTCCCGCCCCGAGCCCACCGCCCCCCCCGCCGAGTCCTTCGGCTTC
GGCGAGGAGATCACCCCCTCCCCCCGCCAGGAGACCAAGGACAAGGAGCAGGGCCCCCCCCTGACCTCCCTGAAGTCCCTGTTCGGCAACGA
CCCCCTGTCCCAGTAA

Fig. 74A 15. 2003_CON_01_AE_gag.PEP

MGARASVLSGGKLDAWEKIRLRPGGKKKYRMKHLVWASRELERFAINPGLLETAEGCQQIIEQLQSTLKTGSEELKSLFNTVATLWCVHQRI
EVKDTKEALDKIEEVQNKSQQKTQAAAGTGSSSKVSQNYPIVQNAQGQMVHQPLSPRTLNAWVKVVEEKGFNPEVIPMFSALSEGATPQDL
NMMLNIVGGHQAAMQMLKETINEEAAEWDRVHPVHAGPIPPGQMREPRGSDIAGTTSTLQEQIGWMTNNPPIPVGDIYKRWIILGLNKIVRM
YSPVSILDIRQGPKEPFRDYVDRFYKTLRAEQATQEVKNWMTETLLVQNANPDCKSILKALGTGATLEEMMTACQGVGGPSHKARVLAEAMS
QAQHANIMMQRGNFKGQKRIKCFNCGKEGHLARNCRAPRKKGCWKCGKEGHQMKDCTERQANFLGKIWPSNKGRPGNFPQSRPEPTAPPAEN
WGMGEEITSLPKQEQKDKEHPPPLVSLKSLFGNDPLSQ$

Fig. 74B

2003_CON_01_AE_gag.OPT

ATGGGCGCCCGCGCCTCCGTGCTGTCCGGCGGCAAGCTGGACGCCTGGGAGAAGATCCGCCTGCGCCCCGGCGGCAAGAAGAAGTACCGCAT
GAAGCACCTGGTGTGGGCCTCCCGCGAGCTGGAGCGCTTCGCCCTGAACCCCGGCCTGCTGGAGACCGCCGAGGGCTGCCAGCAGATCATCG
AGCAGCTGCAGTCCACCCTGAAGACCGGCTCCGAGGAGCTGAAGTCCCTGTTCAACACCGTGGCCACCCTGTGGTGCGTGCACCAGCGCATC
GAGGTGAAGGACACCAAGGAGGCCCTGGACAAGATCGAGGAGGTGCAGAACAAGTCCCAGCAGAAGACCCAGGCCGCCGCCGGCACCGG
CTCCTCCTCCAAGGTGTCCCAGAACTACCCCATCGTGCAGAACGCCCAGGGCCAGATGGTGCACCAGCCCCTGTCCCCCCGCACCCTGAACG
CCTGGGTGAAGGTGGTGGAGGAGAAGGGCTTCAACCCCGAGGTGATCCCCATGTTCTCCGCCCTGTCCGAGGGCGCCACCCCCAGGACCTG
AACATGATGCTGAACATCGTGGGCGGCCACCAGGCCGCCATGCAGATGCTGAAGGAGACCATCAACGAGGAGGCCGCCGAGTGGGACCGCGT
GCACCCCGTGCACGCCGGCCCCATCCCCCCCGGCCAGATGCGCGAGCCCCGCGGCTCCGACATCGCCGGCACCACCTCCACCCTGCAGGAGC
AGATCGGCTGGATGACCAACAACCCCCCCATCCCCGTGGGCGACATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTACAAGACCCTGCGCGCCGA
GCAGGCCACCCAGGAGGTGAAGAACTGGATGACCGAGACCCTGCTGGTGCAGAACGCCAACCCCGACTGCAAGTCCATCCTGAAGGCCCTGG
GCACCGGCGCCACCCTGGAGGAGATGATGACCGCCTGCCAGGGCGTGGGCGGCCCATCCCACAAGGCCCGCGTGCTGGCCGAGGCCATGTCC
CAGGCCCAGCACGCCAACATCATGATGCAGCGCGGCAACTTCAAGGGCCAGAAGCGCATCAAGTGCTTCAACTGCGGCAAGGAGGGCCACCT
GGCCCGCAACTGCCGCGCCCCCCGCAAGAAGGGCTGCTGGAAGTGCGGCAAGGAGGGCCACCAGATGAAGGACTGCACCGAGCGCCAGGCCA
ACTTCCTGGGCAAGATCTGGCCCTCCAACAAGGGCCGCCCCGGCAACTTCCCCCAGTCCCGCCCCGAGCCCACCGCCCCCCCCGCCGAGAAC
TGGGGCATGGGCGAGGAGATCACCTCCCTGCCCAAGCAGGAGCAGAAGGACAAGGAGCACCCCCCCCCTGGTGTCCCTGAAGTCCCTGTT
CGGCAACGACCCCCTGTCCCAGTAA

Fig. 75A 16. 2003_CON_02_AG_gag.PEP

MGARASVLSGGKLDAWEKIRLRPGGKKKYRLKHLVWASRELERFALNPGLLETAEGCQQIMEQLQSALRTGSEELKSLYNTVATLWCVHQRI
DIKDTKEALDKIEEVQNKSKQKTQQAAAATGSSSQNYPIVQNAQGQMTHQSMSPRTLNAWVKVIEEKAFSPEVIPMFSALSEGATPQDLNMM
LNIVGGHQAAMQMLKDTINEEAAEWDRVHPVHAGPIPPGQMREPRGSDIAGTTSTLQEQIGWMTSNPPIPVGEIYKRWIVLGLNKIVRMYSP
VSILDIRQGPKEPFRDYVDRFFKTLRAEQATQEVKNWMTETLLVQNANPDCKSILRALGPGATLEEMMTACQVGGPGHKARVLAEAMSQVQ
QSNIMMQRGNFRGQRTIKCFNCGKEGHLARNCKAPRKKGCWKCGKEGHQMKDCTERQANFLGKIWPSSKGRPGNFPQSRPEPTAPPAESFGM
GEEITSSPKQEPRDKGLYPPLTSLKSLFGNDPS

Fig. 75B

2003_CON_02_AG_gag.OPT

ATGGGCGCGCGCGCCTCCGTGCTGTCCGGCGGCAAGCTGGACGCCTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCGCCGAGGGCTGCCAGCAGATCATGG
AGCAGCTGCAGTCCGCCCTGCGCACCGGCTCCGAGGAGCTGAAGTCCCTGTACAACACCGTGGCCACCCTGTGGTGCGTGCACCAGCGCATC
GACATCAAGGACACCAAGGAGGCCCTGGACAAGATCGAGGAGGTGCAGAACAAGTCCAAGCAGAAGACCCAGCAGGCCGCCGCCGCCACCGG
CTCCTCCTCCCAGAACTACCCCATCGTGCAGAACGCCCAGGGCCAGATGACCCACCAGTCCATGTCCCCCCGCACCCTGAACGCCTGGGTGA
AGGTGATCGAGGAGAAGGCCTTCTCCCCCGAGGTGATCCCCATGTTCTCCGCCCTGTCCGAGGGCGCCACCCCCCAGGACCTGAACATGATG
CTGAACATCGTGGGCGGCCACCAGGCCGCCATGCAGATGCTGAAGGACACCATCAACGAGGAGGCCGCCGAGTGGGACCGCGTGCACCCCGT
GCACGCCGGCCCCATCCCCCCCGGCCAGATGCGCGAGCCCCGCGGCTCCGACATCGCCGGCACCACCTCCACCCTGCAGGAGCAGATCGGCT
GGATGACCTCCAACCCCCCCATCCCCGTGGGCGAGATCTACAAGCGCTGGATCGTGCTGGGCCTGAACAAGATCGTGCGCATGTACTCCCCC
GTGTCCATCCTGGACATCCGCCAGGGCCCCAAGGAGCCCTTCCGCGACTACGTGGACCGCTTCTTCAAGACCCTGCGCGCCGAGCAGGCCAC
CCAGGAGGTGAAGAACTGGATGACCGAGACCCTGCTGGTGCAGAACGCCAACCCCGACTGCAAGTCCATCCTGCGCGCCCTGGGCCCCGGC
GCCACCCTGGAGGAGATGATGACCGCCTGCCAGGTGGGCGGCCCCGGCCACAAGGCCCGCGTGCTGGCCGAGGCCATGTCCCAGGTGCAG
CAGTCCAACATCATGATGCAGCGCGGCAACTTCCGCGGCCAGCGCACCATCAAGTGCTTCAACTGCGGCAAGGAGGGCCACCTGGCCCGCAA
CTGCAAGGCCCCCCGCAAGAAGGGCTGCTGGAAGTGCGGCAAGGAGGGCCACCAGATGAAGGACTGCACCGAGCGCCAGGCCAACTTCCTGG
GCAAGATCTGGCCCTCCTCCAAGGGCCGCCCCGGCAACTTCCCCCAGTCCCGCCCCGAGCCCACCGCCCCGCCAGCCGAGTCCTTCGGCATG
GGCGAGGAGATCACCTCCTCCCCCAAGCAGGAGCCCCGCGACAAGGGCCTGTACCCCCCCCTGACCTCCCTGAAGTCCCTGTTCGGCAACGA
CCCCTAA

Fig. 76A 17. 2003_CON_03_ABG_gag PEP

MGARASVLSGGKLDAWEKIRLRPGGKKKYRIKHLVWASRELERFALNPSLLETSEGCQQILEQLQPTLKTGSEELKSLYNTVATLYCVHQRI
EIKDTKEALDKIEEIQNKSKQTQQAATGTGSSSKVSQNYPIVQNAQGQMTHQSMSPRTLNAWVKVIEEKAFSPEVIPMFSALSEGATPQDL
NMMLNIVGGHQAAMQMLKDTINEEAAEWDRLHPAQAGPFPPGQMREPRGSDIAGTTSTLQEQIGWMTSNPPIPVGDIYKRWIILGLNKIVRM
YSPVSILDIRQGPKEPFRDYVDRFFKTLRAEQATQDVKNWMTETLLVQNANPDCKTILRALGSGATLEEMMTACQGVGGPGHKARVLAEAMS
QVQNANIMMQKSNFRGPKRIKCFNCGKDGHLARNCRAPRKKGCWKCGKEGHQMKDCTERQANFLGRIWPSSKGRPGNFPQSRPEPSAPPAEN
FGMGEEITPSLKQEQKDREQHPPSISLKSLFGNDPLSQ$

Fig. 76B

2003_CON_03_ABG_gag.OPT

ATGGGCGCCCGCGCCTCCGTGCTGTCCGGCGGCAAGCTGGACGCCTGGGAGAAGATCCGCCTGCGCCCCGGCGGCAAGAAGTACCGCAT
CAAGCACCTGGTGTGGGCCTCCCGCGAGCTGGAGCGCTTCGCCCTGAACCCCTCCCTGCTGCTGGAGACCTCCGAGGGCTGCCAGCAGATCCTGG
AGCAGCTGCAGCCCACCCTGAAGACCGGCTCCGAGGAGCTGAAGTCCCTGTACAACACCGTGGCCACCCTGTACTGCGTGCACCAGCGCATC
GAGATCAAGGACACCAAGGAGGCCCTGGACAAGATCGAGGAGATCCAGAACAAGTCCAAGCAGACCCAGCAGGCCGCCACCGGCACCGG
CTCCTCCTCCAAGGTGTCCCAGAACTACCCCATCGTGCAGAACGCCCAGGGCCAGATGACCCACCAGTCCATGTCCCCGCACCCCCAGGACC
CCTGGGTGAAGGTGATCGAGGAGAAGGCCTTCTCCCCCGAGGTGATCCCCATGTTCTCCGCCCTGTCCGAGGGCGCCACCCCCCAGGACCTG
AACATGATGCTGAACATCGTGGGCGGCCACCAGGCCGCCATGCAGATGCTGAAGGACACCATCAACGAGGAGGCCGCCGAGTGGGACCGCCT
GCACCCCGCCCAGGCCGGCCCCTTCCCCCCCGGCCAGATGCGCGAGCCCCGCGGCTCCGACATCGCCGGCACCACCTCCACCCTGCAGGAGC
AGATCGGCTGGATGACCTCCAACCCCCCCATCCCCGTGGGCGACATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGACGTGAAGAACTGGATGACCGAGACCCTGCTGGTGCAGAACGCCAACCCCGACTGCAAGACCATCCTGCGCGCCCTGG
GCTCCGGCGCCACCCTGGAGGAGATGATGACCGCCTGCCAGGGCGTGGGCGGCCCCGGCCACAAGGCCCGCGTGCTGGCCGAGGCCATGTCC
CAGGTGCAGAACGCCAACATCATGATGCAGAAGTCCAACTTCCGCGGCCCCAAGCGCATCAAGTGCTTCAACTGCGGCAAGGACGGCCACCT
GGCCCGCAACTGCCGCGCCCCCCGCAAGAAGGGCTGCTGGAAGTGCGGCAAGGAGGGCCACCAGATGAAGGACTGCACCGAGCGCCAGGCCA
ACTTCCTGGGCCGCATCTGGCCCTCCTCCAAGGGCCGCCCCGGCAACTTCCCCCAGTCCCGCCCCGAGCCCTCCGCCCCCCCCGCCGAGAAC
TTCGGCATGGGCGAGGAGATCACCCCCTCCCTGAAGCAGGAGCAGAAGGACCGCGAGCAGCACCCCCCCTCCATCTCCCTGAAGTCCCTGTT
CGGCAACGACCCCCTGTCCCAGTAA

Fig. 77A 18. 2003_CON_04_CFX_gag.PEP

MGARASVLSGGKLDAWERIRLRPGGKKKYRLKHLVWASRELERFALNPGLLETAEGCQQLMEQLQSTLKTGSEELKSLFNTIATLWCVHQRI
DVKDTKEALDKVEEMQNKSKQTQQAAADTGGSSNVSQNYPIVQNAQGQMVHQSISPRTLNAWVKVIEEKAFSPEVIPMFSALSEGATPQDL
NMMLNIVGGHQAAMQMLKDTINEEAAEWDRAHPVHAGPIPPGQMREPRGSDIAGTTSTLQEQIGWMTSNPPIPVGEIYKRWIILGLNKIVRM
YSPVSILDIRQGPKEPFRDYVDRFFKCLRAEQATQEVKNWMTETLLVQNANPDCKSILKALGTGATLEEMMTACQGVGGPSHKARVLAEAMS
QASNAAAAIMMQKSNFKGQRRIIKCFNCGKEGHLARNCRAPRKKGCWKCGKEGHQMKDCTERQANFLGRMWPSSKGRPGNFLQSRPEPTAPP
AESLEMKEETTSSPKQEPRDKELYPLTSLKSLFGSDPLSQ$

Fig. 77B

2003_CON_04_CFX_gag.OPT

ATGGGCGCCCGCGCCTCCGTCCTGTCTGGCGGCAAGCTGGACGCCTGGGAGCGCATCCGCCTGCGCCCCGGCGGCAAGAAGAAGTACCGCCT
GAAGCACCTGGTGTGGGCCTCCCGCGAGCTGGAGCGCTTCGCCCTGAACCCCGGCCTGCTGGAGACCGCCGAGGGCTGCCAGCAGCTGATGG
AGCAGCTGCAGTCCACCCTGAAGACCGGCTCCGAGGAGCTGAAGTCCCTGTTCAACACCATCGCCACCCTGTGGTGCGTGCACCAGCGCATC
GACGTGAAGGACACCAAGGAGGCCCTGGACAAGGTGGAGGAGATGCAGAACAAGTCCAAGCAGACCCAGCAGGCCGCCGCCGACACCGGCGG
CGGCTCCTCCAACGTGTCCCAGAACTACCCCATCGTGCAGAACGCCCAGGGCCAGATGGTGCACCAGTCCATCTCCCCGCGCACCCTGAACG
CCTGGGTGAAGGTGATCGAGGAGAAGGCCTTCTCCCCCGAGGTGATCCCCATGTTCTCCGCCCTGTCCGAGGGCGCCACCCCCCAGGACCTG
AACATGATGCTGAACATCGTGGGCGGCCACCAGGCCGCCATGCAGATGCTGAAGGACACCATCAACGAGGAGGCCGCCGAGTGGGACCGCGC
CCACCCCGTGCACGCCGGCCCCATCCCCCCAGGCCAGATGCGGGAGCCCCGTGGAGACTACAAGGCCCTTCCGCGACTATCCTGGCCTGAACAAGATCGTGCGCATG
AGATCGGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGTGCCTGCGCGCCGA
GCAGGCCACCCAGGAGGTGAAGAACTGGATGACCGAGACCCTGCTGGTGCAGAACGCCAACCCCGACTGCAAGTCCATCCTGAAGGCCCTGG
GCACCGGCGCCACCCTGGAGGAGATGATGACCGCCTGCCAGGGCGTGGGCGGCCCATCCCACAAGGCCCGCGTGCTGGCCGAGGCCATGTCC
CAGGCCTCCAACGCCGCCGCCGCCATCATGATGCAGAAGTCCAACTTCAAGGGCCAGCGCCGCATCATCAAGTGCTTCAACTGCGGCAAGGA
GGGCCACCTGGCCCGCAACTGCCGCGCCCCCCGCAAGAAGGGCTGCTGGAAGTGCGGCAAGGAGGGCCACCAGATGAAGGACTGCACCGAGC
GCCAGGCCAACTTCCTGGGCCGCATGTGGCCCTCCTCCAAGGGCCGCCCCGGCAACTTCCTGCAGTCCCGCCCCGAGCCCACCGCCCCCCCC
GCCGAGTCCCTGGAGATGAAGGAGGAGACCACCTCCTCCCCCAAGCAGGAGCCCCGCGACAAGGAGCTGTACCCCCTGACCTCCCTGAAGTC
CCTGTTCGGCTCCGACCCCCTGTCCCAGTAA

Fig. 78A

19. 2003_CON_06_CPX_gag.PEP

MGARASVLSGGKLDEWEKIRLRPGGKKKYRLKHLVWASRELERFALNPGLLETAEGCQQIIEQLQSALKTGSEELKSLYNTVATLYCVHQRI
KVTDTKEALDKIEEIQNKSKQKAQQAAAATGNSSNLSQNYPIVQNAQGQMVHQAISPRTLNAWVKVIEEKAFSPEVIPMFSALSEGATPQDL
NMMLNIVGGHQAAMQMLKDTINEEAAEWDRVHPVHAGPIPPGQMREPRGSDIAGTTSTLQEQIGWMTSNPPIPVGEIYKRWIILGLNKIVRM
YSPVSILDIRQGPKEPFRDYVDRFFKTLRAEQATQEVKNWMTDTLLVQNANPDCKTILKALGPGATLEEMMTACQGVGGPGHKARVLAEAMS
QASGTEAAIMMQKSNFKGPKRSIKCFNCGKEGHLARNCRAPRKKGCWKCGKEGHQMKDCTERQANFLGKIWPSNKGRPGNFLQNREPTAPP
AESFGFGEETAPSPKQEPKEKELYPLASLKSLFGNDPS

Fig. 78B

2003_CON_06_CPX_gag.OPT

ATGGGCGCCCGCGCCTCCGTGCTGTCCGGCGGCAAGCTGGACGAGTGGGAGAAGATCCGCCTGCGCCCCGGCGGCAAGAAGAAGTACCGCCT
GAAGCACCTGGTGTGGGCCTCCCGCGAGCTGGAGCGCTTCGCCCTGAACCCTGGCCTGCTGGAGACCGCCGAGGGCTGCCAGCAGATCATCG
AGCAGCTGCAGTCCGCCCTGAAGACCGGCTCCGAGGAGCTGAAGTCCCTGTACAACACCGTGGCCACCCTGTACTGCGTGCACCAGCGCATC
AAGGTGACCGACACCAAGGAGGCCCTGGACAAGATCGAGGAGATCCAGAACAAGTCCAAGCAGGCCAAGCAGGCCGCCGCCGCCACCGG
CAACTCCTCCAACCTGTCCCAGAACTACCCCATCGTGCAGAACGCCCAGGGCCAGATGGTGCACCAGGCCATCTCCCCGCGCACCCTGAACG
CCTGGGTGAAGGTGATCGAAACATCGTGGGCCGGCCATCCCCCGCCGCAGATGCGCGAGCCCCGCGGCTCCGACATCGCCGGCACCACCTCCACCCTGCAGGAGC
AGATCGGCTGGATGACCTCCAACCCTCCGATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTTCAAGACCCTGCGCGCCGA
GCAGGCCACCCAGGAGGTGAAGAACTGGATGACCGACACCCTGCTGGTGCAGAACGCCAACCCCGACTGCAAGACCATCCTGAAGGCCCTGG
GCCCCGGCGCCACCCTGGAGGAGATGATGACCGCCTGCCAGGGCGTGGGCGGCCCCGGCCACAAGGCCCGCGTGCTGGCCGAGGCCATGTCC
CAGGCCTCCGGCACCGAGGCCGCCATCATGATGCAGAAGTCCAACTTCAAGGGCCCCAAGCGCTCCATCAAGTGCTTCAACTGCGGCAAGGA
GGGCCACCTGGCCCGCAACTGCCGCGCCCCCCGCAAGAAGGGCTGCTGGAAGTGCGGCAAGGAGGGCCACCAGATGAAGGACTGCACCGAGC
GCCAGGCCAACTTCCTGGGCAAGATCTGGCCCTCCAACAAGGGCCGCCCCGGCAACTTCCTGCAGAACCGCGAGCCCACCGCCCCCCCCGCC
GCCGAGTCCTTCGGCTTCGGCGAGGAGACCGCCCCCTCCCCCAAGCAGGAGCCCAAGGAGAAGGAGCTGTACCCCCTGGCCTCCCTGAAGTC
CCTGTTCGGCAACGACCCCTAA

Fig. 79A

20. 2003_CON_07_BC_gag.PEP

MGARASILRGGKLDKWEKIRLRPGGKKHYMLKHLVWASRELERFALNPGLLETSEGCKQIIKQLQPALQTGTEELRSLFNTVATLYCVHTEI
DVRDTKEALDKIEEEQNKIQQKTQQAKEADGKVSQNYPIVQNLQGQMVHQPISPRTLNAWVKVVEEKAFSPEVIPMFSALSEGATPQDLNTM
LNTVGGHQAAMQILKDTINEEAAEWDRLHPVHAGPIAPGQMREPRGSDIAGTTSNLQEQIAWMTSNPPVPVGDIYKRWIILGLNKIVRMYSP
TSILDIKQGPKEPFRDYVDRFFKTLRAEQATQDVKNWMTDTLLVQNANPDCKTILRALGPGASIEEMMTACQGVGGPSHKARVLAEAMSQTN
STILMQRSNFKGSKRIVKCFNCGKEGHIARNCRAPRKKGCWKCGKEGHQMKDCTERQANFLGKIWPSHKGRPGNFLQSRPEPTAPPEESFRF
GEETTTPSQKQEPIDKELYPLTSLKSLFGNDPSSQ$

Fig. 79B

2003_CON_07_BC_gag.OPT

ATGGGCGCCCGCGCCTCCATCCTGCGCGGCGGCAAGCTGGACAAGTGGGAGAAGATCCGCCTGCGCCCCGGCGGCAAGAAGCACTACATGCT
GAAGCACCTGGTGTGGGCCTCCCGCGAGCTGGAGCGCTTCGCCCTGAACCCCGGCCTGCTGGAGACCTCCGAGGGCTGCAAGCAGATCATCA
AGCAGCTGCAGCCCGCTCAGCCGCTGCAGACCGGCACCGAGGAGCTGCGCTCCCTGTTCAACACCGTGGCCACCCTGTACTGCGTGCACACCGAGATC
GACGTGCGCGACACCAAGGAGGCCCTGGACAAGATCGAGGAGGAGCAGAACAAGATCCAGCAGAAGACCCAGCAGGCCAAGGAGGCCGACGG
CAAGGTGTCCCAGAACTACCCCATCGTGCAGAACCTGCAGGGCCAGATGGTGCACCAGCCCATCTCCCCGCCACCCTGAACGCTGGGGTGA
AGGTGGTGGAAGAGAAGGCCTTCTCCCCCGAGGTGATCCCCATGTTCTCCGCCCTGTCCGAGGGCGCCACCCCCCAGGACCTGAACACCATG
CTGAACACCGTGGGCGGCCACCAGGCCGCCATGCAGATCCTGAAGGACACCATCAACGAGGAGGCCGAGTGGGACCGCCTGCACCCCGT
GCACGCCGGCCCCATCGCCCCCGGCCAGATGCGCGAGCCCCGCGGCTCCGACATCGCCGGCACCACCTCCAACCTGCAGGAGCAGATCGCCT
GGATGACCTCCAACCCCCCCGTGCCCGTGGGCGACATCTACAAGCGCTGGATCATCCTGGGCCTGAACAAGATCGTGCGCATGTACTCCCCC
ACCTCCATCCTGGACATCAAGCAGGGCCCCAAGGAGCCCTTCCGCGACTACGTGGACCGCTTCTTCAAGACCCTGCGCGCCGAGCAGGCCAC
CCAGGACGTGAAGAACTGGATGACCGACACCCTGCTGGTGCAGAACGCCAACCCCGACTGCAAGACCATCCTGCGCGCCCTGGGCCCCGGCG
CCTCCATCGAGGAGATGATGACCGCCTGCCAGGGCGTGCTGGGCGGCCCATGTCCAAGCGCCGTGCTGGCCGAGGCCATGTCCCAGACCAAC
TCCACCATCCTGATGCAGCGCTCCAACTTCAAGGGCTCCAAGCGCATCGTGAAGTGCTTCAACTGCGGCAAGGAGGGCCACATCGCCCGCAA
CTGCCGCGCCCCCCGCAAGAAGGGCTGCTGGAAGTGCGGCAAGGAGGGCCACCAGATGAAGGACTGCACCGAGCGCCAGGCCAACTTCCTGG
GCAAGATCTGGCCCTCCCACAAGGGCCGCCCCGGCAACTTCCTGCAGTCCCGCCCCGAGCCCACCGCCCCCCCCGAGGAGTCCTTCCGCTTC
GGCGAGGAGACCACCACCCCTCCCAGAAGCAGGAGCCCATCGACAAGGAGCTGTACCCCCTGACCTCCCTGAAGTCCCTGTTCGGCAACGA
CCCCTCCTCCCAGTAA

Figure 21:
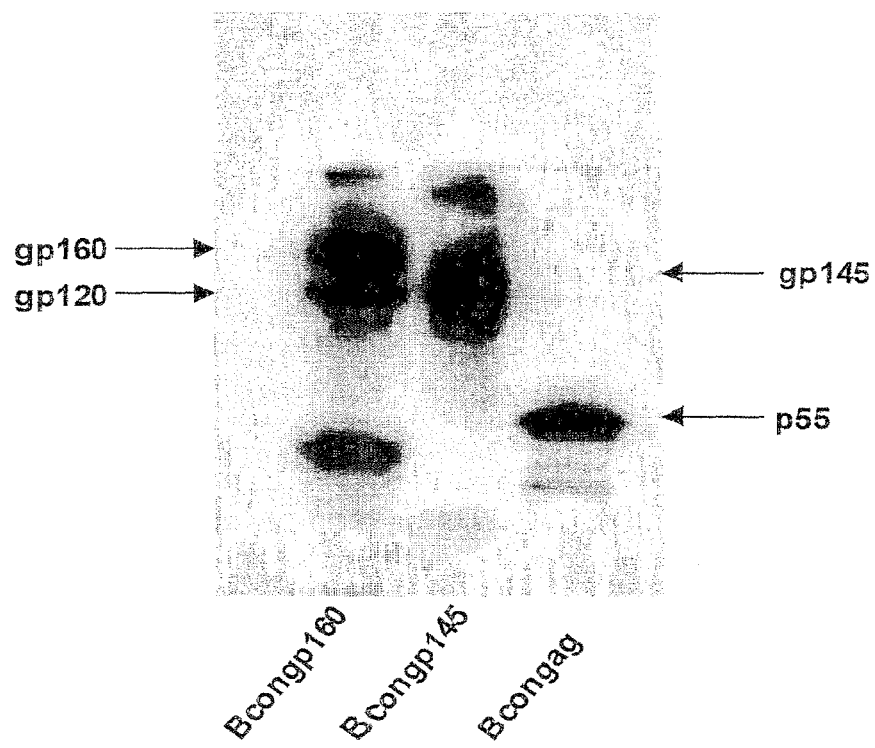

Fig. 80A 21. 2003_CON_08_BC_gag.PEP

MGARASILRGKLDKWEKIRLRPGGKKHYMLKHLVWASRELERFALNPGLLETSEGCKQIIKQLQPALQTGTEELRSLFNTVATLYCVHAEI
EVRDTKEALDKIEEEQNKIQQKTQQAKEADEKVSQNYPIVQNLQGQMVHQPLSPRTLNAWVKVVEEKAFSPEVIPMFTALSEGATPQDLNTM
LNTVGGHQAAMQMLKDTINEEAAEWDRLHPVHAGPVAPGQMREPRGSDIAGTTSTLQEQIGWMTNNPPIPVGEIYKRWIILGLNKIVRMYSP
TSILDIKQGPKEPFRDYVDRFFKTLRAEQATQDVKNWMTDTLLVQNANPDCKTILRALGPGASLEEMMTACQGVGGPSHKARVLAEAMSQTN
NTILMQRSNFKGSKRIVKCFNCGKEGHIAKNCRAPRKKGCWKCGKEGHQMKDCTERQANFLGKIWPSHKGRPGNFLQSRPEPTAPPAESFRF
EETTPAPKQEPKDREPLTSLRSLFGSDPLSQ$

Fig. 80B

2003_CON_08_BC_gag.OPT

ATGGGCGCCCGCGCCTCCATCCTGCGCGGCAAGCTGGACAAGTGGGAGAAGATCCGCCTGCGCCCCGGCGGCAAGAAGCACTACATGCT
GAAGCACCTGGTGTGGGCCAGCCGCGAGCTGGAGCGCTTCGCCCTGAACCCCGGCCTGCTGGAGACCTCCGAGGGCTGCAAGCAGATCATCA
AGCAGCTGCAGCCCGCCCTGCAGACCGGCACCGAGGAGCTGCGCAGCCTGTTCAACACCGTGGCCACCCTGTACTGCGTGCACGCCGAGATC
GAGGTGCGCGACACCAAGGAGGCCCTGGACAAGATCGAGGAGCAGAACAAGATCCAGCAGAAGACCCAGCAGGCCAAGGAGGCCGACGA
GAAGGTGTCCCAGAACTACCCCATCGTGCAGAACCTGCAGGGCCAGATGGTGCACCAGCCCCTGTCCCCCAGGACCCTGAACGCCTGGGTGA
AGGTGGTGGAGGAGAAGGCCTTCTCCCCCGAGGTGATCCCCATGTTCACCGCCCTGAGTGAAGGACCACCATCAAGAGGAGCACCCCCGGA
GCACGCCGCCATGCAGATGCTGAAGGACACCATCAACGAGGAGGCCGCCGAGTGGGACCGCCTGCACCCTGAACAAGATCCGCCAGGAGCT
GGATGACCAACAACCCCATCCCCGTGGGCGAGATCTACAAGCGCTGGATCATCCTGGGCCTGAACAAGATCGTGCGCATGTACTCCCCC
ACCTCCATCCTGGACATCAAGCAGGGCCCTAAGGAGCCCTTCCGCGACTACGTCCGCCGCTTCTTCAAGACCCTGCGCGCCGAGCAGGCCAC
CCAGGACGTGAAGAACTGGATGACCGACACCCTGCTGGTGCAGAACGCCAACCCCGACTGCAAGACCATCCTGCGCGCTGGGCCCCGGCG
CTCCCTGGAGGAGATGATGACCGCCTGCCAGGGCGTGGGCGGCCCCTCCCACAAGGCCCGTGCTGGCCGAGGCCATGTCCCAGACCAACAAC
AACATCCTGATGCAGCGCTCCAACTTCAAGGGCTCCAAGCGCATCGTGAAGTGCTTCAACTGCGGCAAGGAGGGCCACATCGCCAAGAA
CTGCCGCGCCCCCCGCAAGAAGGGCTGCTGGAAGTGCGGCAAGGAGGGCCACCAGATGAAGGACTGCACCGAGCGCCAGGCCAACTTCCTGG
GCAAGATCTGGCCCTCCCACAAGGGCCGCCCCGGCAACTTCCTGCAGTCCCGCCCCGAGCCCACCGCCCCGCCCGAGTCCTTCCGCTTC
GAGGAGACCACCCCCGCCCCCAAGCAGGAGCCCAAGGACCGCGAGCCCCTGACCTCCCTGCGCTCCCTGTTCGGCTCCGACCCCCTGTCCCA
GTAA

Figure 22:
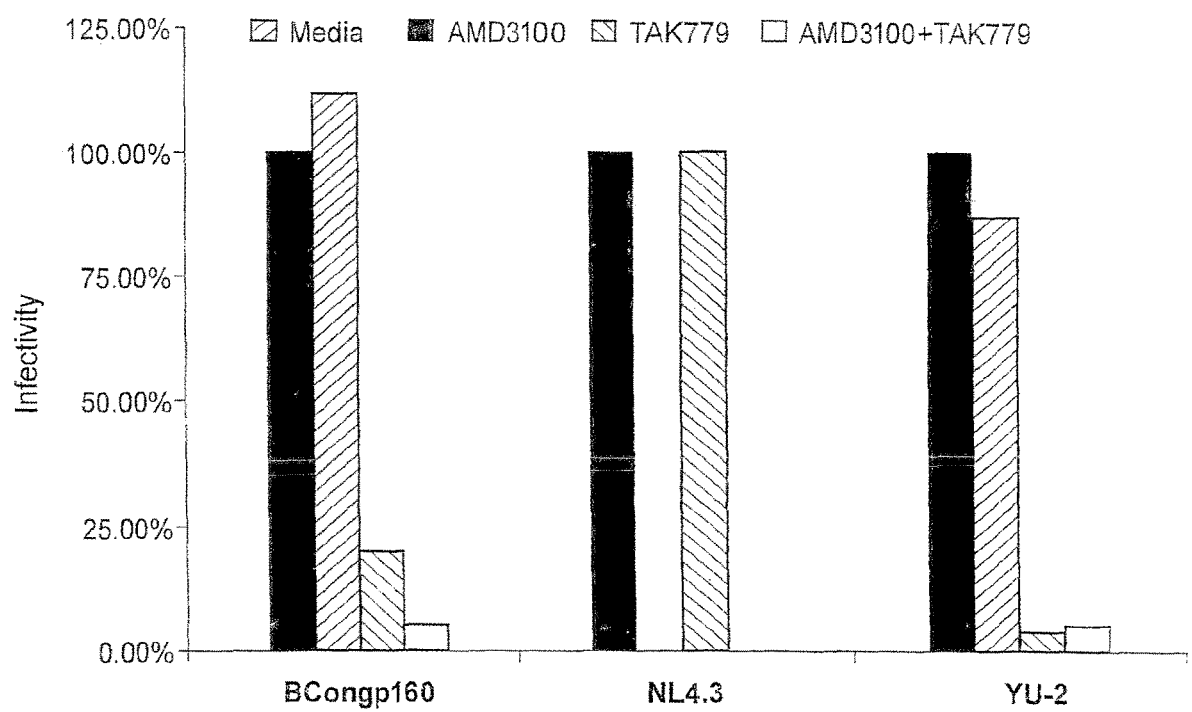

Fig. 81A 22. 2003_CON_10_CD_gag.PEP

MGARASVLSGGKLDEWEKIRLRPGGKKKYRLKHLVWASRELERFAINPGLLETSEGCKQIIGQLQPAIQTGSEEIKSLYNTVATLYCVHERI
KVTDTKEALDKIEEEQTKSKKKAQQATADTGNSSQVSQNYPIVQNLQGQMVHQPLSPRTLNAWVKVIEEKAFSPEVIPMFSALSEGATPQDL
NTMLNTVGGHQAAMQMLKETINEEAAEWDRLHPVQAGPVAPGQIREPRGSDIAGTTSTLQEQIRWMTSNPPIPVGEIYKRWIILGLNKIVRM
YSPVSILDIRQGPKEPFRDYVDRFYKTLRAEQASQDVKNWMTETLLVQNANPDCKTILKALGPAATLEEMTACQGVGGPSHKARVLAEAMS
QATSGNAIMMQRGNFKGPKKIIKCFNCGKEGHIAKNCRAPRKKGCWKCGREGHQMKDCTERQANFLGKIWPSNKGRPGNFLQSRPEPTAPPA
ESFGFGEEITPSQKQEQKDKELHPLASLKSLFGNDPLSQ$

Fig. 81B

2003_CON_10_CD_gag.OPT

ATGGGCGCCCGGGCCTCCGTGCTGTCCGGCGGCAAGCTGGACGAGTGGGAGAAGATCCGCCTGCGCCCCGGCGGCAAGAAGAAGTACCGCCT
GAAGCACCTGGTGTGGGCCTCCCGCGAGCTGGAGCGCTTCGCCATCAACCCCGGCCTGCTGGAGACCTCCGAGGGCTGCAAGCAGATCATCG
GCCAGCTGCAGCCCGCCATCCAGACCGGCTCCGAGGAGATCAAGTCCCTGTACAACGTGGCCACCCTGTACTGCGTGCACGAGCGCATC
AAGGTGACCGACACCAAGGAGGCCCTGGACAAGATCGAGGAGGAGCAGACCAAGTCCAAGAAGAAGGCCCAGCAGGCCACCGCCGACACCGG
CAACTCCTCCCAGGTGTCCCAGAACTACCCCATCGTGCAGAACCTGCAGGGCCAGATGGTGCACCAGCCCCTGTCCCCCCGCACCCTGAACG
CCTGGGTGAAGGTGATCGAGGAGAAGGCCTTCTCCCCCGAGGTGATCCCCATGTTCTCCGCCCTGTCCGAGGGCGCCACCCCCCAGGACCTG
AACACCATGCTGAACACCGTGGGCGGCCACCAGGCCGCCATGCAGATGCTGAAGGAGACCATCAACGAGGAGGCCGCCGAGTGGGACCGCCT
GCACCCCGTGCAGGCCGGCCCCGTGGCCCCCGGCCAGATCCGCGAGCCCCGCGGCTCCGACATCGCCGGCACCACCTCCACCCTGCAGGAGC
AGATCCGCTGGATGACCTCCAACCCCCCCATCCCCGTGGGCGAGATCTACAAGCGCTGGATCATCCTGGGCCTGAACAAGATCGTGCGCATG
TACTCCCCCGTGTCCATCCTGGACATCCGCCAGGGCCCCAAGGAGCCCTTCCGCGACTACGTGGACCGCTTCTACAAGACCCTGCGCGCCGA
GCAGGCCTCCCAGGACGTGAAGAACTGGATGACCGAGACCCTGCTGGTGCAGAACGCCAACCCCGACTGCAAGACCATCCTGAAGGCCCTGG
GCCCCGCCACCCTGGAGGAGATGACCGCCTGCCAGGGCGTGGGCGGCCCCTCCCACAAGGCCCGCGTGCTGGCCGAGGCCATGTCC
CAGGCCACCTCCGGCAACGCCATCATGATGCAGCGCGGCAACTTCAAGGGCCCCAAGAAGATCATCAAGTGCTTCAACTGCGGCAAGGAGG
GCCACATCGCCAAGAACTGCCGCGCCCCCCGCAAGAAGGGCTGCTGGAAGTGCGGCCGCGAGGGCCACCAGATGAAGGACTGCACCGAGCGC
CAGGCCAACTTCCTGGGCAAGATCTGGCCCTCCAACAAGGGCCGCCCCGGCAACTTCCTGCAGTCCCGCCCCGAGCCCACCGCCCCCCCGCC
GAGTCCTTCGGCTTCGGCGAGGAGATCACCCCCTCCCAGAAGCAGGAGCAGAAGGACAAGGAGCTGCACCCCCTGGCCTCCCTGAAGTCCCT
GTTCGGCAACGACCCCCTGTCCCAGTAA

Fig. 82A 23. 2003_CON_11_CPX_gag.PEP
gag.PEPMGARASVLSGGKLDAWEKIRLRPGGKKKYRLKHLVWASRELERFALNPSLLETAEGCQQIMGQLQPALGTEELRSLYNTVATL
YCVHHRIEVKDTKEALDKIEEIQNKSKQKKQQAAADTGNSSKVSQNYPIVQNAQGMVHQAISPRTLNAWVKVVEEKAFSPEVIPMFSALSE
GATPQDLNMMLNIVGGHQAAMQMLKDTINEEAAEWDRVHPVHAGPIPPGQMREPRGSDIAGTTSTLQEQIGWMTGNPPVPVGEIYRRWIILG
LNKIVRMYSPVSILDIRQGPKEPFRDYVDRFFKTLRAEQATQEVKSWMTETLLIQNANPDCKSILRALGPGATLEEMMTACQGVGGPGHKAR
VLAEAMSQVQQTNIMMQRSNFKGQKRIKCFNCGKEGHLARNCRAPRKKGCWKCGKEGHQMKDCTERQANFLGKIWPSSKGRPGNFLQSRPEP
TAPPAESFGFGEEIAPSPKQEPKEKELYPLTSLIKSLFGSDPLSQS

Fig. 82B

2003_CON_11_CPX_gag.OPT
ATGGGCGCCCGCGCCTCCGTGCTGTCCGGCGGCAAGCTGGACGCCTGGGAGAAGATCCGCCTGCGCCCCGGCGGCAAGAAGAAGTACCGCCT
GAAGCACCTGGTGTGCGCCCTCCCCGAGCTGGAGCGCTTCGCCCTGAACCCCTCCCTGCTGGAGACCGCCGAGGGCTGCCAGCAGATCATGG
GCCAGCTGCAGCCCGCCCTGGGCACCGAGGAGCTGCGCTCCCTGTACAACACCGTGGCCACCCTGTACTGCGTGCACCACCGCATC
GAGGTGAAGGACACCAAGGAGGCCCTGGACAAGATCGAGGAGATCCAGAACAAGTCCAAGCAGAAGAAGCAGCAGGCCGCCGCCGACACCGG
CAACTCCTCCAAGGTGTCCCAGAACTACCCCATCGTGCAGAACGCCCAGGGCATGGTGCACCAGGCCATCTCCCCGAGGGCGCCACCCCCCA
CCTGGGTGAAGGTGGTGGAGGAGAAGGCCTTCTCCCCCGAGGTGATCCCCATGTTCTCCGCCCTGTCCGAGGGCACCCCCCAGGACCTG
AACATGATGCTGAACATCGTGGGCGGCCACCAGGCCGCCATGCAGATGCTGAAGGACACCATCAACGAGGAGGCCGCCGAGTGGGACCGCGT
GCACCCCGTGCACGCCGGCCCCATCCCCCCCGGCCAGATGCGCGAGCCCCGTGGGCGAGATCTACCGCCGCTGGATCATCCTGGGCCTGAACAAGATCGTGCGCATG
TACTCCCCCGTGTCCATCCTGGATGTCCTGGATGTGAAGTCTGAGGAGATCATGATGCAGCCCCCCCACCCCCACTGGACGCCGACTGCTGATCCAGAACGCCAACCCCGA
CTGCAAGTCCATCCTGCGCGCCCTGGGCCCCGGCGCCACCCTGGAGGAGATGATGACCGCCTGCCAAGGCGTGGGCGGCCCCGGCCATGTCC
CAGGTGCAGCAGACCAACATCATGATGCAGCGCTCCAACTTCAAGGGCCAGAAGCGCATCAAGTGCTTCAACTGCGGCAAGGAGGGCCACCT
GGCCCGCAACTGCCGCGCCCCCCGCAAGAAGGGCTGCTGGAAGTGCGGCAAGGAGGGCCACCAGATGAAGGACTGCACCGAGCGCCAGGCCA
ACTTCCTGGGCAAGATCTGGCCCTCCTCCAAGGGCCGCCCCGGCAACTTCCTGCAGTCCCGCCCCGAGCCCACCGCCCCCGCCGAGTCC
TTCGGCTTCGGCGAGGAGATCGCCCCCTCCCCCAAGCAGGAGCCCAAGGAGAAGGAGCTGTACCCCCTGACCTCCCTGATCAAGTCCCTGTTCGG
CTCCGACCCCCTGTCCCAGTAA

Fig. 83A 24. 2003_CON_12_BF.gag.PEP

MGARASVLSGGELDRWEKIRLRPGGKKKYRLKHIVWASRELERFAVNPGLLETSEGCRKIIGQIQPSLQTGSEELRSLYNTIAVLYFVHQKV
EVKDTKEALDKLEEEQNKSQQKTQQAAADKGVSQNYPIVQNLQGQMVHQALSPRTLNAWVKVVEEKAFSPEVIPMFSALSEGATPQDLNTML
NTVGGHQAAMQMLKDTINEEAAEWDRLHPVHAGPIPPGQMREPRGSDIAGTTSTLQEQIQWMTSNPPVPVGEIYKRWIILGLNKIVRMYSPV
SILDIRQGPKEPFRDYVDRFFKTLRAEQATQEVKGWMTDTLLVQNANPDCKTILKALGPGATLEEMMTACQGVGGPGHKARVLAEAMSQVTN
TTVMMQKSNFKGQRRIVKCFNCGKEGHIAKNCRAPRKKGCWKCGREGHQMKDCTERQANFLGKIWPSNKGRPGNFLQNRPEPTAPPAESFGF
GEEITPSPKQEQKDEGLYPPLASLKSLFGNDP$

Fig. 83B

2003_CON_12_BF.gag.OPT

ATGGGCGCCCGCGCCTCCGTGCTGTCCGGCGGCGAGCTGGACCGCTGGGAGAAGATCCGCCTGCGCCCGGGCGGCAAGAAGAAGTACCGCCT
GAAGCACATCGTGTGGGCCTCCCGCGAGCTGGAGCGCTTCGCCGTGAACCCCGGCCTGCTGGAGACCTCCGAGGGCTGCCGCAAGATCATCG
GCCAGATCCAGCCCTCCCTGCAGACCGGCTCCGAGGAGCTGCGCTCCCTGTACAACACCATCGCCGTGCTGTACTTCGTGCACCAGAAGGTG
GAGGTGAAGGACACCAAGGAGGCCCTGGACAAGCTGGAGGAGGAGCAGAACAAGTCCCAGCAGAAGACCCAGCAGGCCGCCGCCGACAAGGG
CGTGTCCCAGAACTACCCCATCGTGCAGAACCTGCAGGGCCAGATGGTGCACCAGGCCCTGTCCCCGCGCACCCTGAACGCCTGGGTGAAGG
TGGTGGAGGAGAAGGCCTTCTCCCCCGAGGTGATCCCCATGTTCTCCGCCCTGTCCGAGGGCGCCACCCCCCAGGACCTGAACACCATGCTG
AACACCGTGGGCGGCCATCAGGCCGCCATGCAGATGCTGAAGGACACCATCAACGAGGAGGCCGAGTGGGACCGCCTGCACCCCGTGCA
CGCCGGCCCCATCCCCCCGGGCCAGATGCGCGAGCCCCGCGGCTCCGACATCGCCGGCACCACCTCCACCCTGCAGGAGCAGATCCAGTGGA
TGACCTCCAACCCTCCGGTGCCCGTGGGCGAGATCTACAAGCGCTGGATCATCCTGGGCCTGAACAAGATCGTGCGCATGTACTCCCCCGTG
TCCATCCTGGACATCCGCCAGGGCCCCAAGGAGCCCTTCCGCGACTACGTGGACCGCTTCTTCAAGACCCTGCGCGCCGAGCAGGCCACCCA
GGAGGTGAAGGGCTGGATGACCGACACCCTGCTGGTGCAGAACGCCAACCCCGACTGCAAGACCATCCTGAAGGCCCTGGGCCCGGCCA
CCCTGGAGGAGATGATGACCGCCTGCCAGGGCGTGGGCGGCCCCGGCCACAAGGCCCGCGTGCTGGCCGAGGCCATGTCCCAGGTGACCAAC
ACCACCGTGATGATGCAGAAGTCCAACTTCAAGGGCCAGCGCCGCATCGTGAAGTGCTTCAACTGCGGCAAGGAGGGCCACATCGCCAAGAA
CTGCCGCGCCCGCCGCAAGAAGGGCTGCTGGAAGTGCGGCCGCGAGGGCCACCAGATGAAGGACTGCACCGAGCGCCAGGCCAACTTCCTGG
GCAAGATCTGGCCCTCCAACAAGGGCCGCCCCGGCAACTTCCTGCAGAACCGCCCCGAGCCCACCGCCCCCCCGGCCGAGTCCTTCGGCTTC
GGCGAGGAGATCACCCCCTCCCCCAAGCAGGAGCAGAAGGACGAGGGCCTGTACCCCCCCCTGGCCTCCCTGAAGTCCCTGTTCGGCAACGA
CCCCTAA

Fig. 84A 25. 2003_CON_14_BG_gag.PEP
MGARASVLSGGKLDAWEKIRLRPGGKKKYRMKHLVWASRELERFALNPDLLETAEGCQQIMGQLQPALQTGTEEIRSLFNTVATLYCVHQKI
EVKDTKEALEEVEKAQKKSQKKQQAAMDEGNNSQASQNYPIVQNAQGQMVHQAISPRTLNAWVKVVEEKAFSPEVIPMFSALSEGATPQDLN
TMLNTVGGHQAAMQMLKDTINEEAAEWDRMHPQQAGPIPPGQIREPRGSDIAGTTSTLQEQIRWMTSNPPIPVGEIYKRWIILGLNKIVRMY
SPVSILDIRQGPKEFFRDYVDRFFKTLRAEQATQEVKGWMTDTLLVQNANPDCKTILRALGPGATLEEMMTACQVGGPSHKARVLAEAMSQ
ASGATIMMQKSNFKGPRRNIKCFNCGKEGHLARNCRAPRKKGCWKCGKEGHQMKDCTESKANFLGKIWPSNKGRPGNFLQNRPEPTAPPAES
FGFGEEIAPSPKQEPKEKEIYPLASLKSLFGSDPSSQ$

Fig. 84B

2003_CON_14_BG_gag.OPT
ATGGGCGCCCGGGCCTCCGTGCTGTCCGGCGGCAAGCTGGACGCCTGGGAGAAGATCCGCCTGCGGCCCGGCGGCAAGAAGAAGTACCGCAT
GAAGCACCTGGTGTGGGCCTCCCGCGAGCTGGAGCGCTTCGCCCTGAACCCCGACCTGCTGGAGACCGCCGAGGGCTGCCAGCAGATCATGG
GCCAGCTGCAGCCCGCCCTGCAGACCGGCACCGAGGAGATCCGCTCCCTGTTCAACACCGTGGCCACCCTGTACTGCGTGCACCAGAAGATC
GAGGTGAAGGACACCAAGGAGGCCCTGGAGGAGGTGGAGAAGGCCCAGAAGAAGTCCCAGAAGAAGCAGCAGGCCGCCATGGACGAGGGCAA
CAACTCCCAGGCCTCCCAGAACTACCCCATCGTGCAGAACGCCCAGGGCCAGATGGTGCACCAGGCCATCTCCCCGCGGACCCTGAACGCT
GGGGTGAAGGTGGTGGAGGAGAAGGCCTTCTCCCCCGAGGTGATCCCCATGTTCTCCGCCCTGTCCGAGGGCGCCACCCCCCAGGACCTGAAC
ACCATGCTGAACACCGTGGGCGGCCACCAGGCCGCCATGCAGATGCTGAAGGACACCATCAACGAGGAGGCCGCCGAGTGGGACCGCATGCA
CCCCCAGCAGGCCGGCCCCATCCCCCCCGGCCAGATCCGCGAGCCCCGCGGCTCCGACATCGCCGGCACCACCTCCACCCTGCAGGAGCAGA
TCCGCTGGATGACCTCCAACCCCCCCATCCCCGTGGGCGAGATCTACAAGCGCTGGATCATCCTGGGCCTGAACAAGATCGTGCGCATGTAC
TCCCCCGTGTCCATCCTGGACATCCGCCAGGGCCCCAAGGAGTTCTTCAGAGACTACGTCGACCGCTTCTTCAAGACCCTGCGCGCCGAGCA
GGCCACCCAGGAGGTGAAGGGCTGGATGACCGACACCCTGCTGGTGCAGAACGCCAACCCCGACTGCAAGACCATCCTGCGCGCCCTGGGCC
CCGGCGCCACCCTGGAGGAGATGATGACCGCCTGCCAGGTGGGCGGCCCCTCCCACAAGGCCCGCGTGCTGGCCGAGGCCATGTCCCAG
GCCTCCGGCGCCACCATCATGATGCAGAAGTCCAACTTCAAGGGCCCCAGGCGCAACATCAAGTGCTTCAACTGCGGCAAGGAGGGCCACCT
GGCCCGCAACTGCCGCGCCCCCAGGAAGAAGGGCTGCTGGAAGTGCGGCAAGGAGGGCCACCAGATGAAGGACTGCACCGAGTCCAAGGCCA
ACTTCCTGGGCAAGATCTGGCCCTCCAACAAGGGCCGCCCCGGCAACTTCCTGCAGAACCGCCCCGAGCCCACCGCCCCCCCGAGTCC
TTCGGCTTCGGCGAGGAGATCGCCCCCAGCCCCAAGCAGGAGCCCAAGGAGAAGGAGATCTACCCCCTGGCCTCCCTGAAGTCCCTGTTCGG
CTCCGACCCCTAATCCCAGTAA

Fig. 85A 31. 2003_CONS nef.PEP

MGGKWSKSSIVGWPAVRERIRRTPPAAEGVGAVSQDLDKHGAITSSNTAATNADCAWLEAQEEEVGFPVRPQVPLRPMTYKGAFDLSHFLK
EKGGLDGLIYSKKRQEILDLWVYHTQGYFPDWQNYTPGPGIRYPLTFGWCFKLVPVDPEEVEEANEGENNCLLHPMCQHGMEDEDREVLMWK
FDSRLALRHIARELHPEFYKDC$

Fig. 85B

2003_CONS nef OPT

ATGGGCGGCAAGTGGTCCAAGTCCTCCATCGTGGGCTGGCCCGTGGCCCGCGAGCGCATCCGCCGCACCCCCCCCGCCGAGGGCGTGGG
CGCCGTGTCCCAGGACCTGGACAAGCACGGCGCCATCACCTCCTCCAACACCGCCGCCACCAACGCCGACTGCGCCTGGCTGGAGGCCCAGG
AGGAGGAGGTGGGCTTCCCCGTGCGCCCCCAGGTGCCCCTGCGCCCCATGACCTACAAGGGCGCCTTCGACCTGTCCCACTTCCTGAAG
GAGAAGGGCGGCCTGGACGGCCTGATCTACTCCAAGAAGCGCCAGGAGATCCTGGACCTGTGGGTGTACCACACCCAGGGCTACTTCCCCGA
CTGGCAGAACTACACCCCCGGCCCGGGCATCCGCTACCCCCTGACCTTCGGCTGGTGCTTCAAGCTGGTGCCCGTGGACCCCGAGGAGGTGG
AGGAGGCCAACGAGGGCGAGAACAACTGCCTGCTGCACCCCATGTGCCAGCACGGCATGGAGGACGAGGACCGCGAGGTGCTGATGTGGAAG
TTCGACTCCCGCCTGGCCCTGCGCCACATCGCCCGCGAGCTGCACCCCGAGTTCTACAAGGACTGCTAA

Fig. 86A 32 2003_M_GROUP_anc nef PEP

MGGKWSKSSIVGWPAVRERMRRTAPAAEGVGAVSQDLDKHGAITSSNTAATNADCAWLEAQEEEVGFPVRPQVPLRPMTYKAAFDLSHFLK
EKGGLDGLIYSKKRQEILDLWVYHTQGYFPDWQNYTPGPGIRYPLTFGWCFKLVPVDPEEVEEANEGENNCLLHPMCQHGMEDEEREVLMWK
FDSRLALRHIARELHPEFYKDC$

Fig. 86B

2003_M_GROUP.anc nef OPT

ATGGGCGGCAAGTGGTCCAAGTCCTCCATCGTGGGCTGGCCCGCCGTGCGCGAGCGCATGCGCCGCACCGCCCCCGCCGAGGGCGTGGG
CGCCGTGTCCCAGGACCTGGACAAGCACGGCGCCATCACCTCCTCCAACACCGCCGCCACCAACGCCGACTGCGCCTGGCTGGAGGCCCAGG
AGGAGGAGGTGGGCTTCCCCGTGCGCCCCCAGGTGCCCCTGCGCCCCATGACCTACAAGGCCGCCTTCGACCTGTCCCACTTCCTGAAG
GAGAAGGGCGGCCTGGACGGCCTGATCTACTCCAAGAAGCGCCAGGAGATCCTGGACCTGTGGGTGTACCACACCCAGGGCTACTTCCCCGA
CTGGCAGAACTACACCCCCGGCCCCGGCATCCGCTACCCCCTGACCTTCGGCTGGTGCTTCAAGCTGGTGCCCGTGGACCCCGAGGAGGTGG
AGGAGGCCAACGAGGGCGAGAACAACTGCCTGCTGCACCCCATGTGCCAGCACGGCATGGAGGACGAGGAGCGCGAGGTGCTGATGTGGAAG
TTCGACTCCCGCCTGGCCCTGCGCCACATCGCCCGCGAGCTGCACCCCGAGTTCTACAAGGACTGCTAA

Fig. 87A

33. 2003_CON_A nef.PEP

MGGKWSKSSIVGWPDIRERIRRTPPAAKGVGAVSQDLDKYGAVTINNTAATQASCAWLEAQEEEEVGFPVRPQVPLRPMTFKGAFDLSFFL
KEKGGLDGLIYSQKRQEILDLWVYNTQGYFPDWQNYTPGPGTRFPLTFGWCFKLVPVDPDEVEEATEGENNCLLHPICQHGMDDEEKEVLMW
KFDSRLARRHIALEMHPEFYKDC$

Fig. 87B

2003_CON_A nef.OPT

ATGGGCGGCAAGTGGTCCAAGTCCTCCATCGTGGGCTGGCCCGACATCCGCGAGCGCATCCGCCGCACCCCCCCGGCCGCCAAGGGCGTGGG
CGCCGTGTCCCAGGACCTGGACAAGTACGGCGCCGTGACCATCAACAACACCGCCGCCACCCAGGCCTCCTGCGCCTGGCTGGAGGCCCAGG
AGGAGGAGGAGGTGGGCTTCCCCGTGCGCCCCCAGGTGCCCCTGCGCCCCATGACCTTCAAGGGCGCCTTCGACCTGTCCTTCTTCCTG
AAGGAGAAGGGCGGCCTGGACGGCCTGATCTACTCCCAGAAGCGCCAGGAGATCCTGGACCTGTGGGTGTACAACACCCAGGGCTACTTCCC
CGACTGGCAGAACTACACCCCCGGCCCCGGCACCCGCTTCCCCCTGACCTTCGGCTGGTGCTTCAAGCTGGTGCCCGTGGACCCCGACGAGG
TGGAGGAGGCCACCGAGGGCGAGAACAACTGCCTGCTGCACCCCATCTGCCAGCACGGCATGGACGACGAGGAGAAGGAGGTGCTGATGTGG
AAGTTCGACTCCCGCCTGGCCCGCCGCCACATCGCCCTGGAGATGCACCCCGAGTTCTACAAGGACTGCTAA

Fig. 88A

34. 2003_CON_A1 nef.PEP

MGGKWSKSSIVGWPEVRERMRRTPPAATGVGAVSQDLDKHGAVTSSNINHPSCVWLEAQEEEEVGFPVRPQVPLRPMTYKGALDLSHFLKEK
GGLDGLIYSRKRQEILDLWVYHTQGYFPDWQNYTPGPGIRYPLTFGWCFKLVPVDPDEVEKATEGENNSLLHPICQHGMDDEEREVLKWKFD
SRLALKHRAQELHPEFYKDC$

Fig. 88B

2003_CON_A1 nef.OPT

ATGGGCGGCAAGTGGTCCAAGTCCTCCATCGTGGGCTGGCCCGAGGTGCGCGAGCGCATGCGCCGCACCCCCCCGGCCGCCACCGGCGTGGG
CGCCGTGTCCCAGGACCTGGACAAGCACGGCGCCGTGACCTCCTCCAACATCAACCACCCCTCCTGCGTGTGGCTGGAGGCCCAGGAGGAGG
AGGAGGTGGGCTTCCCCGTGCGCCCCCAGGTGCCCCTGCGCCCCATGACCTACAAGGGCGCCCTGGACCTGTCCCACTTCCTGAAGGAGAAG
GGCGGCCTGGACGGCCTGATCTACTCCCGCAAGCGCCAGGAGATCCTGGACCTGTGGGTGTACCACACCCAGGGCTACTTCCCCGACTGGCA
GAACTACACCCCCGGCCCCGGCATCCGCTACCCCCTGACCTTCGGCTGGTGCTTCAAGCTGGTGCCCGTGGACCCCGACGAGGTGGAGAAGG
CCACCGAGGGCGAGAACAACTCCCTGCTGCACCCCATCTGCCAGCACGGCATGGACGACGAGGAGCGCGAGGTGCTGAAGTGGAAGTTCGAC
TCCCGCCTGGCCCTGAAGCACCGCGCCCAGGAGCTGCACCCCGAGTTCTACAAGGACTGCTAA

Fig. 88C 35 2003_A1.anc_nef.PEP
MGGKWSKSSIVGWPEVRERMRRTPPAAKGVGAVSQDLDKHGAVTSSNTAANNPGCAWLEAQEEEVGFPVRPQVPLRPMTYKGAFDLSHFLK
EKGGLDGLIYSKKRQEILDLWVYHTQGYFPDWQNYTPGPGIRYPLTFGWCFKLVPDPAEVEEATEGENNSLLHPICQHGMDDEEREVLMWK
FDSRLALKHRARELHPEFYKDC$

Fig. 88D

2003_A1.anc_nef.OPT
ATGGGCGGCAAGTGGTCCAAGTCCTCCATCGTGGGCTGGCCTGAAGTGCGCGAGCGCATGCGCCGCACCCCCGCCGCCAAGGGCGTGGG
CGCCGGTGTCCCAGGACCTGGACAAGCACGGCGCCGTGACCAGCAGCAACACCGCCGCCAACAACCCCGGCTGCGCCTGGGAGGCCAGG
AGGAGGAGGTGGGCTTCCCCGTGCGCCCCCAGGTGCCCCTGCGCCCCATGACCTACAAGGGCGCCTTCGACCTGTCCCACTTCCTGAAG
GAGAAGGGCGGCCTGGACGGCCTGATCTACAGCAAGAAGCGCCAGGAGATCCTGGACCTGTGGGTGTACCACACCCAGGGCTACTTCCCCGA
CTGGCAGAACTACACCCCCGGCCCCGGCATCCGCTACCCCCTGCTGACCTTCGGCTGGTGCTTCAAGCTGGTGCCCGACCCCGCCGAGGTGG
AGGAGGCCACCGAGGGCGAGAACAACTCCCTGCTGCACCCCATCTGCCAGCACGGCATGGACGACGAGGAGGCGCGAGGTGCTGATGTGGAAG
TTCGACTCCCGCCTGGCCCTGAAGCACCGCGCCCGAGCTGCACCCCGAGTTCTACAAGGACTGCTAA

Fig. 89A 36. 2003_CON_A2_nef.PEP
MGGKWSKSSIVGWPAIRERMKRTPAAEGVGAVSQDLATRGAVTSSNTAATNPDCAWLEAQEEEVGFPVRPQVPLRPMTFKGAFDLSHFL
KEKGGLDLIYSQKRQDILDLMVYHTQGYFPDWQNYTPGPGTRYPLTFGWCFKLVPVDPSEVEEATEGENNSLLHPICQHGIEDPEREVLRW
KFDSRLALRHRARELHPEFYKDC$

Fig. 89B

2003_CON_A2_nef.OPT
ATGGGCGGCAAGTGGTCCAAGTCCTCCATCGTGGGCTGGCCTGCCATCCGCGAGCGCATGAAGCGCACCCCCGCCGCCGAGGGCGT
GGGCGCCGTGTCCCAGGACCTGGCCACCCGCGGCGCCGTGACCAGCTCCAACACCGCCGCCACCAACCCCGACTGCGCCTGGCTGGAGGCCC
AGGAGGAGGAGGTGGGCTTCCCCGTGCGCCCCCAGGTGCCCCTGCGCCCCATGACCTTCAAGGGCGCCTTCGACCTGTCCCACTTCCTG
AAGGAGAAGGGCGGCCTGGATCTACTCCCAGAAGCGCCAGGACATCCTGGACCTGTGGGTGTACCACACCCAGGGCTACTTCCCC
GACTGGCAGAACTACACCCCCGGCCCCGGCACCCGCTACCCCCTGACCTTCGGCTGTGCTTCAAGCTGGTGCCCGTGGACCCCTCCGAGG
TGGAGGAGGCCACCGAGGGCGAGAACAACTCCCTGCTGCACCCCATCTGCCAGCACGGCATCGAGGACCCCGAGCGCGAGGTGCTGCGCTGG
AAGTTCGACTCCCGCCTGGCCCTGCGCCACCGCGCCCGAGAGTTCTACAAGGACTGCTAA

Fig. 90A

37. 2003_CON_B nef.PEP

MGGKWSKRSVVGWPTVRERMRRAEPAADGVGAVSRDLEKHGAITSSNTAANNADCAWLEAQEEEVGFPVRPQVPLRPMTYKGALDLSHFLK
EKGGLEGLIYSQKRQDILDLWVYHTQGYFPDWQNYTPGPGIRYPLTFGWCFKLVPVEPEKVEEANEGENNSLLHPMSLHGMDDPEREVLVWK
FDSRLAFHHMARELHPEYYKDC$

Fig. 90B

2003_CON-B nef.OPT

ATGGGCGGCAAGTGGTCCAAGCGCTCCGTGGTGGGCTGGCCCACCGTGCGCGAGCGCATGCGCCGCGCCGAGCCCGCCGACGGCGTGGG
CGCCGTGTCCCGCGACCTGGAGAAGCACGGCGCCATCACCTCCTCCAACACCGCCGCCAACAACGCCGACTGCGCCTGGCTGGAGGCCCAGG
AGGAGGAGGTGGGCTTCCCCGTGCGCCCCCAGGTGCCCCTGCGCCCCATGACCTACAAGGGCGCCCTGGACCTGTCCCACTTCCTGAAG
GAGAAGGGCGGCCTGGAGGGCCTGATCTACTCCCAGAAGCGCCAGGACATCCTGGACCTGTGGGTGTACCACACCCAGGGCTACTTCCCCGA
CTGGCAGAACTACACCCCCGGCCCGGGCATCCGCTACCCCCTGACCTTCGGCTGGTGCTTCAAGCTGGTGCCCGTGGAGCCCGAGAAGGTGG
AGGAGGCCAACGAGGGCGAGAACAACTCCCTGCTGCACCCCATGTCCCTGCACGGCATGGACGACCCCGAGCGCGAGGTGCTGGTGTGGAAG
TTCGACTCCCGCCTGGCCTTCCACCACATGGCCCGCGAGCTGCACCCCGAGTACTACAAGGACTGCTAA

Fig. 90C

38. 2003_B.anc nef.PEP

MGGKWSKSSMGGWPAVRERMKRAEPAADGVGAVSRDLEKHGAITSSNTAATNADCAWLEAQEEEVGFPVRPQVPLRPMTYKAALDLSHFLK
EKGGLEGLIYSQKRQDILDLWVYHTQGYFPDWDNYTPGPGIRYPLTFGWCFKLVPVEPEKVEEATEGENNSLLHPMCQHGMDDPEKEVLVWK
FDSRLAFHHMARELHPEYYKDC$

Fig. 90D

2003_B.anc nef.OPT

ATGGGCGGCAAGTGGTCCAAGTCCTCCATGGGCGGCTGGCCCGCCGTGCGCGAGCGCATGAAGCGCGCCGAGCCCGCCGACGGCGTGGG
CGCCGTGTCCCGCGACCTGGAGAAGCACGGCGCCATCACCTCCTCCAACACCGCCACCAACGCCGACTGCGCCTGGCTGGAGGCCCAGG
AGGAGGAGGTGGGCTTCCCCGTGCGCCCCCAGGTGCCCCTGCGCCCCATGACCTACAAGGCCGCCCTGGACCTGTCCCACTTCCTGAAG
GAGAAGGGCGGCCTGGAGGGCCTGATCTACTCCCAGAAGCGCCAGGACATCCTGGACCTGTGGGTGTACCACACCCAGGGCTACTTCCCCGA
CTGGGACAACTACACCCCCGGCCCCGGGCATCCGCTACCCCCTGCTGCACCGGCTGGTGCTTCAAGCTGGTGCCCGTGGAGCCCGAGAAGGTGG
AGGAGGCCACCGAGGGCGAGAACAACTCCCTGCTGCACCCCATGTGCCAGCACGGCATGGACGACCCCGAGAAGGAGGTGCTGGTGTGGAAG
TTCGACTCCCGCCTGGCCTTCCACCACATGGCCCGCGAGCTGCACCCCGAGTACTACAAGGACTGCTAA

Fig. 91A 39. 2003_CON_02_AG nef.PEP

MGGKWSKSSIVGWPKVRERIRQTPPAATGVGAASQDLDRHGAITSSNTAATNADCAWLEAQEEEVGFPVRPQVPLRPMTYKAAVDLSHFLK
EKGGLEGLIYSKKRQEILDLWVYHTQGFPDWQNYTPGPGTRFPLTFGWCFKLVPMDPAEVEEANEGENNSLLHPICQHGMEDEDREVLVWR
FDSSLAFKHRARELHPEFYKDC$

Fig. 91B

2003_CON_02_AG nef.OPT

ATGGGCGGCAAGTGGTCCAAGTCCTCCATCGTGGGCTGGCCCAAGGTGCGCGAGCGCATCCGCCAGACCCCCGCCGCCACCGGCGTGGG
CGCCGCCTCCCAGGACCTGGACCGCCACGGCGCCATCACCTCCTCCAACACCGCCGCCACCAACGCCGACTGCGCCTGCGCCAGG
AGGAGGAGGAGGTGGGCTTCCCCGTGCGCCCCCAGGTGCCCCTGCGCCCCATGACCTACAAGGCCGCCGTGGACCTGTCCCACTTCCTGAAG
GAGAAGGGCGGCCTGGAGGGCCTGATCTACTCCAAGAAGCGCCAGGAGATCCTGGACCTGTGGGTGTACCACACCCAGGGCTTCCCCGA
CTGGCAGAACTACACCCCCGGCCCCGGCACCCGCTTCCCCCTGACCTTCGGCTGCTTCAAGCTGGTGCCCATGGACCCCGCCGAGGTGG
AGGAGGCCAACGAGGGCGAGAACAACTCCCTGCTGCACCCCATCTGCCAGCACGGCATGGAGGACGAGGACCGCGAGGTGCTGGTGTGGCGC
TTCGACTCCTCCCTGGCCTTCAAGCACCGCGCCCGAGCTGCACCCCGAGTTCTACAAGGACTGCTAA

Fig. 92A 40. 2003_CON_C nef.PEP

MGGKWSKSSIVGWPAVRERIRRTEPAAEGVGAASQDLDKHGALTSSNTATNNADCAWLEAQEEEEVGFPVRPQVPLRPMTYKAAFDLSFFL
KEKGGLEGLIYSKKRQEILDLWVYHTQGYFPDWQNYTPGPGVRYPLTFGWCFKLVPVDPREVEEANEGENNCLLHPMSQHGMEDEDREVLKW
KFDSHLARRHMARELHPEYYKDC$

Fig. 92B

2003_CON_C nef.OPT

ATGGGCGGCAAGTGGTCCAAGTCCTCCATCGTGGGCTGGCCCGCCGTGCGCGAGCGCATCCGCCGCACCGAGCCCGCCGCCGAGGGCGTGGG
CGCCGCCTCCCAGGACCTGGACAAGCACGGCGCCCTCACCTCCTCCAACACCGCCACCAACAACGCCGACTGCGCCTGGCTGGAGGCCCAGG
AGGAGGAGGAGGTGGGCTTCCCCGTGCGCCCCCAGGTGCCCCTGCGCCCCATGACCTACAAGGCCGCCTTCGACCTGTCCTTCTTCCTG
AAGGAGAAGGGCGGCCTGGAGGGCCTGATCTACTCCAAGAAGCGCCAGGAGATCCTGGACCTGTGGGTGTACCACACCCAGGGCTACTTCCC
CGACTGGCAGAACTACACCCCCGGCCCCGGCGTGCGCTACCCCCTGACCTTCGGCTGGTGCTTCAAGCTGGTGCCCGTGGACCCCCGCGAGG
TGGAGGAGGCCAACGAGGGCGAGAACAACTGCCTGCTGCACCCCATGTCCCAGCACGGCATGGAGGACGAGGACCGCGAGGTGCTGAAGTGG
AAGTTCGACTCCCACCTGGCCCGCCGCCACATGGCCCGCGAGCTGCACCCCGAGTACTACAAGGACTGCTAA

Fig. 92C 41. 2003_C.anc nef.PEP
MGGKWSKSSIVGWPAVRERMRRTEPAAEGVGAASQDLDKHGALTSSNTAANNADCAWLEAQEEEEVGFPVRPQVPLRPMTYKAAFDLSFFL
KEKGGLDGLIYSKKRQEILDLWVYHTQGYFPDWQNYTPGPGVRYPLTFGWCEILVPVDPREVEEANEGENNCLLHPMSQHGMEDEDREVLKW
KFDSHLARRHMARELHPEYYKDC$

Fig. 92D

2003_C.anc nef.OPT
ATGGGCGGCAAGTGGTCCAAGTCCTCCATCGTGGGCTGGCCCGCCGTGCGCGAGCGCATGCGCCGCACCGAGCCCGCCGAGGGCGTGGG
CGCCGCCTCCCAGGACCTGGACAAGCACGGCGCCCTCACCAGCAGCAACACCGCCAACAACGCCGACTGCGCCTGGCTGGAGGCCCAGG
AGGAGGAGGAGGTGGGCTTCCCCGTGCGCCCCCAGGTGCCCCTGCGCCCCATGACCTACAAGGCCGCCTTCGACCTGTCCTTCTTCCTG
AAGGAGAAGGGCGGCCTGGACGGCCTGATCTACTCCAAGAAGCGCCAGGAGATCCTGGACCTGTGGGTGTACCACACCCAGGGCTACTTCCC
CGACTGGCAGAACTACACCCCCGGCCCCGGCGTGCGCTACCCCCTGACCTTCGGCTGGTGCGAGATCCTGGTGCCCGTGGACCCCCGAGG
TGGAGGAGGCCAACGAGGGCGAGAACAACTGCCTGCTGCACCCCATGTCCCAGCACGGCATGGAGGACGAGGACCGCGAGGTGCTGAAGTGG
AAGTTCGACTCCCACCTGGCCCGCCGCCACATGGCCCGCGAGCTGCACCCCGAGTACTACAAGGACTGCTAA

Fig. 93A 42. 2003_CON_D nef.PEP
MGGKWSKSSIVGWPAIRERIRRTEPAADGVGAVSRDLEKHGAITSSNTAATNADCAWLEAQEEDEEVGFPVRPQVPLRPMTYKAALDLSHFL
KEKGGLEGLVWSQKRQEILDLWVYSNTQGGFFPDWQNYTPGPGIRYPLTFGWCFELVPVDPEEVEEATEGENNCLLHPMCQHGMEDPEREVLMW
RFNSRLAFEHKARVLHPEFYKDC$

Fig. 93B

2003_CON_D nef.OPT
ATGGGCGGCAAGTGGTCCAAGTCCTCCATCGTGGGCTGGCCCGCCATCCGCGAGCGCATCCGCCGCACCGAGCCCGCCGACGGCGTGGG
CGCCGTGTCCCGCGACCTGGAGAAGCACGGCGCCATCACCTCCTCCAACACCGCCGCCACCAACGCCGACTGCGCCTGGCTGGAGGCCCAGG
AGGAGGACGAGGAGGTGGGCTTCCCCGTGCGCCCCCAGGTGCCCCTGCGCCCCATGACCTACAAGGCCGCCCTGGACCTGTCCCACTTCCTG
AAGGAGAAGGGCGGCCTGGAGGGCCTGGTGTGGTCCCAGAAGCGCCAGGAGATCCTGGACCTGTGGGTGTACAACACCCAGGGCTTCTTCCC
CGACTGGCAGAACTACACCCCCGGCCCCGGCATCCGCTACCCCCTGACCTTCGGCTGGTGCTTCGAGCTGGTGCCCGTGGACCCCGAGGAGG
TGGAGGAGGCCACCGAGGGCGAGAACAACTGCCTGCTGCACCCCATGTGCCAGCACGGCATGGAGGACCCCGAGCGCGAGGTGCTGATGTGG
CGCTTCAACTCCCGCCTGGCCTTCGAGCACAAGGCCCGCGTGCTGCACCCCGAGTTCTACAAGGACTGCTAA

Fig. 94A 43. 2003_CON_F1 nef.PEP

MGGKWSKSSIVGWPAVRERMRPTPPAAEGVGAVSQDLERRGAITSSNTGATNPDLAWLEAQEEEVGFPVRPQVPLRPMTYKGAVDLSHFLK
EKGGLEGLIYSKKRQEILDLWVYHTQGYFPDWQNYTPGPIRYPLTFGWCFKLVPVDPEEVEKANEGENNCLLHPMSQHGMEDEDREVLIWK
FDSRLALRHIARERHPEFYQD$

Fig. 94B

2003_CON_F1 nef.OPT

ATGGGCGGCAAGTGGTCCAAGTCCTCCATCGTGGGCTGGCCCGTGCGCGAGCGCATGCGCCCCACCCCCGCCGCCGAGGGCGTGGG
CGCCGTGTCCCAGGACCTGGAGCGCCGCGGCGCCATCACCTCCTCCAACACCGGCGCCACCAACCCCGACCTGGCCTGGCTGGAGGCCCAGG
AGGAGGAGGTGGGCTTCCCCGTGCGCCCCCAGGTGCCCCTGCGCCCCATGACCTACAAGGGCGCCGTGGACCTGTCCCACTTCCTGAAG
GAGAAGGGCGGCCTGGAGGGCCTGATCTACTCCAAGAAGCGCCAGGAGATCCTGGACCTGTGGGTGTACCACACCCAGGGCTACTTCCCCGA
CTGGCAGAACTACACCCCCGGCCCCATCCGCTACCCCCTGACCTTCGGCTGGTGCTTCAAGCTGGTGCCCGTGGACCCCGAGGAGGTGG
AGAAGGCCAACGAGGGCGAGAACAACTGCCTGCTGCACCCCATGTCCCAGCACGGCATGGAGGACGAGGACCGCGAGGTGCTGATCTGGAAG
TTCGACTCCCGCCTGGCCCTGCGCCACATCGCCCGCGAGCGCCACCCCGAGTTCTACCAGGACTAA

Fig. 95A 44. 2003_CON_F2 nef.PEP

MGGKWSKSSIVGWPTIRERIRRTPVAAEGVGAVSQDLDKHGAITSSNTRATNADLAWLEAQEDEEVGFPVRPQVPLRPMTYKAAFDLSHFLK
EKGGLEGLIYSKKRQEILDLWVYHTQGYFPDWQNYTPGPGTRYPLTFGWCFKLVPVDPEEVEKANEGENNCLLHPMSLHGMEDEDREVLKWK
FDSRLALRHIARERHPEYYKD$

Fig. 95B

2003_CON_F2 nef.OPT

ATGGGCGGCAAGTGGTCCAAGTCCTCCATCGTGGGCTGGCCCACCATCCGCGAGCGCATCCGCCGCACCCCCGTGGCCGCCGAGGGCGTGGG
CGCCGTGTCCCAGGACCTGGACAAGCACGGCGCCATCACCTCCTCCAACACCCGCGCCACCAACGCCGACCTGGCCTGGCTGGAGGCCCAGG
AGGACGAGGAGGTGGGCTTCCCCGTGCGCCCCCAGGTGCCCCTGCGCCCCATGACCTACAAGGCCGCCTTCGACCTGTCCCACTTCCTGAAG
GAGAAGGGCGGCCTGGAGGGCCTGATCTACTCCAAGAAGCGCCAGGAGATCCTGGACCTGTGGGTGTACCACACCCAGGGCTACTTCCCCGA
CTGGCAGAACTACACCCCCGGCCCCGGCACCCGCTACCCCCTGACCTTCGGCTGGTGCTTCAAGCTGGTGCCCGTGGACCCCGAGGAGGTGG
AGAAGGCCAACGAGGGCGAGAACAACTGCCTGCTGCACCCCATGTCCCTGCACGGCATGGAGGACGAGGACCGCGAGGTGCTGAAGTGGAAG
TTCGACTCCCGCCTGGCCCTGCGCCACATCGCCCGCGAGCGCCACCCCGAGTACTACAAGGACTAA

Fig. 96A

45. 2003_CON_G nef.PEP

MGGKWSKSSIVGWPEVRERIRQTPPAAEGVGAVSQDLARHGAITSSNTAANNPDCAWLEAQEEDSEVGFPVRPQVPLRPMTYKGAFDLSFFL
KEKGGLDGLIYSKKRQDILDLWVYNTQGFFPDWQNYTPGPGTRFPLTFGWCFKLVPMDPAEVEEANKGENNSLLHPICQHGMEDEDREVLVW
RFDSSLARRHIARELHPEYYKDC$

Fig. 96B

2003_CON_G nef.OPT

ATGGGCGGCAAGTGGTCCAAGTCCTCCATCGTGGGCTGGCCCGAGGTGCGCGAGCGCATCCGCCAGACCCCCCCGGCCGCCGAGGGCGTGGG
CGCCGTGTCCCAGGACCTGGCCCGCCACGGCGCCATCACCTCCTCCAACACCGCCGCCAACAACCCCGACTGCGCCTGGCTGGAGGCCCAGG
AGGAGGACTCCGAGGTGGGCTTCCCCGTGCGCCCCCAGGTGCCCCTGCGCCCCATGACCTACAAGGGCGCCTTCGACCTGTCCTTCTTCCTG
AAGGAGAAGGGCGGCCTGGACGGCCTGATCTACTCCAAGAAGCGCCAGGACATCCTGGACCTGTGGGTGTACAACACCCAGGGCTTCTTCCC
CGACTGGCAGAACTACACCCCCGGCCCCGGCACCCGCTTCCCCCTGCTGACCTTCGGCTGCTGCTTCAAGCTGGTGCCCATGGACCCCGCAGG
TGGAGGAGGCCAACAAGGGCGAGAACAACTCCCTGCTGCACCCCATCTGCCAGCACGGCATGGAGGACGAGGACCGCGAGGTGCTGGTGTGG
CGCTTCGACTCCTCCCTGGCCCGCCGCCACATCGCCCGCGAGCTGCACCCCGAGTACAAGGACTGCTAA

Fig. 97A

46. 2003_CON_H nef.PEP

MGGKWSKSSIGGWPAIRERIRRAEPAAEGVGAVSRDLDRRGAVTINNTASTNPDSAWLEAQEEEEVGFPVRPQVPLRPMTYKGAFDLSHFL
KEKGGLEGLIYSKKRQEILDLWVYNTQGYFPDWQNYTPGPGERYPLTFGWCFKLVPVDPQEVEKANEGENNSLLHPICQHGMEDEREVLMW
KFDSRLAFRHIARELHPEFYKDC$

Fig. 97B

2003_CON_H nef.OPT

ATGGGCGGCAAGTGGTCCAAGTCCTCCATCGGCGGCTGGCCCGCCATCCGCGAGCGCATCCGCCGCGCCGAGCCCGCCGCCGAGGGCGTGGG
CGCCGTGTCCCGCGACCTGGACCGCCGCGGCGCCGTGACCATCAACAACACCGCCTCCACCAACCCCGACTCCGCCTGGCTGGAGGCCCAGG
AGGAGGAGGAGGTGGGCTTCCCCGTGCGCCCCCAGGTGCCCCTGCGCCCCATGACCTACAAGGGCGCCTTCGACCTGTCCCACTTCCTG
AAGGAGAAGGGCGGCCTGGAGGGCCTGATCTACTCCAAGAAGCGCCAGGAGATCCTGGACCTGTGGGTGTACAACACCCAGGGCTACTTCCC
CGACTGGCAGAACTACACCCCCGGCCCCGGCGAGCGCTACCCCCTGACCTTCGGCTGGTGCTTCAAGCTGGTGCCCGTGGACCCCCAGGAGG
TGGAGAAGGCCAACGAGGGCGAGAACAACTCCCTGCTGCACCCCATCTGCCAGCACGGCATGGAGGACGAGCGCGAGGTGCTGATGTGG
AAGTTCGACTCCCGCCTGGCCTTCCGCCACATCGCCCGCGAGCTGCACCCCGAGTTCTACAAGGACTGCTAA

Fig. 98A 47. 2003_CON_01_AE_nef.PEP

MGGKWSKSSIVGWPQVRERIKQTPPATEGVGAVSQDLDKHGAVTSSNMNNADCVWLRAQEEEVGFPVRPQVPLRPMTYKGAFDLSFFLKEK
GGLDGLIYSKKRQEILDLWVYNTQGFFPDWQNYTPGPGIRYPLCFGWCFKLVPVDPREVEEDNKGENNCLLHPMSQHGIEDEEREVLMWKFD
SALARKHIARELHPEYYKDCS

Fig. 98B

2003_CON_01_AE_nef.OPT

ATGGGCGGCAAGTGGTCCAAGTCCTCCATCGTGGGCTGGCCCCAGGTGCGCGAGCGCATCAAGCAGACCCCCGCCACCGAGGGCGTGGG
CGCCGTGTCCCAGGACCTGGACAAGCACGGCGCCGTGACCTCCTCCAACATGAACAACGCCGACTGCGTGTGGCTGCGCGCCCAGGAGGAG
GAGGTGGGCTTCCCCGTGCGCCCCCAGGTGCCCCTGCGCCCCATGACCTACAAGGGCGCCTTCGACCTGTCCTTCTTCCTGAAGGAGAAG
GGCGGCCTGGACGGCCTGATCTACTCCAAGAAGCGCCAGGAGATCCTGGACCTGTGGGTGTACAACACCCAGGGCTTCTTCCCCGACTGGCA
GAACTACACCCCCGGCCCCGGCATCCGCTACCCCCTGTGCTTCGGCTGGTGCTTCAAGCTGGTGCCCGTGGACCCCCGAGGTGGAGGAG
GACAACAAGGGCGAGAACAACTGCCTGCTGCACCCCATGTCCCAGCACGGCATCGAGGACGAGGAGCGCGAGGTGCTGATGTGGAAGTTCGAC
TCCGCCCTGGCCCGCAAGCACATCGCCCGCGAGCTGCACCCCGAGTACTACAAGGACTGCTAA

Fig. 99A 48. 2003_CON_03_AE_nef.PEP

MGGKWSKSSIVGWPQVRERIRRAPAPAARGVGPVSQDLDKYGAVTSSNTAANNADCAWLEAQKEEEVGFPVRPQVPLRPMTYKGAFDLSHFL
KEKGGLDGLIYSKKRQEILDLMVYHTQGYFPDWQNYTPGPGIRFPLTFGWCYKLVPVDPDEVEEATEGENNSLLHPICQHGMDDEEKEVLMW
KFDSRLALTHRARELHPEFYKDCS

Fig. 99B

2003_CON_03_AE_nef.OPT

ATGGGCGGCAAGTGGTCCAAGTCCTCCATCGTGGGCTGGCCCCAGGTGCGCGAGCGCATCCGCCGCGCCCCCGCCCCCGCCGCCCGCGGCGT
GGGCCCCGTGTCCCAGGACCTGGACAAGTACGGCGCCGTGACCTCCTCCAACACCGCCGCCAACAACGCCGACTGCGCCTGGCTGGAGGCCC
AGAAGGAGGAGGAGGTGGGCTTCCCCGTGCGCCCCCAGGTGCCCCTGCGCCCCATGACCTACAAGGGCGCCTTCGACCTGTCCCACTTCCTG
AAGGAGAAGGGCGGCCTGGACGGCCTGATCTACTCCAAGAAGCGCCAGGAGATCCTGGACCTGATGGTGTACCACACCCAGGGCTACTTCCC
CGACTGGCAGAACTACACCCCCGGCCCCGGCATCCGCTTCCCCCTGACCTTCGGCTGGTGCTACAAGCTGGTGCCCGTGGACCCCGACGAGG
TGGAGGAGGCCACCGAGGGCGAGAACAACTCCCTGCTGCACCCCATCTGCCAGCACGGCATGGACGACGAGGAGAAGGAGGTGCTGATGTGG
AAGTTCGACTCCCGCCTGGCCCTGACCCACCGCGCCCGCGAGCTGCACCCCGAGTTCTACAAGGACTGCTAA

Fig. 100A 49. 2003_CON_04_CFX_nef.PEP

MGGKWSKSSIVGWPAIRERMRQRGPAQAEPAAAGVGAVSQDLDKHGAITSSNTAATNPDKAWLEAQEEEEVGFPVRPQVLRPMTFKAALD
LSHFLKEKGGLDGLIYSKKRQEILDLWVYHTQGYFPDWQNYTPGPGERFPLCFGWCFKLVPVDPQEVEEATEGENNCLLHPISQHGMEDEER
EVLKWKFDSRLAYKHIARELHPEFYKDC$

Fig. 100B

2003_CON_04_CFX_nef.OPT

ATGGGCGGCAAGTGGTCCAAGTCCTCCATCGTGGGCTGGCCCGCCATCCGCGAGCGCATGCGCCAGCGCGGCCCCGCCCAGGCCGAGCCCGC
CGCCGCCGGCGTGGGCGCCGTGTCCCAGGACCTGGACAAGCACGGCGCCATCACCTCCTCCAACACCGCCGCCACCAACCCCGACAAGGCCT
GGCTGGAGGCCCAGGAGGAGGAGGAGGTGGGCTTCCCCGTGCGCCCCCAGGTGCTGCGCCCCATGACCTTCAAGGCCGCCCTGGAC
CTGTCCCACTTCCTGAAGGAGAAGGGCCTGGACGGCCTGATCTACTCCAAGAAGCGCCAGGAGATCCTGGACCTGTGGGTGTACAACAC
CCAGGGCTACTTCCCCGACTGGCAGAACTACACCCCCGGCCCCGGCGAGCGCTTCCCCCTGTGCTTCGGCTGGTGCTTCAAGCTGGTGCCCG
TGGACCCCCAGGAGGTGGAGGAGGCCACCGAGGGCGAGAACAACTGCCTGCTGCACCCCATCTCCCAGCACGGCATGGAGGACGAGGAGCGC
GAGGTGCTGAAGTGGAAGTTCGACTCCCGCCTGGCCTACAAGCACATCGCCCGCGAGCTGCACCCCGAGTTCTACAAGGACTGCTAA

Fig. 101A 50. 2003_CON_06_CFX_nef.PEP

MGGKWSKSSIVGWPQVRERMRNPPTEGAAEGVGAVSQDLDKHGAITSSNTATTNAACAWLEAQTEDEVGFPVRPQVLRPMTYKGAFDLSFF
LKEKGGLDGLIYSKKRQEILDLWVYHTQGFFPDWQNYPGPIRYPLTFGWCYKLVPVDPKEVEEDTKGENNCLLHPMCQHGVEDEEREVLM
WKFDSSLARRHIAREMHPEFYKDC$

Fig. 101B

2003_CON_06_CFX_nef.OPT

ATGGGCGGCAAGTGGTCCAAGTCCTCCATCGTGGGCTGGCCCCAGGTGCGCGAGCGCATGCGCAACCCCCCCACCGAGGGCGCCGCCGAGGG
CGTGGGCGCCGTGTCCCAGGACCTGGACAAGCACGGCGCCATCACCTCCTCCAACACCGCCACCACCAACGCCGCCTGCGCCTGGCTGGAGG
CCCAGACCGAGGACGAGGTGGGCTTCCCCGTGCGCCCCCAGGTGCTGCGCCCCATGACCTACAAGGGCGCCTTCGACCTGTCCTTCTTC
CTGAAGGAGAAGGGCCTGGACGGCCTGATCTACTCCAAGAAGCGCCAGGAGATCCTGGACCTGTGGGTGTACCACACCCAGGGCTTCTT
CCCCGACTGGCAGAACTACACCCCCGGGCCCCATCCGCTACCCCCTGACCTTCGGCTGGTGCTACAAGCTGGTGCCCGTGGACCCCAAGG
AGGTGGAGGAGGACACCAAGGGCGAGAACAACTGCCTGCTGCACCCCATGTGCCAGCACGGCGTGGAGGACGAGGAGCGCGAGGTGCTGATG
TGGAAGTTCGACTCCTCCCTGGCCCGCCGCCACATCGCCCGCGAGATGCACCCCGAGTTCTACAAGGACTGCTAA

Fig. 102A 51. 2003_CON_08_BC_nef.PEP
MGGKWSKSSIVGWPATRERIRRTEPAADGVGAVSRDLEKHGAITSSNTADTNADCAWLETQEEEVGFPVRPQVPLRPMTFKGALDLSFFLK
EKGGLEGLIYSKKRQEILDLWVYHTQGYFPDWHNYTPGPGVRFPLTFGWCFKLVPVDPREVEEANEGEDNCLLHPVCQHGMEDEHREVLKWK
FDSQLAHRHRARELHPEFYKDC$

Fig. 102B

2003_CON_08_BC_nef.OPT
ATGGGCGGCAAGTGGTCCAAGTCCTCCATCGTGGGCTGGCCCGCCACCCGAGAGGCCATCCGCCGAGCCGCCGACGCGCGTGGG
CGCCGTGTCCCGCGACCTGGAGAAGCACGGCGCCATCACCTCCTCCAACACCGCCGACACCAACGCCGACTGCGCCTGGCTGGAGACCCAGG
AGGAGGAGGTGGGCTTCCCCGTGCGCCCCCAGGTGCCCCTGCGCCCCATGACCTTCAAGGGCGCCCTGGACCTGTCCTTCTTCCTGAAG
GAGAAGGGCGGCCTGGAGGGCCTGATCTACTCCAAGAAGCGCCAGGAGATCCTGGACCTGTGGGTGTACCACACCCAGGGCTACTTCCCCGA
CTGGCACAACTACACCCCCGGCCGTGCGCTTCCCCCTGACCTTCGGCTGCTTCAAGCTGGTGCCCGTGGACCCCCGAGAGGTGG
AGGAGGCCAACGAGGGCGAGGACAACTGCCTGCTGCACCCCGTGTGCCAGCACGGCATGGAGGACGAGCACCGCGAGGTGCTGAAGTGGAAG
TTCGACTCCCAGCTGGCCCACCGCCACCGCGCCCGCGAGCTGCACCCCGAGTTCTACAAGGACTGCTAA

Fig. 103A 52. 2003_CON_10_CD_nef.PEP
MGGKWSKSSIVGWPAVRERIRRTDPAAEGVGAASRDLEKYGAITSSNTAQTNPDCAWLEAQEEEEVGFPVRPQVPLRPMTYKGAFDLSFFL
KEKGGLEGLIYSKRRQDILDLWVYNTQGFFPDWQNYTPGPGIRYPLTFGWCYKLVPVDPREVEEANEGENNSLLHPMSLHGMEDPHGEVLMW
KFDSNLAHKHMARELHPEYYKDC$

Fig. 103B

2003_CON_10_CD_nef.OPT
ATGGGCGGCAAGTGGTCCAAGTCCTCCATCGTGGGCTGGCCCGCCGTGCGCGAGCGCATCCGCCGCACCGACCCCGCCGAGGGCGTGGG
CGCCGCCTCCCGCGACCTGGAGAAGTACGGCGCCATCACCTCCTCCAACACCGCCCAGACGACCTGCGCCTGGCTGGAGGCCCAGG
AGGAGGAGGAGGTGGGCTTCCCCGTGCGCCCCCAGGTGCCCCTGCGCCCCATGACCTACAAGGGCGCCTTCGACCTGTCCTTCTTCCTG
AAGGAGAAGGGCGGCCTGGAGGGCCTGATCTACTCCAAGCGCCGCCAGGACATCCTGGACCTGTGGGTGTACAACACCCAGGGCTTCTTCCCC
GACTGGCAGAACTACACCCCCGGCCCCGGCATCCGCTACCCCCTGCTGACCTTCGGCTGGTGCTACAAGCTGGTGCCCGTGGACCCCCGAGAGG
TGGAGGAGGCCAACGAGGGCGAGAACAACAGCCTGCTGCACCCCATGTCCCTGCACGGCATGGAGGACCCCCACGGCGAGGTGCTGATGTGG
AAGTTCGACTCCAACCTGGCCCACAAGCACATGGCCCGCGAGCTGCACCCCGAGTACTACAAGGACTGCTAA

Fig. 104A

53. 2003_CON_11_CFX_nef.PEP

MGGKWSKSSIVGWPEIRERLRRTPPTAAAEGVGAVTSSNTAQTNAACAWLEAQEEEVGFPVRPQVPLRPMTYKGAFDLGFF
LKEKGGLDGLIYSKKRQEILDLWVYHTQGYFPDWQNYTPGPGIRYPLCFGWCFKLVPVEPREVEEANEGENNCLLHPMSQHGMDDEEREVLM
WKFDSSLARRHIARELHPDFYKDC$

Fig. 104B

2003_CON_11_CFX_nef.OPT

ATGGGCGGCAAGTGGTCCAAGTCCTCCATCGTGGGCTGGCCCGAGATCCGCGAGCGCCTGCGCCGCACCCCCACCGCCGCCGAGGG
CGTGGGCGCCGTGTCCAGGACCTGGAGACACGGCGCCGTGTCCAAGGACCTGGAGAAGCACGGCGCCGTGACCTCCAACACCGCCCAGACCAACGCCGCCTGCGCTGGCTGGAGG
CCCAGGAGGAGGAGGTGGGCTTCCCTGTGCGCCCACAGGTGCCCCTGCGCCCCATGACCTACAAGGGCGCCTTCGACCTGGGCTTCTTC
CTGAAGGAGAAGGGCGGCCTGGACGGCCTGATCTACAGCAAGAAGCGCCAGGAGATCCTGGACCTGTGGGTGTACCACACCCAGGGCTACTT
CCCCGACTGGCAGAACTACACGCCCGGCCCCGGCATCCGCTACCCCCTGTGCTTCGGCTGGTGCTTCAAGCTGGTGCCCGTGGAGCCCCGCG
AGGTGGAGGAGGCCAACGAGGGCGAGAACAACTGCCTGCTGCACCCCATGTCCCAGCACGGCATGGACGACGAGGAGCGCGAGGTGCTGATG
TGGAAGTTCGACTCCTCCCTGGCCCGCCGCCACATCGCCCGCGAGCTGCACCCCGACTTCTACAAGGACTGCTAA

Fig. 105A

54. 2003_CON_12_BF_nef.PEP

MGGKWSKSSIVGWPDIRERMRRAPPAAEGVGAVSQDLENRGAITSSNTRANNPDLAWLEAQEEEVGFPVRPQVPLRPMTYKGALDLSHFLK
EKGGLEGLIYSKKRQEILDLWVYHTQGYFPDWQNYTPGPGIRYPLTFGWCFKLVPVDPEEVEKANEGENNCLLHPMSQHGMEDEDREVLMWK
FDSRLALRHIAREKHPEFYQDC$

Fig. 105B

2003_CON_12_BF_nef.OPT

ATGGGCGGCAAGTGGTCCAAGTCCTCCATCGTGGGCTGGCCCGACATCCGCGAGCGCATGCGCCGCGCCCCCGCCGCCGAGGGCGTGGG
CGCCGTGTCCCAGGACCTGGAGAACCGCGGCGCCATCACCTCCTCCAACACCCGCGCCAACAACCCCGACCTGGCCTGGCTGGAGGCCCAGG
AGGAGGAGGTGGGCTTCCCCGTGCGCCCCCAGGTGCCCCTGCGCCCCATGACCTACAAGGGCGCCCTGGACCTGTCCCACTTCCTGAAG
GAGAAGGGCGGCCTGGAGGGCCTGATCTACTCCAAGAAGCGCCAGGAGATCCTGGACCTGTGGGTGTACCACACCCAGGGCTACTTCCCCGA
CTGGCAGAACTACACCCCCGGCCCCGGCATCCGCTACCCCCTGACCTTCGGCTGGTGCTTCAAGCTGGTGCCCGTGGACCCCGAGGAGGTGG
AGAAGGCCAACGAGGGCGAGAACAACTGCCTGCTGCACCCCATGTCCCAGCACGGCATGGAGGACGAGGACCGCGAGGTGCTGATGTGGAAG
TTCGACTCCCGCCTGGCCCTGCGCCACATCGCCCGCGAGAAGCACCCCGAGTTCTACCAGGACTGCTAA

Fig. 106A

55. 2003_CON_14_BG_nef.PEP

MGGKWSKCSIVGWPEVRERIRRTPPAAVGVGAVSQDLAKHGAITSSNTAANNPDCAWLEAQEEDSEVGFPVRPQVPLRPMTYKGAFDLSFFL
KEKGGLDGLIYSKQRQDILDLWVYNTQGFFPDWQNYTPGPGTRYPLTFGWCFKLEPVDPAEVEEATKGENNSLLHPICQHGMEDADNEVLIW
RFDSSLARRHIARELHPDFYKDC$

Fig. 106B

2003_CON_14_BG_nef OPT

ATGGGCGGCAAGTGGTCCAAGTGCTCCATCGTGGGCTGGCCCGAGGTGCGCGAGCGCATCCGCCGCACCCCCGCCGCCGTGGGCGTGGG
CGCCGTGTCCCAGGACCTGGCCAAGCACGGCGCCATCACCTCCTCCAACACCGCCGCCAACAACCCCGACTGCGCCTGGCTGGAGGCCCAGG
AGGAGGACTCCGAGGTGGGCTTCCCCGTGCGCCCCCAGGTGCCCCTGCGCCCCATGACCTACAAGGGCGCCTTCGACCTGTCCTTCTTCCTG
AAGGAGAAGGGCGGCCTGGACGGCCTGATCTACTCCAAGCAGCGCCAGGACATCCTGGACCTGTGGGTGTACAACACCCAGGGCTTCTTCCC
CGACTGGCAGAACTACACCCCCGGCCCCGGCACCCGCTACCCCCTGCTGACCTTCGGCTGGTGCTTCAAGCTGGAGCCCGTGGACCCCGCCGAGG
TGGAGGAGGCCACCAAGGGCGAGAACAACTCCCTGCTGCACCCCATCTGCCAGCACGGCATGGAGGACGCCGACAACGAGGTGCTGATCTGG
CGCTTCGACTCCTCCCTGGCCCGCCGCCACATCGCCCGCGAGCTGCACCCCGACTTCTACAAGGACTGCTAA

Fig. 107A

61 2003_2003_CON_S_pol_PEP

FFRENLAFQQGEAREFSSEQTRANSPTSRELRVRGGDNPLSEAGAERQGTVSLSFPQITLWQRPLVTVKIGGQLKEALLDTGADDTVLEEIN
LPGKWKPKMIGGIGGFIKVRQYDQILIEICGKKAIGTVLVGPTPVNIIGRNMLTQIGCTLNFPISPIETVPVKLKPGMDGPKVKQWPLTEEK
IKALTEICTEMEKEGKISKIGPENPYNTPIFAIKKKDSTKWRKLVDFRELNKRTQDFWEVQLGIPHPAGLKKKSVTVLDVGDAYFSVPLDE
DFRKYTAFTIPSINNETPGIRYQYNVLPQGWKGSPAIFQSSMTKILEPFRTQNPEIVIYQYMDDLYVGSDLEIGQHRTKIEELRELLRWGF
TTPDKKHQKEPPFLWMGYELHPDKWTVQPIQLPEKDSWTVNDIQKLVGKLNWASQIYPGIKVKQLCKLLRGAKALTDIVPLTEEAELELAEN
REILKEPVHGVYYDPSKDLIAEIQKQGQDQWTYQIYQEPFKNLKTGKYAKMRSAHTNDVKQLTEAVQKIATESIVIWGKTPKFRLPIQKETW
ETWWTEYWQATWIPEWEFVNTPPLVKLWYQLEKEPIVGAETFYVDGAANRETKLGKAGYVTDRGRQKVVSLTETTNQKTELQAIHLALQDSG
SEVNIVTDSQYALGIIQAQPDKSESELVNQIIEQLIKKEKVYLSWVPAHKGIGGNEQVDKLVSTGIRKVLFLDGIDKAQEEHEKYHSNWRAM
ASDFNLPPIVAKEIVASCDKCQLKGEAMHGQVDCSPGIWQLDCTHLEGKIILVAVHVASGYIEAEVIPAETGQETAYFILKLAGRWPVKVIH
TDNGSNFTSAAVKAACWWAGIQQEFGIPYNPQSQGVVESMNKELKKIIGQVRDQAEHLKTAVQMAVFIHNFKRKGGIGGYSAGERIIDIIAT
DIQTKELQKQITKIQNFRVYYRDSRDPIWKGPAKLLWKGEGAVVIQDNSEIKVVPRRKAKIIRDYGKQMAGDDCVAGRQDED$

Fig. 107B

2003_CON_s_pol.OPT
TTCTTCCGCGAGAACCTGGCCTTCCAGCAGGGCGAGGCCCGAGTTCTCCTCCGAGCAGACCCGCGCCAACTCCCCCACCTCCCCGAGCAGACCCGCGAGCTGCGCCGTGCG
CGGCGGGGACAACCCCGTCGCCAGCTGAAGGAGCCCGAGGGCGCCGGGCCTGGACACCGGCCGACGACACCGTGTCCTCCTTCCCCAGATCACCTGTGGCCCCCCTGGTGACCG
TGAAGATCGGCGGGCCCGAGCTGCGCGGCTTCATCAAGCTGGCGCCCAGATCCCGTGGAGACTGCGCAACTATGATCGAGCTGATCGACCGTGCTGTGGGCCCAC
ATCGCGGCATCGACATCATCGGCCGCAACATGGTGGCCCCCAAGGTGAAGCAGCAGTGGCCCCTGACCGAGAAGATCAAGCCCCTGACCGAGATGTGGAGAGGCAAGATCTCC
GCATGGACGGCCCCCAAGGTGAAGCAGCAGTGGCCCCTGACCGAGAAGATCAAGCCCCTGACCGAGATGTGGAGAGGCAAGATCTCC
AAGATCGGCCCCGAGAACCCCTACAACACCCCATCTTCGCCATCAAGAAGGACTCCACGGTGGCGAAGTCCGTCGTGCTGGGCGACGCCTACT
GCGCACCCAGGACTTCTGGGAGGTGCAGCTCCGCGAAGTACAACGCCCTTCCACCATCCCCTCCACCATGAGATCTGGACCTACCCCCGAGAACCCAACGCCATCCGAGATCTGCACCCTG
CCCCAGGGCTGGAAGGGCTCCCCCGGCCATCTTCCAGTGCCTCCGCCAAAGGATCGCCGTGAAGTTCCGCAAGCAGAACCCCGAGATGGGCGAGAGTCTGGAGGAGCCCTCAGCCTCCCCGAGAAGGAC
CATGACGACCTGTACGTGGGCTCTGTGGGCCACCCAGAAGACACCCAAGAAGCAACCAGATCCAGGCCTCCAAGATCTGGAGGACATGGACGAGCTGACCGGCCAGAGCTGCCGCCCTCCCCCCCTGTCCCCCTCTGCCCCGAGAAGGACTGCCGTGAAGTCCGAGGAGCGCCCCTGGACCCCTGCCCTGTGTTTCCT
TCCTGGACCGTGAACGACATCCAGAAGCTGGTGGGCCCCTGACCTGGCGGCCAAGCTGAACTGACCCCGAGAACCTGGAGCTGGAAGTGCGGGCCCCTGCAAGCTGCG
CGGCGCCAAGGCCCTGAAGGCCGCCTGAACATCCAGGACCCAGATCGATCCGCCGACATCAACAGATCCAGCCCTGGACCCAGATGCCAAGATCCTGCCCTTTCAAGAACCCTGAAGACC
ACTACGACCCCCTCCAAGGACATCGATCCGCCCTGCCCAGCGTGAAGCGTGGGAGACGAGAGCCCGAGCGGTGAACAGCGCCACGAGCTGATCGTGGGCCAA
GGCAAGTACGCCAAGATGCCTCCCGCCAAGTTCCGCAAGGCCGACACCGAGAGGCGAGCAGCCCCTGGATCCCCGATCGCTGGCGCCCAACCGAGACCAAGCTG
GACCCAAGTTCGCCTGCCAAGTCGGTGGTACCAGCTGTGGTACCAGCGCGCCGAGATCGGCGCCAACCGCCGAGACCAAGCTG
CCCCCCTGTGAAGCTGGACGTGCTACAGCTGTGTGGGGCCGCCGAGAGAGGAGCCCACCAACCAGAGCACCTGCAGGCCATGCGAGCTGCAGGCCATCCACCTGGCCCT
GCAAGGCCGGCTACGTGAGCCGAGGCCATCGAGCTGTCCCCTGACCGAAGAACCAGCCCCGCCGCCCCTGGGCCTGGCCGAAGATCAAGCCTGGGCCCCTGTCC
GCAGGACTCCGGCTTCCAGAGTGAACATCGTGACCGACTCCCAGTACGCCCTGGGCATCATCCAGGCGGGCCCCGATCGAGAGCCAGTACGCCCTGGGTGAACC
AGATCATCGAGCAGCTGATCAAGAAGGAGAAGGTGTACCTGGCCTGGCATCCGCCCCCACAAGGGCATCGGTGAAGGGCCAGTCAGATGGACAAGCTGGTGTCC
CCTGCCCCCATCGTGCCAAGGAGATCGTGGCCTCCGCCCCAAGGATCGGCCAAGGGGCTGGACAAGCTGATCAAGCTGGTGTCC
GCCGTCTGGACCTGGCCAAGGAGATCGTGGCCTCCGTGCAAGGTGCCCGTGAAGATGGCCGTGCGAGCGTTCATCCAAAACCCCACCACCCTGAACCCCTGCGACTTCAA
CAGGAGACCGACCCTGCACCCCCTACTTCGGCCCGAGATCCGGAGGGCAAGATCCTGGACGTGTGGCCCCGTGGCCAAGTGCCCGTGAAGGTGAAGCTGAACGTGGACTACCGCTGCTCCCCGATCT
GGCCAAGGTGCGGCTGGCAAGGAGATCGTGGCCTCCGTGAAGGGCCGTGGACTGCCAAGGACTGCCTGGACATGGCCGTGAAGGGCAAGCTGGCCGTGAAGTCCGGCCATCTCCCCGGCATCT
GGCCAAGGCTGGAGTGCACCACCACCTCCGATGCCAAGTGCCGGCCAGTGGACTGCTCCCCCGCGAGACCGGC
CAGGAGACCGACCCTGCACCCCAACTCACCCAGTCCCGGCGTGGTGAGTCATGAACAACCCCAGTCCATGAACCGGCGTGGTGAGTCATGAACAACCCCAGTCCATGAACGCGGCTACTCC
CGGCCAGGTGCGGCCGACCAGCCAGATCGCCACCCTGAAGACCCCGTGCAGATGGCCGTGTTCATCCACCAGATCCGGCCGTGAAGCTGAACGTGCTGAAGTCCGGCCTACTCC
GCCGCCGAGCCGCTACTTCATCGATCGACATCCGGCCATGACCAAGCGCCAAGGACTGCCGTGCTGGTGATCCAGGACCAACTCCGAGATCAAGCCCCGCGCCCCGCC
CTCCCCGGCTCCGGCCAAGCTTCCGAGAAGGCCTGCCCCCCGAGCGGCCCCCCGGAGAAGGGCGACGACTGCCGTGGCCGGCCGACGAGGACGAGGACGAGGACTAA

*Fig. 108A*

62  2003_M_GROUP_anc_pol.PEP
FFRENLAFQQGEAREFSSEQTRANSPTSRELRVRGGDNPLSEAGAERQGTVSFSFPQITLWQRPLVTIKIGGQLREALLDTGADDTVLEEIN
LPGKWKPKMIGGIGGFIKVRQYDQILIEICGKKAIGTVLVGPTPVNIIGRNMLTQIGCTLNFPISPIETVPVKLKPGMDGPKVKQWPLTEEK
IKALTEICTEMEKEGKISKIGPENPYNTPVFAIKKKDSTKWRKLVDFRELNKRTQDFWEVQLGIPHPAGLKKKKSVTVLDVGDAYFSVPLDE
DFRKYTAFTIPSINNETPGIRYQYNVLPQGWKGSPAIFQSSMTKILEPFRTKNPEIVIYQYMDDLYVGSDLEIGQHRAKIEELREHLLRWGF
TTPDKKHQKEPPFLWMGYELHPDKWTVQPIQLPEKDSWTVNDIQKLVGKLNWASQIYPGIKVKQLCKLLRGAKALTDIVPLTEEAELELAEN
REILKEPVHGVYYDPSKDLIAEIQKQGQDQWTYQIYQEPFKNLKTGKYAKMRSAHTNDVKQLTEAVQKIATESIVIWGKTPKFRLPIQKETW
ETWWTEYWQATWIPEWEFVNTPPLVKLWYQLEKEPIVGAETFYVDGAANRETKLGKAGYVTDRGRQKVVSLTETTNQKTELQAIHLALQDSG
SEVNIVTDSQYALGIIQAQPDKSESELVNQIIEQLIKKEKVYLSWVPAHKGIGGNEQVDKLVSSGIRKVLFLDGIDKAQEEHEKYHSNWRAM
ASDFNLPPVVAKEIVASCDKCQLKGEAMHGQVDCSPGIWQLDCTHLEGKVILVAVHVASGYIEAEVIPAETGQETAYFILKLAGRWPVKVIH
TDNGSNFTSAAVKAACWWAGIQQEFGIPYNPQSQGVVESMNKELKKIIGQVRDQAEHLKTAVQMAVFIHNFKRKGGIGGYSAGERIIDIIAT
DIQTKELQKQITKIQNFRVYYRDSRDPIWKGPAKLLWKGEGAVVIQDNSEIKVVPRRKAKIIRDYGKQMAGDDCVAGRQDED$

*Fig. 109A*

63. 2003_CON_A1_pol.PEP
FFRENLAFQQGEARKFSSEQTGANSPTSRDLWDGGRDSLPSEAGAERQGTGPTFSFPQITLWQRPLVTVRIGGQLKEALLDTGADDTVLEDI
NLPGKWKPKMIGGIGGFIKVRQYDQILIEICGKKAIGTVLVGPTPVNIIGRNMLTQIGCTLNFPISPIETVPVKLKPGMDGPKVKQWPLTEE
KIKALTEICTEMEKEGKISKIGPENPYNTPIFAIKKKDSTKWRKLVDFRELNKRTQDFWEVQLGIPHPAGLKKKKSVTVLDVGDAYFSVPLD
ESFRKYTAFTIPSTNNETPGIRYQYNVLPQGWKGSPAIFQSSMTKILEPFRSKNPEIIIYQYMDDLYVGSDLEIGQHRTKIEELRAHLLSWG
FTTPDKKHQKEPPFLWMGYELHPDKWTVQPIELPEKESWTVNDIQKLVGKLNWASQIYAGIKVKQLCKLLRGAKALTDIVTLTEEAELELAE
NREILKDPVHGVYYDPSKDLIAEIQKQGQDQWTYQIYQEPFKNLKTGKYARKRSAHTNDVKQLAEVVQKVMESIVIWGKTPKFKLPIQKET
WETWWMDYWQATWIPEWEFVNTPPLVKLWYQLEKDPIVGAETFYVDGAANRETKLGKAGYVTDRGRQKVVSLTETTNQKTELHAIHLALQDS
GSEVNIVTDSQYALGIIQAQPDRSESELVNQIIEKLIGKDKVYLSWVPAHKGIGGNEQVDKLVSSGIRKVLFLDGIDKAQEEHERYHSNWRA
MASDFNLPPIVAKEIVASCDKCQLKGEAMHGQVDCSPGIWQLDCTHLEGKVILVAVHVASGYIEAEVIPAETGQETAYFLLKLAGRWPVKVV
HTDNGSNFTSAAVKAACWWANIQQEFGIPYNPQSQGVVESMNKELKKIIGQVREQAEHLKTAVQMAVFIHNFKRKGGIGGYSAGERIIDIIA
TDIQTKELQKQITKIQNFRVYRDSRDPTWKGPAKLLWKGEGAVVIQDNSDIKVVPRRKAKIIRDYGKQMAGDDCVAGRQDED$

Fig. 108B

```
2003_M.GROUP anc pol.OPT
TTCTTCCGCGAGAACCTGGCCTTCCAGCAGGGCGAGGCCGAGTTCTCCTCCGAGCAGACCCGCGCCAACTCCCCCACCTCCCCGAGCTGCCGGTGCG
CGGCGGCGACAACCCCGTCGCCGGCCCAGGCCGCGAGCCGGGCGCCGAGCGGCCGTGTCCTTCCTTCCCCAGATCACCCTGTGCCAGCCGCCCCTGGTGACCA
TCAAGATCGGGCGGCCAGCTGCGCGAGGCCCTGCTGGACGACCAGTACGAGATCCTGGAGGAGATCCTGCCCGGCAGTGGAAGCCAAGATG
ATCGGGGCATCGGCGGCTTCATCAAGGTGCGCCAACATGGCTGACCGAGGAGAAGATCAAGGCCCTGACCGAGATCTGCACCGAGATGGAGAAGGAGGGCAAGATCTCC
CCCGTGAACATCATGGCCCCCAAGGTGAACCCCTACAACACCCCGTGTTGCGCATCAAGAAGGACTCCAAGTGGCGAAGCTGGTGGACTTCCGGACTGAACAA
AAGATCGGCCCCGAGACTTCTGGGAGGACTTCCCCGTCCCTGCGCAAGTGCAGACTTCCGGCCAGCTGCCCGCAAGTGCGAACCCCGGCATCCGCTACCAGTGCTG
GCGCACCCAGGAGCTTCTGGGAGGACTTCCCCGTCCCTGCGCAAGTGCAGACTTCCGGCCAGCTGCCCGCAAGTGCGAACCCCGGCATCCGCTACCAGTGCTG
TCTCCGTGCCCCTGCGCGAGAGGGCTCCCCGCCAAGTACACCCTTCCAGGCCATCTTCCAGATCTGGAGATCTGGAAGTCGCACCCCGAGATCGTGATCTACCAGTA
CCCCAGGGCTGAAGGCCTGTACGGTGGGCTCCCCGAGAAGAGCACCCAGAGATCTGGAGATCTGTGATCGCCCGAGATCGGACCTGCCCGAGAAGGAC
CATGGACGACCTGTACGTGGGCTCCGATGGGCTACGAGCCCAAGTGAACTGGTGTGGGCCCAAGTGGCCCTGAACCTGGTGCAACCAGAGATCTACCCGGAGATCGGTGCGC
TCCTGGACCCTGAACGACATCCAGAGAGCCCTGGGTGCCCGAGCTGGAACCTGTGTGCAAGCAGTGTGCCAAGCTGTGCCG
CGGCGCCAAGGCCCTGACCGACATCGTGCCCCTGACCGAGGAGGCCGAGCTGGAGCTGGAGCTGGCCGAGATCAGACCCGATCCCGAGACCAAGTCCACCTGCCCT
ACTACGACCCCTCCAAGGACCTGATCGCCGAGATCCAGAAGCAGGGCCAGGACCAGTGGACCTACCAGATCTACCAGGAGCCCTCAAGAACCTGAAGACC
GGCAAGTACGCCAAGATGCGCTCCGCCCACACCAACGACGTGCGCCAGCTGGCCGAAGTGCGTCTGGAGACTGGCAGAGGACTGGTGTCGTGAACA
GACCCCCAAGTTCCGCCTGCCCATCCAGAAGGAGACCTGGGAGACCTGGGAGACCTGGAGGCCTGGAGCGGCCACCAGGCCGGCCGAGCCGAGATGGAGACCAAGCTG
CCCCCCCCCGTGGTGGCCAAGGAGATCGTGGCCTCCTGTGACAAGTGCCAGCTGAAGGGCGAGGCCATGCACGGCCAGGTGGACTGCTCCCCCGGCATCT
GGCAGCTGGACTGCACCCACCTGGAGGGCAAGGTGATCCTGGTGGCCGTGCACGTGGCCGAGGCCATCGAAGTGGCCTCCCAATTCACCTCCGCCGAGGCC
CAGGAGAGCCGGCTACGTGGAGGTGAACATCGTGACCGACAGCCAGTACGCCCTGGGTATCCCTACCTGTAACAACCCCTGGCTGGAGGTCATGCCCTGAAGGC
CGCCCTGCTGTGGGCGACTACGGCCATCGGCAGGAGTTCGGCATCCCCTACAACCCCCAGGCCAGTCCATGCCCCGTGCAGGAGATCCGAGTCCATGCAGGAGA
TCGGCCAGGTGCGCGACCAGGCCGAGCACCTGAAGACCCGCCCTGGAAAGCAGATCCGAGAAGGGCATCCAGCCCGAAGTCAAGGGCGGCTACTCC
CTCCCCGCGAGATCATCGCCCGCGACTACGGCAAGCAGATGGCCGGCGATGACTGCGTGGCCGGCCGTGCAGATCTCCGAGATCCAAGATCACCACCGCGA
GCAAGGCCAAGATCATCCGCGACTACGGCAAGCAGATGGCCGGCGATGACTGCGTGGCCGGCCGTGCAGATCTCCGAGATCCAAGATCACCACCGCGA
GCAAGGCCAAGGCCTGCTGGCGACTACGGCGACGAGGACTAA
```

*Fig. 109B*

2003_CON_A1 pol.OPT

TTCTTCCGCGAGAACCTGGCCTTCCAGCAGGGCGAGGCCCGCAAGTTCTCCTCCGAGCAGACCGGCGCCAACTCCCCCACCTCCCGCGACCTGTGGGACGG
CGGCCGCGACTCCCTGCCCTCCGAGGCCGGCGCCGAGCGCCAGGGCACCGGCCCCACCTTCTCCTTCCCCCAGATCACCCTGTGGCAGCGCCCCCTGGTGA
CCGTGCGCATCGGCGGCCAGCTGAAGGAGGCCCTGCTGGACACCGGCGCCGACGACACCGTGCTGGAGGACATCAACCTGCCCGGCAAGTGGAAGCCCAAG
ATGATCGGCGGCATCGGCGGCTTCATCAAGGTGAAGCAGTACGACCAGATCCTGATCGAGATCTGCGGCAAGAAGGCCATCGGCACCGTGCTGGTGGGCCC
CACCCCCGTGAACATCATCGGCCGCAACATGCTGACCCAGATCGGCTGCACCCTGAACTTCCCCATCTCCCCCATCGAGACCGTGCCCGTGAAGCTGAAGC
CCGGCATGGACGGCCCCAAGGTGAAGCAGTGGCCCCTGACCGAGGAGAAGATCAAGGCCCTGACCGAGATCTGCACCGAGATGGAGAAGGAGGGCAAGATC
TCCAAGATCGGCCCCGAGAACCCCTACAACACCCCCATCTTCGCCATCAAGAAGAAGGACTCCACCAAGTGGCGCAAGCTGGTGGACTTCCGCGAGCTGAA
CAAGCGCACCCAGGACTTCTGGGAGGTGCAGCTGGGCATCCCCCACCCCGCCGGCCTGAAGAAGAAGAAGTCCGTGACCGTGCTGGACGTGGGCGACGCCT
ACTTCTCCGTGCCCCTGGACGAGTCCTTCCGCAAGTACACCGCCTTCACCATCCCCTCCACCAACAACGAGACCCCCGGCATCCGCTACCAGTACAACGTG
CTGCCCCAGGGCTGGAAGGGCTCCCCCGCCATCTTCCAGTCCTCCATGACCAAGATCCTGGAGCCCTTCCGCTCCAAGAACCCCGAGATCATCATCTACCA
GTACATGGACGACCTGTACGTGGGCTCCGACCTGGAGATCGGCCAGCACCGCACCAAGATCGAGGAGCTGCGCGCCCACCTGCTGTCCTGGGGCTTCACCA
CCCCCGACAAGAAGCACCAGAAGGAGCCCCCCTTCCTGTGGATGGGCTACGAGCTGCACCCCGACAAGTGGACCGTGCAGCCCATCGAGCTGCCCGAGAAG
GAGTCCTGGACCGTGAACGACATCCAGAAGCTGGTGGGCAAGCTGAACTGGGCCTCCCAGATCTACGCCGGCATCAAGGTGAAGCAGCTGTGCAAGCTGCT
GCGCGGCGCCAAGGCCCTGACCGACATCGTGACCCTGACCGAGGAGGCCGAGCTGGAGCTGGCCGAGAACCGCGAGATCCTGAAGGACCCCGTGCACGGCG
TGTACTACGACCCCTCCAAGGACCTGATCGCCGAGATCCAGAAGCAGGGCCAGGACCAGTGGACCTACCAGATCTACCAGGAGCCCTTCAAGAACCTGAAG
ACCGGCAAGTACGCCCGCAAGCGCTCCGCCCACACCAACGACGTGAAGCAGCTGGCCGAGGTGGTGCAGAAGGTGGTGATGGAGTCCATCGTGATCTGGGG
CAAGACCCCCAAGTTCAAGCTGCCCATCCAGAAGGAGACCTGGGAGACCTGGTGGATGGACTACTGGCAGGCCACCTGGATCCCCGAGTGGGAGTTCGTGA
ACACCCCCCCCCTGGTGAAGCTGTGGTACCAGCTGGAGAAGGACCCCATCGTGGGCGCCGAGACCTTCTACGTGGACGGCGCCGCCAACCGCGAGACCAAG
CTGGGCAAGGCCGGCTACGTGACCGACCGCGGCCGCCAGAAGGTGGTGTCCCTGACCGAGACCACCAACCAGAAGACCGAGCTGCACGCCATCCACCTGGC
CCTGCAGGACTCCGGCTCCGAGGTGAACATCGTGACCGACTCCCAGTACGCCCTGGGCATCATCCAGGCCCAGCCCGACCGCTCCGAGTCCGAGCTGGTGA
ACCAGATCATCGAGAAGCTGATCGGCAAGGACAAGGTGTACCTGTCCTGGGTGCCCGCCCACAAGGGCATCGGCGGCAACGAGCAGGTGGACAAGCTGGTG
TCCTCCGGCATCCGCAAGGTGCTGTTCCTGGACGGCATCGACAAGGCCCAGGAGGAGCACGAGCGCTACCACTCCAACTGGCGCGCCATGGCCTCCGACTT
CAACCTGCCCCCCATCGTGGCCAAGGAGATCGTGGCCTCCTGCGACAAGTGCCAGCTGAAGGGCGAGGCCATGCACGGCCAGGTGGACTGCTCCCCCGGCA
TCTGGCAGCTGGACTGCACCCACCTGGAGGGCAAGGTGATCCTGGTGGCCGTGCACGTGGCCTCCGGCTACATCGAGGCCGAGGTGATCCCCGCCGAGACC
GGCCAGGAGACCGCCTACTTCCTGCTGAAGCTGGCCGGCCGCTGGCCCGTGAAGGTGGTGCACACCGACAACGGCTCCAACTTCACCTCCGCCGCCGTGAA
GGCCGCCTGCTGGTGGGCCAACATCCAGCAGGAGTTCGGCATCCCCTACAACCCCCAGTCCCAGGGCGTGGTGGAGTCCATGAACAAGGAGCTGAAGAAGA
TCATCGGCCAGGTGCGCGAGCAGGCCGAGCACCTGAAGACCGCCGTGCAGATGGCCGTGTTCATCCACAACTTCAAGCGCAAGGGCGGCATCGGCGGCTAC
TCCGCCGGCGAGCGCATCATCGACATCATCGCCACCGACATCCAGACCAAGGAGCTGCAGAAGCAGATCACCAAGATCCAGAACTTCCGCGTGTACTACCG
CGACTCCCGCGACCCCATCTGGAAGGGCCCCGCCAAGCTGCTGTGGAAGGGCGAGGGCGCCGTGGTGATCCAGGACAACTCCGACATCAAGGTGGTGCCCC
GCCGCAAGGCCAAGATCATCCGCGACTACGGCAAGCAGATGGCCGGCGACGACTGCGTGGCCGGCCGCCAGGACGAGGACTAA

Fig. 109C

64. 2003_A1.anc_pol.PEP

FFRENLAFQQGEARKFSSEQTRANSPTSRELWDGGRDSLLSEAGAERQGTVPSFSFPQITLWQRPLVTVKIGGQLKEALLDTGADDTVLEDI
NLPGKWKPKMIGGIGGFIKVRQYDQILIEICGKKAIGTVLVGPTPVNIIGRNMLTQIGCTLNFPISPIETVPVKLKPGMDGPKVKQWPLTEE
KIKALTEICTEMEREGKISKIGPENPYNTPVFAIKKKDSTKWRKLVDFRELNKRTQDFWEVQLGIPHPAGLKKKKSVTVLDVGDAYFSVPLD
ESFRKYTAFTIPSINNETPGIRYQYNVLPQGWKGSPAIFQSSMTKILEPFRSKNPEIVIYQYMDDLYVGSDLEIGQHRAKIEELRAHLLSWG
FTTPDKKHQKEPPFLWMGYELHPDKWTVQPIKLPEKDSWTVNDIQKLVGKLNWASQIYAGIKVKQLCKLLRGAKALTDIVTLTEEAELELAE
NREILKDPVHGVYYDPSKDLVAEIQKQGQDQWTYQIYQEFFKNLKTGKYAKKRSAHTNDVKQLTEVVQKVATESIVIWGKTPKFRLPIQKET
WETWWMEYWQATWIPEWEFVNTPPLVKLWYQLEKEPIAGAETFYVDGAANRETKLGKAGYVTDRGRQKVVSLTETTNQKTELHAIHLALQDS
GSEVNIVTDSQYALGIIQAQPDRSESELVNQIIEKLIEKEKVYLSWVPAHKGIGGNEQVDKLVSSGIRKVLFLDGIDKAQEEHEKYHSNWRA
MASDFNLPPIVAKEIVASCDKCQLKGEAMHGQVDCSPGIWQLDCTHLEGKVILVAVHVASGYIEAEVIPAETGQETAYFLLKLAGRWPVKVV
HTDNGSNFTSAAVKAACWWANIQQEFGIPYNPQSQVVESMNKELKKIIGQVREQAEHLKTAVQMAVFIHNFKRKGGIGGYSAGERIIDIIA
TDIQTKELQKQITKIQNFRVYYRDSDIKVVPRRKAKIIRDYGKQMAGDDCVAGRQDED$

Fig. 109D

```
2003_A1.anc_pol.OPT
TTCTTCCCGGAGAACCTGGCCTTCCAGCAGGGCGAGGCCCGCAGGGCCCGGCCAGGACCCGGCGGAGGCCCGAGCGGCCGGAGCAGACCCGGCGCCCAACTCCCCCACCTCCCGCGAGCTGTGGGACGG
CGGCGGACTCCCTGCTGTCCCAGCTGTCCCGAGCCCGGCGCGCCGAGCGCCAGGCACCGGCCGGTGGACATCAACCTGCCCGGCAAGTGGAAGCCCAAG
CCGTGAAGATCGGCGGCCAGCTGAAGGAGGCCCTGCTGTGGAGGACATCTGCGACCAGATCCTGATCGAGACTCCTGAGACTTCCCCATCGACGACCGTGCCCGTGCTGGTGGTGCCC
ATGATCGGCGGCCTGAAACATCGGCGCCAACATGTCGGCTGCAGATCGGCTGCGAGAGAGATCGGCCTGCTGCCCATCTCCCATCTGAAACTTCCCCATCGAGACCGTGCTGCCCGTGAAGCTGAAGC
CACCCCCGTGACGGCCCCAAGGTGAAGCAGTGGCCCCTGACCGGAGAGAGATCAAGGCCCTGACCGGAGATCTGCACCGAGGACTCGCACCGAGCTGGTGCTGGTGCTGCCCAAGCTTCCGCGAGCTGAAGC
TCCAAGATCGGCCCGAGAATCGGCCTGTTCGCTGAAGACTCCAACCCCGTGTTCGCCAAGAAGAAGGACTCCAAGAAGAAGGACTCCGAAGAGAAGAAGCCTGCCCAAGGTGGTGACTTCCGACGTGAA
CAAGGCGCACCCAGGACTTCTGGACGAGTCCTTCGGACAAGTACACCGCCCTTCACCACGCGATCCCCAAGATCCTGGAGCCTTCCGAGCTGCTACCAGTACAACGTG
ACTTCTCCGTGCCCCTGCCAGTGGGAAGGGCTCCGCCATCTTCCAGCTCGACCTGGAGATCGGCCAAGATGCGGCGACCACCGCCTGCTGCCCACCGTGTCCTGGGCTTCACCA
GTACATGGACGACCTGTACGTGGCCTCTGGATGGGCCAAGTGGGCAAGAGGCCATGGAAGTCCCAGCTGGAAAGTCCCCAGATCTACGCCCGAGAACTGGGCGAGAACGCTGGTGCAAGCAGCTGCT
CCCCCCGACAAGAAGCACCAGAAGGAGCCCCCGCCGGTGGCGAGTCCATCAAGGACTGGGAACCGGCAGCGCCCCTGGCCAGTCCAGCGCGCCCATCAAGGTGACACCTGAGAAGTCCTGAAGGATCTGCT
GACTCCTGGACCGTGAAGGACGGCCAAGGCCCTGACCGTTGTGAACCTGTGCGGGGCCCAGCTGGCGCGAGAGATCCGGCCAGCGCGCACCCGAGAACCGGCAGCGCCCAAGGACTGCTGTGCACGGCG
TGTACTACGACCCCCTCCAAGGACCTCCAAGGACCGGGCCCGAGATCTACCCGGAGCTGGTGGGACCAGTCCAGTCCAGTGGACCGGAGCCCCTTTCAAGAACCTGAAGG
ACCGGCAAGTACGCCAAGAAGCCTCCGCCACCAGAGCGCTGACCGCTGAAGCAGTGGTGCAGCAGCGACCTGGTTGGGAGCCTGGATGGAGTACTGGCCAGGCCACCTGGATCCCGAGTGGAGTTCGTGA
CAAGACCCCCAAGTTCCGCCTGCCCATCCGTGCCGAGCTGCGTCCGGGACCTTCTACGTGGACGGCGCCGCCAACCGGGAGACCAAG
ACACCCCCTCCTGGTGAAGCTACGGTGACCAGCGGCGGCCCAGATGTGTCCCTGACCGTGTCCCAGTACCGCCCTGGGCATCATCCGCCCCAAGGGCATCGGCGGCAACTGGCCATCGGCGACTGGCCGGCAACTGGCCATCGGCGACTGGCC
CTGGGCAAGGCTGGACTTCCGGCTCCCGAGGTGAACATCGTGACCGACAGTTCCGAGGACAGCCAGTACTTCCACCGGCTCCGGATCAGGAAGACCCCGAGCGCTCCGAGTCCAGCTGGTGA
CCAGATCATCGAGAAGCTGATCGAGAAGGAGAAGGTGTACCTGTCCTGGGTGCCGCCGAAGGAGCATCGGCGGCAACGAGCAGTGGACAAGCTGTG
TCCTCCGGCATCCGCGAGGTGCTGTTCCTGACGAAGCGAACGAACCACGAAGAAGTACCACTCGAAGGCCGACGAGAAGAAGCCGAGCCCATGGCCTCCGACTT
CAACCTGCCCCATCGTGCCAAGATCGCTGCCCTGCCGACAAGTCGTGGCCTCCGAGGCCCAGCTGAAGGCCGAGGTGACTGCTGCTCCCCGGCA
TCTGGCAGCTGGACTGGCACCCACTGTCGACTGGAGGACAAGGTCAAGGTCAAGGCCGACAAGGCCGGCGCCCAAGGAGGCGACCCCAAGGGGCAAGGTGATCCCCGAGACC
GGCAGGAGACGGCCTACTTCCTGCTGAAGCTGGCCGGCAGGTGGCAACTTCCGGGCCGACCGCGAGGCCGCTCCAACTTCACCTTCCGCCGCCGTGAA
GGCGCCCTGGTGGGCGAGATCAGCGAGTTCGGCAAGGAGAAGAGCCGCATCCCCTACAACCCCGTCATCCCAGTCCGAGTCCTGCATCCCCATGAACGCCGTGGTCCGATCCCCGGGGCCGGCGAGAAGA
TCATCGGCCGCGAGGTGCCGAGCAGGCCGAGCACTCGGCCGTGTTCATCCACAACGATCGAGATGGCCGTGACCAGGACCGCCGGATCCAAGGGCCGACCTGAACGTCGGCGTAC
TCCGCCGGCAGGTGGACACCATCATGCCGACATCATCGCGCAAGATCCTGCTGGCCGTCTGGGAAGGGCCCCAAGGGCAGCTGTGTGGGAAGGGCGATGGCCCAAGGGAAGCCCGACACTGGTGCCCC
GCCCGCAAGGCCGACATCATCCGCGACTACGGCGACCGGCAAGCAGCTGCTGCCGGCGTGCTGCCGGCAAGTGGTGGGACTAA
```

Fig. 110A 65. 2003_CON_A2_pol.PEP

FFRENLAFQQREARKFSSEQNRANSPTSRELRNGGRDNLLSEAGAEEQGTVHSCNFPQITLWQRPLVTVKIEGQLREALLDTGADDTVLEDI
NLPGKWKPKMIGGIGGFIKVRQYDQIAIEICGKRAIGTVLVGPTPVNIIGRNMLVQLGCTLNFPISPIETVPVKLKPGMDGPKVKQWPLTEE
KIKALTEICKEMEKEGKISKIGPENPYNTPVFAIKKKDSTKWRKLVDFRELNKRTQDFWEVQLGIPHPAGLKKKKSVTVLDVGDAYFSVPLH
EDFRKYTAFTIPSINNETPGIRYQYNVLPQGWKGSPAIFQSSMTKILEPFRSKNPEMVIYQYMDDLYVGSDLEIGQHRAKIEELRAHLLRWG
FTTPDKKHQKEPPFLWMGYELHPDKWTVQPIKLPEKDSWTVNDIQKLVGKLNWASQIYAGIKVKQLCKLLRGTKALTDIVTLTKEAELELEE
NREILKNPVHGVYYDPSKDLIAEIQKQGQDWTYQIYQEPFKNLKTGKYAKRKSTHTNDVKQLTEAVQKIAIESIVIWGKTPKFRLPIQKET
WETWWTEYWQATWIPEWEFVNTPPLVKLWYQLETEPIAGAETFYVDGAANRETKLGKAGYVTDRGRQKIVSLTETTNQKTELHAIYLALQDS
GLEVNIVTDSQYALGIIQAQPDRSESELVNQIIEKLIEKERVYLSWVPAHKGIGGNEQVDKLVSSGIRKVLFLDGIDKAQEEHERYHSNWRA
MAHDFNLPPIVAKEIVASCDKCQLKGEAMHGQVDCSPGIWQLDCTHLEGKVILVAVHVASGYIEAEVIPAETGQETAYFILKLAGRWPVKVI
HTDNGPNFTSATVKAACWWAGVQQEFGIPYNPQSQGVVESMNKELKKIIGQVRDQAEHLKTAVQMAVFIHNFKRKGGIGGYSAGERIIDIIA
TDIQTKELQKQIIKIQNFRVYYRDSRDPIWKGPAKLLWKGEGAVVIQDNSDIKVVPRRKAKIIRDYGKQMAGDDCVAGRQDED$

Fig. 111A 66. 2003_CON_B_pol.PEP

FFREDLAFPQGKAREFSSEQTRANSPTRRELQVWGRDNNSLSEAGADRQGTVSFSFPQITLWQRPLVTIKIGGQLKEALLDTGADDTVLEEM
NLPGRWKPKMIGGIGGFIKVRQYDQILIEICGHKAIGTVLVGPTPVNIIGRNLLTQIGCTLNFPISPIETVPVKLKPGMDGPKVKQWPLTEE
KIKALVEICTEMEKEGKISKIGPENPYNTPVFAIKKKDSTKWRKLVDFRELNKRTQDFWEVQLGIPHPAGLKKKKSVTVLDVGDAYFSVPLD
KDFRKYTAFTIPSINNETPGIRYQYNVLPQGWKGSPAIFQSSMTKILEPFRKQNPDIVIYQYMDDLYVGSDLEIGQHRTKIEELRQHLLRWG
FTTPDKKHQKEPPFLWMGYELHPDKWTVQPIVLPEKDSWTVNDIQKLVGKLNWASQIYAGIKVKQLCKLLRGTKALTEVIPLTEEAELELAE
NREILKEPVHGVYYDPSKDLIAEIQKQGQGQWTYQIYQEPFKNLKTGKYARMRGAHTNDVKQLTEAVQKIATESIVIWGKTPKFKLPIQKET
WEAWWTEYWQATWIPEWEFVNTPPLVKLWYQLEKEPIVGAETFYVDGAANRETKLGKAGYVTDRGRQKVVSLTDTTNQKTELQAIHLALQDS
GLEVNIVTDSQYALGIIQAQPDKSESELVSQIIEQLIKKEKVYLAWVPAHKGIGGNEQVDKLVSAGIRKVLFLDGIDKAQEEHEKYHSNWRA
MASDFNLPPVVAKEIVASCDKCQLKGEAMHGQVDCSPGIWQLDCTHLEGKIILVAVHVASGYIEAEVIPAETGQETAYFLLKLAGRWPVKTI
HTDNGSNFTSTTVKAACWWAGIKQEFGIPYNPQSQGVVESMNKELKKIIGQVRDQAEHLKTAVQMAVFIHNFKRKGGIGGYSAGERIVDIIA
TDIQTKELQKQITKIQNFRVYYRDSRDPLWKGPAKLLWKGEGAVVIQDNSDIKVVPRRKAKIIRDYGKQMAGDDCVASRQDED$

Fig. 110B

```
2003_CON_A2 pol.OPT
TTCTTCCGCGAGAACCTGGCCTTCCAGCAGCGGCGAGGCCCGGCAACGTTCTCCTCCGAGCAGAACCGGCCAACTCCCCACCTTCCTCCGAGCTGCCGAACGG
CGGCGGCGACAACCTGCTGTCCGAGGCCGCGCGAGGAGCCGGAGAGCCCGGAGGGCCGCACTCCTGCACTCCCCAGATCACCCTGTGCAGCGCCCCTGTGA
CCGTGAAGATCGAGGGCCAGCTGCGCGGACCCCTGCTCCTGGACACCGGCCCGACCCCCGAGATCGCCGACATCAACCTGCCCGGCAAGTGGAAGCCCAAG
ATGATCGGCGGCATCGGCGGCTTCATCAAGGTGCGCCAGTACGACCAGATCCTGATCGAGATCTGCGGGCACAAGGCCATCGGCACCGTGCTGGTGGGCCC
CACCCCCGTGAACATCATCGGCCGCAACATGCTGACCCAGATCGGCTGCACCCTGAACTTCCCCATCTCCCCCATCGAGACCGTGCCCGTGAAGCTGAAGC
CGGGCATGGACGGCCCCAAGGTGAAGCAGTGGCCCCTGACCGAGGAAGATCAAGGCCCTGACCGAGATCTGCAAGGAGATGGAGAAGGAGGGCAAGATC
TCCAAGATCGGCCCCGAGAACCCCTACAACACCCCGTGTTCGCCATCAAGAAGAAGAAGGACTCCACCAAGTGGCGCAAGCTGGTGGACTTCCGCGAGCTGAA
CAAGCGCACCCAGGACTTCTGGGAGGTGCAGCTGGGCATCCCGCACCCCCGCGGCCTGAAGAAGAAGAAGTCCGTGACCGTGCTGGACGTGGGCGACGCCT
ACTTCTCCGTGCCCCTGGACGAGGACTTCCGCCAAGTACACCGCCTTCACCCATCCTTCCAGTCGACAACCTGGGAGCCCCTTCCAGATCCTCCCGGAGAACCCCGAGATGGTGATCTACCA
CTGCCCCAGGGCTGGAAGGGCTCCCCCGCCATCTTCCAGTCGGATGGGCAAGCTGGACCAGCTGCCCCCATCAAGCGCGCCAAGATCGAGGAGCTGCCCGAGAAG
GTACATGACGACCTGTACGTGGGCTCCGACCTGGAGATCGGCCAGCACCGGACCAAGATCGAGGAGCTGCGCCAGCACCTGCTGCGCTGGGGCCTGACCACC
CCCGACAAGAAGCACCAGAAGGAGCCCCCCTTCCTGTGGATGGGCTACGAGCTGCACCCCGACAAGTGGACCGTGCAGCCCATCGTGCTGCCCGAGAAG
GACTCCTGGACCGTGAACGACATCCAGAAGCTGGTGGCCAAGCTGAACTGGGCCTCGGAGATCTACCCCGGCATCAAGGTGAAGCAGCTGTGCAAGCTGCT
GCGCGGCACCAAGGCCCTGACCGACATCGTGACCCTGACCGAGGAGGCCGAGCTGGAGCTGGCCGAGAACCGCGAGATCCTGAAGGAACCCGTGCACGGCG
TGTACTACGACCCCTCCAAGGACCTGATCGCCGAGATCCAGAAGCAGGGCCAGGGCCAGTGGACCTACCAGATCTACCAGGAGCCCTTCAAGAACCTGAAG
ACCGGCAAGTACGCCAAGCGCAAGTCCACCCACACCAACGACGTGAAGCAGCTGACCGAGGCCGTGCAGAAGATCGCCACCGAGTCCATCGTGATCTGGGG
CAAGACCCCCCAAGTTCCGCCTGCCCATCCAGAAGGAGACCTGGGAGGCCTGGTGGACCGAGTACTGGCAGGCCACCTGGATCCCCGAGTGGGAGTTCGTGA
ACACCCCCCTGGTGAAGCTGTGGTACCAGCTGGAGAAGGAGCCCATCGTGTCCGTGCCAACCAGCCCTGCCCCAACGCCACGCCATCCAGTCCGACCAAG
CTGGGCAAGGCCGGCTACGTGACCGACCGGGCAAATCAGGGTGAACATCGTGACCGACAGCCAGTACGCCCTGGGCATCATCCAGGCCCAGCCCGACCAGAGC
CCTGCAGGACTCCGGCCTGGAAGTGAACATCGTGACCGACAGCCAGTACGCCCTGGGCATCATCCAGGCCCAGCCCGACCGGAGCGAGTCCGAGCTGGTGA
ACCAGATCATCGAGCAGCTGATCAAGAAGGAGAAGGTGTACCTGGCCTGGGTGCCTGCCCATGAGCAGCTGGACAAGCTGGTG
TCCTCCGGCATCCGCAAGGTGCTGTTCCTGGACGGCATCGACAAGGCCCAGGAGGAGCACGAGAAGTACCACTCCAACTGGCGCGCCATGGCCTCCGACTT
CAACCTGCCCCCCGTGGTGGCCAAGGAGATCGTGGCCTCCTGCGACAAGTGCCAGCTGAAGGGCGAGGCCATGCACGGCCAGGTGGACTGCTCCCCCGGCA
TCTGGCAGCTGGACTGCACCCACCTGGAGGGCAAGGTGATCCTGGTGGCCGTGCACGTGGCCTCCGGCTACATCGAGGCCGAGGTGATCCCCGCCGAGACC
GGCCAGGAGACCGCCTACTTCATCCTGAAGCTGGCCGGCCGCTGGCCCGTGAAGACCGTGCACACCGACAACGGCTCCAACTTCACCTCCGCCACCGTGAA
GGCCGCCTGCTGGTGGCCCGGCGTGCAGATGAACACCGCCTACGTGAACCCCTACAACCCCCAGTCCCAGGGCGTGGTGGAGTCCATGAACAAGGAGCTGAAGAAGA
TCATCGGCCAGGTGCGCGACCAGGCCGAGCATCATCGACACCATCGCCTGCGGCGGCATCGTGAAGGCCCACCTGAAGAAGGGCAAGGCCATCGGCGGCTAC
TCCGCCGGCGAGCGCATCGTGGACATCATCGCCACCGACATCCAGACCAAGGAGCTGCAGAAGCAGATCATCAAGATCCAGAACTTCCGCGTGTACTACCG
CGACTCCCGCGACCCCAAGATCCCCCGCGGCAAGCGCTCACGGCGACTGCGTGGCCGGCCGCCAAGATGCCGCCCGAGGGGGCGACTGCTGGCCGTGGTGCCCC
GCCGCAAGGCCAAGATCATCCGCGACTACGGCAAGCAGATGGCCGGCGACGACTGCGTGGCCAGCGGCCAGGACGAGGACCAGAACCAGTAA
```

Fig. 111B

2003_CON_B pol.OPT

TTCTTCCGCGAGGACCTGGCCTTCCCCCAGGGCAAGGCCCGCGAGTTCTCCTCCGAGCAGACCCGCGCCAACTCCCCCACCCGCCGCGAGCTGCAGGTGTG
GGGCCGCGACAACAACTCCCTGTCCGAGGCCGGCGCCGACCGCCAGGGCACCGTGTCCTTCTCCTTCCCCCAGATCACCCTGTGGCAGCGCCCCCTGGTGA
CCATCAAGATCGGCGGCCAGCTGAAGGAGGCCCTGCTGGACACCGGCGCCGACGACACCGTGCTGGAGGAGATGAACCTGCCCGGCCGCTGGAAGCCCAAG
ATGATCGGCGGCATCGGCGGCTTCATCAAGGTGCGCCAGTACGACCAGATCCTGATCGAGATCTGCGGCCACAAGGCCATCGGCACCGTGCTGGTGGGCCC
CACCCCCGTGAACATCATCGGCCGCAACCTGCTGACCCAGATCGGCTGCACCCTGAACTTCCCCATCTCCCCCATCGAGACCGTGCCCGTGAAGCTGAAGC
CCGGCATGGACGGCCCCAAGGTGAAGCAGTGGCCCCTGACCGAGGAGAAGATCAAGGCCCTGGTGGAGATCTGCACCGAGATGGAGAAGGAGGGCAAGATC
TCCAAGATCGGCCCCGAGAACCCCTACAACACCCCCGTGTTCGCCATCAAGAAGAAGGACTCCACCAAGTGGCGCAAGCTGGTGGACTTCCGCGAGCTGAA
CAAGCGCACCCAGGACTTCTGGGAGGTGCAGCTGGGCATCCCCCACCCCGCCGGCCTGAAGAAGAAGAAGTCCGTGACCGTGCTGGACGTGGGCGACGCCT
ACTTCTCCGTGCCCCTGGACAAGGACTTCCGCAAGTACACCGCCTTCACCATCCCCTCCATCAACAACGAGACCCCCGGCATCCGCTACCAGTACAACGTG
CTGCCCCAGGGCTGGAAGGGCTCCCCCGCCATCTTCCAGTCCTCCATGACCAAGATCCTGGAGCCCTTCCGCAAGCAGAACCCCGACATCGTGATCTACCA
GTACATGGACGACCTGTACGTGGGCTCCGACCTGGAGATCGGCCAGCACCGCACCAAGATCGAGGAGCTGCGCCAGCACCTGCTGCGCTGGGGCTTCACCA
CCCCCGACAAGAAGCACCAGAAGGAGCCCCCCTTCCTGTGGATGGGCTACGAGCTGCACCCCGACAAGTGGACCGTGCAGCCCATCGTGCTGCCCGAGAAG
GACTCCTGGACCGTGAACGACATCCAGAAGCTGGTGGGCAAGCTGAACTGGGCCTCCCAGATCTACGCCGGCATCAAGGTGAAGCAGCTGTGCAAGCTGCT
GCGCGGCACCAAGGCCCTGACCGAGGTGATCCCCCTGACCGAGGAGGCCGAGCTGGAGCTGGCCGAGAACCGCGAGATCCTGAAGGAGCCCGTGCACGGCG
TGTACTACGACCCCTCCAAGGACCTGATCGCCGAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAGGCCGTGCAGAAGATCGCCACCGAGTCCATCGTGATCTGGGG
CAAGACCCCCAAGTTCAAGCTGCCCATCCAGAAGGAGACCTGGGAGGCCTGGTGGACCGAGTACTGGCAGGCCACCTGGATCCCCGAGTGGGAGTTCGTGA
ACACCCCCCCCCTGGTGAAGCTGTGGTACCAGCTGGAGAAGGAGCCCATCGTGGGCGCCGAGACCTTCTACGTGGACGGCGCCGCCAACCGCGAGACCAAG
CTGGGCAAGGCCGGCTACGTGACCGACCGCGGCCGCCAGAAGGTGGTGTCCCTGACCGACACCACCAACCAGAAGACCGAGCTGCAGGCCATCCACCTGGC
CCTGCAGGACTCCGGCCTGGAGGTGAACATCGTGACCGACTCCCAGTACGCCCTGGGCATCATCCAGGCCCAGCCCGACAAGTCCGAGTCCGAGCTGGTGT
CCCAGATCATCGAGCAGCTGATCAAGAAGGAGAAGGTGTACCTGGCCTGGGTGCCCGCCCACAAGGGCATCGGCGGCAACGAGCAGGTGGACAAGCTGGTG
TCCGCCGGCATCCGCAAGGTGCTGTTCCTGGACGGCATCGACAAGGCCCAGGAGGAGCACGAGAAGTACCACTCCAACTGGCGCGCCATGGCCTCCGACTT
CAACCTGCCCCCCGTGGTGGCCAAGGAGATCGTGGCCTCCTGCGACAAGTGCCAGCTGAAGGGCGAGGCCATGCACGGCCAGGTGGACTGCTCCCCCGGCA
TCTGGCAGCTGGACTGCACCCACCTGGAGGGCAAGATCATCCTGGTGGCCGTGCACGTGGCCTCCGGCTACATCGAGGCCGAGGTGATCCCCGCCGAGACC
GGCCAGGAGACCGCCTACTTCCTGCTGAAGCTGGCCGGCCGCTGGCCCGTGAAGACCATCCACACCGACAACGGCTCCAACTTCACCTCCACCACCGTGAA
GGCCGCCTGCTGGTGGGCCGGCATCAAGCAGGAGTTCGGCATCCCCTACAACCCCCAGTCCCAGGGCGTGGTGGAGTCCATGAACAAGGAGCTGAAGAAGA
TCATCGGCCAGGTGCGCGACCAGGCCGAGCACCTGAAGACCGCCGTGCAGATGGCCGTGTTCATCCACAACTTCAAGCGCAAGGGCGGCATCGGCGGCTAC
TCCGCCGGCGAGCGCATCGTGGACATCATCGCCACCGACATCCAGACCAAGGAGCTGCAGAAGCAGATCACCAAGATCCAGAACTTCCGCGTGTACTACCG
CGACTCCCGCGACCCCCTGTGGAAGGGCCCCGCCAAGCTGCTGTGGAAGGGCGAGGGCGCCGTGGTGATCCAGGACAACTCCGACATCAAGGTGGTGCCCC
GCCGCAAGGCCAAGATCATCCGCGACTACGGCAAGCAGATGGCCGGCGACGACTGCGTGGCCTCCCGCCAGGACGAGGACTAA

Fig. 111C 67. 2003_B.anc_pol.PEP
FFRENLAFPQGKAREFSSEQTRANSPTRRELQVWGRDNNPLSEAGADRQGTVSFSFPQITLWQRPLVTIKIGGQLKEALLDTGADDTVLEEM
NLPGKWKPKMIGGIGGFIKVRQYDQILIEICGHKAIGTVLVGPTPVNIIGRNLLTQIGCTLNFPISPIETVPVKLKPGMDGPKVKQWPLTEE
KIKALVEICTEMEKEGKISKIGPENPYNTPVFAIKKKDSTKWRKLVDFRELNKRTQDFWEVQLGIPHPAGLKKKKSVTVLDVGDAYFSVPLD
KDFRKYTAFTIPSINNETPGIRYQYNVLPQGWKGSPAIFQSSMTKILEPFRKQNPEIVIYQYMDDLYVGSDLEIGQHRTKIEELREHLLRWG
FTTPDKKHQKEPPFLWMGYELHPDKWTVQPIVLPEKDSWTVNDIQKLVGKLNWASQIYAGIKVKQLCKLLRGTKALTEVVPLTEEAELELAE
NREILKEPVHGVYYDPSKDLIAEIQKQGQGQWTYQIYQEPFKNLKTGKYARMRGAHTNDVKQLTEAVQKIATESIVIWGKTPKFKLPIQKET
WEAWWTEYWQATWIPEWEFVNTPPLVKLWYQLEKEPIVGAETFYVDGAANRETKLGKAGYVTDRGRQKVVSLTDTTNQKTELQAIHLALQDS
GLEVNIVTDSQYALGIIQAQPDKSESELVSQIIEQLIKKEKVYLAWVPAHKGIGGNEQVDKLVSAGIRKVLFLDGIDKAQEEHEKYHSNWRA
MASDFNLPPVVAKEIVASCDKCQLKGEAMHGQVDCSPGIWQLDCTHLEGKIILVAVHVASGYIEAEVIPAETGQETAYFILKLAGRWPVKVI
HTDNGSNFTSTTVKAACWWAGIKQEFGIPYNPQSQGVVESMNKELKKIIGQVRDQAEHLKTAVQMAVFIHNFKRKGGIGGYSAGERIVDIIA
TDIQTKELQKQITKIQNFRVYYRDSRDPLWKGPAKLLMKGEGAVVIQDNSDIKVPRRKAKIIRDYGKQMAGDDCVASRQDED$

Fig. 111D

2003_B.anc pol.OPT

TTCTTCCGCGAGAACCTGGCCTTCCCCCAGGGCAAGGCCCGCGAGTTCTCCTCCGAGCAGACCCGCGCCAACTCCCCCACCCGCCGCGAGCTGCAGGTGTG
GGGCCGCGACAACAACCCCCTGTCCGAGGCCGGCGCCGACCGCCAGGGCACCGTGTCCTTCTCCTTCCCCCAGATCACCCTGTGGCAGCGCCCCCTGGTGA
CCATCAAGATCGGCGGCCAGCTGAAGGAGGCCCTGCTGGACACCGGCGCCGACGACACCGTGCTGGAGGAGATGAACCTGCCCGGCAAGTGGAAGCCCAAG
ATGATCGGCGGCATCGGCGGCTTCATCAAGGTGCGCCAGTACGACCAGATCCTGATCGAGATCTGCGGCCACAAGGCCATCGGCACCGTGCTGGTGGGCCC
CACCCCCGTGAACATCATCGGCCGCAACCTGCTGACCCAGATCGGCTGCACCCTGAACTTCCCCATCTCCCCCATCGAGACCGTGCCCGTGAAGCTGAAGC
CCGGCATGGACGGCCCCAAGGTGAAGCAGTGGCCCCTGACCGAGGAGAAGATCAAGGCCCTGGTGGAGATCTGCACCGAGATGGAGAAGGAGGGCAAGATC
TCCAAGATCGGCCCCGAGAACCCCTACAACACCCCCGTGTTCGCCATCAAGAAGAAGGACTCCACCAAGTGGCGCAAGCTGGTGGACTTCCGCGAGCTGAA
CAAGCGCACCCAGGACTTCTGGGAGGTGCAGCTGGGCATCCCCCACCCCGCCGGCCTGAAGAAGAAGAAGTCCGTGACCGTGCTGGACGTGGGCGACGCCT
ACTTCTCCGTGCCCCTGGACAAGGACTTCCGCAAGTACACCGCCTTCACCATCCCCTCCATCAACAACGAGACCCCCGGCATCCGCTACCAGTACAACGTG
CTGCCCCAGGGCTGGAAGGGCTCCCCCGCCATCTTCCAGTCCTCCATGACCAAGATCCTGGAGCCCTTCCGCAAGCAGAACCCCGAGATCGTGATCTACCA
GTACATGGACGACCTGTACGTGGGCTCCGACCTGGAGATCGGCCAGCACCGCACCAAGATCGAGGAGCTGCGCGAGCACCTGCTGCGCTGGGGCTTCACCA
CCCCCGACAAGAAGCACCAGAAGGAGCCCCCCTTCCTGTGGATGGGCTACGAGCTGCACCCCGACAAGTGGACCGTGCAGCCCATCGTGCTGCCCGAGAAG
GACTCCTGGACCGTGAACGACATCCAGAAGCTGGTGGGCAAGCTGAACTGGGCCTCCCAGATCTACGCCGGCATCAAGGTGAAGCAGCTGTGCAAGCTGCT
GCGCGGCACCAAGGCCCTGACCGAGGTGGTGCCCCTGACCGAGGAGGCCGAGCTGGAGCTGGCCGAGAACCGCGAGATCCTGAAGGAGCCCGTGCACGGCG
TGTACTACGACCCCTCCAAGGACCTGATCGCCGAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAGGCCGTGCAGAAGATCGCCACCGAGTCCATCGTGATCTGGGG
CAAGACCCCCAAGTTCAAGCTGCCCATCCAGAAGGAGACCTGGGAGGCCTGGTGGACCGAGTACTGGCAGGCCACCTGGATCCCCGAGTGGGAGTTCGTGA
ACACCCCCCCCCTGGTGAAGCTGTGGTACCAGCTGGAGAAGGAGCCCATCGTGGGCGCCGAGACCTTCTACGTGGACGGCGCCGCCAACCGCGAGACCAAG
CTGGGCAAGGCCGGCTACGTGACCGACCGCGGCCGCCAGAAGGTGGTGTCCCTGACCGACACCACCAACCAGAAGACCGAGCTGCAGGCCATCCACCTGGC
CCTGCAGGACTCCGGCCTGGAGGTGAACATCGTGACCGACTCCCAGTACGCCCTGGGCATCATCCAGGCCCAGCCCGACAAGTCCGAGTCCGAGCTGGTGT
CCCAGATCATCGAGCAGCTGATCAAGAAGGAGAAGGTGTACCTGGCCTGGGTGCCCGCCCACAAGGGCATCGGCGGCAACGAGCAGGTGGACAAGCTGGTG
TCCGCCGGCATCCGCAAGGTGCTGTTCCTGGACGGCATCGACAAGGCCCAGGAGGAGCACGAGAAGTACCACTCCAACTGGCGCGCCATGGCCTCCGACTT
CAACCTGCCCCCCGTGGTGGCCAAGGAGATCGTGGCCTCCTGCGACAAGTGCCAGCTGAAGGGCGAGGCCATGCACGGCCAGGTGGACTGCTCCCCCGGCA
TCTGGCAGCTGGACTGCACCCACCTGGAGGGCAAGATCATCCTGGTGGCCGTGCACGTGGCCTCCGGCTACATCGAGGCCGAGGTGATCCCCGCCGAGACC
GGCCAGGAGACCGCCTACTTCATCCTGAAGCTGGCCGGCCGCTGGCCCGTGAAGGTGATCCACACCGACAACGGCTCCAACTTCACCTCCACCACCGTGAA
GGCCGCCTGCTGGTGGGCCGGCATCAAGCAGGAGTTCGGCATCCCCTACAACCCCCAGTCCCAGGGCGTGGTGGAGTCCATGAACAAGGAGCTGAAGAAGA
TCATCGGCCAGGTGCGCGACCAGGCCGAGCACCTGAAGACCGCCGTGCAGATGGCCGTGTTCATCCACAACTTCAAGCGCAAGGGCGGCATCGGCGGCTAC
TCCGCCGGCGAGCGCATCGTGGACATCATCGCCACCGACATCCAGACCAAGGAGCTGCAGAAGCAGATCACCAAGATCCAGAACTTCCGCGTGTACTACCG
CGACTCCCGCGACCCCCTGTGGAAGGGCCCCGCCAAGCTGCTGTGGAAGGGCGAGGGCGCCGTGGTGATCCAGGACAACTCCGACATCAAGGTGGTGCCCC
GCCGCAAGGCCAAGATCATCCGCGACTACGGCAAGCAGATGGCCGGCGACGACTGCGTGGCCTCCCGCCAGGACGAGGACTAA

Fig. 112A 68. 2003_CON_C_pol.PEP
FFRENLAFPQGEAREFPSEQTRANSPTSRELQVRGDNPRSEAGAERQGTLNFPQITLWQRPLVSIKVGGQIKEALLDTGADDTVLEEINLPG
KWKPKMIGGIGGFIKVRQYDQILIEICGKKAIGTVLVGPTPVNIIGRNMLTQLGCTLNFPISPIETVPVKLKPGMDGPKVKQWPLTEEKIKA
LTAICEEMEKEGKITKIGPENPYNTPVFAIKKKDSTKWRKLVDFRELNKRTQDFWEVQLGIPHPAGLKKKKSVTVLDVGDAYFSVPLDEGFR
KYTAFTIPSINNETPGIRYQYNVLPQGWKGSPAIFQSSMTKILEPFRAQNPEIVIYQYMDDLYVGSDLEIGQHRAKIEELREHLLKWGFTTP
DKKHQKEPPFLWMGYELHPDKWTVQPIQLPEKDSWTVNDIQKLVGKLNWASQIYPGIKVRQLCKLLRGAKALTDIVPLTEEAELELAENREI
LKEPVHGVYYDPSKDLIAEIQKQGHDQWTYQIYQEPFKNLKTGKYAKMRTAHTNDVKQLTEAVQKIAMESIVIWGKTPKFRLPIQKETWETW
WTDYWQATWIPEWEFVNTPPLVKLWYQLEKEPIAGAETFYVDGAANRETKIGKAGYVTDRGRQKIVSLTETTNQKTELQAIQLALQDSGSEV
NIVTDSQYALGIIQAQPDKSESELVNQIIEQLIKKERVYLSWVPAHKGIGGNEQVDKLVSSGIRKVLFLDGIDKAQEEHEKYHSNWRAMASE
FNLPPIVAKEIVASCDKCQLKGEAIHGQVDCSPGIWQLDCTHLEGKIILVAVHVASGYIEAEVIPAETGQETAYYILKLAGRWPVKVIHTDN
GSNFTSAAVKAACWWAGIQQEFGIPYNPQSQGVVESMNKELKKIIGQVRDQAEHLKTAVQMAVFIHNFKRKGGIGGYSAGERIIDIIATDIQ
TKELQKQIIKIQNFRVYYRDSRDPIWKGPAKLLWKGEGAVVIQDNSDIKVVPRRKAKIIKDYGKQMAGADCVAGRQDED$

Fig. 112B

```
2003_CON_C_pol.OPT
TTCTTCCGCGAGAACCTGGCCTTCCCCCAGGGGCGAGGCCCGAGTTCCCCTCCGAGCAGAGACCCCGCGCCAACTCCCCCACCTTCCCGAGCTGCCAGGTGCG
CGGCGACAACCCCGCTCCGAGGCCGGCCCGCAGGGCCGCCCAGGCCGCCCTGAACTTCCCCGAGATCACCCTGTGGCAGCGCCCCCTGGTGTCCATCAAGTGG
GCCGCCAGATCAAGGAGGCCCTGCTGGACACCGGCCGACACCCTGCTGGAGAGATCAACACCTGCCCGGCAAGTGGAAGCCCAAGATGATCGGCGGC
ATCGGCGGCTTCATCAAGGTGCGCCAAGTAGTCGACCAGTAGCCATCGCCTGATCGAGATCCTGCGGCAGAAGGCCATCGAGACCGTGCCCGTGAAGCTGTGTGGCCCCGTGAA
CATCATCGGCCCAAGTGAAGCTGGCCCTGCCCTGACCGACCAGCAGCCCCTGACCCCTGAACTTCCCCATCTCCCGTGAAGCTGGAAGCCTGGACATGGACG
GCCCCAAGGTGAAGCAGTGGCCCCTGACCGAGGAAGATCAAGGCCCTGACCGACATCCAGCAGGGCATCAAGAAGCTGGTGGAGGCCATCACCAAGATCGGC
CCCGAGAACCCCTACAACACCCCGTGTTCGCCATCAAGAAGAAGGACTCCACCAAGTGGCGCAAGCTGGTGGACTTCCGCGAGCTGAACAAGCGCACCCA
GGACTTCTGGGAGGTGCAGCTGGCCATCCCAGAGAAGAAGAGTCCGTGGCTGGACGTGGGCGACCTGCTGGACGCCCTACTTCTCCGTGC
CCCTGGACGAGGGCTTCCGCAAGTACACCGCCTTCACCATCCCCAGCATCAACAACGAGAGCCCTGCTGAAGTGGGGCTTCACCACCCCCGACAAGA
TGGAAGGGCTCCCCGCAGCCCCCCTTCCTGTGATGGGCAAGCTGGTGGACAAGGGCCAGCTGAACCCCGAGCTGCCGAGAGGACTCCTGGACC
CCTGTACTGGGCCCTGACCAGAAGAGACATCCGTGCCCCGAGATCGCCGAGATCCCCGTGCACCCGAGCTGGCCGAGCTGCTGACCAAGGAGCCCGTGTACTGACC
GTGAACGACATCCAGAAGCTGGTGGCCCCTGAAACTGGGGCGAGCTGAGGAGCCCTCAAGAACCTGAAGACCGGCAAGTAC
GCCAAGATGCGCACCGCCCACACCAACGACCTGAAGCAGCTGACCGAGGCCGTGCAGAAGATCGCCATGGAGTCCATCGTGATCTGGGGCAAGACCCCCAA
GTTCCGCCTGCCCATCCAGAAGGAGACGTGGACCTGGAGAACCGCATCCAGCTGCCCTTGAACACCGAGAAGCTGCCCATCCAGGCCTCCCTGCAGGACTC
TGGTGAAGCTGTGTGACCCGCCGCGCGCCAGAGATCGTGTCCCAAGTGACCCCAGTACCGCCCTGGCAGTAGAGCCCGGCCATCCGACTGTGAACCAGATCATCG
GGGCTCCGAGGTGAACATCGTGACCGACTCCCAGTACGCCCTGGGCATCATCCAGGCCCAGCCGACCTGGTGAACCAGCAGCAGCAGATCGG
AGCAGCTGATCAAGAAGGAGCGCGTGTACCTGTCCTGGGTCCCGGCGCCAAGGCCGACAAGGCAACGAGCAGGTGACAAGCTCCGAGTTCAACCTGCCCC
CGCAAGGTGCTGTTCCTGGACGGCATCGACAAGGCCCAGGAGCACGAAGAGGCCAAGTGCCGACAAGTGCCCAGGCCATGGGCATCTGGCAGCTGG
CATCGTGGCCAAGGAGATCGTGGCCTCCTGCGACAAGTGCCAGCTGAAGGGCGAGGCCATGCACGGCCAGGTGGACTGCTCTCCCCGGCCATCTGGCAGCTGG
ACTGCACCCCACCTGGAGGCCAAGATCATCCTGCGCATCCAGCAGTTCACCGTGCCCGGCCGTGAAGTGATCCTGGCCACCAAGGCGAGCGGCCCTGGAGACC
GCCTACTACATCCTGAAGCTGGCCAAAGGCACCCCGATATCAAGCTGGTGGCCGTGCCCATCCGATCGAAGCTGGGCGATCAACTTCACCTCCCCGCCCTGCTG
GTGCCCGACCAGGCCCAGCGGCCAGCAACATCGTGACCGACATCATCGCCACCGACATCCAGACCAAGGAGCTGCAGAAGCAGATCATCAAGATCCAGAACTTCCGCGTGTACTACCGCGACTCCCGGCCGACCACCTGCCCGAG
TGCGGCAAGGCCCCCGCCAAGGGCCATCAACGAGCGGCTGGATCCCAGTCCCGTGTTCATCCACAACGCCAGATGGCCCGTGCTGTCCCACAACTTCAAGCGGGGCATCGGGGCTACTCCGCGACTCCCTG
CGCGGCAGCAGATCGCCCGACATCATCGCCACCGACATCCAGACCAAGGAGCTGCAGAAGCAGATCATCAAGATCCAGAACTTCCGCGTGTACTACCGCGACTCCCGGCCGACCACCTGCCCGAG
CCCATCTCGGGCCAAGCTGCTGTGGAAGGGCCGAGGGCGCCGTGGTCATCCAGGACAACTCCGACATCAAGGTGGTGCCCCGCCGCAAGGCCA
AGATCATCAAGGACTACGGCAAGCAGATGGCCGCCGACTGCGTGGCCGGCCGCCAAGAAGCTGGGCAAGGACGAGGACTAA
```

Fig. 112C 69. 2003_C.anc_pol.PEP
FFRENLAFPQGEAREFPSEQTRANSPTSRELQVGRDNPRSEAGAERQGTLTLNFPQITLWQRPLVSIKVGGQIKEALLDTGADDTVLEEINL
PGKWKPKMIGGIGGFIKVRQYDQILIEICGKKAIGTVLVGPTPVNIIGRNMLTQLGCTLNFPISPIETVPVKLKPGMDGPKVKQWPLTEEKI
KALTAICEEMEKEGKITKIGPENPYNTPVFAIKKKDSTKWRKLVDFRELNKRTQDFWEVQLGIPHPAGLKKKKSVTVLDVGDAYFSVPLDEG
FRKYTAFTIPSINNETPGIRYQYNVLPQGWKGSPAIFQSSMTKILEPFRAQNPEIVIYQYMDDLYVGSDLEIGQHRAKIEELREHLLKWGFT
TPDKKHQKEPPFLWMGYELHPDKWTVQPIQLPEKDSWTVNDIQKLVGKLNWASQIYPGIKVRQLCKLLRGAKALTDIVPLTEEAELELAENR
EILKEPVHGVYYDPSKDLIAEIQKQGHDQWTYQIYQEPFKNLKTGKYAKMRTAHTNDVKQLTEAVQKIAMESIVIWGKTPKFRLPIQKETWE
TWWTDYWQATWIPEWEFVNTPPLVKLIWYQLEKEPIAGAETFYVDGAANRETKIGKAGYVTDRGRQKIVSLTETTNQKTELQAIQLALQDSGS
EVNIVTDSQYALGIIQAQPDKSESELVNQIIEQLIKKEKVYLSWVPAHKGIGGNEQVDKLVSSGIRKVLFLDGIDKAQEEHEKYHSNWRAMA
SEFNLPPIVAKEIVASCDKCQLKGEAMHGQVDCSPGIWQLDCTHLEGKIILVAVHVASGYIEAEVIPAETGQETAYFILKLAGRWPVKVIHT
DNGSNFTSAAVKAACWWAGIQEEGIPYNPQSQGVVESMNKELKKIIGQVRDQAEHLKTAVQMAVFIHNFKRKGGIGGYSAGERIIDIIATD
IQTKELQKQIIKIQNFRVYYRDSRDPIWKGPAKLLWKGEGAVVIQDNSDIKVVPRRKAKIIRDYGKQMAGADCVAGRQDED$

Fig. 112D

2003_C.anc_pol.OPT

TTCTTCCGGAGAACCTGGCCTTCCCCCAGGGGCGAGGCCGAGGCCGAGTTCCCCTCCGAGCAGACCCCGGCCAACTCCCCCACCTCCCGAGCTGCAGGTGGG
CCGCGACAACCCCGCTCCGAGGCCTCCGAGGCGCCGAGCCGCCAGGCCGCCGAGGCACCCCAGATCGAACTTCCCCGACCCTGAACTCACCCTGCAGGCCCCTGGTGTCATCA
AGGTGGGGCGGCCAGATCAAGGAGGCCCTGCTGGACACACCGGCGCCGATCAACCTGCCCGGCAAGTGAAGCCAAGATGATC
GCGGCATCGGCGGCTTCATCAAGGTGCGCCAGATCCTGATCGAGATCCTGCGGCAAGAAGGCCATCGAGACCTTCCCCCATCGGCGTGCCCGTGAAGCCCGGCA
CGTGAACATCATCGGCCGCAACATGCTGACCTGGGCTGCACCCTGAACTTCCCCATTCTGCGAGGAGATGAAGCCGCAAGATCACCAAG
TGGACGGCCCCAAGTGAAGCAGTGGCCCTGACCAGGAGAGATCAAGGCCCTGAAGCTGGTGACTTCCGGAGCTGAACAAGCG
ATCGGCCCCGAGAACCCTACAACACCCCGTGTTCGCCATCAAGA

Fig. 113A

70. 2003_CON_D_pol.PEP

FFRENLAFPQGKAGELSSEQTRANSPTSRELRVWGGDNPLSETGAERQGTVSFNFPQITLWQRPLVTIKIGGQLKEALLDTGADDTVLEEIN
LPGKWKPKMIGGIGGFIKVRQYDQILIEICGHKAIGTVLVGPTPVNIIGRNLLTQIGCTLNFPISPIETVPVKLKPGMDGPKVKQWPLTEEK
IKALTEICTEMEKEGKISRIGPENPYNTPIFAIKKKDSTKWRKLVDFRELNKRTQDFWEVQLGIPHPAGLKKKKSVTVLDVGDAYFSVPLDE
DFRKYTAFTIPSINNETPGIRYQYNVLPQGWKGSPAIFQSSMTKILEPFRKQNPEIVIYQYMDDLYVGSDLEIGQHRTKIEELREHLLRWGF
TTPDKKHQKEPPFLWMGYELHPDKWTVQPIKLPEKESWTVNDIQKLVGKLNWASQIYPGIKVRQLCKLLRGTKALTEVIPLTEEAELELAEN
REILKEPVHGVYYDPSKDLIAEIQKQGQGQWTYQIYQEPFKNLKTGKYARMRGAHTNDVKQLTEAVQKIAIESIVIWGKTPKFRLPIQKETW
ETWWTEYWQATWIPEWEFVNTPPLVKLWYQLEKEPIIGAETFYVDGAANRETKLGKAGYVTDRGRQKVVPLTDTTNQKTELQAINLALQDSG
LEVNIVTDSQYALGIIQAQPDKSESELVSQIIEQLIKKEKVYLAWVPAHKGIGGNEQVDKLVSNGIRKVLFLDGIDKAQEEHEKYHNNWRAM
ASDFNLPPVAKEIVASCDKCQLKGEAMHGQVDCSPGIWQLDCTHLEGKVILVAVHVASGYIEAEVIPAETGQETAYFLLKLAGRWPVKVVH
TDNGSNFTSAAVKAACWWAGIKQEFGIPYNPQSQGVVESMNKELKKIIGQVRDQAEHLKTAVQMAVFIHNFKRKGGIGGYSAGERIIDIIAT
DIQTKELQKQIIKIQNFRVYYRDSRDPIWKGPAKLLWKGEGAVVIQDNSDIKVVPRRKVKIIRDYGKQMAGDDCVASRQDEDS

Fig. 114A

71. 2003_CON_F1_pol.PEP

FFRENLAFQQGEARKFPSEQTRANSPASRELRVQRGDNPLSEAGAERRGTVPSLSFPQITLWQRPLVTIKIGGQLKEALLDTGADDTVLEDI
NLPGKWKPKMIGGIGGFIKVKQYDHILIEICGHKAIGTVLVGPTPVNIIGRNMLTQIGCTLNFPISPIETVPVKLKPGMDGPRVKQWPITEE
KIKALTEICTEMEKEGKISKIGPENPYNTPVFAIKKKDSTKWRKLVDFRELNKRTQDFWEVQLGIPHPAGLKKKKSVTVLDVGDAYFSVPLD
KDFRKYTAFTIPSVNNETPGIRYQYNVLPQGWKGSPAIFQCSMTKILEPFFRTKNPDIVIYQYMDLYVGSDLEIGQHRTKIEELRELHLLKWG
FTTPDKKHQKEPPFLWMGYELHPDKWTVQPIQLPDKDSWTVNDIQKLVGKLNWASQIYPGIKVKQLCKLLRGAKALTDIVPLTAEAELELAE
NREILKEPVHGVYYDPSKDLIAEIQKQGQGQWTYQIYQEPFKNLKTGKYAKMRSAHTNDVKQLTEAVQKIALESIVIWGKTPKFRLPILKET
WDTWWTDYWQATWIPEWEFVNTPPLVKLWYQLETEPIVGAETFYVDGASNRETKKGKAGYVTDRGKQKVVSLTETTNQKAELQAIHLALQDS
GSEVNIVTDSQYALGIIQAQPDKSESELVNQIIEQLIQKEKVYLSWVPAHKGIGNEQVDKLVSAGIRKILFLDGIDKAQEEHEKYHNNWRAI
MASDFNLPPVVAKEIVASCDKCQLKGEAMHGQVDCSPGIWQLDCTHLEGKIILVAVHVASGYIEAEVIPAETGQETAYFILKLAGRWPVKII
HTDNGSNFTSAAVKAACWWAGIQQEFGIPYNPQSQGVVESMNKELKKIIGQVRDQAEHLKTAVQMAVFIHNFKRKGGIGGYSAGERIIDIIA
TDIQTKELQKQITKIQNFRVYYRDSRDPVWKGPAKLLWKGEGAVVIQDNSEIKVVPRRKAKIIRDYGKQMAGDDCVAGRQDEDS

Fig. 113B

2003_CON_D_pol.OPT

TTCTTCCGGAGAACCTGGCCTTCCCCCAGGGCAAGGCCGGCGAGCTGTGTCCTCCGAGCAGACCCGGCGCCAACTCCCCACCTCCCGAGCTGCCGCGTGTG
GGGCGGCGACAACCCCCTGTCCAGCTGAAGGAGCCGGCCCTGCTGGACGACGAACCGTGCTGGCACCGATCACCTTCCCCAGAGGAGATCAACCTGCTGGAAGCCCCCTGGTGACCA
TCAAGATCGGCGGCCAGCTGAAGGAGGCCCTGCTGGACAACGGCCCGCGACGACCGGCCCTGCTGGCCCGGCAAGTGAAGTGGGCAGCCCAAGATG
ATCGCGGCCATCGGCGCTTCATCAAGGTGCTGACCCAGATCTGCGCGACCTGAAGCCTGATCGAGATCTGCGGCCACAAGGCCATGGACCGTGCCGTGCTGGTGGTGACCCAC
CCCGTGAACATCATGGCCGCCAAGGTGAAGCAGTGCCCCCTGACCGAGAGATCAAGGCCCTGACCGAGATCTGCACCGAGATCTGCCCCGAGATCTGCCGTGCCGTGAAGCCGTGCCGTGAAGCCGAC
GCATGGACGGCCCCGAGAACCCCTACAACACCCCCATCTTCGCCATCAAGAAGAAGAAGAAGAACTCAAGTGGCGACTGTGAGCTTCCGCGAGCTGAACAA
CGCCACCCAGGACTTCTGGGAGGTGCAGCTGGGCATCCCCCATGAACACCGAGAAGATCTGGAGGCCCCTGACCGTGACCGTGGGCGACGCCTACT
TCTCCGTGCCCCTGGACGAGGGCTTCCGCCGCAAGTACGCCTTCCGCCATCTTCCAGTGATCCTCCATGACCAGATCCCGCAAGCAGAACCCGCTGCTGCGCGTGACCAACGTGCTG
CCCAGGGGCTGGAAGGCTCCCCCGGCCTCCGACCTGTGGGCTCCGAGATCGGCCAGCTGGCGACGAGCTGCCCAGCCGTGCGCGACGTGGACGGCATCTACCCCGAGAAGGAG
CATGGACGACCTGTACGTGGCACGAAGCACCGAATCTCAGAAGCCCCCTGAGCTGGAGCTGAATGGGCCAAGCCGAGAGGAGGCAGGGCGAGAAGACGCGAGATCTGCCAAGCTGTGCCGGCGT
CCGACAAGAAGCGACATCCAGAAGCCCCTTCCTGTGATGGGCCAAGCTGGGTCCCCGGAGAGGCAGGGCGAGCTGCAGGGCCAGTGATCGCCGAGATCTACCAGGACCTCAGATCGCCAGATCTACCAGGACC
TCCTGGACCGGCGAACCGACATCCAGAAGCCCTTCCTGTGATGGGCCAAGCTGGTGCCCGAGAAGGACACCAAGCTGGGCCCAGAGGAGGCAGGGCGAGCTGCAGGGCCAGTGATCGCCGAGATCTACCAGGACCCG
CGGCACCCAAGGCCCCTGACCGAGGTGATCCCCCTGACCGAGGAGGTGATCGCCCCAGAGCTGGGCGACCCCCAAGATCGCGCCGTGCGCGACGTGGT
ACTACGACCCCTCCAAGGACCTGATCGCCAGACCTGGCACCCCGAGCGTGAAGACCGGCAAGCTACCCAGAGAAAGGCCCCTCAAGGAGCCCTTCAAGAACCTGAAGACC
GGCAAGTACGCCCGCATGCGCGGCGCCACACCAGAAGGAGACCAACGACGTGAAGCAGCTGACCGAGGCAGCAGCAGATCGCCATGCGCCATCGAGTCCGATCTGGGGCAA
GACCCCAAGTTCCGCCTGCCATCCAGAGAGATCTGGAGGGGACGAGCCCCATCATCCCAGATCTGCCAGGCACCTGGAAGCGGCAGAGTTCGTGAACA
CCCCCCCCCTGGTGAAGTTGTGGTACCAGCTGTGGACCAGCCGGCCGAGACCGAGAAGACCAACCAGAAGACCGAGCTGCAGGCAGCCAAGACCCCGCCGCGGCCCAAGCTGG
GGCAAGGCCGGCTACGTGACCGACCGGCGGCCCAGCGGGTGTGCCCTGAGACCACTGGCTGCCCCTCCAGTACGACCCTGGGCGCCCTGGGTCCCC
GCAGGACTCCGGCTGGAGGTGAACATCGTGACCGACAGGCACCGGGACGCCCTTCAGCGGCAACACTGGCGCCCATGCCCGCCATGGCCATTCCGCACTTCAA
AGATCATCGAGACCTGATCAAGAAGGAGAAGGTGTACCTGGCCTGGGTGCCCGCCGCCCATGGCCGCCCCGAGTGGGCCTCCGACTCCAAGCTTCAA
AACGGCCCCGGCAAGGTGCCTGTTCCTGGACGGCATCGACAAGGCCCAGGACCACCACGAGGAAGTACCACAGCAACTGGCGCGCCATGGCCGCCCCTCCATGCCCGCCCATGGCGCCCACGAGGAGTACCACAGCAACTGGCGCGCCATGGCCGCCCATGCCGCGCCATGGCGCCATGGCCTCCCATGCCCGCCATCTCTCCAA
CCTGCCCCCCATCGTGGCCAAGGAGATCGTGGCCTCCTGCGACAAGTGCCAGCTGAAGGGCGAGGCCATGCACGGCCAGGTGGACTGTAGCCCCGGCATCT
GGCAGCTGGACTGCACCCACCTGGAGGGCAAGGTGATCCTGGTGGCCGTCCATGTGGCCAGCGGCTACATCGAGGCCGAGGTGATCCCCCGCGAGACCGGC
CAGGAGACCGCCTACTTCCTGCTGAAGCTGGCCGCCATCATGGCCAGACCAGCCATCATCGACACATCATCAAGCCGGCGTGAAGAGCTGAAGAAGATCA
TCGGCCAGGTGCGCGACCAGGCCGAGCACCTGAAGACCGCCGTGCAGATGGCCGTGTTCATCCACAACTTCAAGCGCAAGGGCGGCATCGGCGGCTACTCC
GCCGGCGAGCGCATCGTGGACATCATCGCCACCGACATCCAGACCAAGGAGCTGCAGAAGCAGATCATCAAGATCCAGAACTTCCGCGTGTACTACCGCGA
CTCCCGCGACCCCATCTGGAAGGGCCCCGCCAAGCTGCTGTGGAAGGGCGAGGGCGCCGTGGTGATCCAGGACAACTCCGACATCAAGGTGGTGCCCCGCC
GCAAGGTGAAGATCATCCGCGACTACGGCAAGCAGATGGCCGGCGACGACTGCGTGGCCAGCAGACAAGCAGAAGACGAAGCTAA

Fig. 114B

```
2003_CON_F1_pol.OPT
TTCTTCCGGAGAACCTGGCCTTCCAGCAGGGCGAGGCCCGAGCAGACCCGGCGCCAACTCCCCGGCCTCCCGAGCTGCCGTGCA
GCGGCGACAACCCCGTCGGCGGCCAGCTGAAGGAGCCGCTGCCGAGCCGCTGTCCCCAGATCACCCTGTGGCAGCCCCCTGTGA
CCATCAAGATCGGCGGCCAGCTGAAGGAGGCCCTGCTGGACAACCGGTCGCCGAGACAGTCGGCGCCAAGTGGAAGCCCAAG
ATGATCGGCGGGATCCGGCGGCGCTTCATCGGCCGCAACATGCTGACCCAGATCGGCTGCAACTCCCCCATCTGCGACCTGAAGC
CACCCCCGTGAACATCATCGGCGCCAAGGTGCCCCAAGGTGAAGCAGTGGCCCCTGACCGAGGAGAAGATCAAGGCCCTGACCGAGATCTGCACCGAGATGGAGAAGGAGGGCAAGATC
CGGGCATGGACGGGCCCCAAGGTGAAGCAGTGGCCCCTGACCGAGGAGAAGATCAAGGCCCTGGTGGAGATCTGCACCGAGATGGAGAAGGAGGGCAAGATC
TCCAAGATCGGCCCAGAGAACTTCGGAGAGCCCCATCAAGAAGAAGAAGGACTCCAAGAAGTGGCGCAAGCTGGTGGACGCCCT
CAAGCGCACCCAGGACTTCCTGACAAGGACTTCCGCAAGTACCACGCCTTCACCACCGCCCTCAACGAGCCCCTGTGACCGTGACCGCTACCAGTACACGTG
ACTTCTCCGTGCCCCTGGACAAGGGCTCTCCCCCGCCATCTTCCAGTGCTCTTCCGACACCACCCAAGAACCCCGACATCGTGATCTACCA
CTGCCCCAGGGCTGGAAGGGCTCTACCGTGGCGCTCCCCGACACCATCGAGAGCTGCGGACAAGATCGAGAGCTGCCGAGCAAGTGGGGCCTTCACCA
GTACATGGACGACCTGTACGTGGGCAGTGACCTGGAGATCGGCCAGCACCGGACCAAGATCGAGGAGCTGCGGCAGCTGCTGCTCGACAAG
CCCCGACAAGAGCACCAGGAAGAGCCCCTTCCTGTGGATGGGCTACGAGCTGAACCCCGACAAGTGGACCGTGCAGCCCATCGAGCTGCCCGACAAG
GACTCCCTGAACGACCTGAAGACATCCAGAAGACCGTGGGCCAAGCTGAACTGGGCCCTGCCCGAGGCCAGGCCAGGCCAGCCGCGGGACCAGGCC
GCGCGGCGCCAAGGCCCCCTGACCGAGGTGATCCAGCTGACCCGAGAGGCCGAGCTGGAGCTGGCCGAGAACCGCGAGATCCTGAAGGAGCCCCTTCAAGAACCTGAAC
TGTACTACGACCCCCTCCAAGGACCTGATCGCCGAGAAGCTGCCGCCCACACCGAGGCCAGCCAGGCCCTGAGTCCATCGTGATCTGGGG
ACCGGCAAGTACGCCAAGATGCGCTCCGCCCACACCAACGACGTGAAGCAGCTGACCGAAGCTGGGCCGAGCTGAAGCAGTCTCGCAGCAGTGGCAAGCAGCCCGAGCAGCAGCCATCCACCTGGC
CAAGACCCCCAAGTTCCGCCCGACCAAGCCCCTTGAAGGAGACCTGGGAGACCTGGTGGGCGCGGCAGCCCGAGAGCCACCGCCCACCTGGC
ACACCCCCCCCCTGGTGAAGCTGTGGTACCAGCTGGAAGAAGGTGTCCCTGACCGACCCCTGACCGACTCATCGGCAGGACTGACCCTGACGAGTGGGCCAGCCAGTCCGAGCTGGTGA
AAGGGCCAAGGCCGGCTACGTGACCGACCGGGGCCGCCAGAAGGTGGTCCCTGACCCTGGACAAGGCCGAGCGGACCCTGACCGCCATCCCAGCCAGCCAGCCAGCCCACCGGC
CCTGCAGGACTTCCGGCTGGAGCTCCGAGGTGAACATCGTGACCGACTCGCCCACTACCGGCCCCTGCCGAGGGCCATCGGCGCCAACCTGGCGCCATGGCCTTCCGACTTT
ACCAGAGATCATCGAGCAGCTGATCAAGGAGAAGGGTCCTTCCTGGACAAGAAGTTGGCCCTGAAGCGGCCATCATGCGCTCCCGGACTT
CAACCTGCCCCCCGTGGTGGCCAAAGAGATCGTGGCCAGCTGCGACAAGTGCCAGCTGAAGGGCGGAGCCCATGCATGCACTGGCAG
TCTGGCAGCTGGACTGCACCCACCTGGGGCAGCCCCTGACCCTGAAGTCCATCGAGGCCCTACACCCGCCTGCCCTGGCAGCGCAGCGCAAGAAGATCATCCGGGACTACGGCAAGCAGATGGCCCGGACCTGCATGACCAAGAGGGCAGCTTCCACCCAAGATCGGCAAG
TCATCGGCCAGGCCAACAGGCCAAGACCATCGACATCATCGCCAACGACATCCAGCACCAGCCTGGAGGTGGTGCAGAGCAGGCCAAGCTGTGTGTTGATCGGCCAGGGCCGTGGGAGGCCCATCGCAAGCAAGGGGGCCATGCGGGTACTACCG
CGACTCCCGGGACCCCCTCTGGAAAGGCCCCGGAAAGCTGCTGTGGAAGGGCGAAGGGCCTGTTCATCCTGAAGCTGGCCGGCCGCGACAAGCTGAAGGTCCATCCTCCACCATCAGCCAACCGGGGCTGTGAAGGGCCAAGCTCGCTGTGTGTGTGATCGGCCAGGTCGCAGGGCCGTGGGAGGCCCATCGCAAGCAAGGGGGCCATGCGGGTACTACCG
GCCGCAAGGCCAAGGCCAAGATCATCCGCGACTACGGCAAGCAGATGGCCGGCGACGACTGCGTGGCCGGCCGTGCAGGTGGTGCCCC
GCCGCAAGGCCAAGATCATCCGCGACTACGGCAAGCAGATGGCCGGCGACGACTGCGTGGCCGGCCGTGCAGGTGGTGCCCC
GCCGCAAGGCCAAGATCATCCGCGACTACGGCAAGCAGATGGCCGGCGACGACTGCGTGGCCGGCCGTGCAGGTGGTGCCCC
```

Fig. 115A

72. 2003_CON_F2 pol.PEP

FERENLAFQQGEARKFSSEQTRANSPASRELRVRRGDNSLPEAGAERQGTGSSLDFPQITLWQRPLVTIKVGGQLREALLDTGADDTVLEDI
NLPGKWKPKMIGGIGGFIKVRQYDQIPIEICGQKAIGTVLVGPTPVNIIGRNMLTQIGCTLNFPISPIETVPVKLKPGMDGPKVKQWPLTEE
KIKALTEICTEMEKEGKISKIGPENPYNTPVFAIKKKDSTKWRKLVDFRELNKRTQDFWEVQLGIPHPAGLKKKKSVTVLDVGDAYFSVPLD
KEFRKYTAFTIPSINNETPGIRYQYNVLPQGWKGSPAIFQSSMTKILEPFRAKNPEIVIYQYMDDLYVGSDLEIGQHRTKIEELREHLLRWG
FTTPDKKHQKEPPFLWMGYELHPDKWTVQAIQLPDKSSWTVNDIQKLVGKLNWASQIYPGIRVKHLCKLLRGAKALTDVVPLTAEAELELAE
NREILKEPVHGVYYDPSKDLIAEIQKQGHDQWTYQIYQEPHKNLKTGKYARRKSAHTNDVKQLTEVVQKIATEGIVIWGKVPKFRLPIQKET
WEIWWTEYWQATWIPEWEFVNTPPLVKLWYQLETETPIVGAETYVDGAANRETKLGKAGYVTDRGRQKVVPLTETTNQKTELQAIHLALQDS
GSEVNIVTDSQYALGIIQAHPDKSESELVNQIEQLIQKERVYLSWVPAHKGIGGNEQVDKLVSTGIRKVLFLDGIDKAQEEHEKYHSNWRA
MASDFNLPPVVAKEIVASCDKCQLKGEAMHGQVDCSPGIWQLDCTHLEGKIILVAVHVASGYIEAEVIPAETGQETAYFILKLAGRWPVKII
HTDNGSNFTSTVVKAACWWAGIQQEFGIPYNPQSQGVVESMNKELKKIIGQVRDQAEHLKTAVQMAVFIHNFKRKGGIGGYSAGERIIDIIA
TDIQTKELQKQITKIQNFRVYFRDSRDPVWKGPAKLLWKGEGAVVIQDNNEIKVVPRRKAKIIRDYGKQMAGDDCVAGRQDED$

Fig. 116A

73. 2003_CON_G pol.PEP

FFRENLAFQQGEAREFSSEQARANSPTRRELRVRRGDSPLPEAGAEGKGAISLSFPQITLWQRPLVTVKIGGQLIEALLDTGADDTVLEEIN
LPGKWKPKMIGGIGGFIKVRQYDQILIEISGKKAIGTVLVGPTPINIIGRNMLTQIGCTLNFPISPIETVPVKLKPGMDGPKVKQWPLTEEK
IKALTEICTEMEKEGKISKIGPENPYNTPIFAIKKKDSTKWRKLVDFRELNKRTQDFWEVQLGIPHPAGLKKKKSVTVLDVGDAYFSVPLDE
NFRKYTAFTIPSTNNETPGIRYQYNVLPQGWKGSPAIFQSSMTKILEPFRTKNPEIVIYQYMDDLYVGSDLEIGQHRAKIEELRELLRWGF
TTPDKKHQKEPPFLWMGYELHPDKWTVQPIQLPDKESWTVNDIQKLVGKLNWASQIYPGIKVKQLCKLLRGAKALTDIVPLTAEAELELAEN
REILKEPVHGVYYDPSKELIAEVQKQGLDQWTYQIYQEPYKNLKTGKYAKRGSAHTNDVKQLTEVVQKIATESIVIWGKTPKFKLPIRKETW
EVWWTEYWQATWIPEWEFVNTPPLVKLWYRLETETPIPGAETYYVDGAANRETKLGKAGYVTDKGKQKIITLTETTNQKAELQAIHLALQDSG
SEVNIVTDSQYALGIIQAQPDRSESELVNQIIEQLIKKEKVYLSWVPAHKGIGGNEQVDKLVSSGIRKVLFLDGIDKAQEEHERYHSNWRAM
ASDFNLPPIVAKEIVASCDKCQLKGEAMHGQVDCSPGIWQLDCTHLEGKIILVAVHVASGYIEAEVIPAETGQETAYFILKLAGRWPVKVIH
TDNGSNFTSAAVKAACWWANITQEFGIPYNPQSQGVVESMNKELKKIIGQVRDQAEHLKTAVQMAVFIHNFKRKGGIGGYSAGERIIDIIAS
DIQTKELQKQITKLQNFRVYYRDSRDPIWKGPAKLLWKGEGAVVIQDNNEIKVVPRRKAKIIRDYGKQMAGDDCVAGRQDED$

Fig. 115B

2003_CON_F2 pol.OPT

TTCTTCCGCGAGAACCTGGCCTTCCAGCAGGGCGAGGCCCGCAAGTTCTCCTCCGAGCAGACCCGCGCCAACTCCCCCGCCTCCCGCGAGCTGCGCGTGCG
CCGCGGCGACAACTCCCTGCCCGAGGCCGGCGCCGAGCGCCAGGGCACCGGCTCCTCCCTGGACTTCCCCCAGATCACCCTGTGGCAGCGCCCCCTGGTGA
CCATCAAGGTGGGCGGCCAGCTGCGCGAGGCCCTGCTGGACACCGGCGCCGACGACACCGTGCTGGAGGACATCAACCTGCCCGGCAAGTGGAAGCCCAAG
ATGATCGGCGGCATCGGCGGCTTCATCAAGGTGCGCCAGTACGACCAGATCCCCATCGAGATCTGCGGCCAGAAGGCCATCGGCACCGTGCTGGTGGGCCC
CACCCCCGTGAACATCATCGGCCGCAACATGCTGACCCAGATCGGCTGCACCCTGAACTTCCCCATCTCCCCCATCGAGACCGTGCCCGTGAAGCTGAAGC
CCGGCATGGACGGCCCCAAGGTGAAGCAGTGGCCCCTGACCGAGGAGAAGATCAAGGCCCTGACCGAGATCTGCACCGAGATGGAGAAGGAGGGCAAGATC
TCCAAGATCGGCCCCGAGAACCCCTACAACACCCCCGTGTTCGCCATCAAGAAGAAGGACTCCACCAAGTGGCGCAAGCTGGTGGACTTCCGCGAGCTGAA
CAAGCGCACCCAGGACTTCTGGGAGGTGCAGCTGGGCATCCCCCACCCCGCCGGCCTGAAGAAGAAGAAGTCCGTGACCGTGCTGGACGTGGGCGACGCCT
ACTTCTCCGTGCCCCTGGACAAGGAGTTCCGCAAGTACACCGCCTTCACCATCCCCTCCATCAACAACGAGACCCCCGGCATCCGCTACCAGTACAACGTG
CTGCCCCAGGGCTGGAAGGGCTCCCCCGCCATCTTCCAGTCCTCCATGACCAAGATCCTGGAGCCCTTCCGCGCCAAGAACCCCGAGATCGTGATCTACCA
GTACATGGACGACCTGTACGTGGGCTCCGACCTGGAGATCGGCCAGCACCGCACCAAGATCGAGGAGCTGCGCGAGCACCTGCTGCGCTGGGGCTTCACCA
CCCCCGACAAGAAGCACCAGAAGGAGCCCCCCTTCCTGTGGATGGGCTACGAGCTGCACCCCGACAAGTGGACCGTGCAGGCCATCCAGCTGCCCGACAAG
TCCTCCTGGACCGTGAACGACATCCAGAAGCTGGTGGGCAAGCTGAACTGGGCCTCCCAGATCTACCCCGGCATCCGCGTGAAGCACCTGTGCAAGCTGCT
GCGCGGCGCCAAGGCCCTGACCGACGTGGTGCCCCTGACCGCCGAGGCCGAGCTGGAGCTGGCCGAGAACCGCGAGATCCTGAAGGAGCCCGTGCACGGCG
TGTACTACGACCCCTCCAAGGACCTGATCGCCGAGATCCAGAAGCAGGGCCACGACCAGTGGACCTACCAGATCTACCAGGAGCCCCACAAGAACCTGAAG
ACCGGCAAGTACGCCCGCCGCAAGTCCGCCCACACCAACGACGTGAAGCAGCTGACCGAGGTGGTGCAGAAGATCGCCACCGAGGGCATCGTGATCTGGGG
CAAGGTGCCCAAGTTCCGCCTGCCCATCCAGAAGGAGACCTGGGAGATCTGGTGGACCGAGTACTGGCAGGCCACCTGGATCCCCGAGTGGGAGTTCGTGA
ACACCCCCCCCCTGGTGAAGCTGTGGTACCAGCTGGAGACCGAGCCCATCGTGGGCGCCGAGACCTTCTACGTGGACGGCGCCGCCAACCGCGAGACCAAG
CTGGGCAAGGCCGGCTACGTGACCGACCGCGGCCGCCAGAAGGTGGTGCCCCTGACCGAGACCACCAACCAGAAGACCGAGCTGCAGGCCATCCACCTGGC
CCTGCAGGACTCCGGCTCCGAGGTGAACATCGTGACCGACTCCCAGTACGCCCTGGGCATCATCCAGGCCCACCCCGACAAGTCCGAGTCCGAGCTGGTGA
ACCAGATCATCGAGCAGCTGATCCAGAAGGAGCGCGTGTACCTGTCCTGGGTGCCCGCCCACAAGGGCATCGGCGGCAACGAGCAGGTGGACAAGCTGGTG
TCCACCGGCATCCGCAAGGTGCTGTTCCTGGACGGCATCGACAAGGCCCAGGAGGAGCACGAGAAGTACCACTCCAACTGGCGCGCCATGGCCTCCGACTT
CAACCTGCCCCCCGTGGTGGCCAAGGAGATCGTGGCCTCCTGCGACAAGTGCCAGCTGAAGGGCGAGGCCATGCACGGCCAGGTGGACTGCTCCCCCGGCA
TCTGGCAGCTGGACTGCACCCACCTGGAGGGCAAGATCATCCTGGTGGCCGTGCACGTGGCCTCCGGCTACATCGAGGCCGAGGTGATCCCCGCCGAGACC
GGCCAGGAGACCGCCTACTTCATCCTGAAGCTGGCCGGCCGCTGGCCCGTGAAGATCATCCACACCGACAACGGCTCCAACTTCACCTCCACCGTGGTGAA
GGCCGCCTGCTGGTGGGCCGGCATCCAGCAGGAGTTCGGCATCCCCTACAACCCCCAGTCCCAGGGCGTGGTGGAGTCCATGAACAAGGAGCTGAAGAAGA
TCATCGGCCAGGTGCGCGACCAGGCCGAGCACCTGAAGACCGCCGTGCAGATGGCCGTGTTCATCCACAACTTCAAGCGCAAGGGCGGCATCGGCGGCTAC
TCCGCCGGCGAGCGCATCATCGACATCATCGCCACCGACATCCAGACCAAGGAGCTGCAGAAGCAGATCACCAAGATCCAGAACTTCCGCGTGTACTTCCG
CGACTCCCGCGACCCCGTGTGGAAGGGCCCCGCCAAGCTGCTGTGGAAGGGCGAGGGCGCCGTGGTGATCCAGGACAACAACGAGATCAAGGTGGTGCCCC
GCCGCAAGGCCAAGATCATCCGCGACTACGGCAAGCAGATGGCCGGCGACGACTGCGTGGCCGGCCGCCAGGACGAGGACTAA

Fig. 116B

2003_CON_G_pol.OPT

TTCTTCCGCGAGAACCTGGCCTTCCAGCAGGGCGAGGCCGAGTTCTCCTCCGAGCAGGCCCGGCCAACTCCCCCACCCGGCGCCCGCGAGCTGCGCGTGCG
CCGGCGGACTCCCCCCTGCCCGAGGCCGGCGAGGCCGAGGCAAGACCGGGAGCCCATCCAGATCACCCTGTGGCAGCGCCCCCTGGTGACCG
TGAAGATCGGCGGCGCCAGCTGATCGAGGCCTGCCACCAAGGGCGACACCGTCGCCCGGCAAGTGCCCGGCAAGTGGAAGCCCAAGATG
ATCGGCGGCATCGGCGGCTTCATCAAGGTGCGCCAACATGCTGAGCACCAGATCCTGCACCCTGAACTTCCCCATCCCCGAGAAGCCCAC
CCCCATCAACATCATGGCCGCCAAGGTGAAGCAGTGGCCCCTGACCGAGGAGAAGATCAAGGCCCTGACCGAGATCTGCACCGAGATGGAGAAGGAGGGCAAGATCTCC
AAGATCGGCCCCGAGAACCCTACAACACCCCTGCACCTTCGCCATCAAGAAGAAGACCCTCCAACCACCACCGCCGCAAGTGGCGCAAGTGGTGACCTTCCGCGAGCTGAACAA
GCGCACCCAGGACTTCTGGGAGGTGCAGCTGGGCATCCCCCACCCCGCCGGCCTGAAGAAGAAGAAGAGTCCGTGACCGTGCTGACCGAGACGCCTACT
TCTCCGTGCCCCTGGACGAGAACTTCCGCAAGTACACCGCCTTCACCATCCCCAGCAAGAACCGCGCTACCAGTACAACGTGCTG
CCCCAGGCCGAGGGCTGAAGGGCTCCCCGCCATCTTCCAGTCTCCATGACAAGATCTGGAGATCGGAGAGATCGCTGCGCTGGGCTTCACCACCC
CATGACGAGGACCTGTACGTGGGCTCCGTGGATGGGCCTACGAGCTGAAGTGGCAAGTGCAGCGCGATCCAGCTGTGTCACCCGCGAGAACCGGAG
TCCCTGGACCCCAGCAACGACATCCAGAGCCGTGACAAGTGGGCTGCCCCTGACCGGCGCTGGAGAGCCCGGCCTGAGCGTCGAAGAGCAGGTGCTGCGCCTGCGGCAG
CGGCCCAAGGCCGTGAAGGCCCCTGACGCATCGTGCCGCGACATCCCGAGAGGCCAGGCCGACAAGAACCTGAAGAACCTGAAAACCGAGAAGAAGAAGAC
ACTACGAGCCCCTCCAAGGAGCTGATCGCCGAGCTGCAGAAGCAGGGCCTGGACGAAATCGTTCGAGGGCCGCCTACAAGAACCTGAAGAACCCTGGGGGCCAA
GGCAAGTACGCCGCCAAGCGCGCCCGCTGCCGCCAACGGCTGTGGCCAGCCGAGGTGGTGCAGAATGCCGCCGTGCTGAGCACCGAGGGCTGATCTGGGGCAA
GACCCCAAGTTCAAGCTGCCCATCCAGAAGGAGACCTGGGAGACCTGGACCTGGACAGCCAACGCCACCTGGACCAACGCCGAGACCCGAGAGACCTGGGAGTCGTGAACA
CCCCCCCCCCTGGTGAAGCTGTGGTACCAAGCTGGAAGCCGAGATCATCCCACCTGACAAGGCCGAGGCCGAGACCGCCTACCTGGCCCAACCTGGAAGGCCCATCCACCTGGCCCT
GGCAAGGCCGGCTACGTGACCGACAAGGCCCAGAGGGTGAACATCGTGACCGACAGCCAGTACGCCCTGGGCATCATCCAGCTGCGCCTCCGGAGTCCGAGCTGGTGAACC
AGATCATCGAGCAGCTGATCAAGAAGAAGGTGTACCTGTGTCCTGGACGGCATCGAACAAGGCCGAGCAGCTGACCCAACTGGCCTCCTCCGACTTCAA
TCCCGCATCCCCTCGTGTTCCTGGACGGGATCGTCGGGCCTCTGCCGACAAGTGCCAGCTGCCCGACAACTTCGCCGACCTTCATCCACCGGCATCT
CCTGCCCCCATCGTGGCCAAGGAGATCGTGGCCAGCTGCGACAAGTGCCAAGTGCCAGCGTGCCGAGGGCCCCCGCCGAGACCGGGC
GGCAGCTGGACTGCACCCCAGGGTCAAGGGCAGCAAGATCATCCGTGGCGCCGTGCAGCGCTACATCGAGGCGGAGCTGATCCCGCGCGTGAAGGC
CAGGAGACCGGCTACGTGACCGACAAGGGCCGAGCTCCCCGCGAGTTCGGCATCCCCTACAACCCCCAGAGCCAGGGCGTGGTGGAGTCCATGAACAAGGAGCTGAAGAAGATCA
TCGGCCAGGTGCGGCCAACATCCAGCAGGCCGAGCACCTGAAGACCGCCGTGCAGATGGCCGTTCATCCACAACTTCAAGCGCAAGGGCCGGCATCGGCGGCTACTCC
GCCGGCGAGCGCATCGACACCAAGGTGCTCGACTGGAAGGGCCCCGCCCAAGATCAAGCAGCTGCCCGAAGAACTTCGGCATCCAGACCGAGGAGCTGAAGC
CTCCCCGGCTGGTGTGAAGGGCCCGAGACCGCGGCCGCGCGGCCAAGCAGATGGCCGTTCGGCGCGCCAGGACTAA

Fig. 117A

74. 2003_CON_H_pol.PEP

FFRENLAFQQREARKFSPEQARANSPTSRELRVRGDDPLSEAGAEGQGTSLSFPQITLWQRPLVTVKIEGQLREALLDTGADDTVLEEINL
PGKWKPKMIGGIGGFIKVRQYEQVAIEICGKKAIGTVLVGPTPVNIIGRNILTQIGCTLNFPISPIETVPVKLKPGMDGPKVKQWPLTEEKI
KALTEICIEMEKEGKISKIGPENPYNTPIFAIKKKDSTKWRKLVDFRELNKRTQDFWEVQLGIPHPAGLKKKKSVSVLDVGDAYFSVPLDKD
FRKYTAFTIPSINNETPGIRYQYNVLPQGWKGSPAIFQSSMTKILEPFRKQNPEMIIYQYMDDLYVGSDLEIGQHRAKIEELRAHLLRWGFT
TPDKKHQKEPPFLWMGYELHPDKWTVQPVKLPEKDSWTVNDIQKLVGKLNWASQIYPGIKVKQLCKLLRGAKALTDIVPLTKEAELELAENR
EILREPVHGVYYDPSKDLIAEIQKQGPDQWTYQIYQEPFKNLKTGKYAKMRTAHTNDVKQLTEAVQKIATESIVIWGKIPKFRLPIQKETWE
TWWTEHWQATWIPEWEFVNTPHLVKLWYQLETEPIAGAETYYVDGAANRETKIGKAGYVTDRGKQKVVSLTETTNQKTELQAIYLALQDSGL
EVNIVTDSQYALGIIQAQPDKSESELVNQIIEELIKKEKVYLSWVPAHKGIGGNEQVDKLVSSGIRKVLFLDGIDKAQEEHERYHNNWRAMA
SDFNLPPIVAKEIVASCDKCQLKGEAMHGQVDCSPGIWQLDCTHLEGKVILVAVHVASGYIEAEVIPAETGQETAYFLLKLAGRWPVKMIHT
DNGSNFTSAAVKAACWWADIQQEFGIPYNPQSQGVVESMNKELKKIIGQVRDQAEHLRTAVQMAVFIHNFKRKGGIGGYSAGERIIDIIATD
IQTKELQKQISKIQKFRVYRDSRDPIWKGPAKLLWKGEGAVVIQDNSEIKVVPRRKAKIIRDYGKQMAGDDCVAGRQDED$

Fig. 118A

75. 2003_CON_01_AE_pol.PEP

FFRENLAFQQGKAGEFSSEQTRANSPTSRKLGDGGRDNLLTEAGAERQGTSSSFSFPQITLWQRPLVTVKIGGQLKEALLDTGADDTVLEDI
NLPGKWKPKMIGGIGGFIKVRQYDQILLEICGKKAIGTVLVGPTPVNIIGRNMLTQIGCTLNFPISPIDTVPVTLKPGMDGPKVKQWPLTEE
KIKALTEICKEMEEEGKISKIGPENPYNTPVEAIKKKDSTKWRKLVDFRELNKRTQDFWEVQLGIPHPAGLKKKKSVTVLDVGDAYFSVPLD
ESFRKYTAFTIPSINNETPGIRYQYNVLPQGWKGSPAIFQSSMTKILEPFRIKNPEMVIYQYMDDLYVGSDLEIGQHRTKIEELRAHLLSWG
FTTPDKKHQKEPPFLWMGYELHPDRWTVQPIELPEKDSWTVNDIQKLVGKLNWASQIYAGIKVKQLCKLLRGAKALTDIVPLTEEAELELAE
NREILKTPVHGVYYDPSKDLVAEVQKQGQDQWTYQIYQEPFKNLKTGKYARKRSAHTNDVRQLTEVVQKIATESIVIWGKTPKFRLPIQRET
WETWWMEYWQATWIPEWEFVNTPPLVKLWYQLEKDPIVGAETFYVDGAASRETKLGKAGYVTDRGRQKVVSLTETTNQKTELHATHLALQDS
GSEVNIVTDSQYALGIIQAQPDRSESEVVNQIIEELIKKEKVYLSWVPAHKGIGGNEQVDKLVSSGIRKVLFLDGIDKAQEEHERYHSNWRT
MASDFNLPPIVAKEIVANCDKCQLKGEAMHGQVDCSPGIWQLDCTHLEGKIIIGQVREQAEHLKTAVQMAVFIHNFKRKGGIGGYSAGERII
HTDNGSNFTSAAVKAACWANVRQEFGIPYNPQSQGVVESMNKELKKIIGQVRQDNSDIKVVPRRKAKIIRDYGKQMAGDDCVAGRQDED$
TDIQTKELQKQITKIQNFRVYRDSRDPIWKGPAKLLWKGEGAVVIQDNSDIKVVPRRKAKIIRDYGKQMAGDDCVAGRQDED$

Fig. 117B

```
2003_CON_H_pol.OPT
TTCTTCCGGAGAACCTGGCCTTCCAGCAGCCCGAGGCCCGCAAGTTCTCCCCCACCTCCCCGAGCAGGCCCGGCCAACTCCCCGAGCTGCCGGTGCG
CCGCGGCGACGACCCCTGTCGCGCGAGGCCGAGGGCCGAGGGCCGGCGCCCCCCAGATCACCCTGGCAGCCGCCCCTGTGACCGTGA
AGATCGAGGGCCAGGGCCAGACCGGCCCTGCTGGACACCGGCGACGACCGTGCTGCCGGCAAGTGGAAGCCCAAGATGATC
GGGCATCGGGCGGCTTCATCATCAAGGTGCCGCAGCATCCGACCATCGGCTACGACCGTCGGCCCGTGCTGGTGGCCCACCCC
CGTGAACATCGGCCGCGCAAGATCGCTGACCCTGAGGAGAAGATCGCTGAGATCTGCCCCCATCGAGACCCGTGCCCGTGAAGCCCGGCA
TGGACGGCCCCAAGGTGAAGCAGTGGCCCCTGACCGGCGACCCCTGACCGAGATCTGCATGCCCAAGTGGCGCAAGTGTGACTTCCGGACCAG
ATCGGCCCCGAGAACCCTACAACCCCCCCATCCTTCGCCATCAAGAGAAAGACCCGCCGGCATCCCCTGAAGAAGAAGTCCGTGTCGTGGCGACGCCTACTTCT
CACCCAGGACTTCTGGAGGTGCAGTTCCGCAAGACCGTCCGCCAAGTACACCCGCCTTCACCATCCCCGCCATCGACCGAGACAACGTGCTGCCC
CGGGCTGGAAGGGCTCCCCCCGCCATCTCCAGTCCTCCAAGATCCTGGAGATCGGCCAAGCAGAACCCTTCGCGCGCCACCTGCTGCGCCGGGCTTCACCACCCCG
GACGACCTGTACGTGGGGCTTCCCTGGAGATGGCCAGCCCCCTTCCTGTGATGGGCAAGCTGGTGGACGACGCTCAAGGTGCAGCAGTGTGCAAGCTGCTGCGGG
ACAAGAAGCACCAGAAGGAGCCCCCCGTTCCTGTGTGGGATGGGCCAAGCTGGTGGCCCCTGAACTGGGCCTGACCGAGAACGGCGAAGATCCGCCGAGAAGGACTCC
TGGACCGTGAACGACGATCCAGAAGCTGGTGGCCCTGACCAAGGTGGACTACACCCGGAACTGGGCCTGCGAGATCCTGCGAGCTGTGCACGGG
CGCCAAGGCCCTGACGAGATCGTGCCCGAGAAGAGCCAGGGCCCAGGAGAAGCAGGCCGAGAATCTACCAGGAGGACCCCTTCAAGAACCTGAAGACCGGC
ACGACCCCCCTCCAAGGACCTGATCGCCGAGATCAGCAGCCCCACACGAGAAGCGTGAGGAGCAGCTGACCCGTGAACGCCGAGTCCATCGTGATCTGGGGCAAGAT
AAGTACGCCAAGATGCGCACCGCCCGGAAGAACGACCTGAACGACCCAGAGAAGATCGCCAGGAGCAGGCGATCGCCACCTGGACGCACTGTACCACCC
CCCCAAGTTCCGCTGCCCATCCAGAAGGAGATCCTCGCAGAAGTGCCAGCTGCCGACAAGTGCCCAGTGGAGGCCCAGTGACTTCGTGAACACCGG
CCACCCTGGTGTGACCGTGTGTGGTGACCGGCCAAGTGTGCTACTAGCTGCGCGGCCCAGCCGAGAGACCAAGATCGGC
AAGGCCGGCTACGTGACCGACCGGGGAAGCGCCGCAAGAAGGTGGTGTCCCTGACCGAGACCACCAACCAGAAGACCGAGCTGCAGGCCATCCAGCTGCA
GGACTCCGGCGCTGGAAGCTGAACATCGTGACCGACTCCCAGTACGCCCTGGGTGTTGCCCAGGCCCAGCCCGACAAGAGCGAGTCCGAGCTGGTGAACCAGA
TCATCGAGAGACTGATCAAGAAGAGAAGGTGTACCTGGCCTGGGTGCCCGCCCACAAGGCATGCGGCAACGAGCAGGTGGACAAGCTGGTGTCCTCC
GGCATCGGGCTGCTGTTCCTGGACGGCATCGACAAGGCGCAAGGCGATGGCAGAGCGTGTGGAGACCAAGTCTGAGACCACCAACCCGCCAGGCCCGGTGGCCGCTGACTCCGAGACCACCCCCCGAGACCGGCCAGATCG
AGATCGGCCTACTCCCAGACCCAAGCGGCAAGATCATCCCGCCGACCATCCAGGAGACTGGGCAACGTGGTGCAGGCCATGCTGACAAGGGCTGCCGCTGTTCGGCGCTACACCGACACCGGGTGATCCCCTACAGCGG
CTGCTGGCCCAGGACCGGCCCGACAAGAGCGAGAGCGAGCTGGTCAACCAGATCATCGAGCAGCTGATCAAGAAGGAGAAGGTGTACCTGGCCTGGGTGCCCGCCCAC
GCCAGGTGCCGCGCCGGCATCCGCAAGGTGCTGTTCCTGGACGGCATCGACAAGGCGCAAGGCGATGGCAGAGCGTGTGG
GCGAGCGCATCGACGTGAAGGGCCCCCGAAGCCCCCGACCAAGGGCGTGGGCGGCAACGAGCAGGTGGACAAGCTGGTGTCC
CCGGCGACCCATCTGGTGGCCCAGGACCAGTCCCAGGCCTGCGGAGCTGGTGCGGCAGATGGCGACGGCCTGCCGGACGGCACCAACAACCCCGGCCGTGTCCA
AGGCCAAGATCATCCGCGACTACGGCAAGCAGATGGCCGGCGACGACTGCGTGGCGGGCGAGCTGCCTGGCCGTGGGGCGACGAGGACGAGGACTAA
```

Fig. 118B

2003_CON_01_AE pol.OPT
TTCTTCCGGAGAACCTGGCCTTCTCCTCCGAGCAGGGCAAGGCCGGCGAGTTCTCCTCCGAGCAGAACCCGGCGCCAACTCCCCCACCTCCCCGCAAGCTGGGCGACGG
CGGCCGCGACAACCTGGCTGACGAGGCCGGCGAGGCGCGCGAGGCCCAGTCGAAGGAGGCCCTGCTGGACACCGGGCAGCCTCCTTCCTCGAGATCAACTCACCCTGGTGA
CCGTGAAGATCGGCGGCCAGCTCGTGGCGCGGCTTCATCAAGGTGCGGCTTCATCAAGGCCGTGCTGGAGGACATCAAGACCGTGCGCGAAGAAGGCCATCGACGAGATCTGCGCCAAGTGGAAGCCCAAG
ATGATCGGCGGCATCGGCTACACGCCGTGAACATGCTACGGCGCCAACATGCTGGCCAACATGCTCCCCGCCAACATGCTGGCCAACATCTCCCCATGCGACACCTCGAAGCTTCCCGATCGCGCCCTGAAGC
CACCCCGTGAAGATGAACATCGGCCCCAACATGCTGGCCCAAGTGAAGCTGAAGATCGGCGAGAGAGATCGGCGAGAGAGATCAAGGCCCCCTGACCGAGAGATCAAGGCCCCTGACCGAGAGATCAAGGCCCCTGACCGAGAGATCAAGG
CCGGCATGGACGGCCCCAAGGTGAAGCAGTGGCCCCTGACCGAGGAGAAGATCAAGGCCCTGACGAGATCAAGGCCCTGACGAGATCAAGGCCCTGACGAGATCTGCAAGGAGATCTGCAAGGAGAGGCCAAGATC
TCCAAGATCGGCCAGGGCCCGAGAACCCCTACAACACCCCCGTGTTCGCCATCAAGAAGAAGGACTCCAAGAGTGGCGCAAGCTGGTGGACTTCCGCGAGCTGAA
CAAGCGCACCCAGGACTTCTGGGAGGTCAGCTGGTCCGAGAGTCCCTTCCGGCCATCTTCCAGTCCAGTGAGATCCTGACCGTGACGGCGCGTGACGTGGGCGACGCCT
ACTTCTCCGTGCCCCCTGGAAGGCGCGACTGCGGTGGTGCTGGGTGCAAGTACACGACCGCCTTCCAGTCCGTGCCCCTGGACCGCGAAGATCCTGGAGCCCTTCAGGGGCTTCACCA
CTACATGGACGACCTGTACGTGGGCAGCGACCTGGAGATCGGCGACCGGCAGCGTCTCCCCATCAACGAGATCCTGGAGCGCATCCGCAGCAAGATCGGCCCCGAGAAG
CCCCGCCACAAGAAGCAGCACGATCCAGAGGGCACCCAGAAGGTGCGAGCTCGACACGGCCTCGACAGCAGCCCCAGGGCCCGCACGAGACCCATCGACGTGGAGTTCGTGA
GACTCCTGACCGTGAACCCTGAAGCAGCCCCCCGAGAGCTGGCGACCTGCGCGGCGGCAGATCGTGAAGTGGCCGTGCGCAGATCTGGCGCCCCGAGAACCGGCCATCCACCTGGC
GCGCGGCGCCAAGGCCCTGACCGACGTGATCCCTGGAGCTGCGGGCCTGGCCCCCAGACGACCCCTGGGACTTCATCAAGGGCAAGCTGCTCCGAGTCGAGGTGGTGA
TGTACTACGACCCCCTCAAGGACCTGGTGGCGGAGGTGGAGCAGGCCCAGGACGAGAAGCAGCGCTACCCCGAGCCCCTGCCGGTGCACGCCGAGCAGGTGCGAGCTGAAG
ACCGGCAAGTACCCCCGCAAGCGCTCCGCCCATCCGGGACGTGCTGCGCCAGCTCCACCAAGACCGGAGCACACCGCCTGCGCCACGGTGCGGACGTGCTCCCCGGAGACCAAG
CAAGACCCCCCAAGTTCCGCCATCGTGCTGAAGCTGTGGCAGCTGGAGGATCTGGATGGCGCCGCCGAGAGAGATCCGGCACGGCAGAGAGAGCCCGCATCGAGACCGGCAACCAAG
ACACCCCCCCCCGGTGTTCCGCAAGCTGGATCTTCCTACCGCTGAAGGTGGTGCCTGACCGAGATCCTCCAGATCATCGAGCCCTCCCGACCAACGGCCATCCACCTGGC
CTGCAAGGCCGTGAAGCTCGTGGGCCAGCGCGAGCTGCAGGAACATCGTGAACCCCCAGGTACGCCCCTGGGCACCAACCATCTGGACCGCGCGACCCATCCGAGGTGGTGA
CCTGCAGGACTTCCGGGTGTTCCTGAAGATGTGCTTCCGAAGACCTGCGGACACCCCGGCGCGGCTCCAGGAAGCTCCTGACCCATGGCCCTTCGACTTT
TCCTCGGCATCCCCCCAGCTGTGGCCGAAGGAGATCGTGGCCCCAGCTGCGCAAGGTGCTGCCTGAATCTCTCCCCGGGCGCGAGGTGGACTGGCCAGCCTCTCCCCCGGCA
CAACCTGCCCCCCATCGTGGCCAAGGAGATCGTGGCCAGCTGCGACAAGTGCCAACTGCGCCAAGTGCGAGGCCCAGGTGCGACTGCTCCCCCGGCA
TCTGGCAGGCCGACTGCACCCACCTGGAGGGCAAGGTGATCCTGGTGGCCGTGCACGTGGCCAGCCCGAGGCCGAGGCCCGTGATCCCCGCCGAGACC
GCCAGGAGGAGCTGCTGAAGTTCCTGTGCTGCTGGAAGCTGCCCCGAGCAGGCCACCCCCAGGGCCGCCAGGGCCGCCAGGGCCGCCAGGTCCATGACGGCGGTGAGTCGACAGAGAAGA
GGCCAGCCTGGTGGCGAGAGGCCGCTACGAGGCCCGTGGAAGCTCCAACTTCACCTCCCGCCGTGAAGAGCGCCTACTACCG
TCATCCGGCCGCCATCATGCACAACTTCCGCAAGCAGATCAAGACCATCGCCCAGAAGTACCTCCCAAGCATGAAGGGGCATCCAAGCGCAAGGTGGTGCCCCAGCCGCAAAGG
CGACTCCCGCGACCTGCTCAAGCTGGCGAGGGCCGGCGTGGTGCGGGACGACATCAACCGGCAGCGAACTCCGACATCCAGACCAGCGAGGACGAGG
GCCGCAAGCCCAAGATCATCCGCGACTACGGCAAGCAGATGGCCGGCGACGACTGCGTGGCCGGGCCGGCAAGATCGTGCCCCGCCGAGAGCGGATAA

Fig. 119A 76. 2003_CON_02_AG pol.PEP
FFRENLAFQQGEARKFSSEQTGTNSPTSRELWDGGRDNLLSEAGTEGQGTISSSFNFPQITLWQRPLVTVRIGGQLIEALLDTGADDTVLEEI
NLPGKWKPKMIGGIGGFIKVRQYDQILIEICGKKAIGTVLVGPTPVNIIGRNMLTQIGCTLNFPISPIETVPVKLKPGMDGPKVKQWPLTEE
KIKALTDICTEMEKEGKISKIGPENPYNTPVFAIKKKDSTKWRKLVDFRELNKRTQDFWEVQLGIPHPAGLKKKKSVTVLDVGDAYFSVPLD
KDFRKYTAFTIPSVNNETPGIRYQYNVLPQGWKGSPAIFQASMTKILEPFRTKNPEIVIYQYMDDLYVGSDLEIGQHRAKIEELREHLLRWG
FTTPDKKHQKEPPFLWMGYELHPDKWTVQPIQLPEKDSWTVNDIQKLVGKLNWASQIYAGIKVKQLCKLLRGAKALTDIVTLTEEAELELAE
NREILKEPVHGVYYDPTKDLIAEIQKQGQDQWTYQIYQEPFKNLKTGKYAKMRSAHTNDVKQLTEVVQKVATESIVIWGKTPKFRLPIQRET
WEAWWMEYWQATWIPEWEFVNTPPLVKLWYQLEKDPIVGAETFYVDGAANRETKLGKAGYVTDRGRQKVVSLTETTNQKTELHAIHLALQDS
GSEVNIVTDSQYALGIIQAQPDRSESELVNQIIEKLIEKDKVYLSWVPAHKGIGGNEQVDKLVSNGIRKVLFLDGIDKAQEEHERYHSNWRA
MASDFNLPPIVAKEIVASCDKCQLKGEAMHGQVDCSPGIWQLDCTHLEGKIILVAVHVASGYIEAEVIPAETGQETAYFILKLAGRWPVKVI
HTDNGSNFTSAAVKAACWWANVTQEFGIPYNPQSQGVVESMNKELKKIIGQVRDQAEHLKTAVQMAVFIHNFKRKGIGGYSAGERIIDIIA
SDIQTKELQKQITKIQNFRVYYRDSRDPIWKGPAKLLWKGEGAVVIQDNSDIKVPRRKAKIIRDYGKQMAGDDCVAGRQDED$

Fig. 120A 77. 2003_CON_03_AB pol.PEP
FFRENLAFQQREARKFSSEQTRAISPTSRKLWDGGRDNPLPETGTERQGTASSFNFPQITLWQRPLVTVRIGGQLKEALLDTGADDTVLEDI
NLPGKWKPKMIGGIGGFIKVRQYDQILIEICGKKAIGTVLVGPTPVNIIGRNMLTQLGCTLNFPISPIETVPVTLKPGMDGPKVKQWPLTEE
KIKALTDICKEMEKEGKISKIGPENPYNTPVFAIKKKDSTKWRKLVDFRELNKRTQDFWEVQLGIPHPAGLKKKKSVTVLDVGDAYFSVPLD
QDFRKYTAFTIPSTNNETPGIRYQYNVLPQGWKGSPAIFQSSMTKILEPFRKQNPEIVIYQYMDDLYVGSDLEIGQHRTKIEELREHLLRWG
FTTPDKKHQKEPPFLWMGYELHPDKWTVQPIVLPEKDSWTVNDIQKLVGKLNWASQIYAGIKVRQLCKLLRGAKALTEVIPITAEAELELAE
NREILKEPVHGVYYDPSKDLIVAEIQKQGQGQWTYQIYQEPFKNLKTGKYARLRGAHTNDVKQLTEAVQKIATESIVIWGKTPKFKLPIQKET
WETWWTEYWQATWIPEWEFVNTPPLVKLWYQLEKEPIVGAETFYVDGAANRETKSGKAGYVTDRGRQKVVSLTDTTNQKTELQAIHLALQDS
GLEVNIVTDSQYALGIIQAQPDKSESELVSQIIEQLIKKEKVYLAWVPAHKGIGGNEQVDKLVSAGIRKVLFLDGIDKAQEAHEKYHSNWRA
MASDFNLPPVVAKEIVASCDKCQLKGEAMHGQVDCSPGIWQLDCTHLEGKIILVAVHVASGYIEAEVIPAETGQETAYFVLKLAGRWPVKII
HTDNGSNFISTAVKAACWAGIKQEFGIPYNPQSQGVVESMNKQLKQIIGQVRDQAEHLKTAVQMAVFIHNFKRKGGIGGYSAGERIIDIIA
TDIQTKELQKQIIKIQNFRVYYRDSRDPIWKGPAKLLWKGEGAVVIQDNNDIKVPRRKAKIIRDYGKQMAGDDCVASRQDED$

Fig. 119B

2003_CON_02_AG_pol.OPT
TTCTTCCGGAGAACCTGGCCTTCCAGCAGGGCGAGGCCCCAAGTTCTCCTCCGAGCAGACCGGCACCAACCTCCCCGCCACCTCCCGCGAGCTGTGGGACGG
CGGCCGCGACAACCTGCTGTCCGAGGCCGGCACCGAGGGCCACCATCCCCCAGATCACCCTGTGCAAGATCACCCTGTGA
CCGTGCGCATCGGCGGCCAGCTGATCGAGGCCCTGCTGGACACCGTGCTGGAGACGACCGGCAAGTGGAAGCCCAAG
ATGATCGGGGCCATCGGCGGCTTCATCAAGGTGCGCCGACCAACATGCCGCAACATCGGCTGCTGCACATCGGCTGCCCATCGAGACCGAGCTGAAGC
CACCCCGTGAACATGGCCCCAAGGTGAAGCAGGGCCCCAAGGTGAAGCAGTGGCCCCTGACCGAGGAGATCAAGGCCCTGACCGAGGAGGCAAGATC
CGGGCATGGACGGCCCCAAGGTGAAGCAGTGGCCCCTGACCGAGGAGATCAAGGCCCTGACCGAGGAGGCAAGATC
TCCAAGATCGGCCCCGAGAACCCCTACAACACCCCGTGTTCGCCATCAAGAAGAAGGACTCCACCAAGTGGCGCAAGCTTCCGCGACGCCT
CAAGCGCACCGGGCCCCCAGGACTTCTGGGAGGTGCAGCTTCCGCCAAGTACACCGCCTTCACCACCCCGGGAGGTGCAGCTGACCGTGCTCCAGTACAACGTG
ACTTCTCCGTGCCCCCTGGACAAGGACTTCCGGGCTCCCCCGCCCTCCCAGGCCTCAGGCCTCGGCCTTCCAGCGGCTGAGAGATCGAGAACCCTGAGAAG
CTGCCCCAGGGCTGGAAGGGCTCCCCCGCCATCTTCCAGGCCTGCCCAGATCGGCGACAAGCTGGGTCTCCGTGGATGGGCAAGCTCCGAGCTCACCA
GTACATGGACGACCTGTACGTGGCCCTGGACAAGGACATCAAGGAACCAGATCGAGCTGCCCAGATCTACGCCGAGATCTACGCCAAGAACGGC
CCCCCCCCGGACAAGAAGCACCAGAAGGAGCCCCCCTTCCTGTGGATGGGCTACGAGCTGCACCCCGACAAGTGGACAGTCTCCCAGATCGGGGCAAGAG
GACTCCTGGACCGTGAACGATCCAGAAGATCCAGAATGGGCCTGGAACCTGTGACGAGCAGCAGGCCAGGCCCTTCAAGAACCTGAACAAGACCTTAACCATC
GCGGCGCAAGGCCCTGACCGAGGTGCTGCCCCTGAGCAAGGAGGCCGAGCTGGAACTGAACAACCCCTGCGGCTGGAAGCCCCGAGCTGCTGAAGGACGAGCCAACCAAG
TGTATACGACGCCCACCAAGGACCTGATCGCCCGAGATCCAGAAGCAGGGCCAGCGCGATCTACCAGATCTACCAGGAGCCTTCAAGAACCTGAAGC
ACCGGCAAGTACGCCAAGATGCGCTCCGCCCACACCAACGACGTGAAGCAGCTGACCGAGGTGGTGCAGAAGGTGGCCACCGAGAGCATCGTGATCTGGGG
CAAGACCCCCAAGTTCCGCCTGCCCATCCAGAAAGAGCACCGAGCAGCCTGGACGCCCAGGACCTGGATGCAGGCCAGCCAGCCCTTCTACGTGGAGTTCGTGA
ACACCCCCCCCTGGTGAAGCTGTGGTACCAGCTGGAGAAGGAAGATCCCAGAGGAAGTGCTCCCAGTGGTGTCCCTGACCGAGACCACCAACCAGAAGACCGAGCTGCACCGCCATCCACCTGGC
CTGCAGGACCTCCCGGTCCGGAGTGAACATCGTGACCGACAGCCAGTACGCCCTGGGCATCATCCAGGCCCAGCCCGACCGCAGCGAGCAGTGGGACG
ACCAGATCATCGAGCAGCTGATCAAGAAGGAAGAAGGAAGCAAGGTGTACCTGTCCTGGGTGCCCGCCCACAAAGGCATCGGCGGCAACGAGCAGGTGGACAAGCTGGTG
TCCAACGGCATCCGCAAGGTGCTGTTCCTGGACGGCATCGACAAGGCCCAGGACGAGCACGAGAAGTACCACAGCAACTGGCGCGCCATGGCCTCTCCGACTTT
CAACCTGCCCCCAGTTCGCGACAAGATCGTGGCCAGCTGCGACAAGTGCCAGCTGAAGGGCGAAGCCATGCACGGCAGGTGGACTGCTCCCCCGGCA
TCTGGCAGCTGGACTGCACCACCTCCACCTTCATCCTGAAGGGCAAGATCATCCTGGTGGCCGTGCCGACCATGAGCGGCTACATCGAGGCCGAGGTGATCCCCGCCGAGACC
GGCCAGGAGAGACGCGCCATCATGCGACGTGGGTTGCGGCAGTTCGGACTGAAGCCGGCCACCCTGCAGGGCGTGGTGAGCTGGTCATGAACCAAGGAGCTGAAGAGA
TCATCGGCCAGGTGCGGGAGCCAGCGACCGAGCATCATCGCCCACGAGTTCGGCATTCCTTCAAGGCCGCCCAAGGGCCCATCGGCCGCTACTAC
TCCGCCGGCGAGCGCATCATCGACATCATCGCCACCGACATCCAGACCAAGGAGCTGCAGAAGCAGATCACCAAGATCCAGAACTTCCGCGTGTACTACCG
CGACTCCCGCGATCCCGTGGAGGCCACCGGCAAGCAGATGCCCGTGCTGTGGGAGAAGGCGAGCTGGTAAACACAGGACAATCCGACACTTCAAGGGCCCC
GCCGCAAGGCCGTGGACGACTGCGTGGCCGGCCAGCAAGCAGCAGGACGAGGACTAA

Fig. 120B

2003_CON_03_AB_pol.OPT
TTCTTCCCGCGAGAACCTGGCCTTCCAGCAGCGGCCGAGGCCCGCAAGTTCTCCTCCGAGCAGAGACCCGCGCCATCTCCCCACCTCCCCGCAAGCTGTGGGACGG
CGGCCGCGACAACCCCTCGGCCGCAGCTGCCCGAGACCGGCGACCGAGCGCACCGAGGCCCTGCGCCCTTCAACTTCACCGTGGCCAGCATCACCCTGGTGA
CCGTGCCGATCGGCGGCGGCATCGGCGGTCCAGCTGAAGGAGGCCCTGCTCGGACAACCGGCCGATCAAACCTGCCCCGGCAAGTGGAAGCCAAG
ATGATCGGCGCGGTGAACATCGGCGCCAACATGTCCCCCAAGGTGCCCCCAAAGGTGAAGCAGTGGCCCCTGAACCGCCAACATCTCCCCATCTGCGAGATCTGCGGGCGG
CACCCCGTGGACGACATCATCGGCCGCAACATGTCCCCCAAGGTGAAGCAGTGGCCCCTGAACCGCCAACATCTCCCCATCTGCGAGATCTGCGGGCGG
CGGGCATGGACGGCCCCAAGGTGAAGCAGTGGCCCCTGACCGAGGAGATCAAGGCCCTGACCGAGATCGTGGAGAAGCTGGAGAAGGAGGGCAAGATC
TCCAAGATCGGCCCCGAGAACCCCTACAACACCCCCGTGTTCGCCATCAAGAAGAAGGACTCCACCAAGTGGCGCAAGCTGGTGGACTTCCGCGAGCTGAA
CAAGCGCACCCAGGACTTCTGGGAGGTGCAGCTCGGCATCCCCCACCCCGCCGGCCTGAAGAAGAAGAAGTCCGTGACCGTCTGAACGTGCGACGCCT
ACTTCTCCGTGCCCCTGGACGAGGACTTCCGCAAGTACACCGCCTTCACCCTGCCCTCCATCAACAACGAGACCCCCGGAGATCCGGGCTTCACCA
CTGCCCAGGGCTGGAAGGGCTCCCCCGCCATCTTCCAGTCCAGCATGACCAAGATCCTGGAGCCCTTCCGCAAGCAGAACCCTGACCGTGCTGCCCGAGAAG
GTACATGACGACGACCTGTACGTGGGCTCCGACCTGGAGATCGGCCAGCACCGAGCACTGAGGCCCTGGAGCAGTGCCGGCCACCGTCAACGTGCGCAGCTGCT
CCCCGACAAGAAGCACCAGAAGACATCCAGAAGCTCGGGCCGCAGCTGGTGCCCCTGACCGAGGAGATCCAGAAACTGATCGCCAGCTGTCGCCGAGAAG
GACTCCTGGACCGTGAACGCCCCTGAAGGGCCCCAAGCTGGTGCCCCTGACCGAGGAGATCCAGAAACTGATCCTGCACCCGCCCTGGAACCCTGACGG
GCGGGCGCGCAAGGCCCTGACCGAGGTGATCCCCGAGGGCCCGCGAGCTACCCAGGACTCCCAGTGGACCTGCCCGAGTCCGAGCTGGTGT
TGTACTACGACCCCTCCAAGGACCTGATCGGCGAGTACGGCAAGCTGACCAAGAGCAGGCCTACCAGATCTACCAGAGCCCCCTTCAAGAACCTGAAG
ACCGGCAAGTACGCCCGCCTGCGCGCACACCCAGAAGACGTCTGAAGCAGCTGGCCGGCCAGCAGTTCATCGTCCATCGGAGTCGTGGGG
CAAGACCCCCAAGTTCAAGCTGCCCATCCAGAAGGAGACCTGGGAGACCTGGTGGACCGAGTACCCCGGCTGATCGGGCCACCTGGGAGTTCGTGA
ACACCCCCCCCCTGGTGAAGCTGTGGTACCAGCTGGAGAAGGAGCCCATCGTGGGCGCCGAGACCTTCTACGTGGACGCCTCCTGCAACCGCGAGACCAAG
TCCGGCAAGGCCGGCTACGTGACCGATCGGCGGAAGAAGGCCGTGAAGCCCATCCTGAGACCTGGGCCAGCGCCAGTCGAGATCCGAGCTGGTGT
CCTGCAGGACTCCCGGTTCGGCTTCCTGTGCTCAGGAGAGTGAACATCGTGACCGACTCCCAGTACGCCCTGGGTATCCGCCTGCGCTGGACAAGCTGGTG
CCAGATCATCGAGCAGCTGATCAAGAAGGAGAAGGTGTACCTGGCCTGGGTGCCCGCCCACAAGGGCATCGGCGGCAACGAGCAGGTGGACAAGCTGGTG
TCCGCCGGCATCCGCAAGGTGCTGTTCCTGGACGGCATCGACAAGGCCCAGGACGAGCACGAGAAGTACCACTCCAACTGGCGCGCCATGGCCTCCGACTT
CAACCTGCCCCCGGTGGTGGCCAAGGAGATCGTGGCCTCCTGCGACAAGTGCCAGCTGAAGGGCGAGGCCATGCACGGCCAGGTGGACTGCTCCCCGGCA
TCTGGCAGCTGGACTGCACCCACCTTGAGCTGCTGTGTGACCAAGGGCCAGAGATCATCCTGGGTGGCCGTGCACGTGGCCTCCGGCTACATCGAGGCCGAGGTGATCCCCGCCGAGACC
GGCCAGGAGACAGCCTACTTCGTGCTGAAGCTGGCCGGCAGATGTTCGGAGTTCAAGCGCCGAGATCCAACTTCAAGATCCAGAACTTCCGCGTGTACTACCG
GGCCCCTGCTGTGGGCCATCAAGGCCCGAGCCAGCCGAGAGTTCGGGCCACCTGCCCACCCCAGTCCCCAGTGGTGAGTCCAACTTCAAGCGCAAGGGCGGCATCGGCGGCTAC
TCCGCCGGGAGCGCCTGGTGGACGTGGGTCCCAGACCGACGCGCAGCAAGGCCCCCAAGCCAAGCAAGCAGGCCCGTGTGAGGCGCGGCGACTGGCGTGGGAGATGGCCGGCCAAGGCCAAGGAAGGGCGAGGCCTCCCCGCCCGCGAGACC
GCCGCAAGGCCAAGATCATCCGCGACTACGGCAAGCAGGTGGCCGGCGACGACTGCGTGGCCAGCCGGCAAGGAACGAGGCCTCCCCGCCCGCGAGACC

Fig. 121A 78. 2003_CON_04_CPX_pol.PEP

FFRENVAFQQREARKFSSEQARANSPARRELRDERGDNLLSEAGTEGQGTISENFPQITLWQRPLVTIKIGGQIREALLDTGADDTVLEEIN
LPGKWKPKMIGGIGGFIKVRQYDQIPIEICGKKAIGTVLVGPTPVNIIGRNMLTQLGCTLNFPISPIETVPVKLKPGMDGPKVKQWPLTEEK
IKALTEICTEMEKEGKISKIGPENPYNTPIFAIKKKNSTRWRKLVDFRELNKRTQDFWEVQLGIPHPAGLKKKKSVTVLDVGDAYFSVPLDP
EFRKYTAFTIPSTNNETPGIRYQYNVLPQGWKGSPAIFQCSMTKILEPFRTKNPEIVIYQYMDDLYVGSDLEIGQHRAKIEELRELHLLRWGF
STPDKKHQKEPPFLWMGYELHPDKWTVQPIQLAEKDSWTVNDIQKLVGKLNWASQIYPGIKVKQLCKLLRGAKALTDIVPLTTEAELELAEN
REILKEPVHGAYDPSKDLIAEIQKQGQGQWTYQIYQEPYKNLKTGKYAKTRSAHTNDVRQLTEAVQKIAMECIVIWGKTPKFRLPIQKETW
DTWWTEYWQATWIPEWEFVNTPPLVKLWYQLETDPIAGAETFYVDGAASRETKQGKAGYVTDRGRQKVVSLSETTNQKTELQAIYLALQDSG
SEVNIVTDSQYAIGIIQAPDRSESDLVNQIIEQLIQKDKVYLSWVPAHKGIGNEQVDKLVSNGIRKVLFLDGIDKAQEEHEKYHNNWRAM
ASDFNLPPVVAKEIVASCNKCQLKGEAMHGQVDCSPGIWQLDCTHLEGKIILVAVHVASGYIEAEVIPAETGQETAYFILKLAGRWPVKIIH
TDNGPNFTSAAVKAACWWADIQQEFGIPYNPQSQGVVESMNKELKKIIGQVRDQAEHLKTAVQMAVFIHNFKRKGGIGGYSAGERIIDIIAS
DIQTKELQKQITKIQNFRVYYRDSRDPIWKGPAKLLWKGEGAVVIQDNSDIKVPRRKAKIIRDYGKQMAGDDCVAGRQDEDS

Fig. 122A 79. 2003_CON_06_CPX_pol.PEP

FFRENLAFQQGEAREFSSEQARANSPTRRELRVRRGDSPLPEAGAEGQGAISLSFPQITLWQRPLVTVRIGGQLIEALLDTGADDTVLEDIN
LPGKWKPKMIGGIGGFIKVRQYDQILIEICGKKAIGTVLVGPTPVNIIGRNMLTQIGCTLNFPISPIETVPVKLKPGMDGPKVKQWPLTEEK
IKALTEICTEMEKEGKISKIGPENPYNTPIFAIKKKDSTKWRKLVDFRELNKRTQDFWEVQLGIPHPAGLKKKKSVTVLDVGDAYFSVPLDE
DFRKYTAFTIPSINNETPGIRYQYNVLPQGWKGSPAIFQSSMIKILEPFRIKNPEIVIYQYMDDLYVGSDLEIGQHRAKIEELRELHLLKWGF
TTPDKKHQKEPPFLWMGYELHPDKWTVQPIQLPDKDSWTVNDIQKLVGKLNWASQIYPGIKVKQLTEAVQKIALESIVIWGKTPKFRLPIQKETW
ETWWTEYWQATWIPEWEFVNTPPLVKLWYQLETETPIVGAETFYVDGAANRETKKGKAGYVTDRGRQKVVSLTETTNQKTELQAINLALQDSG
SEVNIVTDSQYALGIIQAPDKSESELVNQIIEQLIKKEKVYLSWVPAHKGIGNEQVDKLVSTGIRKVLFLDGIDKAQEDHERYHSNWRAM
ASDFNLPPIVAKEIVASCDKCQLKGEAMHGQVDCSPGIWQLDCTHLEGKIILVAVHVASGYIEAEVIPAETGQETAYFILKLAGRWPVKVIH
TDNGSNFTSAAVKAACWWANITQEFGIPYNPQSQGVVESMNKELKKIIGQVRDQAEHLKTAVQMAVFIHNFKRKGGIGGYSAGERIIDIIAS
DIQTKELQKQITKIQNFRVYYRDSRDPIWKGPAKLLWKGEGAVVIQDNSEIKVPRRKAKIIRDYGKQMAGDDCVAGRQDEDS

Fig. 121B

2003_CON_04_CPX_pol.OPT
TTCTTCCGGAGAACGTGGCCTTCCGAGCAGCGCGAGGCCCGGCGCAACTCCCCCGGCGCGAGGCCCGGCGAGCTGCGCGACGA
GCGGCGGCGACAACCTGCTGTCCGAGGCCGGCACCGAGGGCCGGGCCGAGGCCCTGCTGGACACCCTGCTGGCAGCGCCCTGTGACCA
TCAAGATCGGCGGCCAGATCCGCGAGGCCGGCGGCTTCATCATCAAGGTGCGCCAGTACGACCAGATCTGCGAGAAGGCCACCTGCCGTGTGAAGATG
ATCGGCGCGGCCGGCTTCATCATCAAGGTGCGCCAGTACGACCAGATCTGCGAGAAGGCCACCTGCCGTGTGTGAAGCTGAAGCCCAC
CCCGTGAACATCATCGGCGCAACATGGCCCAGCTGGGCTGCACCCTGAACTTCCCCATCTCCCCATCGAGACTCCCCCGTGCCCGTGAAGCTG
GCATGGACGGCCCCAAGTGAAGCAGTGGCCCCTGACCGAGAAGATCAAGGCCCTGACCGAGATCTGCACCGAGATGTGACCGAGAAGGGCCAAGATCTCC
AAGATCGGCCCCGAGAACCCTGCACACACCCCCATCTTCGCCATCAAGAAGAACTCCAAGCCCTGCCCAAGCTGGTGTGGACTTCCGCGAGCTGAACAA
GCGCACCCAGGACTTCTGGGAGGTGCAGCTGGGCATCCCCCACCCCGCGCCCCTGTGGCCCTGAAGATCTGGCCCGCTGGGCGACGCCTACT
TCTCCGTGCTGGACCCCGAGTTCCGCAAGTTCCGCAAGTACACACCGAGTCCGCCATCGACACCCCGAGATCCGCTACCAGTGTACACCGTG
CCCCAGGGCTGGAAGGGCTCCCCCGGGCCTCCGACATCAAGACCTGCCCAAGCTCTGGAGCCTGGTGCGCTGGGGCTTCTCCACCC
CATGGACGACCTGTACGTGGGCTACAATCCAGAAGGAGCCCCCATCCAGAAGAACCGTGCCCGAAGCTGGAAGCGAGATCCAGGACCAGCTGTGCAAGGAC
TCCTGGACCGTGAACGACATCCAGAAGCTGGTGGCCAAGCTGAACTGGGCCTCCCAGATCTACCCCGGCATCAAGGTGCAAGCAGTGTGCAAGGCCCGTGCC
CGGCCGCCAAGGCCCTGACCGACGTGATCCCCCTGACCGAGGAGGCCGAGCTGGAGCTGGCCGAGAACCGGAGCCGAGCCGTGGCCCTGCAAGGCCCGTGCACGGCGCCT
ACTACGACCCCCTCCAAGGACCTGATCGCCCAGAAGCAGGGCCAGTGATGGCCCAGATCGACCAGATCTACCCAGGAGCCCCTACAAGAACCTGAAGACC
GGCAAGTACGCCAAGATGCGCGGCGCCCACAACGACGTGCGCCAGCTGACCGAGGCGGTGGCCCAGAAGCTGATCGCGATCGTGATCTGGGGCAA
GACCCCCCAAGTTCCGCCTGCCCATCCAGAAGGAGACCTGGGAGATCTGGTGGACCACTGATCGCCGGGCCCAGGAGCCTTCTACGTGGATCGGCCCCCGGAGATCAAGCAG
CCCCCCCCCGTGTGAAGCTACGTGGCCTCCGAGAGCGAGCTCCGAGCTCCCAAGAGACCAGGCCTCGGCGCAGACCGGCCCCCGGAGACCAAGCAG
GGCCTGCTGTGGAAGCCGGCTACGTCCGAGGTGAACATCGTGACCGACAAGGTGTACCTGTCCCAGGCGCTCCCAGTTCGGCTTCCGCCAGCCAGTCCCAGCCTCTGGCCCT
GCAGGACTCCGGCCCTGAGGTGAACATCGTGACCGACAAGGTGTACCTGTCCTGGGTGCCCGCGCACAAGGGCATCGGCGGCAACGAGCAGGTGGACAAGCTGGTGAACC
AGATCATCGAGCAGCTGATCAAGAAGGAGAAGGTGTATCCAGAGGAGCATCGCCCGGGCGCCATGGCGCCACGATGCGCCCCCGGATCAGAGTCCCAGACTTCAA
AACGGCATCCGGCAAGTGCTGTTCCTGGACGGCATCGACAAGGCCCAGGAGGAGCACGAGAAGTACCACAGCACCGAGGCCCGCCACAACTGGCGCGCGCCATGGCCTCCGACTTCAA
CCTGCCCCCCGTGGTGGCCAAGGAGATCGTGGCCTCCTGCAACAAGTGCCAGCTGAAGGGCGAGGCCATGCACGGCCAGGTGGACTGCTCCCCCGGCATCT
GGCAGCTGGACTGCACCCACCTGAGCCCGCAAGATCATCCTGGTGGCTGTCCAGCACCACATCTCCGGCATCATCGAGGCCCAAGGGCCGAGGTGAT
CAGGAGAGCAACTCCGCCTACTTCATCATCGGAGAGTTCGGCATCCCCTACAACCCCCAGTCCCAGGGCGTGGTGGAGTCCATGAACAAGGAGCTGAAGAAGATCA
TCGGCCAGGTGCGCGACCAGGCCGAGCACCTGAAGACCGCCGTGCAGATGGCCGTGTTCATCCACAACTTCAAGCGCAAGGGCGGCATCGGCGGCTACTCC
GCCGGCGAGCGCATCGTGGACATCATCGCCACGGCAGATCAAGCAGTTCGCCCCGCCCCCAAGGCCCCCGACATCATCAGGACAACTCCGACATCAAGGTGGTGCCCCGCC
CTCCCCGGCCAGATCATCCGCGACTACGCCAAGCCCCCGACGACTGCGCTGGCCCGACGACGAGGACTAA

Fig. 122B

2003_CON_06_CPX pol.OPT

TTCTTCCGCGAGAACCTGGCCTTCCAGCAGGGCGAGGCCCGCGAGTTCTCCTCCGAGCAGGCCCGCGCCAACTCCCCCACCCGCCGCGAGCTGCGCGTGCG
CCGCGGCGACTCCCCCCTGCCCGAGGCCGGCGCCGAGGGCCAGGGCGCCATCTCCCTGTCCTTCCCCCAGATCACCCTGTGGCAGCGCCCCCTGGTGACCG
TGCGCATCGGCGGCCAGCTGATCGAGGCCCTGCTGGACACCGGCGCCGACGACACCGTGCTGGAGGACATCAACCTGCCCGGCAAGTGGAAGCCCAAGATG
ATCGGCGGCATCGGCGGCTTCATCAAGGTGCGCCAGTACGACCAGATCCTGATCGAGATCTGCGGCAAGAAGGCCATCGGCACCGTGCTGGTGGGCCCCAC
CCCCGTGAACATCATCGGCCGCAACATGCTGACCCAGATCGGCTGCACCCTGAACTTCCCCATCTCCCCCATCGAGACCGTGCCCGTGAAGCTGAAGCCCG
GCATGGACGGCCCCAAGGTGAAGCAGTGGCCCCTGACCGAGGAGAAGATCAAGGCCCTGACCGAGATCTGCACCGAGATGGAGAAGGAGGGCAAGATCTCC
AAGATCGGCCCCGAGAACCCCTACAACACCCCCATCTTCGCCATCAAGAAGAAGGACTCCACCAAGTGGCGCAAGCTGGTGGACTTCCGCGAGCTGAACAA
GCGCACCCAGGACTTCTGGGAGGTGCAGCTGGGCATCCCCCACCCCGCCGGCCTGAAGAAGAAGAAGTCCGTGACCGTGCTGGACGTGGGCGACGCCTACT
TCTCCGTGCCCCTGGACGAGGACTTCCGCAAGTACACCGCCTTCACCATCCCCTCCATCAACAACGAGACCCCCGGCATCCGCTACCAGTACAACGTGCTG
CCCCAGGGCTGGAAGGGCTCCCCCGCCATCTTCCAGTCCTCCATGATCAAGATCCTGGAGCCCTTCCGCATCAAGAACCCCGAGATCGTGATCTACCAGTA
CATGGACGACCTGTACGTGGGCTCCGACCTGGAGATCGGCCAGCACCGCGCCAAGATCGAGGAGCTGCGCGAGCACCTGCTGAAGTGGGGCTTCACCACCC
CCGACAAGAAGCACCAGAAGGAGCCCCCCTTCCTGTGGATGGGCTACGAGCTGCACCCCGACAAGTGGACCGTGCAGCCCATCCAGCTGCCCGACAAGGAC
TCCTGGACCGTGAACGACATCCAGAAGCTGGTGGGCAAGCTGAACTGGGCCTCCCAGATCTACCCCGGCATCAAGGTGAAGCAGCTGTGCAAGCTGCTGCG
CGGCGCCAAGGCCCTGACCGACATCGTGCCCCTGACCGCCGAGGCCGAGCTGGAGCTGGCCGAGAACCGCGAGATCCTGAAGGAGCCCGTGCACGGCGTGT
ACTACGACCCCTCCAAGGACCTGATCGCCGAGATCCAGAAGCAGGGCCAGGGCCAGTGGACCTACCAGATCTACCAGGAGCCCCACAAGAACCTGAAGACC
GGCAAGTACGCCCGCATCAAGTCCGCCCACACCAACGACGTGAAGCAGCTGACCGAGGCCGTGCAGAAGATCGCCCTGGAGTCCATCGTGATCTGGGGCAA
GACCCCCAAGTTCCGCCTGCCCATCCAGAAGGAGACCTGGGAGACCTGGTGGACCGAGTACTGGCAGGCCACCTGGATCCCCGAGTGGGAGTTCGTGAACA
CCCCCCCCCTGGTGAAGCTGTGGTACCAGCTGGAGACCGAGCCCATCGTGGGCGCCGAGACCTTCTACGTGGACGGCGCCGCCAACCGCGAGACCAAGAAG
GGCAAGGCCGGCTACGTGACCGACCGCGGCCGCCAGAAGGTGGTGTCCCTGACCGAGACCACCAACCAGAAGACCGAGCTGCAGGCCATCAACCTGGCCCT
GCAGGACTCCGGCTCCGAGGTGAACATCGTGACCGACTCCCAGTACGCCCTGGGCATCATCCAGGCCCAGCCCGACAAGTCCGAGTCCGAGCTGGTGAACC
AGATCATCGAGCAGCTGATCAAGAAGGAGAAGGTGTACCTGTCCTGGGTGCCCGCCCACAAGGGCATCGGCGGCAACGAGCAGGTGGACAAGCTGGTGTCC
ACCGGCATCCGCAAGGTGCTGTTCCTGGACGGCATCGACAAGGCCCAGGAGGACCACGAGCGCTACCACTCCAACTGGCGCGCCATGGCCTCCGACTTCAA
CCTGCCCCCCATCGTGGCCAAGGAGATCGTGGCCTCCTGCGACAAGTGCCAGCTGAAGGGCGAGGCCATGCACGGCCAGGTGGACTGCTCCCCCGGCATCT
GGCAGCTGGACTGCACCCACCTGGAGGGCAAGATCATCCTGGTGGCCGTGCACGTGGCCTCCGGCTACATCGAGGCCGAGGTGATCCCCGCCGAGACCGGC
CAGGAGACCGCCTACTTCATCCTGAAGCTGGCCGGCCGCTGGCCCGTGAAGGTGATCCACACCGACAACGGCTCCAACTTCACCTCCGCCGCCGTGAAGGC
CGCCTGCTGGTGGGCCAACATCACCCAGGAGTTCGGCATCCCCTACAACCCCCAGTCCCAGGGCGTGGTGGAGTCCATGAACAAGGAGCTGAAGAAGATCA
TCGGCCAGGTGCGCGACCAGGCCGAGCACCTGAAGACCGCCGTGCAGATGGCCGTGTTCATCCACAACTTCAAGCGCAAGGGCGGCATCGGCGGCTACTCC
GCCGGCGAGCGCATCATCGACATCATCGCCTCCGACATCCAGACCAAGGAGCTGCAGAAGCAGATCACCAAGATCCAGAACTTCCGCGTGTACTACCGCGA
CTCCCGCGACCCCATCTGGAAGGGCCCCGCCAAGCTGCTGTGGAAGGGCGAGGGCGCCGTGGTGATCCAGGACAACTCCGAGATCAAGGTGGTGCCCCGCC
GCAAGGCCAAGATCATCCGCGACTACGGCAAGCAGATGGCCGGCGACGACTGCGTGGCCGGCCGCCAGGACGAGGACTAA

Fig. 123A 80. 2003_CON_08_BC_pol.PEP
FFREILAFPQGEAREFPPEQTRANSPTSRELQVRGDNPSSEAGTERQGTLNFPQITIWQRPLVSIKVGGQIKEALLDTGADDTVLEEVNLPG
KWKPKMIGGIGGFIKVRQYEQIPIEICGKKAIGTVLVGPTPVNIIGRNMLTQLGCTLNFPISPIETVPVKLKPGMDGPKVKQWPLTEEKIKA
LTAICDEMEKEGKITKIGPDNPYNTPIFAIRKKDSSKWRKLVDFRELNKRTQDFWEVQLGIPHPAGLKKKKSVTVLDGDAYFSVPLDKDFR
KYTAFTIPSVNNETPGIRYQYNVLPQGWKGSPAIFQCSMTKILEPFRKQNPDIVIYQYMDDLYVGSDLEIGQHRTKIEELREHLLKWGFTTP
DKKHQKEPPFLWMGYELHPDKWTVQPIQLPEKDSWTVNDIQKLVGKLNWASQIYPGIKVRQLCKLLRGAKALTDIVPLTEEAELELAENREI
LKEPVHGAYYDPSKELLIAEIQKQGQDQWTYQIYQEPFKNLKTGKYAKMRTAHTNDVKQLTEAVQKIAMESIVIWGKIPKFRLPIQKETWETW
WTDYWQATWIPEWEFVNTPPLVKLWYQLEKDPIAGVETFYVDGAANRETKIGKAGYVTDRGRKKIVSLTDTTNQKTELQAIYIALQDSGSEV
NIVTDSQYALGIIQAQPDKSESELVNQIIEQLIKKERVYLSWVPAHKGIGNEQVDKLVSNGIRKVLFLDGIDKAQEEHEKYHSNWRAMASD
FNLPPIVAKEIVASCDQCQLKGEAMHGQVDCSPGIWQLDCTHLEGKIILVAVHVASGYIEAEVIPAETGQETAYFILKLAGRWPVKVIHTDN
GSNFTSAAVKAACWWAGIQQEFGIPYNPQSQGVVESMNKELKKLIGQVRDQAEHLKTAVQMAVFIHNFKRKGGIGGYSAGERIVDIIATDIQ
TRELQKQIIKIQNFRVYYRDSRDPIWKGPAKLLWKGEGAVVIQDNSDIKVVPRRKAKIIKDYGKQMAGADCVAGRQDED$

Fig. 124A 81. 2003_CON_10_CD_pol.PEP
FFRENLAFQQRKARELPSEQTRANSPTSRELRVWGGDNTLSETGAERQGAVSLSFPQITLWQRPLVTVKIGGQLKEALLDTGADDTVLEEMN
LPGKWKPKMIGGIGGFIKVRQYDQILIEICGYKAIGTVLVGPTPVNIIGRNLLTQIGCTLNFPISPIETVPVKLKPGMDGPKVKQWPLTEEK
IKALTEICTEMEKEGKISRIGPENPYNTPIFAIKKKDSTKWRKLVDFRELNKRTQDFWEVQLGIPHPAGLKKKKSVTVLDVGDAYFSVPLYE
DFRKYTAFTIPSINNETPGIRYQYNVLPQGWKGSPAIFQSSMTKILEPFRKQNPEMVIYQYMDDLYVGSDLEIGQHRIKIEELRGHLLKWGF
TTPDKKHQKEPPFLWMGYELHPDKWTVQPIQLPEKDSWTVNDIQKLVGKLNWASQIYPGIKVRQLCKLLRGAKALTDIVPLTEEAELELAEN
REILKEPVHGVYYDPSKDLIAEIQKQGQDQWTYQIYQEPHKNLKTGKYAKRRTAHTNDVKQLTEAVQKIAQESIVIWGKTPKFRLPIQKETW
ETWWTDYWQATWIPEWEFVNTPPLVKLWYQLEKEPIVGAETFYVDGAANRETKLGKAGYVTDRGRQKVISITDTTNQKTELQAINLALQDSG
SEVNIVTDSQYALGIIQAQPDKSESELVNQIIEQLIKKEKVYLSWVPAHKGIGGNEQVDKLVSSGIRKVLFLDGIDKAQEEHEKYHNNWRAM
ASDFNLPPVVAKEIVASCDKCQLKGEALHGQVDCSPGIWQLDCTHLEGKVILVAVHVASGYIEAEVIPAETGQETAYFLLKLAGRWPVKVVH
TDNGSNFTSAAVKAACWWAGIKQEFGIPYNPQSQGVVESMNKELKKIIGQVRDQAEHLKTAVQMAVFIHNFKRKGGIGGYSAGERIIDIIAT
DIQTKELQKQIIKIQNFRVYYRDSDIKVVPRRKVKIIKDYGKQMAGADCVASRQDEDQ

Fig. 123B

2003_CON_08_BC_pol.OPT

```
TTCTTCCGCGAGATCCTGGCCTTCCCCCAGGGGCGAGGCCCGAGTTCCCCCCAGGCAGACCCGGCAGGCCCGAGCTGCCGAGTGTGCG
CGGCGACAACCCCTCCTCCGAGGCCGGCCAGCCGCCAGGCCACCGAGCGCCCAGATCACCCTGTGCAGCGCCCCTGTGTCCATCAAGTGG
GCGGCCAGAGATCAAGGAGGCCCTGCTGGACACCGGCCGACACCTGCTGGAGGAGGTGAACCTGCCCGGCAAGTGGAAGCCCAAGATGATCGGCGGC
ATCGGCGGCTTCATCAAGGTGCGCCAGTACGAGCAGATCCCCGTCGAGCTTCCCCATCTCCCCATGGACCGTGCCCGTGAAGCCGGCATGGACG
CATCATGGCCCAAGCATGCTGACCAGCTGGCCCCTGACCGAGGAGAAGATCAAGGCCCTGACCGAGATCTGCAAGGACATGGAGGAGGCCAAGATCACCAAGATCGGC
GCCCAAGGTGAAGCAGTGGCCCCTGACCGAGGAGAAGATCAAGGCCCTGACCGAGATCTGCAAGGACCTGGAGAAGGAGGGCAAGATCAGCAAGATCGGC
CCCGACAACCCCTACAACACCCCCATCTTCGCCATCAAGAAGAAGGACTCCTCCAAGTGGCGCAAGCTGGTGGACTTCCGCGAGCTGAACAAGCGCACCCA
GGACTTTCTGGGAGGTGCAGCTTCCGCAAGTACACCGCCTTCACCATCCCCTCGTGAACAGCCTGTGCGACGTCCGGCGACCCCTACTTCTCCGTGC
CCCTGGACGAAGGACTTCCGCAAGTACACCGCCTTCACCATCCCCCTCCGTGAACAGCCTGTGCGACGTCCGGCGACCCCTACTTCTCCGTGC
TGGAAGGGCTCCCCGGCCATCTCCAGTGCTCCATGACCAGCACCTGGAGCTGGCCTTCACCCCCGACAAGAGCTGCTGCGAGGACTCCTGGACC
CCTGTACGTGGGCTCCCCCGACCTGGAGACTGGCGAGATCGGCGATGGGCCAAGCTGACTGAACTGGGGCCAGAGGAGCTGTGCCGAGCTCGACGA
AGCACCCAGAAGGAGCATCCCGAGGATCCTGTGGATGGGCCAGCTGGAGGAGGCCAGTGGTCCGAGATCTACCGGGCCTACAGGGCCCAGTAC
GTGAACGACATCCAGAAGCTGTGCCCCCTGACCAGTGGGCCGAGCTGAACTGGGGCCAGCTGGAGGAGGCCCTTCAAGGAACCTGAAGAACCTGAAGAACCTGGAAGTAC
GGCCCCCTGACCGACATCGTGCCCCTGACCGAGGAGCAGCTGGACGACCTGACCAGGACCGAGCCGTGACCAGCGTGTGCCGGCCTACTACGACC
CGGCTCCGAGGTGAACATCGTGACCGACTCCCAGTACGCCCTGGGCATCATCCAGGCCCAGCCGACAAGTCCGAGTCGTGAACCAGATCATCG
AGCAGCTGATCAAGAAGGAGCGCGTGTACCTGTGTCCTGGTGCCCGCGGCAGCATCCCCAAAGGGCCATGCCCAAGAGCTGGACAAGCTGGTGTCCACTTCAACGGCATC
CGCCAAGATGCTGTTCCTGACGGCATCCGACAAGGCCACACTCCACTCCAACTGCCCATGCCTTCCCCCCGCCATCTGGCCAGCTGG
GTTCCCGCGACCAGCTGTTCCCTGACGGCATCCGACAAGGCCACACTCCACTCCAACTGCCCATGCCTTCCCCCCGCCATCTGGCCAGCTGG
TGGTGAAGCTGTGTGGTGACCGGCGGCCGCCAAGAGATCGTGCCCGGGCACTCCCGGCCCTGACCGAGGAGGTGATCCCCGCCGAGACCGGCCAGGAGACC
GGCTACGTGGACCGCGGCCGCCAAGAGATCGTGCCCCTGACCGAGGGCATCCGAGGCTGGTGGCCCTGACCGAGGAGGTGATCCCCGCCGAGACCGGCCAGGAGACC
CGGCTCCGAGGTGAACATCGTGACCGACTCCCAGTACGCCCTGGGCATCATCCAGGCCCAGCCGACAAGTCCGAGTCGTGAACCAGATCATCG
AGCAGCTGATCAAGAAGGAGCGCGTGTACCTGTCCTGGTGCCCGCGGCAGCATCCCCCAAGGGCCATGCCCAAGAGCTGGACAAGCTGGTGTCCACTTCAACGGCATC
CGCCAAGATGCTGTTCCTGACGGCATCCGACAAGGCCACACTCCACTCCAACTGCCCATGCCTTCCCCCCGCCATCTGGCCAGCTGG
GTTCCCGCGACCAGCTGTTCCCTGACGGCATCCGACAAGGCCACACTCCACTCCAACTGCCCATGCCTTCCCCCCGCCATCTGGCCAGCTGG
TGGTGAAGCTGTGTGGTGACCGGCGGCCGCCAAGAGATCGTGCCCGGGCACTCCCGGCCCTGACCGAGGAGGTGATCCCCGCCGAGACCGGCCAGGAGACC
GGCTACGTGGACCGCGGCCGCCAAGAGATCGTGCCCCTGACCGAGGAGCAGCTGGACGACCTGACCAGGACCGAGCCGTGACCAGCGTGTGCCGGCCTACTACGACC
CGGCTCCGAGGTGAACATCGTGACCGACTCCCAGTACGCCCTGGGCATCATCCAGGCCCAGCCGACAAGTCCGAGTCGTGAACCAGATCATCG
AGCAGCTGATCAAGAAGGAGCGCGTGTACCTGTCCTGGTGCCCGCGGCAGCATCCCCCAAGGGCCATGCCCAAGAGCTGGACAAGCTGGTGTCCACTTCAACGGCATC
TGCCGCCAGCCGCCGAGCCGAGCCGAGCCGTGTTCATCCAGATGGCCGTGTTCATCCACAACTTCAAGCGCAAGGGCGGCATCGGCGGCTACTCCGCGGCGAG
CGCATCGTCGATGACATCATCGCCACCGACATCCAGACCAAGGAGCTGCAGAAGCAGATCATCAAGATCCAGAACTTCCGCGTGTACTACCGGGACTCCCGCGA
CCCCATCTGGAAGGGCCCAGCTGCGTGTGGAAGGCCGAGGGCGCCGTGGTGATCCAGGACAACTCCGACATCAAGGTGGTGCCCCGCCGCAAGGCCA
AGATCATCAAGGACTACGGCAAGCAAGCAGATGGCCGCCGGCGACTGCGTGGCGGGCCGCCAGGACGAGGACTAA
```

Fig. 124B

2003_CON_10_CD_pol.OPT
TTCTTCCCGGAGAACCTGGCCTTCCAGCAGCAGCGCCTTCCGAGCTGCCCTCCCCACCTCCCCGAGCTGCCGCTGTG
GGGCGGCGACAACACCCTGTCCGAGACCCGTCCTCTTCCCCAGCAGCACCCTGTGGCAGCGCCCCCTGGTGACCG
TGAAGATCGGCGGCGACCCCTGAAGGAGGCCCGCAGTGCCGGCAAGTGAACCTGCCCGGCAAGTGGAAGCCAAGATG
ATCGGCGGCATCGGCGGCTTCATCAAGGCCGCAACCTGCTGCGCCAGATCCTGATCGAGATCTGCGGCTACAAGGCCGACCCAC
CCCGTGAACATCATCGGCCAAGGTGAAGCAGTGGCCCTGACCGAGGAGAAGATCAAGGCCCTGACCGAGATCTGCACCGAGATCTGC
GCATGGACGGCCCCAAGGTGAAGCAGTGGCCCTGACCGAGGAGAAGATCAAGGCCCTGACCGAGATCTGCACCGAGATCTCC
CGCATCGGCCGCCCCGAGAACCCCTACAACACCCCCATTCGCCATCAAGAAGAAGACTCCGAGCTGGTGGACTTCCGAGCTGAACAA
GCGCACCCAGGAGACTTCTGGGAGTGCAAGTGCAAGTTCCGCAAGTGGACTACACCGCGCTGACCCGTGACCGTGGGGCGACCGCTACT
TCTCCGTGCCCCTGTGAAGGGCTCCCCGCAGAGATCTTCCAGTCCATGATGACCAGCAGAACCCCGAGATGGTGATCTACCAGTA
CCCAGGGCTGGAAGGGCTCCCCGCCATCTTCCAGTCCATGATGACCAGCAGAACCCCGAGATGGTGATCTACCAGTA
CATGACGACCTGTACGTGGACTTCCCCGCAAGTGACCTGGAGATCGGCCAGCACCTGGAGATGGGCTACGAGCTGCACCGCCATCAGCTGCCGAGAAGGAC
CCGACAAGAAGCACCAGAAGACATCCAGAACGACCTGGGAGCCGCTGGTGGACCTGATCGGCCAACCGAGATCTGGGAGTTCGTGAACA
GACCCCCAAGTTCCGCCTGCCCATCCAGAAGGAGACCTGGGAGACCTGGTGGACCGTGTACGTGGACCTCCTATGGACCCGCCGACTGGATCCCGAGAAGACCAAGCTG
TCCTGGACCGTGAACGACATCCAGAAGACATCGTGCCCCTGAGAAGGTGATCGCCCGAGCTGCAGGACCTGATCATCCAGAAGGTGATCGTGCTGGCCCAGGAAGGTCCAGGAGAACTGAAGGTCATCATCAACATCAGGGGGACCCCAAGCTGTCTGGACCAGAAGGGAGAACCTGAAGCGAGCTGGTGAACC
ACTACGACCCTCCAAGGACCTGATCGCCGAGATCTGATCGCCGCCCAGATCCAGAACGACCTGCAGGAGAGCTCGCAGGGGACTACGACCCCAGTCCATCGTGCCCAGGAGCAGGCCATCGGCGGCAACAACTGGCCGCGCAACAACTGGCCTGCGTGATCTGGGGCAA
GGCAAGTACGCCAAGGCCGCCCACCGGCGCCTGCCCATCCAGAAGGAGACGTGAAGCAGTGCTGGTGGAGAGTCCCCGAGTGGATCGCCGCCGACTACTGGCAGGCCGACCTGGAGGCCGACCTGGAGGTTCGTGAACA
GACCCCCAAGTTCCGCCTGCCCATCCAGAAGGAGACCTGGGAGACCTGGTGGACCGTACTGGCAGGCCGACCTGGAGGCCGACCTGGAGGTTCGTGAACA
CCCCCCCCAAGTTCCTGGTGACCGTGTGTACGAGCTGCTGAAGGTCATCATCAACATCAGGGGCCCAACCGAGACCAAGCTGGCCCT
GGCAAGGCCGGCTACGTGACGTGAACATCGTCCCGAGGTGAACATCGTGAACATCAGTGAACATCAGTGAACTGTTCGCCATCCAGATCTCCGGCATCT
GCAGGAGACCGCTCACTTCCTGCTGAAGCAGGTTCGGCATCATCGACACATCATCGCCCGCGAGAGTTCGGCATCATCGACACATCATCGCCGAGGTGATCAGCGCTTCAACTTCGAGGGCCTCCCGCGTGAAGGC
CAGGAGAACGCCTACTTCCTGCTGAAGCAGGTTCGGCATCATCGACACATCATCGCCCGCGAGAGTTCGGCATCATCGACACATCATCGCCGAGGTGATCAGCGCTTCAACTTCGAGGGCCTCCCGCGTGAAGGC
CGCCATGCTGTGGGCGCCCAGCCGAGCCTGCACCCAGGAGTTCGGCATCATCGACACATCATCGCCCGCGAGAGTTCGGCATCATCGACACATCATCGCCGAGGTGATCAGCGCTTCAACTTCGAGGGCCTCCCGCGTGAAGGC
TCCCCGCGAGCGCACCCCATCTGGAAGGCCGAGCATCGCCGACCGACCATCATCCCGCGAGAAGCTGCTGTGTGAAGGCCCAAGCCCAGGACTACCCCAAGCGGTCATCATCAAGTGGTGCCCGCC
CTCCCCGCGAGCGCACCCCATCTGGAAGGCCGAGCATCGCCGACCGACCATCATCCCGCGAGAAGCTGCTGTGTGAAGGCCCAAGCCCAGGACTACCCCAAGCGGTCATCATCAAGTGGTGCCCGCC
GCAAGGTGAAGATCATCAAGGACTACGGCAAGCAGTACGGCCCCTGCCCTGGCCTGCGCGCCGAGGACCAG

Fig. 125A

82. 2003_CON_11_CPX_pol.PEP
FFRENLAFQQGEAREFSPEQARANSPTSRELRVRGGDSPLPETGAEGEGAISFNFPQITLWQRPLVTIKVAGQLKEALLDTGADDTVLEEID
LPGRWKPKMIGGIGGFIKVRQYEEIIIEIEGKKAIGTVLVGPTPVNIIGRNMLTQIGCTLNFPISPIDTVPVKLKPGMDGPKVKQWPLTEEK
IKALTEICTEMEKEGKISKIGPENPYNTPVFAIKKKDSTKWRKLVDFRELNKRTQDFWEVQLGIPHPAGLKKKKSVTVLDVGDAYFSVPLDE
SFRKYTAFTIPSINNETPGIRYQYNVLPQGWKGSPAIFQSSMTKILEPFRTQNPEIVIYQYMDDLYVGSDLEIGQHREKVEELRKHLLKWGF
TTPDKKHQKEPPFLWMGYELHPDKWTVQPIQLPDKECWTVNDIQKLVGKLNWASQIYPGIKVKQLCKLLRGTKALTDIVPLTAEAELELAEN
REILKEPVHGVYYDPSKDLIAEVQKGQLDQWTYQIYQEPFKNLKTGKYAKRRTAHTNDVRQLAEVVQKISMESIVIWGKIPKFRLPIQRETW
ETWWTDYWQATWIPEWEFVNTPLVKLWYQLEKEPIIGAETFYVDGAANRETKLGKAGYVTDKGRQKVVTLTETTNQKTELEAIHLALQDSG
LEVNIVTDSQYALGIIQAQPDKSESELVSQIIEQLIKKEKVYLSWVPAHKGIGGNEQVDKLVSSGIRKVLFLDGIDKAQEEHERYHSNWRAM
ASDFNLPPIVAKEIVASCDKCQLKGEAMHGQVDCSPGIWQLDCTHLEGKIILVAVHVASGYIEAEVIPAETGQETAYFILKLAGRWPVKIH
TDNGSNFTSAAVKAACWWANIQQEFGIPYNPQSQGVVESMNKELKKIIGQVREQAEHLKTAVQMAVFIHNFKRKGGIGGYSAGERIVDIIAT
DLQTKELQKQITKIQNFRVYYRDSRDPIWKGPAKLLWKGEGAVVIQDNSDIKVVPRRKAKIIRDYGKQMAGDDCVAGRQDED$

Fig. 126A

83 2003_CON_12_BF_pol.PEP
FFRENLAFQQGEARKFPSEQARANSPASRELWVRRGDNPLSEAGAERRGTVPSLSFPQITLWQRPLVTIKVGGQLKEALLDTGADDTVLEDI
NLPGWKPKMIGGIGGFIKVKQYDNILIEICGHKAIGTVLVGPTPVNIIGRNLLTQLGCTLNFPISPIETVPVKLKPGMDGPKVKQWPLTEE
KIKALTEICTEMEKEGKISKIGPENPYNTPVFAIKKKDSTKWRKLVDFRELNKRTQDFWEVQLGIPHPAGLKKKKSVTVLDVGDAYFSVPLD
KDFRKYTAFTIPSVNNETPGIRYQYNVLPQGWKGSPAIFQSSMTKILEPFRKQNPDIVIYQYMDDLYVGSDLEIGQHRTKIEELRQHLLRWG
FTTPDKKHQKEPPFLWMGYELHPDKWTVQPIVLPEKDSWTVNDIQKLVGKLNWASQIYPGIKVKQLCRLLRGTKALTEVIPLTKEAELELAE
NREILKEPVHGVYYDPSKDLIAEIQKQGQGQWTYQIYQEPFKNLKTGKYARMRGAHTNDVKQLTEAVQKITTESIVINGKTPKFRLPILKET
WDTWWTEYWQATWIPEWEFVNTPPLVKLWYQLETEPIAGAETFYVDGASNRETKKGKAGYVTDRGRQKAVSLTETTNQKAELHAIQLALQDS
GSEVNIVTDSQYALGIIQAQPDKSESELVNQIIEQLIKKEKVYLSWVPAHKGIGGNEQVDKLVSAGIRKILFLDGIDKAQEEHEKYHNNWRA
MASDFNLPPVVAKEIVASCDKCQLKGEAMHGQVDCTHLEGKIILVAVHVASGYLEAEVIPAETGQETAYFILKLAGRWPVKTI
HTDNGPNFSSAAVKAACWAGIQQEFGIPYNPQSQGVVESMNKELKKIIRQVRDQAEHLKTAVQMAVFIHNFKRKGGIGGYSAGERIIDIIS
TDIQTRELQKQIIKIQNFRVYYRDSRDPVWKGPAKLLWKGEGAVVIQDNSEIKVVPRRKAKIIRDYGKQMAGDDCVAGRQDED$

Fig. 125B

```
2003_CON_11_CPX_pol.OPT
TTCTTCCCGCGAGAACCTGGCCTTCCAGCAGGGCGAGGGCGAGAGTTCTCCCCGAGCAGCCCGGCCAACTCCCCCACCTCCCCGAGAGCTGCCGGTGCC
CGGCGGCGACTCCCCCTGCCCGAGACCGGCGCGCCGAGGGCGAGGGCGCCGAGGGCGCGGCCCATCCTTCAACTTCTGTGGCAGCGCCCCTGGTGACCA
TCAAGGTGGCCGGCGACTCCCAGCTGCCCGGCCTGAAGGAGGCCCTGCTGCCGACCACCGTGCTGGACGACACCATCGAGATCATCGACCTGCCAAGATG
ATCGGCGGCGAAACATCATCGGCCGCCTTCATCAAGGTGCTGCCGCAACATGGCTGACCAGATCGGCTGCGAGGAGATCATCATCGAACTTCCCCATCTG
CCCCGTGAACTGGCCCCAAGGTGAAGCAGTGGCCCCCTGACCCCTGACCCCCTGTTCGCCATCAAGAAGAAGGACTCACCAAGTGGCGCAAGTTCCGCAA
GCATGGACGGCCCCAAGGTGAAGCAGTGGCCCCTGACCCCTGAAGAGAAGATCAAGGCCCTGACCGAGATCTGCACCGAGATGGAGAAGGAGGGCAAGATCTCC
AAGATCGGCCCCGAGAACCCCTACAACACCCCCGTGTTCGCCATCAAGAAGAAGGACTCCACCAAGTGGCGCAAGCTGGTGGACTTCCGCGAGCTGAACAA
GCGCACCCAGGACTTCTGGGAGGTGCAGCTGGGCATCCCGCACCCCGCCGGCCTGAAGAAGAAGAAGAGCAGTCCGTGACCGTGCTGGACGTGGGCGACGCCTACT
TCTCCGTGCCCTGGACGAGTCCTTCCGCAAGTACACCGCCTTCACCATCCCCTCCATCAACGAGAACGAGAGCCCCGGCATCCGCTACCAGTACAACGTGCTG
CCCCAGGGCTGGAAGGGCTCCCCCGCCATCTTCCAGTCCTCCATGACCAAGATCCTGGAGCCCTTCCGCAAGCAGAACCCCGAGATCGTGATCTACCAGTA
CATGGACGACCTGTACGTGGGCTCCGACCTGGAGATCGGCCAGCACCGCACCAAGATCGAAGAGGTGGAGAGCCTGCTGCGCAAGCCTGACGACCTCCACCACCC
CGACAAGAAGCACCAGAACGACATCCAGAAGCTGGTGGGCAAGCTGAACTGGGCCTCCCAGATCTACCCCGGCATCAAGGTGAAGCAGCTGTGCAAGCTGCTGCG
TGGCTGGACCCGTGAACGACATCGACCAGCTGACCGAGGCCGTCCTGGGGCCTGAGCCTGCCGCGAGAACCGTGCACGGCGTGT
CGGCACCAAGGCCCTGACCGAGGTGCTCCCCCTGACCGAAGAGCCGGCCGCAGAAGCCCGAGAGCCGGCCCTGACGCCCTGCTGAAGAACCTGAAGACC
ACTACGACCCCCTCCAAGGACCTGATCGCCGAGATCCAGAAGCAGGGCGCCAGTGACCAGAGATCGGCGCACAGCATCAACGACCACTCCGACTGGCC
GGCAAGTACGCCAAGCGCCCCACACGACTGGTACCTGTCCTGGGTGCCCAAGGCCCACGAGGCCCTACACCGACCCCTGAAGGCGCAACTCCAACTGGCCTCCGACTTCAA
GATCCCCAAGTTCCGCCGCTGCCCCATCAGCGACCAAGAGCCGGGAGATCGTGCGCGGCCTTCCTAGTGGCCAGCGCCGACCCGGGGACGGAGACCGGGCAAGCTG
CCTGCCCCCTGGTGAAGCTGGTGCACCACCTGTGCCCGGCTGGTGGTACCAGAAGGCCTGCCGCAAGATCTGTGGCCCCCTGCCTCCTCCATCCTGACGTGCCAT
GGCAGCTGCCGGCTACGTGACCGACCGAGGGCCAAGATCAAGGGCCTGGGCGCCTACAAGGCCGAGGCGTGATCCATCCAGCCGGCCTACTCCGGCCCCGGCAAGCC
CAGGAGAGACCGGCTGAACATCAAGCCCAGAGAGTTGATCGACGAGGCTGCTGGTGGCCGTGCCGGCCCCTAACCTTCACCACAACCGGGGCATGGCGCAAGGC
CGCCTGCTGGGCGACGTTCGGCTGAAGAAGGGGGGCCGGCATCCCCCTACAACCCCCAGGGCGTGTTCATCCAGCAGAACCCCAGATGGCCAAGGGCAACCGGGCTACTCC
GCCGGCGAGCGCATCGTGGACATCATCGCCACCGACATCCAGACCAAGGAGCTGCAGAAGCAGATCACCAAGATCCAGAACTTCCGCGTGTACTACCGGGA
CTCCCGGGACCCCTGTGGGCGGGAAGGCCGCCGAAGCTGCCTGGCTGGAAGCCGGCCGATGGCCGGCCGTGCCCGGCCCCCGCC
GCAAGGCCAAGATCATCCGCGACTACGGCAAGCAGATGGCCGGCGACGACTGCGTCGCCCCCGCCCCAAGGCCGAGGACTAA
```

Fig. 126B

```
2003_CON_12_BF_pol.OPT
TTCTTCCGGAGAACCTGGCCTTCCAGCAGGGCGAGGCCCGCCAACTTCCCCTCCGCCTCCCCGAGCTGTGGGTGCG
CCGCGGGACAACCCCTGTCCAGGGCCGGCGGCCGAGCCGGACACCTGTCCTTCCCCGAGATCACCTGTGGCCAGCGCCCCTGTGA
CCATCAAGGTGGGGGCGCAGCTGGAAGGAGGCCCTGCTGTGGACGACATCAACCTGCCCGGCAAGTGGAAGCCAAG
ATGATCGGCGGCATCGGCGGCTTCATCAAGGTGAAGCAGTACGACAAATCCTGATCTGCGGCAAGCCCGTGCTGGTGGCCC
CACCCCCGTGAACATCATCGGCCGCCAAGTGCTGGACCCCAAGCTCCCCATCTCCCAATCTGAACCTGCCCGTGCGCAGCTGAAGC
CGGGCATGGACGGCCCCAAGGTGAAGCAGTGGCCCCTGACCGAGGAGATCAAGGCCCTGACCGAGATCTGCACCGAGATGGAGAAGGAGGCAAGATC
TCCAAGATCGGCCCCGAGAACCCCTACAACACCCCCGTGTTCGCCATCAAGAAGAAGGACTCCACCAAGTGGCGCAAGCTGGTGGACTTCCGCGAGCTGAA
CAAGCGCACCCAGGACTTCTGGGAGTGCAGTTCCGCAAGGAATTCGCCCCCAATCCCCGGCCTGAAGAAGAAGTCCGTGACGTGGGCGACGCCT
ACTTCTCCGTGCCCCTGGACGAAGACTTCCGCAAGTACACCGCCTTCACCATCCCATGACCAGCCCTTCCGGAGCCCTTCGGAGCTGGAGCTGATCTACCA
CTGCCCCAGGGCTGGAAGGCTCCCCCGAAGATCTTCCAGTCCATGATGACCAGGAATCGGCGCAGCTGGGGATGGGCCAAGAAGCTGCACCCTGACCCCGCCATCTGATCTACCA
GTACATGGACGACCTGTACGTGGGCTCCGACCTGGAGATCGGCCAGCACCGGACCAAGATCGAGGAGCTGCGCCAGCACCTGCTGCGCTGGGGCCTTCACCA
CCCCGACAAGAAGCACCAGAAGGAGCCCCCTTCCTGTGGATGGGCTACGAGCTGCACCCCGACAAGTGGACCGTGCAGCCCATCGTGCTGCCCGAGAAG
GACTCCTGGACCGTGAACGACATCCAGAAGCTGGTGGGCAAGCTGAACTGGGCCTCCCAGATCTACCCCGGGGCAATCCTGAAGCTGAAGGAGCCCTGCT
GCGCGGCACCAAGGCCCTGACCGAGGTGATCCCCCTGACCGAGGAGCCGGAGCTGGAGCTGGCCGAGAACCGCGAGATCCTGAAGGAGCCCGTGCACGGCGTG
TGTACTACGACCCCTCCAAGGACCTGATCGCCGAGATCCAGAAGCAGGGCCAGGGCCAGTGGACCTACCAGATCTACCAGGAGCCCTTCAAGAACCTGAAG
ACCGGCAAGTACGCCCGCATGCGCGGCGCCCACACCAACGACGTGAAGCAGCTGACCGAAGCAGTGCGTGCAGGACACCATCGGCACCACCGTGATCTGGGG
CAAGACCCCAAGTTCCGCCTGGCCGAGAACCGCGAGACCTGGGACACCTGGTGGACAGCTGGTGCGCGGGACACCTGGACCGAGGCCCTCCAACCGCCATCCAGCTGGC
ACACCCCCCCCGGTGGTGTGACCGAGGCGCCGTGCCGGCCCAGAGGCCACGCCCTGACGTGTCCCTGACCGCCCGAGACCCACCATCATCCGAGTCGAGCCGCCAG
AAGGGCCAAGGCCGGCTGGTCCGGCTCCAGATCGTCCGAGGTGAACATCGTGACCGACTCCCAGTACGCCCTGGGTGCCCGACAAGCTGGTGAGCCAGTACAAGCTGGTG
CCTGCAGGATCCCGGCCCTGATCAAGGACTGAATCCTGTTCCTGGACGGAAGTGTACCTGTCCTGGGTGCCCCGCCCATGCCCTCCGACTT
TCCAGCCATCCCCCCCCGGTGCCCAAGATCGTGCGCACAAGCTGCCGACAAGTGCGAGGGCCCCAGAACAATGGCCGGCCAGTGCCTCCCCGGCA
CAACCTGCCCCCGGCGAAGCCCGACTGAAGCCCTGCGCAAGCAAGTCGTGCCGACAAGCCGGAGCTGTCCGGCTGGAGGCGCCAGTGACTGATCCCGCGAGACC
TCTGGCAGCTGGACTGCACCCACCTGGAAGCGCGCAAGATCATCCTGGAGGCCCTCCGGCTGGTGGCCGTGGCCCCGTGAAGACCATCCACACCGACAACGGCCCCGGCC
GGCCTGCTGCTGGTGCGGCCATCGGCCAGGCCCGACGACAGCCAGGAGGTTCGGCATCCCTACAACCCCCCAGTCCCAGTCCACCACACCAATCTCAGAACCAAGGAGCTGAAGAGA
TCATCCGCCAGGTGCGGCGACCAGGCCGGAGCACGTGAAGAGACCCGTGTTCATCCACAACTTCAAGCGCAAGGGCGGCATCGGCGGCTAC
TCCGCCGGCAGGAGCGCATCGTCGACATCATCGCCACCGACATCAAGACAGAGCTGCAGAAGCAGATCATCAAGATCCAGAATTCCGCGATCAAGGTGTACTACCG
CGACTCCCGCGATCCCCGGTGTGGAAGGCCGTGCTGCGCCCACGCCAAGCTGCGTGATGGCCGGTGGCAAGCAACTCCAGCGACAACAACTCCAGATTCCCAGATTCCGAGATCAAGGTGGTGCCCC
GCCGCAAGGCCAAGATCATCCGCGACTACGGCAAGCAGCAGATGGCCGGTGCCCGAGTGGCGCCCGCCGGCCCCGGACCGGAGGACTAA
```

Fig. 127A 84. 2003_CON_14_BG_pol.PEP
FFRENLAFQQGEAREFSPEQARANSPTRRELMVRRGDSPLPEARAEGKGDIPLSLPQITLMQRPLVTVRIGGQLIEALLDTGADDTVLEDIN
LPGKWKPKMIGGIGGFIKVRQYDQLLEICGKKAIGTVLVGPTPINIIGRNMLTQIGCTLNFPISPIETVPVKLKPGMDGPKVKQWPLTEEK
IKALTDICTEMEREGKISKIGPENPYNTPIFAIKKKDSTKWRKLVDFRELNKRTQDFWEVQLGIPHPSGLKKKKSVTVLDVGDAYFSVPLDE
SFRKYTAFTIPSTNNETPGIRYQYNVLPQGWKGSPAIFQSSMTKILEPFRIKNPEIVIYQYMDDLYVGSDLEIGQHRAKIEELRKHLLSWGF
TTPDKKHQKEPPFLWMGYELHPDKWTVQPIQLPDKESWTVNDIQKLVGKLNWASQIYPGIKVKQLCKLLRGAKALTDIVPLTAEAELELAEN
REILKEPVHGVYYEPSKELIAEVQKQGLDQWTYQIYQEPYKNLKTGKYAKRGSAHTNDVKQLTEVVQKTATESIVIWGKTPKFKLPIRKETW
EVWWTEYWQATWIPDWEFVNTPPLVKLWYRLETEPIAGAETYYVDGAANRETKLGKAGYVTDKGKQKIITLTETTNQKAELQAIHIALQDSG
SEVNIVTDSQYALGIIQAQPDRSESESEVVNQIIEQLIKKEKVYLSWVPAHKGIGGNEQVDKLVSSGIRKVLFLDGIDKAQEEHEKYHSNWRAM
ASDFNLPPVVAKEIVASCDKCQLKGEAMHGQVDCSPGIWQLDCTHLEGKIILVAVHVASGYIEAEVIPAETGQETAYFILKLAGRWPVKIIH
TDNGSNFTSAAVKAACWWANITQEFGIPYNPQSQGVVESMNKELKKIIGQVRDQAEHLKTAVQMAVFIHNFKRKGGIGGYSAGERIIDIIAS
DIQTKELQKQITKIQNFRVYFRDSRDPIWKGPAKLLWKGEGAVVIQDNNEIKVVPRRKAKIIRDYGKQMAGDDCVAGRQDED$

Fig. 127B

2003_CON_14_BG_pol.OPT
TTCTTCCGCGAGAACCTGGCCTTCCAGCAGGGCGAGGGCCGCGAGTTCTCCCCCGAGCAGGCCCGGCCAACTCCCCACCCGCCGCGAGCTGTGGGTGCG
CCGCGGCGACTCCCCCTGCCCCTGAGGCCCGCGAGGGCGAGGGCCGAGGGCAAGCTGCCCCAGATCACCCTGTGCCAGCGCCCCCTGGTGACCG
TGCGCATCGGCGGGCAGCTGATCGAGGGCCTGTACCCCGACGACGACACCGTGCTGGAGGACATCAACCTGCCCCGGCAAGTGGAAGCCAAGATG
ATCGGCGGCATCGGCGGCTTCATCAAGGTGCGCCAGTACGACCAGATCCTGATCGAGATCTGCGGCAAGAAGGCCATCGGCACCGTGCTGGTGGGACCCAC
CCCATCAACATCATCGGCCAAGGTGAAGCAGTGGCCCCTGACCGAGGAGAAGATCAAGGCCCTGACCGACATCTGCACCGAGATGGAGAAGGAAGCCCG
GCATGGACGGCCCCAAGGTGAAGCAGTGGCCCCTGACCGAGGAGAAGATCAAGGCCCTGACCGAGATGGAGCGCGAGGGCAAGATCTCC
AAGATCGGCCCCGAGAACCCCTACAACACCCCCATCTTCGCCATCAAGAAGAAGGACTCCACCAAGTGGCGCAAGCTGGTGGACTTCCGCGAGCTGAACAA
GCGCACCCAGGACTTCTGGGAGGTGCAGCTGGGCATCCCGCGCCAATCCCCGGCTACACCCCGAGAAGATCGAGAAGCCCTTCCGCAAGCAGAACCCGGACATCGTGATCTACCAGTA
TCCCAGGGCTGGAAGGGCTCCCCCGCCATCTTCCAGTCCTCCATGACCAAGATCCTGGAGCCCTTCCGCAAGCAGAACCCCGACATCGTGATCTACCAGTA
CATGGACGACCTGTACGTGGGCTCCGACCTGGAGATCGGGCAGCATGGGCCGAAGACTGAGGAGTCGACACCCCGAGAACCGCGAAGCAGCTGTGCAAGCTGCTGCG
CGGACAAGAAGCACCAAGGAGCCCCCTTCCGTGTGGGCAAGCTGGTGCCCCTGACGCGCCGAGCTGCCCGAGCTGGGCCTGAGCCTCACCCCCGAGAACCGCGAAGCAGCTGCTGCG
TCCTGGACCCTGAAGCCCGAGCAGAAGGAGCCCCCTTCCGTGTGGGATGGCCAAGCTGGTGCCCCTGACCGAGCTGGGCCTGAGCGCCGCCTGCCCGAGAACCGCGTGCACGGCGTGT
CGGCGCCAAGGCCCTGACCGAGGTGATCCCGCTGACCGAGGAAGCAGGCCGAGAAGCCCTGGATTGCCCCCTGGACCTGTCCTGGTGCCGGAGCAGCTGCAGCTGGACAACCTGAAGACC
ACTACGAGCGCCTCCAAGGACTACCTGACCGAGGTGATCCAGCTGACCCGCCGCGCACCGCCCCTGGGTGCCCCGGAGGAGCACGAGAAGTACCACTCCAACTGGCGCGCCATGGCCTCCGACTTCAA
GACCCCCAAGTTCAAGCTGCCCATCCAGAAAGAGACCTGGGAGACCTGGGTGTGCAGCTGGGCAAGGGCGAGCCCGCCGAGCGCCATCGTCATCAAGGCCCTCCCCCGGCATCT
CCTGCCCCCTGGTGTGCTACCGCCTGACCAAGGGGCCAAGATCATCCTGGAGGGGCAAGAGCTGCTGTGGGCCCGTGTGAAGATCATCCACCACCGCGGGCATCGCCGCCAGGACCGGC
CAGGAGACCGCCGTCACTTCATCCGAGGTGATCATCAGGGCCAAGGCACCTGCCTGCCCCAGATGAAGATCAACCCCCAGTCCCAGGGCGGTGGTGAGTGCATGAACAAGGAGCTGAAGAAGATCA
TCGGGCCAGGTGCGGCGACCAGGCCGAGCACCTGAAGACCCGCGTGCAGATGGCCGTTCATCCACACAGCCGCAAGGGCGGCATCGGCGGCTACTCC
GCCGCCGAGCGCATCGTGGACATCATCGCCCCAGATCGCGATCCAGCTGCCAAGCTGGGCAAGGCCCCAAGCGACCACTGAGAAGGTGGCTGGCCCCCGCC
CTCCCCCAAGGATCATCCGCGACTACGGCAAGCAGATGGCCGGCGACTGCGTGGCCGGCCGGCAAGCAGGACGAGGACTAA

CONSENSUS/ANCESTRAL IMMUNOGENS

This application is a Continuation of U.S. application Ser. No. 13/137,517, filed Aug. 23, 2011, which is a Continuation of U.S. application Ser. No. 10/572,638, filed Dec. 22, 2006, which is a National Stage Application under 35 U.S.C. section 371 of PCT/US2004/030397, filed Sep. 17, 2004, which claims priority from U.S. Provisional Application No. 60/503,460, filed Sep. 17, 2003, and U.S. Provisional Application No. 60/604,722, filed Aug. 27, 2004, the entire contents of which are incorporated herein by reference in their entireties.

SEQUENCE LISTING

The instant application contains a Sequence Listing which has been filed electronically in ASCII format and is hereby incorporated by reference in its entirety. Said ASCII copy, created on Jun. 28, 2018, is named 2933311-030-US7_SL.txt and is 1,108,293 bytes in size.

TECHNICAL FIELD

The present invention relates, in general, to an immunogen and, in particular, to an immunogen for inducing antibodies that neutralize a wide spectrum of HIV primary isolates and/or to an immunogen that induces a T cell immune response. The invention also relates to a method of inducing anti-HIV antibodies, and/or to a method of inducing a T cell immune response, using such an immunogen. The invention further relates to nucleic acid sequences encoding the present immunogens.

BACKGROUND

The high level of genetic variability of HIV-1 has presented a major hurdle for AIDS vaccine development. Genetic differences among HIV-1 groups M, N, and O are extensive, ranging from 30% to 50% in gag and env genes, respectively (Gurtler et al, J. Virol. 68:1581-1585 (1994), Vanden Haesevelde et al, J. Virol. 68:1586-1596 (1994), Simon et al, Nat. Med. 4:1032-1037 (1998), Kuiken et al, Human retroviruses and AIDS 2000: a compilation and analysis of nucleic acid and amino acid sequences (Theoretical Biology and Biophysics Group, Los Alamos National Laboratory, Los Alamos, N. Mex.)). Viruses within group M are further classified into nine genetically distinct subtypes (A-D, F-H, J and K) (Kuiken et al, Human retroviruses and AIDS 2000: a compilation and analysis of nucleic acid and amino acid sequences (Theoretical Biology and Biophysics Group, Los Alamos National Laboratory, Los Alamos, New Mex., Robertson et al, Science 288:55-56 (2000), Robertson et al, Human retroviruses and AIDS 1999: a compilation and analysis of nucleic acid and amino acid sequences, eds. Kuiken et al (Theoretical Biology and Biophysics Group, Los Alamos National Laboratory, Los Alamos, N. Mex.), pp. 492-505 (2000)). With the genetic variation as high as 30% in env genes among HIV-1 subtypes, it has been difficult to consistently elicit cross-subtype T and B cell immune responses against all HIV-1 subtypes. HIV-1 also frequently recombines among different subtypes to create circulating recombinant forms (CRFs) (Robertson et al, Science 288: 55-56 (2000), Robertson et al, Human retroviruses and AIDS 1999: a compilation and analysis of nucleic acid and amino acid sequences, eds. Kuiken et al (Theoretical Biology and Biophysics Group, Los Alamos National Laboratory, Los Alamos, N. Mex.), pp. 492-505 (2000), Carr et al, Human retroviruses and AIDS 1998: a compilation and analysis of nucleic acid and amino acid sequences, eds. Korber et al (Theoretical Biology and Biophysics Group, Los Alamos National Laboratory, Los Alamos, N. Mex.), pp. III-10-III-19 (1998)). Over 20% of HIV-1 isolates are recombinant in geographic areas where multiple subtypes are common (Robertson et al, Nature 374:124-126 (1995), Cornelissen et al, J. virol. 70:8209-8212 (1996), Dowling et al, AIDS 16:1809-1820 (2002)), and high prevalence rates of recombinant viruses may further complicate the design of experimental HIV-1 immunogens.

To overcome these challenges in AIDS vaccine development, three computer models (consensus, ancestor and center of the tree) have been used to generate centralized HIV-1 genes to (Gaschen et al, Science 296:2354-2360 (2002), Gap et al, Science 299:1517-1518 (2003), Nickle et al, Science 299:1515-1517 (2003), Novitsky et al, J. Virol. 76:5435-5451 (2002), Ellenberger et al, Virology 302:155-163 (2002), Korber et al, Science 288:1789-1796 (2000)). The biology of HIV gives rise to star-like phylogenies, and as a consequence of this, the three kinds of sequences differ from each other by 2-5% (Gao et al, Science 299:1517-1518 (2003)). Any of the three centralized gene strategies will reduce the protein distances between immunogens and field virus strains. Consensus sequences minimize the degree of sequence dissimilarity between a vaccine strain and contemporary circulating viruses by creating artificial sequences based on the most common amino acid in each position in an alignment (Gaschen et al, Science 296:2354-2360 (2002)). Ancestral sequences are similar to consensus sequences but are generated using maximum-likelihood phylogenetic analysis methods (Gaschen et al, Science 296: 2354-2360 (2002), Nickle et al, Science 299:1515-1517 (2003)). In doing so, this method recreates the hypothetical ancestral genes of the analyzed current wild-type sequences (FIG. 26). Nickle et al proposed another method to generate centralized HIV-1 sequences, center of the tree (COT), that is similar to ancestral sequences but less influenced by outliers (Science 299:1515-1517 (2003)).

The present invention results, at least in part, from the results of studies designed to determine if centralized immunogens can induce both T and B cell immune responses in animals. These studies involved the generation of an artificial group M consensus env gene (CON6), and construction of DNA plasmids and recombinant vaccinia viruses to express CON6 envelopes as soluble gp120 and gp140CF proteins. The results demonstrate that CON6 Env proteins are biologically functional, possess linear, conformational and glycan-dependent epitopes of wild-type HIV-1, and induce cytokine-producing T cells that recognize T cell epitopes of both HIV subtypes B and C. Importantly, CON6 gp120 and gp140CF proteins induce antibodies that neutralize subsets of subtype B and C HIV-1 primary isolates.

The iterative nature of study of the centralized HIV-1 gene approach is derived from the rapidly expanding evolution of HIV-1 sequences, and the fact that sequences collected in the HIV sequence database (that is, the Los Alamos National Database) are continually being updated with new sequences each year. The CON6 gp120 envelope gene derives from Year 1999 Los Alamos National Database sequences, and Con-S derives from Year 2000 Los Alamos National Database sequences. In addition, CON6 has Chinese subtype C V1, V2, V4, and V5 Env sequences, while Con-S has all group M consensus Env constant and variable regions, that have been shortened to minimal-length variable loops. Codon-optimized genes for a series of Year 2003 group M and subtype consensus sequences have been designed, as have a corresponding series of wild-type HIV-1 Env genes for comparison, for use in inducing broadly reactive T and B cell responses to HIV-1 primary isolates.

SUMMARY OF THE INVENTION

The present invention relates to an immunogen for inducing antibodies that neutralize a wide spectrum of HIV primary isolates and/or to an immunogen that induces a T cell immune response, and to nucleic acid sequences encoding same. The invention also relates to a method of inducing anti-HIV antibodies, and/or to a method of inducing a T cell immune response, using such an immunogen.

Objects and advantages of the present invention will be clear from the description that follows.

BRIEF DESCRIPTION OF THE DRAWINGS

FIGS. 1A-1D: Generation and expression of the group M consensus env gene (CON6). The complete amino acid sequence of CON6 gp160 is shown. (FIG. 1A) (SEQ ID NO: 1) The five regions from the wild-type CRF08_BC (98CN006) env gene are indicated by underlined letters. Variable regions are indicated by brackets above the sequences. Potential N-liked glycosylation sites are highlighted with bold-faced letters. (FIG. 1B) Constructs of CON6 gp120 and gp140CF. CON6 gp120 and gp140CF plasmids were engineered by introducing a stop codon after the gp120 cleavage site or before the transmembrane domain, respectively. The gp120/gp41 cleavage site and fusion domain of gp41 were deleted in the gp140CF protein. (FIG. 1C) Expression of CON6 gp120 and gp140CF. CON6 gp120 and gp140CF were purified from the cell culture supernatants of rVV-infected 293T cells with *galanthus Nivalis* argarose lectin columns. Both gp120 and gp140CF were separated on a 10% SDS-polyarylamide gel and stained with Commassie blue. (FIG. 1D.) (SEQ ID NO: 2) CON6 env gene optimized based on codon usage for highly expressed human genes.

FIGS. 2A-2E. Binding of CON6 gp120 gp140 CF to soluble CD4 (sCD4) and anti-Env mAbs. (FIGS. 2A-2B) Each of the indicated mabs and sCD4 was covalently immobilized to a CM5 sensor chip (BIAcore) and CON6 gp120 (FIG. 2A) or gp140CF (FIG. 2B) (100 μg/ml and 300 μg/ml, respectively) were injected over each surface. Both gp120 and gp140CF proteins reacted with each anti-gp120 mabs tested except for 17b mab, which showed negligible binding to both CON6 gp120 and gp140CF. To determine induction of 17b mab binding to CON6 gp120 and gp140CF, CON6 gp120 (FIG. 2C) or gp140CF (FIG. 2D) proteins were captured (400-580 RU) on individual flow cells immobilized with sCD4 or mabs A32 or T8. Following stabilization of each of the surface, mAb 17b was injected and flowed over each of the immobilized flow cells. Overlay of curves show that the binding of mab 17b to CON6 Env proteins was markedly enhanced on both sCD4 and mab A32 surfaces but not on the T8 surface (FIGS. 2C-2D). To determine binding of CON6 gp120 and gp140CF to human mabs in ELISA, stock solutions of 20: g/ml of mabs 447, F39F, A32, IgG1b12 and 2F5 on CON6 gp120 and gp140CF were tittered (FIG. 2E). Mabs 447 (V3), F39F (V3) A32 (gp120) and IgG1b12 (CD4 binding site) each bound to both CON6 gp120 and 140 well, while 2F5 (anti-gp41 ELDKWAS) (SEQ ID NO: 321) only bound gp140CF. The concentration at endpoint titer on gp120 for mab 447 and F39F binding was <0.003 μg/ml and 0.006 μg/ml, respectively; for mab A32 was <0.125 μg/ml; for IgG1b12 was <0.002 μg/ml; and for 2F5 was 0.016 μg/ml.

FIGS. 3A and 3B. Infectivity and coreceptor usage of CON6 envelope. (FIG. 3A) CON6 and control env plasmids were cotransfected with HIV-1/SG3Δenv backbone into human 293T cells to generate Env-pseudovirions. Equal amounts of each pseudovirion (5 ng p24) were used to infect JC53-BL cells. The infectivity was determined by counting the number of blue cells (infectious units, IU) per microgram of p24 of pseudovirons (IU/μg p24) after staining the infected cells for β-gal expression. (FIG. 3B) Coreceptor usage of the CON6 env gene was determined on JC53BL cells treated with AMD3100 and/or TAK-799 for 1 hr (37° C.) then infected with equal amounts of p24 (5 ng) of each Env-pseudovirion. Infectivity in the control group (no blocking agent) was set as 100%. Blocking efficiency was expressed as the percentage of IU from blocking experiments compared to those from control cultures without blocking agents. Data shown are mean±SD.

FIG. 4. Western blot analysis of multiple subtype Env proteins against multiple subtype antisera. Equal amount of Env proteins (100 ng) were separated on 10% SDS-polyacrylamide gels. Following electrophoresis, proteins were transferred to Hybond ECL nitrocellulose membranes and reacted with sera from HIV-1 infected patients (1:1,000) or guinea pigs immunized with CON6 gp120 DNA prime, rVV boost (1:1,000). Protein-bound antibody was probed with fluorescent-labeled secondary antibodies and the images scanned and recorded on an infrared imager Odyssey (Li-Cor, Lincoln, Nebr.). Subtypes are indicated by single-letters after Env protein and serum IDs. Four to six sera were tested for each subtype, and reaction patterns were similar among all sera from the same subtype. One representative result for each subtype serum is shown.

FIG. 5. T cell immune responses induced by CON6 Env immunogens in mice. Splenocytes were isolated from individual immunized mice (5 mice/group). After splenocytes were stimulated in vitro with overlapping Env peptide pools of CON6 (black column), subtype B (hatched column), subtype C (white column), and medium (no peptide; gray column), INF-γ producing cells were determined by the ELISPOT assay. T cell IFN-γ responses induced by either CON6 gp120 or gp140CF were compared to those induced by subtype specific Env immunogens (JRFL and 96ZM651). Total responses for each envelope peptide pool are expressed as SFCs per million splenocytes. The values for each column are the mean±SEM(of IFN-γ SFCs (n=5 mice/group).

FIGS. 6A-6E. Construction of codon usage optimized subtype C ancestral and consensus envelope genes (FIGS. 6A and 6B, respectively) (SEQ ID NOS 3-4). Ancestral and consensus amino acid sequences (FIGS. 6C and 6D, respectively) (SEQ ID NOS 5-6) were transcribed to mirror the codon usage of highly expressed human genes. Paired oligonucleotides (80-mers) overlapping by 20 bp were designed to contain 5' invariant sequences including the restriction enzyme sites EcoRI, BbsI, Bam HI and BsmBI. BbsI and BsmBI are Type II restriction enzymes that cleave outside of their recognition sequences. Paired oligomers were linked individually using PCR and primers complimentary to the 18 bp invariant sequences in a stepwise fashion, yielding 140 bp PCR products. These were subcloned into pGEM-T and sequenced to confirm the absence of inadvertant mutations/deletions. Four individual pGEM-T subclones containing the proper inserts were digested and ligated together into pcDNA3.1. Multi-fragment ligations occurred repeatly amongst groups of fragments in a stepwise manner from the 5' to the 3' end of the gene until the entire gene was reconstructed in pcDNA3.1. (See schematic in FIG. 6E.)

FIG. 7. JC53-BL cells are a derivative of HeLa cells that express high levels of CD4 and the HIV-1 coreceptors CCR5 and CXCR4. They also contain the reporter cassettes of luciferase and β-galactosidase that are each expressed from an HIV-1 LTR. Expression of the reporter genes is dependent on production of HIV-1 Tat. Briefly, cells are seeded into 24 or 96-well plates, incubated at 37° C. for 24 hours and treated with DEAE-Dextran at 37° C. for 30 minutes. Virus is serially diluted in 1% DMEM, added to the cells incubating in DEAE-Dextran, and allowed to incubate for 3 hours at 37° C. after which an additional cell media is added to each well. Following a final 48-hour incubation at 37° C., cells are either fixed, stained using X-Gal to visualize β-galactosidase expressing blue foci or frozen-thawed three times to measure luciferase activity.

FIG. 8. Sequence alignment of subtype C ancestral and consensus env genes. Alignment of the subtype C ancestral (bottom line) (SEQ ID NO: 8) and consensus (top line) (SEQ ID NO: 7) env sequences showing a 95.5% sequence homology; amino acid sequence differences are indicated. One noted difference is the addition of a glycosylation site in the C ancestral env gene at the base of the V1 loop. A plus sign indicates a within-class difference of amino acid at the indicated position; a bar indicates a change in the class of amino acid. Potential N-glycosylation sites are marked in blue. The position of truncation for the gp140 gene is also shown.

FIG. 9. Expression of subtype C ancestral and consensus envelopes in 293T cells. Plasmids containing codon-optimized gp160, gp140, or gp120 subtype C ancestral and consensus genes were transfected into 293T cells, and protein expression was examined by Western Blot analysis of cell lysates. 48-hours post-transfection, cell lysates were collected, total protein content determined by the BCA protein assay, and 2 µg of total protein was loaded per lane on a 4-20% SDS-PAGE gel. Proteins were transferred to a PVDF membrane and probed with HIV-1 plasma from a subtype C infected patient.

Figure 10A:
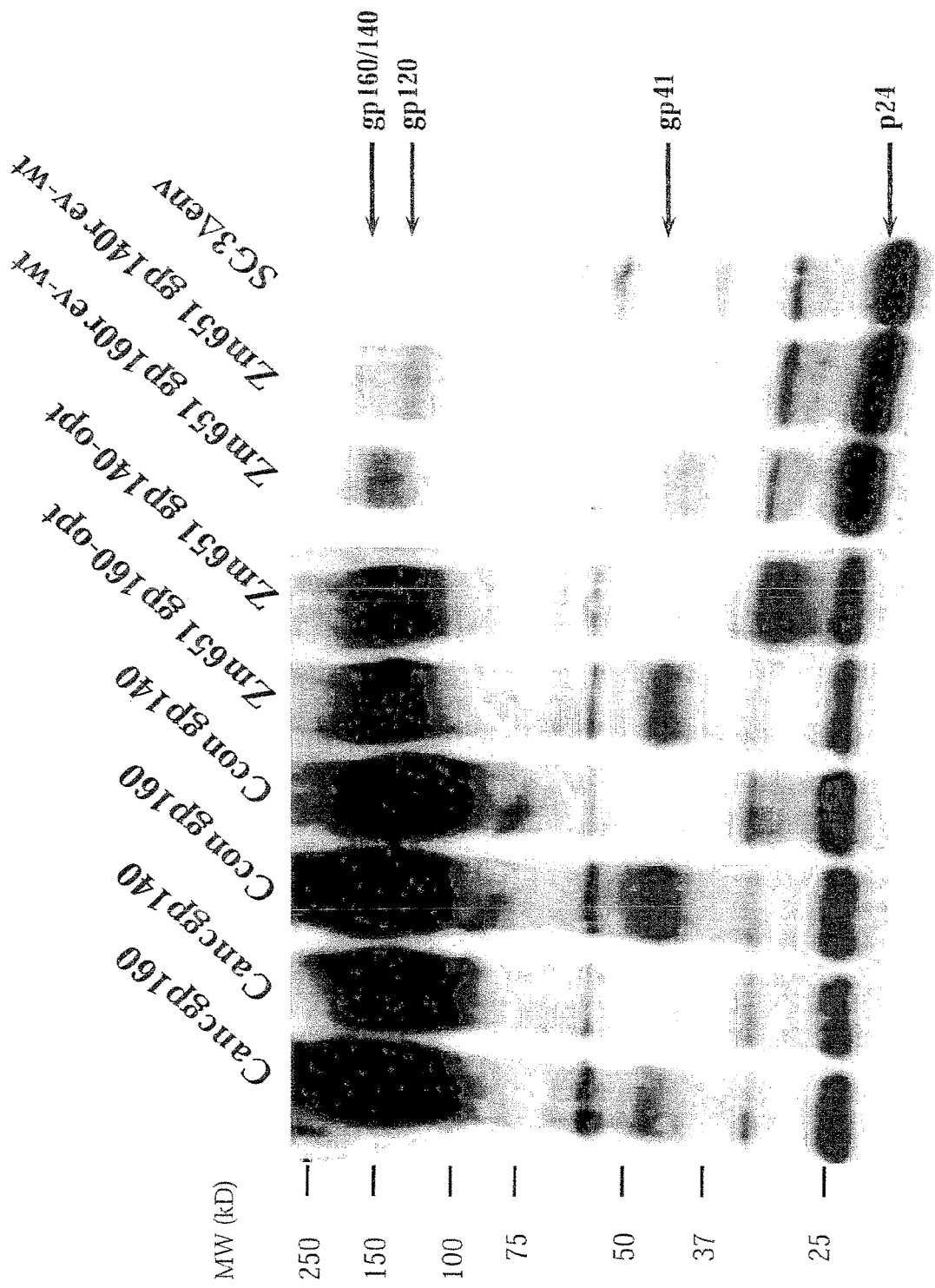
Figure 10B:
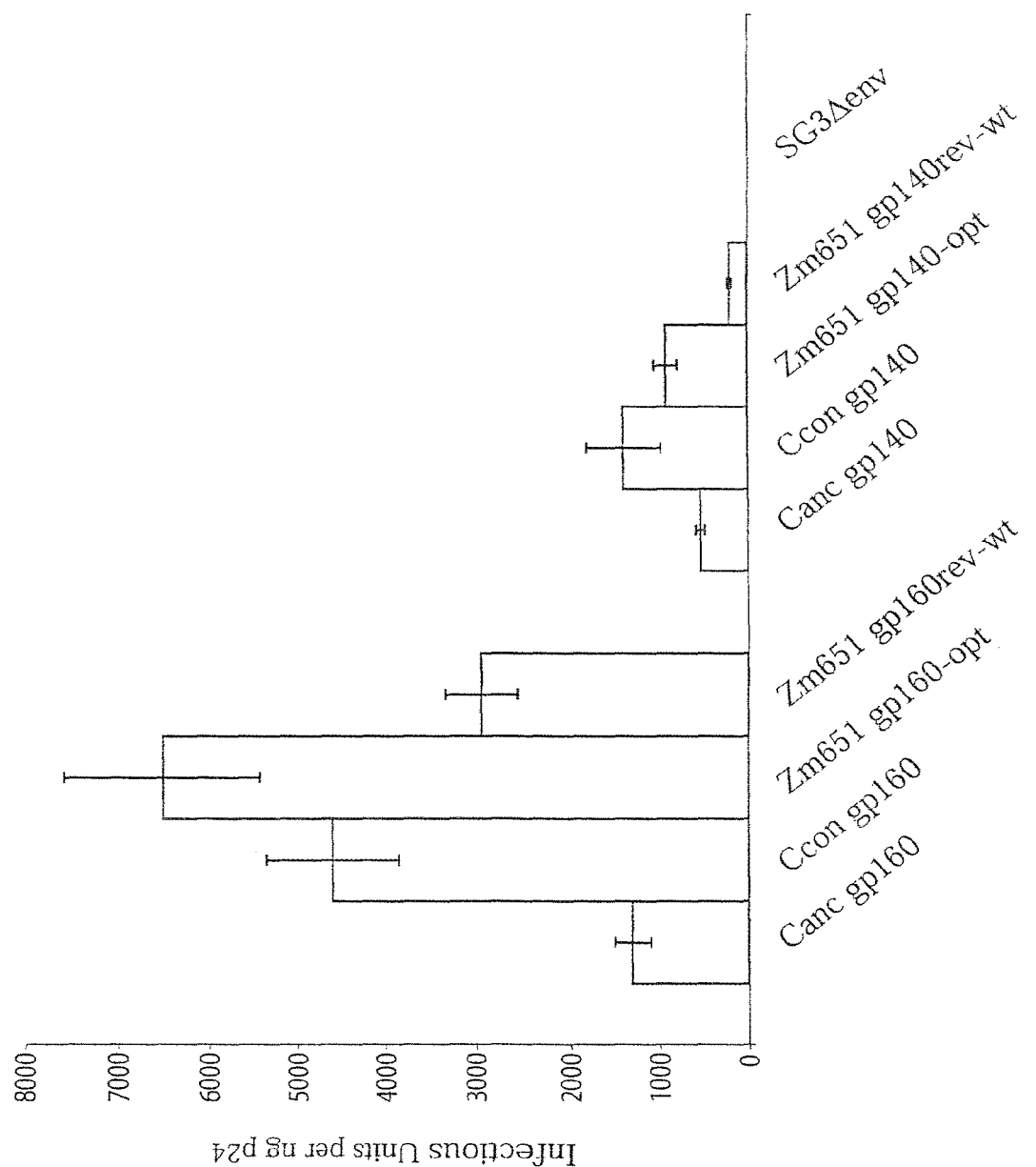

FIGS. 10A and 10B. FIG. 10A. Trans complementation of env-deficient HIV-1 with codon-optimized subtype C ancestral and consensus gp160 and gp140. Plasmids containing codon-optimized, subtype C ancestral or consensus gp160 or gp140 genes were co-transfected into 293T cells with an HIV-1/SG3Δenv provirus. 48 hours post-transfection cell supernatants containing pseudotyped virus were harvested, clarified by centrifugation, filtered through at 0.2 µM filter, and pelleted through a 20% sucrose cushion. Quantification of p24 in each virus pellet was determined using the Coulter HIV-1 p24 antigen assay; 25 ng of p24 was loaded per lane on a 4-20% SDS-PAGE gel for particles containing a codon-optimized envelope. 250 ng of p24 was loaded per lane for particles generated by co-transfection of a rev-dependent wild-type subtype C 96ZAM651env gene. Differences in the amount of p24 loaded per lane were necessary to ensure visualization of the rev-dependent envelopes by Western Blot. Proteins were transferred to a PVDF membrane and probed with pooled plasma from HIV-1 subtype B and subtype C infected individuals. FIG. 10B. Infectivity of virus particles containing subtype C ancestral and consensus envelope glycoproteins. Infectivity of pseudotyped virus containing ancestral or consensus gp160 or gp140 envelope was determined using the JC53-BL assay. Sucrose cushion purified virus particles were assayed by the Coulter p24 antigen assay, and 5-fold serial dilutions of each pellet were incubated with DEAE-Dextran treated JC53-BL cells. Following a 48-hour incubation period, cells were fixed and stained to visualize β-galactosidase expressing cells. Infectivity is represented as infectious units per ng of p24 to normalize for differences in the concentration of the input pseudovirions.

FIG. 11. Co-receptor usage of subtype C ancestral and consensus envelopes. Pseudotyped particles containing ancestral or consensus envelope were incubated with DEAE-Dextran treated JC53-BL cells in the presence of AMD3100 (a specific inhibitor of CXCR4), TAK779 (a specific inhibitor of CCR5), or AMD3000+TAK779 to determine co-receptor usage. NL4.3, an isolate known to utilize CXCR4, and YU-2, a known CCR5-using isolate, were included as controls.

FIGS. 12A-12C. Neutralization sensitivity of subtype C ancestral and consensus envelope glycoproteins. Equivalent amounts of pseudovirions containing the ancestral, consensus or 96ZAM651 gp160 envelopes (1,500 infectious units) were preincubated with a panel of plasma samples from HIV-1 subtype C infected patients and then added to the JC53-BL cell monolayer in 96-well plates. Plates were cultured for two days and luciferase activity was measured as an indicator of viral infectivity. Virus infectivity is calculated by dividing the luciferase units (LU) produced at each concentration of antibody by the LU produced by the control infection. The mean 50% inhibitory concentration ($IC_{50}$) and the actual % neutralization at each antibody dilution are then calculated for each virus. The results of all luciferase experiments are confirmed by direct counting of blue foci in parallel infections.

FIGS. 13A-13F. Protein expression of consensus subtype C Gag (FIG. 13A) and Nef (FIG. 13B) following transfection into 293T cells. Consensus subtype C Gag and Nef amino acid sequences are set forth in FIGS. 13C and 13D (SEQ ID NOS: 9-10), respectively, and encoding sequences are set forth in FIGS. 13E and 13F (SEQ ID NOS: 11-12), respectively.

FIGS. 14A-14C. FIGS. 14A and 14B show the Con-S Env amino acid sequence and encoding sequence, respectively (SEQ ID NOS: 13-14). FIG. 14C shows expression of Group M consensus Con-S Env proteins using an in vitro transcription and translation system.

FIGS. 15A and 15B. Expression of Con-S env gene in mammalian cells. (FIG. 15A—cell lysate, FIG. 15B—supernatant.)

FIGS. 16A and 16B. Infectivity (FIG. 16A) and coreceptor usage (FIG. 16B) of CON6 and Con-S env genes.

FIGS. 17A-17C. Env protein incorporation in CON6 and Con-S Env-pseudovirions. (FIG. 17A—lysate, FIG. 17B—supernatant, FIG. 17C pellet.)

Figures 18C, 18D, 19:
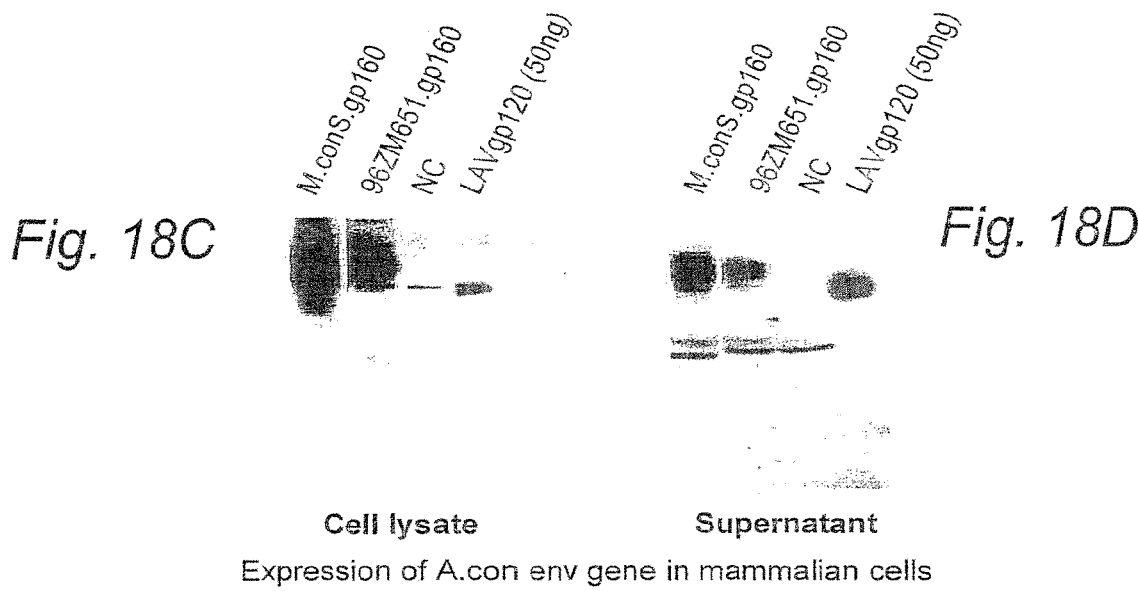

FIGS. 18A-18D. FIGS. 18A and 18B show subtype A consensus Env amino acid sequence and nucleic acid sequence encoding same, respectively (SEQ ID NOS: 15-16). FIGS. 18C and 18D show expression of A.con env gene in mammalian cells (FIG. 18C—cell lysate, FIG. 18D—supernatant).

FIGS. 19A-19H. M.con.gag (FIG. 19A) (SEQ ID NO: 17), M.con.pol (FIG. 19B) (SEQ ID NO: 18), M.con.nef (FIG. 19C) (SEQ ID NO: 19) and C.con.pol (FIG. 19D) (SEQ ID NO: 20) nucleic acid sequences and corresponding encoded amino acid sequences (FIGS. 19E-19H, respectively) (SEQ ID NOS: 21-24).

FIGS. 20A-20D. Subtype B consensus gag (FIG. 20A) (SEQ ID NO: 25) and env (FIG. 20B) (SEQ ID NO: 26)

genes. Corresponding amino acid sequences are shown in FIGS. 20C and 20D (SEQ ID NOS: 28-29).

FIG. 21. Expression of subtype B consensus env and gag genes in 293T cells. Plasmids containing codon-optimized subtype B consensus gp160, gp140, and gag genes were transfected into 293T cells, and protein expression was examined by Western Blot analysis of cell lysates. 48-hours post-transfection, cell lysates were collected, total protein content determined by the BCA protein assay, and 2 μg of total protein was loaded per lane on a 4-20% SDS-PAGE gel. Proteins were transferred to a PVDF membrane and probed with serum from an HIV-1 subtype B infected individual.

FIG. 22. Co-receptor usage of subtype B consensus envelopes. Pseudotyped particles containing the subtype B consensus gp160 Env were incubated with DEAE-Dextran treated JC53-BL cells in the presence of AMD3100 (a specific inhibitor of CXCR4), TAK779 (a specific inhibitor of CCR5), and AMD3000+TAK779 to determine co-receptor usage. NL4.3, an isolate known to utilize CXCR4 and YU-2, a known CCR5-using isolate, were included as controls.

FIGS. 23A and 23B. Trans complementation of env-deficient HIV-1 with codon-optimized subtype B consensus gp160 and gp140 genes. Plasmids containing codon-optimized, subtype B consensus gp160 or gp140 genes were co-transfected into 293T cells with an HIV-1/SG3Δenv provirus. 48-hours post-transfection cell supernatants containing pseudotyped virus were harvested, clarified in a tabletop centrifuge, filtered through a 0.2 μM filter, and pellet through a 20% sucrose cushion. Quantification of p24 in each virus pellet was determined using the Coulter HIV-1 p24 antigen assay; 25 ng of p24 was loaded per lane on a 4-20% SDS-PAGE gel. Proteins were transferred to a PVDF membrane and probed with anti-HIV-1 antibodies from infected HIV-1 subtype B patient serum. Trans complementation with a rev-dependent NL4.3 env was included for control. FIG. 23B. Infectivity of virus particles containing the subtype B concensus envelope. Infectivitiy of pseudotyped virus containing consensus B gp160 or gp140 was determined using the JC53-BL assay. Sucrose cushion purified virus particles were assayed by the Coulter p24 antigen assay, and 5-fold serial dilutions of each pellet were incubated with DEAE-Dextran treated JC53-BL cells. Following a 48-hour incubation period, cells were fixed and stained to visualize β-galactosidase expressing cells. Infectivity is expressed as infectious units per ng of p24.

Figure 24A:
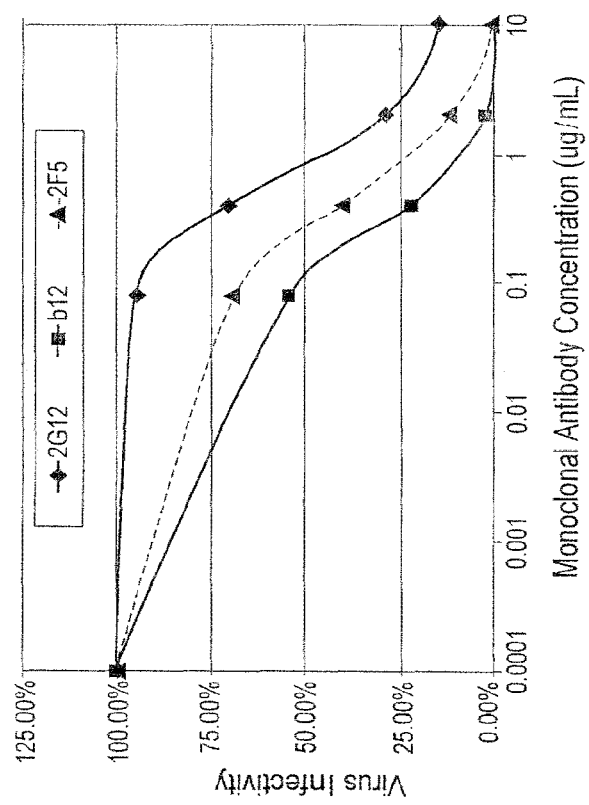
Figure 24B:
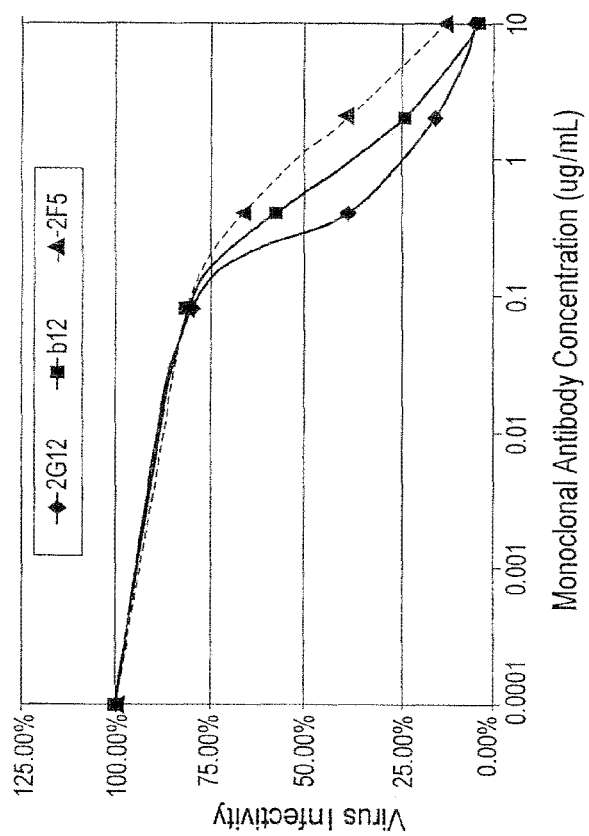

FIGS. 24A-24D. Neutralization sensitivity of virions containing subtype B consensus gp160 envelope. Equivalent amounts of pseudovirions containing the subtype B consensus or NL4.3 Env (gp160) (1,500 infectious units) were preincubated with three different monoclonal neutralizing antibodies and a panel of plasma samples from HIV-1 wubtype B infected individuals, and then added to the JC53-BL cell monolayer in 96-well plates. Plates were cultured for two days and luciferase activity was measured as an indicator of viral infectivity. Virus infectivity was calculated by dividing the luciferase units (LU) produced at each concentration of antibody by the LU produced by the control infection. The mean 50% inhibitory concentration ($IC_{50}$) and the actual % neutralization at each antibody dilution were then calculated for each virus. The results of all luciferase experiments were confirmed by direct counting of blue foci in parallel infections. FIG. 24A. Neutralization of Pseudovirions containing Subtype B consensus Env (gp160). FIG. 24B. Neutralization of Pseudovirions containing NL4.3 Env (gp160).

Figure 24C:
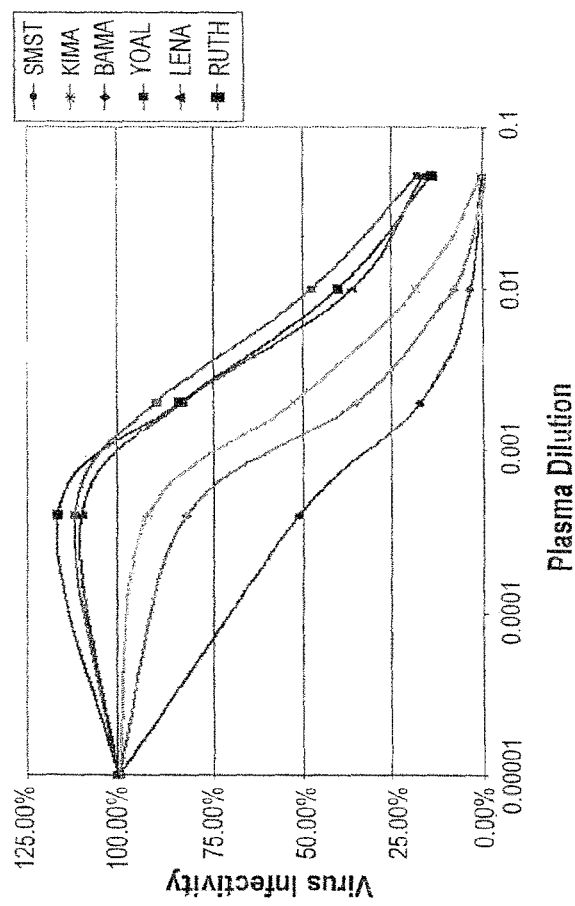
Figure 24D:
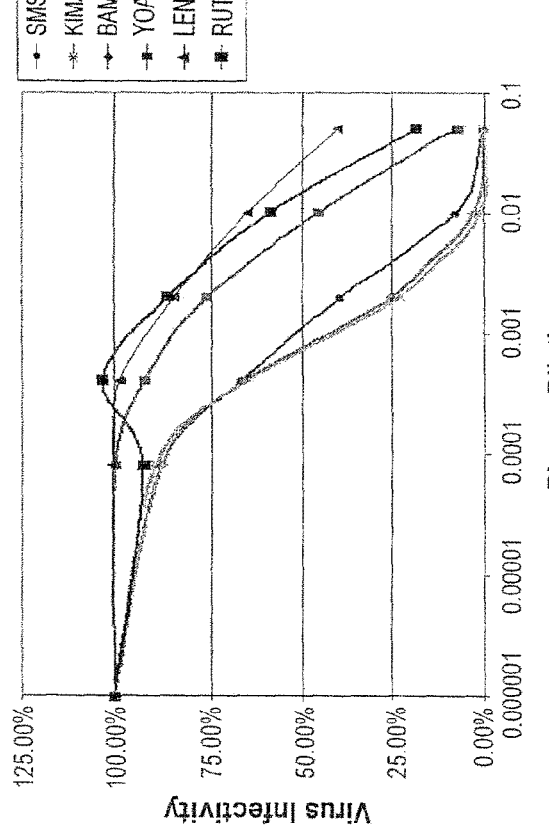

FIG. 24C. Neutralization of Pseudovirions containing Subtype B consensus Env (gp160). FIG. 24D. Neutralization of Pseudovirions containing NL4.3 Env (gp160).

Figure 25A:
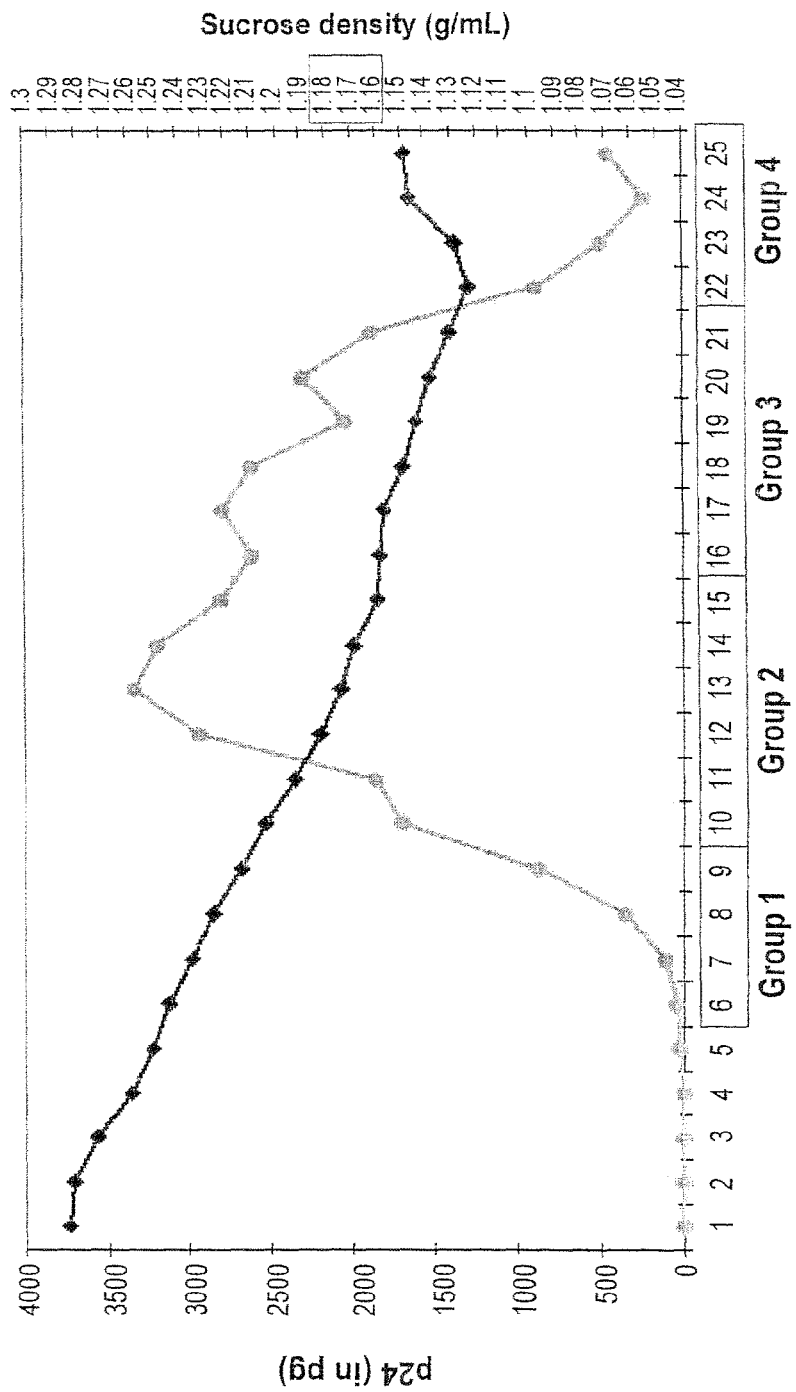
Figure 25B:
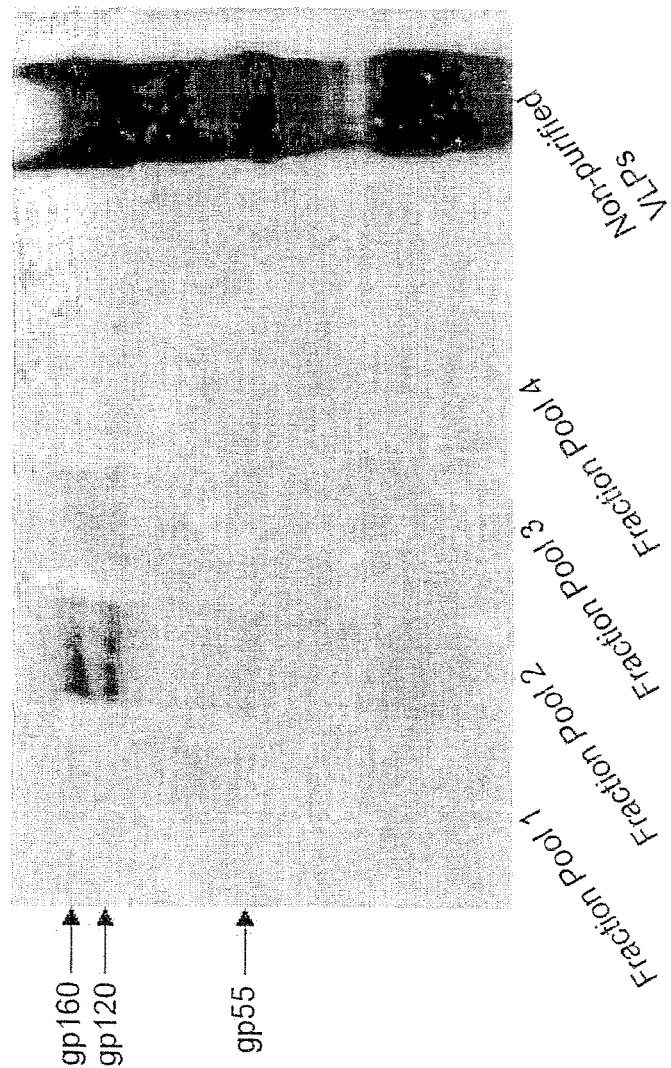

FIGS. 25A and 25B. FIG. 25A. Density and p24 analysis of sucrose gradient fractions. 0.5 ml fractions were collected from a 20-60% sucrose gradient. Fraction number 1 represents the most dense fraction taken from the bottom of the gradient tube. Density was measured with a refractometer and the amount of p24 in each fraction was determined by the Coulter p24 antigen assay. Fractions 6-9, 10-15, 16-21, and 22-25 were pooled together and analyzed by Western Blot. As expected, virions sedimented at a density of 1.16-1.18 g/ml.

FIG. 25B. VLP production by co-transfection of subtype B consensus gag and env genes. 293T cells were co-transfected with subtype B consensus gag and env genes. Cell supernatants were harvested 48-hours post-transfection, clarified through at 20% sucrose cushion, and further purified through a 20-60% sucrose gradient. Select fractions from the gradient were pooled, added to 20 ml of PBS, and centrifuged overnight at 100,000×g. Resuspended pellets were loaded onto a 4-20% SDS-PAGE gel, proteins were transferred to a PVDF membrane, and probed with plasma from an HIV-1 subtype B infected individual.

FIGS. 26A and 26B. FIG. 26A. 2000 Con-S 140CFI.ENV (SEQ ID NO: 30). FIG. 26B. Codon-optimized Year 2000 Con-S 140CFI.seq (SEQ ID NO: 31).

Figure 27:
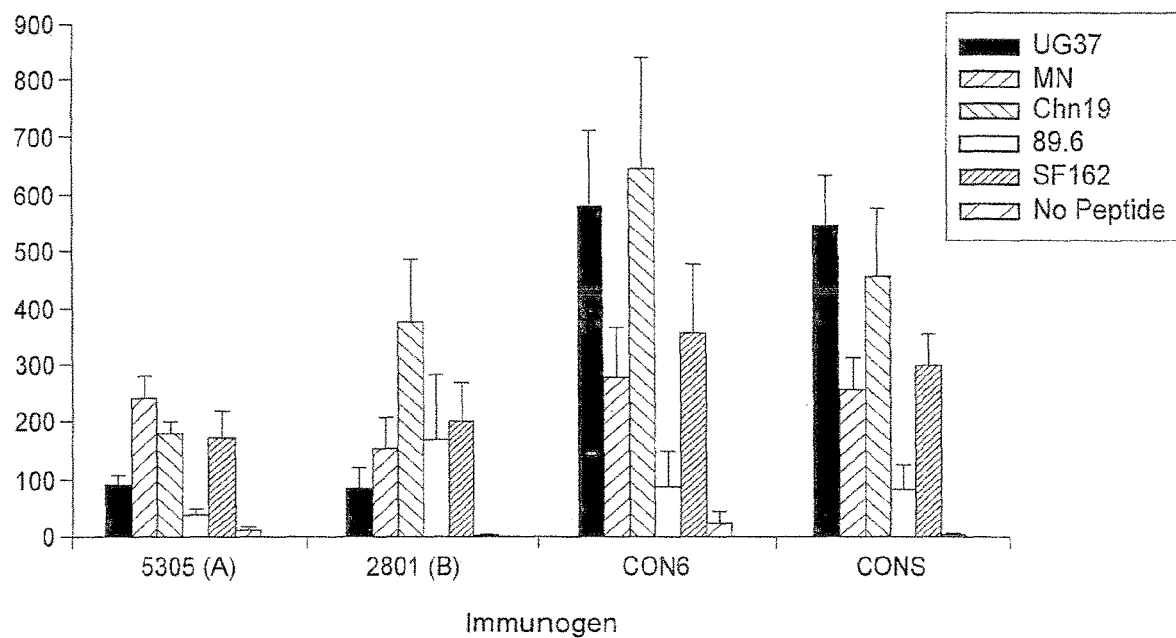

FIG. 27. Individual C57BL/6 mouse T cell responses to HIV-1 envelope peptides. Comparative immunogenicity of CON6 gp140CFI and Con-S gp140CFI in C57BL/C mice. Mice were immunized with either HIV5305 (Subtype A), 2801 (Subtype B), CON6 or Con-S Envelope genes in DNA prime, rVV boost regimens, 5 mice per group. Spleen cells were assayed for IFN-γ spot-forming cells 10 days after rVV boost, using mixtures of overlapping peptides from Envs of HIV-1 UG37(A), MN(B), Ch19(C), 89.6(B) SF162(B) or no peptide negative control.

FIGS. 28A-28C. FIG. 28A. Con-B 2003 Env. pep (841 a.a.) (SEQ ID NO: 32). Amino acid sequence underlined is the fusion domain that is deleted in 140CF design and the "W" underlined is the last amino acid at the C-terminus, all amino acids after the "W" are deleted in the 140CF design. FIG. 28B. Con-B-140CF.pep (632 a.a.) (SEQ ID NO: 33). Amino acids in bold identify the junction of the deleted fusion cleavage site. FIG. 28C. Codon-optimized Con-B 140CF.seq (1927 nt.) (SEQ ID NO: 34).

FIGS. 29A-29C. FIG. 29A. CON_OF_CONS-2003 (829 a.a.) (SEQ ID NO: 35). Amino acid sequence underlined is the fusion domain that is deleted in 140CF design and the "W" underlined is the last amino acid at the C-terminus, all amino acids after the "W" are deleted in the 140CF design. FIG. 29B. ConS-2003 140CF.pep (620 a.a.) (SEQ ID NO: 36). Amino acids in bold identify the junction of the deleted fusion cleavage site. FIG. 29C. CODON-OPTIMIZED ConS-2003 140CF.seq (1891 nt.) (SEQ ID NO: 37).

FIGS. 30A-30C. FIG. 30A. CONSENSUS_A1-2003 (845 a.a.) (SEQ ID NO: 38). Amino acid sequence underlined is the fusion domain that is deleted in 140CF design and the "W" underlined is the last amino acid at the C-terminus, all amino acids after the "W" are deleted in the 140CF design. FIG. 30B. Con-A1-2003 140CF.pep (629 a.a.) (SEQ ID NO: 39). Amino acids in bold identify the junction of the deleted fusion cleavage site. FIG. 30C. CODON-OPTIMIZED Con-A1-2003.seq (SEQ ID NO: 40).

FIGS. 31A-31C. FIG. 31A. CONSENSUS_C-2003 (835 a.a.) (SEQ ID NO: 41). Amino acid sequence underlined is the fusion domain that is deleted in 140CF design and the "W" underlined is the last amino acid at the C-terminus, all amino acids after the "W" are deleted in the 140CF design. FIG. 31B. Con-C 2003 140CF.pep (619 a.a.) (SEQ ID NO: 42). Amino acids in bold identify the junction of the deleted fusion cleavage site. FIG. 31C. CODON-OPTIMIZED Con-C-2003 (140 CF (1,888 nt.) (SEQ ID NO: 43).

FIGS. 32A-32C. FIG. 32A. CONSENSUS_G-2003 (842 a.a.) (SEQ ID NO: 44). Amino acid sequence underlined is the fusion domain that is deleted in 140CF design and the "W" underlined is the last amino acid at the C-terminus, all amino acids after the "W" are deleted in the 140CF design. FIG. 32B. Con-G-2003 140CF.pep (626 a.a.) (SEQ ID NO: 45). Amino acids in bold identify the junction of the deleted fusion cleavage site. FIG. 32C. CODON-OPTIMIZED Con-G-2003.seq (SEQ ID NO: 46).

FIGS. 33A-33C. FIG. 33A. CONSENSUS_01_AE-2003 (854 a.a.) (SEQ ID NO: 47). Amino acid sequence underlined is the fusion domain that is deleted in 140CF design and the "W" underlined is the last amino acid at the C-terminus, all amino acids after the "W" are deleted in the 140CF design. FIG. 33B. Con-AE01-2003 140CF.pep (638 a.a.) (SEQ ID NO: 48). Amino acids in bold identify the junction of the deleted fusion cleavage site. FIG. 33C, CODON-OPTIMIZED Con-AE01-2003.seq. (1945 nt.) (SEQ ID NO: 49).

FIGS. 34A-34C. FIG. 34A. Wild-type subtype A Env. 00KE MSA4076-A (Subtype A, 891 a.a.) (SEQ ID NO: 50). Amino acid sequence underlined is the fusion domain that is deleted in 140CF design and the "W" underlined is the last amino acid at the C-terminus, all amino acids after the "W" are deleted in the 140CF design. FIG. 34B. 00KE MSA4076-A 140CF.pep (647 a.a.) (SEQ ID NO: 51). Amino acids in bold identify the junction of the deleted fusion cleavage site. FIG. 34C. CODON-OPTIMIZED 00KE MSA4076-A 140CF.seq. (1972 nt.) (SEQ ID NO: 52).

FIGS. 35A-35C. FIG. 35A. Wild-type subtype B. QH0515.1g gp160 (861 a.a.) (SEQ ID NO: 53). Amino acid sequence underlined is the fusion domain that is deleted in 140CF design and the "W" underlined is the last amino acid at the C-terminus, all amino acids after the "W" are deleted in the 140CF design. FIG. 35B. QH0515.1g 140CF (651 a.a.) (SEQ ID NO: 54). Amino acids in bold identify the junction of the deleted fusion cleavage site. FIG. 35C. CODON-OPTIMIZED QH0515.1g 140CF.seq (1984 nt.) (SEQ ID NO: 55).

FIGS. 36A-36C. FIG. 36A. Wild-type subtype C. DU123.6 gp160 (854 a.a.) (SEQ ID NO: 56). Amino acid sequence underlined is the fusion domain that is deleted in 140CF design and the "W" underlined is the last amino acid at the C-terminus, all amino acids after the "W" are deleted in the 140CF design. FIG. 36B. DU123.6 140CF (638 a.a.) (SEQ ID NO: 57). Amino acids in bold identify the junction of the deleted fusion cleavage site. FIG. 36C. CODON-OPTIMIZED DU123.6 140CF.seq (1945 nt.) (SEQ ID NO: 58).

FIGS. 37A-37C. FIG. 37A. Wild-type subtype CRF01_AE. 97CNGX2F-AE (854 a.a.) (SEQ ID NO: 59). Amino acid sequence underlined is the fusion domain that is deleted in 140CF design and the "W" underlined is the last amino acid at the C-terminus, all amino acids after the "W" are deleted in the 140CF design. FIG. 37B. 97CNGX2F-AE 140CF.pep (629 a.a.) (SEQ ID NO: 60). Amino acids in bold identify the junction of the deleted fusion cleavage site. FIG. 37C. CODON-OPTIMIZED 97CNGX2F-AE 140CF.seq (1921 nt.) (SEQ ID NO: 61).

FIGS. 38A-38C. FIG. 38A. Wild-type DRCBL-G (854 a.a.) (SEQ ID NO: 62). Amino acid sequence underlined is the fusion domain that is deleted in 140CF design and the "W" underlined is the last amino acid at the C-terminus, all amino acids after the "W" are deleted in the 140CF design. FIG. 38B. DRCBL-G 140CF.pep (630 a.a.) (SEQ ID NO: 63). Amino acids in bold identify the junction of the deleted fusion cleavage site. FIG. 38C. CODON-OPTIMIZED DRCBL-G 140CF.seq (1921 nt.) (SEQ ID NO: 64).

FIGS. 39A and 39B. FIG. 39A. 2003 Con-S Env (SEQ ID NO: 65). FIG. 39B. 2003 Con-S Env.seq.opt. (Seq.opt.=codon optimized encoding sequence.) (SEQ ID NO: 72)

FIGS. 40A and 40B. FIG. 40A. 2003 M. Group.Anc Env (SEQ ID NO: 66). FIG. 40B. 2003 M. Group.anc Env.seq.opt. (Seq.opt.=codon optimized encoding sequence.) (SEQ ID NO: 67)

FIGS. 41A and 41B. FIG. 41A. 2003 CON_A1 Env (SEQ ID NO: 68). FIG. 41B. 2003 CON_A1 Env.seq.opt. (Seq.opt.=codon optimized encoding sequence.) (SEQ ID NO: 70)

FIGS. 42A and 42B. FIG. 42A. 2003 A1.Anc Env (SEQ ID NO: 69). FIG. 42B. 2003 A1.anc Env.seq.opt. (Seq.opt.=codon optimized encoding sequence.) (SEQ ID NO: 71)

FIGS. 43A and 43B. FIG. 43A. 2003 CON_A2 Env (SEQ ID NO: 73). FIG. 43B. 2003 CON_A2 Env.seq.opt. (Seq.opt.=codon optimized encoding sequence.) (SEQ ID NO: 75)

FIGS. 44A and 44B. FIG. 44A. 2003 CON_B Env (SEQ ID NO: 74). FIG. 44B. 2003 CON_B Env.seq.opt. (Seq.opt.=codon optimized encoding sequence.) (SEQ ID NO: 76)

FIGS. 45A and 45B. FIG. 45A. 2003 B.anc Env (SEQ ID NO: 77). FIG. 45B. 2003 B.anc Env.seq.opt. (Seq.opt.=codon optimized encoding sequence.) (SEQ ID NO: 79)

FIGS. 46A and 46B. FIG. 46A. 2003 CON_C Env (SEQ ID NO: 78). FIG. 46B. 2003 CON_C Env.seq.opt. (Seq.opt.=codon optimized encoding sequence.) (SEQ ID NO: 80)

FIGS. 47A and 47B. FIG. 47A. 2003 C.anc Env (SEQ ID NO: 81). FIG. 47B. 2003 C.anc Env.seq.opt. (Seq.opt.=codon optimized encoding sequence.) (SEQ ID NO: 83)

FIGS. 48A and 48B. FIG. 48A. 2003 CON_D Env (SEQ ID NO: 82). FIG. 48B. 2003 CON D Env.seq.opt. (Seq.opt.=codon optimized encoding sequence.) (SEQ ID NO: 84)

FIGS. 49A and 49B. FIG. 49A. 2003 CON_F1 Env (SEQ ID NO: 85). FIG. 49B. 2003 CON_F1 Env.seq.opt. (Seq.opt.=codon optimized encoding sequence.) (SEQ ID NO: 87)

FIGS. 50A and 50B. FIG. 50A. 2003 CON_F2 Env (SEQ ID NO: 86). FIG. 50B. 2003 CON_F2 Env.seq.opt. (Seq.opt.=codon optimized encoding sequence.) (SEQ ID NO: 88)

FIGS. 51A and 51B. FIG. 51A. 2003 CON_G Env (SEQ ID NO: 89). FIG. 51B. 2003 CON_G Env.seq.opt. (Seq.opt.=codon optimized encoding sequence.) (SEQ ID NO: 91)

FIGS. 52A and 52B. FIG. 52A. 2003 CON_H Env (SEQ ID NO: 90). FIG. 52B. 2003 CON_H Env.seq.opt. (Seq.opt.=codon optimized encoding sequence.) (SEQ ID NO: 92)

FIGS. 53A and 53B. FIG. 53A. 2003_CON_01_AE Env (SEQ ID NO: 93). FIG. 53B. 2003_CON_01_AE Env.seq.opt. (Seq.opt.=codon optimized encoding sequence.) (SEQ ID NO: 95)

FIGS. 54A and 54B. FIG. 54A. 2003 CON_02_AG Env (SEQ ID NO: 94). FIG. 54B. 2003 CON_02_AG Env.seq.opt. (Seq.opt.=codon optimized encoding sequence.) (SEQ ID NO: 96)

FIGS. 55A and 55B. FIG. 55A. 2003 CON_03_AB Env (SEQ ID NO: 97). FIG. 55B. 2003 CON_03_AB Env.seq.opt. (Seq.opt.=codon optimized encoding sequence.) (SEQ ID NO: 99)

FIGS. 56A and 56B. FIG. 56A. 2003 CON_04_CPX Env (SEQ ID NO: 98). FIG. 56B. 2003 CON_04_CPX Env.seq.opt. (Seq.opt.=codon optimized encoding sequence.) (SEQ ID NO: 100)

FIGS. 57A and 57B. FIG. 57A. 2003 CON_06_CPX Env (SEQ ID NO: 101). FIG. 57B. 2003 CON_06_CPX Env.seq.opt. (Seq.opt.=codon optimized encoding sequence.) (SEQ ID NO: 103)

FIGS. 58A and 58B. FIG. 58A. 2003 CON_08_BC Env (SEQ ID NO: 102). FIG. 58B. 2003 CON_08_BC Env.seq.opt. (Seq.opt.=codon optimized encoding sequence.) (SEQ ID NO: 104)

FIGS. 59A and 59B. FIG. 59A. 2003 CON_10_CD Env (SEQ ID NO: 105). FIG. 59B. 2003 CON_10_CD Env.seq.opt. (Seq.opt.=codon optimized encoding sequence.) (SEQ ID NO: 107)

FIGS. 60A and 60B. FIG. 60A. 2003 CON_11_CPX Env (SEQ ID NO: 106). FIG. 60B. 2003 CON_11_CPX Env.seq.opt. (Seq.opt.=codon optimized encoding sequence.) (SEQ ID NO: 108)

FIGS. 61A and 61B. FIG. 61A. 2003 CON_12_BF Env (SEQ ID NO: 109). FIG. 61B. 2003 CON_12_BF Env.seq.opt. (Seq.opt.=codon optimized encoding sequence.) (SEQ ID NO: 111)

FIGS. 62A and 62B. FIG. 62A. 2003 CON_14_BG Env (SEQ ID NO: 110). FIG. 62B. 2003 CON_14_BG Env.seq.opt. (Seq.opt.=codon optimized encoding sequence.) (SEQ ID NO: 112)

FIGS. 63A and 63B. FIG. 63A. 2003_CON_S gag.PEP (SEQ ID NO: 113). FIG. 63B. 2003_CON_S gag.OPT. (OPT=codon optimized encoding sequence.) (SEQ ID NO: 114)

FIGS. 64A and 64B. FIG. 64A. 2003_M.GROUP.anc gag.PEP (SEQ ID NO: 115). FIG. 64B. 2003_M.GROUP.anc gag.OPT. (OPT=codon optimized encoding sequence.) (SEQ ID NO: 116)

FIGS. 65A-65D. FIG. 65A. 2003_CON_A1 gag.PEP (SEQ ID NO: 117). FIG. 65B. 2003_CON_A1 gag.OPT (SEQ ID NO: 118). FIG. 65C. 2003_A1.anc gag.PEP (SEQ ID NO: 119). FIG. 65D. 2003_A1.anc gag.OPT (SEQ ID NO: 120). (OPT=codon optimized encoding sequence.)

FIGS. 66A and 66B. FIG. 66A. 2003_CON_A2 gag.PEP (SEQ ID NO: 121), FIG. 66B. 2003_CON_A2 gag.OPT. (OPT=codon optimized encoding sequence.) (SEQ ID NO: 122)

FIGS. 67A-67D. FIG. 67A. 2003_CON_B gag.PEP (SEQ ID NO: 123). FIG. 67B. 2003_CON_B gag.OPT (SEQ ID NO: 124). FIG. 67C. 2003_B, anc gag.PEP (SEQ ID NO: 125). FIG. 67D. 2003_B.anc gag.OPT. (OPT=codon optimized encoding sequence.) (SEQ ID NO: 126)

FIGS. 68A-68D. FIG. 68A. 2003_CON_C gag.PEP (SEQ ID NO: 127). FIG. 68B. 2003_CON_C gag.OPT (SEQ ID NO: 128). FIG. 68C. 2003_C.anc.gag.PEP (SEQ ID NO: 129). FIG. 68D. 2003_C.anc.gag.OPT. (OPT=codon optimized encoding sequence.) (SEQ ID NO: 130)

FIGS. 69A and 69B. FIG. 69A. 2003_CON_D gag.PEP (SEQ ID NO: 131). FIG. 69B. 2003_CON_D gag.OPT. (OPT=codon optimized encoding sequence.) (SEQ ID NO: 132)

FIGS. 70A and 70B. FIG. 70A. 2003_CON_F gag.PEP (SEQ ID NO: 133). FIG. 70B. 2003_CON_F gag.OPT. (OPT=codon optimized encoding sequence.) (SEQ ID NO: 134)

FIGS. 71A and 71B. FIG. 71A. 2003_CON_G gag.PEP (SEQ ID NO: 135). FIG. 71B. 2003_CON_G gag.OPT. (OPT=codon optimized encoding sequence.) (SEQ ID NO: 136)

FIGS. 72A and 72B. FIG. 72A. 2003_CON_H gag.PEP (SEQ ID NO: 137). FIG. 72B. 2003_CON_H gag.OPT. (OPT=codon optimized encoding sequence.) (SEQ ID NO: 138)

FIGS. 73A and 73B. FIG. 73A. 2003_CON_K gag.PEP (SEQ ID NO: 139). FIG. 73B. 2003_CON_K gag.OPT. (OPT=codon optimized encoding sequence.) (SEQ ID NO: 140)

FIGS. 74A and 74B. FIG. 74A. 2003_CON_01_AE gag.PEP (SEQ ID NO: 141). FIG. 7B. 2003_CON_01_AE gag.OPT. (OPT=codon optimized encoding sequence.) (SEQ ID NO: 142)

FIGS. 75A and 75B. FIG. 75A. 2003_CON_02_AG gag.PEP (SEQ ID NO: 143). FIG. 75B. 2003_CON_02_AG gag.OPT. (OPT=codon optimized encoding sequence.) (SEQ ID NO: 144)

FIGS. 76A and 76B. FIG. 76A. 2003_CON_03_ABG gag.PEP (SEQ ID NO: 145). FIG. 76B. 2003_CON_03_ABG gag.OPT. (OPT=codon optimized encoding sequence.) (SEQ ID NO: 146)

FIGS. 77A and 77B. FIG. 77A. 2003_CON_04_CFX gag.PEP (SEQ ID NO: 147). FIG. 77B. 2003_CON_04_CFX gag.OPT. (OPT=codon optimized encoding sequence.) (SEQ ID NO: 148)

FIGS. 78A and 78B. FIG. 78A. 2003_CON_06_CPX gag.PEP (SEQ ID NO: 150). FIG. 78B. 2003_CON_06_CPX gag.OPT. (OPT=codon optimized encoding sequence.) (SEQ ID NO: 151)

FIGS. 79A and 79B. FIG. 79A. 2003_CON_07_BC gag.PEP (SEQ ID NO: 152). FIG. 79B. 2003_CON_07_BC gag.OPT. (OPT=codon optimized encoding sequence.) (SEQ ID NO: 153)

FIGS. 80A and 80B. FIG. 80A. 2003_CON_08_BC gag.PEP (SEQ ID NO: 154). FIG. 80B. 2003_CON_08_BC gag.OPT. (OPT=codon optimized encoding sequence.) (SEQ ID NO: 155)

FIGS. 81A and 81B. FIG. 81A. 2003_CON_10_CD gag.PEP (SEQ ID NO: 156). FIG. 81B. 2003_CON_10_CD gag.OPT. (OPT=codon optimized encoding sequence.) (SEQ ID NO: 157)

FIGS. 82A and 82B. FIG. 82A. 2003_CON_11_CPX gag.PEP (SEQ ID NO: 158). FIG. 82B. 2003_CON_11_CPX gag.OPT. (OPT=codon optimized encoding sequence.) (SEQ ID NO: 159)

FIGS. 83A and 83B. FIG. 83A. 2003_CON_12_BF.gag.PEP (SEQ ID NO: 160) FIG. 83B. 2003_CON_12_BF.gag.OPT. (OPT=codon optimized encoding sequence.) (SEQ ID NO: 161)

FIGS. 84A and 84B. FIG. 84A. 2003_CON_14_BG gag.PEP (SEQ ID NO: 162). FIG. 84B. 2003_CON_14_BG gag.OPT. (OPT=codon optimized encoding sequence.) (SEQ ID NO: 163)

FIGS. 85A and 85B. FIG. 85A. 2003_CONS nef.PEP (SEQ ID NO: 164). FIG. 85B. 2003_CONS nef.OPT. (OPT=codon optimized encoding sequence.) (SEQ ID NO: 165)

FIGS. 86A and 86B. FIG. 86A. 2003_M GROUP.anc nef.PEP (SEQ ID NO: 166). FIG. 86B. 2003 M GROUP.anc.nef OPT. (OPT=codon optimized encoding sequence.) (SEQ ID NO: 167)

FIGS. 87A and 87B. FIG. 87A. 2003_CON_A nef.PEP (SEQ ID NO: 168). FIG. 87B. 2003_CON_A nef OPT. (OPT=codon optimized encoding sequence.) (SEQ ID NO: 169)

FIGS. 88A-88D. FIG. 88A. 2003_CON_A1 nef.PEP (SEQ ID NO: 170). FIG. 88B. 2003_CON_A1 nef.OPT (SEQ ID NO: 171). FIG. 88C. 2003_A1.anc nef.PEP (SEQ ID NO: 172). FIG. 88D. 2003_A1.anc nef.OPT. (OPT=codon optimized encoding sequence.) (SEQ ID NO: 173)

FIGS. 89A and 89B. FIG. 89A. 2003_CON_A2 nef.PEP (SEQ ID NO: 174). FIG. 89B. 2003_CON_A2 nef.OPT. (OPT=codon optimized encoding sequence.) (SEQ ID NO: 175)

FIGS. 90A-90D. FIG. 90A. 2003_CON_B nef PEP (SEQ ID NO: 176). FIG. 90B. 2003_CON-B nef OPT (SEQ ID NO: 177). FIG. 90C. 2003_B.anc nef.PEP (SEQ ID NO: 178). FIG. 90D. 2003_B.anc nef.OPT. (OPT=codon optimized encoding sequence.) (SEQ ID NO: 179)

FIGS. 91A and 91B. FIG. 91A. 2003_CON_02_AG nef.PEP (SEQ ID NO: 180). FIG. 91B. 2003_CON_02_AG nef.OPT. (OPT=codon optimized encoding sequence.) (SEQ ID NO: 181)

FIGS. 92A-92D. FIG. 92A. 2003_CON_C nef PEP (SEQ ID NO: 182). FIG. 92B. 2003_CON_C nef OPT (SEQ ID NO: 183). FIG. 92C. 2003_C.anc nef PEP (SEQ ID NO: 184). FIG. 92D. 2003_C.anc nef.OPT. (OPT=codon optimized encoding sequence.) (SEQ ID NO: 185)

FIGS. 93A and 93B. FIG. 93A. 2003_CON_D nef.PEP (SEQ ID NO: 186). FIG. 93B. 2003_CON_D nef OPT. (OPT=codon optimized encoding sequence.) (SEQ ID NO: 187)

FIGS. 94A and 94B. FIG. 94A. 2003_CON_F1 nef PEP (SEQ ID NO: 188). FIG. 94B. 2003_CON_F1 nef OPT. (OPT=codon optimized encoding sequence.) (SEQ ID NO: 189)

FIGS. 95A and 95B. FIG. 95A. 2003_CON_F2 nef.PEP (SEQ ID NO: 190). FIG. 95B. 2003_CON_F2 nef.OPT. (OPT=codon optimized encoding sequence.) (SEQ ID NO: 191)

FIGS. 96A and 96B. FIG. 96A. 2003_CON_G nef.PEP (SEQ ID NO: 192). FIG. 96B. 2003_CON_G nef OPT. (OPT=codon optimized encoding sequence.) (SEQ ID NO: 193)

FIGS. 97A and 97B. FIG. 97A. 2003_CON_H nef.PEP (SEQ ID NO: 194). FIG. 97B. 2003_CON_H nef.OPT. (OPT=codon optimized encoding sequence.) (SEQ ID NO: 195)

FIGS. 98A and 98B. FIG. 98A. 2003_CON_01_AE nef.PEP (SEQ ID NO: 196). FIG. 98B. 2003_CON_01_AE nef OPT. (OPT=codon optimized encoding sequence.) (SEQ ID NO: 197)

FIGS. 99A and 99B. FIG. 99A. 2003_CON_03_AE nef.PEP (SEQ ID NO: 198). FIG. 99B. 2003_CON_03_AE nef OPT. (OPT=codon optimized encoding sequence.) (SEQ ID NO: 199)

FIGS. 100A and 100B. FIG. 100A. 2003_CON_04_CFX nef.PEP (SEQ ID NO: 200). FIG. 100B. 2003_CON_04_CFX nef.OPT. (OPT=codon optimized encoding sequence.) (SEQ ID NO: 201)

FIGS. 101A and 101B. FIG. 101A. 2003_CON_06_CFX nef.PEP (SEQ ID NO: 202). FIG. 101B. 2003_CON_06_CFX nef.OPT. (OPT=codon optimized encoding sequence.) (SEQ ID NO: 203)

FIGS. 102A and 102B. FIG. 102A. 2003_CON_08_BC nef.PEP (SEQ ID NO: 204). FIG. 102B. 2003_CON_08_BC nef OPT. (OPT=codon optimized encoding sequence.) (SEQ ID NO: 205)

FIGS. 103A and 103B. FIG. 103A. 2003_CON_10_CD nef.PEP (SEQ ID NO: 206). FIG. 103B. 2003_CON_10_CD nef.OPT. (OPT=codon optimized encoding sequence.) (SEQ ID NO: 207)

FIGS. 104A and 104B. FIG. 104A. 2003_CON_11_CFX nef.PEP (SEQ ID NO: 208). FIG. 104B. 2003_CON_11_CFX nef.OPT. (OPT=codon optimized encoding sequence.) (SEQ ID NO: 209)

FIGS. 105A and 105B. FIG. 105A. 2003_CON_12_BF nef.PEP (SEQ ID NO: 210). FIG. 105B. 2003_CON_12_BF nef.OPT. (OPT=codon optimized encoding sequence.) (SEQ ID NO: 211)

FIGS. 106A and 106B. FIG. 106A. 2003_CON_14_BG nef.PEP (SEQ ID NO: 212). FIG. 106B. 2003_CON_14_BG nef.OPT. (OPT=codon optimized encoding sequence.) (SEQ ID NO: 213)

FIGS. 107A and 107B. FIG. 107A. 2003_CON_S pol. PEP (SEQ ID NO: 214). FIG. 107B. 2003_CON_S pol.OPT. (OPT=codon optimized encoding sequence.) (SEQ ID NO: 215)

FIGS. 108A and 108B. FIG. 108A. 2003_M GROUP anc pol.PEP (SEQ ID NO: 216). FIG. 108B. 2003_M.GROUP anc pol.OPT. (OPT=codon optimized encoding sequence.) (SEQ ID NO: 218)

FIGS. 109A-109D. FIG. 109A. 2003_CON_A1 pol.PEP (SEQ ID NO: 217). FIG. 109B. 2003_CON_A1 pol.OPT (SEQ ID NO: 219). FIG. 109C. 2003_A1.anc pol.PEP (SEQ ID NO: 220). FIG. 109D. 2003_A1.anc pol.OPT (SEQ ID NO: 221). (OPT=codon optimized encoding sequence.)

FIGS. 110A and 110B. FIG. 110A. 2003_CON_A2 pol. PEP (SEQ ID NO: 222). FIG. 110B. 2003_CON_A2 pol.OPT. (OPT=codon optimized encoding sequence.) (SEQ ID NO: 224)

FIGS. 111A-111D. FIG. 111A. 2003_CON_B pol.PEP (SEQ ID NO: 223). FIG. 111B. 2003_CON_B pol.OPT (SEQ ID NO: 225). FIG. 111C. 2003_B.anc pol.PEP (SEQ ID NO: 226). FIG. 111D. 2003_B.anc pol.OPT (SEQ ID NO: 227). (OPT=codon optimized encoding sequence.)

FIGS. 112A-112D. FIG. 112A. 2003_CON_C pol.PEP (SEQ ID NO: 228). FIG. 112B. 2003_CON_C pol.OPT (SEQ ID NO: 229). FIG. 112C. 2003_C.anc pol.PEP (SEQ ID NO: 230). FIG. 112D. 2003_C.anc pol.OPT. (OPT=codon optimized encoding sequence.) (SEQ ID NO: 231)

FIGS. 113A and 113B. FIG. 113A. 2003_CON_D pol. PEP (SEQ ID NO: 232). FIG. 113B. 2003_CON_D pol.OPT. (OPT=codon optimized encoding sequence.) (SEQ ID NO: 224)

FIGS. 114A and 114B. FIG. 114A. 2003_CON_F1 pol. PEP (SEQ ID NO: 233). FIG. 114B. 2003_CON_F1 pol.OPT. (OPT=codon optimized encoding sequence.) (SEQ ID NO: 235)

FIGS. 115A and 115B. FIG. 115A. 2003_CON_F2 pol. PEP (SEQ ID NO: 236). FIG. 115B. 2003_CON_F2 pol.OPT. (OPT=codon optimized encoding sequence.) (SEQ ID NO: 238)

FIGS. 116A and 116B. FIG. 116A. 2003_CON_G pol. PEP (SEQ ID NO: 237). FIG. 116B. 2003_CON_G pol.OPT. (OPT=codon optimized encoding sequence.) (SEQ ID NO: 239)

FIGS. 117A and 117B. FIG. 117A. 2003_CON_H pol. PEP (SEQ ID NO: 240). FIG. 117B. 2003_CON_H pol.OPT. (OPT=codon optimized encoding sequence.) (SEQ ID NO: 242)

FIGS. 118A and 118B. FIG. 118A. 2003_CON_01_AE pol.PEP (SEQ ID NO: 241). FIG. 118B. 2003_CON_01_AE pol.OPT. (OPT=codon optimized encoding sequence.) (SEQ ID NO: 243)

FIGS. 119A and 119B. FIG. 119A. 2003_CON_02_AG pol.PEP (SEQ ID NO: 244). FIG. 119B. 2003_CON_02_AG pol.OPT. (OPT=codon optimized encoding sequence.) (SEQ ID NO: 246)

FIGS. 120A and 120B. FIG. 120A. 2003_CON_03_AB pol.PEP (SEQ ID NO: 245). FIG. 120B. 2003_CON_03_AB pol.OPT. (OPT=codon optimized encoding sequence.) (SEQ ID NO: 247)

FIGS. 121A and 121B. FIG. 121A. 2003_CON_04_CPX pol.PEP (SEQ ID NO: 248). FIG. 121B. 2003_CON_04_CPX pol.OPT. (OPT=codon optimized encoding sequence.) (SEQ ID NO: 250)

FIGS. 122A and 122B. FIG. 122A. 2003_CON_06_CPX pol.PEP (SEQ ID NO: 249). FIG. 122B. 2003_CON06_CPX pol.OPT. (OPT=codon optimized encoding sequence.) (SEQ ID NO: 251)

FIGS. 123A and 123B. FIG. 123A. 2003_CON_08_BC pol.PEP (SEQ ID NO: 252). FIG. 123B. 2003_CON_08_BC pol.OPT. (OPT=codon optimized encoding sequence.) (SEQ ID NO: 254)

FIGS. 124A and 124B. FIG. 124A. 2003_CON_10_CD pol.PEP (SEQ ID NO: 253). FIG. 124B. 2003_CON_10_CD pol.OPT. (OPT=codon optimized encoding sequence.) (SEQ ID NO: 255)

FIGS. 125A and 125B. FIG. 125A. 2003_CON_11_CPX pol.PEP (SEQ ID NO: 256). FIG. 125B. 2003_CON_11_CPX pol.OPT. (OPT=codon optimized encoding sequence.) (SEQ ID NO: 258)

FIGS. 126A and 126B. FIG. 126A. 2003_CON_12_BF pol.PEP (SEQ ID NO: 257). FIG. 126B. 2003_CON_12_BF pol.OPT. (OPT=codon optimized encoding sequence.) (SEQ ID NO: 259)

FIGS. 127A and 127B. FIG. 127A. 2003_CON_14_BG pol.PEP (SEQ ID NO: 260). FIG. 127B. 2003_CON_14_BG pol.OPT. (OPT=codon optimized encoding sequence.) (SEQ ID NO: 261)

DETAILED DESCRIPTION OF THE INVENTION

The present invention relates to an immunogen that induces antibodies that neutralize a wide spectrum of human immunodeficiency virus (HIV) primary isolates and/or that induces a T cell response. The immunogen comprises at least one consensus or ancestral immunogen (e.g., Env, Gag, Nef or Poly, or portion or variant thereof. The invention also relates to nucleic acid sequences encoding the consensus or ancestral immunogen, or portion or variant thereof. The invention further relates to methods of using both the immunogen and the encoding sequences. While the invention is described in detail with reference to specific consensus and ancestral immunogens (for example, to a group M consensus Env), it will be appreciated that the approach described herein can be used to generate a variety of consensus or ancestral immunogens (for example, envelopes for other HIV-1 groups (e.g., N and O)).

In accordance with one embodiment of the invention, a consensus env gene can be constructed by generating consensus sequences of env genes for each subtype of a particular HIV-1 group (group M being classified into subtypes A-D, F-H, J an K), for example, from sequences in the Los Alamos HIV Sequence Database (using, for example, MASE (Multiple Aligned Sequence Editor)). A consensus sequence of all subtype consensuses can then be generated to avoid heavily sequenced subtypes (Gaschen et al, Science 296:2354-2360 (2002), Korber et al, Science 288:1789-1796 (2000)). In the case of the group M consensus env gene described in Example 1 (designated CON6), five highly variable regions from a CRF08_BC recombinant strain (98CN006) (V1, V2, V4, V5 and a region in cytoplasmic domain of gp41) are used to fill in the missing regions in the sequence (see, however, corresponding regions for Con-S). For high levels of expression, the codons of consensus or ancestral genes can be optimized based on codon usage for highly expressed human genes. (Haas et al, Curr. Biol. 6:315-324 (2000), Andre et al, J. Virol. 72:1497-1503 (1998)).

With the Year 1999 consensus group M env gene, CONE, it has been possible to demonstrate induction of superior T cell responses by CONE versus wild-type B and C env by the number of ELISPOT γ-interferon spleen spot forming cells and the number of epitopes recognized in two strains of mice (Tables 1 and 2 show the data in BALB/c mice). The ability of CON6 Env protein to induce neutralizing antibodies to HIV-1 primary isolates has been compared to that of several subtype B Env. The target of neutralizing antibodies induced by CON6 includes several non-B HIV-1 strains.

TABLE 1

T cell epitope mapping of CON6, JRFL and 96ZM651 Env immunogen in BALB/c mice.
Table 1 discloses SEQ ID NOS: 262-287, respectively, in order of appearance.

| | | Immunogen | | | |
|---|---|---|---|---|---|
| | Peptide | CON6 | JRFL (B) | 96ZM651 (C) | T cell response |
| CON 6 (group M consensus) | | | | | |
| 16 | DTEVHNVWATHACVP | + | | + | CD4 |
| 48 | KNSSEYYRLINCNTS | + | | + | CD4 |
| 49 | EYYRLINCNTSAITQ | | | | |
| 53 | CPKVSFEPIPIHYCA | + | | | CD4 |
| 54 | SFEPIPIHYCAPAGF | | | | |

TABLE 1-continued

T cell epitope mapping of CON6, JRFL and
96ZM651 Env immunogen in BALB/c mice.
Table 1 discloses SEQ ID NOS: 262-287,
respectively, in order of appearance.

| Peptide | | CON6 | JRFL (B) | 96ZM651 (C) | T cell response |
|---|---|---|---|---|---|
| 62 | NVSTVQCTHGIKPVV | + | | | CD4 |
| 104 | ETITLPCRIKQIINM | + | | | CD8 |
| 105 | LPCRIKQIINMWQGV | | | | |
| 130 | GIVQQQSNLLRAIEA | + | | | CD4 |
| 131 | VQQSNLLRAIEAQQHL | | | | |
| 134 | AQQHLLQLTVWGIKQLQ | + | | | CD4 |
| 135 | LQLTVWGIKQLQARVL | | | | |
| Subtype B (MN) | | | | | |
| 6223 | AKAYDTEVHNVWATQ | + | | | CD4 |
| 6224 | DTEVHNVWATQACVP | | | | |
| 6261 | ACPKISFEPIPIHYC | + | | | CD4 |
| 6262 | ISFEPIPIHYCAPAG | | | | |
| 6286 | RKRIHIGPGRAFYTT | | + | | CD8 |
| 6287 | HIGPGRAFYTTKNII | | | | |
| 6346 | IVQQQNNLLRAIEAQ | + | | | CD4 |
| 6347 | QNNLLRAIEAQQHML | | | | |
| Subtype C (Chn19) | | | | | |
| 4834 | VPVWKEAKTTLFCASDAKSY | | | + | CD4 |
| 4836 | GKEVHNVWATHACVPTDPNP | + | | + | CD4 |
| 4848 | SSENSSEYYRLINCNTSAIT | + | | + | CD4 |
| 4854 | STVQCTHGIKPVVSTQLLLN | + | | | CD4 |
| 4884 | QQSNLLRAIEAQQHLLQLTV | + | | | CD4 |
| 4885 | AQQHLLQLTVWGIKQLQTRV | + | | | CD4 |

TABLE 2

T cell epitope mapping of CON6.gp120
immunogen in C57BL/6 mice.
Table 2 discloses SEQ ID NOS: 288-304,
respectively, in order of appearance.

| Peptide | Peptide sequence | T cell response |
|---|---|---|
| CON 6 (consensus) | | |
| 2 | GIQRNCQHLWRWGTM | CD8 |
| 3 | NCQHLWRWGTMILGM | |
| 16 | DTEVENVWATHACVP | CD4 |
| 53 | CPKVSFEPIPIHYCA | CD4 |
| 97 | FYCNTSGLFNSTWMF | CD8 |
| 99 | FNSTWMFNGTYMFNG | CD8 |
| Subtype B (MN) | | |
| 6210 | GIRRNYQHWWGWGTM | CD8 |
| 6211 | NYQHWWGWGTMLLGL | |
| 6232 | NMWKNNMVEQMHEDI | CD4 |
| 6262 | ISFEPIPIHYCAPAG | CD4 |
| 6290 | NIIGTIRQAHCNISR | CD4 |
| 6291 | TIRQAHCNISRAKWN | |
| Subtype C (Chn 19) | | |
| 4830 | MRVTGIRKNYQHLWRWGTML | CD8 |
| 5446 | RWGTMLLGMLMICSAAEN | CD8 |
| 4836 | GKEVNVWATHACVPTDPNP | CD4 |
| 4862 | GDIRQAHCNISKDKWNETLQ | CD4 |
| 4888 | LLGIWGCSGKLICTTTVPWN | CD8 |

For the Year 2000 consensus group M env gene, Con-S, the Con-S envelope has been shown to be as immunogenic as the CON6 envelope gene in T cell γ interferon ELISPOT assays in two strains of mice (the data for C57BL/6 are shown in FIG. 27). Furthermore, in comparing CON6 and Con-S gp140 Envs as protein immunogens for antibody in guinea pigs (Table 3), both gp140 Envs were found to induce antibodies that neutralized subtype B primary isolates. However, Con-S gp140 also induced robust neutralization of the subtype C isolates TV-1 and DU 123 as well as one subtype A HIV-1 primary isolate, while CON6 did not.

TABLE 3

Ability of Group M Consensus CON6 and Con-S Envs to Induce Neutralization of HIV-1 Primary Isolates

| HIV-1 Isolate | CON6 gp140CF | | | | CON6 gp140 CFI | | | | CONS gp140 CFI | | | |
|---|---|---|---|---|---|---|---|---|---|---|---|---|
| | Guinea Pig Number | | | | | | | | | | | |
| (Subtype) | 770 | 771 | 772 | 775 | 781 | 783 | 784 | 786 | 776 | 777 | 778 | 780 |
| BX08(B) | 520 | 257 | 428 | 189 | 218 | 164 | >540 | 199 | >540 | >540 | >540 | >5 |
| QH0692 (B) | 46 | 55 | 58 | 77 | <20 | 91 | 100 | 76 | 109 | <20 | <20 | <20 |
| SS1196(B) | 398 | 306 | 284 | 222 | 431 | 242 | >540 | 351 | >540 | 296 | >540 | >540 |
| JRLFL(B) | <20 | <20 | <20 | <20 | <20 | 169 | <20 | <20 | <20 | <20 | <20 | <20 |
| BG1168(B) | <20 | <20 | <20 | <20 | <20 | <20 | <20 | <20 | <20 | <20 | <20 | <20 |
| 3988(B) | <20 | <20 | <20 | <20 | <20 | <20 | <20 | <20 | <20 | <20 | <20 | <20 |
| 6101(B) | <20 | <20 | <20 | <20 | <20 | <20 | <20 | <20 | <20 | <20 | <20 | <20 |
| TV-1(C) | <20 | <20 | <20 | <20 | <20 | <20 | <20 | <20 | 356 | 439 | >540 | >540 |
| DU123(C) | <20 | <20 | 71 | 74 | <20 | 72 | <20 | <20 | 176 | 329 | 387 | 378 |
| DU172(C) | <20 | <20 | 96 | 64 | <20 | <20 | <20 | <20 | <20 | 235 | <20 | 213 |
| ZM18108.6(C) | ND | ND | ND | ND | <20 | <20 | <20 | <20 | 84 | 61 | 86 | 43 |
| ZM14654.7(C) | ND | ND | ND | ND | <20 | <20 | <20 | <20 | <20 | <20 | 30 | <20 |
| DU151(C) | <20 | <20 | <20 | <20 | <20 | <20 | <20 | <20 | <20 | <20 | <20 | <20 |
| DU422(C) | <20 | <20 | <20 | <20 | <20 | <20 | <20 | <20 | <20 | <20 | <20 | <20 |
| DU156(C) | <20 | <20 | <20 | <20 | <20 | <20 | <20 | <20 | <20 | <20 | <20 | <20 |
| 92RWO20(A) | <20 | <20 | <20 | <20 | <20 | <20 | <20 | <20 | 116 | 204 | 95 | 117 |
| 92UG037(A) | <20 | <20 | 30 | <20 | <20 | 44 | <20 | <20 | <20 | <20 | <20 | <2 |

‡ 50% Neutralization titers after 4th or 5th immunizations
Year 2000 Con-S 140CFI.ENV sequence is shown in FIG. 26A. Gp140 CFI refers to an HIV-1 envelope design in which the cleavage-site is deleted (c), the fusion-site is deleted (F) and the gp41 immunodominant region is deleted (I), in addition to the deletion of transmembrane and cytoplasmic domains. The codon-optimized Year 2000 Con-S 140 CFI sequence is shown in FIG. 26B.

As the next iteration of consensus immunogens, and in recognition of the fact that a practical HIV-1 immunogen can be a polyvalent mixture of either several subtype consensus genes, a mixture of subtype and consensus genes, or a mixture of centralized genes and wild type genes, a series of 11 subtype consensus, and wild type genes have been designed from subtypes A, B, C, CRF AE01, and G as well as a group M consensus gene from Year 2003 Los Alamos National Database sequences. The wild type sequences were chosen either because they were known to come from early transmitted HIV-1 strains (those strains most likely to be necessary to be protected against by a vaccine) or because they were the most recently submitted strains in the database of that subtype. These nucleotide and amino acid sequences are shown in FIGS. 28-38 (for all 140CF designs shown, 140CF gene can be flanked with the 5' sequence "TTCAGTCGACGGCCACC" (SEQ ID NO: 305) that contains a Kozak sequence (GCCACCATGG/A) (SEQ ID NO: 306) and SalI site and 3' sequence of TAAAGATCTTACAA (SEQ ID NO: 307) containing stop codon and BglII size). Shown in FIGS. 39-62 are 2003 centralized (consensus and ancestral) HIV-1 envelope proteins and the codon optimized gene sequences.

Major differences between CONE gp140 (which does not neutralize non-clade B HIV strains) and Con-S gp140 (which does induce antibodies that neutralize non-clade B HIV strains) are in Con-S V1, V2, V4 and V5 regions. For clade B strains, peptides of the V3 region can induce neutralizing antibodies (Haynes et al, J. Immunol. 151:1646-1653 (1993)). Thus, construction of Th-V1, Th-V2, Th-V4, Th-V5 peptides can be expected to give rise to the desired broadly reactive anti-non-clade B neutralizing antibodies. Therefore, the Th-V peptides set forth in Table 4 are contemplated for use as a peptide immunogen(s) derived from Con-S gp140. The gag Th determinant (GTH, Table 4) or any homologous GTH sequence in other HIV strains, can be used to promote immunogenicity and the C4 region of HIV gp120 can be used as well (KQIINMWQVVGKA-MYA) (SEQ ID NO: 308) or any homologous C4 sequence from other HIV strains (Haynes et al, J. Immunol. 151:1646-1653 (1993)). Con-S V1, V2, V4, V5 peptides with an N-terminal helper determinant can be used singly or together, when formulated in a suitable adjuvant such as Corixa's RC529 (Baldridge et al, J. Endotoxin Res. 8:453-458 (2002)), to induce broadly cross reactive neutralizing antibodies to non-clade B isolates.

TABLE 4

1) GTH Con-S V1    YKRWIILGLNKIVRMYTNVNVTNTTNNT
   132-150         EEKGEIKN

2) GTH Con-S V2    YKRWIILGLNKIVRMYTEIRDKKQKVYA
   157-189         LFYRLDVVPIDDNNNNSSNYR

3) GTH Con-S V3    YKRWIILGLNKIVRMYTRPNNNTRKSIR
   294-315         IGPGQAFYAT

4) GTH Con-S V4    YKRWIILGLNKIVRMYNTSGLFNSTWIG
   381-408         NGTKNNNNTNDTITLP

5) GTH Con-S V5    YKRWIILGLNKIVRMYRDGGNNNTNETE
   447-466         IFRPGGGD

6) GTH Con-6 V1    YKRWIILGLNKIVRMYNVRNVSSNGTET
   132-150         DNEEIKN

7) GTH Con-6 V2    YKRWIILGLNKIVRMYTELRDKKQKVYA
   157-196         LFYRLDVVPIDDKNSSEISGKNSSEYYR

8) GTH-Con 6 V3    YKRWIILGLNKIVRMYTRPNNNTRKSIH
   301-322         IGPGQAFYAT

TABLE 4-continued

| 9) | GTH Con-6 V4 388-418 | YKRWIILGLNKIVRMYNTSGLFNSTWMF NGTYMFNGTKDNSETITLP |
|---|---|---|
| 10 | GTH Con 6 V5 457-477 | YKRWIILGLNKIVRMYRDGGNNSNKNKT ETFRPGGGD |

It will be appreciated that the invention includes portions and variants of the sequences specifically disclosed herein. For example, forms of codon optimized consensus encoding sequences can be constructed as gp140CF, gp140 CFI, gp120 or gp160 forms with either gp120/41 cleaved or uncleaved. For example, and as regards the consensus and ancestral envelope sequences, the invention encompasses envelope sequences devoid of V3. Alternatively, V3 sequences can be selected from preferred sequences, for example, those described in U.S. application Ser. No. 10/431,596 and U.S. Provisional Application No. 60/471, 327. In addition, an optimal immunogen for breadth of response can include mixtures of group M consensus gag, pol, nef and env encoding sequences, and as well as consist of mixtures of subtype consensus or ancestral encoding sequences for gag, pol, nef and env HIV genes. For dealing with regional differences in virus strains, an efficacious mixture can include mixtures of consensus/ancestral and wild type encoding sequences.

A consensus or ancestral envelope of the invention can be been "activated" to expose intermediate conformations of neutralization epitopes that normally are only transiently or less well exposed on the surface of the HIV virion. The immunogen can be a "frozen" triggered form of a consensus or ancestral envelope that makes available specific epitopes for presentation to B lymphocytes. The result of this epitope presentation is the production of antibodies that broadly neutralize HIV. (Attention is directed to WO 02/024149 and to the activated/triggered envelopes described therein.)

The concept of a fusion intermediate immunogen is consistent with observations that the gp41 HR-2 region peptide, DP178, can capture an uncoiled conformation of gp41 (Furata et al, Nature Struct. Biol. 5:276 (1998)), and that formalin-fixed HIV-infected cells can generate broadly neutralizing antibodies (LaCasse et al, Science 283:357 (1997)). Recently a monoclonal antibody against the coiled-coil region bound to a conformational determinant of gp41 in HR1 and HR2 regions of the coiled-coil gp41 structure, but did not neutralize HIV (Jiang et al, J. Virol. 10213 (1998)). However, this latter study proved that the coiled-coil region is available for antibody to bind if the correct antibody is generated.

The immunogen of one aspect of the invention comprises a consensus or ancestral envelope either in soluble form or anchored, for example, in cell vesicles or in liposomes containing translipid bilayer envelope. To make a more native envelope, gp140 or gp160 consensus or ancestral sequences can be configured in lipid bilayers for native trimeric envelope formation. Alternatively, triggered gp160 in aldrithio 1-2 inactivated HIV-1 virions can be used as an immunogen. The gp160 can also exist as a recombinant protein either as gp160 or gp140 (gp140 is gp160 with the transmembrane region and possibly other gp41 regions deleted). Bound to gp160 or gp140 can be recombinant CCR5 or CXCR4 co-receptor proteins (or their extracellular domain peptide or protein fragments) or antibodies or other ligands that bind to the CXCR4 or CCR5 binding site on gp120, and/or soluble CD4, or antibodies or other ligands that mimic the binding actions of CD4. Alternatively, vesicles or liposomes containing CD4, CCR5 (or CXCR4), or soluble CD4 and peptides reflective of CCR5 or CXCR4 gp120 binding sites. Alternatively, an optimal CCR5 peptide ligand can be a peptide from the N-terminus of CCR5 wherein specific tyrosines are sulfated (Bormier et al, Proc. Natl. Acad. Sci. USA 97:5762 (2001)). The triggered immunogen may not need to be bound to a membrane but may exist and be triggered in solution. Alternatively, soluble CD4 (sCD4) can be replaced by an envelope (gp140 or gp160) triggered by CD4 peptide mimetopes (Vitra et al, Proc. Natl. Acad. Sci. USA 96:1301 (1999)). Other HIV co-receptor molecules that "trigger" the gp160 or gp140 to undergo changes associated with a structure of gp160 that induces cell fusion can also be used. Ligation of soluble HIV gp140 primary isolate HIV 89.6 envelope with soluble CD4 (sCD4) induced conformational changes in gp41.

In one embodiment, the invention relates to an immunogen that has the characteristics of a receptor (CD4)-ligated consensus or ancestral envelope with CCR5 binding region exposed but unlike CD4-ligated proteins that have the CD4 binding site blocked, this immunogen has the CD4 binding site exposed (open). Moreover, this immunogen can be devoid of host CD4, which avoids the production of potentially harmful anti-CD4 antibodies upon administration to a host.

The immunogen can comprise consensus or ancestral envelope ligated with a ligand that binds to a site on gp120 recognized by an A32 monoclonal antibodies (mab) (Wyatt et al, J. Virol. 69:5723 (1995), Boots et al, AIDS Res. Hum. Retro. 13:1549 (1997), Moore et al, J. Virol. 68:8350 (1994), Sullivan et al, J. Virol. 72:4694 (1998), Fouts et al, J. Virol. 71:2779 (1997), Ye et al, J. Virol. 74:11955 (2000)). One A32 mab has been shown to mimic CD4 and when bound to gp120, upregulates (exposes) the CCR5 binding site (Wyatt et al, J. Virol. 69:5723 (1995)). Ligation of gp120 with such a ligand also upregulates the CD4 binding site and does not block CD4 binding to gp120. Advantageously, such ligands also upregulate the HR-2 binding site of gp41 bound to cleaved gp120, uncleaved gp140 and cleaved gp41, thereby further exposing HR-2 binding sites on these proteins—each of which are potential targets for anti-HIV neutralizing antibodies.

In a specific aspect of this embodiment, the immunogen comprises soluble HIV consensus or ancestral gp120 envelope ligated with either an intact A32 mab, a Fab2 fragment of an A32 mab, or a Fab fragment of an A32 mab, with the result that the CD4 binding site, the CCR5 binding site and the HR-2 binding site on the consensus or ancestral envelope are exposed/upregulated. The immunogen can comprise consensus or ancestral envelope with an A32 mab (or fragment thereof) bound or can comprise consensus or ancestral envelope with an A32 mab (or fragment thereof) bound and cross-linked with a cross-linker such as 0.3% formaldehyde or a heterobifunctional cross-linker such as DTSSP (Pierce Chemical Company). The immunogen can also comprise uncleaved consensus or ancestral gp140 or a mixture of uncleaved gp140, cleaved gp41 and cleaved gp120. An A32 mab (or fragment thereof) bound to consensus or ancestral gp140 and/or gp120 or to gp120 non-covalently bound to gp41, results in upregulation (exposure) of HR-2 binding sites in gp41, gp120 and uncleaved gp140. Binding of an A32 mab (or fragment thereof) to gp120 or gp140 also results in upregulation of the CD4 binding site and the CCR5 binding site. As with gp120 containing complexes, complexes comprising uncleaved gp140 and an A32 mab (or fragment thereof) can be used as an immunogen uncross-linked or cross-linked with cross-linker such as 0.3% formaldehyde or DTSSP. In one embodiment, the invention relates to an immunogen comprising soluble uncleaved consensus or ancestral gp140 bound and cross linked to a Fab fragment or whole A32 mab, optionally bound and cross-linked to an HR-2 binding protein.

The consensus or ancestral envelope protein triggered with a ligand that binds to the A32 mab binding site on gp120 can be administered in combination with at least a second immunogen comprising a second envelope, triggered by a ligand that binds to a site distinct from the A32 mab binding site, such as the CCR5 binding site recognized by mab 17b. The 17b mab (Kwong et al, Nature 393:648 (1998) available from the AIDS Reference Repository, NIAID, NIH) augments sCD4 binding to gp120. This second immunogen (which can also be used alone or in combination with triggered immunogens other than that described above) can, for example, comprise soluble HIV consensus or ancestral envelope ligated with either the whole 17b mab, a Fab2 fragment of the 17b mab, or a Fab fragment of the 17b mab. It will be appreciated that other CCR5 ligands, including other antibodies (or fragments thereof), that result in the CD4 binding site being exposed can be used in lieu of the 17b mab. This further immunogen can comprise gp120 with the 17b mab, or fragment thereof, (or other CCR5 ligand as indicated above) bound or can comprise gp120 with the 17b mab, or fragment thereof, (or other CCR5 ligand as indicated above) bound and cross-linked with an agent such as 0.3% formaldehyde or a heterobifunctional cross-linker, such as DTSSP (Pierce Chemical Company). Alternatively, this further immunogen can comprise uncleaved gp140 present alone or in a mixture of cleaved gp41 and cleaved gp120. Mab 17b, or fragment thereof (or other CCR5 ligand as indicated above) bound to gp140 and/or gp120 in such a mixture results in exposure is of the CD4 binding region. The 17b mab, or fragment thereof, (or other CCR5 ligand as indicated above) gp140 complexes can be present uncross-linked or cross-linked with an agent such as 0.3% formaldehyde or DTSSP.

Soluble HR-2 peptides, such as T649Q26L and DP178, can be added to the above-described complexes to stabilize epitopes on consensus gp120 and gp41 as well as uncleaved consensus gp140 molecules, and can be administered either cross-linked or uncross-linked with the complex.

A series of monoclonal antibodies (mabs) have been made that neutralize many HIV primary isolates, including, in addition to the 17b mab described above, mab IgGlb12 that binds to the CD4 binding site on gp120 (Roben et al, J. Virol. 68:482 (1994), Mo et al, J. Virol. 71:6869 (1997)), mab 2G12 that binds to a conformational determinant on gp120 (Trkola et al, J. Virol. 70:1100 (1996)), and mab 2F5 that binds to a membrane proximal region of gp41 (Muster et al, J. Virol. 68:4031 (1994)).

As indicated above, various approaches can be used to "freeze" fusogenic epitopes in accordance with the invention. For example, "freezing" can be effected by addition of the DP-178 or T-649Q26L peptides that represent portions of the coiled coil region, and that when added to CD4-triggered consensus or ancestral envelope, result in prevention of fusion (Rimsky et al, J. Virol. 72:986-993 (1998)). HR-2 peptide bound consensus or ancestral gp120, gp140, gp41 or gp160 can be used as an immunogen or crosslinked by a reagent such as DTSSP or DSP (Pierce Co.), formaldehyde or other crosslinking agent that has a similar effect.

"Freezing" can also be effected by the addition of 0.1% to 3% formaldehyde or paraformaldehyde, both protein cross-linking agents, to the complex, to stabilize the CD4, CCR5 or CXCR4, HR-2 peptide gp160 complex, or to stabilize the "triggered" gp41 molecule, or both (LaCasse et al, Science 283:357-362 (1999)).

Further, "freezing" of consensus or ancestral gp41 or gp120 fusion intermediates can be effected by addition of heterobifunctional agents such as DSP (dithiobis[succimidylproprionate]) (Pierce Co. Rockford, Ill., No. 22585ZZ) or the water soluble DTSSP (Pierce Co.) that use two NHS esters that are reactive with amino groups to cross link and stabilize the CD4, CCR5 or CXCR4, HR-2 peptide gp160 complex, or to stabilize the "triggered" gp41 molecule, or both.

Analysis of T cell immune responses in immunized or vaccinated animals and humans shows that the envelope protein is normally not a main target for T cell immune response although it is the only gene that induces neutralizing antibodies. HIV-1 Gag, Pol and Nef proteins induce a potent T cell immune response. Accordingly, the invention includes a repertoire of consensus or ancestral immunogens that can induce both humoral and cellular immune responses. Subunits of consensus or ancestral sequences can be used as T or B cell immunogens. (See Examples 6 and 7, and Figures referenced therein, and FIGS. 63-127.

The immunogen of the invention can be formulated with a pharmaceutically acceptable carrier and/or adjuvant (such as alum) using techniques well known in the art. Suitable routes of administration of the present immunogen include systemic (e.g. intramuscular or subcutaneous). Alternative routes can be used when an immune response is sought in a mucosal immune system (e.g., intranasal).

The immunogens of the invention can be chemically synthesized and purified using methods which are well known to the ordinarily skilled artisan. The immunogens can also be synthesized by well-known recombinant DNA techniques. Nucleic acids encoding the immunogens of the invention can be used as components of, for example, a DNA vaccine wherein the encoding sequence is administered as naked DNA or, for example, a minigene encoding the immunogen can be present in a viral vector. The encoding sequence can be present, for example, in a replicating or non-replicating adenoviral vector, an adeno-associated virus vector, an attenuated *Mycobacterium tuberculosis* vector, a *Bacillus* Calmette Guerin (BCG) vector, a vaccinia or Modified Vaccinia Ankara (MVA) vector, another pox virus vector, recombinant polio and other enteric virus vector, Salmonella species bacterial vector, *Shigella* species bacterial vector, Venezuelean Equine Encephalitis Virus (VEE) vector, a Semliki Forest Virus vector, or a Tobacco Mosaic Virus vector. The encoding sequence, can also be expressed as a DNA plasmid with, for example, an active promoter such as a CMV promoter. Other live vectors can also be used to express the sequences of the invention. Expression of the immunogen of the invention can be induced in a patient's own cells, by introduction into those cells of nucleic acids that encode the immunogen, preferably using codons and promoters that optimize expression in human cells. Examples of methods of making and using DNA vaccines are disclosed in U.S. Pat. Nos. 5,580,859, 5,589,466, and 5,703,055.

The composition of the invention comprises an immunologically effective amount of the immunogen of this invention, or nucleic acid sequence encoding same, in a pharmaceutically acceptable delivery system. The compositions can be used for prevention and/or treatment of immunodeficiency virus infection. The compositions of the invention can be formulated using adjuvants, emulsifiers, pharmaceutically-acceptable carriers or other ingredients routinely provided in vaccine compositions. Optimum formulations can be readily designed by one of ordinary skill in the art and can include formulations for immediate release and/or for sustained release, and for induction of systemic immunity and/or induction of localized mucosal immunity (e.g, the formulation can be designed for intranasal administration). The present compositions can be administered by any convenient route including subcutaneous, intranasal, oral, intramuscular, or other parenteral or enteral route. The immunogens can be administered as a single dose or multiple doses. Optimum immunization schedules can be readily determined by the ordinarily skilled artisan and can vary with the patient, the composition and the effect sought.

The invention contemplates the direct use of both the immunogen of the invention and/or nucleic acids encoding same and/or the immunogen expressed as minigenes in the vectors indicated above. For example, a minigene encoding the immunogen can be used as a prime and/or boost.

The invention includes any and all amino acid sequences disclosed herein and, where applicable, CF and CFI forms thereof, as well as nucleic acid sequences encoding same (and nucleic acids complementary to such encoding sequences).

Certain aspects of the invention can be described in greater detail in the non-limiting Examples that follows.

Example 1

Artificial HIV-1 Group M Consensus Envelope Experimental Details

Expression of CONE gp120 and gp140 proteins in recombinant vaccinia viruses (VV). To express and purify the secreted form of HIV-1 CON6 envelope proteins, CON6 gp120 and gp140CF plasmids were constructed by introducing stop codons after the gp120 cleavage site (REKR) (SEQ ID NO: 319) and before the transmembrane domain (YIKIFIMIVGGLIGLRIVFAVLSIVN) (SEQ ID NO: 320), respectively. The gp120/gp41 cleavage site and fusion domain of gp41 were deleted in the gp140CF protein. Both CON6 gp120 and gp140CF DNA constructs were cloned into the pSC65 vector (from Bernard Moss, NIH, Bethesda, Md.) at SalI and KpnI restriction enzyme sites. This vector contains the lacZ gene that is controlled by the p7.5 promoter. A back-to-back P E/L promoter was used to express CON6 env genes. BSC-1 cells were seeded at $2\times10^5$ in each well in a 6-well plate, infected with wild-type vaccinia virus (WR) at a MOI of 0.1 pfu/cell, and 2 hr after infection, pSC65-derived plasmids containing CON6 env genes were transfected into the VV-infected cells and recombinant (r) VV selected as described (Moss and Earl, Current Protocols in Molecular Biology, eds, Ausubel et al (John Wiley & Sons, Inc. Indianapolis, Ind.) pp. 16.15.1-16.19.9 (1998)). Recombinant VV that contained the CON6 env genes were confirmed by PCR and sequencing analysis. Expression of the CON6 envelope proteins was confirmed by SDS-PAGE and Western blot assay. Recombinant CON6 gp120 and gp140CF were purified with agarose *galanthus Nivalis* lectin beads (Vector Labs, Burlingame, Calif.), and stored at 70° C. until use. Recombinant VV expressing JRFL (vCB-28) or 96ZM651 (vT241R) gp160 were obtained from the NIH AIDS Research and Reference Reagent Program (Bethesda, Md.).

Monoclonal Antibodies and gp120 Wild-type Envelopes. Human mabs against a conformational determinant on gp120 (A32), the gp120 V3 loop (F39F) and the CCR5 binding site (17b) were the gifts of James Robinson (Tulane Medical School, New Orleans, La.) (Wyatt et al, Nature 393; 705-711 (1998), Wyatt et al, J. Virol. 69:5723-5733 (1995)). Mabs 2F5, 447, b12, 2G12 and soluable CD4 were obtained from the NIH AIDS Research and Reference Reagent Program (Bethesda, Md.) (Gorny et al, J. Immunol. 159:5114-5122 (1997), Nyambi et al, J. Virol. 70:6235-6243 (1996), Purtscher et al, AIDS Res. Hum. Retroviruses 10:1651-1658 (1994), Trkola et al, J. Virol 70:1100-1108 (1996)). T8 is a murine mab that maps to the gp120 C1 region (a gift from P. Earl, NIH, Bethesda, Md.). BaL (subtype B), 96ZM651 (subtype C), and 93TH975 (subtype E) gp120s were provided by QBI, Inc. and the Division of AIDS, NIH. CHO cell lines that express 92U037 (subtype A) and 93BR029 (subtype F) gp140 (secreted and uncleaved) were obtained from NICBS, England.

Surface Plasmon Resonance Biosensor (SPR) Measurements and ELISA. SPR biosensor measurements were determined on a BIAcore 3000 instrument (BIAcore Inc., Uppsala, Sweden) instrument and data analysis was performed using BIAevaluation 3.0 software (BIAcore Inc, Upsaala, Sweden). Anti-gp120 mabs (T8, A32, 17b, 2G12) or sCD4 in 10 mM Na-acetate buffer, pH 4.5 were directly immobilized to a CM5 sensor chip using a standard amine coupling protocol for protein immobilization. FPLC purified CON6 gp120 monomer or gp140CF oligomer recombinant proteins were flowed over CM5 sensor chips at concentrations of 100 and 300 μg/ml, respectively. A blank in-line reference surface (activated and de-activated for amine coupling) or non-bonding mab controls were used to subtract non-specific or bulk responses. Soluble 89.6 gp120 and irrelevant IgG was used as a positive and negative control respectively and to ensure activity of each mab surface prior to injecting the CON6 Env proteins. Binding of CON6 envelope proteins was monitored in real-time at 25° C. with a continuous flow of PBS (150 mM NaCl, 0.005% surfactant P20), pH 7.4 at 10-30 μl/min. Bound proteins were removed and the sensor surfaces were regenerated following each cycle of binding by single or duplicate 5-10 μpulses of regeneration solution (10 mM glycine-HCl, pH 2.9). ELISA was performed to determine the reactivity of various mabs to CON6 gp120 and gp140CF proteins as described (Haynes et al, AIDS Res. Hum. Retroviruses 11:211-221 (1995)). For assay of human mab binding to rgp120 or gp140 proteins, end-point titers were defined as the highest titer of mab (beginning at 20 μg/ml) at which the mab bound CON6 gp120 and gp140CF Env proteins ≥3 fold over background control (non-binding human mab).

Infectivity and coreceptor usage assays. HIV-1/SG3Δenv and CON6 or control env plasmids were cotransfected into human 293T cells. Pseudotyped viruses were harvested, filtered and p24 concentration was quantitated (DuPont/NEN Life Sciences, Boston, Mass.). Equal amounts of p24 (5 ng) for each pseudovirion were used to infect JC53-BL cells to determine the infectivity (Derdeyn e al, J. Virol. 74:8358-8367 (2000), Wei et al, Antimicrob Agents Chemother. 46:1896-1905 (2002)). JC53-BL cells express CD4, CCR5 and CXCR4 receptors and contain a β-galactosidase (β-gal) gene stably integrated under the transcriptional control of an HIV-1 long terminal repeat (LTR). These cells can be used to quantify the infectious titers of pseudovirion stocks by staining for β-gal expression and counting the number of blue cells (infectious units) per microgram of p24 of pseudovirons (IU/μg p24) (Derdeyn e al, J. Virol. 74:8358-8367 (2000), Wei et al, Antimicrob Agents Chemother. 46:1896-1905 (2002)). To determine the coreceptor usage of the CON6 env gene, JC53BL cells were treated with 1.2 μM AMD3100 and 4 μM TAK-799 for 1 hr at 37° C. then infected with equal amounts of p24 (5 ng) of each Env pseudotyped virus. The blockage efficiency was expressed as the percentage of the infectious units from blockage experiments compared to that from control culture without blocking agents. The infectivity from control group (no blocking agent) was arbitrarily set as 100%.

Immunizations. All animals were housed in the Duke University Animal Facility under AALAC guidelines with animal use protocols approved by the Duke University Animal Use and Care Committee. Recombinant CON6 gp120 and gp140CF glycoproteins were formulated in a stable emulsion with RIBI-CWS adjuvant based on the protocol provided by the manufacturer (Sigma Chemical Co., St. Louis, Mo.). For induction of anti-envelope antibodies, each of four out-bred guinea pigs (Harlan Sprague, Inc., Chicago, Ill.) was given 100 µg either purified CON6 gp120 or gp140CF subcutaneously every 3 weeks (total of 5 immunizations). Serum samples were heat-inactivated (56° C., 1 hr), and stored at −20° C. until use.

For induction of anti-envelope T cell responses, 6-8 wk old female BALB/c mice (Frederick Cancer Research and Developmental Center, NCI, Frederick, Md.) were immunized i.m. in the quadriceps with 50 µg plasmid DNA three times at a 3-week interval. Three weeks after the last DNA immunization, mice were boosted with $10^7$ PFU of rVV expressing Env proteins. Two weeks after the boost, all mice were euthanized and spleens were removed for isolation of splenocytes.

Neutralization assays. Neutralization assays were performed using either a MT-2 assay as described in Bures et al, AIDS Res. Hum. Retroviruses 16:2019-2035 (2000), a luciferase-based multiple replication cycle HIV-1 infectivity assay in 5.25.GFP.Luc.M7 cells using a panel of HIV-1 primary isolates (Bures et al, AIDS Res. Hum. Retroviruses 16:2019-2035 (2000), Bures et al, J. Virol. 76:2233-2244 (2002)), or a syncytium (fusion from without) inhibition assay using inactivated HIV-1 virions (Rossio et al, J. Virol. 72:7992-8001 (1998)). In the luciferase-based assay, neutralizing antibodies were measured as a function of a reduction in luciferase acitivity in 5.25.EGFP.Luc.M7 cells provided by Nathaniel R. Landau, Salk Institute, La Jolla, Calif. (Brandt et al, J. Biol. Chem. 277:17291-17299 (2002)). Five hundred tissue culture infectious dose 50 ($TCID_{50}$) of cell-free virus was incubated with indicated serum dilutions in 150 µl (1 hr, at 37° C.) in triplicate in 96-well flat-bottom culture plates. The 5.25.EGFP.Luc.M7 cells were suspended at a density of $5\times10^5$/ml in media containing DEAE dextran (10 µg/ml). Cells (100 µl) were added and until 10% of cells in control wells (no test serum sample) were positive for GFP expression by fluorescence microscopy. At this time the cells were concentrated 2-fold by removing one-half volume of media. A 50 µl suspension of cells was transferred to 96-well white solid plates (Costar, Cambridge, Mass.) for measurement of luciferase activity using Bright-Glo™ substrate (Promega, Madison, Wis.) on a Wallac 1420 Multilabel Counter (PerkinElmer Life Sciences, Boston, Mass.). Neutralization titers in the MT-2 and luciferase assays were those where ≥50% virus infection was inhibited. Only values that titered beyond 1:20 (i.e. >1:30) were considered significantly positive. The syncytium inhibition "fusion from without" assay utilized HIV-1 aldrithiol-2 (AT-2) inactivated virions from HIV-1 subtype B strains ADA and AD8 (the gift of Larry Arthur and Jeffrey Lifson, Frederick Research Cancer Facility, Frederick, Md.) added to SupT1 cells, with syncytium inhibition titers determined as those titers where ≥90% of syncytia were inhibited compared to prebleed sera.

Enzyme linked immune spot (ELISPOT) assay. Single-cell suspensions of splenocytes from individual immunized mice were prepared by mincing and forcing through a 70 µm Nylon cell strainer (BD Labware, Franklin Lakes, N.J.). Overlapping Env peptides of CON6 gp140 (159 peptides, 15mers overlapping by 11) were purchased from Boston Bioscence, Inc (Royal Oak, Mich.). Overlapping Env peptides of MN gp140 (subtype B; 170 peptides, 15mers overlapping by 11) and Chn19 gp140 (subtype C; 69 peptides, 20mers overlapping by 10) were obtained from the NIH AIDS Research and Reference Reagent Program (Bethesda, Md.). Splenocytes (5 mice/group) from each mouse were stimulated in vitro with overlapping Env peptides pools from CON6, subtype B and subtype C Env proteins. 96-well PVDF plates (MultiScreen-IP, Millipore, Billerica, Mass.) were coated with anti-IFN-γ mab (5 µg/ml, AN18; Mabtech, Stockholm, Sweden). After the plates were blocked at 37° C. for 2 hr using complete Hepes buffered RPMI medium, 50 µl of the pooled overlapping envelope peptides (13 CON6 and MN pools, 13-14 peptides in each pool; 9 Chn19 pool, 7-8 peptide in each pool) at a final concentration of 5 µg/ml of each were added to the plate. Then 50 µl of splenocytes at a concentration of $1.0\times10^7$/ml were added to the wells in duplicate and incubated for 16 hr at 37° C. with 5% $CO_2$. The plates were incubated with 100 µl of a 1:1000 dilution of streptavidin alkaline phosphatase (Mabtech, Stockholm, Sweden), and purple spots developed using 100 µl of BCIP/NBT (Plus) Alkaline Phosphatase Substrate (Moss, Pasadena, Md.). Spot forming cells (SFC) were measured using an Immunospot counting system (CTL Analyzers, Cleveland, Ohio). Total responses for each envelope peptide pool are expressed as SFCs per $10^6$ splenocytes.

Results

CON6 Envelope Gene Design, Construction and Expression. An artificial group M consensus env gene (CON6) was constructed by generating consensus sequences of env genes for each HIV-1 subtype from sequences in the Los Alamos HIV Sequence Database, and then generating a consensus sequence of all subtype consensuses to avoid heavily sequenced subtypes (Gaschen et al, Science 296:2354-2360 (2002), Korber et al, Science 288:1789-1796 (2000)). Five highly variable regions from a CRF08_BC recombinant strain (98CN006) (V1, V2, V4, V5 and a region in cytoplasmic domain of gp41) were then used to fill in the missing regions in CON6 sequence. The CON6 V3 region is group M consensus (FIG. 1A). For high levels of expression, the codons of CON6 env gene were optimized based on codon usage for highly expressed human genes (Haas et al, Curr. Biol. 6:315-324 (2000), Andre et al, J. Virol. 72:1497-1503 (1998)). (See FIG. 1D.) The codon optimized CON6 env gene was constructed and subcloned into pcDNA3.1 DNA at EcoR I and BamH I sites (Gao et al, AIDS Res. Hum. Retroviruses, 19:817-823 (2003)). High levels of protein expression were confirmed with Western-blot assays after transfection into 293T cells. To obtain recombinant CON6 Env proteins for characterization and use as immunogens, rVV was generated to express secreted gp120 and uncleaved gp140CF (FIG. 1B). Purity for each protein was ≥90% as determined by Coomassie blue gels under reducing conditions (FIG. 1C).

Figure 2B:
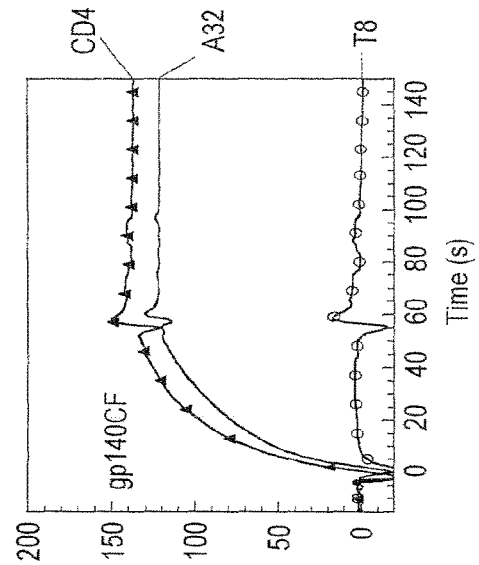
Figure 2C:
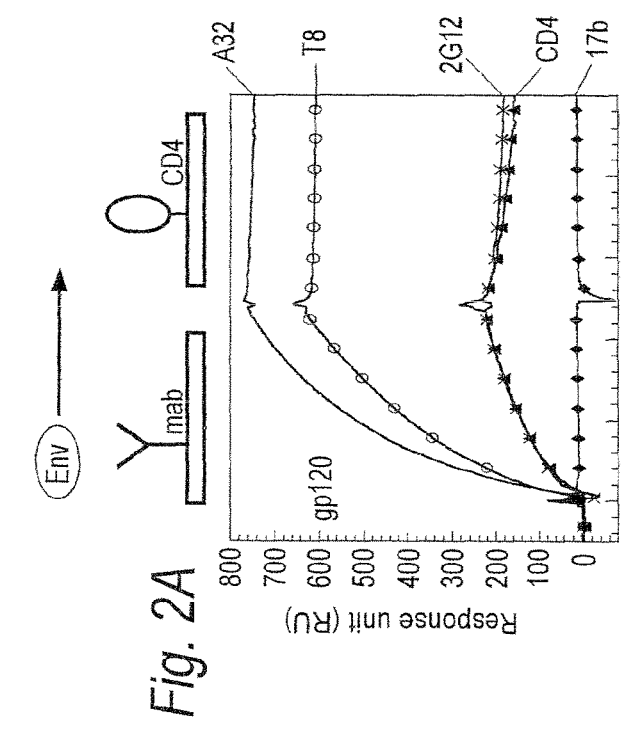
Figure 2D:
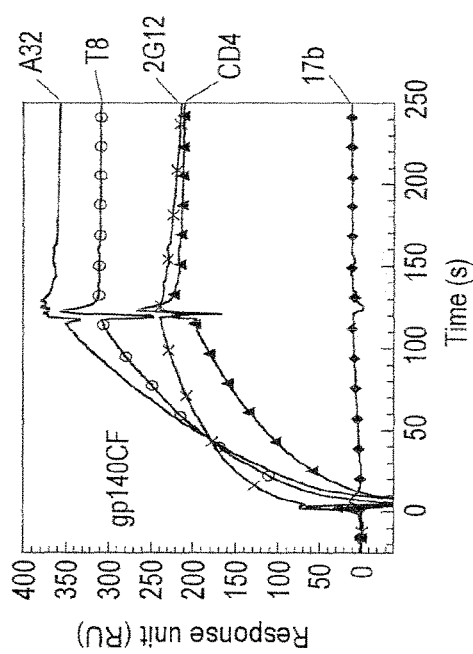
Figure 2E:
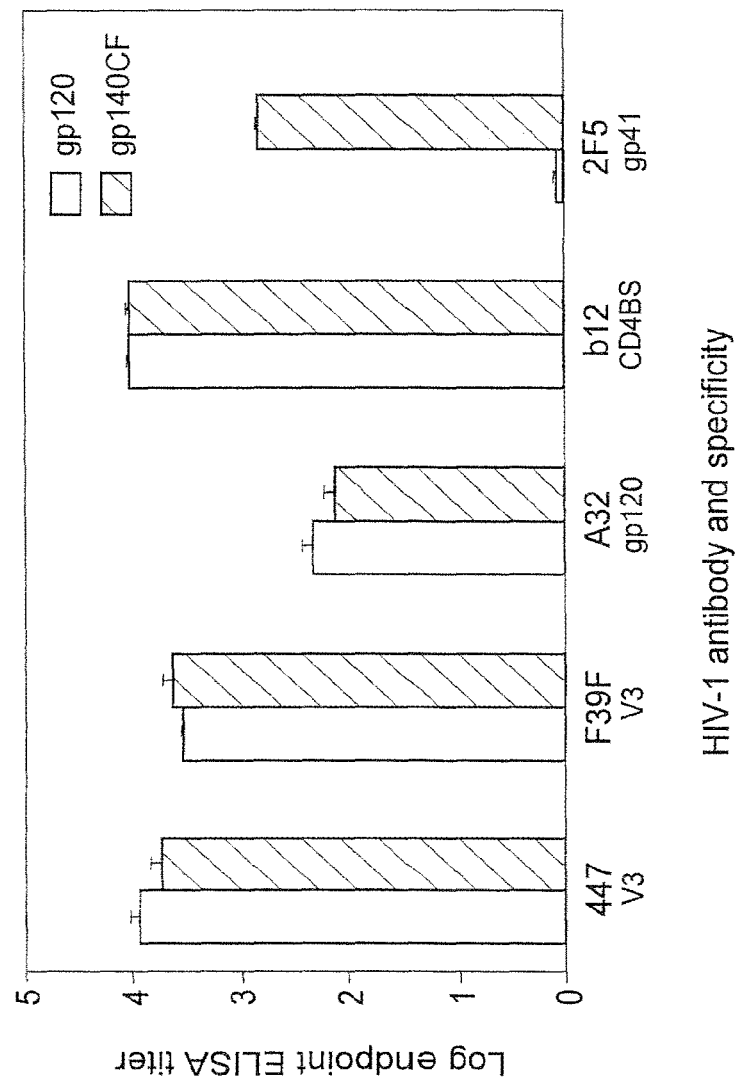

CD4 Binding Domain and Other Wild-type HIV-1 Epitopes are Preserved on CON6 Proteins. To determine if CON6 proteins can bind to CD4 and express other wild-type HIV-1 epitopes, the ability of CON6 gp120 and gp140CF to bind soluble(s) CD4, to bind several well-characterized anti-gp120 mabs, and to undergo CD4-induced conformational changes was assayed. First, BIAcore CM5 sensor chips were coated with either sCD4 or mabs to monitor their binding activity to CON6 Env proteins. It was found that both monomeric CON6 gp120 and oligomeric gp140CF efficiently bound sCD4 and anti-gp120 mabs T8, 2G12 and A32, but did not constitutively bind mab 17b, that recognizes a CD4 inducible epitope in the CCR5 binding site of gp120 (FIGS. 2A and 2B). Both sCD4 and A32 can expose the 17b binding epitope after binding to wild-type gp120 (Wyatt et al, Nature 393; 705-711 (1998), Wyatt et al, J. Virol. 69:5723-5733 (1995)). To determine if the 17b epitope could be induced on CON6 Envs by either sCD4 or A32, sCD4, A32 and T8 were coated on sensor chips, then CON6 gp120 or gp140CF captured, and mab 17b binding activity monitored. After binding sCD4 or mab A32, both CON6 gp120 and gp140CF were triggered to undergo conformational changes and bound mab 17b (FIGS. 2C and 2D). In contrast, after binding mab T8, the 17b epitope was not exposed (FIGS. 2C and 2D). ELISA was next used to determine the reactivity of a panel of human mabs against the gp120 V3 loop (447, F39F), the CD4 binding site (b12), and the gp41 neutralizing determinant (2F5) to CON6 gp120 and gp140CF (FIG. 2E). Both CON6 rgp120 and rgp140CF proteins bound well to neutralizing V3 mabs 447 and F39F and to the potent neutralizing CD4 binding site mab b12. Mab 2F5, that neutralizes HIV-1 primary isolates by binding to a C-terminal gp41 epitope, also bound well to CON6 gp140CF (FIG. 2E).

Figure 3A:
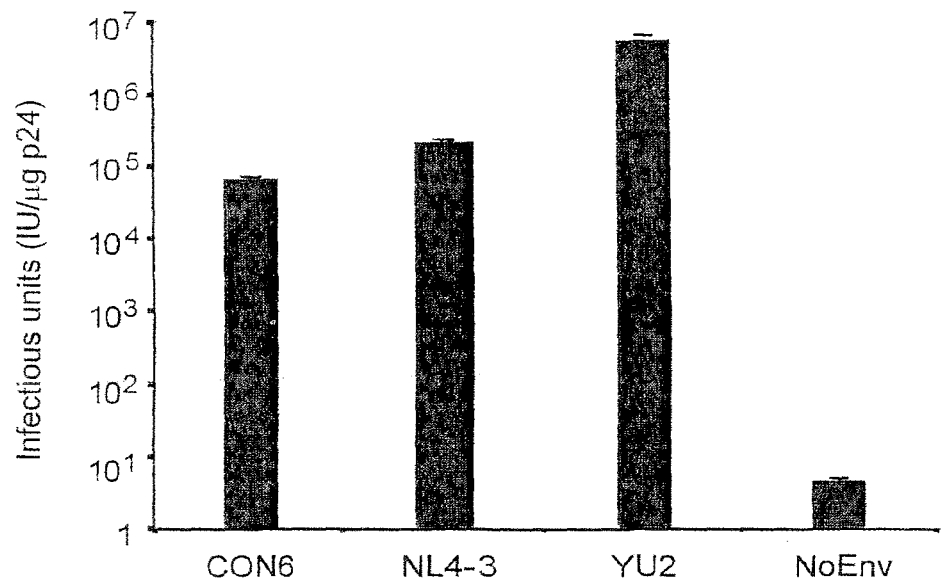

CON6 env Gene is Biologically Functional and Uses CCR5 as its Coreceptor. To determine whether CON6 envelope gene is biologically functional, it was co-transfected with the env-defective SG3 proviral clone into 293T cells. The pseudotyped viruses were harvested and JC53BL cells infected. Blue cells were detected in JC53-BL cells infected with the CON6 Env pseudovirions, suggesting that CON6 Env protein is biologically functional (FIG. 3A). However, the infectious titers were 1-2 logs lower than that of pseudovirions with either YU2 or NL4-3 wild-type HIV-1 envelopes.

Figure 3B:
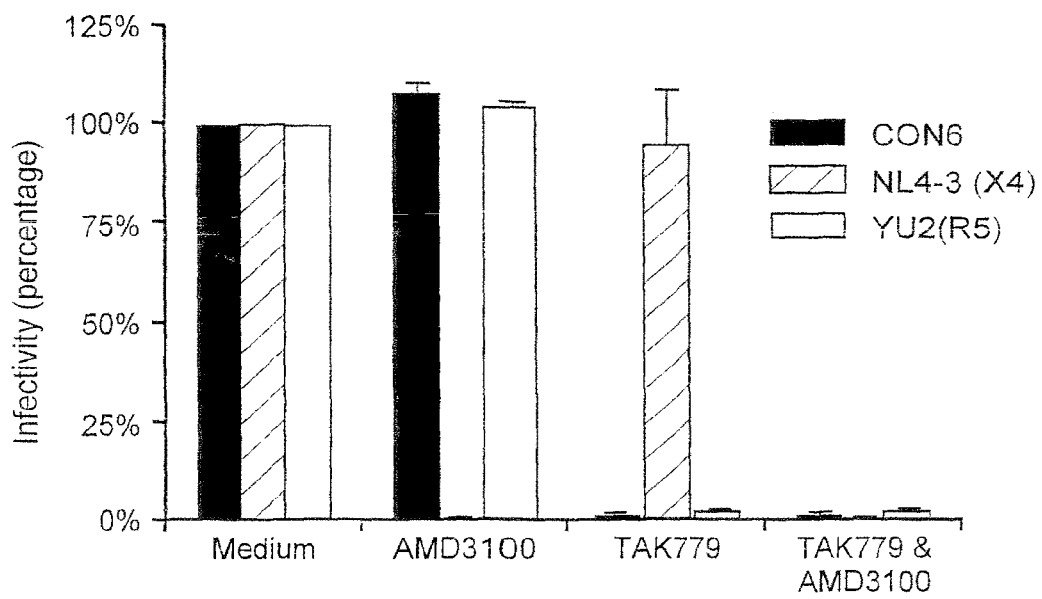

The co-receptor usage for the CON6 env gene was next determined. When treated with CXCR4 blocking agent AMD3100, the infectivity of NL4-3 Env-pseudovirons was blocked while the infectivity of YU2 or CON6 Env-pseudovirons was not inhibited (FIG. 3B). In contrast, when treated with CCR5 blocking agent TAK-779, the infectivity of NL4-3 Env-pseudovirons was not affected, while the infectivity of YU2 or CON6 Env-pseudovirons was inhibited. When treated with both blocking agents, the infectivity of all pseudovirions was inhibited. Taken together, these data show that the CON6 envelope uses the CCR5 co-receptor for its entry into target cells.

Reaction of CON6 gp120 With Different Subtype Sera. To determine if multiple subtype linear epitopes are preserved on CON6 gp120, a recombinant Env protein panel (gp120 and gp140) was generated. Equal amounts of each Env protein (100 ng) were loaded on SDS-polyacrylamide gels, transferred to nitrocellulose, and reacted with subtype A through G patient sera as well as anti-CON6 gp120 guinea pig sera (1:1,000 dilution) in Western blot assays. For each HIV-1 subtype, four to six patient sera were tested. One serum representative for each subtype is shown in FIG. 4.

It was found that whereas all subtype sera tested showed variable reactivities among Envs in the panel, all group M subtype patient sera reacted equally well with CON6 gp120 Env protein, demonstrating that wild-type HIV-1 Env epitopes recognized by patient sera were well preserved on the CON6 Env protein. A test was next made as to whether CON6 gp120 antiserum raised in guinea pigs could react to different subtype Env proteins. It was found that the CON6 serum reacted to its own and other subtype Env proteins equally well, with the exception of subtype A Env protein (FIG. 4).

Induction of T Cell Responses to CON6, Subtype B and Subtype C Envelope Overlapping Peptides. To compare T cell immune responses induced by CON6 Env immunogens with those induced by subtype specific immunogens, two additional groups of mice were immunized with subtype B or subtype C DNAs and with corresponding rVV expressing subtype B or C envelope proteins. Mice immunized with subtype B (JRFL) or subtype C (96ZM651) Env immunogen had primarily subtype-specific T cell immune responses (FIG. 5). IFN-γ SFCs from mice immunized with JRFL (subtype B) immunogen were detected after stimulation with subtype B (MN) peptide pools, but not with either subtype C (Chn19) or CON6 peptide pools. IFN-γ SFCs from mice immunized with 96ZM651 (subtype C) immunogen were detected after the stimulation with both subtype C (Chn19) and CON6 peptide pools, but not with subtype B (MN) peptide pools. In contrast, IFN-γ SFCs were identified from mice immunized with CON6 Env immunogens when stimulated with either CON6 peptide pools as well as by subtype B or C peptide pools (FIG. 5). The T cell immune responses induced by CON6 gp140 appeared more robust than those induced by CON6 gp120. Taken together, these data demonstrated that CON6 gp120 and gp140CF immunogens were capable of inducing T cell responses that recognized T cell epitopes of wild-type subtype B and C envelopes.

Induction of Antibodies by Recombinant CON6 gp120 and gp140CF Envelopes that Neutralize HIV-1 Subtype B and C Primary Isolates. To determine if the CON6 envelope immunogens can induce antibodies that neutralize HIV-1 primary isolates, guinea pigs were immunized with either CON6 gp120 or gp140CF protein. Sera collected after 4 or 5 immunizations were used for neutralization assays and compared to the corresponding prebleed sera. Two AT-2 inactivated HIV-1 isolates (ADA and AD8) were tested in syncytium inhibition assays (Table 5A). Two subtype B SHIV isolates, eight subtype B primary isolates, four subtype C, and one each subtype A, D, and E primary isolates were tested in either the MT-2 or the luciferase-based assay (Table 5B). In the syncytium inhibition assay, it was found that antibodies induced by both CON 6 gp120 and gp140CF proteins strongly inhibited AT-2 inactivated ADA and AD8-induced syncytia (Table 5A). In the MT-2 assay, weak neutralization of 1 of 2 SHIV isolates (SHIV SF162P3) by two gp120 and one gp140CF sera was found (Table 5B). In the luciferase-based assay, strong neutralization of 4 of 8 subtype B primary isolates (BXO8, SF162, SS1196, and BAL) by all gp120 and gp140CF sera was found, and weak neutralization of 2 of 8 subtype B isolates (6101, 0692) by most gp120 and gp140CF sera was found. No neutralization was detected against HIV-1 PAVO (Table 5B). Next, the CON6 anti-gp120 and gp140CF sera were tested against four subtype C HIV-1 isolates, and weak neutralization of 3 of 4 isolates (DU179, DU368, and S080) was found, primarily by anti-CON6 gp120 sera. One gp140CF serum, no. 653, strongly neutralized DU179 and weakly neutralized S080 (Table 5B). Finally, anti-CON6 Env sera strongly neutralized a subtype D isolate (93ZR001), weakly neutralized a subtype E (CM244) isolate, and did not neutralize a subtype A (92RW020) isolate.

TABLE 5A

Ability of HIV-1 Group M Consensus Envelope CON6 Proteins to Induce Fusion Inhibiting Antibodies

| Guinea Pig No. | Immunogen | Syncytium Inhibition antibody titer[1] | |
|---|---|---|---|
| | | AD8 | ADA |
| 646 | gp120 | 270 | 270 |
| 647 | gp120 | 90 | 90 |
| 648 | gp120 | 90 | 270 |
| 649 | gp120 | 90 | 90 |
| Geometric Mean Titer | | 119 | 156 |
| 650 | gp140 | 270 | 270 |
| 651 | gp140 | 90 | 90 |
| 652 | gp140 | ≥810 | 810 |
| 653 | gp140 | 270 | 90 |
| Geometric Mean Titer | | 270 | 207 |

[1]Reciprocal serum dilution at which HIV-induced syncytia of Sup T1 cells was inhibited by >90% compared to pre-immune serum.
All prebleed sera were negative (titer <10).

TABLE 5B

Ability of Group M Consensus HIV-1 Envelope CON6 gp120 and gp140CF Proteins to Induce Antibodies that Neutralize HIV Primary Isolates

| HIV Isolate (Subtype) | CON6 gp120 Protein Guinea Pig No. | | | | | CON6 gp140CF Protein Guinea Pig No. | | | | | Controls | | |
|---|---|---|---|---|---|---|---|---|---|---|---|---|---|
| | 646 | 647 | 648 | 649 | GMT | 650 | 651 | 652 | 653 | GMT | TriMab$_2$‡ | CD4-IgG2 | HIV + Serum |
| SHIV 89.6P*(B) | <20 | <20 | <20 | <20 | <20 | <20 | <20 | <20 | <20 | <20 | NT | NT | NT |
| SHIV SF162P3*(B) | <20 | 30 | 48 | <20 | <20 | 27 | <20 | <20 | <20 | <20 | NT | 0.2 µg/ml | NT |
| BX08(B) | 270 | 183 | 254 | 55 | 102 | 199 | 64 | 229 | 150 | 187 | 0.7 µg/ml | NT | 2384 |
| 6101(B) | <20 | 38 | 35 | <20 | <20 | <20 | 90 | 72 | 73 | 39 | 1.1 µg/ml | NT | NT |
| BG1168(B) | <20 | <20 | <20 | <20 | <20 | 40 | <20 | <20 | 25 | <20 | 2.7 µg/ml | NT | NT |
| 0692(B) | 31 | 32 | 34 | <20 | 24 | 28 | 33 | 30 | 45 | 33 | 0.8 µg/ml | NT | 769 |
| PAVO(B) | <20 | <20 | <20 | <20 | <20 | <20 | <20 | <20 | <20 | <20 | 2.9 µg/ml | NT | NT |
| SF162(B) | 2,146 | 308 | 110 | 282 | 379 | 206 | 5,502 | 15,098 | 174 | 1,313 | NT | NT | >540 |
| SS1196(B) | 206 | 26 | 148 | 59 | 83 | 381 | 401 | 333 | 81 | 253 | NT | NT | 301# |
| BAL(B) | 123 | 90 | 107 | 138 | 113 | 107 | 146 | 136 | 85 | 116 | NT | NT | 3307 |
| 92RW020(A) | <20 | <20 | <20 | <20 | <20 | <20 | <20 | <20 | <20 | <20 | NT | NT | 693 |
| DU179(C) | <20 | 43 | <20 | 24 | <20 | <20 | <20 | 24 | 515 | 33 | NT | 0.8 µg/ml | NT |
| DU368(C) | 25 | 35 | 62 | <20 | 27 | <20 | <20 | <20 | 23 | <20 | NT | 2.3 µg/ml | NT |
| S021(C) | <20 | <20 | 33 | <20 | <20 | <20 | <20 | <20 | <20 | <20 | NT | 8.3 µg/ml | NT |
| S080(C) | 24 | 37 | 70 | 41 | 40 | <20 | <20 | <20 | 52 | <20 | NT | 3.4 µg/ml | NT |
| 93ZR001(D) | 275 | 144 | 126 | 114 | 154 | 306 | 195 | 129 | 173 | 191 | NT | NT | 693 |
| CM244(E) | 35 | 43 | 64 | ND | 46 | 31 | 25 | 27 | 25 | 26 | NT | NT | 693 |

*MT-2 Assay; All other HIV isolates were tested in the M7-luciferase assay.
HIV-1 isolates QH0692, SS1196, SF162, 6101, BX08, BG1168, BAL were assayed with post-injection 5 serum; other HIV-1 isolates were assayed with post-injection 4 serum. ND = not done.
HIV + sera was either HIV-1 + human serum (LEH3) or an anti-gp120 guinea pig serum (#) with known neutralizing activity for HIV-1 isolate SS1196. GMT = geometric mean titer of four animals per group. Neutralizing titers reported are after subtraction of any background neutralization in prebleed sera.
‡TriMab$_2$ = a mixture of human mabs 2F5, b12, 2G12.

Conclusions

The production of an artificial HIV-1 Group M consensus env genes (encoding sequences) (CONE and Con-S) have been described that encodes a functional Env protein that is capable of utilizing the CCR5 co-receptor for mediating viral entry. Importantly, these Group M consensus envelope genes could induce T and B cell responses that recognized epitopes of subtype B and C HIV-1 primary isolates. In addition, Con-S induces antibodies that strongly neutralize Subtype-C and A HIV-1 strains (see Table 3).

The correlates of protection to HIV-1 are not conclusively known. Considerable data from animal models and studies in HIV-1-infected patients suggest the goal of HIV-1 vaccine development should be the induction of broadly-reactive CD4+ and CD8+ anti-HIV-1 T cell responses (Letvin et al, Annu. Rev. Immunol. 20:73-99 (2002)) and high levels of antibodies that neutralize HIV-1 primary isolates of multiple subtypes (Mascola et al, J. Viral. 73:4009-4018 (1999), Mascola et al, Nat. Med. 6:270-210 (2000)).

The high level of genetic variability of HIV-1 has made it difficult to design immunogens capable of inducing immune responses of sufficient breadth to be clinically useful. Epitope based vaccines for T and B cell responses (McMichael et al, Vaccine 20:1918-1921 (2002), Sbai et al, Curr. Drug Targets Infect, Disord. 1:303-313 (2001), Haynes, Lancet 348:933-937 (1996)), constrained envelopes reflective of fusion intermediates (Fouts et al, Proc. Natl. Acad. Sci. USA 99:11842-22847 (2002)), as well as exposure of conserved high-order structures for induction of anti-HIV-1 neutralizing antibodies have been proposed to overcome HIV-1 variability (Roben et al, J. Virol. 68:4821-4828 (1994), Saphire et al, Science 293:1155-1159 (2001)). However, with the ever-increasing diversity and rapid evolution of HIV-1, the virus is a rapidly moving complex target, and the extent of complexity of HIV-1 variation makes all of these approaches problematic. The current most common approach to HIV-1 immunogen design is to choose a wild-type field HIV-1 isolate that may or may not be from the region in which the vaccine is to be tested. Polyvalent envelope immunogens have been designed incorporating multiple envelope immunogens (Bartlett et al, AIDS 12:1291-1300 (1998), Cho et al, J. Virol. 75:2224-2234 (2001)).

The above-described study tests a new strategy for HIV-1 immunogen design by generating a group M consensus env gene (CON6) with decreased genetic distance between this candidate immunogen and wild-type field virus strains. The CON6 env gene was generated for all subtypes by choosing the most common amino acids at most positions (Gaschen et al, Science 296:2354-2360 (2002), Korber et al, Science 288:1789-1796 (2000)). Since only the most common amino acids were used, the majority of antibody and T cell epitopes were well preserved. Importantly, the genetic distances between the group M consensus env sequence and any subtype env sequences was about 15%, which is only half of that between wild-type subtypes (30%) (Gaschen et al, Science 296:2354-2360 (2002)). This distance is approximately the same as that among viruses within the same subtype. Further, the group M consensus env gene was also about 15% divergent from any recombinant viral env gene, as well, since CRFs do not increase the overall genetic divergence among subtypes.

Infectivity of CON6-Env pseudovirions was confirmed using a single-round infection system, although the infectivity was compromised, indicating the artificial envelope was not in an "optimal" functional conformation, but yet was able to mediate virus entry. That the CON6 envelope used CCR5 (R5) as its coreceptor is important, since majority of HIV-1 infected patients are initially infected with R5 viruses.

BIAcore analysis showed that both CON6 gp120 and gp140CF bound sCD4 and a number of mabs that bind to wild-type HIV-1 Env proteins. The expression of the CON6 gp120 and 140CF proteins that are similar antigenically to wild-type HIV-1 envelopes is an important step in HIV-1 immunogen development. However, many wild-type envelope proteins express the epitopes to which potent neutralizing human mabs bind, yet when used as immunogens themselves, do not induce broadly neutralizing anti-HIV-1 antibodies of the specificity of the neutralizing human mabs.

The neutralizing antibody studies were encouraging in that both CON6 gp120, CON6 gp140CF and Con-S gp140CFI induced antibodies that neutralized select subtype B, C and D HIV-1 primary isolates, with Con-S gp140CFI inducing the most robust neutralization of non-subtype B primary HIV isolates. However, it is clear that the most difficult-to-neutralize primary isolates (PAVO, 6101, BG1168, 92RW020, CM244) were either only weakly or not neutralized by anti-CON6 gp120 or gp140 sera (Table 4b). Nonetheless, the Con-S envelope immunogenicity for induction of neutralizing antibodies is promising, given the breadth of responses generated with the Con-S subunit gp140CFI envelope protein for non-subtype B HIV isolates. Previous studies with poxvirus constructs expressing gp120 and gp160 have not generated high levels of neutralizing antibodies (Evans et al, J. Infect. Dis. 180:290-298 (1999), Polacino et al, J. Virol. 73:618-630 (1999), Ourmanov et al, J. Virol. 74:2960-2965 (2000), Pal et al, J. Virol 76:292-302 (2002), Excler and Plotkin, AIDS 11(Suppl A):S127-137 (1997). rVV expressing secreted CON6 gp120 and gp140 have been constructed and antibodies that neutralize HIV-1 primary isolates induced. An HIV neutralizing antibody immunogen can be a combination of Con-S gp140CFI, or subunit thereof, with immunogens that neutralize most subtype B isolates.

The structure of an oligomeric gp140 protein is critical when evaluating protein immunogenicity. In this regard, study of purified CON6 gp140CF proteins by fast performance liquid chromatography (FPLC) and analytical ultracentrifiguration has demonstrated that the purified gp140 peak consists predominantly of trimers with a small component of dimers.

Thus, centralized envelopes such as CON6, Con-S or 2003 group M or subtype consensus or ancestral encoding sequences described herein, are attractive candidates for preparation of various potentially "enhanced" envelope immunogens including CD4-Env complexes, constrained envelope structures, and trimeric oligomeric forms. The ability of CON6-induced T and B cell responses to protect against HIV-1 infection and/or disease in SHIV challenge models will be studied in non-human primates.

The above study has demonstrated that artificial centralized HIV-1 genes such as group M consensus env gene (CON6) and Con-S can also induce T cell responses to T cell epitopes in wild-type subtype B and C Env proteins as well as to those on group M consensus Env proteins (FIG. 5). While the DNA prime and rVV boost regimen with CON6 gp140CF immunogen clearly induced IFN-γ producing T cells that recognized subtype B and C epitopes, further studies are needed to determine if centralized sequences such as are found in the CON6 envelope are significantly better at inducing cross-clade T cell responses than wild-type HIV-1 genes (Ferrari et al, Proc. Natl. Acad. Sci. USA 94:1396-1401 (1997), Ferrari et al, AIDS Res. Hum. Retroviruses 16:1433-1443 (2000)). However, the fact that CON6 (and Con-S, env encoding sequence) prime and boosted splenocyte T cells recognized HIV-1 subtype B and C T cell epitopes is an important step in demonstration that CON6 (and Con-S) can induce T cell responses that might be clinically useful.

Three computer models (consensus, ancestor and center of the tree (COT)) have been proposed to generate centralized HIV-1 genes (Gaschen et al, Science 296:2354-2360 (2002), Gao et al, Science 299:1517-1518 (2003), Nickle et al, Science 299:1515-1517 (2003), Korber et al, Science 288:1789-1796 (2000). They all tend to locate at the roots of the star-like phylogenetic trees for most HIV-1 sequences within or between subtypes. As experimental vaccines, they all can reduce the genetic distances between immunogens and field virus strains. However, consensus, ancestral and COT sequences each have advantages and disadvantages (Gaschen et al, Science 296:2354-2360 (2002), Gao et al, Science 299:1517-1518 (2003), Nickle et al, Science 299: 1515-1517 (2003). Consensus and COT represent the sequences or epitopes in sampled current wild-type viruses and are less affected by outliers HIV-1 sequences, while ancestor represents ancestral sequences that can be significantly affected by outlier sequences. However, at present, it is not known which centralized sequence can serve as the best immunogen to elicit broad immune responses against diverse HIV-1 strains, and studies are in progress to test these different strategies.

Taken together, the data have shown that the HIV-1 artificial CON6 and Con-S envelope can induce T cell responses to wild-type HIV-1 epitopes, and can induce antibodies that neutralize HIV-1 primary isolates, thus demonstrating the feasibility and promise of using artificial centralized HIV-1 sequences in HIV-1 vaccine design.

Example 2

HIV-1 Subtype C Ancestral and Consensus Envelope Glycoproteins
Experimental Details HIV-1 subtype C ancestral and consensus env genes were obtained from the Los Alamos HIV Molecular Immunology Database (http://hiv-web.lanl.gov/immunology), codon-usage optimized for mammalian cell expression, and synthesized (FIG. 6). To ensure optimal expression, a Kozak sequence (GCCGCCGCC) was inserted immediately upstream of the initiation codon. In addition to the full-length genes, two truncated env genes were generated by introducing stop codons immediately after the gp41 membrane-spanning domain (IVNR) and the gp120/gp41 cleavage site (REKR), generating gp140 and gp120 form of the glycoproteins, respectively (FIG. 8).

Genes were tested for integrity in an in vitro transcription/translation system and expressed in mammalian cells. To determine if the ancestral and consensus subtype C envelopes were capable of mediating fusion and entry, gp160 and gp140 genes were co-transfected with an HIV-1/SG3Δenv provirus and the resulting pseudovirions tested for infectivity using the JC53-BL cell assay (FIG. 7). Co-receptor usage and envelope neutralization sensitivity were also determined with slight modifications of the JC53-BL assay. Codon-usage optimized and rev-dependent 96ZAM651 env genes were used as contemporary subtype C controls.

Results

Codon-optimized subtype C ancestral and consensus envelope genes (gp160, gp140, gp120) express high levels of env glycoprotein in mammalian cells (FIG. 9).

Codon-optimized subtype C gp160 and gp140 glycoproteins are efficiently incorporated into virus particles. Western Blot analysis of sucrose-purified pseudovirions reveals tenfold higher levels of virion incorporation of the codon-optimized envelopes compared to that of a rev-dependent contemporary envelope controls (FIG. 10A).

Virions pseudotyped with either the subtype C consensus gp160 or gp140 envelope were more infectious than pseudovirions containing the corresponding gp160 and gp140 ancestral envelopes. Additionally, gp160 envelopes were consistently more infectious than their respective gp140 counterparts (FIG. 10B).

Both subtype C ancestral and consensus envelopes utilize CCR5 as a co-receptor to mediate virus entry (FIG. 11).

The infectivity of subtype C ancestral and consensus gp160 containing pseudovirions was neutralized by plasma from subtype C infected patients. This suggests that these artificial envelopes possess a structure that is similar to that of native HIV-1 env glycoproteins and that common neutralization epitopes are conserved. No significant differences in neutralization potential were noted between subtype C ancestral and consensus env glycoproteins (gp160) (FIG. 12).

Conclusions

HIV-1 subtype C viruses are among the most prevalent circulating isolates, representing approximately fifty percent of new infections worldwide. Genetic diversity among globally circulating HIV-1 strains poses a challenge for vaccine design. Although HIV-1 Env protein is highly variable, it can induce both humoral and cellular immune responses in the infected host. By analyzing 70 HIV-1 complete subtype C env sequences, consensus and ancestral subtype C env genes have been generated. Both sequences are roughly equidistant from contemporary subtype C strains and thus expected to induce better cross-protective immunity. A reconstructed ancestral or consensus sequence derived-immunogen minimizes the extent of genetic differences between the vaccine candidate and contemporary isolates. However, consensus and ancestral subtype C env genes differ by 5% amino acid sequences. Both consensus and ancestral sequences have been synthesized for analyses. Codon-optimized subtype C ancestral and consensus envelope genes have been constructed and the in vitro biological properties of the expressed glycoproteins determined. Synthetic subtype C consensus and ancestral env genes express glycoproteins that are similar in their structure, function and antigenicity to contemporary subtype C wild-type envelope glycoproteins.

Example 3

Codon-Usage Optimization of Consensus of Subtype C gag and nef Genes (C.con.gag and C.con.nef)

Subtype C viruses have become the most prevalent viruses among all subtypes of Group M viruses in the world. More than 50% of HIV-1 infected people are currently carrying HIV-1 subtype C viruses. In addition, there is considerable intra-subtype C variability: different subtype C viruses can differ by as much as 10%, 6%, 17% and 16% of their Gag, Pol, Env and Nef proteins, respectively. Most importantly, the subtype C viruses from one country can vary as much as the viruses isolated from other parts of the world. The only exceptions are HIV-1 strains from India/China, Brazil and Ethiopia/Djibouti where subtype C appears to have been introduced more recently. Due to the high genetic variability of subtype C viruses even within a single country, an immunogen based on a so single virus isolate may not elicit protective immunity against other isolates circulating in the same area.

Thus gag and nef gene sequences of subtype C viruses were gathered to generate consensus sequences for both genes by using a 50% consensus threshold. To avoid a potential bias toward founder viruses, only one sequence was used from India/China, Brazil and Ethiopia/Djibouti, respectively, to generate the subtype C consensus sequences (C.con.gag and C.con.nef). The codons of both C.con.gag and C.con.nef genes were optimized based on the codon usage of highly expressed human genes. The protein expression following transfection into 293T cells is shown in FIG. 13. As can be seen, both consensus subtype C Gag and Nef proteins were expressed efficiently and recognized by Gag- and Nef-specific antibodies. The protein expression levels of both C.con.gag and C.con.nef genes are comparable to that of native subtype env gene (96ZM651).

Example 4

Synthesis of a Full Length "Consensus of the Consensus env Gene with Consensus Variable Regions" (CON-S)

In the synthesized "consensus of the consensus" env gene (CON6), the variable regions were replaced with the corresponding regions from a contemporary subtype C virus (98CN006). A further con/con gene has been designed that also has consensus variable regions (CON-s). The codons, of the Con-S env gene were optimized based on the codon usage of highly expressed human genes. (See FIGS. 14A and 14B for amino acid sequences and nucleic acid sequences, respectfully.)

Paired oligonucleotides (80-mers) which overlap by 20 bp at their 3' ends and contain invariant sequences at their 5' and 3' ends, including the restriction enzyme sites EcoRI and BbsI as well as BsmBI and BamHI, respectively, were designed. BbsI and BamHI are Type II restriction enzymes that cleave outside of their recognition sequences. They have been positioned in the oligomers in such a way that they cleave the first four resides adjacent to the 18 bp invariant region, leaving 4 base 5' overhangs at the end of each fragment for the following ligation step. 26 paired oligomers were linked individually using PCR and primers complimentary to the 18 bp invariant sequences. Each pair was cloned into pGEM-T (Promega) using the T/A cloning method and sequenced to confirm the absence of inadvertent mutations/deletions. pGEM-T subclones containing the proper inserts were then digested, run on a 1% agarose gel, and gel purified (Qiagen). Four individual 108-mers were ligated into pcDNA3.1 (Invitrogen) in a multi-fragment ligation reaction. The four-way ligations occurred among groups of fragments in a stepwise manner from the 5' to the 3' end of the gene. This process was repeated until the entire gene was reconstructed in the pcDNA3.1 vector.

A complete Con-S gene was constructed by ligating the codon usage optimized oligo pairs together. To confirm its open reading frame, an in vitro transcription and translation assay was performed. Protein products were labeled by $S^{35}$-methionine during the translation step, separated on a 10% SDS-PAGE, and detected by radioautography. Expected size of the expressed Con-S gp160 was identified in 4 out of 7 clones (FIG. 14C).

CONs Env protein expression in the mammalian cells after transfected into 293T cells using a Western blot assay (FIG. 15). The expression level of Con-S Env protein is very similar to what was observed from the previous CON6 env clone that contains the consensus conservative regions and variable loops from 98CN006 virus isolate.

The Env-pseudovirons was produced by cotransfecting Con-S env clone and env-deficient SG3 proviral clone into 293T cells. Two days after transfection, the pseudovirions were harvested and infected into JC53BL-13 cells. The infectious units (IU) were determined by counting the blue cells after staining with X-gal in three independent experiments. When compared with CON6 env clone, Con-S env clones produce similar number of IU in JC53BL-13 cells (FIG. 16). The IU titers for both are about 3 log higher than the SG3 backbone clone control (No Env). However, the titers are also about 2 log lower than the positive control (the native HIV-1 env gene, NL4-3 or YU2). These data suggest that both consensus group M env clones are biologically functional. Their functionality, however, has been compromised. The functional consensus env genes indicate that these Env proteins fold correctly, preserve the basic conformation of the native Env proteins, and are able to be developed as universal Env immunogens.

It was next determined what coreceptor Con-S Env uses for its entry into JC53-BL cells. When treated with CXCR4 blocking agent AMD3100, the infectivity of NL4-3 Env-pseudovirons was blocked while the infectivity of YU2, Con-S or CON6 Env-pseudovirons was not inhibited. In contrast, when treated with CCR5 blocking agent TAK779, the infectivity of NL4-3 Env-pseudovirons was not affected, while the infectivity of YU2, Con-S or CON6 Env-pseudovirons was inhibited. When treated with both blocking agents, the infectivity of all pseudovirions was inhibited. Taken together, these data show that the Con-S as well as CON6 envelope uses the CCR5 but not CXCR4 co-receptor for its entry into target cells.

It was next determined whether CON6 or Con-S Env proteins could be equally efficiently incorporated in to the pseudovirions. To be able precisely compare how much Env proteins were incorporated into the pseudovirions, each pseudovirions is loaded on SDS-PAGE at the same concentraion: 5 μg total protein for cell lysate, 25 ng p24 for cell culture supernatant, or 150 ng p24 for purified virus stock (concentrated pseudovirions after super-speed centrifugation). There was no difference in amounts of Env proteins incorporated in CON6 or Con-S Env-pseudovirions in any preparations (cell lysate, cell culture supernatant or purified virus stock) (FIG. 17).

Example 5

Synthesis of a Consensus Subtype A Full Length env (A.con.env) Gene

Subtype A viruses are the second most prevalent HIV-1 in the African continent where over 70% of HIV-1 infections have been documented. Consensus gag, env and nef genes for subtype C viruses that are the most prevalent viruses in Africa and in the world were previously generated. Since genetic distances between subtype A and C viruses are as high as 30% in the env gene, the cross reactivity or protection between both subtypes will not be optimal. Two group M consensus env genes for all subtypes were also generated. However, to target any particular subtype viruses, the subtype specific consensus genes will be more effective since the genetic distances between subtype consensus genes and field viruses from the same subtype will be smaller than that between group M consensus genes and these same viruses. Therefore, consensus genes need to be generated for development of subtype A specific immunogens. The codons of the A.con.env gene were optimized based on the codon usage of highly expressed human genes. (See FIGS. 18A and 18B for amino acid and nucleic acid sequences, respectively.)

Each pair of the oligos has been amplified, cloned, ligated and sequenced. After the open reading frame of the A.con env gene was confirmed by an in vitro transcription and translation system, the A.con env gene was transfected into the 293T cells and the protein expression and specificity confirmed with the Western blot assay (FIG. 18). It was then determined whether A.con envelope is biologically functional. It was co-transfected with the env-defective SG3 proviral clone into 293T cells. The pseudotyped viruses were harvested and used to infect JC53BL cells. Blue cells were detected in JC53-BL cells infected with the A.con Env-pseudovirions, suggesting that A.con Env protein is biologically functional (Table 6). However, the infectious titer of A.con Env-psuedovirions was about 7-fold lower than that of pseudovirions with wild-type subtype C envelope (Table 6). Taken together, the biological function A.con Env proteins suggests that it folds correctly and may induce linear and conformational T and B cell epitopes if used as an Env immunogen.

TABLE 6

Infectivity of pseudovirons with A.con env genes JC53BL13 (IU/ul)

| | Mar. 31, 2003 non filtered supt. | Apr. 7, 2003 0.22 μm filtered | Apr. 25, 2003 0.22 μm filtered |
|---|---|---|---|
| A.con + SG3 | 4 | 8.5 | 15.3 |
| 96ZM651 + SG3 | 87 | 133 | 104 |
| SG3 backbone | 0 | 0.07 | 0.03 |
| Neg control | 0 | 0.007 | 0 |

Example 6

Design of Full Length "Consensus of the Consensus gag, pol and nef Genes" (M.con.gag, M.con.pol and M.con.nef) and a Subtype C Consensus pol Gene (C.con.pol)

For the group M consensus genes, two different env genes were constructed, one with virus specific variable regions (CON6) and one with consensus variable regions (Con-S). However, analysis of T cell immune responses in immunized or vaccinated animals and humans shows that the env gene normally is not a main target for T cell immune response although it is the only gene that will induce neutralizing antibody. Instead, HIV-1 Gag, Pol and Nef proteins are found to be important for inducing potent T cell immune responses. To generate a repertoire of immunogens that can induce both broader humoral and cellular immune responses for all subtypes, it may be necessary to construct other group M consensus genes other than env gene alone. "Consensus of the consensus" gag, pol and nef genes (M.con.gag., M.con.pol and M.con.nef) have been designed. To generate a subtype consensus pol gene, the subtype C consensus poi gene (C.con.pol) was also designed. The codons of the M.con.gag., M.con.pol, M.con.nef and C.con.pol. genes were optimized based on the codon usage of highly expressed human genes. (See FIG. 19 for nucleic acid and amino acid sequences.)

Example 7

Synthetic Subtype B Consensus gag and env Genes
Experimental Details

Subtype B consensus gag and env sequences were derived from 37 and 137 contemporary HIV-1 strains, respectively, codon-usage optimized for mammalian cell expression, and synthesized (FIGS. 20A and 20B). To ensure optimal expression, a Kozak sequence (GCCGCCGCC) was inserted immediately upstream of the initiation codon. In addition to the full-length env gene, a truncated env gene was generated by introducing a stop codon immediately after the gp41 membrane-spanning domain (IVNR) to create a gp145 gene. Genes were tested for integrity in an in vitro transcription/translation system and expressed in mammalian cells. (Subtype B consensus Gag and Env sequences are set forth in FIGS. 20C and 20D, respectively.)

To determine if the subtype B consensus envelopes were capable of mediating fusion and entry, gp160 and gp145 genes were co-transfected with an HIV-1/SG3Δenv provirus and the resulting pseudovirions were tested for infectivity using the JC53-BL cell assay. JC53-BL cells are a derivative of HeLa cells that express high levels of CD4 and the HIV-1 coreceptors CCR5 and CXCR4. They also contain the reporter cassettes of luciferase and β-galactosidase that are each expressed from an HIV-1 LTR. Expression of the reporter genes is dependent on production of HIV-1 Tat. Briefly, cells are seeded into 24-well plates, incubated at 37° C. for 24 hours and treated with DEAE-Dextran at 37° C. for 30 min. Virus is serially diluted in 1% DMEM, added to the cells incubating in DEAE-dextran, and allowed to incubate for 3 hours at 37° C. after which an additional 500 μL of cell media is added to each well. Following a final 48-hour incubation at 37° C., cells are fixed, stained using X-Gal, and overlaid with PBS for microscopic counting of blue foci. Counts for mock-infected wells, used to determine background, are subtracted from counts for the sample wells. Co-receptor usage and envelope neutralization sensitivity were also determined with slight modifications of the JC53-BL assay.

To determine whether the subtype B consensus Gag protein was capable of producing virus-like particles (VLPs) that incorporated Env glycoproteins, 293T cells were co-transfected with subtype B consensus gag and env genes. 48-hours post-transfection, cell supernatants containing VLPs were collected, clarified in a tabletop centrifuge, filtered through a 0.2 mM filter, and pellet through a 20% sucrose cushion. The VLP pellet was resuspended in PBS and transferred onto a 20-60% continuous sucrose gradient. Following overnight centrifugation at 100,000×g, 0.5 ml fractions were collected and assayed for p24 content. The refractive index of each fraction was also measured. Fractions with the correct density for VLPs and containing the highest levels of p24 were pooled and pellet a final time. VLP-containing pellets were re-suspended in PBS and loaded on a 4-20% SDS-PAGE gel. Proteins were transferred to a PVDF membrane and probed with serum from a subtype B HIV-1 infected individual.

Results

Codon-usage optimized, subtype B consensus envelope (gp160, gp145) and gag genes express high levels of glycoprotein in mammalian cells (FIG. 21).

Subtype B gp160 and gp145 glycoproteins are efficiently incorporated into virus particles. Western Blot analysis of sucrose-purified pseudovirions suggests at least five-fold higher levels of consensus B envelope incorporation compared to incorporation of a rev-dependent contemporary envelope (FIG. 23A). Virions pseudotyped with either the subtype B consensus gp160 or gp145 envelope are more infectious than pseudovirions containing a rev-dependent contemporary envelope (FIG. 23 B).

Subtype B consensus envelopes utilize CCR5 as the co-receptor to gain entry into CD4 bearing target cells (FIG. 22).

The infectivity of pseudovirions containing the subtype B consensus gp160 envelope was neutralized by plasma from HIV-1 subtype B infected patients (FIG. 24C) and neutralizing monoclonal antibodies (FIG. 24A). This suggests that the subtype B synthetic consensus B envelopes is similar to native HIV-1 Env glycoproteins in its overall structure and that common neutralization epitopes remain intact. FIGS. 24B and 24D show neutralization profiles of a subtype B control envelope (NL4.3 Env).

Subtype B consensus Gag proteins are able to bud from the cell membrane and form virus-like particles (FIG. 25A). Co-transfection of the codon-optimized subtype B consensus gag and gp160 genes produces VLPs with incorporated envelope (FIG. 25B).

Conclusions

The synthetic subtype B consensus env and gag genes express viral proteins that are similar in their structure, function and antigenicity to contemporary subtype B Env and Gag proteins. It is contemplated that immunogens based on subtype B consensus genes will elicit CTL and neutralizing immune responses that are protective against a broad set of HIV-1 isolates.

All documents and other information sources cited above are hereby incorporated in their entirety by reference. Also incorporated by reference is Liao et al, J. Virol. 78:5270 (2004)).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10946090B2). An electronic copy of the "Sequence Listing" will also be available from the USPTO upon request and payment of the fee set forth in 37 CFR 1.19(b)(3).

What is claimed is:

1. A nucleic acid comprising a nucleotide sequence that encodes a group M consensus Env comprising SEQ ID NO: 13, or a Cons-S gp140CFI Env comprising SEQ ID NO: 30, or a CON-S gp140CF Env comprising SEQ ID NO: 36.

2. The nucleic acid according to claim 1, wherein said nucleotide sequence comprises codons optimized for expression in human cells.

3. The nucleic acid according to claim 2, wherein said nucleic acid comprises the nucleotide sequence set forth in SEQ ID NO: 14.

4. The nucleic acid according to claim 2, wherein said nucleic acid comprises the nucleotide sequence set forth in SEQ ID NO: 31.

5. The nucleic acid according to claim 2, wherein said nucleic acid comprises the nucleotide sequence set forth in SEQ ID NO: 37.

6. A nucleic acid comprising a nucleotide sequence that encodes a recombinant gp120 envelope protein, wherein the recombinant gp120 envelope protein comprises the consecutive amino acid sequence represented by amino acid numbers 30 to 503 of SEQ ID NO: 13.

7. The nucleic acid of claim 6 comprising the consecutive nucleotide sequence from SEQ ID NO: 14 that encodes the consecutive amino acid sequence represented by amino acid numbers 30 to 503 of SEQ ID NO: 13, wherein said nucleotide sequence comprises codons optimized for expression in human cells.

8. A vector comprising the nucleic acid according to claim 1.

9. An isolated mammalian cell comprising a nucleic acid according to claim 1 for recombinant protein expression.

10. A vector comprising the nucleic acids of claim 6.

11. A composition comprising the nucleic acid according to claim 1 and a carrier.

12. A method of inducing an immune response in a mammal, the method comprising administering to said mammal the composition of claim 11 in an amount sufficient to effect such induction.

13. A composition comprising the nucleic acid according to claim 1 and a carrier, wherein the nucleic acid comprises a nucleotide sequence that encodes a group M consensus Env comprising SEQ ID NO: 13 and a carrier.

14. A composition comprising the nucleic acid according to claim 6 and a carrier.

15. An isolated mammalian cell comprising the nucleic acid according to claim 1, wherein the nucleic acid comprises a nucleotide sequence that encodes a group M consensus Env comprising SEQ ID NO: 13 or recombinant protein expression.

16. An isolated mammalian cell comprising the nucleic acid according to claim 6 for recombinant protein expression.

17. A method of inducing an immune response in a mammal, the method comprising administering to said mammal the composition of claim 13 in an amount sufficient to effect such induction.

18. A method of inducing an immune response in a mammal, the method comprising administering to said mammal the composition of claim 14 in an amount sufficient to effect such induction.

* * * * *